United States Patent [19]

Amparo et al.

[11] Patent Number: 5,698,538
[45] Date of Patent: Dec. 16, 1997

[54] BORONIC ACID AND ESTER INHIBITORS OF THROMBIN

[75] Inventors: Eugene Cruz Amparo, West Chester; William Henry Miller, Schwenksville, both of Pa.; Gregory James Pacofsky, Raleigh, N.C.; John Wityak, West Grove; Patricia Carol Weber, Yardley, both of Pa.; John Jonas Vytautas Duncia, Wilmington, Del.; Joseph Basil Santella, III, Springfield, Pa.

[73] Assignee: The DuPont Merck Pharmaceutical Company, Wilmington, Del.

[21] Appl. No.: 690,220

[22] Filed: Jul. 26, 1996

Related U.S. Application Data

[60] Division of Ser. No. 364,338, Dec. 27, 1994, Pat. No. 5,563,127, which is a continuation-in-part of Ser. No. 348,029, Dec. 1, 1994, abandoned, which is a continuation-in-part of Ser. No. 318,029, Oct. 4, 1994, abandoned, which is a continuation-in-part of Ser. No. 36,377, Mar. 24, 1993, abandoned.

[51] Int. Cl.$^6$ .............. A61K 31/69; C07D 5/04
[52] U.S. Cl. .............. 514/64; 558/286; 558/287; 558/288; 558/289; 558/298; 562/7; 562/806; 564/8; 564/9; 564/10; 568/1; 568/6
[58] Field of Search .............. 558/286, 287, 558/288, 289, 298; 562/7, 806; 564/8, 9, 10; 568/1, 6; 514/64

[56] References Cited

U.S. PATENT DOCUMENTS 4,963,655  10/1990  Kinder et al. .............. 530/331

OTHER PUBLICATIONS

CA87:163396u Amino methaneboronic acids. Synthesis . . . substrates. Lindquist et al., p. 195, 1977.
CA101:225600z Benzamidomethane boronic acid: . . . chymotrypsin. Amiri et al., p. 341, 1984.
CA108:218119r β-lactamase . . . boronic acids. Crompton et al., p. 243, 1988.
CA 121:136648s Liquid . . . enzyme stability. Labeque et al., p. 140, 1994.

Primary Examiner—Joseph McKane

[57] ABSTRACT

Novel boronic acid and ester and carboxyl-modified amino acid compounds of the Formula I, which are inhibitors of trypsin-like enzymes, are disclosed:

$$R^1-Z-CHR^2-A,$$

where $R^1$, Z, $R^2$ and A are defined within.

7 Claims, No Drawings

BORONIC ACID AND ESTER INHIBITORS OF THROMBIN

This is a division of application Ser. No. 08/364,338, filed Dec. 27, 1994, now U.S. Pat. No. 5,563,127 which is a continuation-in-part of U.S. patent application Ser. No. 8/348/029, filed Dec. 1, 1994, now abandoned, which is a continuation-in-part of U.S. patent application Ser. No. 08/318/029, filed Oct. 4, 1994, now abandoned, which is a continuation-in-part of U.S. patent application Ser. No. 08/036/377, filed Mar. 24, 1993, now abandoned.

FIELD OF THE INVENTION

This invention relates to the discovery of new boronic acid derivatives which are inhibitors of thrombin and pharmaceutical compositions thereof.

BACKGROUND OF THE INVENTION

Hemostasis is the normal physiological process in which bleeding from an injured blood vessel is arrested. It is a dynamic and complex process in which proteolytic enzymes such as thrombin play a key role. Blood coagulation may occur through either of two cascades of zymogen activations, the extrinsic and intrinsic pathways of the coagulation cascade. Factor VIIa in the extrinsic pathway, and Factor IXa in the intrinsic pathway are important determinants of the activation of factor X to factor Xa, which itself catalyzes the activation of prothrombin to thrombin. The last protease in each pathway is thrombin, which acts to hydrolyze four small peptides (two FpA and two FpB) from each molecule of fibrinogen, thus deprotecting its polymerization sites. Once formed, the linear fibrin polymers may be cross-linked by factor XIIIa, which is itself activated by thrombin. In addition, thrombin is a potent activator of platelets, upon which it acts at specific receptors. Thrombin activation of platelets leads to aggregation of the cells and secretion of additional factors that further accelerate the creation of a hemostatic plug. Thrombin also potentiates its own production by the activation of factors V and VIII (see Hemker and Beguin in: Jolles, et. al., "Biology and Pathology of Platelet Vessel Wall Interactions," pp. 219–26 (1986), Crawford and Scrutton in: Bloom and Thomas, "Haemostasis and Thrombosis," pp. 47–77, (1987), Bevers, et. al., *Eur. J. Biochem.* 1982, 122, 429–36, Mann, *Trends Biochemo Sci.* 1987, 12, 229–33).

Thrombosis may be regarded as the pathological condition wherein improper activity of the hemostatic mechanism results in intravascular thrombus formation. Etiological factors such as the presence of atherosclerotic plaque, phlebitis and septicemia may cause thrombosis, leading to impaired blood flow to the effected tissues and possible serious pathological consequences. Thrombosis may be reduced by inhibition of the normal process of blood coagulation by anticoagulants. Anticoagulants act by reducing the amount of thrombin which is generated, or by inhibiting with the proteolytic actions of thrombin.

Currently, two of the most effective classes of drugs in clinical use as anticoagulants are the heparins and the vitamin K antagonists. The heparins are ill-defined mixtures of sulfated polysaccharides that bind to, and thus potentiate the action of antithrombin III. Antithrombin III is a naturally occurring inhibitor of the activated clotting factors IXa, Xa, XIa, thrombin and probably XIIa (see Jaques, *Pharmacol. Rev.* 1980, 31, pp. 99–166). The vitamin K antagonists, of which warfarin is the most well-known example, act indirectly by inhibiting the post-ribosomal carboxylations of the vitamin K dependent coagulation factors II, VII, IX and X (see Hirsch, *Semin. Thromb. Hemostasis* 1986, 12, 1–11). While effective therapies for the treatment of thrombosis, heparins and vitamin K antagonists have the unfortunate side effects of bleeding and marked interpatient variability, resulting in a small and unpredictable therapeutic safety margin. The use of direct acting thrombin inhibitors is expected to alleviate these problems.

Anticoagulants are also necessary in the processing of blood for therapeutic or diagnostic purposes or for the production of blood products or fragments, since contact of blood with the surfaces commonly used for blood collection and storage causes activation of coagulation leading to thrombin formation and clot formation.

The coagulation proteases thrombin, factor Xa, factor VIIa, and factor IXa are serine proteases having trypsin-like specificity for the cleavage of sequence-specific Arg-Xxx peptide bonds. As with other serine proteases, the cleavage event begins with an attack of the active site serine on the scissile bond of the substrate, resulting in the formation of a tetrahedral intermediate. This is followed by collapse of the tetrahedral intermediate to form an acyl enzyme and release of the amino terminus of the cleaved sequence. Hydrolysis of the acyl enzyme then releases the carboxy terminus.

A number of naturally occurring thrombin inhibitors have been reported. These include nazumamide A from *Theonella sp.* (see Fusetani, et. al., *Tetrahedron Lett.* 1991, 32, 707314 4), cyclotheonamide A from *Theonella sp.* (see Fusetani, et. al., *J. Am. Chem. Soc.* 1990, 112, 7053–4), amblyommin from *Amblyomma hebraeum* (see Bonin, et. al., EP 345614), hirudin from *Hirudo medicinalis*, recombinant versions of hirudin and hirudin fragments (see Rigbl and Jackson, EP 352903, Koerwer, WO 9109946, Meyer, et. al., WO 9108233, Dawson, et. al., WO 9109125, Maraganore, et. al., WO 9102750 and Maraganore, EP 333356).

Synthetic thrombin inhibitors have also been disclosed. Arylsulfonylarginine amides such as (2R,4R)-4-methyl-1-[N²-{(3-methyl-1,2,3,4-tetrahydro-8-quinolinyl)sulfonyl}-L-arginyl]-2-piperidinecarboxylate have been shown to be effective inhibitors of thrombin (see Okamoto, et. al. *Thromb Res.* 1976, 8, 77–82, Ohshiro, et. al., *Blood Vessel* 1983, 14, 216–8), as have compounds containing constrained arginine mimics such as (2-naphthylsulfonylglycyl)-4-amidino-phenylalanyl piperidide (see Stuerzebecher, et. al., *Thromb. Res.* 1983, 29, 635–42), 1-[2-[5-(dimethylamino)naphth-1-ylsulfonamido]-3-(2-iminohexahydropyrimidin-5-yl)propanoyl]-4-methylpiperidine dihydrochloride (see Ishikawa, JP 88227572 and Ishikawa and Inamura, JP 88227573), N-(trans-4-amino-methylcyclohexylcarbonyl)-4-O-(2-picolyl)-L-tyrosine 4-acetanilide dihydrochloride (see Okamoto, et. al., EP 217286) and 4-[(aminoiminomethyl) amino]benzoic acid esters (see Fuji, et. al., DE 3005580, Matsuoka, et. al., *Jpn. J. Pharmacol.* 1989, 51, 455–63, and Takeshita, et. al., EP 435235).

Inhibitor design has benefitted from the knowledge of the mechanism of action and of the peptide sequences which are thought to bind in the catalytic site of thrombin, e.g., -Gly-Val-Arg-Gly- of fibrinogen (see Blomback, et. al., *J. Biol. Chem.*, 1972, 247, 1496–512), Ile-Pro-Arg-Ser- of prothrombin (see Magnussen, et. al., in: Reich, et. al., "Proteases and Biological Control," pp. 123–149 (1975)) and -Val-Pro-Arg-Gly- of factor XIII (see Takagi and Doolittle, *Biochemistry* 1974, 13, 750–6 and Nakamura, et. al., *Biochemo Biophys. Res. Commun.* 1974, 58, 250–256).

This class of mechanism-based inhibitors are exemplified by the tripepride aldehyde D-Phe-Pro-N-Me-Arg-H (see Bajusz, et. al., *J. Med. Chem.* 1990, 33, 1729–35), the chloromethyl ketone Ac-D-Phe-Pro-ArgCH$_2$Cl (see Kettner and Shaw, *Thromb. Res.* 1979, 14, 969–73) and the trifluoromethyl ketone D-Phe-Pro-ArgCF$_3$ (see Kolb, et. al., U.S. Pat. No. 697,987).

Kettner and Shenvi (EP 293881, published Jun. 12, 1988), disclose peptide boronic acid inhibitors of trypsin-like proteases of formula (1)

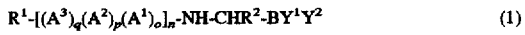
$$R^1-[(A^3)_q(A^2)_p(A^1)_o]_n-NH-CHR^2-BY^1Y^2 \quad (1)$$

wherein Y$^1$ and Y$^2$, independently, are hydroxyl or fluoro or, taken together, form a moiety derived from a dihydroxy compound having at least two hydroxy groups separated by at least two connecting atoms in a chain or ring, said chain or ring comprising 1 to about 20 carbon atoms and, optionally, a heteroatom which can be N, S, or O; R$^2$ is a substituted alkyl selected from the group consisting of —(CH$_2$)$_z$—X, —(CH(CH$_3$)—(CH$_2$)$_2$—X, —CH$_2$—CH—(CH$_3$)—CH$_2$—X, —(CH$_2$)$_2$—CH (CH$_3$)—X and —(CH$_2$)$_2$—CH(CH$_3$)$_2$—X, where X is —NH$_2$, —NH—C(NH)—NH$_2$ or —S—C(NH)—NH$_2$, and z is 3 to 5; n, o, p and q are, independently, either 0 or 1; A$^1$, A$^2$ and A$^3$ are, independently, amino acids of L- or D-configuration selected from the group consisting of Ala, Arg, Asn, Asp, Cys, Gln, Glu, Gly, His, Ile, Leu, Lys, Met, Phe, Pro, Ser, Thr, Trp, Tyr and Val; and R$^1$ is a peptide comprised of 1 to about 20 amino acids, an acyl or a sulfonyl group comprised of 1 to about 20 carbon atoms, H, or an N-terminal protecting group. In this disclosure, Kettner and Shenvi demonstrated that the pinanediol esters of boropeptides are pharmacogolically equivalent to the corresponding boronic acids. Metternich (EP 0471651 A2) discloses borolysine thrombin inhibitors of formula (2)

$$W-Y-NR^4-CHR^5-BQ^1Q^2 \quad (2)$$

wherein W is an N-protecting group; Y is a sequence of n amino acids such that the n+1 amino acid peptide Y-Lys or Y-Arg has an affinity for the active site of a trypsin-like protease; where n is an integer of from 1 to 10 and in which at least one amino acid is an unnatural amino acid having a hydrophobic side chain; Q$^1$ and Q$^2$ are the same or different and are selected from —OH, —COR$_1$, —CONR$_1$R$_2$, —NR$_1$R$_2$ or —OR$_3$ of Q$^1$ and Q$^2$ taken together form a diol residue; R$_1$, R$_2$ and R$_3$ which may be the same or different, are C$_{1-10}$alkyl, C$_{6-10}$aryl, C$_{6-10}$aralkyl, or phenyl substituted by up to three groups selected from C$_{1-4}$alkyl, halogen and C$_{1-4}$alkoxy; R$_4$ is hydrogen or C$_{1-10}$alkyl; R$_5$ is a group —A—X; wherein A is —(CH$_2$)$_z$— in which z is 2, 3, 4 or 5; —CH(CH$_3$)—(CH$_2$)$_2$—; —CH$_2$—CH(CH$_3$)—CH$_2$—; —(CH$_2$)$_2$—CH(CH$_3$)—; —(CH$_2$)$_2$—C(CH$_3$)$_2$—; CH(CH$_3$)—(CH$_2$)$_3$—; —CH$_2$—CH(CH$_3$)—(CH$_2$)$_2$—; —CH$_2$—CH$_2$—CH(CH$_3$)—CH$_2$—; —(CH$_2$)$_3$—CH(CH$_3$)—; —(CH$_2$)$_3$—C(CH$_3$)$_2$; C$_{6-10}$aryl C$_{6-10}$aralkyl and X is —NH$_2$, —NH—C(NH)—NH$_2$, —S—C(NH)—NH$_2$, N$_3$, -C$_{1-4}$alkoxy, C$_{1-4}$alkylthio or Si(CH$_3$)$_3$ or R$_4$ and R$_5$ taken together form a trimethylene group and the asymmetric carbon atom may have the D- or L-configuration or represent any mixture of these.

Surprising for their lack of a basic residue at P$_1$ are tripeptide thrombin inhibitors comprised of 1-aminoboronic and 1-aminophosphonic acid analogs of 3-methoxypropylglycine (see Claeson, et. al., U.S. Ser. No. 07-245428) and pentylglycine (see Cheng, et. al., "Symposium on Thrombosis and Hemostasis," 1991, Amsterdam, Abstract 2150).

In addition to thrombin inhibition, boropeptides have been disclosed with utility as a treatment for tumors, viral infections and arthritis (U.S. Pat. No. 4,963,655 and EP 354522A), emphysema (U.S. Pat. No. 4,499,082), hypertension (EP 315574A) and as factor VII/VIIa inhibitors (WO 8909612A). Kleemann, et. al. (AU A-24693/88) disclose renin-inhibiting 1-amino boronic acid derivatives of formula (3)

$$A^1-A^2-HN-CHR^2-BXR^3(YR^4) \quad (3)$$

in which A$^1$ denotes a radical of formulae (4–8).

$$R^1NR^6-CHR^5-C=O- \quad (4)$$

$$R^1CHR^{12}-CHR^5-C=O- \quad (5)$$

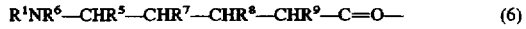
$$R^1NR^6-CHR^5-CHR^7-CHR^8-CHR^9-C=O- \quad (6)$$

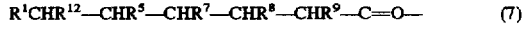
$$R^1CHR^{12}-CHR^5-CHR^7-CHR^8-CHR^9-C=O- \quad (7)$$

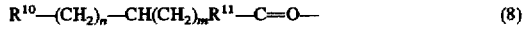
$$R^{10}-(CH_2)_n-CH(CH_2)_mR^{11}-C=O- \quad (8)$$

Despite the foregoing, more efficacious and specific inhibitors of coagulation proteases are needed as potentially valuable therapeutic agents for the treatment of thrombosis. None of the cited references describe or suggest the new thrombin-inhibiting boronic acid derivatives of the present invention.

SUMMARY OF THE INVENTION

This invention pertains to novel compounds of formula (I):

$$R^1-Z-CHR^2-A \quad (I)$$

wherein
A is
- a) —BY$^1$Y$^2$,
- b) —C(=O)CF$_3$,
- c) —C(=O)CHF$_2$,
- d) —C(=O)CH$_2$F,
- e) —C(=O)CH$_2$Cl,
- f) —C(=O)OR$^3$,
- g) —C(=O)NR$^{15}$R$^{16}$,
- h) —C(=O)R$^3$,
- i) —C(=O)COOR$^3$,
- j) —C(=O)C(=O)NR$^{15}$R$^{16}$,
- k) —C(=O)C(=O)R$^3$,
- l) —C(=O)CY$^3$Y$^4$COOR$^3$,
- m) —C(=O)CY$^3$Y$^4$C(=O)NR$^{15}$R$^{16}$,
- n) —C(=O)CY$^3$Y$^4$C(=O)R$^3$,
- o) —PO$_3$H$_2$, or
- p) —CHO;

Y$^1$ and Y$^2$ are independently
- a) —OH,
- b) —F,
- c) —NR$^3$R$^4$, or
- d) C$_1$–C$_8$ alkoxy;

Y$^1$ and Y$^2$ can be taken together to form:
- e) a cyclic boron ester where said chain or ring contains from 2 to 20 carbon atoms and, from 0–3 heteroatoms which can be N, S, or O,
- f) a cyclic boron amide where said chain or ring contains from 2 to 20 carbon atoms and, from 0–3 heteroatoms which can be N, S, or O, g) a cyclic boron amide-ester where said chain or ring contains from 2 to 20 carbon atoms and, from 0–3 heteroatoms which can be N, S, or O;

$Y^3$ and $Y^4$ are independently
a) —OH or
b) —F;

Z is
a) —$(CH_2)_m CONR^8$—,
b) —$(CH_2)_m CSNR^8$—,
c) —$(CH_2)_m SO_2NR^8$—,
d) —$(CH_2)_m CO_2$—,
e) —$(CH_2)_m C(S)O$—, or
f) —$(CH_2)_m SO_2O$—;

$R^1$ is
a) —$(CH_2)_p$-aryl, wherein aryl is phenyl, naphthyl or biphenyl substituted with one, two or three substituents selected from the group consisting of:
halo (F, Cl, Br, I), methylenedioxy, —$R^8$, —$NR^8COR^9$, $C_2$-$C_6$-alkenyl, $C_2$-$C_6$-alkynyl, —$(CH_2)_w$—$OR^8$, -($C_1$-$C_6$)-perfluoroalkyl, —$(CH_2)_w CN$, —$(CH_2)_w NC$, —$(CH_2)_w NO_2$, —$(CH_2)_w CF_3$, —$(CH_2)_w S(O)_r R^7$, —$(CH_2)_w NR^8R^9$, —$(CH_2)_w COR^8$, —$(CH_2)_w CHO$; —$(CH_2)_w CO_2R^8$, —$(CH_2)_w CONR^8R^9$, —$(CH_2)_w SO_2NH$—$(C_1$-$C_5)$-alkyl, —$(CH_2)_w SO_2NH_2$, —$(CH_2)_w SO_2NH$—CO—$(C_1$-$C_6)$-alkyl, —$(CH_2)_w SO_2NH$—$CO_2$—$(C_1$-$C_6)$-alkyl, —$(CH_2)_w NHSO_2$—$(C_1$-$C_6)$-alkyl, —$(CH_2)_w NHSO_2$—$(C_1$-$C_6)$-perfluoroalkyl, —$(CH_2)_w NHSO_2$-phenyl, —$(CH_2)_w NHSO_2$-perfluorophenyl, —$(CH_2)_w CN^4H$, —$O(CH_2)_w CN$, —$NH(CH_2)_w CN$, —$S(CH_2)_w CN$, —$(CH_2)_w NH$—CO—$(C_1$-$C_6$-alkyl ), —$(CH_2)_w NH$—CO—$(C_1$-$C_6$-perfluoroalkyl), —$(CH_2)_w NH$—CO—(phenyl), —$(CH_2)_w NH$—$CO_2$—$(C_1$-$C_6$-alkyl), —$(CH_2)_w NH$—$CO_2$—$(C_1$-$C_6$-perfluoroalkyl), —$(CH_2)_w NH$—$CO_2$—(phenyl), —$O(C=O)$—$(C_1$-$C_5$-alkyl),

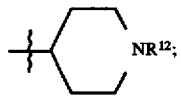

b) heteroaryl, wherein heteroaryl is an unsubstituted, monosubstituted or disubstituted:
i) quinolinyl,
ii) isoquinolinyl,
iii) benzopyranyl,
iv) benzothiophenyl,
v) benzofuranyl,
vi) 5,6,7,8-tetrahydroquinolinyl,
vii) 5,6,7,8-tetrahydroisoquinolinyl,
and wherein the substituents are selected from the group consisting of halo (F, Cl, Br, I), —CN, $C_1$-$C_{10}$-alkyl, $C_3$-$C_8$-cycloalkyl, $C_2$-$C_{10}$-alkenyl, $C_2$-$C_{10}$-alkynyl, $R^8$, —$OR^8$, —$NO_2$, —$CF_3$, —$S(O)_r R^7$, —$NR^8R^9$, —$COR^8$, —$CO_2R^8$, —$CONHR^8$, $NR^8COR^9$, $NR^8CO_2R^9$,

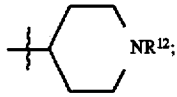

c)

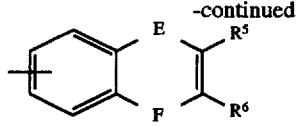

d) 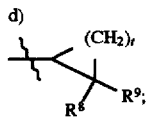

e) 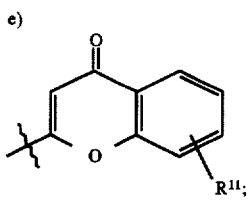

f) 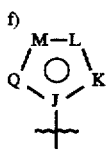

wherein J is N or C and K, L, M and Q are independently selected at each occurrence from the group consisting of N, $CR^{13}$, S or O, provided that:
i) there may be only one S or O present in the ring at a time;
ii) there may only be 1–2N present when there is an O or S present;
iii) there may be only 1–4N present;

g)

wherein W, R, T, U and V are selected from the group consisting of: $CR^{13}$ or N, provided that there be no less than 1 and no more than 3N present;

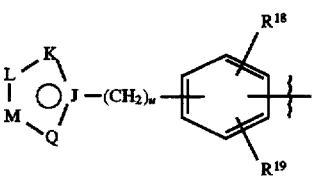 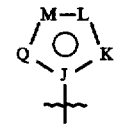

wherein is as defined above;

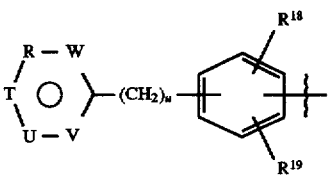 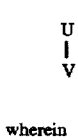

wherein is as defined above;

j)
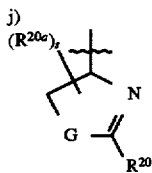

wherein G is O, S, or NP, where P is an amine protecting group selected from the group consisting of: —R³, —C(=O)R³, —SO₂R³, —C(=O)OR³);

k)
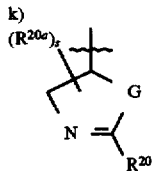

wherein G is O, S, or NP, where P is an amine protecting group selected from the group consisting of: —R³, —C(=O)R³, —SO₂R³, —C(=O)OR³);

R² is
 a) —(C₁–C₁₂ alkyl)—X,
 b) —(C₂–C₁₂ alkenyl)—X, or c)
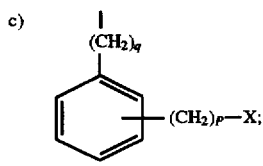

X is
 a) halogen (F, Cl, Br, I),
 b) —CN,
 c) —NO₂,
 d) —CF₃,
 e) —S(O)ᵣR¹⁴,
 f) —NHR¹⁴
 g) —NHS(O)ᵣR¹⁴,
 h) —NHC(NH)H,
 i) —NHC(NH)NHOH,
 j) —NHC(NH)NSCN,
 k) —NHC(NH)NHR¹⁴,
 l) —NHC(NH)NHCOR¹⁴,
 m) —C(NH)NHR¹⁴,
 n) —C(NH)NHCOR¹⁴,
 o) —C(O)NHR¹⁴,
 p) —C(O)NHC(O)R¹⁴,
 q) —C(O)OR¹⁴,
 r) —OR¹⁴,
 s) —OC(O)R¹⁴,
 t) —OC(O)OR¹⁴,
 u) —OC(O)NHR¹⁴,
 v) —OC(O)NHC(O)R¹⁴,
 w) —SC(=NH)NHR¹⁴, or
 x) —SC(=NH)NHC(=O)R¹⁴;
R³ is
 a) hydrogen,
 b) C₁–C₈ alkyl,
 c) —(C₁–C₄ alkyl)-aryl,
 d) C₅–C₇ cycloalkyl,
 e) phenyl; or
R⁴ is
 a) hydrogen,
 b) C₁–C₈ alkyl,
 c) -(C₁–C₄ alkyl)-aryl,
 d) C₅–C₇ cycloalkyl,
 e) phenyl, or
 f) phenylsulfonyl;
R⁵ and R⁶ are hydrogen or when taken together form a six membered aromatic ring optionally substituted with one, two or three substituents selected from the group consisting of halo (F, Cl, Br, I), —CN, C₁–C₁₀-alkyl, C₃–C₈-cycloalkyl, C₂–C₁₀-alkenyl, C₂–C₁₀-alkynyl, —OR⁸, —NO₂, —CF₃, —S(O)ᵣR⁷, —NR⁸R⁹, —COR⁸, —CO₂R⁸, —CONR⁸R⁹, phenyl, benzyl, phenylethyl;
R⁷ is
 a) phenyl,
 b) C₁–C₈-alkyl,
 c) C₁–C₄-alkoxy,
 d) —CF₃, or
 e) benzyl;
R⁸ and R⁹ are independently
 a) H, b)
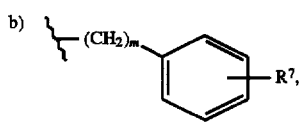

c) C₃–C₇ cycloalkyl, or
 d) C₁–C₈-alkyl;
R¹¹ is
 a) halo (F, Cl, Br, I),
 b) —CN,
 c) C₁–C₁₀-alkyl,
 d) C₃–C₈-cycloalkyl,
 e) C₂–C₁₀-alkenyl,
 f) C₂–C₁₀-alkynyl,
 g) —OR⁸,
 h) —NO₂,
 i) —CF₃,
 j) —S(O)ᵣR⁷,
 k) —NR⁸R⁹,
 l) —COR⁹,
 m) —CO₂R⁸,
 n) —CONR⁸R⁹, or
 o) H
R¹² is
 H, C₁–C₄ alkyl, phenyl, benzyl, —COR⁷, or —S(O)ᵣR⁷;
R¹³ is
 H, halogen (F, Cl, Br, I), (C₁–C₈)alkyl, (C₁–C₆)-perfluoroalkyl, —(CH₂)ᵣ—D, C₃–C₈ cycloalkyl, C₂–C₆-alkenyl, C₂–C₆-alkynyl, methylenedioxy, —(CH₂)ᵥᵥ—OR⁸, —(CH₂)ᵥᵥNC, —(CH₂)ᵥᵥCN, —(CH₂)ᵥᵥNO₂, —(CH₂)ᵥᵥCF₃, —(CH₂)ᵥᵥS(O)ᵣR⁷, —(CH₂)ᵥᵥNR⁸R⁹, —(CH₂)ᵥᵥCOR⁸, —(CH₂)ᵥᵥCO₂R⁸, —(CH$_2$)$_w$CONR$^8$R$^9$, —(CH$_2$)$_w$SO$_2$NH—(C$_1$-C$_6$)-alkyl, —(CH$_2$)$_w$SO$_2$NH$_2$, —(CH$_2$)$_w$SO$_2$NH—CO—(C$_1$-C$_6$)-alkyl, —(CH$_2$)$_w$SO$_2$NH—CO$_2$—(C$_1$-C$_6$)-alkyl, —(CH$_2$)$_w$SO$_2$NH, —(CH$_2$)$_w$NHSO$_2$—(C$_1$-C$_6$)-alkyl, —(CH$_2$)$_w$NHSO$_2$—(C$_1$-C$_6$)-perfluoroalkyl, —(CH$_2$)$_w$NHSO$_2$-phenyl, —(CH$_2$)$_w$NHSO$_2$-perfluorophenyl, —(CH$_2$)$_w$CN$^4$H, —O(C=O)—(C$_1$-C$_5$-alkyl), —O(CH$_2$)$_w$CN, —NH(CH$_2$)$_w$CN, —S(CH$_2$)$_w$CN, —(CH$_2$)$_w$NH—CO—(C$_1$-C$_6$-alkyl), —(CH$_2$)$_w$NH—CO—(C$_1$-C$_6$-perfluoroalkyl), —(CH$_2$)$_w$ NH—CO—(phenyl), —(CH$_2$)$_w$NH—CO$_2$—(C$_1$-C$_6$-alkyl), —(CH$_2$)$_w$NH—CO$_2$—(C$_1$-C$_6$-perfluoroalkyl), —(CH$_2$)$_w$NH—CO$_2$—(phenyl), —(CH$_2$)$_u$phenyl wherein the phenyl contains 0–3 substituents selected from R$^{18}$, —S—(CH$_2$)$_u$phenyl wherein the phenyl contains 0–3 substituents selected from R$^{18}$, or —O—(CH$_2$)$_u$phenyl wherein the phenyl contains 0–3 substituents selected from R$^{18}$;

R$^{14}$ is
a) —H,
b) —CF$_3$
c) -C$_1$-C$_4$ alkyl,
d) —(CH$_2$)$_q$-aryl, wherein aryl is phenyl, biphenyl, naphthyl, or fluorenyl unsubstituted or substituted with one to three substituents selected from the group consisting of:
halogen (F, Cl, Br, I),
—CF$_3$,
-(C$_1$-C$_4$ alkyl),
—(CH$_2$)$_x$R$^{15}$,
—(CH$_2$)$_x$CO(CH$_2$)$_y$R$^{15}$,
—(CH$_2$)$_x$C(O)O(CH$_2$)$_y$R$^{15}$,
—(CH$_2$)$_x$C(O)N[(CH$_2$)$_y$R$^{15}$][(CH$_2$)$_y$R$^{16}$],
-methylenedioxy,
—(C$_1$-C$_4$ alkoxy),
—(CH$_2$)$_x$O(CH$_2$)$_y$R$^{15}$,
—(CH$_2$)$_x$OCO(CH$_2$)$_y$R$^{15}$,
—(CH$_2$)$_x$OC(O)O(CH$_2$)$_y$R$^{15}$,
—(CH$_2$)$_x$OC(O)N[(CH$_2$)$_y$R$^{15}$][(CH$_2$)$_y$R$^{16}$],
—(CH$_2$)$_x$OC(O)N[(CH$_2$)$_y$R$^{15}$][CO(CH$_2$)$_y$R$^{16}$],
—(CH$_2$)$_x$S(O)$_r$(CH$_2$)$_y$R$^{15}$,
—(CH$_2$)$_x$S(O)$_r$(CH$_2$)$_y$COR$^{15}$,
—(CH$_2$)$_x$S(O)$_r$(CH$_2$)$_y$C(O)OR$^{15}$,
—(CH$_2$)$_x$S(O)$_r$N[(CH$_2$)$_y$R$^{15}$][(CH$_2$)$_y$R$^{16}$]
—(CH$_2$)$_x$N[(CH$_2$)$_y$R$^{15}$][(CH$_2$)$_y$R$^{16}$],
—(CH$_2$)$_x$N[(CH$_2$)$_y$R$^{15}$][CO(CH$_2$)$_y$R$^{16}$],
—(CH$_2$)$_x$N[(CH$_2$)$_y$R$^{15}$][C(O)O(CH$_2$)$_y$R$^{16}$],
—(CH$_2$)$_x$N[(CH$_2$)$_y$R$^{15}$]CON[(CH$_2$)$_y$R$^{15}$][(CH$_2$)$_y$R$^{16}$],
—(CH$_2$)$_x$N[(CH$_2$)$_y$R$^{15}$]CON[(CH$_2$)$_y$R$^{15}$]—[CO(CH$_2$)$_y$R$^{16}$],
—(CH$_2$)$_x$N[(CH$_2$)$_y$R$^{15}$][S(O)$_r$(CH$_2$)$_y$R$^{16}$];

R$^{15}$ and R$^{16}$ are independently
a) hydrogen,
b) C$_1$-C$_8$ alkyl,
c) -(C$_1$-C$_4$ alkyl)-aryl, where aryl is defined above,
d) C$_5$-C$_7$ cycloalkyl,
e) phenyl, substituted by 0–3 R$^{18}$,
f) benzyl, substituted by 0–3 R$^{18}$, or
g) -(C$_1$-C$_4$ alkoxy);

R$^{15}$ and R$^{16}$ can be taken together to form a ring:

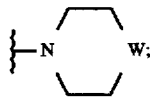

R$^{18}$ and R$^{19}$ are independently H, halo (F, Cl, Br, I), C$_1$-C$_8$-alkyl, C$_3$-C$_8$ cycloalkyl, C$_2$-C$_6$-alkenyl, C$_2$-C$_6$-alkynyl, —(CH$_2$)$_w$—OR$^8$, —(CH$_2$)$_w$CN, —(CH$_2$)$_w$NC, —(CH$_2$)$_w$NO$_2$, —(CH$_2$)$_w$CF$_3$, —(CH$_2$)$_w$S(O)$_r$R$^7$, —(CH$_2$)$_w$NR$^8$R$^9$, —(CH$_2$)$_w$COR$^8$, —(CH$_2$)$_w$CO$_2$R$^8$, —(CH$_2$)$_w$$^{CONR8}$R9, —(CH$_2$)$_w$SO$_2$NH—(C$_1$-C$_6$)-alkyl, —(CH$_2$)$_w$SO$_2$NH$_2$, —(CH$_2$)$_w$SO$_2$NH—CO—(C$_1$-C$_6$)-alkyl, —(CH$_2$)$_w$SO$_2$NH—CO$_2$—(C$_1$-C$_6$)-alkyl, —(CH$_2$)$_w$ SO$_2$NH—, —(CH$_2$)$_w$NHSO$_2$—(C$_1$-C$_6$)-alkyl, —(CH$_2$)$_w$ NHSO$_2$—(C$_1$-C$_6$)-perfluoroalkyl, —(CH$_2$)$_w$ NHSO$_2$-phenyl, —(CH$_2$)$_w$NHSO$_2$-perfluorophenyl, —(CH$_2$)$_w$ CN$^{4H}$, —O(C=O)—(C$_1$-C$_5$-alkyl), —O(CH$_2$)$_w$ CN, —NH(CH$_2$)$_w$CN, —S(CH$_2$)$_w$CN, —(CH$_2$)$_w$NH—CO—(C$_1$-C$_6$-alkyl), —(CH$_2$)$_w$NH—CO—(C$_1$-C$_6$-perfluoroalkyl), —(CH$_2$)$_w$NH—CO—(C$_1$-C$_6$-phenyl), —(CH$_2$)$_w$NH—CO$_2$—(C$_1$-C$_6$-alkyl), —(CH$_2$)$_w$NH—CO$_2$—(C$_1$-C$_6$-phenyl), or —O(C=O) phenyl;

R$^{18}$ and R$^{19}$ can be taken together to form a methylenedioxy group;

R$^{20}$ and R$^{20a}$ are independently (C$_1$-C$_8$)alkyl, —(CH$_2$)$_u$phenyl wherein the phenyl contains 0–3 substituents selected from R$^{18}$, (C$_1$-C$_6$)-perfluoroalkyl, or —(CH$_2$)$_r$—D;

m is 0 to 6;
n is 1 to 2;
p is 0 to 2;
q is 0 to 4,
r is 0 to 2;
s is 0 to 3;
t is 1 to 5;
u is 0 to 5;
v is 0 to 5;
w is 0 to 5;
x is 0 to 6;
y is 0 to 6;
D is fur-2-yl, fur-3-yl, thiophen-2-yl, thiophen-3-yl, oxazol-2-yl, oxazol-4-yl, thiazol-2-yl, thiazol-4-yl, isoxazol-3-yl, isoxazol-4-yl, isoxazol-5-yl, pyrid-2-yl, pyrid-4-yl, pyridazin-3-yl, pyridazin-4-yl, pyrimidin-2-yl, pyrimidin-4-yl, pyrazin-2-yl, or tetrazolyl;
E is —CO—, —SO$_2$—, —CH$_2$— or a single bond;
F is —CO—;
W is
a) —O—,
b) —S(O)$_r$—,
c) —NR$^4$—,
d) —NC(=O) R$^3$—,
e) a bond, or
f) —(CH$_2$)$_n$—;
or prodrugs or pharmaceutically acceptable salts thereof.
Preferred compounds of formula (I) are those compounds wherein:
Z is
a) —(CH$_2$)$_m$CONR$^8$—,
b) —(CH$_2$)$_m$CSNR$^8$—,
c) —(CH$_2$)$_m$SO$_2$NR$^8$—,
R$^1$ is
a) —(CH$_2$)$_p$-aryl, wherein aryl is phenyl, naphthyl or biphenyl substituted with one, two or three substituents selected from the group consisting of:

halo (F, Cl, Br, I), methylenedioxy, —R$^8$, —NR$^8$COR$^9$, C$_2$-C$_6$-alkenyl, C$_2$-C$_6$-alkynyl, —(CH$_2$)$_w$—OR$^8$, -(C$_1$-C$_6$)-perfluoroalkyl, —(CH$_2$)$_w$CN, —(CH$_2$)$_w$NC, —(CH$_2$)$_w$NO$_2$, —(CH$_2$)$_w$CF$_3$, —(CH$_2$)$_w$S(O)$_r$R$^7$, —(CH$_2$)$_w$NR$^8$R$^9$, —(CH$_2$)$_w$COR$^8$, —(CH$_2$)$_w$CO$_2$R$^8$, —(CH$_2$)$_w$CONR$^8$R$^9$, —(CH$_2$)$_w$SO$_2$NH—(C$_1$-C$_6$)-alkyl, —(CH$_2$)$_w$SO$_2$NH$_2$, —(CH$_2$)$_w$SO$_2$NH—CO—(C$_1$-C$_6$)-alkyl, —(CH$_2$)$_w$SO$_2$NH—CO$_2$—(C$_1$-C$_6$)-alkyl, —(CH$_2$)$_w$NHSO$_2$—(C$_1$-C$_6$)-alkyl, —(CH$_2$)$_w$NHSO$_2$—(C$_1$-C$_6$)-perfluoroalkyl, —(CH$_2$)$_w$NHSO$_2$-phenyl, —(CH$_2$)$_w$NHSO$_2$-perfluorophenyl, —(CH$_2$)$_w$CN$^4$H, e—O(CH$_2$)$_w$CN, —NH(CH$_2$)$_w$CN, —S(CH$_2$)$_w$CN, —(CH$_2$)$_w$NH—CO—(C$_1$-C$_6$-alkyl), —(CH$_2$)$_w$NH—CO—(C$_1$-C$_6$-perfluoroalkyl), —(CH$_2$)$_w$NH—CO—(phenyl), —(CH$_2$)$_w$NH—CO$_2$—(C$_1$-C$_6$-alkyl), —(CH$_2$)$_w$NH—CO$_2$—(C$_1$-C$_6$-perfluoroalkyl), or —(CH$_2$)$_w$NH—CO$_2$—(phenyl), —O(C=O—(C$_1$-C$_5$ alkyl);

b) heteroaryl, wherein heteroaryl is an unsubstituted, monosubstituted or disubstituted:
   i) quinolinyl,
   ii) isoquinolinyl,
   iii) benzopyranyl,
   iv) benzothiophenyl,
   v) benzofuranyl,
   vi) 5,6,7,8-tetrahydroquinolinyl,
   vii) 5,6,7,8-tetrahydroisoquinolinyl,
   and wherein the substituents are selected from the group consisting of halo (F, Cl, Br, I), —CN, C$_1$-C$_{10}$-alkyl, C$_3$-C$_8$-cycloalkyl, C$_2$-C$_{10}$-alkenyl, C$_2$-C$_{10}$-alkynyl, R$^8$, —OR$^8$, —NO$_2$, —CF$_3$, —S(O)$_r$ R$^7$, —NR$^8$R$^9$, —COR$^8$, —CO$_2$R$^8$, —CONR$^8$H, NR$^8$COR$^9$, NR$^8$CO$_2$R$^9$;

c)
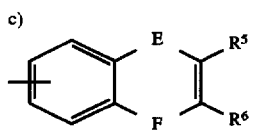

d)
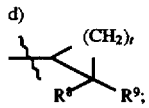

e)
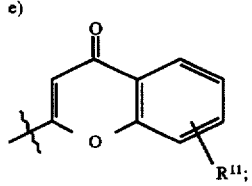

f) wherein the ring

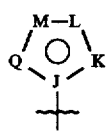

represented by —J—K—L—M—Q— is a group selected from:
1) —N—C(R$^{13}$)=C(R$^{13}$)—C(R$^{13}$)=C(R$^{13}$)—,
2) —N—C(R$^{13}$)=C(R$^{13}$)—C(R$^{13}$)=N—,
3) —N—C(R$^{13}$)=C(R$^{13}$)—N=C(R$^{13}$)—,
4) —N—C(R$^{13}$)=N—C(R$^{13}$)=N—,
5) —N—C(R$^{13}$)=C(R$^{13}$)—N=N—
6) —N—C(R$^{13}$)=N—N=N—,
7) —N—N=C(R$^{13}$)—N=N—,
8) =C—O—C(R$^{13}$)=N—C(R$^{13}$)=,
9) —C=C(R$^{13}$)—O—C(R$^{13}$)=N—,
10) =C—O—C(R$^{13}$)=C(R$^{13}$)—N=,
11) —C=C(R$^{13}$)—C(R$^{13}$)=N—O—,
12) =C—C(R$^{13}$)=C(R$^{13}$)—O—N=,
13) —C=C(R$^{13}$)—O—N=C(R$^{13}$)—,
14) =C—S—C(R$^{13}$)=N—C(R$^{13}$)=,
15) —C=C(R$^{13}$)—S—C(R$^{13}$)=N—,
16) =C—S—C(R$^{13}$)=C(R$^{13}$)—N=,
17) —C=N—S—N=C(R$^{13}$)—,
18) —C=N—S—C(R$^{13}$)=N—,
19) =C—S—N=C(R$^{13}$)—N=,
20) =C—S—C(R$^{13}$)=C(R$^{13}$)—C(R$^{13}$)=,
21) —C=C(R$^{13}$)—S—C(R$^{13}$)=C(R$^{13}$)—,
22) =C—O—C(R$^{13}$)=C(R$^{13}$)—C(R$^{13}$)=, or
23) —C=C(R$^{13}$)—O—C(R$^{13}$)=C(R$^{13}$)—;

g) wherein the ring

represented by —C—W—R—T—U—V— is a group selected from:
1) —C=N—C(R$^{13}$)=C(R$^{13}$)—C(R$^{13}$)=C(R$^{13}$)—,
2) —C=C(R$^{13}$)—N=C(R$^{13}$)—C(R$^{13}$)=C(R$^{13}$)—,
3) —C=C(R$^{13}$)—C(R$^{13}$)=N—C(R$^{13}$)=C(R$^{13}$)—,
4) —C=N—N=C(R$^{13}$)—C(R$^{13}$)=C(R$^{13}$)—,
5) —C=C(R$^{13}$)—N=N—C(R$^{13}$)=C(R$^{13}$)—,
6) —C=N—C(R$^{13}$)=C(R$^{13}$)—C(R$^{13}$)=N—,
7) —C=N—C(R$^{13}$)=C(R$^{13}$)—N=C(R$^{13}$)—,
8) —C=N—C(R$^{13}$)=N—C(R$^{13}$)—N=C(R$^{13}$)—,
9) —C=C(R$^{13}$)—N=C(R$^{13}$)—N=C(R$^{13}$)—,
10) —C=N—C(R$^{13}$)=N—N=C(R$^{13}$)—,
11) —C=N—C(R$^{13}$)=C(R$^{13}$)—N=N—, or
12) —C=C(R$^{13}$)—N=C(R$^{13}$)—N=N—;

h)
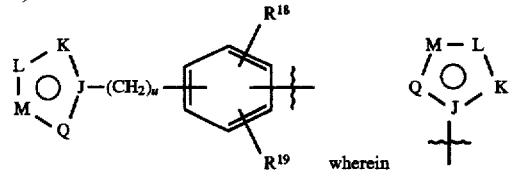
wherein is as defined above;

i)
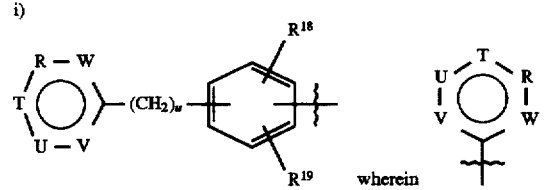
wherein is as defined above;

j)
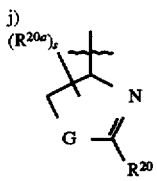

wherein G is O, S, or NP (where P is an amine protecting group selected from the group consisting of: —$R^3$, —$C(=O)R^3$, —$SO_2R^3$, —$C(=O)OR^3$;

k)
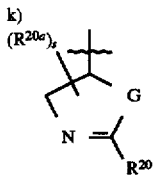

wherein G is O, S, or NP (where P is an amine protecting group selected from the group consisting of: —$R^3$, —$C(=O)R^3$, —$SO_2R^3$, —$C(=O)OR^3$;

$R^{14}$ is
a) —H,
b) —$CF_3$
c) -$C_1$-$C_4$ alkyl,
d) —$(CH_2)_q$-aryl, wherein aryl is phenyl, biphenyl, naphthyl, or fluorenyl unsubstituted substituted with one to three substituents selected from the group consisting of:
halogen (F, Cl, Br, I),
—$CF_3$,
-($C_1$-$C_4$ alkyl),
-methylenedioxy,
-($C_1$-$C_4$ alkoxy),
—$(CH_2)_xN[(CH_2)_yR^{15}][(CH_2)_yR^{16}]$; and all other required substituents of formula (I) are as defined in Claim 1.

More preferred compounds of the formula (I) are those compounds wherein:

A is
a) —$BY^1Y^2$,
b) —$C(=O)CF_3$,
c) —$C(=O)CHF_2$,
d) —$C(=O)CH_2F$,
e) —$C(=O)CH_2Cl$,
f) —$C(=O)R^3$,
g) —$C(=O)NR^{15}R^{16}$,
h) —$C(=O)R^3$,
i) —$C(=O)COOR^3$,
j) —$C(=O)C(=O)NR^{15}R^{16}$,
k) —$C(=O)C(=O)R^3$,
l) —CHO;

$Y^1$ and $Y^2$ are independently
a) —OH, or
b) $C_1$-$C_8$ alkoxy;

$Y^1$ and $Y^2$ can be taken together to form a cyclic boron ester where said chain or ring contains from 2 to 20 carbon atoms and, from 0–3 heteroatoms which can be N, S, or O, Z is a) —$(CH_2)_mCONR^8$—,
b) —$(CH_2)_mCSNR^8$—, or
c) —$(CH_2)_mSO_2NR^8$—;

$R^1$ is a) —$(CH_2)_p$-aryl, wherein aryl is phenyl, naphthyl or biphenyl substituted with one, two or three substituents independently selected at each occurrence from the group consisting of:
halo (F, Cl, Br, I), methylenedioxy, —$R^8$, —$NR^8COR^9$, $C_2$-$C_6$-alkenyl, $C_2$-$C_6$-alkynyl, —$(CH_2)_w$—$OR^8$, —($C_1$-$C_6$)-perfluoroalkyl, —$(CH_2)_wCN$, —$(CH_2)_w$NC, —$(CH_2)_wNO^2$, —$(CH_2)_wCF_3$, —$(CH_2)_wS(O)_rR^7$, —$(CH_2)_wNR^8R^9$, —$(CH_2)_wCOR^8$, —$(CH_2)_w$ $CO_2R^8$, —$(CH_2)_wCONR^8R^9$, —$(CH_2)_w$ $SO_2NH$—($C_1$-$C_6$)-alkyl, —$(CH_2)_wSO_2NH_2$, —$(CH_2)_w$ $SO_2NH$—CO—($C_1$-$C_6$)-alkyl, —$(CH_2)_w$ $SO_2NH$—$CO_2$—($C_1$-$C_6$)-alkyl, —$(CH_2)_w$ $SO_2NH$—, —$(CH_2)_wNHSO_2$—($C_1$-$C_6$)-alkyl, —$(CH_2)_wNHSO_2$—($C_1$-$C_6$)-perfluoroalkyl, —$(CH_2)_wNHSO_2$-phenyl, —$(CH_2)_wNHSO_2$-perfluorophenyl, —$(CH_2)_wCN^4H$, —$O(CH_2)_wCN$, —$NH(CH_2)_wCN$, —$S(CH_2)_wCN$, —$(CH_2)_wNH$—CO—($C_1$-$C_6$-alkyl), —$(CH_2)_wNH$—CO—($C_1$-$C_6$-perfluoroalkyl), —$(CH_2)_wNH$—CO—(phenyl), —$(CH_2)_wNH$—$CO_2$—($C_1$-$C_6$-alkyl), —$(CH_2)_w$ $NH$—$CO_2$—($C_1$-$C_6$-perfluoroalkyl), or —$(CH_2)_w$ $NH$—$CO_2$—(phenyl), —$O(C=O)$—$C_1$-$C_5$-alkyl);

b) heteroaryl, wherein heteroaryl is an unsubstituted, monosubstituted or disubstituted:
i) quinolinyl,
ii) isoquinolinyl,
iii) benzopyranyl,
iv) benzothiophenyl,
v) benzofuranyl,
vi) 5,6,7,8-tetrahydroquinolinyl,
vii) 5,6,7,8-tetrahydroisoquinolinyl,
wherein the substituents are members selected from the group consisting of: halo (F, Cl, Br, I), —CN, $C_1$-$C_{10}$-alkyl, $C_3$-$C_8$-cycloalkyl, $C_2$-$C_{10}$-alkenyl, $C_2$-$C_{10}$-alkynyl, $R^8$, —$OR^8$, —$NO_2$, —$CF_3$, —$S(O)_r$ $R^7$, —$NR^8R^9$, —$COR^8$, —$CO_2R^8$, —$CONR^8H$, $NR^8COR^9$, $NR^8CO_2R^9$;

c)
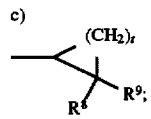

d)
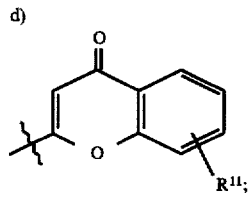

e)
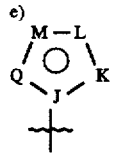

wherein the ring represented by —J—K—L—M—Q— is a group selected from:
1) —N—$C(R^{13})$=$C(R^{13})$—$C(R^{13})$=$C(R^{13})$—, 2) —N—C(R$^{13}$)=C(R$^{13}$)—C(R$^{13}$)=N—,
3) —N—C(R$^{13}$)=C(R$^{13}$)—N=C(R$^{13}$)—,
4) —N—C(R$^{13}$)=N—C(R$^{13}$)=N—,
5) —N—C(R$^{13}$)=C(R$^{13}$)—N=N—
6) —N—C(R$^{13}$)=N—N=N—,
7) —N—N=C(R$^{13}$)—N=N—,
8) =C—O—C(R$^{13}$)=N—C(R$^{13}$)=,
9) —C=C(R$^{13}$)O—C(R$^{13}$)=N—,
10) =C—C(R$^{13}$)=C(R$^{13}$)—N=,
11) —C=C(R$^{13}$)—C(R$^{13}$)=N—O—,
12) =C=C(R$^{13}$)=C(R$^{13}$)—O—N=,
13) =C=C(R$^{13}$)—O—N=C(R$^{13}$)—,
14) =C—S—C(R$^{13}$)=N—C(R$^{13}$)=,
15) =C=C(R$^{13}$)—S—C(R$^{13}$)=N—,
16) =C—S—C(R$^{13}$)=C(R$^{13}$)—N=,
17) =C—S—C(R$^{13}$)=C(R$^{13}$)—C(R$^{13}$)=,
18) —C=C(R$^{13}$)—S—C(R$^{13}$)=C(R$^{13}$)—,
19) =C—O—C(R$^{13}$)=C(R$^{13}$)—C(R$^{13}$)=, or
20) —C=C(R$^{13}$)—O—C(R$^{13}$)=C(R$^{13}$)—;

f)

wherein the ring represented by —C—W—R—T—U—V— is a group selected from:
1)—C=N—C(R$^{13}$)=C(R$^{13}$)—C(R$^{13}$)=C(R$^{13}$)—,
2)—C=C(R$^{13}$)—N=C(R$^{13}$)—C(R$^{13}$)=C(R$^{13}$)—,
3)—C=C(R$^{13}$)—C(R$^{13}$)=N—C(R$^{13}$)=C(R$^{13}$)—,
4)—C=N—N=C(R$^{13}$)—C(R$^{13}$)=C(R$^{13}$)—,
5)—C=C(R$^{13}$)—N=N—C(R$^{13}$)=C(R$^{13}$)—,
6)—C=N—C(R$^{13}$)=C(R$^{13}$)—C(R$^{13}$)=N—
7)—C=N—C(R$^{13}$)=C(R$^{13}$)—N=C(R13)—,
8)—C=N—C(R$^{13}$)=N—C(R$^{13}$)=C(R$^{13}$)—,
9)—C=C(R$^{13}$)—N=C(R$^{13}$)—N=C(R13)—,
10)—C=N—C(R$^{13}$)=N—N=C(R$^{13}$)—,
11)—C=N—C(R$^{13}$)=C(R$^{13}$)—N=N—, or
12)—C=C(R$^{13}$)—N=C(R$^{13}$)—N=N—;

g)

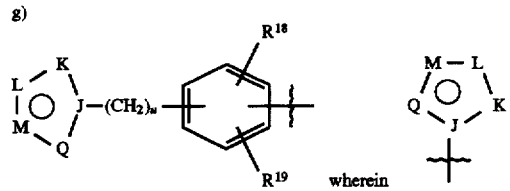 wherein is as defined above;

h)

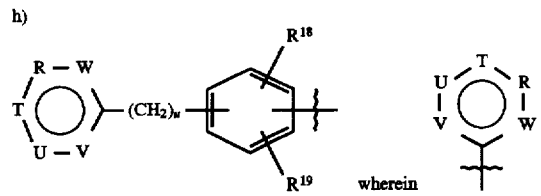 wherein is as defined above; or i)

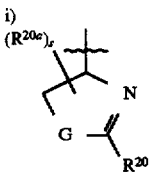

wherein G is O, S, or NP (where P is an amine protecting group selected from the group consisting of: —R$^3$, —C(=O)R$^3$, —SO$_2$R$^3$, —C(=O)OR$^3$);

R$^2$ is
a) -(C$_1$–C$_{12}$ alkyl)—X,
b) -(C$_2$–C$_{12}$ alkenyl)—X, or c)

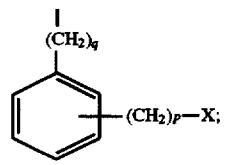

X is
a) halogen (F, Cl, Br, I),
b) —CN,
c) —NO$_2$,
d) —CF$_3$,
e) —NHR$^{14}$
f) —NHS(O)$_r$R$^{14}$,
g) —NHC(NH)H,
h) —NHC(NH)NHOH,
i) —NHC(NH)NHCN,
j) —NHC(NH)NHR$^{14}$,
k) —NHC(NH)NHCOR$^{14}$,
l) —C(NH)NHR$^{14}$,
m) —C(NH)NHCOR$^{14}$,
n) —C(O)NHR$^{14}$,
o) —C(O)NHC(O)R$^{14}$,
p) —C(O)OR$^{14}$,
q) —OR$^{14}$
r) —OC(O)R$^{14}$,
s) —OC(O)OR$^{14}$,
t) —OC(O)NHR$^{14}$,
u) —OC(O)NHC(O) R$^{14}$,
v) —SC(=NH)NHR$^{14}$, or
w) —SC(=NH)NHC(=O) R$^{14}$;

R$^{13}$ is
H, halogen (F, Cl, Br, I), (C$_1$-C$_6$) alkyl, —(CH$_2$)$_r$—D, methylenedioxy, —(CH$_2$)$_w$—OR$^8$, —(CH$_2$)$_w$CONR$^8$R$^9$, —(CH$_2$)$_w$NC, —(CH$_2$)$_w$CN, —(CH$_2$)$_w$NO$^2$, —(CH$_2$)$_w$S(O)$_r$R$^7$, —(CH$_2$)$_w$COR$^8$, —(CH$_2$)$_w$CO$_2$R$^8$, —(CH$_2$)$_w$CONR$^8$R$^9$, —(CH$_2$)$_w$SO$_2$NH—(C$_1$-C$_5$)-alkyl, —(CH$_2$)$_w$SO$_2$NH$_2$, —(CH$_2$)$_w$SO$_2$NH—CO—(C$_1$-C$_6$)-alkyl, —(CH$_2$)$_w$SO$_2$NH—CO$_2$—(C$_1$-C$_6$)-alkyl, —(CH$_2$)$_w$NHSO$_2$—(C$_1$-C$_6$)-alkyl, —(CH$_2$)$_w$NHSO$_2$—(C$_1$-C$_6$)-perfluoroalkyl, —(CH$_2$)$_w$NHSO$_2$ —phenyl, —(CH$_2$)$_w$NHSO$_2$-perfluorophenyl, —(CH$_2$)$_w$CN$^4$H, —O(C=O)—(C$_1$-C$_5$-alkyl), —O(CH$_2$)$_w$CN, —NH (CH$_2$)$_w$CN, —S (CH$_2$)$_w$CN, —(CH$_2$)$_w$NH—CO—(C$_1$-C$_6$-alkyl), —(CH$_2$)$_w$NH—CO—(C$_1$-C$_6$-perfluoroalkyl), —(CH$_2$)$_w$ NH—CO—(C$_1$-C$_6$-phenyl), —(CH$_2$)$_w$ NH—CO$_2$—(C$_1$-C$_6$-alkyl), —(CH$_2$)$_w$NH—CO$_2$—(C$_1$-C$_6$-phenyl), —(CH$_2$)$_w$phenyl wherein the phenyl contains 0–3 substituents selected from R$^{18}$, or —O(C=O)phenyl wherein the phenyl contains 0–3 substituents selected from R$^{18}$;

R$^{14}$ is
a) —H,
b) —CF$_3$
c) -C$_1$-C$_4$ alkyl,
d) —(CH$_2$)$_q$-aryl, wherein aryl is phenyl, biphenyl, naphthyl, or fluorenyl are optionally substituted with one to three substituents selected from the group consisting of:
halogen (F, Cl, Br, I),
—CF$_3$,
-(C$_1$-C$_4$ alkyl),
-methylenedioxy,
-(C$_1$-C$_4$ alkoxy), or
—CH$_2$)$_p$N[(CH$_2$)$_r$R$^{15}$][CH$_2$)$_s$R$^{16}$];

R$^{18}$ and R$^{19}$ are independently
H, halo (F, Cl, Br, I, C$_1$-C$_6$-alkyl, —(CH$_2$)$_w$—OR$^8$, —(CH$_2$)$_w$CN, —(CH$_2$ WCN, —(CH$_2$)$_w$NO$_2$, —(CH$_2$)$_w$ S(O)$_r$R$^7$, —(CH$_2$)$_w$NR$^8$R$^9$, —(CH$_2$)$_w$COR$^8$, —(CH$_2$)$_w$ CO$_2$R$^8$, —(CH$_2$)$_w$CONR$^8$R$^9$, —(CH$_2$)$_w$ SO$_2$NH—(C$_1$-C$_5$)-alkyl, —(CH$_2$)$_w$SO$_2$NH$_2$, —(CH$_2$)$_w$ SO$_2$NH—CO—(C$_1$-C$_6$)-alkyl, —(CH$_2$)$_w$ SO$_2$NH—CO$_2$—(C$_1$-C$_6$)-alkyl, —(CH$_2$)$_w$NHSO$_2$—(C$_1$-C$_6$)-alkyl, —(CH$_2$)$_w$NHSO$_2$—(C$_1$-C$_6$)-perfluoroalkyl, —(CH$_2$)$_w$NHSO$_2$-phenyl, —(CH$_2$)$_w$NHSO$_2$-perfluorophenyl, —(CH$_2$)$_w$CN$^4$H, —O(C=O)—(C$_1$-C$_5$-alkyl), —O(CH$_2$)$_w$CN, —NH(CH$_2$)$_w$CN, —S(CH$_2$)$_w$CN, —(CH$_2$)$_w$NH—CO—(C$_1$-C$_6$-alkyl), —(CH$_2$)$_w$NH—CO—(C$_1$-C$_6$-perfluoroalkyl), —(CH$_2$)$_w$ NH—CO—(C$_1$-C$_6$-phenyl), —(CH$_2$)$_w$ NH—CO$_2$(C$_1$-C$_6$-alkyl), —(CH$_2$)$_w$NH—CO$_2$—(C$_1$-C$_6$-phenyl), or —O(C=O)phenyl;

R$^{18}$ and R$^{19}$ can be taken together to form a methylenedioxy group;

R$^{20}$ and R$^{20a}$ are independently (C$_1$-C$_8$)alkyl, —(CH$_2$)$_u$ phenyl wherein the phenyl contains 0–3 substituents selected from R$^{18}$, (C$_1$-C$_6$)-perfluoroalkyl, or —(CH$_2$)$_t$—D;

D is fur-2-yl, fur-3-yl, thiophen-2-yl, thiophen-3-yl, oxazol-2-yl, oxazol-4-yl, thiazol-2-yl, thiazol-4-yl, pyrid-2-yl, pyrid-4-yl, pyrimidin-2-yl, or pyrimidin-4-yl;

W is
a) —O—,
b) —NR$^4$—,
c) a bond, or
d) —(CH$_2$)$_n$—;

and all other required substituents of formula (I) are as defined in Claim 2.

Most preferred compounds of the formula (I) are those compounds wherein:
A is —BY$^1$Y$^2$;
Y$^1$ and Y$^2$ are —OH;
Y$^1$ and Y$^2$ can be taken together to form a cyclic boron ester where said chain or ring contains from 2 to 20 carbon atoms and, from 0–3 heteroatoms which can be N, S, or O,
Z is —(CH$_2$)$_m$CONR$^8$—;
R$^1$ is
a) —(CH$_2$)$_p$-aryl, wherein aryl is phenyl, naphthyl or biphenyl substituted with one, two or three substituents selected from the group consisting of:

halo (F, Cl, Br, I), methylenedioxy, —R$^8$, —NR$^8$COR$^9$, C$_2$-C$_6$-alkenyl, C$_2$-C$_6$-alkynyl, —(CH$_2$)$_w$—OR$^8$, —(C$_1$-C$_6$)-perfluoroalkyl, —(CH$_2$)$_w$CN, —(CH$_2$)$_w$ NC, —(CH$_2$)$_w$NO$_2$, —(CH$_2$)$_w$CF$_3$, —(CH$_2$)$_w$S (O)$_r$R$^7$, —(CH$_2$)$_w$NR$^8$R$^9$, —(CH$_2$)$_w$COR$^8$, (CH$_2$)$_w$ CO$_2$R$^8$, —(CH$_2$)$_w$CONR$^8$R$^9$, —(CH$_2$)$_w$SO$_2$NH—(C$_1$-C$_6$)-alkyl, —(CH$_2$)$_w$SO$_2$NH$_2$, —(CH$_2$)$_w$ SO$_2$NH—CO—(C$_1$-C$_6$)-alkyl, —(CH$_2$)$_w$ SO$_2$NH—CO$_2$—(C$_1$-C$_6$)-alkyl, —(CH$_2$)$_w$ NHSO$_2$—(C$_1$-C$_6$)-alkyl, —(CH$_2$)$_w$NHSO$_2$—(C$_1$-C$_6$)-perfluoroalkyl, —(CH$_2$)$_w$NHSO$_2$-phenyl, —(CH$_2$)$_w$NHSO$_2$-perfluorophenyl, —(CH$_2$)$_w$CN$^4$H, —O(CH$_2$)$_w$CN, —NH(CH$_2$)$_w$CN, —S(CH$_2$)$_w$CN, —(CH$_2$)$_w$NH—CO—(C$_1$-C$_6$-alkyl), —(CH$_2$)$_w$NH—CO—(C$_1$-C$_6$-perfluoroalkyl), —(CH$_2$)$_w$NH—CO—(C$_1$-C$_6$-phenyl), —(CH$_2$)$_w$NH—CO$_2$—(C$_1$-C$_6$-alkyl), —(CH$_2$)$_w$NH—CO$_2$—(C$_1$-C$_6$-perfluoroalkyl), or —(CH$_2$)$_w$NH—CO$_2$—(C$_1$-C$_6$-phenyl);

b) heteroaryl, wherein heteroaryl is an unsubstituted, monosubstituted or disubstituted isoquinolinyl wherein the substituents are members selected from the group consisting of:
halo (F, Cl, Br, I), —CN, C$_1$-C$_{10}$-alkyl, C$_3$-C$_8$-cycloalkyl, C$_2$-C$_{10}$-alkenyl, C$_2$-C$_{10}$-alkynyl, R$^8$, —OR$^8$, —NO$_2$, —CF$_3$, —S(O)$_r$R$^7$, —NR$^8$R$^9$, —COR$^8$, —CO$_2$R$^8$, —CONR$^8$R$^9$, NR$^8$COR$^9$, NR$^8$CO$_2$R$^9$, c)

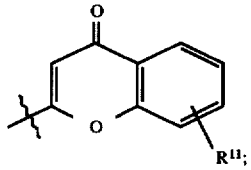

d)

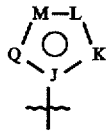

wherein the ring represented by —J—K—L—M—Q— is a group selected from:
1) —N—C(R$^{13}$)=N—C(R$^{13}$)=N—,
2) —N—C(R$^{13}$)=C(R$^{13}$)—N=N—,
3) —N—N=C(R$^{13}$)—N=N—,
5) —N—C(R$^{13}$)=N—N=N—,
6) =C—S—C(R$^{13}$)=C(R$^{13}$)—C(R$^{13}$)=, or
7) =C—O—C(R$^{13}$)=C(R$^{13}$)—C(R$^{13}$)=;

e)

wherein the ring represented by —C—W—R—T—U—V— is a group selected from:
1) —C=N—C(R$^{13}$)=C(R$^{13}$)=C(R$^{13}$)—C(R13)=C (R$^{13}$)—,
1) —C=C(R$^{13}$)—N=C(R$^{13}$)—C(R$^{13}$)=C(R$^{13}$)—, 2) —C=C(R$^{13}$)—C(R$^{13}$)=N—C(R$^{13}$)=C(R$^{13}$)—,
3) —C=C(R$^{13}$)—N=C(R$^{13}$)—N=C(R$^{13}$)—,
4) —C=N—C(R$^{13}$)=C(R$^{13}$)—C(R$^{13}$)=N—, or
5) —C=N—C(R$^{13}$)=N—C(R$^{13}$)=C(R$^{13}$)—;

f)

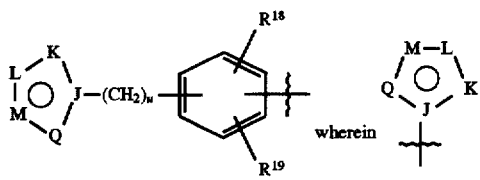

is as defined above;

g)

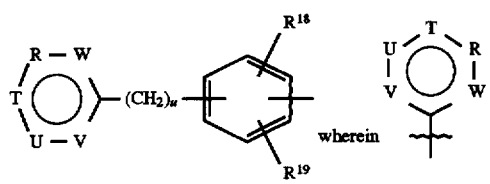

is as defined above; or h)

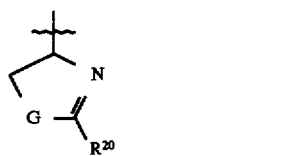

wherein G is S;
R$^2$ is
a) —(C$_1$–C$_{12}$ alkyl)—X, or b)

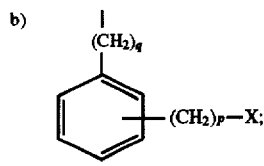

X is
a) halogen (F, Cl, Br, I),
b) —CN,
c) —NHR$^{14}$
d) —NHC(NH)H,
e) —NHC(NH)NHR$^{14}$,
f) —C(NH)NHR$^{14}$,
g) —OR$^{14}$, or
h) —SC(=NH)NHR$^{14}$;
R$^{11}$ is H;
R$^{13}$ is H, halogen (F, Cl, Br, I), —(CH$_2$)$_w$NO$_2$, C$_1$–C$_6$)alkyl, —(CH$_2$)$_r$—D, —(CH$_2$)$_w$—OR$^8$, —(CH$_2$)$_w$CONR$^8$R$^9$, —(CH$_2$)$_w$CN, —(CH$_2$)$_w$NC, —(CH$_2$)$_w$NR$^8$R$^3$, —(CH$_2$)$_w$S (O)$_2$R$^7$, —(CH$_2$)$_w$SO$_2$NHCO—(C$_1$–C$_6$)-alkyl, —(CH$_2$)$_w$NHSO$_2$-phenyl—(CH$_2$)$_w$SO$_2$NH—(C$_1$–C$_5$)-alkyl, —(CH$_2$)$_w$SO$_2$NH$_2$, —(CH$_2$)$_w$ SO$_2$NHCO$_2$(C$_1$–C$_6$)-alkyl, —(CH$_2$)$_w$NHSO$_2$—(C$_1$C$_6$) -alkyl, —(CH$_2$)$_w$NHSO$_2$—(C$_1$–C$_6$)-perfluoroalkyl, —(CH$_2$)$_w$CN$^4$H, —O(C=O)—(C$_1$–C$_5$-alkyl), —O(CH$_2$)$_t$CN, —NH (CH$_2$)$_t$CN, —S (CH$_2$)$_t$CN, —(CH$_2$)$_w$NH—CO—(C$_1$–C$_6$-alkyl), —(CH$_2$)$_w$NH—CO—(C$_1$–C$_6$-perfluoroalkyl), or —(CH$_2$)$_w$phenyl wherein the phenyl contains 0–3 substituents selected from R$^{18}$;

R$^{14}$ is —H;
R$^{18}$ and R$^{19}$ are independently

H, halo (F, Cl, Br, I), C$_1$–C$_6$-alkyl, —(CH$_2$)$_w$—OR$^8$, —(CH$_2$)$_w$CN, —(CH$_2$)$_w$NC, —(CH$_2$)$_w$NO$_2$, (CH$_2$)$_w$S (O)$_t$R$^7$, —(CH$_2$)$_w$NR$^8$R$^9$, —(CH$_2$)$_w$COR$^8$, —(CH$_2$)$_w$CO$_2$R$^8$, —(CH$_2$)$_w$CONR$^8$R$^9$, —(CH$_2$)$_w$SO$_2$NH—(C$_1$–C$_5$)-alkyl, —(CH$_2$)$_w$SO$_2$NH$_2$, —(CH$_2$)$_w$ SO$_2$NH—CO—(C$_1$–C$_6$)-alkyl, —(CH$_2$)$_w$SO$_2$NH—CO$_2$—(C$_1$–C$_6$)-alkyl, —(CH$_2$)$_w$NHSO$_2$—(C$_1$–C$_6$)-alkyl, —(CH$_2$)$_w$NHSO$_2$—(C$_1$–C$_6$)-perfluoroalkyl, —(CH$_2$)$_w$NHSO$_2$ -phenyl, —(CH$_2$)$_w$NHSO$_2$-perfluorophenyl, —(CH$_2$)$_w$CN$_4$H, —O(C=O)—(C$_1$–C$_5$-alkyl), —O(CH$_2$)$_t$CN, —NH (CH$_2$)$_t$CN, —S (CH$_2$)$_t$CN, —(CH$_2$)$_w$NH—CO—(C$_1$–C$_6$-alkyl), —(CH$_2$)$_w$NH—CO—(C$_1$–C$_6$-perfluoroalkyl), —(CH$_2$)$_w$ NH—CO—(C$_1$–C$_6$-phenyl), —(CH$_2$)$_w$ NH—CO$_2$—(C$_1$–C$_6$-alkyl), —(CH$_2$)$_w$NH—CO$_2$—(C$_1$–C$_6$-phenyl), or —O(C=O)phenyl;

R$^{18}$ and R$^{19}$ can be taken together to form a methylenedioxy group;

R$^{20}$ is selected from the group consisting of:

(CH$_2$)$_r$—D, or —(CH$_2$)$_w$phenyl wherein the phenyl contains 0–3 substituents selected from R$^{18}$;

and all other required substituents of formula (I) are defined as in Claim 3.

Specifically preferred are those most preferred compounds listed below:

N$^1$-(4-phenylbenzoyl)-(R)-boroarginine, hydrochloride
N$^1$-(3-phenoxybenzoyl)-(R)-boroarginine, hydrochloride
N$^1$-(1-fluorenonyl)-(R)-boroarginine, hydrochloride
N$^1$-(4-[1-butyl]benzoyl)-(R)-boroarginine, hydrochloride
N$^1$-(2-benzoylbenzoyl)-(R)-boroarginine, hydrochloride
N$^1$-(5-phenyl-2-furoyl)-(R)-boroarginine, hydrochloride
N$^1$-(3-[N-benzyloxycarbonyl-N-methylamino]-4-[1-butyl]-benzoyl)-(R)-boroarginine, hydrochloride
N$^1$-(2-phenyl-4-isoquinoloyl)-(R)-boroarginine, hydrochloride
N$^1$-(4-cyclohexylbenzoyl)-(R)-boroarginine, hydrochloride
N$^1$-(2-methyl-4-phenylbenzoyl)-(R)-boroarginine, hydrochloride
N$^1$-[4-phenyl-2-nitrobenzoyl]boroArg, (+)-pinanediol ester
N$^1$-[4-phenyl-2-fluorobenzoyl]boroArg, (+)-pinanediol ester
N$^1$-[4-phenyl-2-aminobenzoyl]boroArg, (+)-pinanediol ester
N$^1$-[4-phenyl-2-(methylsulfonamido)benzoyl]boroArg, (+)-pinanediol ester
N$^1$-[4-phenyl-2-(cyanomethylamino)benzoyl]boroArg, (+)-pinanediol ester
N$^1$-[4-phenyl-2-(cyanomethyl)benzoyl]boroArg, (+)-pinanediol ester
N$^1$-[4-phenyl-2-(diethylamino)benzoyl]boroArg, (+)-pinanediol ester
N$^1$-[4-[2-(t-butylaminosulfonyl)phenyl]-2-methyl-benzoyl]boroArg, (+)pinanediol ester N¹-[4-[2-(aminosulfonyl)phenyl]-2-methyl-benzoyl]
boroArg, (+)pinanediol ester N¹-[4-[2-(methoxycarbonylaminosulfonyl)phenyl]-2-
methyl-benzoyl]boroArg, (+)-pinanediol ester N¹-[4-[2-(t-butylaminosulfonyl)phenyl]benzoyl]
boroArg, (+)-pinanediol ester N¹-[4-[2-(t-butylaminosulfonyl)phenyl]benzoyl]
boroArg-OH N¹-[4-[2-(n-butoxycarbonylaminosulfonyl)phenyl]-2-
methyl-benzoyl]boroArg, (+)-pinanediol ester N¹-[4-[2-(diethylaminosulfonyl)phenyl]-2-methyl-
benzoyl]boroArg, (+)pinanediol ester N¹-[4-[2-(t-butylaminosulfonyl)phenyl]-2-fluoro-
benzoyl]boroArg, (+)-pinanediol ester N¹-[4-[2-(aminosulfonyl)phenyl]-2-fluoro-benzoyl]
boroArg, (+)pinanediol ester N¹-[4-[2-(methoxycarbonylaminosulfonyl)phenyl]-2-
fluoro-benzoyl]boroArg, (+)-pinanediol ester N¹-[4-[2-(t-butylaminosulfonyl)phenyl]-2-nitro-benzoyl]
boroArg, (+)pinanediol ester N¹-[4-[2-(aminosulfonyl)phenyl]-2-nitro-benzoyl]
boroArg, (+)pinanediol ester N¹-[4-[2-(methoxycarbonylaminosulfonyl)phenyl]-2-
nitro-benzoyl]boroArg, (+)-pinanediol ester N¹-(3-phenylbenzoyl)boroarg, (+)-pinanediol N¹-[4-(3-BOCNHphenyl)₂-methylbenzoyl]boroarg, (+)-
pinanediol N¹-(5-phenyl-2-furoyl)boroarg, (+)-pinanediol N¹-(5-phenyl-2-thienyl)boroarg, (+)-pinanediol N¹-[4-(3-nitrophenyl)benzoyl]boroarg, (+)-pinanediol N¹-[4-(3-aminophenyl)benzoyl]boroarg, (+)-pinanediol N¹-(3-phenylbenzoyl)borolys, (+)-pinanediol N¹-(5-phenyl-2-furoyl)boroarg-OH N¹-(3-phenylbenzoyl)boroIrg, (+)-pinanediol (R)-[5-amino-1-[[[5-(phenylmethyl)-1H-1,2,4-triazol-1-
yl]acetyl]amino]-pentyl]boronic acid hydrochloride

[3aS-[2(S*),3aα,4β,6β]]-(1,1-dimethylethyl) [3-[5-[[[4-[
(amino-iminomethyl)amino]-1-(hexahydro-3a,5,5-
trimethyl-4,6-methano-1,3,2-benzo-dioxaborol-2-yl)
butyl]amino]carbonyl]-2-thienyl]phenyl]carbamate
hydrochloride

[3aS-[2(S*),3aα,4β,6β,7aα]]-N-[5-amino-1-(hexahydro-
3a,5,5-trimethyl-4,6-methano- 1,3,2-benzodioxaborol-
2-yl) pentyl]-5-(phenyl-methyl)-3-(2H-tetrazol-5-
ylmethyl)-1H-1,2,4-triazole-1-acetamide
hydrochloride

[3aS-[2(S*),3a,4β,6β,7aα]]-1-[2-[[5-amino-1-
(hexahydro-3a, 5,5-trimethyl-4,6-methano-1,3,2-
benzodioxaborol-2 -yl) pentyl]amino]-2-oxoethyl]-5-
(phenylmethyl)-1H-1,2,4-triazole-3-acetic acid
hydrochloride 1:1 with [3aS-[2(S*), 3aα,4β,6β,7aα]]-
1-[2-[[5-amino-1-(hexahydro-3a, 5,5-trimethyl-4,6-
methano-1,3,2-benzodioxaborol-2-yl)pentyl]amino]-2-
oxoethyl]-3-(phenylmethyl)-1H-1,2,4-triazole-5-acetic
acid hydrochloride

[3aS-[2(S*),3aα,4β,6β,7aα]]-methyl 1-[2-[[5-amino-1-
(hexahydro-3a, 5,5-trimethyl-4,6-methano-1,3,2-
benzodioxaborol-2-yl) pentyl]-amino]-2-oxoethyl]-5-
(phenylmethyl)-1H-1,2,4-triazole-3-acetate
hydrochloride

[3aS-[2(S*),3aα,4β,6β,7aα]]-methyl 1-[2-[[5-amino-1-
(hexahydro-3a, 5,5-trimethyl-4,6-methano-1,3,2-
benzodioxaborol-2-yl)pentyl]-amino]-2-oxoethyl]-3-
(phenylmethyl)-1H-1,2,4-triazole-5-acetate
hydrochloride

[3aS-[2(S*), 3aα,4β,6β,7aβ]]-N-[5-amino-1-(hexahydro-
3a,5,5-trimethyl-4,6-methano-1,3,2-benzodioxaborol-
2-yl) pentyl]-3-phenyl-5-(phenyl -methyl)-1H-1,2,4-
triazole-1-acetamide hydrochloride (R)-[5-amino-1-[[[3-phenyl-5-(phenylmethyl)-1H-1,2,4-
triazol-1-yl]acetyl]-amino]pentyl]boronic acid hydro-
chloride

[3aS-[2(S*), 3aα,4β,6β,7aβ]]-N-[5-amino-1-(hexahydro-
3a,5,5-trimethyl-4,6-methano-1,3,2-benzodioxaborol-
2-yl) pentyl]-3-(3-nitro-phenyl)-5-(phenylmethyl)-1H-
1, 2,4-triazole-1-acetamide hydrochloride

[3aS-[2(S*), 3aα,4β,6β,7aβ]]-N-[4-[(aminoiminomethyl)
-amino]-1-(hexahydro-3a,5,5-trimethyl-4,6-methano-
1,3,2-benzodioxaborol-2-yl) butyl]-3-(3-nitrophenyl)-
5-(phenylmethyl)-1H-1,2,4-triazole-1-acetamide
hydrochloride

[3aS-[2(S*),3aα,4β,6β,7aβ]]-N-[5-amino-1-(hexahydro-
3a,5,5-trimethyl-4,6-methano-1,3,2-benzodioxaborol-
2-yl)pentyl]-3,5-bis(phenyl-methyl)-1H-1,2,4-triazole-
1-acetamide hydrochloride

[3aS-[2(S*),3aα,4β,6β,7aβ]]-N-[4-[(aminoiminomethyl)
-amino]-1-(hexahydro-3a,5,5-trimethyl-4,6-methano-
1,3,2-benzodioxaborol-2-yl)butyl]-3,5-bis
(phenylmethyl)-1H-1,2,4-triazole-1-acetamide
hydrochloride

[3aS-[2(S*),3aα,4β,6β,7aβ]]-N-[5-amino-1-(hexahydro-
3a,5,5-trimethyl-4,6-methano-1,3,2-benzodioxaborol-
2-yl)pentyl]-3-(phenylmethyl)-1H-1,2,4-triazole-1-
acetamide (R)-[5-amino-1-[[[3-(phenylmethyl)-1H-1,2,4-triazol-1-
yl]acetyl]amino]-pentyl]boronic acid hydrochloride

[3aS-[2(S*),3aα,4β,6β,7aβ]]-N-[5-amino-1-(hexahydro-
3a,5,5-trimethyl-4,6-methano-1,3,2-benzodioxaborol-
2-yl)pentyl]-5-methyl-3-(phenylmethyl)-1H-1,2,4-
triazole-1-acetamide hydrochloride

[3aS-[2(R*),3aα,4β,6β]]-N-[5-amino-1-(hexahydro-3a,5,
5-tri-methyl-4,6-methano-1,3,2-benzodioxaborol-2-yl)
pentyl]-5-[(phenyl-methoxy)ₘethyl]-3-(phenylmethyl)
-1H-1,2,4-triazole-1-acetamide hydrochloride

[3aS-[2(S*),3aα,4β,6β,7aβ]]-N-[5-amino-1-(hexahydro-
3a,5,5-trimethyl-4,6-methano-1,3,2-benzodioxaborol-
2-yl)pentyl]-5-(cyanomethyl)-3-(phenylmethyl)-1H-1,
2,4-triazole-1-acetamide hydrochloride

[3aS-[2(S*),3aα,4β,6β,7aβ]]-N-[5-amino-1-(hexahydro-
3a,5,5-trimethyl-4,6-methano-1,3,2-benzodioxaborol-
2-yl)pentyl]-3-(phenylmethyl)-5-propyl-1H-1,2,4-
triazole-1-acetamide hydrochloride

[3aS-[2(S*),3aα,4β,6β,7aβ]]-N-[5-amino-1-(hexahydro-
3a,5,5-trimethyl-4,6-methano- 1,3,2-benzodioxaborol-
2-yl)pentyl]-5-phenyl-3-(phenylmethyl)-1H-1,2,4-
triazole-1-acetamide hydrochloride (R)-[5-amino-1-[[[5-methyl-3-(phenylmethyl)-1H-1,2,4-
triazol-1-yl]acetyl]-amino]pentyl]boronic acid hydro-
chloride

[3aS-[2(S*), 3aα,4β,6β,7β]]-N-[5-amino-1-(hexahydro-
3a,5,5-trimethyl-4,6-methano-1,3,2-benzodioxaborol-
2-yl) pentyl]-3-phenyl-1H-1,2,4-triazole-1-acetamide
hydrochloride

[3aS-[2(S*), 3aα,4β,6β,7aβ]]-N-[5-amino-1-(hexahydro-
3a, 5,5-trimethyl-4,6-methano-1,3,2-benzodioxaborol-
2-yl) pentyl]-5-methyl -3-phenyl -1H-1,2,4-triazole-1-
acetamide hydrochloride

[3aS-[2(S*), 3aα,4β,6β,7aβ]]-N-[5-amino-1-(hexahydro-3a,5,5-trimethyl-4,6-methano-1,3,2-benzodioxaborol-2-yl) pentyl]-5-(2-phenyl-ethyl)-1H-1,2,4-triazole-1-acetamide (R)-[5-amino-1-[[[5-(2-phenylethyl)-1H-1,2,4-triazol-1-yl]acetyl]amino]-pentyl]boronic acid hydrochloride

[3aS-[2(S*),3aα,4β,6β,7aβ]]-N-[5-amino-1-(hexahydro-3a,5,5-trimethyl-4,6-methano-1,3,2-benzodioxaborol-2-yl)pentyl]-3,5-bis(2-phenyl-ethyl)-1H-1,2,4-triazole-1-acetamide hydrochloride (R)-[5-amino-1-[[[3,5-bis(2-phenylethyl)-1H-1,2,4-triazol-1-yl]acetyl]amino]-pentyl]boronic acid hydrochloride

[3aS-[2(S*), 3aα,4β,6β,7aβ]]-N-[5-amino-1-(hexahydro-3a,5,5-trimethyl-4,6-methano-1,3,2-benzodioxaborol-2-yl) pentyl]-3-(2-phenylethyl)-1H-1,2,4-triazole-1-acetamide (R)-[5-amino-1-[[[3-(2-phenylethyl)-1H-1,2,4-triazol-1-yl]acetyl]amino]-pentyl]boronic acid hydrochloride

[3aS-[2(S*), 3aα,4β,6β,7aβ]]-N-[5-amino-1-(hexahydro-3a,5,5-trimethyl-4,6-methano-1,3,2-benzodioxaborol-2-yl) pentyl]-3-(3-phenyl-propyl)-1H-1,2,4-triazole-1-acetamide (R)-[5-amino-1-[[[5-(3-phenylpropyl)-1H-1,2,4-triazol-1-yl]acetyl]amino]-pentyl]boronic acid hydrochloride (R)-[5-amino-1-[[[3-(3-phenylpropyl)-1H-1,2,4-triazol-1-yl]acetyl]amino]-pentyl]boronic acid hydrochloride

[3aS-[2(S*),3aα,4β,6β,7aβ]]-N-[5-amino-1-(hexahydro-3a,5,5-trimethyl-4,6-methano-1,3,2-benzodioxaborol-2-yl)pentyl]-1,5-bis(phenyl-methyl)-1H-1,2,4-triazole-3-acetamide hydrochloride 2:8 with (R)-[5-amino-1-[[[1,5-bis(phenylmethyl)-1H-1,2,4-triazol-3-yl]acetyl]amino]-pentyl]boronic acid hydrochloride

[3aS-[2(S*),3aα,4β,6β,7aβ]]-N-[5-amino-1-(hexahydro-3a,5,5-trimethyl-4,6-methano-1,3,2-benzodioxaborol-2-yl)pentyl]-4-methyl-2-phenyl-5-pyrimidinecarboxamide hydrochloride

[3aS-[2(S*),3aα,4β,6β,7aβ]]-N-[5-amino-1-(hexahydro-3a,5,5-trimethyl-4,6-methano-1,3,2-benzodioxaborol-2-yl)pentyl]-2,4-diphenyl-5-pyrimidinecarboxamide hydrochloride

[3aS-[2(S*),3aα,4β,6β,7aβ]]-N-[4-[(amimoiminomethyl)amino]-1-(hexahydro-3a,5,5-trimethyl-4,6-methano-1,3,2-benzodioxaborol-2-yl)-butyl]-4-methyl-2-phenyl-5-pyrimidinecarboxamide hydrochloride

[3aS-[2(S*),3α,4β,6β,7aβ]]-N-[5-amino-1-(hexahydro-3a,5,5-trimethyl-4,6-methano-1,3,2-benzodioxaborol-2-yl)pentyl]-6-phenyl-3-pyridinecarboxamide hydrochloride (R)-[5-amino-1-[[(6-phenyl-3-pyridinyl)carbonyl]amino] pentyl]boronic acid dihydrochloride Illustrative of the compounds of this invention are the following:

$N^1$-(4-phenylbenzoyl)-(R)-boroarginine (+)-pinanediol, bisulfite $N^1$-(3-phenylbenzoyl)-(R)-boroarginine (+)-pinanediol, bisulfite $N^1$-(3-phenoxybenzoyl)-(R)-boroarginine (+)-pinanediol, bisulfite $N^1$-(4-[4-pyridyl]benzoyl)-(R)-boroarginine (+)-pinanediol, bisulfite $N^1$-(2-benzoylbenzoyl)-(R)-boroarginine (+)-pinanediol, bisulfite $N^1$-(3-benzoylbenzoyl)-(R)-boroarginine (+)-pinanediol, bisulfite $N^1$-(4-benzoylbenzoyl)-(R)-boroarginine (+)-pinanediol, bisulfite $N^1$-(3-[N-benzyloxycarbonyl]aminobenzoyl)-(R)-boroarginine (+)-pinanediol, bisulfite $N^1$-(3-[N-benzyloxycarbonyl-N-methyl]aminobenzoyl)-(R)-boroarginine (+)-pinanediol, bisulfite $N^1$-(4-ethylbenzoyl)-(R)-boroarginine (+)-pinanediol, bisulfite $N^1$-(4-n-propylbenzoyl)-(R)-boroarginine (+)-pinanediol, bisulfite $N^1$-(4-isopropylbenzoyl)-(R)-boroarginine (+)-pinanediol, bisulfite $N^1$-(4-n-butylbenzoyl)-(R)-boroarginine (+)-pinanediol, bisulfite $N^1$-(4-tert-butylbenzoyl)-(R)-boroarginine (+)-pinanediol, bisulfite $N^1$-(4-n-hexylbenzoyl)-(R)-boroarginine (+)-pinanediol, bisulfite $N^1$-(4-cyclohexylbenzoyl)-(R)-boroarginine (+)-pinanediol, bisulfite $N^1$-(2-[N-(2-phenylethyl)carbonyl]aminobenzoyl)-(R)-boroarginine (+)-pinanediol, bisulfite $N^1$-(4-n-butyloxybenzoyl)-(R)-boroarginine (+)-pinanediol, bisulfite $N^1$-(4-[N-cyclopropylcarbonyl]aminobenzoyl)-(R)-boroarginine (+)-pinanediol, bisulfite $N^1$-(4-[N-cyclohexylcarbonyl]aminobenzoyl)-(R)-boroarginine (+)-pinanediol, bisulfite $N^1$-(4-[N-(4-methoxy)benzoyl]aminobenzoyl)-(R)-boroarginine (+)-pinanediol, bisulfite $N^1$-(4-[4-methoxy]phenylbenzoyl)-(R)-boroarginine (+)-pinanediol, bisulfite $N^1$-(2-[2-phenyl]benzyloxycarbonylbenzoyl)-(R)-boroarginine (+)-pinanediol, bisulfite $N^1$-(2-[1-naphthyl]benzoyl)-(R)-boroarginine (+)-pinanediol, bisulfite $N^1$-(4-[4-carboxy]phenylbenzoyl)-(R)-boroarginine (+)-pinanediol, bisulfite $N^1$-(4-phenylbenzoyl)-(R)-borothioarginine (+)-pinanediol, hydrobromide $N^1$-(3-phenylbenzoyl)-(R)-borothioarginine (+)-pinanediol, hydrobromide $N^1$-(3-phenoxybenzoyl)-(R)-borothioarginine (+)-pinanediol, hydrobromide $N^1$-(2-benzoylbenzoyl)-(R)-borothioarginine (+)-pinanediol, hydrobromide $N^1$-(3-benzoylbenzoyl)-(R)-borothioarginine (+)-pinanediol, hydrobromide $N^1$-(4-benzoylbenzoyl)-(R)-borothioarginine (+)-pinanediol, hydrobromide $N^1$-(3-[N-benzyloxycarbonyl]aminobenzoyl)-(R)-borothioarginine (+)-pinanediol, hydrobromide $N^1$-(3-[N-benzyloxycarbonyl-N-methyl]aminobenzoyl)-(R)-borothioarginine (+)-pinanediol, hydrobromide $N^1$-(4-ethylbenzoyl)-(R)-borothioarginine (+)-pinanediol, hydrobromide $N^1$-(4-n-propylbenzoyl)-(R)-borothioarginine (+)-pinanediol, hydrobromide $N^1$-(4-isopropylbenzoyl)-(R)-borothioarginine (+)-pinanediol, hydrobromide $N^1$-(4-n-butylbenzoyl)-(R)-borothioarginine (+)-pinanediol, hydrobromide $N^1$-(4-tert-butylbenzoyl)-(R)-borothioarginine (+)-pinanediol, hydrobromide $N^1$-(4-n-hexylbenzoyl)-(R)-borothioarginine (+)-pinanediol, hydrobromide $N^1$-(4-cyclohexylbenzoyl)-(R)-borothioarginine (+)-pinanediol, hydrobromide $N^1$-(2-[N-(2-phenylethyl)carbonyl]aminobenzoyl)-(R)-borothioarginine (+)-pinanediol, hydrobromide $N^1$-(4-n-butyloxybenzoyl)-(R)-borothioarginine (+)-pinanediol, hydrobromide $N^1$-(4-[N-cyclopropylcarbonyl]aminobenzoyl)-(R)-borothioarginine (+)-pinanediol, hydrobromide $N^1$-(4-[N-cyclohexylcarbonyl]aminobenzoyl)-(R)-borothioarginine (+)-pinanediol, hydrobromide $N^1$-(4-[N-(4-methoxy)benzoyl]aminobenzoyl)-(R)-borothioarginine (+)-pinanediol, hydrobromide $N^1$-(4-[4-methoxy]phenylbenzoyl)-(R)-borothioarginine (+)-pinanediol, hydrobromide $N^1$-(2-[2-phenylbenzyloxycarbonyl]benzoyl)-(R)-borothioarginine (+)-pinanediol, hydrobromide $N^1$-(2-[1-naphthyl]benzoyl)-(R)-borothioarginine (+)-pinanediol, hydrobromide $N^1$-(4-[4-carboxy]phenylbenzoyl)-(R)-borothioarginine (+)-pinanediol, hydrobromide $N^1$-([2-anthraquinonyl]carbonyl)-(R)-boroarginine (+)-pinanediol, bisulfite $N^1$-([2-dioxothioxanthinonyl]carbonyl)-(R)-boroarginine (+)-pinanediol, bisulfite $N^1$-([2-anthraquinonyl]carbonyl)-(R)-borothioarginine (+)-pinanediol, hydrobromide $N^1$-([2-dioxothioxanthinonyl]carbonyl)-(R)-borothioarginine (+)-pinanediol, hydrobromide $N^1$-([2-fluoren-9-onyl]carbonyl)-(R)-borothiohomoarginine (+)-pinanediol, hydrobromide $N^1$-([2-fluoren-9-onyl]carbonyl)-(R)-boroarginine (+)-pinanediol, bisulfite $N^1$-([2-fluoren-9-onyl]carbonyl)-(R)-borothioarginine (+)-pinanediol, hydrobromide $N^1$-([3-fluoren-9-onyl]carbonyl)-(R)-borothioarginine (+)-pinanediol, hydrobromide $N^1$-([3-fluoren-9-onyl]carbonyl)-(R)-boroarginine (+)-pinanediol, bisulfite $N^1$-([4-fluoren-9-onyl]carbonyl)-(R)-borothioarginine (+)-pinanediol, hydrobromide $N^1$-([4-fluoren-9-onyl]carbonyl)-(R)-boroarginine (+)-pinanediol, bisulfite $N^1$-(1-naphthoyl)-(R)-borothioarginine (+)-pinanediol, hydrobromide $N^1$-(1-naphthoyl)-(R)-boroarginine (+)-pinanediol, bisulfite $N^1$-(2-methyl-4-phenyl-5-methoxybenzoyl)-(R)-borothioarginine (+)-pinanediol, hydrobromide $N^1$-(2-methyl-4-phenyl-5-carboxamidobenzoyl)-(R)-borothioarginine (+)-pinanediol, hydrobromide $N^1$-(2-methyl-4-phenyl-5-fluorobenzoyl)-(R)-borothioarginine (+)-pinanediol, hydrobromide $N^1$-(2-methyl-4-phenyl-5-trifluoromethylbenzoyl)-(R)-borothioarginine (+)-pinanediol, hydrobromide $N^1$-(2-methyl-4-phenyl-5-chlorobenzoyl)-(R)-borothioarginine (+)-pinanediol, hydrobromide $N^1$-(2-methyl-4-phenyl-5-hydroxybenzoyl)-(R)-borothioarginine (+)-pinanediol, hydrobromide $N^1$-(2-methyl-4-[4-carboxy]phenyl-5-methoxybenzoyl)-(R)-borothioarginine (+)-pinanediol, hydrobromide $N^1$-(2-methyl-4-[4-carboxy]phenyl-5-carboxamidobenzoyl)-(R)-borothioarginine (+)-pinanediol, hydrobromide $N^1$-(2-methyl-4-[4-carboxy]phenyl-5-fluorobenzoyl)-(R)-borothioarginine (+)-pinanediol, hydrobromide $N^1$-(2-methyl-4-[4-carboxy]phenyl-5-trifluoromethylbenzoyl)-(R)-borothioarginine (+)-pinanediol, hydrobromide $N^1$-(2-methyl-4-[4-carboxy]phenyl-5-chlorobenzoyl)-(R)-borothioarginine (+)-pinanediol, hydrobromide $N^1$-(2-methyl-4-[4-carboxy]phenyl-5-hydroxybenzoyl)-(R)-borothioarginine (+)-pinanediol, hydrobromide $N^1$-(2-methyl-4-phenyl-5-methoxybenzoyl)-(R)-boroarginine (+)-pinanediol, bisulfite $N^1$-(2-methyl-4-phenyl-5-carboxamidobenzoyl)-(R)-boroarginine (+)-pinanediol, bisulfite $N^1$-(2-methyl-4-phenyl-5-fluorobenzoyl)-(R)-boroarginine (+)-pinanediol, bisulfite $N^1$-(2-methyl-4-phenyl-5-trifluoromethylbenzoyl)-(R)-boroarginine (+)-pinanediol, bisulfite $N^1$-(2-methyl-4-phenyl-5-chlorobenzoyl)-(R)-boroarginine (+)-pinanediol, bisulfite $N^1$-(2-methyl-4-phenyl-5-hydroxybenzoyl)-(R)-boroarginine (+)-pinanediol, bisulfite $N^1$-(2-methyl-4-[4-carboxy]phenyl-5-methoxybenzoyl)-(R)-boroarginine (+)-pinanediol, bisulfite $N^1$-(2-methyl-4-[4-carboxy]phenyl-5-carboxamidobenzoyl)-(R)-boroarginine (+)-pinanediol, bisulfite $N^1$-(2-methyl-4-[4-carboxy]phenyl-5-fluorobenzoyl)-(R)-boroarginine (+)-pinanediol, bisulfite $N^1$-(2-methyl-4-[4-carboxy]phenyl-5-trifluoromethylbenzoyl)-(R)-boroarginine (+)-pinanediol, bisulfite $N^1$-(2-methyl-4-[4-carboxy]phenyl-5-chlorobenzoyl)-(R)-boroarginine (+)-pinanediol, bisulfite $N^1$-(2-methyl-4-[4-carboxy]phenyl-5-hydroxybenzoyl)-(R)-boroarginine (+)-pinanediol, bisulfite $N^1$-(2-[5-phenyl]furylcarbonyl)-(R)-boroarginine (+)-pinanediol, bisulfite $N^1$-(2-[5-phenyl]thiophen-ylcarbonyl)-(R)-boroarginine (+)-pinanediol, bisulfite $N^1$-(2-[5-phenyl]furylcarbonyl)-(R)-borothioarginine (+)-pinanediol, hydrobromide $N^1$-(2-[5-phenyl]thiophen-ylcarbonyl)-(R)-borothioarginine (+)-pinanediol, hydrobromide $N^1$-(3-[6-phenyl]pyridylcarbonyl)-(R)-boroarginine (+)-pinanediol, bisulfite $N^1$-(3-[5-benzyloxy]pyridylcarbonyl)-(R)-boroarginine (+)-pinanediol, bisulfite $N^1$-(3-[6-phenyl]pyridylcarbonyl)-(R)-borothioarginine (+)-pinanediol, hydrobromide $N^1$-(3-[5-benzyloxy]pyridylcarbonyl)-(R)-borothioarginine (+)-pinanediol, hydrobromide $N^1$-(2-benzopyronylcarbonyl)-(R)-boroarginine(+)-pinanediol, bisulfite $N^1$-(2-benzopyronylcarbonyl)-(R)-borothioarginine (+)-pinanediol, hydrobromide $N^1$-(3-isoquinolinylcarbonyl)-(R)-boroarginine (+)-pinanediol, bisulfite $N^1$-(2-phenyl-4-isoquinolinylcarbonyl)-(R)-boroarginine (+)-pinanediol, bisulfite $N^1$-(3-isoquinolinylcarbonyl)-(R)-borothioarginine (+)-pinanediol, hydrobromide $N^1$-(2-phenyl-4-isoquinolinylcarbonyl)-(R)-borothioarginine (+)-pinanediol, hydrobromide $N^1$-(2-isoquinolinylcarbonyl)-(R)-boroarginine(+)-pinanediol, bisulfite $N^1$-(2-isoquinolinylcarbonyl)-(R)-borothioarginine (+)-pinanediol, hydrobromide $N^1$-(4-phenylbenzoyl)-(R)-boroarginine, hydrochloride $N^1$-(3-phenylbenzoyl)-(R)-boroarginine, hydrochloride $N^1$-(3-phenoxybenzoyl)-(R)-boroarginine, hydrochloride $N^1$-(4-[4-pyridyl]benzoyl)-(R)-boroarginine, hydrochloride $N^1$-(2-benzoylbenzoyl)-(R)-boroarginine, hydrochloride $N^1$-(3-benzoylbenzoyl)-(R)-boroarginine, hydrochloride $N^1$-(4-benzoylbenzoyl)-(R)-boroarginine, hydrochloride $N^1$-(3-[N-benzyloxycarbonyl]aminobenzoyl)-(R)-boroarginine, hydrochloride $N^1$-(3-[N-benzyloxycarbonyl-N-methyl]aminobenzoyl)-(R)-boroarginine, hydrochloride $N^1$-(4-ethylbenzoyl)-(R)-boroarginine, hydrochloride $N^1$-(4-n-propylbenzoyl)-(R)-boroarginine, hydrochloride $N^1$-(4-isopropylbenzoyl)-(R)-boroarginine, hydrochloride $N^1$-(4-tert-butylbenzoyl)-(R)-boroarginine, hydrochloride $N^1$-(4-n-hexylbenzoyl)-(R)-boroarginine, hydrochloride $N^1$-(4-cyclohexylbenzoyl)-(R)-boroarginine, hydrochloride $N^1$-(2-[N-(2-phenylethyl)carbonyl]aminobenzoyl)-(R)-boroarginine, hydrochloride $N^1$-(4-n-butyloxybenzoyl)-(R)-boroarginine, hydrochloride $N^1$-(4-[N-cyclopropylcarbonyl]aminobenzoyl)-(R)-boroarginine, hydrochloride $N^1$-(4-[N-cyclohexylcarbonyl]aminobenzoyl)-(R)-boroarginine, hydrochloride $N^1$-(4-[N-(4-methoxy)benzoyl]aminobenzoyl)-(R)-boroarginine, hydrochloride $N^1$-(4-[4-methoxy]phenylbenzoyl)-(R)-boroarginine, hydrochloride $N^1$-(2-[2-phenyl]benzyloxycarbonylbenzoyl)-(R)-boroarginine, hydrochloride $N^1$-(2-[1-naphthyl]benzoyl)-(R)-boroarginine, hydrochloride $N^1$-(4-[4-carboxy]phenylbenzoyl)-(R)-boroarginine, hydrochloride $N^1$-([2-anthraquinonyl]carbonyl)-(R)-boroarginine, hydrochloride $N^1$-([2-dioxothioxanthinonyl]carbonyl)-(R)-boroarginine, hydrochloride $N^1$-([2-fluoren-9-onyl]carbonyl)-(R)-boroarginine, hydrochloride $N^1$-([3-fluoren-9-onyl]carbonyl)-(R)-boroarginine, hydrochloride $N^1$-(1-naphthoyl)-(R)-boroarginine, hydrochloride $N^1$-([4-fluoren-9-onyl]carbonyl)-(R)-boroarginine, hydrochloride $N^1$-(2-methyl-4-phenyl-5-methoxybenzoyl)-(R)-boroarginine, hydrochloride $N^1$-(2-methyl-4-phenyl-5-carboxamidobenzoyl)-(R)-boroarginine, hydrochloride $N^1$-(2-methyl-4-phenyl-5-fluorobenzoyl)-(R)-boroarginine, hydrochloride $N^1$-(2-methyl-4-phenyl-5-trifluoromethylbenzoyl)-(R)-boroarginine, hydrochloride $N^1$-(2-methyl-4-phenyl-5-chlorobenzoyl)-(R)-boroarginine, hydrochloride $N^1$-(2-methyl-4-phenyl-5-hydroxybenzoyl)-(R)-boroarginine, hydrochloride $N^1$-(2-methyl-4-[4-carboxy]phenyl-5-methoxybenzoyl)-(R)-boroarginine, hydrochloride $N^1$-(2-methyl-4-[4-carboxy]phenyl-5-carboxamidobenzoyl)-(R)-boroarginine, hydrochloride $N^1$-(2-methyl-4-[4-carboxy]phenyl-5-fluorobenzoyl)-(R)-boroarginine, hydrochloride $N^1$-(2-methyl-4-[4-carboxy]phenyl-5-trifluoromethylbenzoyl)-(R)-boroarginine, hydrochloride $N^1$-(2-methyl-4-[4-carboxy]phenyl-5-chlorobenzoyl)-(R)-boroarginine, hydrochloride $N^1$-(2-methyl-4-[4-carboxy]phenyl-5-hydroxybenzoyl)-(R)-boroarginine, hydrochloride $N^1$-(2-[5-phenyl]furylcarbonyl)-(R)-boroarginine, hydrochloride $N^1$-(2-[5-phenyl]thiophen-ylcarbonyl)-(R)-boroarginine, hydrochloride $N^1$-(2-benzopyronylcarbonyl)-(R)-boroarginine, hydrochloride $N^1$-(2-isoquinolinylcarbonyl)-(R)-boroarginine, hydrochloride $N^1$-(3-isoquinolinylcarbonyl)-(R)-boroarginine, hydrochloride $N^1$-(2-phenyl-4-isoquinolinylcarbonyl)-(R)-boroarginine, hydrochloride $N^1$-(4-phenylbenzoyl)-(R)-borothioarginine, hydrochloride $N^1$-(3-phenylbenzoyl)-(R)-borothioarginine, hydrochloride $N^1$-(3-phenoxybenzoyl)-(R)-borothioarginine, hydrochloride $N^1$-(2-benzoylbenzoyl)-(R)-borothioarginine, hydrochloride $N^1$-(3-benzoylbenzoyl)-(R)-borothioarginine, hydrochloride $N^1$-(4-benzoylbenzoyl)-(R)-borothioarginine, hydrochloride $N^1$-(3-[N-benzyloxycarbonyl]aminobenzoyl)-(R)-borothioarginine, hydrochloride $N^1$-(3-[N-benzyloxycarbonyl-N-methyl]aminobenzoyl)-(R)-borothioarginine, hydrochloride $N^1$-(4-ethylbenzoyl)-(R)-borothioarginine, hydrochloride $N^1$-(4-n-propylbenzoyl)-(R)-borothioarginine, hydrochloride $N^1$-(4-isopropylbenzoyl)-(R)-borothioarginine, hydrochloride $N^1$-(4-n-butylbenzoyl)-(R)-borothioarginine, hydrochloride $N^1$-(4-tert-butylbenzoyl)-(R)-borothioarginine, hydrochloride $N^1$-(4-n-hexylbenzoyl)-(R)-borothioarginine, hydrochloride $N^1$-(4-cyclohexylbenzoyl)-(R)-borothioarginine, hydrochloride $N^1$-(2-[N-(2-phenylethyl)carbonyl]aminobenzoyl)-(R)-borothioarginine, hydrochloride $N^1$-(4-n-butyloxybenzoyl)-(R)-borothioarginine, hydrochloride $N^1$-(4-[N-cyclopropylcarbonyl]aminobenzoyl)-(R)-borothioarginine, hydrochloride $N^1$-(4-[N-cyclohexylcarbonyl]aminobenzoyl)-(R)-borothioarginine, hydrochloride $N^1$-(4-[N-(4-methoxy)benzoyl]aminobenzoyl)-(R)-borothioarginine, hydrochloride $N^1$-(4-[4-methoxy]phenylbenzoyl)-(R)-borothioarginine, hydrochloride $N^1$-(2-[2-phenylbenzyloxycarbonyl]benzoyl)-(R)-borothioarginine, hydrochloride $N^1$-(2-[1-naphthyl]benzoyl)-(R)-borothioarginine, hydrochloride $N^1$-(4-[4-carboxy]phenylbenzoyl)-(R)-borothioarginine, hydrochloride $N^1$-[(2-anthraquinonyl)carbonyl)-(R)-borothioarginine, hydrochloride $N^1$-[(2-dioxothioxanthinonyl]carbonyl)-(R)-borothioarginine, hydrochloride $N^1$-[(2-fluoren-9-onyl]carbonyl)-(R)-borothiohomoarginine, hydrochloride $N^1$-[(2-fluoren-9-onyl]carbonyl)-(R)-borothioarginine, hydrochloride $N^1$-[(3-fluoren-9-onyl]carbonyl)-(R)-borothioarginine, hydrochloride $N^1$-[(4-fluoren-9-onyl]carbonyl)-(R)-borothioarginine, hydrochloride $N^1$-(1-naphthoyl)-(R)-borothioarginine, hydrochloride $N^1$-(2-methyl-4-phenyl-5-methoxybenzoyl)-(R)-borothioarginine, hydrochloride $N^1$-(2-methyl-4-phenyl-5-carboxamidobenzoyl)-(R)-borothioarginine, hydrochloride $N^1$-(2-methyl-4-phenyl-5-fluorobenzoyl)-(R)-borothioarginine, hydrochloride $N^1$-(2-methyl-4-phenyl-5-trifluoromethylbenzoyl)-(R)-borothioarginine, hydrochloride $N^1$-(2-methyl-4-phenyl-5-chlorobenzoyl)-(R)-borothioarginine, hydrochloride $N^1$-(2-methyl-4-phenyl-5-hydroxybenzoyl)-(R)-borothioarginine, hydrochloride $N^1$-(2-methyl-4-[4-carboxy]phenyl-5-methoxybenzoyl)-(R)-borothioarginine, hydrochloride $N^1$-(2-methyl-4-[4-carboxy]phenyl-5-carboxamidobenzoyl)-(R)-borothioarginine, hydrochloride $N^1$-(2-methyl-4-[4-carboxy]phenyl-5-fluorobenzoyl)-(R)-borothioarginine, hydrochloride $N^1$-(2-methyl-4-[4-carboxy]phenyl-5-trifluoromethylbenzoyl)-(R)-borothioarginine, hydrochloride $N^1$-(2-methyl-4-[4-carboxy]phenyl-5-chlorobenzoyl)-(R)-borothioarginine, hydrochloride $N^1$-(2-methyl-4-[4-carboxy]phenyl-5-hydroxybenzoyl)-(R)-borothioarginine, hydrochloride $N^1$-(2-[5-phenyl]furylcarbonyl)-(R)-borothioarginine, hydrochloride $N^1$-(2-[5-phenyl]thiophenylcarbonyl)-(R)-borothioarginine, hydrochloride $N^1$-(3-[6-phenyl]pyridylcarbonyl)-(R)-boroarginine, hydrochloride $N^1$-(3-[5-benzyloxy]pyridylcarbonyl)-(R)-boroarginine, hydrochloride $N^1$-(3-[6-phenyl]pyridylcarbonyl)-(R)-borothioarginine, hydrochloride $N^1$-(3-[5-benzyloxy]pyridylcarbonyl)-(R)-borothioarginine, hydrochloride $N^1$-(2-benzopyronylcarbonyl)-(R)-borothioarginine, hydrochloride $N^1$-(3-isoquinolinylcarbonyl)-(R)-borothioarginine, hydrochloride $N^1$-(2-phenyl-4-isoquinolinylcarbonyl)-(R)-borothioarginine, hydrochloride $N^1$-(2-isoquinolinylcarbonyl)-(R)-borothioarginine, hydrochloride $N^1$-(4-phenylbenzoyl)-(R)-borolysine (+)-pinanediol, hydrochloride $N^1$-(3-phenylbenzoyl)-(R)-borolysine (+)-pinanediol, hydrochloride $N^1$-(3-phenoxybenzoyl)-(R)-borolysine (+)-pinanediol, hydrochloride $N^1$-(4-[4-pyridyl]benzoyl)-(R)-borolysine (+)-pinanediol, hydrochloride $N^1$-(2-benzoylbenzoyl)-(R)-borolysine (+)-pinanediol, hydrochloride $N^1$-(3-benzoylbenzoyl)-(R)-borolysine (+)-pinanediol, hydrochloride $N^1$-(4-benzoylbenzoyl)-(R)-borolysine (+)-pinanediol, hydrochloride $N^1$-(3-[N-benzyloxycarbonyl]aminobenzoyl)-(R)-borolysine (+)-pinanediol, hydrochloride $N^1$-(3-[N-benzyloxycarbonyl-N-methyl]aminobenzoyl)-(R)-borolysine (+)-pinanediol, hydrochloride $N^1$-(4-ethylbenzoyl)-(R)-borolysine (+)-pinanediol, hydrochloride $N^1$-(4-n-propylbenzoyl)-(R)-borolysine (+)-pinanediol, hydrochloride $N^1$-(4-isopropylbenzoyl)-(R)-borolysine (+)-pinanediol, hydrochloride $N^1$-(4-tert-butylbenzoyl)-(R)-borolysine (+)-pinanediol, hydrochloride $N^1$-(4-n-hexylbenzoyl)-(R)-borolysine (+)-pinanediol, hydrochloride $N^1$-(4-cyclohexylbenzoyl)-(R)-borolysine (+)-pinanediol, hydrochloride $N^1$-(2-[N-(2-phenylethyl)carbonyl]aminobenzoyl)-(R)-borolysine (+)-pinanediol, hydrochloride $N^1$-(4-n-butyloxybenzoyl)-(R)-borolysine (+)-pinanediol, hydrochloride $N^1$-(4-[N-cyclopropylcarbonyl]aminobenzoyl)-(R)-borolysine (+)-pinanediol, hydrochloride $N^1$-(4-[N-cyclohexylcarbonyl]aminobenzoyl)-(R)-borolysine (+)-pinanediol, hydrochloride $N^1$-(4-[N-(4-methoxy)benzoyl]aminobenzoyl)-(R)-borolysine (+)-pinanediol, hydrochloride $N^1$-(4-[4-methoxy]phenylbenzoyl)-(R)-borolysine (+)-pinanediol, hydrochloride $N^1$-(2-[2-phenylbenzyloxycarbonylbenzoyl)-(R)-borolysine (+)-pinanediol, hydrochloride $N^1$-(2-[1-naphthyl]benzoyl)-(R)-borolysine (+)-pinanediol, hydrochloride $N^1$-(4-[4-carboxy]phenylbenzoyl)-(R)-borolysine (+)-pinanediol, hydrochloride $N^1$-([2-anthraquinonyl]carbonyl)-(R)-borolysine (+)-pinanediol, hydrochloride $N^1$-([2-dioxothioxanthinonyl]carbonyl)-(R)-borolysine (+)-pinanediol, hydrochloride $N^1$-([2-fluoren-9-onyl]carbonyl)-(R)-borolysine (+)-pinanediol, hydrochloride $N^1$-([3-fluoren-9-onyl]carbonyl)-(R)-borolysine (+)-pinanediol, hydrochloride $N^1$-(1-naphthoyl)-(R)-borolysine (+)-pinanediol, hydrochloride $N^1$-([4-fluoren-9-onyl]carbonyl)-(R)-borolysine (+)-pinanediol, hydrochloride $N^1$-(2-methyl-4-phenyl-5-methoxybenzoyl)-(R)-borolysine (+)-pinanediol, hydrochloride $N^1$-(2-methyl-4-phenyl-5-carboxamidobenzoyl)-(R)-borolysine (+)-pinanediol, hydrochloride $N^1$-(2-methyl-4-phenyl-5-fluorobenzoyl)-(R)-borolysine (+)-pinanediol, hydrochloride $N^1$-(2-methyl-4-phenyl-5-trifluoromethylbenzoyl)-(R)-borolysine (+)-pinanediol, hydrochloride $N^1$-(2-methyl-4-phenyl-5-chlorobenzoyl)-(R)-borolysine (+)-pinanediol, hydrochloride $N^1$-(2-methyl-4-phenyl-5-hydroxybenzoyl)-(R)-borolysine (+)-pinanediol, hydrochloride $N^1$-(2-methyl-4-[4-carboxy]phenyl-5-methoxybenzoyl)-(R)-borolysine (+)-pinanediol, hydrochloride $N^1$-(2-methyl-4-[4-carboxy]phenyl-5-carboxamidobenzoyl)-(R)-borolysine (+)-pinanediol, hydrochloride $N^1$-(2-methyl-4-[4-carboxy]phenyl-5-fluorobenzoyl)-(R)-borolysine (+)-pinanediol, hydrochloride $N^1$-(2-methyl-4-[4-carboxy]phenyl-5-trifluoromethylbenzoyl)-(R)-borolysine (+)-pinanediol, hydrochloride $N^1$-(2-methyl-4-[4-carboxy]phenyl-5-chlorobenzoyl)-(R)-borolysine (+)-pinanediol, hydrochloride $N^1$-(2-methyl-4-[4-carboxy]phenyl-5-hydroxybenzoyl)-(R)-borolysine (+)-pinanediol, hydrochloride $N^1$-(2-[5-phenyl]furylcarbonyl)-(R)-borolysine (+)-pinanediol, hydrochloride $N^1$-(2-[5-phenyl]thiophen-ylcarbonyl)-(R)-borolysine (+)-pinanediol, hydrochloride $N^1$-(2-benzopyronylcarbonyl)-(R)-borolysine (+)-pinanediol, hydrochloride $N^1$-(2-isoquinolinylcarbonyl)-(R)-borolysine (+)-pinanediol, hydrochloride $N^1$-(3-isoquinolinylcarbonyl)-(R)-borolysine (+)-pinanediol, hydrochloride $N^1$-(2-phenyl-4-isoquinolinylcarbonyl)-(R)-borolysine (+)-pinanediol, hydrochloride $N^1$-(4-phenylbenzoyl)-(R)-borolysine, hydrochloride $N^1$-(3-phenylbenzoyl)-(R)-borolysine, hydrochloride $N^1$-(3-phenoxybenzoyl)-(R)-borolysine, hydrochloride $N^1$-(4-[4-pyridyl]benzoyl)-(R)-borolysine, hydrochloride $N^1$-(2-benzoylbenzoyl)-(R)-borolysine, hydrochloride $N^1$-(3-benzoylbenzoyl)-(R)-borolysine, hydrochloride $N^1$-(4-benzoylbenzoyl)-(R)-borolysine, hydrochloride $N^1$-(3-[N-benzyloxycarbonyl]aminobenzoyl)-(R)-borolysine, hydrochloride $N^1$-(3-[N-benzyloxycarbonyl-N-methyl]aminobenzoyl)-(R)-borolysine, hydrochloride $N^1$-(4-ethylbenzoyl)-(R)-borolysine, hydrochloride $N^1$-(4-n-propylbenzoyl)-(R)-borolysine, hydrochloride $N^1$-(4-isopropylbenzoyl)-(R)-borolysine, hydrochloride $N^1$-(4-tert-butylbenzoyl)-(R)-borolysine, hydrochloride $N^1$-(4-n-hexylbenzoyl)-(R)-borolysine, hydrochloride $N^1$-(4-cyclohexylbenzoyl)-(R)-borolysine, hydrochloride $N^1$-(2-[N-(2-phenylethyl)carbonyl]aminobenzoyl)-(R)-borolysine, hydrochloride $N^1$-(4-n-butyloxybenzoyl)-(R)-borolysine, hydrochloride $N^1$-(4-[N-cyclopropylcarbonyl]aminobenzoyl)-(R)-borolysine, hydrochloride $N^1$-(4-[N-cyclohexylcarbonyl]aminobenzoyl)-(R)-borolysine, hydrochloride $N^1$-(4-[N-(4-methoxy)benzoyl]aminobenzoyl)-(R)-borolysine, hydrochloride $N^1$-(4-[4-methoxy]phenylbenzoyl)-(R)-borolysine, hydrochloride $N^1$-(2-[2-phenyl]benzyloxycarbonylbenzoyl)-(R)-borolysine, hydrochloride $N^1$-(2-[1-naphthyl]benzoyl)-(R)-borolysine, hydrochloride $N^1$-(4-[4-carboxy]phenylbenzoyl)-(R)-borolysine, hydrochloride $N^1$-([2-anthraquinonyl]carbonyl)-(R)-borolysine, hydrochloride $N^1$-([2-dioxothioxanthinonyl]carbonyl)-(R)-borolysine, hydrochloride $N^1$-([2-fluoren-9-onyl]carbonyl)-(R)-borolysine, hydrochloride $N^1$-([3-fluoren-9-onyl]carbonyl)-(R)-borolysine, hydrochloride $N^1$-(1-naphthoyl)-(R)-borolysine, hydrochloride $N^1$-([4-fluoren-9-onyl]carbonyl)-(R)-borolysine, hydrochloride $N^1$-(2-methyl-4-phenyl-5-methoxybenzoyl)-(R)-borolysine, hydrochloride $N^1$-(2-methyl-4-phenyl-5-carboxamidobenzoyl)-(R)-borolysine, hydrochloride $N^1$-(2-methyl-4-phenyl-5-fluorobenzoyl)-(R)-borolysine, hydrochloride $N^1$-(2-methyl-4-phenyl-5-trifluoromethylbenzoyl)-(R)-borolysine, hydrochloride $N^1$-(2-methyl-4-phenyl-5-chlorobenzoyl)-(R)-borolysine, hydrochloride $N^1$-(2-methyl-4-phenyl-5-hydroxybenzoyl)-(R)-borolysine, hydrochloride $N^1$-(2-methyl-4-[4-carboxy]phenyl-5-methoxybenzoyl)-(R)-borolysine, hydrochloride $N^1$-(2-methyl-4-[4-carboxy]phenyl-5-carboxamidobenzoyl)-(R)-borolysine, hydrochloride $N^1$-(2-methyl-4-[4-carboxy]phenyl-5-fluorobenzoyl)-(R)-borolysine, hydrochloride $N^1$-(2-methyl-4-[4-carboxy]phenyl-5-trifluoromethylbenzoyl)-(R)-borolysine, hydrochloride $N^1$-(2-methyl-4-[4-carboxy]phenyl-5-chlorobenzoyl)-(R)-borolysine, hydrochloride $N^1$-(2-methyl-4-[4-carboxy]phenyl-5-hydroxybenzoyl)-(R)-borolysine, hydrochloride $N^1$-(2-[5-phenyl]furylcarbonyl)-(R)-borolysine, hydrochloride N¹-(2-[5-phenyl]thiophenylcarbonyl)-(R)-borolysine, hydrochloride N¹-(2-benzopyronylcarbonyl)-(R)-borolysine, hydrochloride N¹-(2-isoquinolinylcarbonyl)-(R)-borolysine, hydrochloride N¹-(3-isoquinolinylcarbonyl)-(R)-borolysine, hydrochloride N¹-(2-phenyl-4-isoquinolinylcarbonyl)-(R)-borolysine, hydrochloride N¹-(2-methyl-4-phenylbenzoyl-R-borolysine, hydrochloride N¹-(2-methyl-4-phenylbenzoyl-R-borolysine, (+)-pinanediol, hydrochloride N¹-(2-methyl-4-phenylbenzoyl-R-borothioarginine, hydrobromide N¹-(2-methyl-4-phenylbenzoyl-R-borothioarginine, (+)-pinanediol, hydrochloride N¹-(2-methyl-4-phenylbenzoyl-R-boroarginine, hydrochloride N¹-(2-methyl-4-phenylbenzoyl-R-boroarginine, (+)-pinanediol, bisulfite N¹-[4-phenyl-2-nitrobenzoyl]boroArg(Me), (+)-pinanediol ester N¹-[4-phenyl-2-fluorobenzoyl]boroArg(Me), (+)-pinanediol ester N¹-[4-phenyl-2-aminobenzoyl]boroArg(Me), (+)-pinanediol ester N¹-[4-phenyl-2-(methylsulfonamido)benzoyl]boroArg(Me), (+)-pinanediol ester N¹-[4-phenyl-2-(cyanomethylamino)benzoyl]boroArg(Me), (+)-pinanediol ester N¹-[4-phenyl-2-(cyanomethyl)benzoyl]boroArg(Me), (+)-pinanediol ester N¹-[4-phenyl-2-(diethylamino)benzoyl]boroArg(Me), (+)-pinanediol ester N¹-[4-[2-(t-butylaminosulfonyl)phenyl]-2-methyl-benzoyl]boroArg (Me), (+) pinanediol ester N¹-[(4-[2-(aminosulfonyl)phenyl]-2-methyl-benzoyl]boroArg (Me), (+) pinanediol ester N¹-[4-[2-(methoxycarbonylaminosulfonyl)phenyl]-2-methyl-benzoyl]boroArg(Me), (+)-pinanediol ester N¹-[4-[2-(t-butylaminosulfonyl)phenyl]benzoyl]boroArg (Me), (+)-pinanediol ester N¹-[4-[2-(t-butylaminosulfonyl)phenyl]benzoyl]boroArg (Me)—OH N¹-[4-[2-(n-butoxycarbonylaminosulfonyl)phenyl]-2-methyl-benzoyl]boroArg(Me), (+)-pinanediol ester N¹-[4-[2-(diethylaminosulfonyl)phenyl]-2-methyl-benzoyl]boroArg(Me), (+)pinanediol ester N¹-[4-[2-(t-butylaminosulfonyl)phenyl]-2-fluoro-benzoyl]boroArg(Me), (+)pinanediol ester N¹-[4-[2-(aminosulfonyl)phenyl]-2-fluoro-benzoyl]boroArg(Me), (+)pinanediol ester N¹-[4-[2-(methoxycarbonylaminosulfonyl)phenyl]-2-fluoro-benzoyl]boroArg(Me), (+)-pinanediol ester N¹-[4-[2-(t-butylaminosulfonyl)phenyl]-2-nitro-benzoyl]boroArg(Me), (+)-pinanediol ester N¹-[4-[2-(aminosulfonyl)phenyl]-2-nitro-benzoyl]boroArg(Me), (+)pinanediol ester N¹-[4-[2-(methoxycarbonylaminosulfonyl)phenyl]-2-nitro-benzoyl]boroArg(Me), (+)-pinanediol ester N¹-[4-phenyl-2-nitrobenzoyl]boroMPG, (+)-pinanediol ester N¹-[4-phenyl-2-fluorobenzoyl]boroMPG, (+)-pinanediol ester N¹-[4-phenyl-2-aminobenzoyl]boroMPG, (+)-pinanediol ester N¹-[4-phenyl-2-(methylsulfonamido)benzoyl]boroMPG, pinanediol ester N¹-[4-phenyl-2-(cyanomethylamino)benzoyl]boroMPG, (+)-pinanediol ester N¹-[4-phenyl-2-(cyanomethyl)benzoyl]boroMPG, (+)-pinanediol ester N¹-[4-phenyl-2-(diethylamino)benzoyl]boroMPG, (+)-pinanediol ester N¹-[4-[2-(t-butylaminosulfonyl)phenyl]-2-methyl-benzoyl]boroMPG, (+)pinanediol ester N¹-[4-[2-(aminosulfonyl)phenyl]-2-methyl-benzoyl]boroMPG, (+)pinanediol ester N¹-[4-[2-(methoxycarbonylaminosulfonyl)phenyl]-2-methyl-benzoyl]boroMPG, (+)-pinanediol ester N¹-[4-[2-(t-butylaminosulfonyl)phenyl]benzoyl]boroMPG, (+)-pinanediol ester N¹-[4-[2-(t-butylaminosulfonyl)phenyl]benzoyl]boroMPG—OH N¹-[4-[2-(n-butoxycarbonylaminosulfonyl)phenyl]-2-methyl-benzoyl]boroMPG, (+)-pinanediol ester N¹-[4-[2-(diethylaminosulfonyl)phenyl]-2-methyl-benzoyl]boroMPG, (+)pinanediol ester N¹-[4-[2-(t-butylaminosulfonyl)phenyl]-2-fluoro-benzoyl]boroMPG, (+)pinanediol ester N¹-[4-[2-(aminosulfonyl)phenyl]-2-fluoro-benzoyl]boroMPG, (+)pinanediol ester N¹-[4-[2-(methoxycarbonylaminosulfonyl)phenyl]-2-fluoro-benzoyl]boroMPG, (+)-pinanediol ester N¹-[4-[2-(t-butylaminosulfonyl)phenyl]-2-nitro-benzoyl]boroMPG, (+)pinanediol ester N¹-[4-[2-(aminosulfonyl)phenyl]-2-nitro-benzoyl]boroMPG, (+)pinanediol ester N¹-[4-[2-(methoxycarbonylaminosulfonyl)phenyl]-2-nitro-benzoyl]boroMPG, (+)-pinanediol ester N¹-[4-phenyl-2-nitrobenzoyl]boroACA, (+)-pinanediol ester N¹-[4-phenyl-2-fluorobenzoyl]boroACA, (+)-pinanediol ester N¹-[4-phenyl-2-aminobenzoyl]boroACA, (+)-pinanediol ester N¹-[4-phenyl-2-(methylsulfonamido)benzoyl]boroACA, (+)-pinanediol ester N¹-[4-phenyl-2-(cyanomethylamino)benzoyl]boroACA, (+)-pinanediol ester N¹-[4-phenyl-2-(cyanomethyl)benzoyl]boroACA, (+)-pinanediol ester N¹-[4-phenyl-2-(diethylamino)benzoyl]boroACA, (+)-pinanediol ester N¹-[4-[2-(t-butylaminosulfonyl)phenyl]-2-methyl-benzoyl]boroACA, (+)pinanediol ester N¹-[4-[2-(aminosulfonyl)phenyl]-2-methyl-benzoyl]boroACA, (+)pinanediol ester N¹-[4-[2-(methoxycarbonylaminosulfonyl)phenyl]-2-methyl-benzoyl]boroACA, (+)-pinanediol ester N¹-[4-[2-(t-butylaminosulfonyl)phenyl]benzoyl]boroACA, (+)-pinanediol ester N¹-[4-[2-(t-butylaminosulfonyl)phenyl]benzoyl]
boroACA-OH N¹-[4-[2-(n-butoxycarbonylaminosulfonyl)phenyl]-2-
methyl-benzoyl]boroACA, (+)-pinanediol ester N¹-[4-[2-(diethylaminosulfonyl)phenyl]-2-methyl-
benzoyl]boroACA, (+)pinanediol ester N¹-[4-[2-(t-butylaminosulfonyl)phenyl]-2-fluoro-
benzoyl]boroACA, (+)pinanediol ester N¹-[4-[2-(aminosulfonyl)phenyl]-2-fluoro-benzoyl]
boroACA, (+)pinanediol ester N¹-[4-[2-(methoxycarbonylaminosulfonyl)Phenyl]-2-
fluoro-benzoyl]boroACA, (+)-pinanediol ester N¹-[4-[2-(t-butylaminosulfonyl)phenyl]-2-nitro-benzoyl]
boroACA, (+)pinanediol ester N¹-[4-[2-(aminosulfonyl)phenyl]-2-nitro-benzoyl]
boroACA, (+)pinanediol ester N¹-[4-[2-(methoxycarbonylaminosulfonyl)phenyl]-2-
nitro-benzoyl]boroACA, (+)-pinanediol ester N¹-[4-phenyl-2-nitrobenzoyl]boroLys, (+)-pinanediol
ester N¹-[4-phenyl-2-fluorobenzoyl]boroLys, (+)-pinanediol
ester N¹-[4-phenyl-2-aminobenzoyl]boroLys, (+)-pinanediol
ester N¹-[4-phenyl-2-(methylsulfonamido)benzoyl]boroLys,
(+)-pinanediol ester N¹-[4-phenyl-2-(cyanomethylamino)benzoyl]boroLys,
(+)-pinanediol ester N¹-[4-phenyl-2-(cyanomethyl)benzoyl]boroLys, (+)-
pinanediol ester N¹-[4-phenyl-2-(diethylamino)benzoyl]boroLys, (+)-
pinanediol ester N¹-[4-[2-(t-butylaminosulfonyl)phenyl]-2-methyl-
benzoyl]boroLys, (+)pinanediol ester N¹-[4-[2-(aminosulfonyl)phenyl]-2-methyl-benzoyl]
boroLys, (+)pinanediol ester N¹-[4-[2-(methoxycabonylaminosulfonyl)phenyl]-2-
methyl-benzoyl]boroLys, (+)-pinanediol ester N¹-[4-[2-(t-butylaminosulfonyl)phenyl]benzoyl]boroLys,
(+)-pinanediol ester N¹-[4-[2-(t-butylaminosulfonyl)phenyl]benzoyl]
boroLys—OH N¹-[4-[2-(n-butoxycarbonylaminosulfonyl)phenyl]-2-
methyl-benzoyl]boroLys, (+)-pinanediol ester N¹-[4-[2-(diethylaminosulfonyl)phenyl]-2-methyl-
benzoyl]boroLys, (+)pinanediol ester N¹-[4-[2-(t-butylaminosulfonyl)phenyl]-2-fluoro-
benzoyl]boroLys, (+)pinanediol ester N¹-[4-[2-(aminosulfonyl)phenyl]-2-fluoro-benzoyl]
boroLys, (+)pinanediol ester N¹-[4-[2-(methoxycarbonylaminosulfonyl)phenyl]-2-
fluoro-benzoyl]boroLys, (+)-pinanediol ester N¹-[4-[2-(t-butylaminosulfonyl)phenyl]-2-nitro-benzoyl]
boroLys, (+)pinanediol ester N¹-[4-[2-(aminosulfonyl)phenyl]-2-nitro-benzoyl]
boroLys, (+)pinanediol ester N¹-[4-[2-(methoxyaminosulfonyl)phenyl]-2-nitro-
benzoyl]boroLys, (+)-pinanediol ester.

DETAILED DESCRIPTION OF THE INVENTION

Throughout the specification, the following conventional three-letter abbreviations for amino acid residues or amino acids apply:

Ala=alanine
Arg=arginine
Asn=asparagine
Asp=aspartic acid
Cys=cysteine
Gln=glutamine
Glu=glutamic acid
Gly=glycine
His=histidine
Ile=isoleucine
Leu=leucine
Lys=lysine
Met=methionine
Phe=phenylalanine
Pro=proline
Ser=serine
Thr=threonine
Trp=tryptophan
Tyr=tyrosine
Val=valine
Irg=arginine where the guanidine is replaced with an isothiouronium (—SC(=NH)NH$_2$)
Arg(Me)=arginine with the guanidino group methylated
MPG=5-methoxy-propylglycine
ACA=3-(4-amino)cyclohexylalanine The prefix "boro" indicates amino acid residues where the carboxy group is replaced by a boronic acid (Formula I, Y¹ and Y²=—OH).

The pinanediol boronic acid ester and the pinacol boronic acid ester are abbreviated "-C$_{10}$H$_{16}$-" and -C$_6$H$_{12}$-" respectively. Other illustrations of diols useful for deriving a boronic acid orthoesters are 1,2-ethanediol, 1,3-propanediol, 1,2-propanediol, 2,3-butanediol, 1,2-diisopropylethanediol, 5,6-decanediol, 1,2-dicyclohexylethanediol.

The formamidino modified amino group is abbreviated (CH=NH). For example, the formamidino analog of -boroOrn—OH {—NH—CH[(CH$_2$)$_3$—NH—CH(NH)H]B(OH)$_2$} is -boroOrn(CH=NH)—OH. Analogs containing sidechain substituents are described by indicating the substituent in parenthesis following the name of the parent residue. For example the analog of boroPhenylalanine containing a meta cyano group is -boroPhe(mCN)-. N-alkyl substituents on the guanidino group of boroArg- or on the isothiouronium analogs (boroIrg) are also put in parenthesis in a similar manner.

Other abbreviations are: Z, benzyloxycarbonyl; BSA, benzene sulfonic acid; THF, tetrahydrofuran; Boc-, g-butoxycarbonyl-; Ac-, acetyl; pNA, p-nitro-aniline; DMAP, 4-N,N-dimethylaminopyridine; Tris, Tris (hydroxymethyl)aminomethane; MS, mass spectrometry; FAB/MS, fast atom bombardment mass spectrometry. LRMS(NH$_3$—Cl) and HRMS(NH$_3$—Cl) are low and high resolution mass spectrometry, respectively, using NH$_3$ as an ion source As used herein, the structure

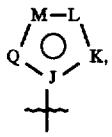

wherein J is N or C and K, L, M and Q are independently selected at each occurrence from the group consisting of N, CR¹³, S or O, provided that:

i) there may be only one S or O present in the ring at a time;

ii) there may only be 1–2N present when there is an O or S present;

iii) there may be only 1–4N present; is used as a substituent definition for $R^1$. This substituent may be exemplified by the following structures where —J—K—L—M—Q— is:

1) —N—C($R^{13}$)=C($R^{13}$)—C($R^{13}$)=C($R^{13}$)—,
2) —N—C($R^{13}$)=C($R^{13}$)—C($R^{13}$)=N—,
3) —N—C($R^{13}$)=C($R^{13}$)—N=C($R^{13}$)—,
4) —N—C($R^{13}$)=N—C($R^{13}$)=N—,
5) —N—C($R^{13}$)=C($R^{13}$)—N=N—
6) —N—C($R^{13}$)=N—N=N—,
7) —N—N=C($R^{13}$)—N=N—,
8) =C—O—C($R^{13}$)=N—C($R^{13}$)=,
9) —C=C($R^{13}$)—O—C($R^{13}$)=N—,
10) =C—O—C($R^{13}$)=C($R^{13}$)—N=,
11) —C=C($R^{13}$)—C($R^{13}$)=N—O—,
12) =C—C($R^{13}$)=C($R^{13}$)—O—N=,
13) —C=C($R^{13}$)—O—N=C($R^{13}$)—,
14) =C—S—C($R^{13}$)=N—C($R^{13}$)=,
15) —C=C($R^{13}$)—S—C($R^{13}$)=N—,
16) =C—S—C($R^{13}$)=C($R^{13}$)—N=,
17) —C=N—S—N=C($R^{13}$)—,
18) —C=N—S—C($R^{13}$)=N—,
19) =C—S—N=C($R^{13}$)—N=,
20) =C—S—C($R^{13}$)=C($R^{13}$)—C($R^{13}$)=,
21) —C=C($R^{13}$)—S—C($R^{13}$)=C($R^{13}$)—,
22) =C—O—C($R^{13}$)=C($R^{13}$)—C($R^{13}$)=, or
23) —C=C($R^{13}$)—O—C($R^{13}$)=C($R^{13}$)—.

As used herein, the structure

wherein in W, R, T, U and V are independently selected at each occurrence from the group consiting of: $CR^{13}$ or N, provided that there may be only 1–3N present, is used as a substituent definition for $R^1$. This substituent may be exemplified by the following structures where —C—W—R—T—U—V— is:

1) —C=N—C($R^{13}$)=C($R^{13}$)—C($R^{13}$)=C($R^{13}$)—,
2) —C=C($R^{13}$)—N=C($R^{13}$)—C($R^{13}$)=C($R^{13}$)—,
3) —C=C($R^{13}$)—C($R^{13}$)=N—C($R^{13}$)=C($R^{13}$)—,
4) —C=N—N=C($R^{13}$)—C($R^{13}$)=C($R^{13}$)—,
5) —C=C($R^{13}$)—N=N—C($R^{13}$)=C($R^{13}$)—,
6) —C=N—C($R^{13}$)=C($R^{13}$)—C($R^{13}$)=N—,
7) —C=N—C($R^{13}$)=C($R^{13}$)—N=C($R^{13}$)—,
8) —C=N—C($R^{13}$)=N—C($R^{13}$)=C($R^{13}$)—,
9) —C=C($R^{13}$)—N=C($R^{13}$)—N=C($R^{13}$)—,
10) —C=N—C($R^{13}$)=N—N=C($R^{13}$)—,
11) —C=N—C($R^{13}$)=C($R^{13}$)—N=N—, or
12) —C=C($R^{13}$)—N=C($R^{13}$)—N=N—.

"Amino acid residues" as used herein, refers to natural or unnatural amino acids of either D- or L-configuration. Natural amino acids residues are Ala, Arg, Asn, Asp, Aze, Cys, Gln, Glu, Gly, His, Ile, Irg Leu, Lys, Met, Orn, Phe, Phe(4-fluoro), Pro, Sar, Ser, Thr, Trp, Tyr, and Val. Roberts and Vellaccio, The Peptides, Vol 5; 341–449 (1983), Academic Press, New York, discloses numerous suitable unnatural amino acids and is incorporated herein by reference for that purpose.

"Amino acids residues" also refers to various amino acids where sidechain functional groups are coupled with appropriate protecting groups known to those skilled in the art. "The Peptides", Vol 3, 3–88 (1981) discloses numerous suitable protecting groups and is incorporated herein by reference for that purpose.

The reactions of the synthetic methods claimed herein are carried out in suitable solvents which may be readily selected by one of skill in the art of organic synthesis, said suitable solvents generally being any solvent which is substantially nonreactive with the starting materials (reactants), the intermediates, or products at the temperatures at which the reactions are carried out, i.e., temperatures which may range from the solvent's freezing temperature to the solvent's boiling temperature. A given reaction may be carried out in one solvent or a mixture of more than one solvent. Depending on the particular reaction step, suitable solvents for a particular reaction step may be selected.

The compounds herein described may have asymmetric centers. All chiral, diastereomeric, and racemic forms are included in the present invention. Many geometric isomers of olefins, C=N double bonds, and the like can also be present in the compounds described herein, and all such stable isomers are contemplated in the present invention. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. Also, it is realized that cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomer form is specifically indicated.

When any variable (for example, $R^1$ through $R^{20}$, $R^{20a}$, m, n, D, E, F, W, X, etc.) occurs more than one time in any constituent or in Formula (I), its definition on each occurrence is independent of its definition at every other occurrence. Thus, for example, if a group is shown to be substituted with 0–3 $R^{11}$, then said group may optionally be substituted with up to three $R^{11}$ and $R^{11}$ at each occurrence is selected independently from the defined list of possible $R^{11}$. Also, for example, in -N($R^{15}$)$_2$, each of the $R^{15}$ substituents may be independently selected from the list of possible $R^{20}$ groups defined. Also, combinations of substituents and/or variables are permissible only if such combinations result in stable compounds. Similarly, by way of example, for the group —C($R^{11}$)$_2$—, each of the two $R^{11}$ substituents on C is independently selected from the defined list of possible $R^{11}$.

As used herein, "alkyl" is intended to include both branched and straight-chain saturated aliphatic hydrocarbon groups having the specified number of carbon atoms; "haloalkyl" is intended to include both branched and straight-chain saturated aliphatic hydrocarbon groups having the specified number of carbon atoms, substituted with 1 or more halogen (for example -$C_vF_w$ where v=1 to 3 and w=1 to (2v+1)); "alkoxy" represents an alkyl group of indicated number of carbon atoms attached through an oxygen bridge; "cycloalkyl" is intended to include saturated ring groups, including mono-,bi- or poly-cyclic ring systems, such as cyclopropyl, cyclobutyl, cyclopentyl, cyclohexyl, cycloheptyl, adamantyl and cyclooctyl; and "bicyloalkyl" is intended to include saturated bicyclic ring groups such as [3.3.0]bicyclooctane, [4.3.0]bicyclononane,

[4.4.0]bicyclodecane (decalin), [2.2.2]bicyclooctane, and so forth. "Alkenyl" is intended to include hydrocarbon chains of either a straight or branched configuration and one or more unsaturated carbon—carbon bonds which may occur in any stable point along the chain, such as ethenyl, propenyl, and the like; and "alkynyl" is intended to include hydrocarbon chains of either a straight or branched configuration and one or more triple carbon-carbon bonds which may occur in any stable point along the chain, such as ethynyl, propynyl and the like.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "aryl" or "aromatic residue" is intended to mean phenyl or naphthyl; the term "arylalkyl" represents an aryl group attached through an alkyl bridge. By way of examples: the term "$C_7$–$C_{10}$ arylalkyl" is intended to refer to an aryl group attached through a $C_1$–$C_4$ alkyl bridge to the residue of the indicated compound; the term "($C_1$–$C_3$ alkyl) aryl" is intended to refer to a $C_1$–$C_3$ alkyl group which is attached through an aryl ring to the residue of the indicated compound; the term "aryl($C_1$–$C_3$ alkyl)" is intended to refer to an aryl group attached through a $C_1$–$C_3$ alkyl group to the residue of the indicated compound.

As used herein, "carbocycle" or "carbocyclic residue" is intended to mean any stable 3- to 8-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" is intended to mean a stable 5- to 7-membered monocyclic or bicyclic or 7- to 10-membered bicyclic heterocyclic ring which is saturated and consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The term "heteroaryl" is intended to mean an aromatic form of a heterocyclic ring. Unless otherwise specified, the heterocyclic and heteroaryl rings described herein may be substituted on carbon or on a nitrogen atom if the resulting compound is stable. Unless otherwise specified, examples of such heterocycles include, but are not limited to, pyridinyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H, 6H-1,5,2-dithiazinyl, thiophenyl, thianthrenyl, pyranyl, isobenzofuranyl, chromenyl, xanthenyl, phenoxathiinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, or isatinoyl. Also included are fused ring and spiro compounds containing, for example, the above heterocycles.

When a bond to a substituent is shown to cross the bond connecting two atoms in a ring, then such substituent may be bonded to any atom on the ring. When a substituent is listed without indicating the atom via which such substituent is bonded to the rest of the compound of formula I, then such substituent may be bonded via any atom in such substituent. For example, when the substituent is piperazinyl, piperidinyl, or tetrazolyl, unless specified otherwise, said piperazinyl, piperidinyl, tetrazolyl group may be bonded to the rest of the compound of formula (I) via any atom in such piperazinyl, piperidinyl, tetrazolyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that an one or more hydrogen on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

As used herein, the term "any group that, when administered to a mammalian subject, cleaves to form a free hydroxyl, amino or sulfhydryl" means any group bonded to an O, N, or S atom, respectively, which is cleaved from the O, N, or S atom when the compound is administered to a mammalian subject to provide a compound having a remaining free hydroxyl, amino, or sulfhydryl group, respectively. Examples of groups that, when administered to a mammalian subject, are cleaved to form a free hydroxyl, amino or sulfhydryl, include but are not limited to, phosphate esters, $C_1$–$C_6$ alkyl substituted with 0–3 $R^{11}$, $C_3$–$C_6$ alkoxyalkyl substituted with 0–3 $R^{11}$, $C_1$–$C_6$ alkylcarbonyl substituted with 0–3 $R^{11}$, $C_1$–$C_6$ alkoxycarbonyl substituted with 0–3 $R^{11}$, $C_1$–$C_6$ alkylaminocarbonyl substituted with 0–3 $R^{11}$, benzoyl substituted with 0–3 $R^{12}$, phenoxycarbonyl substituted with 0–3 $R^{12}$, phenylaminocarbonyl substituted with 0–3 $R^{12}$, or heteroarylcarbonyl. Examples of groups that, when administered to a mammalian subject, are cleaved to form a free hydroxyl, amino or sulfhydryl, may include hydroxy, amine or sulfhydryl protecting groups, respectively.

As used herein, the term "amine protecting group" means any group known in the art of organic synthesis for the protection of amine groups. Such amine protecting groups include those listed in Greene and Wuts, "Protective Groups in Organic Synthesis" John Wiley & Sons, New York (1991) and "The Peptides: Analysis, Synthesis, Biology, Vol. 3, Academic Press, New York (1981), the disclosure of which is hereby incorporated by reference. Any amine protecting group known in the art can be used. Examples of amine protecting groups include, but are not limited to, the following: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1- methylethoxycarbonyl, and 9-fluorenylmethoxycarbonyl (Fmoc); 3) aliphatic carbamate types such as tertbutyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl.

The term "amino acid" as used herein means an organic compound containing both a basic amino group and an acidic carboxyl group. Included within this term are natural amino acids, modified and unusual amino acids, as well as amino acids which are known to occur biologically in free or combined form but usually do not occur in proteins. Included within this term are modified and unusual amino acids, such as those disclosed in, for example, Roberts and Vellaccio (1983) The Peptides, 5: 342–429, the teaching of which is hereby incorporated by reference. Modified or unusual amino acids which can be used to practice the invention include, but are not limited to, D-amino acids, hydroxylysine, 4-hydroxyproline, an N—Cbz-protected amino acid, ornithine, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The term "peptide" as used herein means a compound that consists of two or more amino acids (as defined herein) that are linked by means of a peptide bond. The term "peptide" also includes compounds containing both peptide and non-peptide components, such as pseudopeptide or peptide mimetic residues or other non-amino acid components. Such a compound containing both peptide and non-peptide components may also be referred to as a "peptide analog".

The term "peptide bond" means a covalent amide linkage formed by loss of a molecule of water between the carboxyl group of one amino acid and the amino group of a second amino acid.

As used herein, "pharmaceutically acceptable salts" refer to derivatives of the disclosed compounds wherein the parent compound of formula (I) is modified by making acid or base salts of the compound of formula (I). Examples of pharmaceutically acceptable salts include, but are not limited to, mineral or organic acid salts of basic residues such as amines; alkali or organic salts of acidic residues such as carboxylic acids; and the like.

"Prodrugs" are considered to be any covalently bonded carriers which release the active parent drug according to formula (I) in vivo when such prodrug is administered to a mammalian subject. Prodrugs of the compounds of formula (I) are prepared by modifying functional groups present in the compounds in such a way that the modifications are cleaved, either in routine manipulation or in vivo, to the parent compounds. Prodrugs include compounds of formula (I) wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate, or benzoate derivatives of alcohol and amine functional groups in the compounds of formula (I); phosphate esters, dimethylglycine esters, aminoalkylbenzyl esters, aminoalkyl esters and carboxyalkyl esters of alcohol and phenol functional groups in the compounds of formula (I); and the like.

The pharmaceutically acceptable salts of the compounds of formula (I) include the conventional non-toxic salts or the quaternary ammonium salts of the compounds of formula (I) formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of formula (I) which contain a basic or acidic moiety by conventional chemical methods. Generally, such salts can be prepared by reacting the free acid or base form of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in water or in an organic nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

The disclosures of all of the references cited herein are hereby incorporated herein by reference in their entirety.

SYNTHESIS

The compounds of formula (I) can be prepared using the reactions and techniques described below. The reactions are performed in a solvent appropriate to the reagents and materials employed and suitable for the transformations being affected. It will be understood by those skilled in the art of organic synthesis that the functionality present on the molecule should be consistent with the chemical transformations proposed and this will sometimes require judgment as to the order of synthetic steps or selection of particular process scheme used from that shown below in order to obtain a desired compound of the invention.

Scheme 1
Synthesis of Thrombin Inhibitors

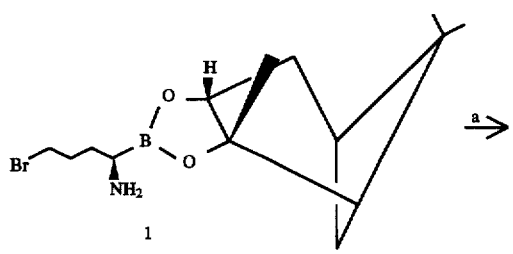

-continued
Scheme 1
Synthesis of Thrombin Inhibitors

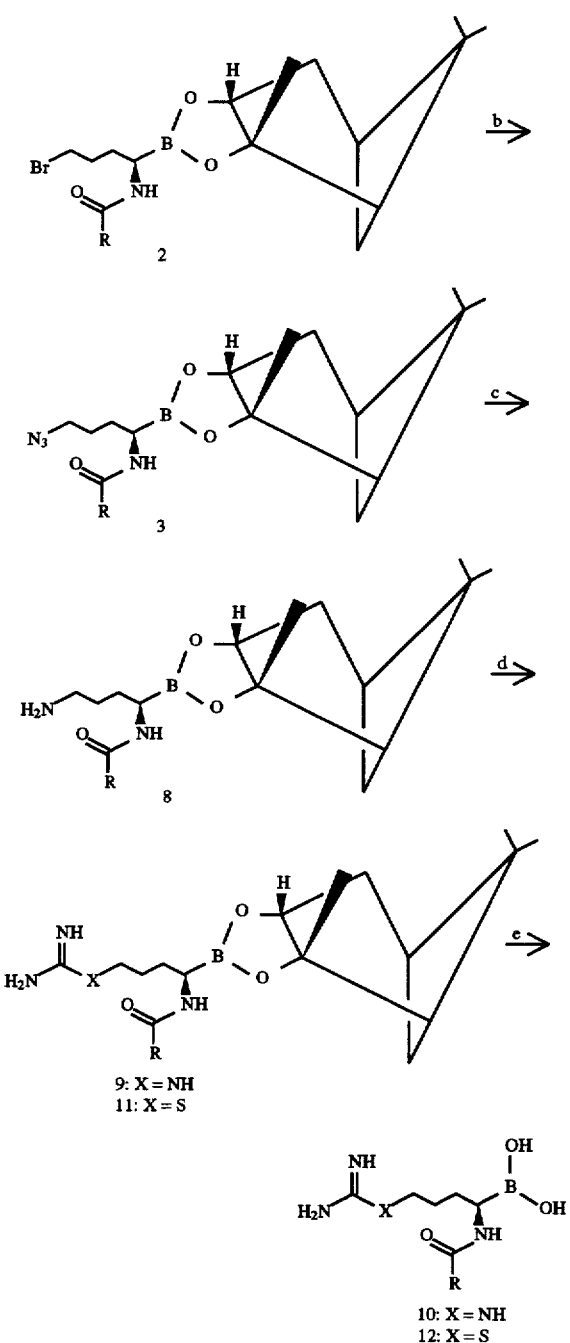

9: X = NH
11: X = S

10: X = NH
12: X = S

Reagents: a. IBCF, NMM, RCO₂H, Et₃N, 0° C.,
b. NaN₃, c. H₂, Pd(OH)₂/C, HCl,
d. DMAP, aminoiminomethanesulfonic acid,
e. phenylboronic acid Amine hydrochloride 1 is readily available via the procedure of Kettner and Shenvi (EP 0293881 A2).

There are numerous synthetic methods by which to prepare amide 2, however, competing with amide formation is the cyclization of 1 to afford a complex mixture containing the desired amide and the corresponding N-acylboroproline. Since purification at this stage is unfeasible, choosing the correct method for amide formation is crucial to obtaining 2 in a purity suitable for subsequent synthetic transformations.

Three methods are preferred for the preparation of 2. In the first, a solution of 1 in tetrahydrofuran or dichloromethane at 0° C. is treated sequentially with the desired acid chloride followed by two equivalents of triethylamine. The mixture is then allowed to warm to room temperature overnight. The second method is the mixed anhydride procedure of Anderson, et. al. (*J. Am Chem. Soc.* 1967, 89, 5012). In this method the isobutyl mixed anhydride is generated by dissolving the carboxylic acid component in tetrahydrofuran and adding one equivalent of N-methylmorpholine. The solution is cooled to 0° C. and one equivalent of isobutyl chloroformate is added. After 5 minutes, a solution of 1 in chloroform is added, followed by the addition of one equivalent of triethylamine. The mixture is typically stirred at 0° C. for one hour followed by one to several hours at room temperature. The third method for amide formation is the hydroxybenzotriazole/DCC method of König and Geiger (*Chem. Ber.* 1970, 103, 788–98). Thus, to a solution of 1 and the carboxylic acid component in dimethylformamide or tetrahydrofuran at 0° C. is added N-methylmorpholine, 1-hydroxybenzotriazole hydrate (2 eq) and DCC (1.05 eq). The solution is allowed to warm to room temperature overnight.

The preferred method for the preparation of azide 3 is by reaction of 2 with sodium azide (1.1 eq) in dimethylformamide at 70° C. for 2 hours.

The azide displacement may also be performed prior to amide formation. This is the preferred method in cases where the rate of amide formation is slow relative to the rate of cyclization. Azide 4 is prepared by a modification of the procedure of Kettner and Shenvi (EP 0293881 A2) as shown in Scheme 2. Thus, bromide 5 is reacted with sodium azide, followed by homologation to give 6, chloride displacement to afford 7 and acidic hydrolysis to give 4. Amide formation between 4 and the carboxylic acid component then affords 3 directly.

Scheme 2
Synthesis of Azide 4

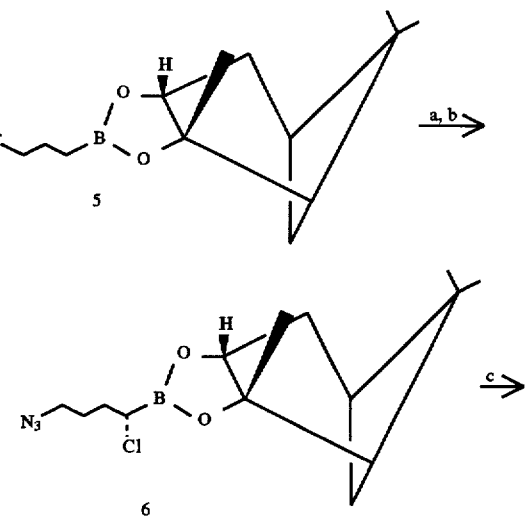

45

-continued
Scheme 2
Synthesis of Azide 4

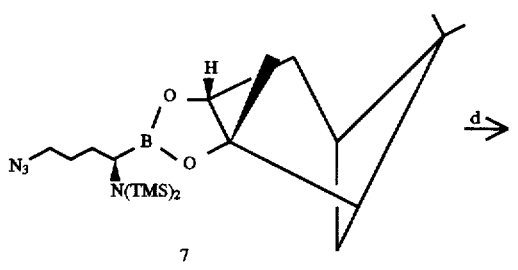

4

Reagents: a. NaN₃ b. CHCl₂Li, ZnCl₂,
c. LiN(TMS)₂, d. 4M HCl, dioxane

Reduction of azide 3 to amine 8 may be accomplished by hydrogenation over precious metal catalysts. The preferred catalyst for this transformation is Pearlman's catalyst (palladium hydroxide on carbon). The amine is typically isolated as the hydrochloride salt. Isolation of 8 as the free base typically results in lowered yields. Salts of 8 which may confer superior physical properties may be preferred over the hydrochloride salt.

Formamidination of amine 8 may be accomplished using cyanamide. Due to the low reactivity of amine 8, however, the preferred method for this transformation is reaction with 4-dimethylamin-opyridine (DMAP) and aminoiminomethanesulfonic acid (AMSA, prepared by the method of Kim, et. al., *Tetrahedron Lett.* 1988, 29, 3183–6). This affords guanidine 9, which is isolated as the bisulfite or hydrochloride salt.

Cleavage of pinanediol ester 9 may be accomplished using anhydrous boron trichloride according to the procedure of Matteson and Ray (*J. Am. Chem. Soc.* 1980, 102, 7588). This method, however, is strongly Lewis acidic and leads to partial destruction of the substrate. The preferred method for water soluble boronic acids is a transesterification reaction that is run in the presence of excess phenylboronic acid. The free boronic acid 10 may then be isolated using cation exchange chromatography.

The isothiouronium functionalized analogs 11/12 are prepared from bromide 2 according to the procedure of Kettner and Shenvi (EP 0293881 A2).

Inhibitors containing a sulfonamide in place of a carboxamide are prepared from either 1 or 4 by reaction with a sulfonyl chloride in the presence of a hindered amine (Scheme 3). The product sulfonamide 13 is then converted to the guanidinium 14 or isothiouronium 15 in the same manner as the corresponding carboxamides.

Scheme 3
Synthesis of Sulfonamides

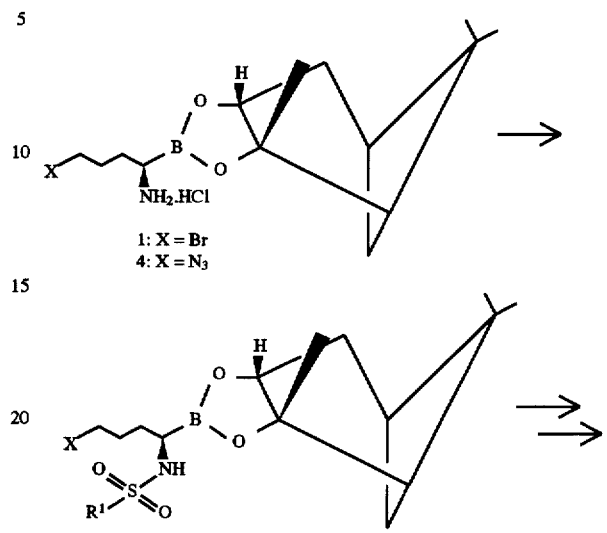

1: X = Br
4: X = N₃

13

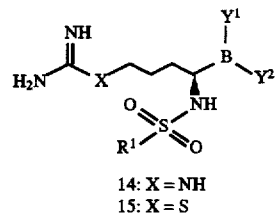

14: X = NH
15: X = S

Inhibitors containing the borolysine moiety are prepared analogously to those containing boroarginine according to Kettner and Shenvi (EP 0293881 A2).

Novel biaryls synthesized in this invention are prepared through palladium catalyzed coupling of an appropriate arylmetal species to the aryl halide of choice using the methods described in Negishi, et. al., *Org. Synth.* 1987, 66, 67–74, and references cited within.

Synthetic approaches toward construction of pyrroles are numerous: R. J. Sundberg in "Comprehensive Heterocyclic Chemistry", A. R. Katritzky (Ed.), Pergamon Press, New York (1984), Vol. 4, p. 705; *Synthesis*, 1946, 281. The following discussion is restricted to the most common and reliable methods towards the synthesis of pyrroles within the general scope of the invention.

Compounds where R¹ is a pyrrole can be synthesized as shown on Scheme 4.

Scheme 4

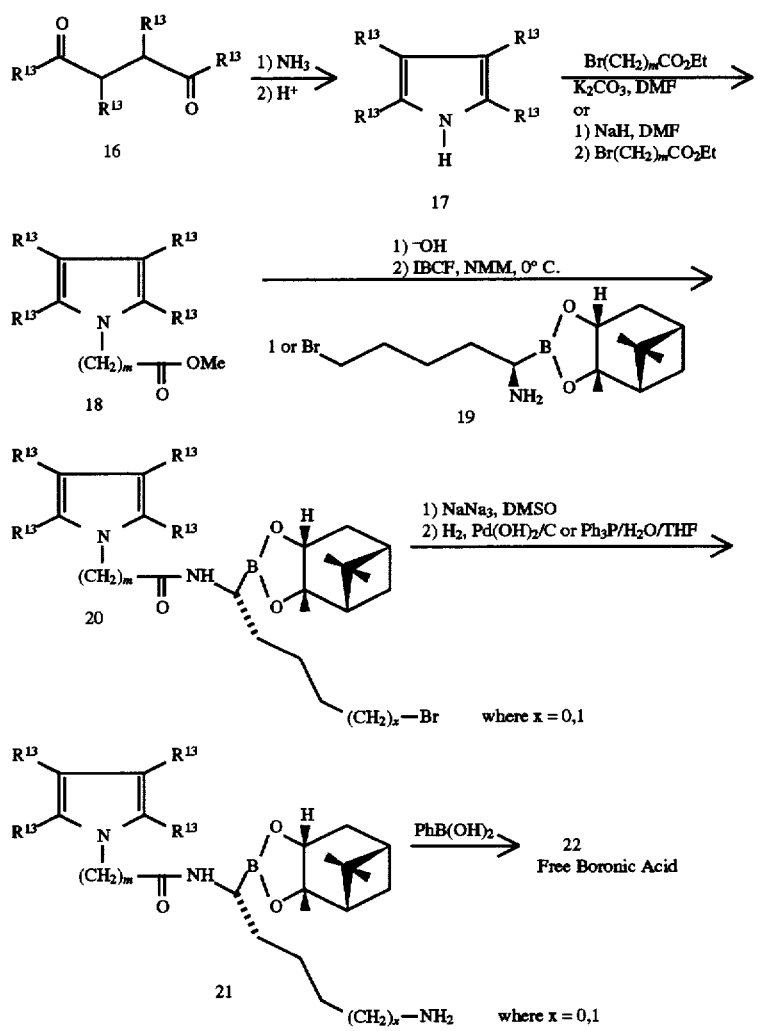

Starting material diketone 16 may or may not have its substituents $R^{13-16}$ in final form as defined in the scope. These substituents might be in protected forms or in the form of suitable precursors which make the heterocyclic portion, for example, amenable to synthesis. These precursor forms can then be converted to their final forms later on in the synthesis using procedures familiar to one skilled in the art.

The cyclization condensation of 1,4-dicarbonyl compounds with ammonia, primary amines or related compounds, the Paal-Knorr reaction, is one of the most general and widely applicable pyrrole syntheses, R. A. Jones and G. P. Bean, "The Chemistry of Pyrroles", Academic Press, London, 1977; p. 77–81. The generality of this approach is primarily determined by the availability of the dicarbonyl precursors, 16, as illustrated by Scheme 4. By heating such diketones with ammonia or amines in a solvent like benzene, toluene or methylene chloride with a catalyst such as sulfuric acid, acetic acid, p-toluenesulfonic acid, alumina or even titanium tetrachloride, pyrroles like 17 may be prepared.

Subsequent alkylation of pyrrole 17 with a bromoester, for example, leads to the alkylated heterocycle 18. Alkylation conditions include either first deprotonating with NaH or KH in DMF followed by addition of the alkylating agent or simply stirring the heterocycle with the alkylaning agent in an inert solvent such as DMF or DMSO at 0° C. to 100° C. in the presence of an acid scavenger such as $K_2CO_3$.

Saponification of ester 18 followed by coupling aminoboronic ester 1 or 19 as discussed previously yields compound 20. This bromide may be either elaborated to the lysine side-chain 21 (X=1) or if X=0, into the corresponding ornithine side-chain or any other side-chain discussed previously. Subsequent hydrolysis of the boronic ester yields the boronic acid as discussed previously too.

The cyclization of diynes 23 with amines has been reported and an adaptation of this method is shown in Scheme 5 (K. E. Schulte et al., Chem. Ber (1965) 98; A. J. Chalk Tet. Lett. $(1972)_{3487}$). The diynes are made via transition metal catalyzed coupling of alkynes, i.e., the Cadio-Chodkiewicz reaction (W. Chodkiewicz Ann. Chim. (Paris) (1957)2 81g).

Scheme 5

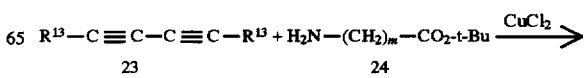

Scheme 5

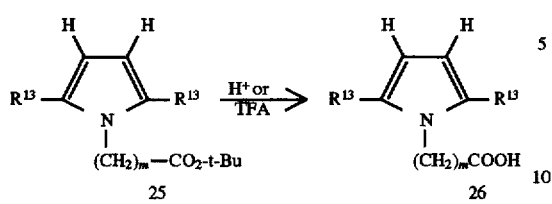

Scheme 6

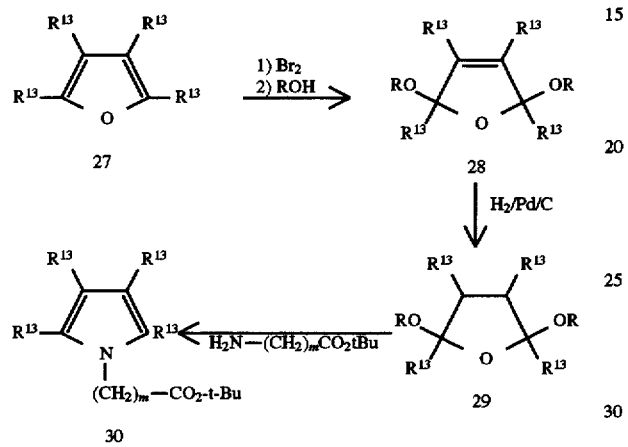

Furans (27) have been converted directly to pyrroles by treatment with amines but the harsh conditions required (400° C./Al$_2$O$_3$) precludes its generality. 2,5-Dialkoxytetrahydrofurans (29) have been more commonly employed as furan (or 1,4-dicarbonyl) equivalents and react readily with aliphatic or aromatic amines (and even weakly nucleophilic sulfonamides) to give pyrroles as shown in Scheme 6, J. W. F. Wasley and K. Chan, *Synth. Commun.* 3, 303 (1973). Although commercially available 2,5-dialkoxytetrahydrofurans (29) (R$^1$=R$^2$=H))generally restrict one to preparing 1-substituted pyrroles, more highly substituted systems may be obtained by a three-step alcoholysis of the appropriate furans (27) to the more highly substituted 2,5-dialkoxytetrahydrofurans (29) as shown in Scheme 6, N. L. Weinberg and H. R. Weinberg, *Chem. Rev.*, 68, 449 (1968); N. Elming, *Adv. Org. chem.*, 2, 67 (1960).

The Hantzsch synthesis utilizes the condensation of β-haloketones (30a) and β-ketoesters (31) in the presence of ammonia or a primary amine to give pyrroles such as (32), as shown in Scheme 7, A. Hantzsch, *Chem. Ber.*, 23, 1474 (1980); D. C. von Beelen, J. Walters, and S. von der Gen, *Rec Trav. Chem.* 98, 437 (1979). Among the numerous modifications reported over the years, the substitution of (30a) with the readily available α-hydroxyaldehydes or nitroalkenes has expanded the versatility and generality of this important method, D. M. McKinnon, *Can. J. Chem.* 43, 2628 (1965); H. George and H. J. Roth, *Arch. Pharm.* 307, 699 (1974); C. A. Grok and K. Camenisch, *Helv. Chem. Acta*, 36, 49 (1953).

Scheme 7

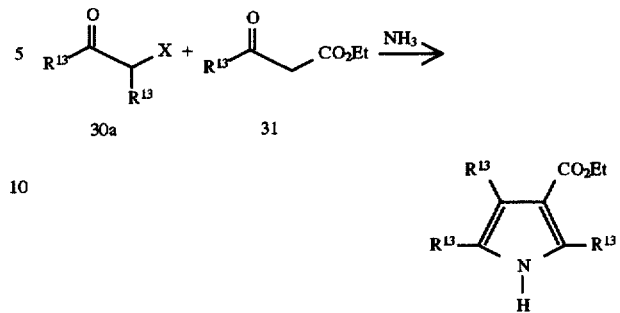

Scheme 8

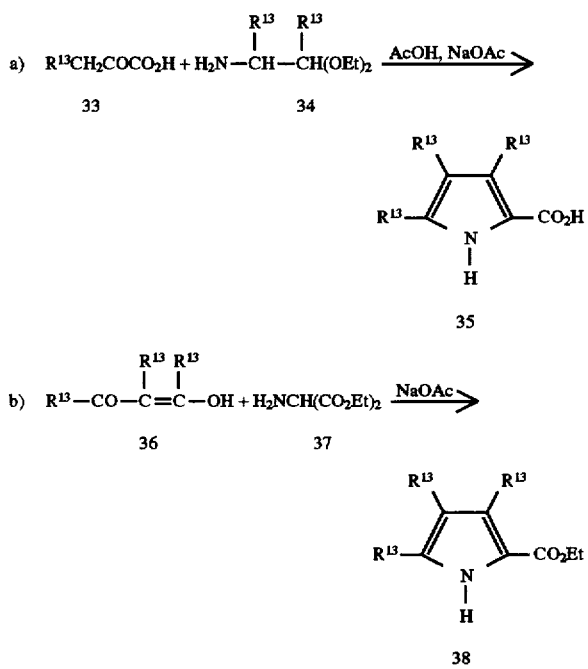

The closely related Knorr condensation involves the reaction between amino carbonyl compounds (or their precursors) and carbonyl (or dicarbonyl) compounds, J. M. Patterson, *Synthesis*, 282 (1976). Representative methods for preparing substituted pyrroles (35 and 38) are shown by Scheme 8, equations a) and b), S. Umio et al., Jap. Pat. 7018653, Fujisawa Pharmaceutical Co., Ltd., 1970 (*C.A.* 73, 77039, 1970); K. Tanaka, K. Kariyone, S. Umio, *Chem. Phram. Bull (Tokyo)*), 17, 611 (1969).

The elaboration of an appropriately functionalized pyrrole is another method for preparing pyrroles of general formula I. Methyl (or ethyl) 5-formyl-1H-pyrrole-2-carboxylate (43) is a particularly useful intermediate with regards to pyrroles claimed in this invention and has been prepared by a number of methods as shown by Scheme 9, eq. a, W. A. Davies, A. R. Pinder and I. G. Morris, *Tetrahedron* 18, 405 (1962); *Org Syn.*, vol 36, p. 74; *Org. Syn.*, vol. 51.

More recently, Ullrich has extended the Vilsmeyer-Haack formylation of pyrroles to include vinylogous systems such as (46) by using the 3-(N,N-dimethylformamide derivative, as shown by Scheme 9, eq. b, F. W. Ullrich and E.

Breitmaier, *Synthesis*, 641 (1983); W. Heinz, et al., *Tetrahedron*, 42, 3753 (1986).

An especially attractive approach to pyrroles claimed in this invention has recently been reported, whereby lithiation of the 6-dimethylamino-1-azafulvene dimer (49) followed by treatment with an appropriate electrophile and subsequent hydrolysis leads to 5-substituted pyrrole-2-carboxaldehydes (51), as illustrated in Scheme 10, J. M. Muchowski and P. Hess, *Tetrahedron Lett*, 29, 777 (1988). The carboxylic acid, ester and aldehyde side-chains depicted in Schemes 9–10 can be readily converted to $R^{13-16}$ by methods familiar to one skilled in the art.

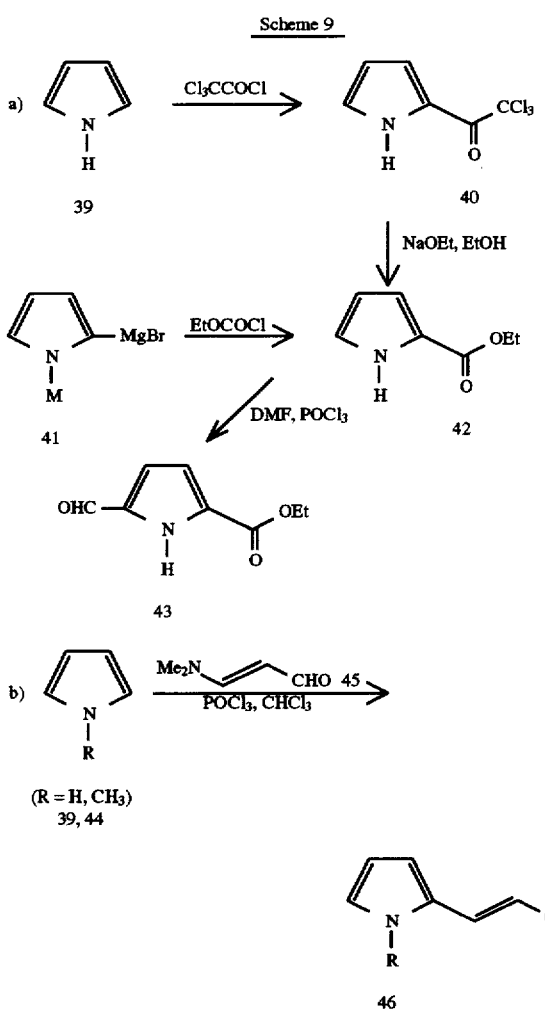

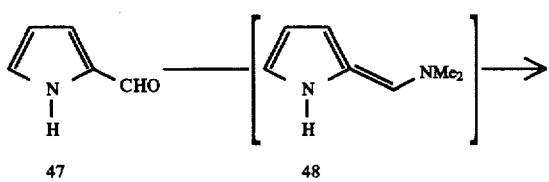

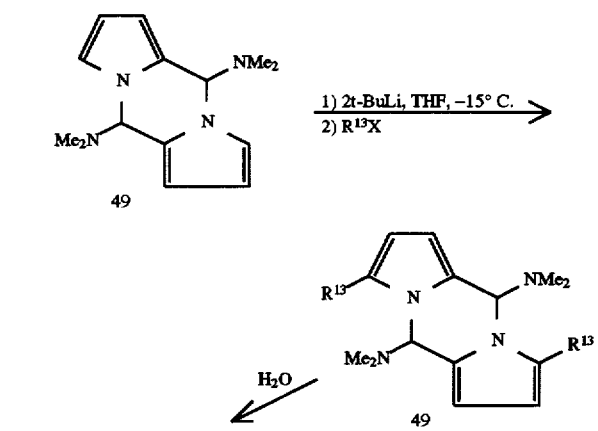

A general and versatile approach to pyrazoles ($R^1$ = pyrazole) involves condensation of a 1,3-difunctional compound (usually dicarbonyl) with hydrazine or its derivatives, as shown in Scheme 11 for pyrazoles of the formula 53 and reviewed by G. Corspeau and J. Elguerv, *Bull. Soc. Chim. Fr.*, 2717 (1970). Rarely have pyrazoles have been prepared in which the N—N bond is the last step of the ring closure, J. Elguerv in *Comprehensive Heterocyclic Chemistry*, S. R. Katritzky (Ed.) Pergamon Press, New York, Vol. 5 (1984), p. 274; J. Barluenga, *J. Chem. Soc, Perkin Trans.1*, 2275 (1983).

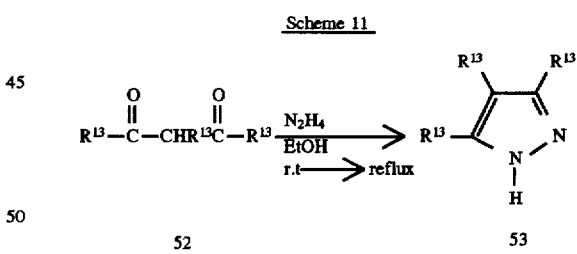

The condensation of 1,3-dicarbonyl compounds with hydrazine hydrate derivatives is generally carried out by admixture of the two components in a suitable solvent like a lower alcohol, ether, or THF at 0° C. to the reflux temperature for 1–18 hours.

The synthesis of 1,3-dicarbonyl compounds has received considerable attention in the literature and most of the major approaches towards 1,3-diketones 52 of interest in this invention are illustrated by Scheme 12.

Scheme 12

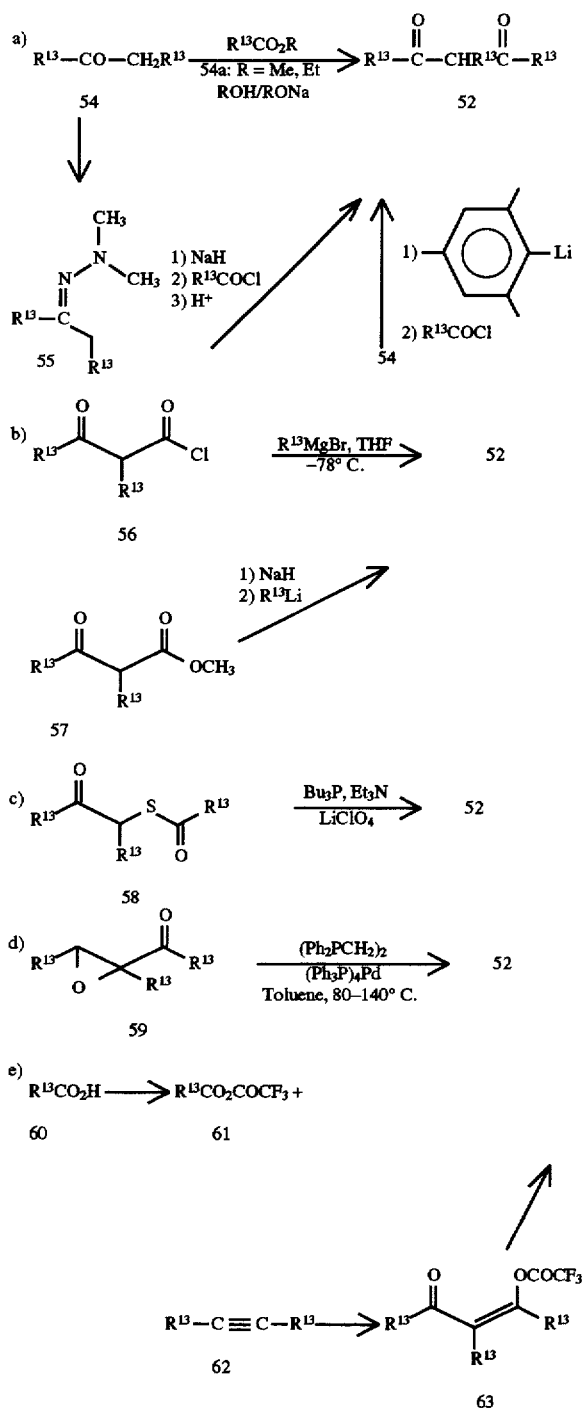

Esters 54a can be reacted with ketones 54 using bases like sodium ethoxide, sodium hydride or sodium amide in a suitable solvent like alcohol, DMF, DMSO or benzene at 0° C. to reflux for 4–18 hours with 30–70% efficiency, J. M. Sprague, Lo J. Beckham and H. Adkins, *J. Amer. Chem. Soc.*, 56, 2665 (1934). Metallation of hydrazines 55 with n-BuLi followed by reaction with carboxylic acid chlorides and subsequent hydrolysis affords 52, D. Enders and P. Wenster, *Tetrahedron Lett.*, 2853 (1978). Metallation of 54 with the non-nucleophilic mesityl lithium followed by acylation also affords 52, A. K. Beck, M. S. Hoelstein and D. Seebach, *Tetrahedron Lett.*, 1187 (1977); D. Seebach, *Tetrahedron Lett.*, 4839; (1976).

As shown in Scheme 12, equation b, the addition of Grignard reagents to β-keto carboxylic acid chlorides may be limited to monoaddition at low temperatures to provide 52, C. D. Hurd and G. D. Kelso, *J. Amer. Amer. Soc.* 62, 1548 (1940); F .Sato, M. Trone. K. Oyuro, and M. Sato, *Tetrahedron Lett.* 4303 (1979). Lithium dialkyl copper reagents ($R^2$ CuLi) have also been used, Luong-Thi and Riviero, *J. Organomet. Chem.* 77, C52 (1974). Analogously, addition of alkyllithium reagents ($R^{15}$Li) to the monoanions of β-keto esters 57 also give rise to 1,3-diketones, S. N. Huckin and L. Weiler, *Can. J. Chem.* 52, 1379 (1974).

Eschenmoser has demonstrated a synthesis of β-diketones through a sulfur extrusion reaction of keto thioesters 58 with tributylphosphine, triethylamine and lithium perchlorate, S. Eshenmoser, *Helv. Chim. Acta.*, 54, 710 (1971).

The rearrangement of α,β-epoxy ketones 59 to β-diketones 52 catalyzed by Pd° has been reported, R. Noyori, *J. Amer. Chem. Soc.* 102, 2095 (1980).

Mixed anhydrides such as 61, available from carboxylic acids 60 and trifluoroacetic anhydride, have been shown to acylate alkynes 62 to produce the enol trifluoroacetate of a β-diketone 63. Transesterification by refluxing with methanol liberates the β-diketone 52, A. L. Henne and J. M. Tedder, *J. Chem. Soc.* 3628 (1953).

Scheme 13

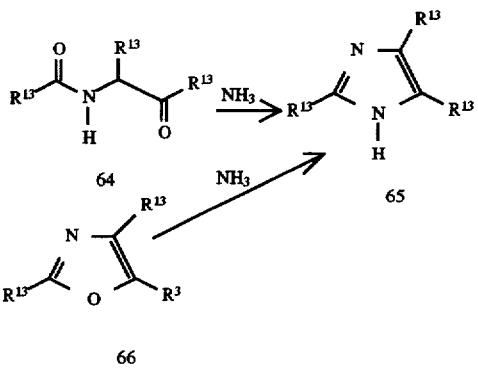

Scheme 14 a)

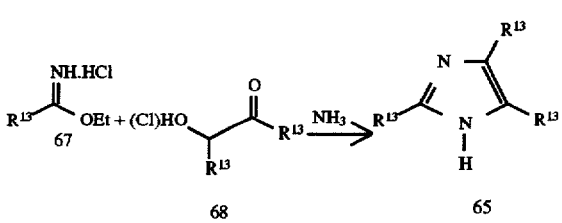

-continued
Scheme 14 b)
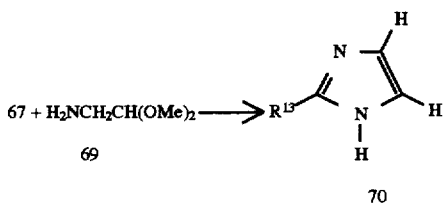

c)
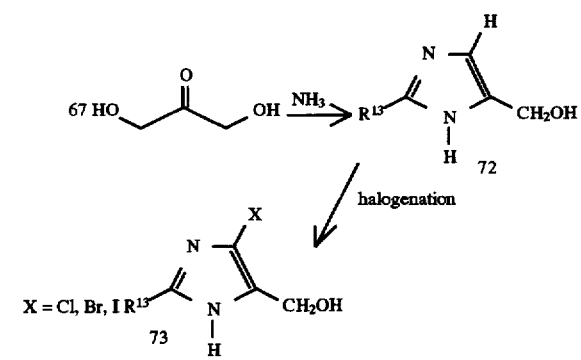

d)
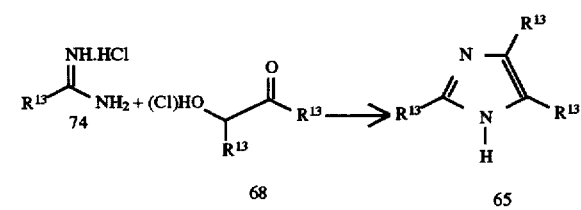

e)
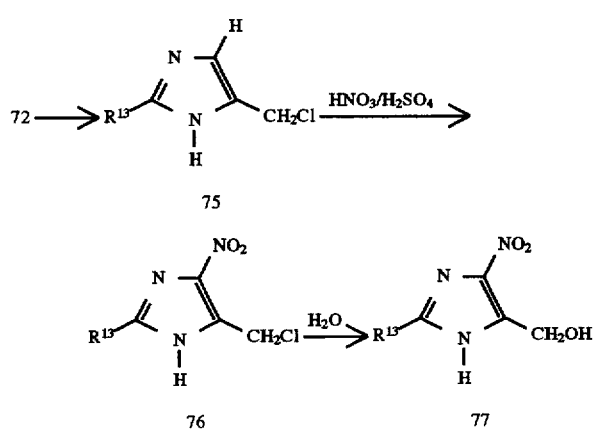

f)
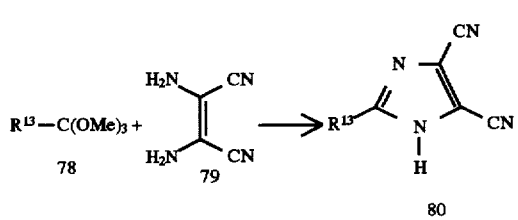

-continued
Scheme 14 g)
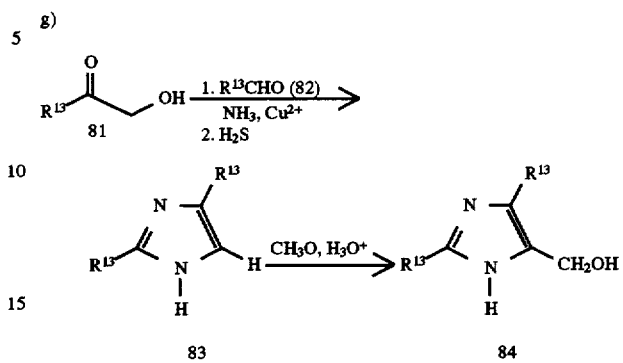

Compounds where R¹= imidazole, such as 65, are readily available by any of a number of standard methods. For example, acylaminoketone 64 can be cyclized with ammonia or equivalents thereof, D. Davidson, et al., *J. Org. Chem.*, 2, 319 (1937) to the to corresponding imidazole as shown in Scheme 13. The corresponding oxazole 66 can also be converted to imidazole 65 by action of ammonia or amines in general, H. Bredereck, et. al., Ber., 88, 1351 (1955); J. W. Cornforth and R. H. Cornforth, *J. Chem. Soc.*, 96, (1947).

Several alternative routes to imidazoles 65 are illustrated in Scheme 14. As shown in Scheme 14 equation a), reaction of the appropriate $R^{13}$ substituted imidate esters 67 with an appropriately substituted α-hydroxy- or α-haloketone or aldehyde 68 in ammonia leads to imidazoles of formula 65, P. Dziuron, and W. Schunack, *Archive, Pharmaz.*, 307 and 470 (1974).

The starting imidazole compounds 65 wherein $R^{13}$ is hydrogen can be prepared as shown in equation b) by reaction of the appropriate $R^{13}$-substituted imidate ester 67 with α-aminoacetaldehyde dimethyl acetal, M. R. Grimmett, *Adv. Heterocyclic Chem.*, 12, 103 (1970).

As shown in equation c), imidazole 72 (wherein $R^{13}$= hydrogen and $CH_2OH$) can be prepared by treatment of the imidate ester 67 with 1,3-dihydroxyacetone 71 in ammonia by the procedure described in *Archive der Pharmazie*, 307, 470 (1974). Halogenation of imidazole 72 or any imidazole wherein $R^{13}$ is hydrogen is preferably accomplished by reaction with one to two equivalents of N-halosuccinimide in a polar solvent such as dioxane or 2-methoxyethanol at a temperature of 40°–100° C. for 1–10 hours.

Compounds of formula 73 can also be prepared from 70 by reaction with formaldehyde as described in E. F. Godefroi, et al., *Recueil*, 91, 1383 (1972) followed by halogenation as was described above.

As shown in equation d) the imidazoles 65 can also be prepared by reaction of $R^{13}$ substituted amidines 74 with an α-hydroxy- or α-haloketone or aldehyde 68 as described by F. Kunckel, *Ber.*, 34, 637, (1901).

As shown in equation e), preparation of the nitroimidazoles (65, $R^{13}=NO_2$) is preferably accomplished by heating the appropriate starting imidazole in a 3:1 mixture of conc. sulfuric acid/conc. nitric acid at 60°–100° C. for 1–6 hours. Nitration of the imidazole can be achieved by first converting the hydroxmethylimidazole to the corresponding chloromethylimidazole 75 employing thionyl chloride or oxalyl chloride. Nitration, as described above, followed by hydrolysis provides the nitroimidazoles 77.

Imidazoles 80 where $R^{13}$=CN can be prepared as shown in equation f) by reaction of $R^{13}$ substituted ortho esters, ortho acids or aldehydes (followed by oxidation of the aldehyde) with diaminomaleonitrile 79 by the procedure described by R. W. Begland et al., *J. Org. Chem.*, 39, 2341 (1974). Likewise, $R^{13}$ substituted imidate esters 67 also react with diaminomaleonitrile to give 4,5-dicyanoimidazoles 80. The nitrile groups can be further elaborated into other functional groups by methods familiar to one skilled in the art.

Compounds wherein $R^{13}$=alkyl of 1–6 (straight or branched), phenyl, phenalkyl where alkyl is 1–3 carbon atoms, etc. and another $R^{13}$=CH$_2$OH can be prepared as shown in equation g). The imidazoles 83 were prepared as described in L A. Reiter, *J. Org. Chem.*, 52, 2714 (1987), Hydroxymethylation of 83 as described by U. Kempe, et al. in U.S. Pat. No. 4,278,801 provides the hydroxymethylimidazoles 84.

The CH$_2$OH group, as in imidazolemethanol 72, is a versatile synthon for other functional groups. Scheme 15 shows some of these transformations, all of which are familiar to one skilled in the art.

A suitably protected imidazole 85 may undergo selective halogen-metal exchange followed by quenching 5 with electrophiles to yield trisubstituted imidazoles (Scheme 16) (M. Groziak and L. Wei *J. Org. Chem.* (1992) 57, 3776). This strategy can be used to add several $R^{13}$ groups onto the imidazole ring. By changing the order in which the electrophiles are added, one may change the position to which the electrophile gets attached onto the imidazole ring.

Scheme 15

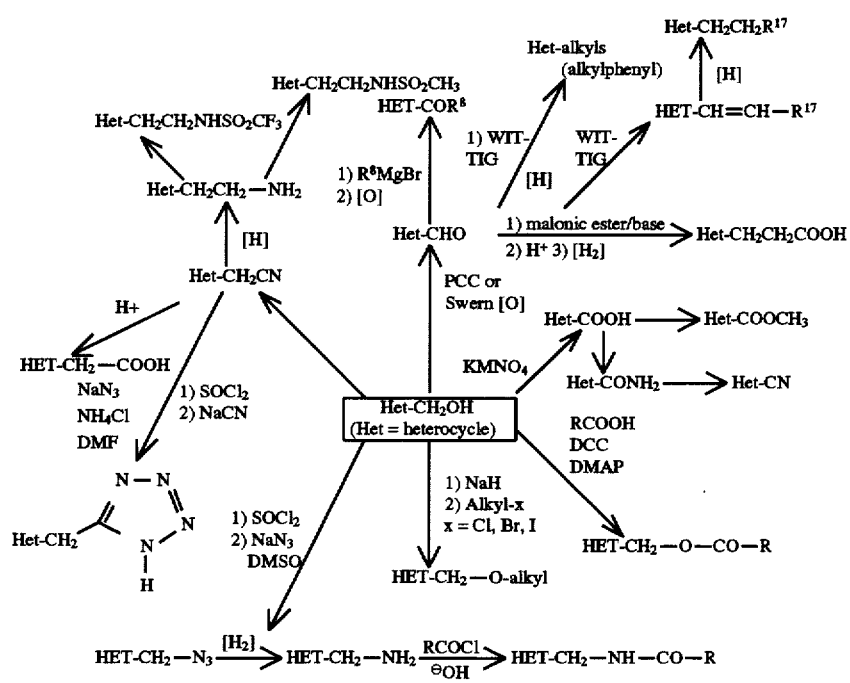

Scheme 16

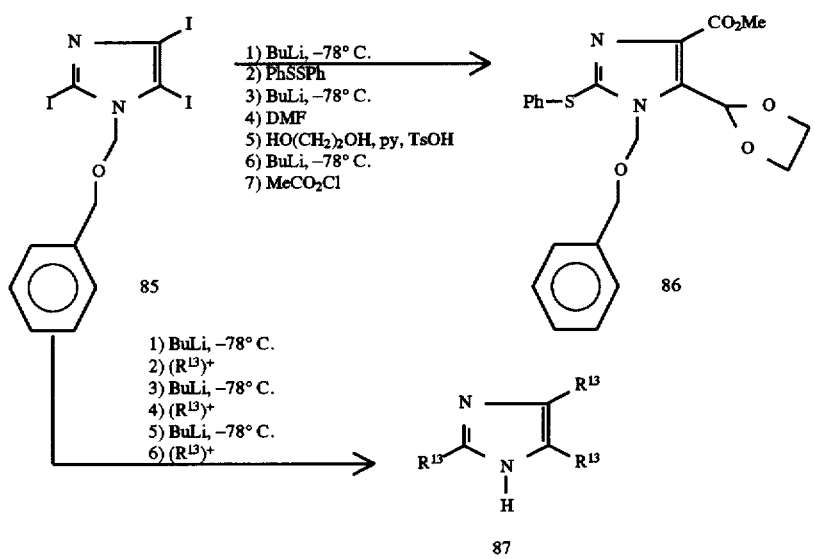

where (R¹³)+ is a suitable electrophilic precursors to R¹³.

The pyrazoles and imidazoles disclosed previously and other heterocycles which will be mentioned later in this specification may undergo alkylation onto a nitrogen Scheme 17

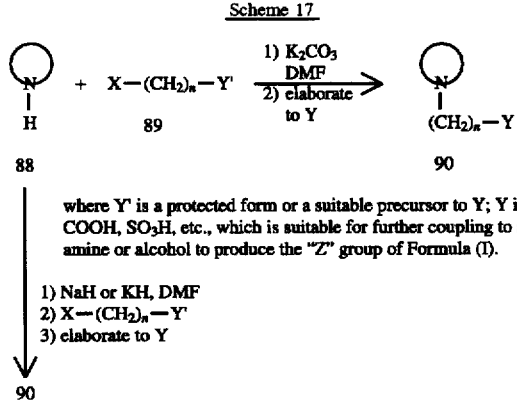

atom just as the pyrrole in Scheme 4 by simply stirring a mixture of the heterocycle 88 and alkylbromide, iodide, mesylate or tosylate 89 in the presence of an acid scavanger such as potassium carbonate in an inert solvent such as THF or DMF for several hours to several days at room temperature or up to the reflux temperature of the solvent (Scheme 17).

Another way to make 9Q involves first deprotonation of the N—H of heterocycle 88 with a base such as NaH, KH, n-BuLi, t-BuLi, etc., followed by displacement of the X-leaving group of 89 to yield 90.

This sequence can be performed in inert solvents such as ether or THF. NaH and KH can also be employed in DMF and DMSO at room temperature or at a higher temperature. Alkylation sometimes yields regioisomers when more than one nitrogen atom is present in the heterocycle. These isomers can be separated by standard methods such as crystallization or chromatography. Once alkylated, the Y group can be coupled to the boronic acid moiety and all protecting groups removed to yield compounds of Formula I by procedures described previously.

Compounds where R¹=1,2,4-triazole can be prepared by the route of H. Paul, G. Hilgetag and G. Jahnchen, *Chem. Ber.*, 101, 2033 (1968) which is depicted in Scheme 18. Imidate ester 92 is formed from nitrile 91 by the method of P. Keynaud and R. D. Moreau *Bull. Soc. Chim. France*, 2997 (1964). Hydrazide 99 is easily Scheme 18

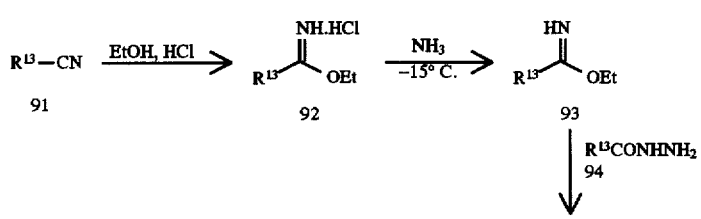

-continued
Scheme 18

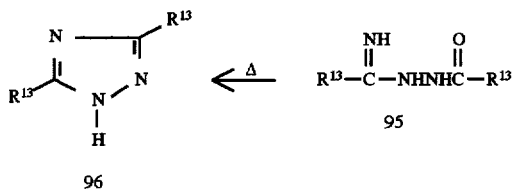

prepared via the action of hydrazine on the corresponding methyl ester precursor. It is understood that $R^{13}$ of 91 and 94 do not necessarily have to be in their final form, for example, and 98 when the $R^{13}$ groups are not identical. These intermediates can be converted into final products in the usual fashion as shown in Scheme 19.

Scheme 19

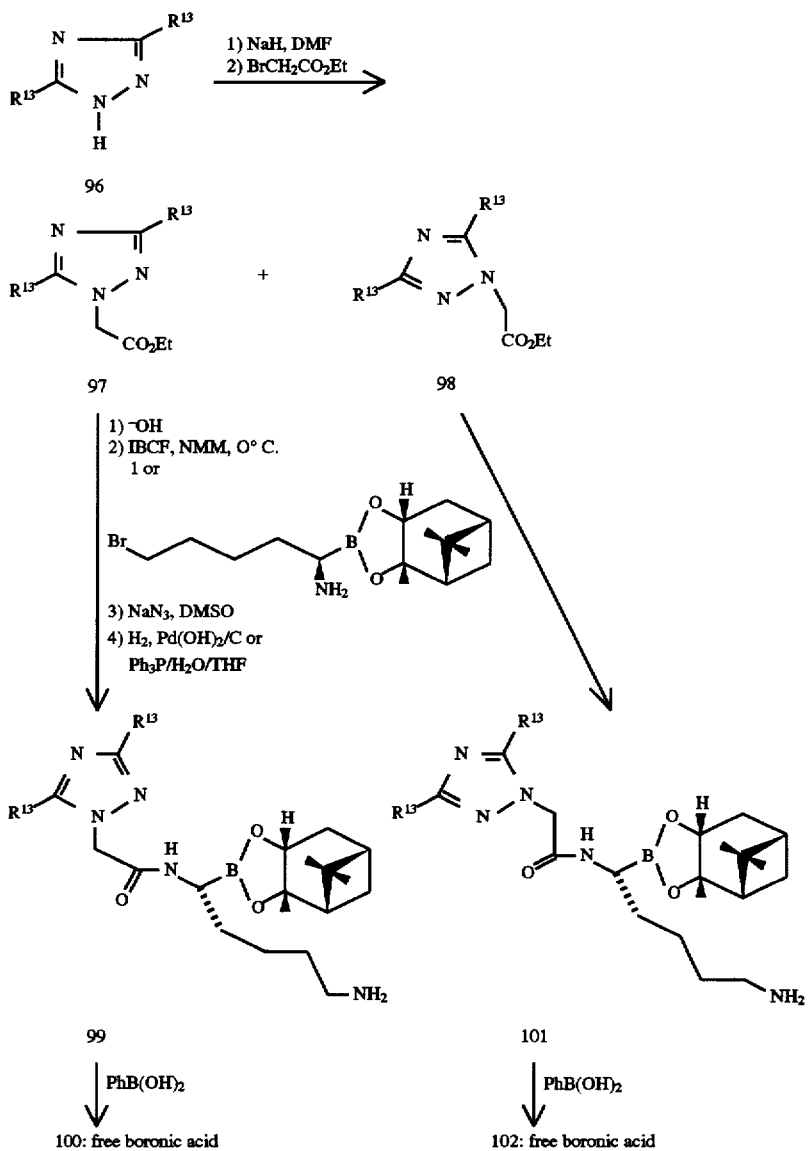

In each case, they can exist as either a protected species or in the form of a precursor to $R^{13}$.

Alkylation of triazole 96 yields two isomeric products 97

The regioselective syntheses of both 97 and 98 are shown in Scheme 20. Imidate ester 93 is reacted with hydrazine to form amidrazone 103. Alkylation with methyl μ-bromoacetate yields 194. Ring closure with either an ortho-ester, acid chloride or anhydride yields triazole 98. For a similar triazole synthesis, see David B. Reitz, European Patent Application 508, 445, published 14.10.92., G. D. Searle & Co. For schemes 20, and 22, the different $R^{13}$ groups are differentiated from one another by the placement of a prime symbol next to one of the $R^{13}$ groups, i.e. $R^{13'}$.

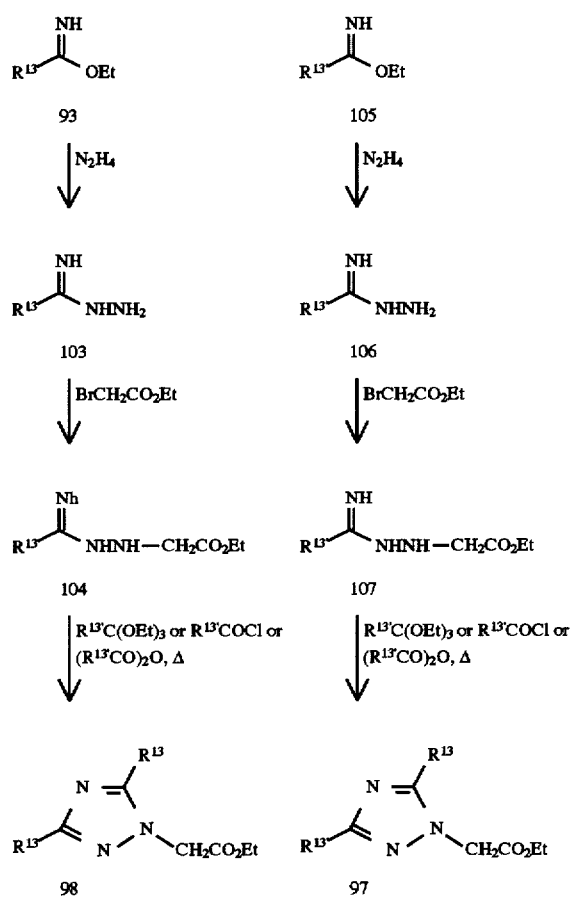

Yet another regioselective synthesis of 97 or 98 is depicted in Scheme 21 following a similar sequence as was shown in Scheme 20 (D. B. Reitz, ibid.).

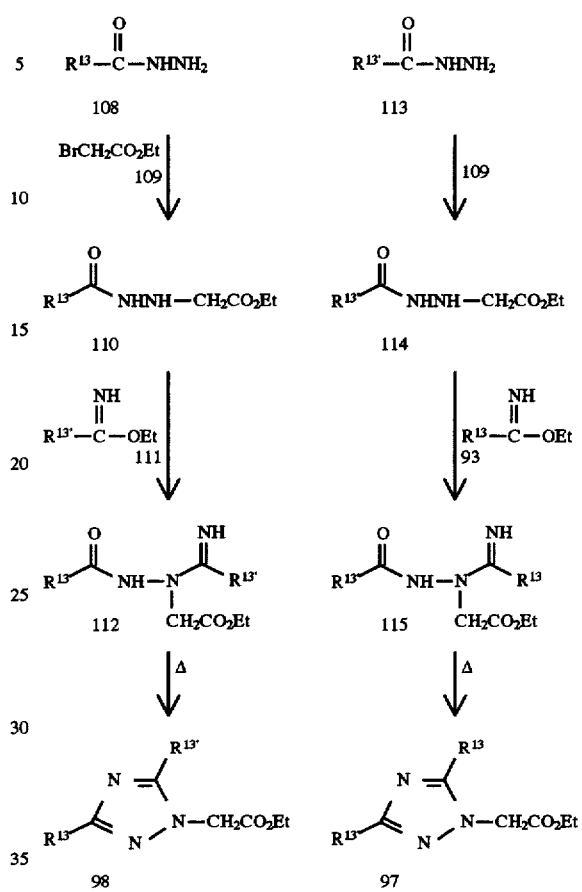

1,2,4-Triazoles also undergo selective metalation at the 5-position when the nitrogen at the 1-position is suitably protected. The metallated triazole can then be quenched through the addition of an electrophile to result in a newly functionalized triazole at the 5-position. Suitable protecting groups are benzyl and trityl. (D. K. Anderson, et al., *J. Heterocyclic Chem.*, 23, 1257 (1986) as well as diethoxymethyl (S. Ohta, et al., *Chem. Pharm. Bull.*, 41, 1226 (1993). The 3-position can also be metallated if the 5-position is suitably protected (S. Ohta et al., ibid.). Thus here we have two other methods for introducing $R^{13}$ substituents at the 5- or 3-positions of the 1,2,4-triazoles.

Compounds where $R^1$=1,2,3-triazole can be synthesized via the 1,3-dipolar cycloaddition of an azide to an alkyne as shown in Scheme 22 (for an example of this cycloaddition reaction, see W. Kirmse and L. Horner *Justus Liebigs Ann. Chem.* (1958) 614, 1).

Scheme 22

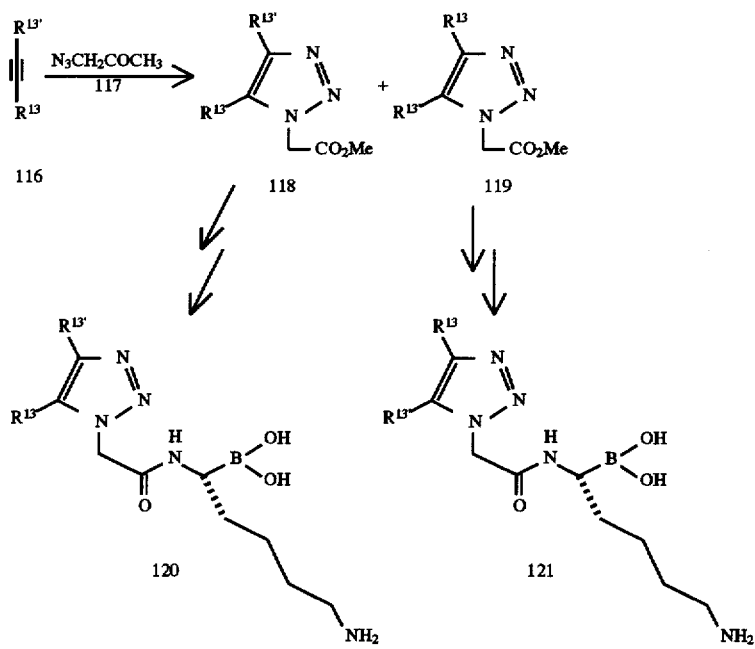

Compounds where R¹=tetrazole can be synthesized by the methods outlined in Scheme 23. In line a, three methods are given for the conversion of a nitrile into a tetrazole (ammonium chloride/sodium azide: W. G. Finnegan et al., *J. Am. Chem. Soc.* 1958, 80, 3908; trialkyltin azides: J. G. Luitjen et al., *Rec. Tray. Chim. Pays-Bas*; dialkyltin oxide: S. Wittenberger and B. G. Donner, *J. Org. Chem.*, 1993, 58, 4139).

In Scheme 23, line b, two procedures are given for the regioselective synthesis of 1,5-disubstituted tetrazoles (DEAD, Ph₃P, TMSN₃: J. V. Duncia, M. E. Pierce, J. B. Santella III, *J. Org. Chem.* 1991, 56 2395; Tf₂O/NaN₃: E. W. Thomas *Synthesis*, 1993, 767) which can be more difficult to synthesize due to the steric crowding of the substituents.

Compounds where R¹ is an oxazole may be synthesized by a variety of methods including those outlined in Scheme 24. The oldest synthesis and one of the most versatile is shown on line a), namely the cyclodehydration of 2-acylaminoketones (The Robinson-Gabriel Synthesis) (see I. J. Turchi in *Oxazoles*, Turchi, I. J., ed. John Wiley and Sons, New York (1986) p. 1). The 2-acylaminoketone starting materials may be synthesized from the Dakin-West reaction and modifications thereof (G. H. Cleland and F. S. Bennett *Synthesis* (1985)₆₈₁ and references therein). Some cyclodehydration agents include PCl₅, H₂SO₄, P₂O₅, SOCl₂, etc).

Scheme 23

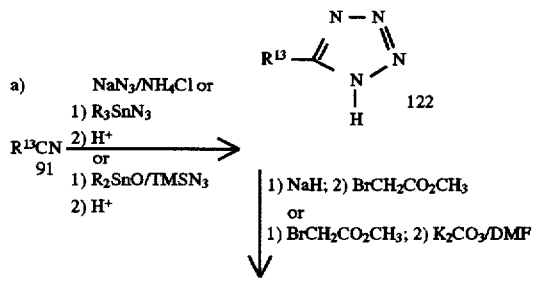

-continued
Scheme 23
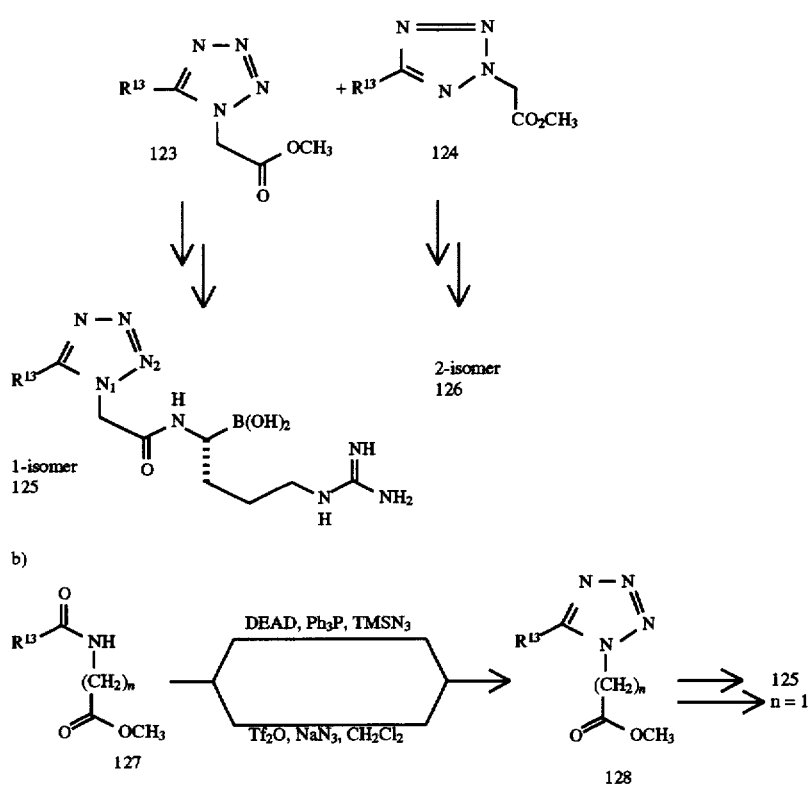
Scheme 24
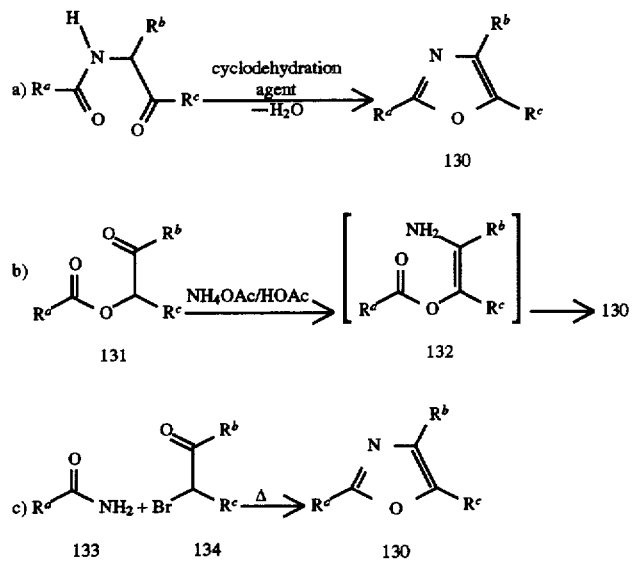

-continued
Scheme 24

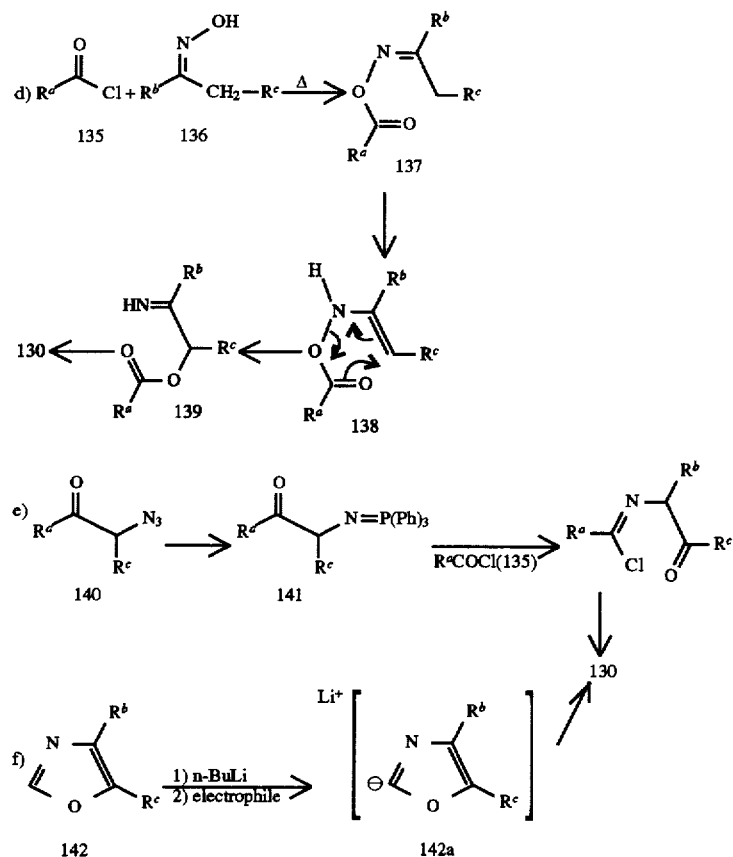

$R^a$, $R^b$ and $R^c$ are equal to $R^{13}$ which is described in the scope of this application. $R^{13}$ in Scheme 24 does not have to be in finalized form as it appears in the scope, but can be in protected form or in the form of suitable precursors. It is understood that only when the entire molecule of formula I is synthesized do all of the substituents have to appear in their final forms as stated in the scope. Protected forms and suitable precursors to $R^{13}$ are readily recognized by one skilled in the art of organic synthesis.

In line b, the reaction of α-acylketones 131 with ammonium acetate/acetic acid also yields oxazole 130 (D. Davidson, M. Weiss, M. Jelling J. Org. Chem. (1937), 328). In line c, we find the regioselective formation of oxazole 130 from the reaction of an α-haloketone 134 with amide 133 (R. Lakham, B. Ternai, Adv, Heterocycl. Chem. (1974) 17, 99; I. J. Turchi, M. J. S. Dewar, Chem. Rev. (1975), 75, 389). Acid chlorides 135 react with oximes 136 to yield after a [3,3] sigmatropic rearrangement (138) oxazole 130 as shown in line d (G. S. Reddy and M. V. Bhatt Ind. J. Chem. (1981) 208, 322; M. V. Bhatt, G. S. Reddy Tet. Lett. (1980) 21, 2359). In line e, μ-azidoketones (140), after reaction with triphenylphosphine to yield 141, react with acid chloride 135 to yield oxazole 130 (E. Zbiral, E. Bauer, J. Stroh Monatsh. Chem. (1971) 102, 168). Finally, oxazoles undergo deprotonation with strong bases such as n-BuLi at the 2-position when the 4 and 5 positions are blocked and after quenching with an electrophile can yield oxazole 130 (R. Schroder, V. Schollkopf, E. Blume, I. Hoppe Liebigs Ann. Chem., (1975) 533). As stated earlier, $R^{13}$ can be either in final form as defined in the scope of this application or in the form of precursor functionality which later on can be elaborated into final form by methods familiar to one skilled in the art. This holds true not only for the oxazoles discussed here, but for all of the other heterocyclic systems in this application where $R^{13}$ appears as substituents.

Oxazoles are most readily brominated at the 5-position followed by the 4-position and finally the 2-position. A brominated oxazole (as well as other brominated heterocycles in this application) can undergo aryl cross-coupling reactions catalyzed by transition metals to yield aryl-or heteroaryl-substituted oxazoles (See for example E.-I. Negishi; A. O. King; N. Okukado J. Org. Chem. (1977) 42, 1821).

Compounds where $R^1$ is an isoxazole may be synthesized by the methods outlined in Scheme 25. In line a, reaction of 1,3-diketone 143 with hydroxylamine yields oxazoles 144 and 145. Nitrile oxide 146 can also add across the triple bond of alkyne 147 to yield isoxazoles 144 and 145. (See P. Grunanger and P. Vita-Finsi Isoxazoles, v. 49 pt. 1 of The Chemistry of Heterocyclic Compounds, E. C. Taylor and A. Weissberger, eds., John Wiley and Sons (New York: 1991) p. 126).

Scheme 25 a) 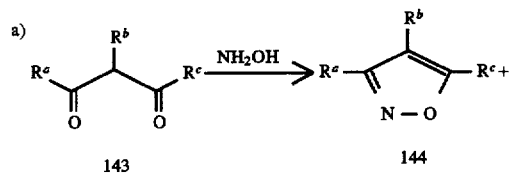

b) R¹³—C≡N—O + R¹³—C≡C—R¹³ ⟶ 144 + 145
   146              147

As discussed previously R$^a$, R$^b$ and R$^c$ in Scheme 25 are again equal to R$^{13}$ and are not necessarily in final form as they appear in the scope of this application.

Compounds wherein R$^1$ is a thiazole may be synthesized by the method depicted in Scheme 26, which mimics the route of Scheme 24c) describing a route for oxazoles. Thus thioamide 148 reacts with α-halocarbonyl compound 134 to yield thiazole 149. Again as for the oxazole, R$^a$, R$^b$, and R$^c$ have the same definitions. For the synthesis of thiazoles, by the route depicted in Scheme 26, see G. Vernin "General Synthetic Methods for Thiazole and Thiazolium Salts" in *Thiazole and Its Derivatives*, J. V. Metzger, ed., volume 34, pt. 1 in *The Chemistry of Heterocyclic Compounds*, A. Weissberger and E. C. Taylor, eds. John Wiley and Sons (New York:1979) p. 180.

Scheme 26

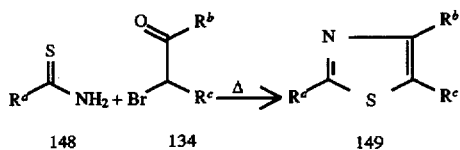

Compounds wherein R$^1$ is a 1,2,5-thiadiazole may be synthesized by the methods shown in Scheme 27. Diamine 150 may be reacted with sulfur monochloride to yield 1,2,5-thiadiazole 151. Likewise, α-diketone 152 may be converted into bisoxime 153 which also reacts with S$_2$Cl$_2$ to yield 151 (L. M. Weinstock, P. Davis, B. Handelsman, R. Tull *J. Org. Chem.* (1967) 32, 2823). Z is defined in Scheme 24.

Scheme 27 a) 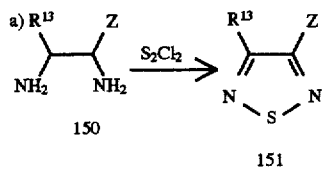

b) 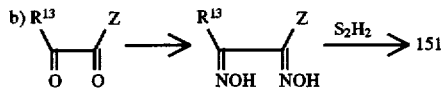

Scheme 28

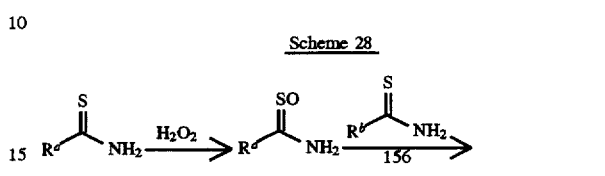

Compounds wherein R$^1$ is a 1,2,4-thiadiazole may be synthesized by the method depicted in Scheme 28. Oxidation of thioamide 154 with hydrogen peroxide yields S-oxide 155 which must be stored at 0° C. Further reaction of the S-oxide intermediate with thioamide 156 yields thioacylamidine 157 which cyclizes to product 158 (V. Goerdeler, H. Porrmann *Chem. Ber.* (1962) 95, 627). R$^a$ and R$^b$ are as defined previously in Scheme 24.

Compounds where R$^1$ is a furan may be synthesized by the methods shown in Scheme 29, but as understood by one skilled in the art, not limited thereto, as in the case as for all of the schemes in this patent application. In line a, cyclodehydration of 1,4-dicarbonyl compound 159 yields furan 160 (L. D. Krasnoslobodskaya, Ya. L Gol'dfarb *Russ. Chem. Rev.* (Engl. Trans.) 1969, 38, 389). In line b, α-bromoketone or aldehyde 161 protected as its dimethyl ketal or acetal reacts with trimethylsilylenol ether 162 to yield intermediate 163 which cyclizes to furan 160 (T. Mukaiyama, H. Ishihara, K. Inomata *Chem. Lett.*, 1975, 527). R$^a$, R$^b$, R$^c$, and R$^d$ are R$^{13}$ which is described in the scope of this application and with similar limitations as were described under Scheme 24 for R$^{13}$ with regards to being in final form or not.

Compounds where R$^1$ is a thiophene may be synthesized by the methods shown in Scheme 30. In line a, 1,4-dicarbonyl compound 159 is reacted with a phosphorous sulfide (phosphorous pentasulfide, phosphorous trisulfide, phosphorous heptasulfide, etc.) to yield thiophene 164 (H. D. Hartough, *Chem. Heterocycl. Compd.*, 1952, 3, 1). The dicarbonyl compound 159 also reacts with H$_2$S to favor thiophenes at lower temperatures (−50° C.) (F. Duus *Tetrahedron*, 1976, 32, 2817). Reaction of alkenes 165 or 166 (line b) with sulfur and heat also yield thiophene 16 (A. S. Broun, M. G. Voronkov *J. Gen. Chem. USSR*, (Engl. Trans.) (1947) 17, 1162; M. g. Voronkov, A. S. Broun, ibid, (1948) 18, 700; J. Schmitt., M. Suquet, R. Fallard (C. R. Hebd, Seances Acad, Sci. (1956) 242, 1738. $R^a$, $R^b$, $R^c$ and $R^d$ are as defined in Scheme 29.

Scheme 29

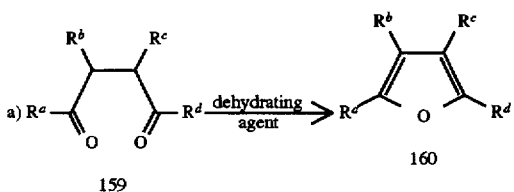

dehydrating agents include $H_2SO_4$, HCl, polyphosphoric acid, $PCl_3$, $ZnCl_2$, DMSO, phosphoric esters, etc.

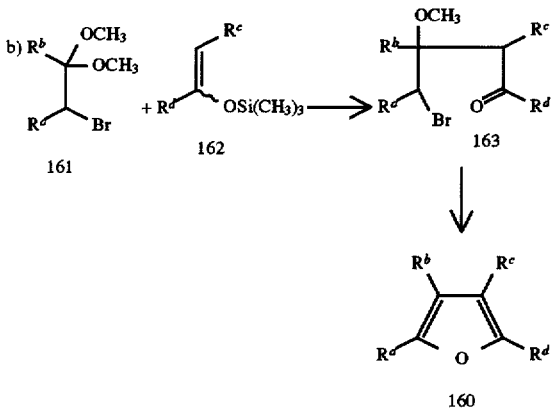

Scheme 30

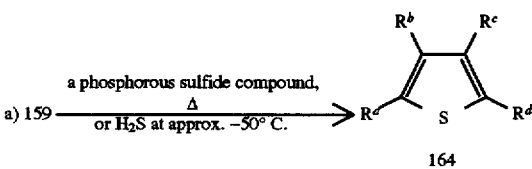

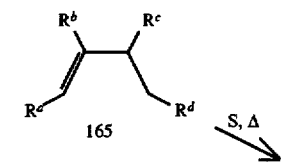

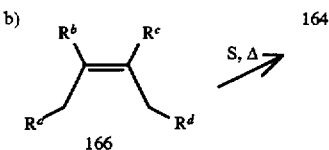

Compounds where $R^1$ is a pyridine may be synthesized by the methods shown in Scheme 31. It is to be understood that each scheme and each reaction has its own scope and limitations and that no one synthesis is universally applicable. It is also to be understood that one skilled in the art will be able to determine which synthesis is best suited for his or her needs. In line a, reaction of enamine 167 with ethynyl ketone 168 will cyclize to pyridine 170 (F. Bohlmann, D. Rahtz Chem. Ber. (1957)90, 2265). Enamino ketones 171 (line b) condense with 1,3-diketones or beta-keto esters 172 to yield pyridine 174 where R is alkyl, aryl or alkoxy and aryloxy (N. K. Kachetkov, A. Gonsales, A.

Nesmeyanov Dokl. Akad, Navk, SSSR (1951) 79, 609; S. Auricchio, R. Bernardi, A. Ricca Tet. Lett. (1976) 9831; H. Henecka Chem. Ber. (1949) 82, 41).

The Hantsch dihydropyridine synthesis can be used in the synthesis of pyridines as shown in line c. There are many modifications of this synthesis of which only one is shown. Reaction of 175 with beta-aminocrotonate 176 yields dihydropyridine 177 (F. Bassett, H. Meyer, E. Wehinger Angew. Chem. Int. Ed. Engl. (1981) 20, 762). Further oxidation with, for example, dilute nitric acid yields pyridine 178 where R and $R^1$ can be different alkoxy groups (E. Knoevenagel, W. Rushhaupt Ber. (1898) 31 1025). Cycloaddition of oxazole 179 with alkene 180 can also yield a pyridine (182) (M. Ya Karpeiskii, V. L. Florent'ev Russ. Chem. Rev. (Engl. Trans.) (1969) 38, 540; R. Lakhan, B. Ternai Adv. Heterocyl. Chem. (1974) 17, 99). In all of these pyridine synthesis, $R^a$, $R^b$, $R^c$, and $R^d$ are as described for Scheme 29. All of the substituents around the pyridine ring can be in final form or in the form of a precursor to a given functional group as would be recognized by one skilled in the art. Finally, in line e, hydroxypyridines, such as 183, may be triflated and coupled with an aryl-or heteroarylboronic acid or aryl-or heteroaryl-trialkylstannane using a transition metal catalyst such as Pd to yield aryl or heteroarylpyridinecarboxylic acids, such as 186. This in turn may be coupled to aminoboronic acid esters as discussed previously to yield compounds of Formula I. Halogens, such as Br or I may be used instead of triflate in compound 184 to undergo what is known as the Suzuki coupling reaction. R and $R^{1'}$ in line e) are any of the allowed phenyl substituents in the scope of this application (Suzuki reactions: A. Suzuki Pure Appl. Chem. (1985) 57, 1749).

Scheme 31

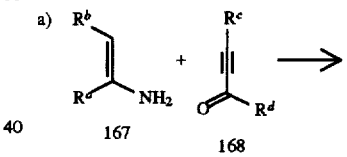

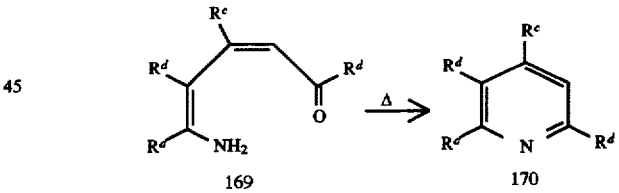

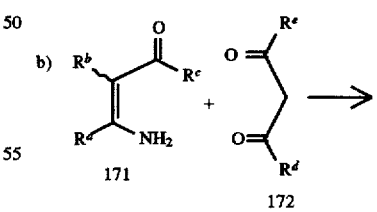

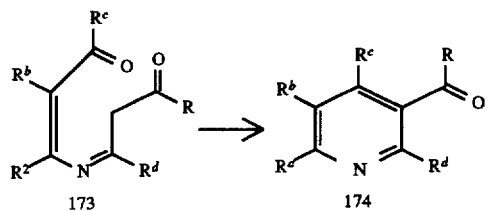

Scheme 31 (continued)

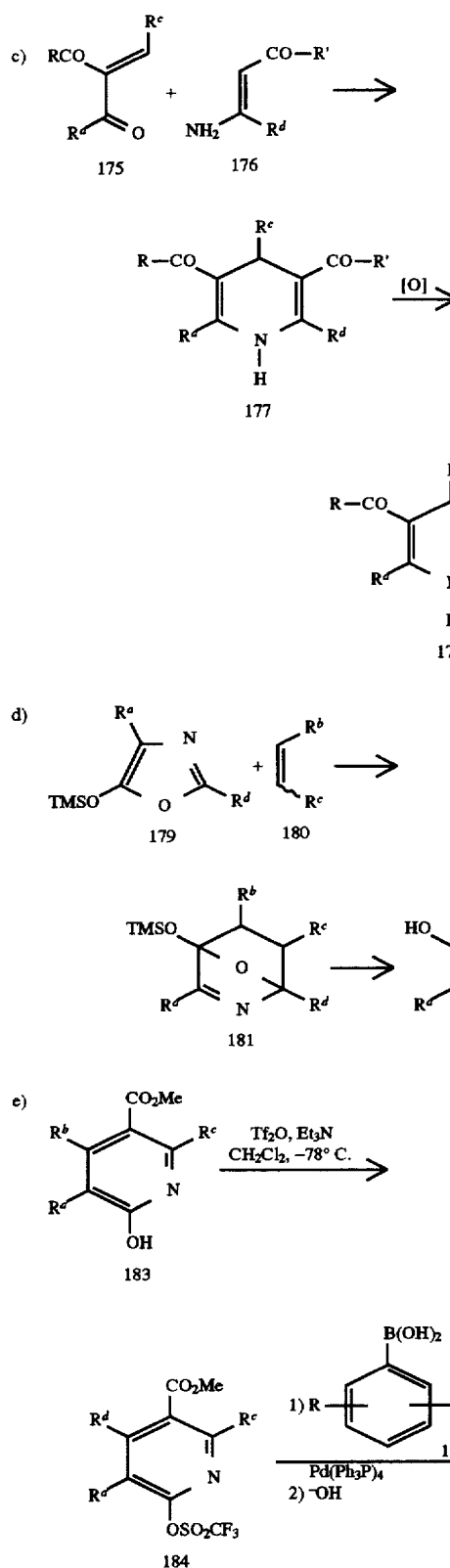

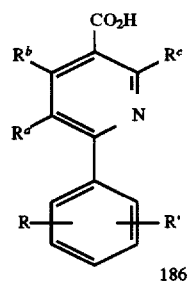

Compounds where $R^1$ is a pyridazine may be synthesized by the routes shown in Scheme 32. Reaction of 1,4-carbonyl compound 187 with hydrazine yields pyridazine 188. If the 1,4-dicarbonyl compound is saturated as in line b (compound 159), then the product from the reaction with hydrazine 189 must be oxidized to yield pyridazine 188 (K. C. Nicolaou, W. E. Barnette, R. L. Magolda *J. Am. Chem. Soc.* (1979) 101, 766;

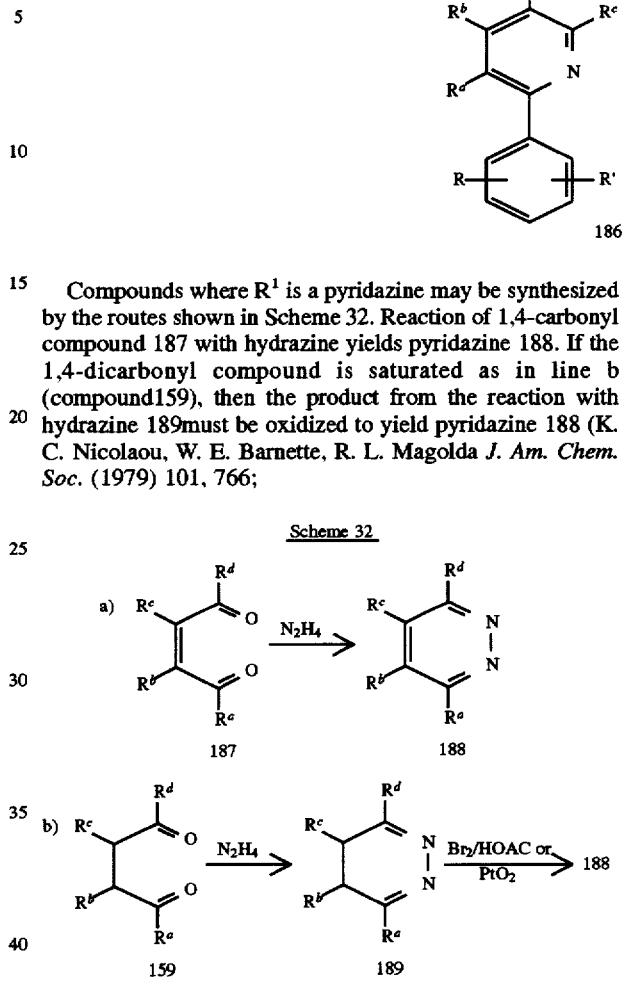

M. Tisler, B. Stanovnik "Pyridazines and their Benzo Derivatives" in A. R. Katrizky, C W. Rees *Comprehensive Heterocyclic Chemistry*, v.3 (Pergamon Press: Oxford), 1984, p. 45). Halopyridazines or hydroxypyridazines may also undergo the same aromatic cross-coupling reactions as were described for pyridines. $R^a$, $R^b$, $R^c$ and $R^d$, etc., are defined the same as in the pyridine case.

Compounds wherein $R^1$ is a pyrimidine may be synthesized by the methods shown in Scheme 33. Reaction of 1,3-dicarbonyl compound 190 with amidine 191 yields pyrimidine 192 (D. J. Brown, S. F. Mason *The Pyrimidines* in A. Weissberger ed. *The Chemistry of Heterocyclic Compounds*, (John Wiley: New York) 1962, p. 31).

Scheme 33

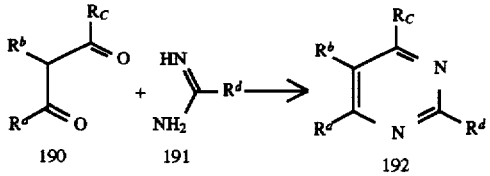

Scheme 33

-continued

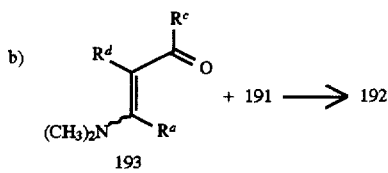

Reaction of amidine 191 with 193 also yields pyrimidines (P. Schenone, L. Sansebastiano, L. Mosti *J. Heterocyclic Chem.* (1990) 27, 295). $R^a$, $R^b$, $R^c$, and $R^d$ are as defined previously in Scheme 32. Halopyrimidines or hydroxypyrimidines may also undergo the same aromatic cross-coupling reactions as were described for pyridines.

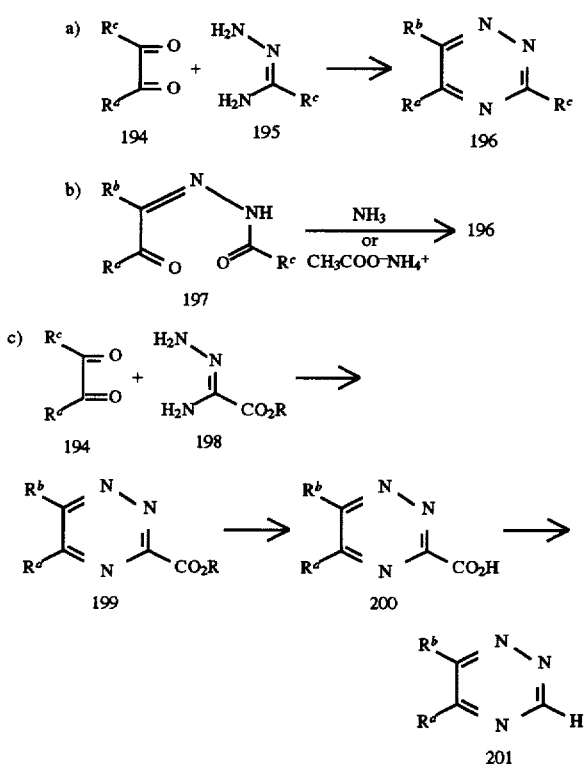

Compounds in which $R^1$ is a 1,2,4-triazine my be synthesized by the procedures outlined in Scheme 34. In line a, 1,3-dicarbonyl compound 194 is condensed with amidrazone 195 to yield triazine 196 (H. Neunhoeffer and P. F. Wiley *Chemisrty of 1,2,3-Triazines and 1,2,4-Triazines and Pentazines*, v. 33 in A. Weissberger, E. C. Taylor, eds., *The Chemistry of Hetrocyclic Compounds* John Wiley and Sons (New York: 1978) pp 194–200 and p. 524). In line b, cyclization of acylhydrazone 197 with ammonia or ammonium acetate leads to triazine 196 (H. Neunhoeffer, P. F. Wiley, ibid., p. 196, 197). In line c, reaction 1,2-dicarbonyl compound 194 with oxalamidrazonates 198 yields 1,2,4-triazine ester 199. Saponification of 199 yields 200 which can be decarboxylated to yield 1,2,4-triazine 201 (H. Neunhoeffer, P. F. Wiley, ibid., p. 526). $R^a$, $R^b$, and $R^c$ are as defined in the pyridine case. Halotriazines or hydroxytriazines may undergo the same aromatic cross-coupling reactions as were described earlier for pyridines.

Compounds in which $R^1$ is as described in lines k and l in the scope of this application may be synthesized by the methods described in Scheme 35. If heterocycle —J—K—L—M—Q— 202 contains a bromine, iodine or a hydroxyl group (which can be triflated) designated by X, then it can undergo a Suzuki coupling to yield 204 where u is 0 (A. Suzuki, ibid) (Scheme 35, line a). If instead of $B(OH)_2$ a trialkyltin group is present, then a Stille coupling can be performed when X=triflate (J. K. Stille *Angew. Chem. Int. Ed. Engl.* (1986) 25 508; J. K. Stille *Pure Appl. Chem.* (1985) 57, 1771).

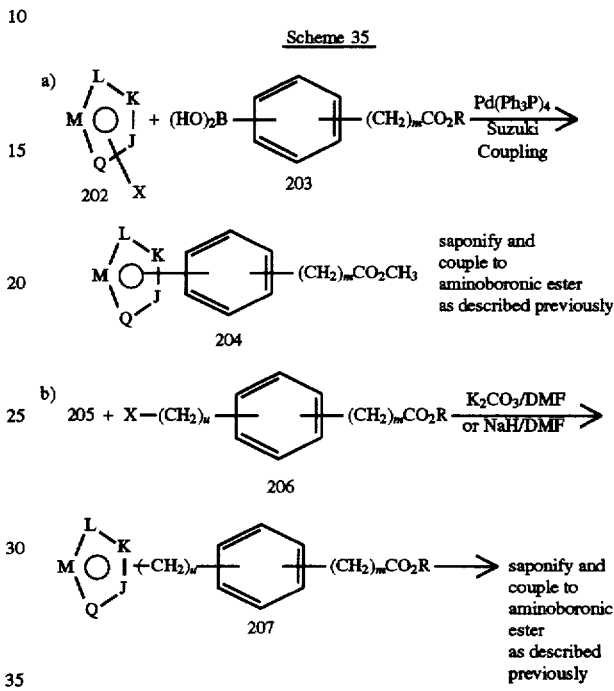

The X and $B(OH)_2$ (or trialkyltin) moieties may be reversed so that now $X=B(OH)_2$ (or $R_3Sn$) and the phenyl of 203 contains halogen or triflate group. The same coupling procedures may be used in synthesizing compounds where $R^1$ is described by line 1 and u is 0 as were used in synthesizing compounds where $R^1$ is described by line k and u is 0.

When u is not 0, heterocycle 205 and its six-membered ring counterpart —C—W—R—T—U—V— (described in line 1) must be synthesized from scratch by the methods described heretofore, with the —$(CH_2)_u$-Phenyl—$(CH_2)_m CO_2R$ group being one of the substituents in final or precursor form. If heterocycle 205 contains an N—H which is alkylatable, then alkylation with 206 where X is Cl, Br, I, mesylate tosylate or triflate yields 207 (Scheme 35, line b). The esters 204 and 297 can then be hydrolyzed to the free acid and coupled with aminoboronic acid ester derivative as described in Scheme 4, for example, to yield boronic acid esters which can also be hydrolyzed to the corresponding free boronic acid products.

A general method (Scheme 36) for the synthesis of 4-carboxydihydroheterocycles (oxazolines, thiazolines, imidazolines) utilizes the condensation of an α-amino acid ester (210) with an imidate (211) to provide 212, see: Meyers, A. I.; Hanagan, M. A.; Mazzu, A. L. *Heterocycles* 1981, 15, 361; Meyers, A. I.; Whitten, C. E. *Heterocycles* 1976, 1, 1687; North, M.; Pattenden, G. *Tetrahedron* 1990, 46, 8267; Jones, R. C. F.; Ward, G. J. *Tetrahedron Lett.* 1988, 29, 3853. In the case where $R^{20}$=H, the cyclization might be conducted with trimethyl orthoformate instead of 211, see: Martin, P. K. et al. *J. Org. Chem.* 1968, 33, 3758. For compounds that are substituted only at the 2-position of the heterocycle, serine or cysteine might be used as the amino acid ester partner. The dihydroimidazole-based materials would be prepared from an N$^\alpha$-monoprotected diaminopropionic acid to prevent tautomerization of the double bond once the cyclic system of 212 has been formed, see: Martin, P. K. et al. *J. Org. Chem.* 1968, 33, 3758. Hydrolysis of the ester then affords carboxylic acid 213.

Scheme 36: Synthesis of 4-Carboxyheterocycles.

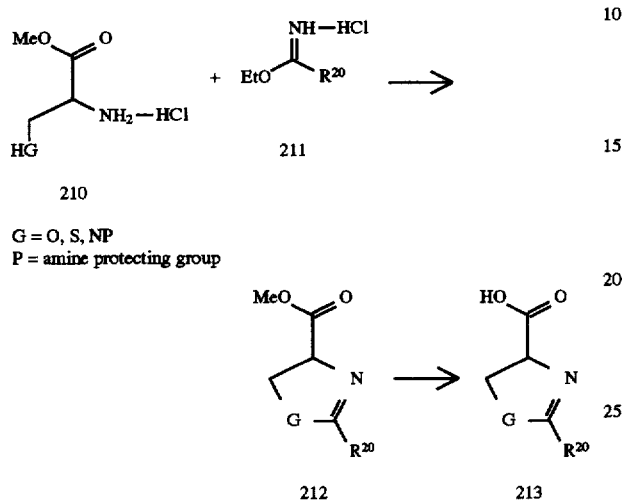

G = O, S, NP
P = amine protecting group

It may be desirable to prepare more highly substituted heterocycles as well (Scheme 37). An approach to the oxazoline class could utilize reaction between the anion of 215 and formaldehyde to provide adducts 216 as recorded by Kanemasa, S. et al. *Tetrahedron Lett.* 1993, 34, 677 and Ito, Y. et al. *Tetrahedron* 1988, 44, 5253. Hydrolysis of the imine should deliver 217, an example of an G-substituted α-amino acids, as a mixture of isomers. Condensation as before with imidate (211) should generate cyclic moieties of general structure 218 which are hydrolyzed to 219.

The corresponding thiazolines should be available by installing a sulfhydryl group prior to cyclocondensation. To that end, N—protection of 217, followed by reaction with a sulfur nucleophile, a thiol ester or an inorganic salt thereof, based on the work reported by Mitsunobu, O. *Synthesis* 1981, 1, and Yuan, W. et al. *J. Med. Chem.* 1993, 36, 211, should provide the substituted cysteine (220) upon premoval of the N-protecting group. Subsequent reaction with the imidate should deliver 221 and ultimately 222, after hydrolysis of the ester.

Scheme 37: Synthesis of Substituted Heterocycles.

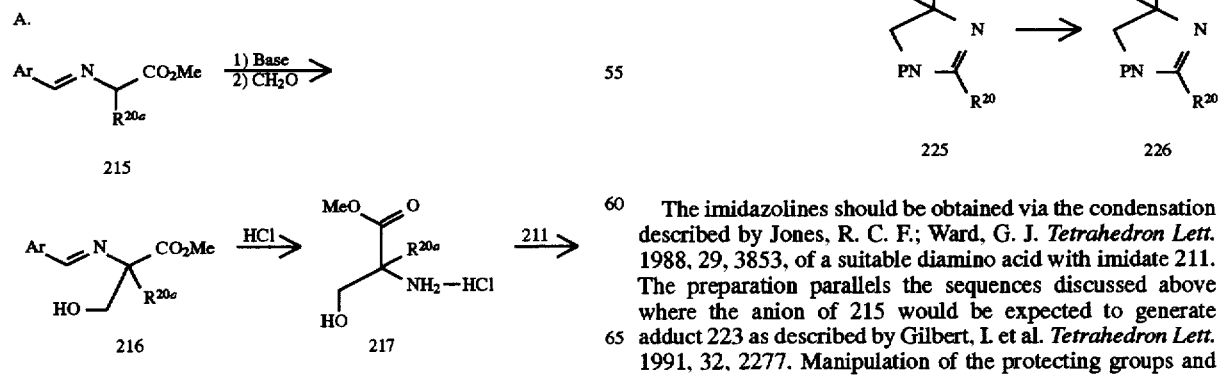

The imidazolines should be obtained via the condensation described by Jones, R. C. F.; Ward, G. J. *Tetrahedron Lett.* 1988, 29, 3853, of a suitable diamino acid with imidate 211. The preparation parallels the sequences discussed above where the anion of 215 would be expected to generate adduct 223 as described by Gilbert, L et al. *Tetrahedron Lett.* 1991, 32, 2277. Manipulation of the protecting groups and implementation of the aforementioned cyclization should give imidazoline 225 which may be converted to the corresponding carboxylic acid 226.

Using an analogous synthetic sequence (Scheme 38), the polysubstituted versions of these heterocycles should also be accessible. For the oxazo—or imidazo—type compounds, reaction of the anion of 215 with an electrophile 227 should deliver 228, as reported by Kanemasa, S. et al. *Tetrahedron Lett.* 1993, 34, 677 [cf. Meyer, R. et al. *Liebigs Ann. Chem.* 1977, 1183], and liberation of the a -amino group should then provide 229, as a mixture of isomers. Application of the now standard cyclocondensation should complete the synthesis of 231 upon hydrolysis of 230.

A similar sequence should provide an entry into the thiazolines series (235). However, in the case where $R^{3b}$=H, this material would be prepared by converting 232 to the corresponding mercaptan 233 using the conditions described earlier; the ester in 234 could then be hydrolyzed to afford 235. This reaction sequence would be preferred to avoid use of a presumably unstable thioaldehyde (227 where U=S and $R^{3b}$=H), see: Takahashi, T. et al. *Heterocycles* 1993, 36, 1601 and references therein.

SCHEME 38: Polysubstituted Heterocycles, Synthesis I.

A.

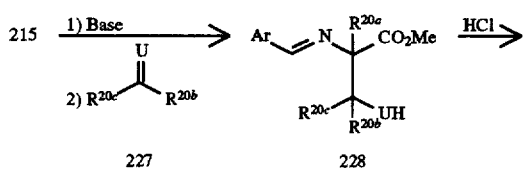

U = O, S, NP
(if U = S, then $R^{20b} \neq$ H)

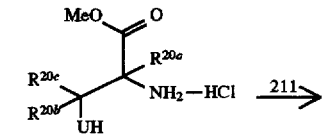

229

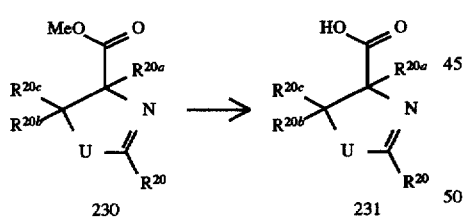

230    231

B.

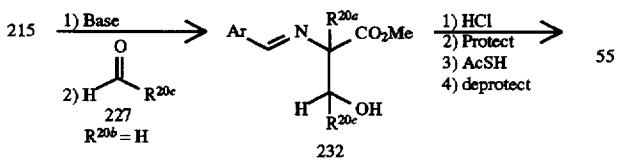

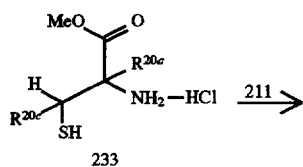

233

-continued
SCHEME 38: Polysubstituted Heterocycles, Synthesis I.

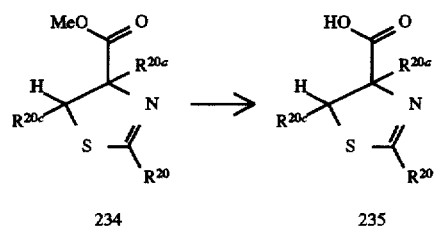

234    235

Alternative methods for the preparation of these polysubstitutued heterocycles employ (Scheme 39) the addition of the anion of isocyanide 236 to an electrophile 227 to provide the heterocycle 237, see: Ito, Y. et al. *Tetrahedron Lett.* 1989, 30, 4681; Ito, Y. et al. *Tetrahedron Lett.* 1988, 29, 6321, 235; Ito, Y. et al. *Tetrahedron Lett.* 1987, 28, 6215; Ito, Y. et al. *Tetrahedron* 1988, 44, 5253; Meyer, R. et al. *Liebigs Ann. Chem.* 1977, 1183. The carboxylic ester may be manipulated at this time, however the preferred sequence would implement either an exchange reaction mediated by a transition metal catalyst as reported by Ito, Y. et al. *Tetrahedron* 1988, 44, 5253 to provide derivatives 238; standard hydrolysis followed by reaction with imidate 211 would also yield 238. Subsequent conversion to the carboxylic acid 239 should proceed smoothly. For cyclic compounds (243) where $R^{20}$= H, the preferred sequence would involve the sequential hydrolysis of adduct 240, transformation of the hydroxyl group into a sulfhydryl function, cyclocondensation to thiazoline 242 and finally hydrolysis to afford the desired carboxylic acid 243.

SCHEME 39: Polysubstituted Heterocycles, Synthesis II.

A.

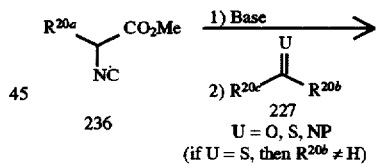

236

U = O, S, NP
(if U = S, then $R^{20b} \neq$ H)

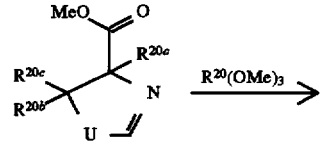

237

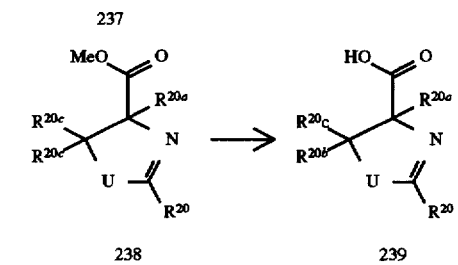

238    239

B.

SCHEME 39: Polysubstituted Heterocycles, Synthesis II.
(-continued)

SCHEME 40: Alternative Syntheses of Oxazolines and Thiazolines.

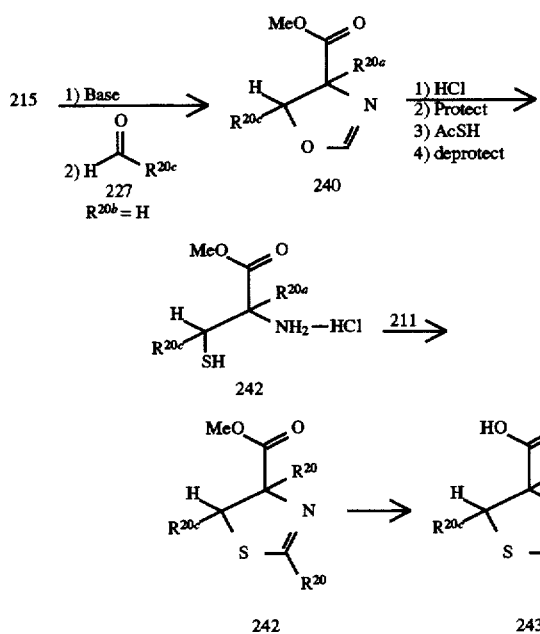

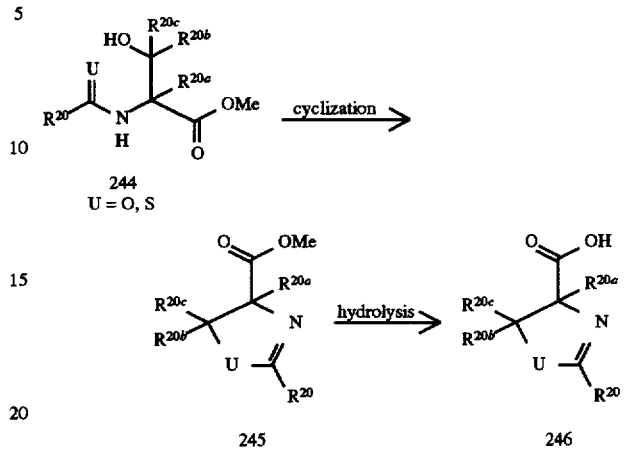

Another noteworthy method (Scheme 40) for the assembly of oxazolines and thiazolines utilizes an appropriate N-acyl-β-hydroxy-α-amino acid (244) which reacts intramolecularly by cyclization of the amide carbonyl onto the hydroxyl group of the amino acid. This transformation may occur upon treatment with triphenylphosphine and an azodicarboxylate, as reported by Wipf, P.; Miller, C. P. *Tetrahedron Lett.* 1992, 33, 6267, 907 and Galéotti, N. et al. *Ibid.*, 2807, or through the use of diphenyl sulfoxide and triflic anhydride, as demonstrated by Yokokawa, F. et al. *Synlett* 1992, 153, to generate the requisite ring system; in 245. Hydrolysis of the ester then provides 246. Alternatively, this cyclization may be effected by intramolecular displacement of the corresponding halo derivative (—OH→halogen in 244), which is generated in situ, to provide the oxazoline (245), see: Evans, D. A. et al. *J. Org. Chem.* 1992, 57, 1961.

The regioisomeric 5-carboxyheterocycles may be synthesized (Scheme 41) by condensation of an appropriate α-functionalized β-amino acid with imidate 211; for an example of this type of cyclization, see: Wolfe, S. et al. *Tetrahedron Lett.* 1979, 3913. In the event, nucleophilic opening of an a, b-epoxy acid (247) with an inorganic azide such as lithium azide according to Chong, J. M.; Sharpless, K. B. J. *Org. Chem.* 1985, 50, 1563 should provide 248; the corresponding esters also participate in this reaction, see: Commerçon, A. et al. *Tetrahedron Lett.* 1992, 33, 5185. Reduction should give the requisite (α-hydroxy-β-amino acid 249. Alternatively, it may be desirable to prepare 249 from an a—amino acid directly as described by Poss, M. A.; Reid J. A. *Tetrahedron Lett.* 1992, 33, 1411, by reaction of the appropriate N-BOC compound (250) with 2-furyllithium to provide vicinal amino alcohol (251); manipulation of the furan moiety and deprotection then generates 249. A similar approach using 2-ithiothiazoles may also be useful, see: Dondoni, A.; Perrone, D. *Tetrahedron Lett.* 1992, 33, 7259.

SCHEME 41: Regioisomeric Heterocycles, Synthesis I.

A.

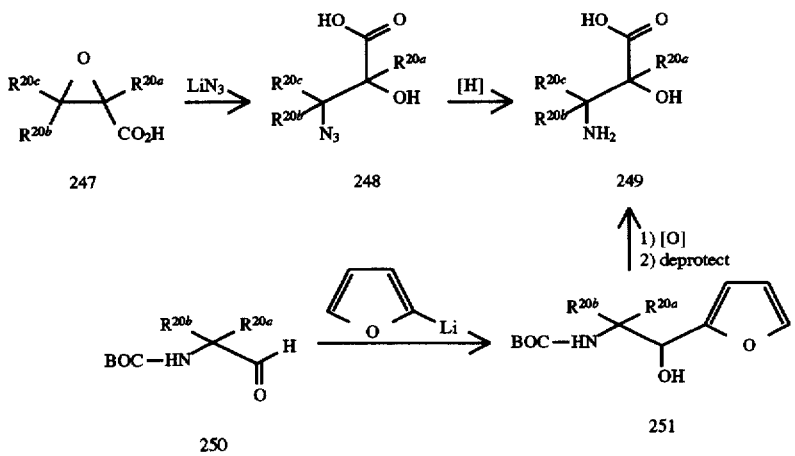

SCHEME 41: Regioisomeric Heterocycles, Synthesis I.
-continued

B.

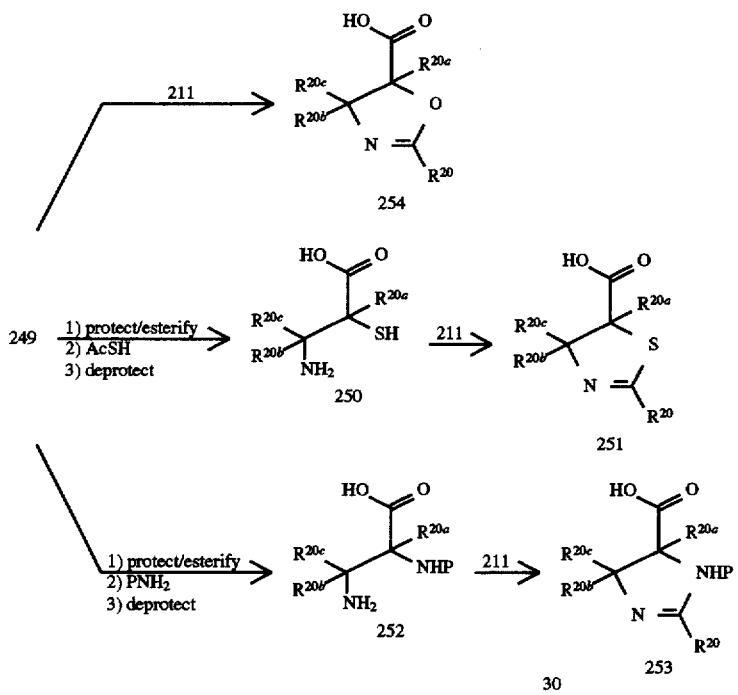

Completion of the syntheses of the heterocycles should follow precedent. Reaction with of 249 with 211 should provide oxazoline 254 directly. This alcohol may also be used in a sequence described previously to allow for incorporartion of sulfur and ultimately provide 250; this mercaptan should lead to thiazoline 251. Additionally, 249 could be employed as a substrate for reaction with a nitrogen based nucleophile, see: Mitsunobu, O. *Synthesis* 1981, 1 [cf. Cardani, S. et al. *Tetrahedron* 1988, 44, 5563], to deliver 252 as a precursor for imidazoline 253.

The regioisomeric imiodazolines should be available from other routes as well (Scheme 42). One method would call for hydrolysis of imine 223, discussed earlier in Scheme 37, followed by protection of the newly liberated α-amino group to give 254. Cleavage of the phthaloyl residue and reaction with imidate 211 should provide 255 which is hydrolyzed to 256. An alternative approach calls for reaction of an α-bromo-α,β-unsaturated ester (257) with an amidine (258) [sterically hindered (P is large ) materials do not react]to generate 259 in a single step as reported by Marsura, A. et al. *Synthesis* 1985, 537; hydrolysis of the ester should yield the acid 260.

SCHEME 42: Alternative Preparations of Imidazolines.

A.

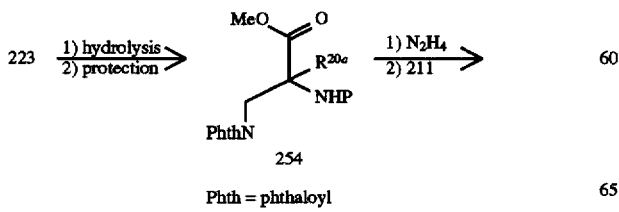

Phth = phthaloyl

-continued
SCHEME 42: Alternative Preparations of Imidazolines.

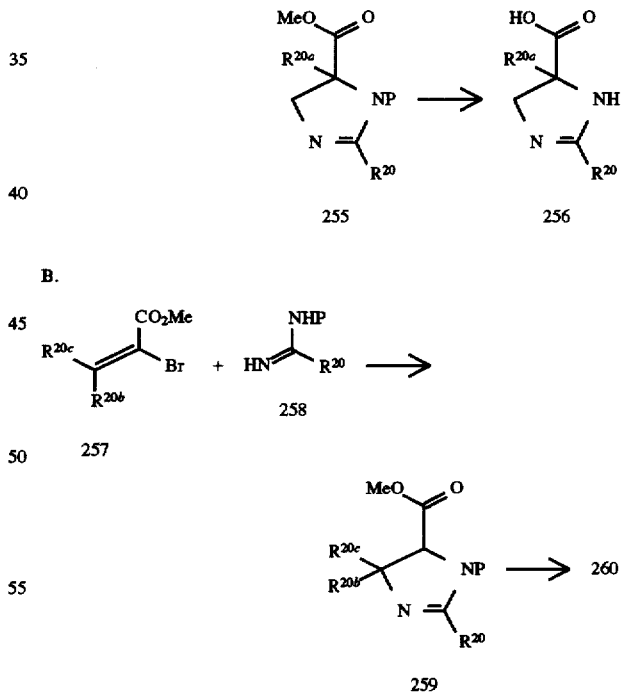

The several types of inhibitors disclosed in this invention can be broadly classified by their electrophilic functional group A, as defined in Formula (I). The compounds described below, unlike the boron containing peptides, utilize a highly electrophilic carbon atom at A to interact with the active site serine of thrombin. The precursor for the electrophilic carbon inhibitors is the appropriately protected amino acid (261) of Scheme 43.

Scheme 43

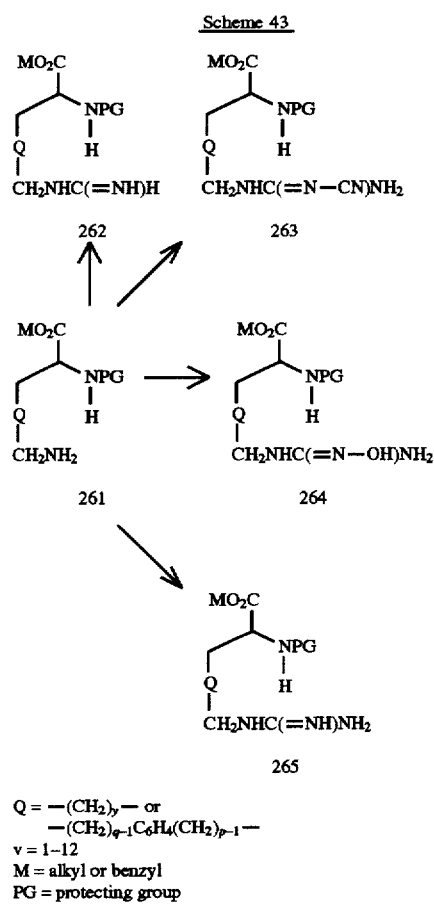

Q = —(CH₂)ᵥ— or
—(CH₂)ᵩ₋₁C₆H₄(CH₂)ₚ₋₁—
v = 1–12
M = alkyl or benzyl
PG = protecting group The preparation of (261) can be found in the general chemical literature, one such reference being the review by Morrison and Mosher (1976). According to Scheme 43 various terminal functional groups are available from (261): the formamidino-(262), cyanoguanidino-(263), hydroxyguanidino-(264) and guanidino-analogs (265).

The preparation of amidine derivative (267) and phenylguanidines of formula (269) from amino acids (266) and (268), respectively, is shown in Scheme 44. The conditions used to prepare amidines of formula (267) is discussed for (303) of Scheme 53 while the method for formamidinylation of (268) to give (269) is the same as that described to prepare (295) of Scheme 52.

Scheme 44.

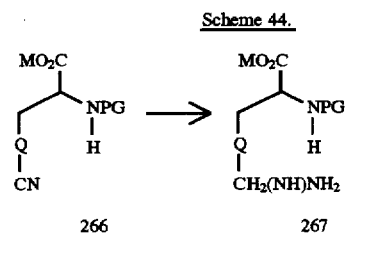

Q = —(CH₂)ᵥ— or —(CH₂)ᵩ₋₁C₆H₄(CH₂)ᵩ₋₁—

-continued
Scheme 44.

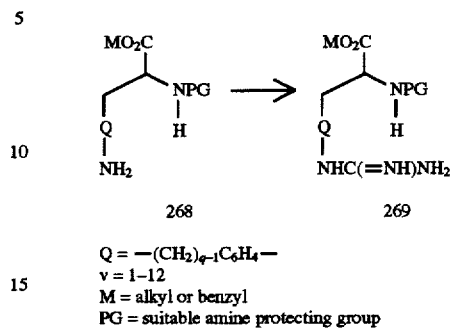

Q = —(CH₂)ᵩ₋₁C₆H₄—
v = 1–12
M = alkyl or benzyl
PG = suitable amine protecting group As shown in Scheme 45, appropriately protected derivatives of formulae (261–269), wherein M is an alkyl or benzyl group can be coupled with N,N-disubstituted acid (270) or (271) (wherein M is hydrogen). The X group in compounds of formulae (261) through (269) and (272) in Scheme 45, as well as in compounds illustrated in the Schemes to follow, is a protected version of the terminal functional group X, as defined by Formula (I), unless deprotection is indicated to obtain the final compound of the sequence.

Scheme 45.

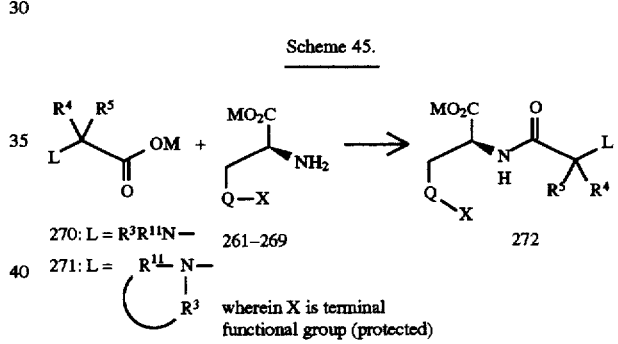

wherein X is terminal functional group (protected)

It is understood that the protecting group(s) used should compatible with the conditions of the process discussed; a good source for information on protecting group chemistry is Greene and Wuts (1991).

The preparation of the thrombin inhibitors trihalomethyl ketone (274) and α-ketoester (275) are shown in Scheme 46. The coupled ester (272), wherein M is alkyl or benzyl can be converted to the acid (M is hydrogen) by the methodology appropriate for the particular ester functionality as described in Greene and Wuts (1984). The aldehyde (273) can be prepared by selective reduction of the acid (272, M is hydrogen) to the primary alcohol followed by oxidation.

Scheme 46.

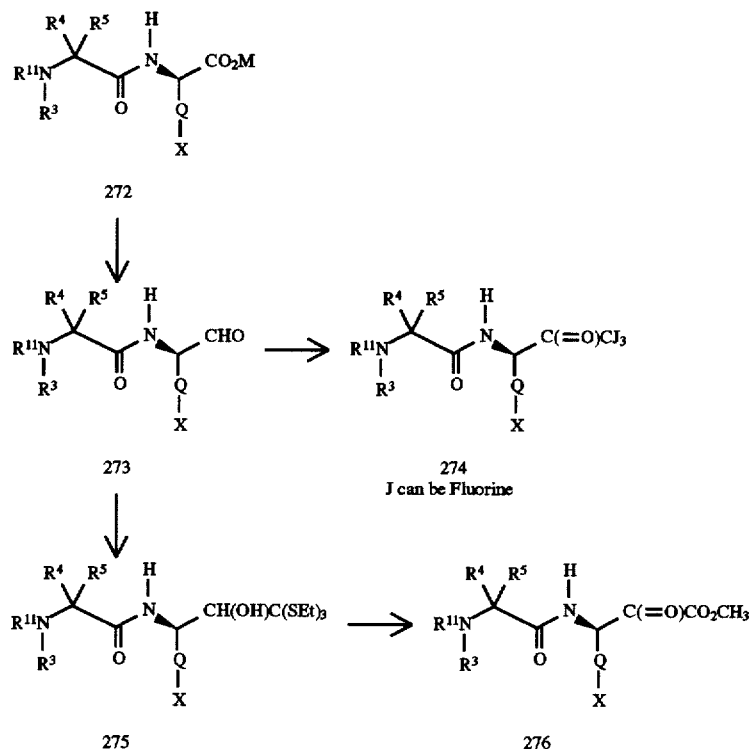

274
J can be Fluorine

To obtain the primary alcohol, the acid can be transformed to the mixed anhydride by condensation of the trialkylammonium salt of the acid with an alkyl- or arylchloroformate in an inert non-polar solvent such as tetrahydrofuran, 1,2-dimethoxyethane or toluene at −78° C. to room temperature. The solution of the resulting mixed anhydride is filtered and reduced to the peptidyl alcohol with an excess of a borohydride reducing agent in a compatible solvent like water or an alcohol at −78° C. to room temperature according to the method of Rodriguez et. al., Tetrahedron Lett. 32, 923 (1991). The peptidyl alcohol can be oxidized to aldehyde (273) without over oxidation by a variety of procedures, as detailed by Hudlicky in Oxidations in Organic Chemistry, American Chemical Society, p. 114 (1991); the preferred methods include Swern oxidation described by Omura and Swern, Tetrahedron 34, 1651 (1978); and the Pfitzner-Moffat oxidation described by Fearon et al. in J. Med. Chem. 30, 1617 (1987). A two step protocol reported by Edwards, Tetrahedron Lett. 33, 4279 (1992) can be used to prepare the trifluoromethyl ketones (274) (J is fluorine) from aldehyde (273). In this procedure a metallated trifluoromethyl anion is generated from an excess of trifluoromethyliodide or -bromide and an active metal such as zinc, magnesium, lithium or cadmium in inert, anhydrous solvents like tetrahydrofuran or N,N-dimethylformamide at temperatures of −100° C. up to the reflux point of the solvent. Alternatively, the metallated trifluoromethyl anion may be generated by the transmetallation of trifluoromethyliodide or -bromide with an organometallic compound such as a Grignard reagent or alkyllithium compound in an inert solvent like tetrahydrofuran, hexane or ether at temperatures ranging from −78° C. up to the reflux point of the selected solvent. Aldehyde (273) can be added to the solution of the metallated trifluoromethyl anion to form the trifluoroethanol derivative at temperatures of −100° C. or higher. To obtain the trifluoromethyl ketone (274) where J is fluoro, the alcohol is oxidized by the Pfitzner-Moffat or Swern procedure. Removal of the protecting group(s) on terminal group X by the appropriate method will provide the thrombin inhibitors of formulae (274).

Trihalomethyl analogs of (274), where J is fluoro can also be prepared from aldehyde (273) by a different method. The trihalomethyl ketones are prepared by treating aldehyde (273) with either the trimethylsilyl trihaloacetate or the potassium or sodium trihaloacetate in a polar solvent such as an alcohol, N,N-dimethylformamide or methylsulfoxide with or without a base such as a trialkyl amine, potassium carbonate or sodium hydroxide at temperatures of −78° C. or higher according to the method of Beaulieu, Tetrahedron Lett. 32, 1031 (1991); Shell Int. Res., European Patent Application EP 16504). The resulting α,α,α-trihaloethanol is oxidized and group X can be deprotected as above to give the thrombin inhibitors or formulae (274).

The α-ketoester thrombin inhibitors, exemplified by (276), are prepared according to a route disclosed by Iwanowicz et. al. in Bioorgan. Med. Chem. Lett. 12, 1607 (1992). The tris(ethylthio)methyl anion is added to the peptidyl aldehyde (273) in a solvent such as tetrahydrofuran, 1,2-dimethoxyethane or toluene at −100° C. or higher to give the alcohol (275). The α-hydroxyl ester is generated from (275) by treatment with a mixture of mercuric salts, such as mercuric chloride and mercuric oxide, in an alcohol or water. Swern or Pfitzner-Moffat oxidation of the s-hydroxyl ester followed by the deprotection of substituent X protecting group provides thrombin inhibitors of formula (276).

Another method for the preparation of compound (276) substitutes a 1-lithio-1-alkoxyethene or 1-magnesio-1-alkoxyethene for the tris(ethylthio)methyl anion of Scheme 15 in an addition reaction with peptidyl aldehyde (273). There can be obtained an adduct analogus to the tris (ethylthio)hydroxyethyl compound (275) when excess 1-magnesio- or 1-lithio-1-alkoxyethene anion is stirred at temperatures ranging from −100° C. to ambient temperature with (273) in anhydrous solvents such as diethyl ether or tetrahydrofuran. This alkoxyolefin product may then be transformed to (276) by oxidative cleavage with reagents such as ozone or periodate in an inert solvent such as a halohydrocarbon, lower alkyl ketone, an alcohol or water at temperatures ranging from −100° C. to ambient temperature, followed by oxidation of the intervening α-hydroxyester and deprotection as described above.

The preparation of the α,α-dihalomethylketone thrombin inhibitors of this invention is outlined in Scheme 47.

Scheme 47.

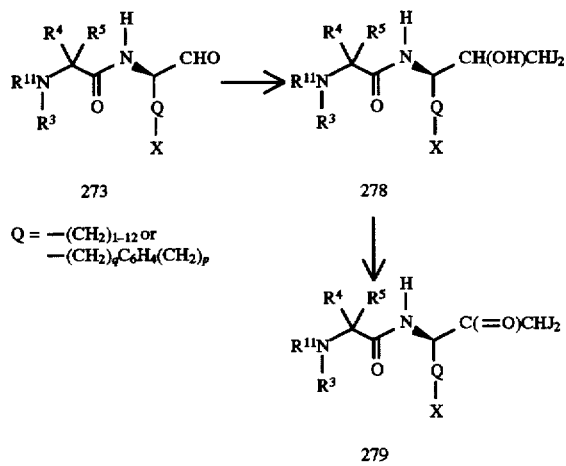

The α,α-dihalomethylketone (279), where J is fluoro can be prepared from the aldehyde (273) by selective reaction of the aldehyde with the anion of the corresponding dihalomethane. The metallated dihalomethane anion is generated from one equivalent each of a strong hindered base, such as lithium tetramethylpiperidide or tertbutyllithium, and the selected dihalomethane in an anhydrous, inert solvent like tetrahydrofuran or 1,2-dimethoxyethane at −100° C. or higher according to the method of Taguchi et. al. *Bull. Chem. Soc. Jpn.*, 50, 1588 (1977). The metallated dihalomethane anion can be added to the aldehyde (273) at −100° C. or higher. Alternatively, the dihalomethane anion is generated from a dihalomethyl(trimethyl)silane and an anhydrous fluoride ion source such as tris(diethylamino)sulfonium difluoromethyl silicate in an inert solvent like benzene, acetonitrile or tetrahydrofuran at −78° C. or higher, then (273) can be added to give dihaloethanol (278) according to the method of Fujita and Hiyama, *J. Am. Chem. Soc.* 107, 4085 (1985). The resulting dihaloethanol can be oxidized to ketone (279) by the Swern or Pfitzner-Moffat procedure. Removal of the protecting group(s) on substituent X of (279) gives the α,α-dihalomethylketone thrombin inhibitors.

α-Halomethylketone thrombin inhibitors can be prepared by the process illustrated in Scheme 48. The acid chloride (281) can be prepared from acid (272), wherein M is hydrogen or its trialkylammonium, sodium or potassium salt with a chlorinating agent such as thionyl chloride, oxalyl chloride or dichloromethylmethyl ether in a solvent like tetrahydrofuran or dichloromethane with or without a catalytic amount of N,N-dimethylformamide at −78° C. or higher. Alternatively, the mixed anhydride of (272)$_m$ay be prepared as described for (272) in Scheme 46. Compound (281) or the mixed anhydride of (272) can be treated with an ether solution of diazomethane and either anhydrous hydrogen fluoride or hydrogen chloride gas according to that described by McPhee and Klingsbury, *Org. Synth. Coll.* III, 119 (1955); or hydrogen bromide according to the method Miescher and Kaji, *Helv. Chim. Acta.* 24, 1471 (1941).

Scheme 48.

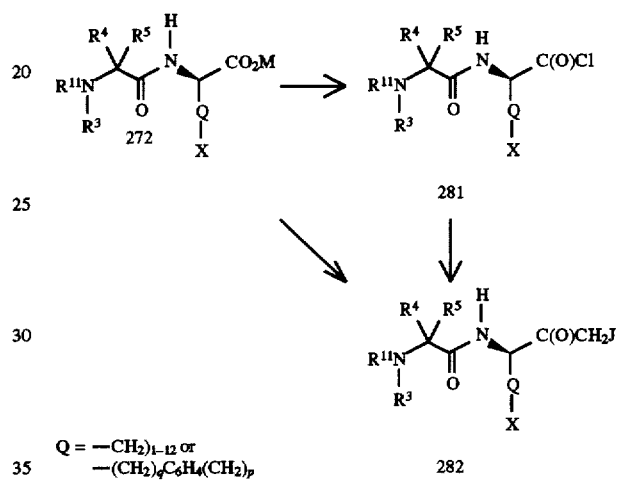

Selection of the hydrogen fluoride gas will give the α-fluoromethylketone analog, (282) wherein J is fluoro; and hydrogen chloride gas gives the α-chloromethylketone analog (282) wherein J is chloro. Deprotection of X gives the corresponding thrombin inhibitors of (282).

The general preparative route for the α,β-diketoester, -amide and -ketone thrombin inhibitors of this invention is exemplified in Scheme 49. Compound (281) or the mixed anhydride of (272) can be reacted with a Wittig reagent such as methyl (triphenyl-phosphoranylidene)acetate in a solvent like tetrahydrofuran or acetonitrile at temperatures ranging from 0° C. to the reflux point of the solvent to give (284). Oxidative cleavage of the phosphoranylidene (284) with an oxidizing agent like ozone or OXONE™ in an inert solvent such as tetrahydrofuran, dichloromethane or water at temperatures of −78° C. or higher gives the vicinal tricarbonyl compound (285), analogous to that described by Wasserman and Vu, *Tetrahedron Lett.* 31, 5205 (1990). Cleavage of the protecting group can provide thrombin inhibitors of formula (285).

Scheme 49.

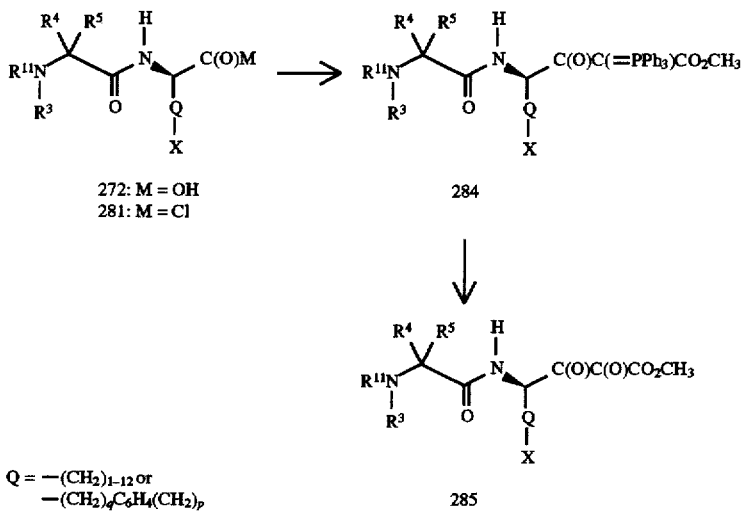

Q = —(CH$_2$)$_{1-12}$ or
—(CH$_2$)$_o$C$_6$H$_4$(CH$_2$)$_p$

The preparative routes for the synthesis of the α-mono- and α,α-dihalo-β-ketoester -amide and ketone thrombin inhibitors of this invention are summarized in Scheme 50. The exemplified β-ketoester (287) is available from the acid derivative (272). The acid (272) can be treated with carbonyl diimidazole in an inert solvent such as tetrahydrofuran or dichloromethane at 0° C. or higher to form the acyl imidazole. This acyl imidazole, or the mixed anhydride of (272), can be further reacted with lithioethylacetate in solvents such as 1,2-dimethoxyethane or tetrahydrofuran/hexane at temperatures ranging from –100° C. to ambient temperature, according to the method of Dow, *J. Org. Chem.* 55, 386 (1990) to give β-ketoester (287).

the reflux point of the selected solvent according to the methods of Uhle, *J. Am. Chem. Soc.* 83, 1460 (1961); and DeKimpe et. al., Synthesis 2, 188 (1987). The α,α-dihalo analog (289) where J is chloro is available from halogenation with molecular chlorine in a halogenated solvent at temperatures of –20° C. or higher according to the method of Bigelow and Hanslick, *Org. Syn. Coll.* II, 244 (1943). Reagents such as N-fluorobis[(trifluoromethyl sulfonyl] imide are useful for the preparation of mono- and difluoro analogs (288) and (289) by reacting the appropriate stoichiometry of this reagent with (287) in a halogenated solvent at temperatures of –78° C. or higher according to the method of Resnati and DesMarteau, *J. Org. Chem.* 56, 4925 (1991).

Scheme 50.

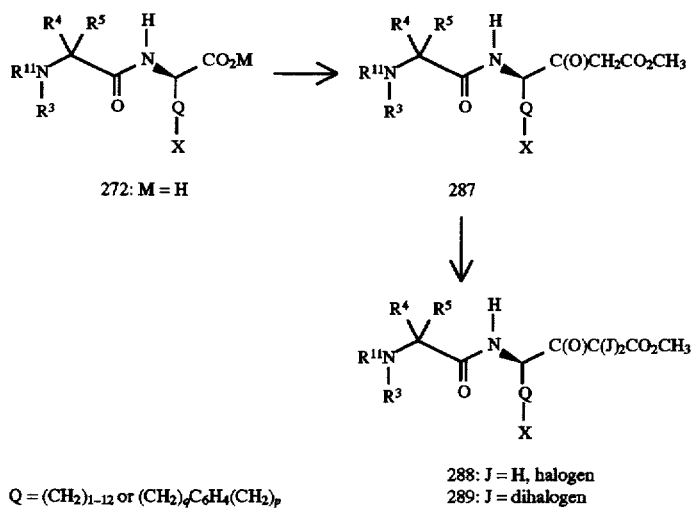

Q = (CH$_2$)$_{1-12}$ or (CH$_2$)$_o$C$_6$H$_4$(CH$_2$)$_p$

288: J = H, halogen
289: J = dihalogen

Compound (287) serves as a substrate for both mono- and dihalogenation. The α-monochloro analog of (288), where J is each chlorine and hydrogen, can be prepared by controlled halogenation reactions with reagents like N-chlorosuccinimide or thionyl chloride in an inert halogenated solvent and at temperatures ranging from –20° C. to Deprotection of substituent X of the halogenation products (288) and (289) can provide the corresponding thrombin inhibitors.

Compounds of formula (287) also serves as a substrate for the preparation of tricarbonyl derivatives such as (285) (Scheme 49). Condensation of (287) with an aldehyde, such as benzaldehyde, gives an β-ene-α,γdione. This ene-dione can be oxidatively cleaved with reagents like ozone or periodate to give tricarbonyl analog (285).

The preparation of the mono- and dihalomethylketone thrombin inhibitors is outlined in Scheme 51. The intermediates formed in the preparation of the α-mono- and α,α-dihalo-β-ketoester thrombin inhibitors of Scheme 49 can be used in these preparations.

The decarboxylation of these halogenation products, (288) and (289), can be effected by saponification of the ester with mild aqueous base such as potassium carbonate or sodium hydroxide in water miscible solvents like an alcohol, tetrahydrofuran or N,N-dimethylformamide, followed by adjusting the pH to a range of 4 to 6. This mixture can be either stirred at ambient temperatures or heated at various temperatures up to the reflux point of the solvent chosen until the formation of (279) or (282) is complete and is similar to that reported in Matsuda et. al., *Tetrahedron Lett.* 30, 4259 (1989). Removal of protecting group(s) can provide thrombin inhibitors corresponding to (279) or (282).

A process for the preparation of the boropeptide thrombin inhibitors of this invention from intermediates (291) and (292) is disclosed in Scheme 52. Compound (291) serves as a starting point for isothiouronium thrombin inhibitors (296) and (297). The boronic ester (296) is prepared by stirring a solution of (291) and thiourea in an inert polar solvent, such as an alcohol or N,N-dimethylformamide, at temperatures ranging from ambient to the reflux temperature of the selected solvent. It is understood that a boronic acid ester like compound (296) is an effective thrombin inhibitor, however, it may be transformed to the corresponding free boronic acid (297) without a loss of biological activity. Compound (297) is derived from the boron ester (296 by transesterification under equilibrium conditions.

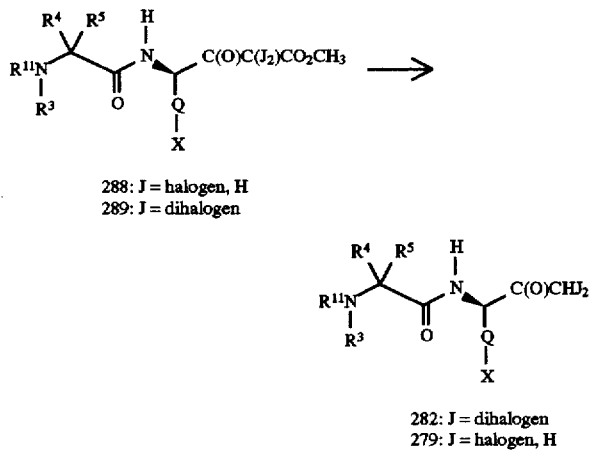

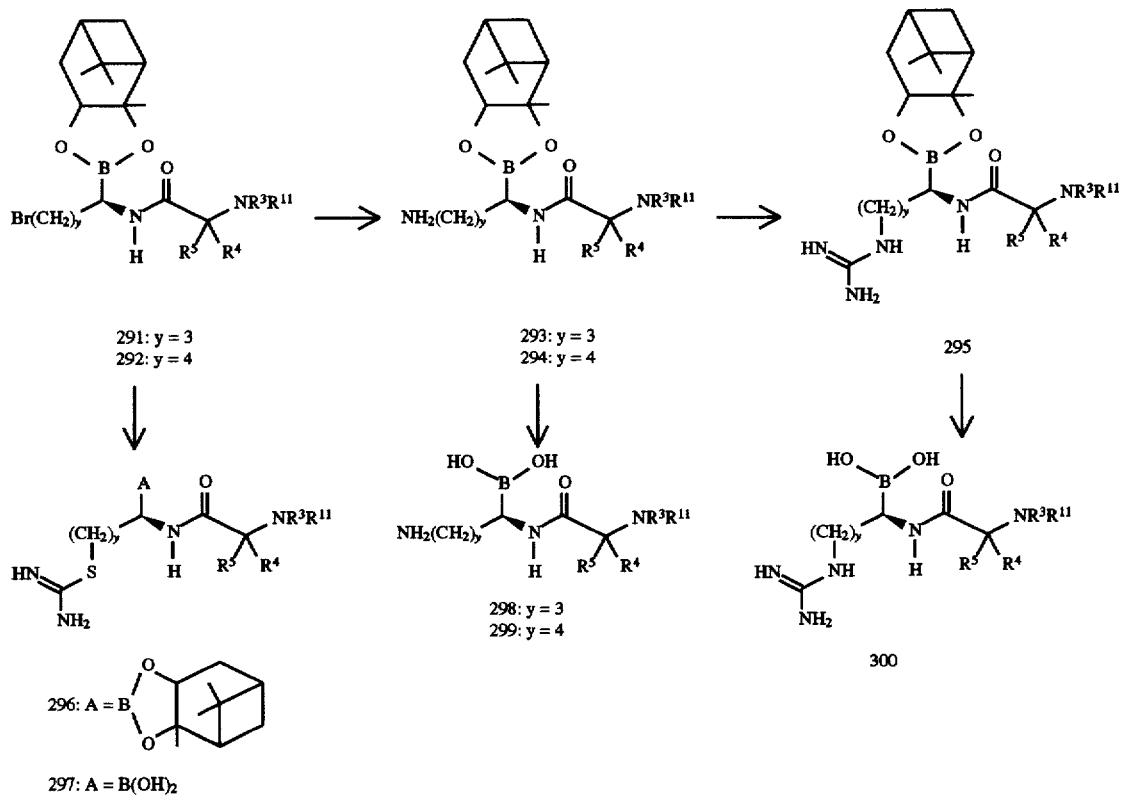

Thus stirring ester (296) with an excess of an alkyl- or aryl boric acid in a biphasic mixture of neutral or acidic water and an immiscible solvent, such as ethyl ether or toluene, gives (297) after several hours at ambient temperature. The conditions generally preferred use 5 to 10 equivalents of phenylboric acid in ethyl ether/water at neutral pH. Thrombin inhibitors (293) to (299) are obtained by reduction of an azide intermediate prepared from (291) or (292). The azide intermediate is prepared by heating either (291) or (292) with an inorganic azide, such as sodium or potassium azide, in an anhydrous polar aprotic solvent, such as acetone, dimethylformamide or methyl sulfoxide at temperatures ranging from ambient to 130° C. Alternatively, phase transfer conditions may be employed to prepare the azide intermediate from (291) or (292). For example, a tetraalkylammonium azide in a non-polar aprotic solvent, such as tetrahydrofuran or toluene, or a crown ether and inorganic azide in biphasic mixtures of water and an immiscible solvent, such as benzene, toluene or xylene, can be stirred at room temperature or heated up to the reflux point of the selected solvent. The primary amines (293) and (294) are most conveniently obtained from the catalytic hydrogenation of the azide in an inert solvent, such as an alcohol, ethyl acetate or tetrahydrofuran with a transition metal catalyst such as platinum or palladium on carbon under an atmosphere of hydrogen gas. A variety of alternative methods are also useful and can be found in the monograph by Hudlicky (1984, pp. 76). The acid salt of the resulting amines (293) and (294) may be formed by the addition of one equivalent of the desired acid to the hydrogenation mixture. Phenylboric acid mediated hydrolysis of esters (293) and (294) gives the free boronic acid thrombin inhibitors (298) and (299), compounds of formula (I) of the invention.

Compounds containing a primary guanidine or N-alkyl guanidine functionality may be prepared by the alternative process outlined in Scheme 52. As illustrated with primary amine (293), the transformation to (295) is effected with a guanidinylation agent, such as an S-alkyl thiourea, aminoiminomethane sulfonic acid reported by Miller and Bischoff *Synthesis* 9, 777 (1986), cyanamide reported by Kettner et al. (1990) or their N-alkyl derivatives. This mixture is stirred at room temperature or higher with a base, such as potassium carbonate, triethylamine or N,N-dimethylaminopyridine in an inert solvent like water, alcohol, N,N-dimethylformamide or acetone. The guanidine boronic acid esters (295) can be deesterified to give the corresponding boronic acid (300) by the phenylboric acid procedure described above.

According to Scheme 53, the bromide (292) is converted to the corresponding alkylnitrile (302) upon exposure to the cyanide anion under a variety of conditions.

Scheme 53

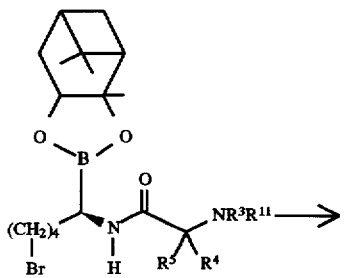

-continued
Scheme 53

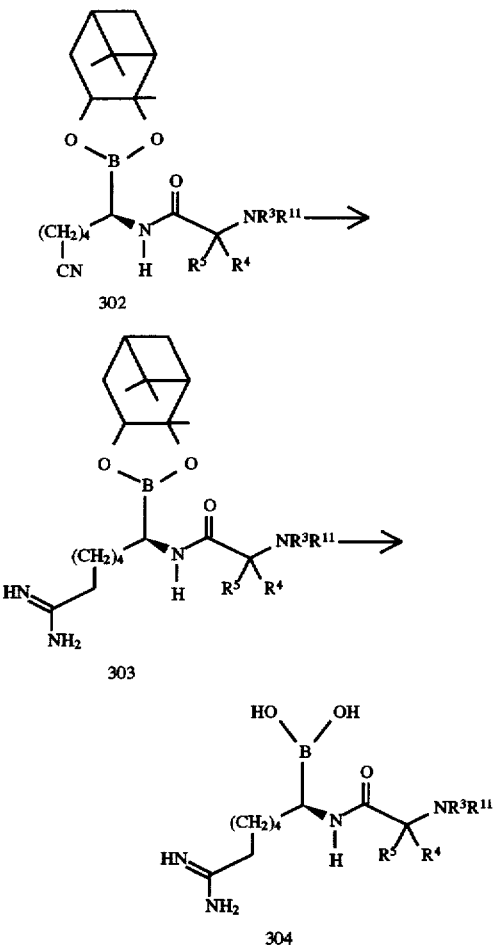

Effective methods include the use of potassium or sodium cyanides in polar aprotic solvents, such as N,N-dimethylformamide, methylsulfoxide, acetone or ethylmethyl ketone, at temperatures ranging from ambient up to the reflux point of the selected solvent. More useful, however, are conditions employing phase transfer agents such as tetrabutylammonium cyanide in a nonpolar aprotic solvent such as tetrahydrofuran or toluene, or a biphasic mixture of a crown ether and an inorganic cyanide in water with an immiscible solvent like benzene, toluene or xylene. These mixtures can be stirred at ambient temperature or heated up to the reflux temperature of the selected solvent. An amidine like (303) is prepared by first treating nitrile (302) with a saturated solution of a mineral acid such as hydrogen chloride in an alcohol solvent at room temperature or lower. The intermediate O-alkylimidate can be exposed to ammonia, or a primary or secondary amine under anhydrous conditions with or without an inert solvent. As illustrated in Scheme 5, compound (303) is produced by treating the O-alkylimidate formed from (302) with neat anhydrous ammonia at reflux. The free boronic acid (304) is obtained by transesterification of (303) with phenylboric acid in a mixture of water and diethyl ether.

EXAMPLE 1

$N^1$-(4-Phenylbenzoyl)boroarginine (+)-Pinanediol, Bisulfite

Part A: (+)-Pinanediol 4-bromo-1(R)-(4-phenylbenzo-yl)-aminobutane-1-boronate.

To a solution of (+)-pinanediol 4-bromo-1(R)-aminobutane-1-boronate hydrochloride (5.00 g, 13.6 mmol) in dichloromethane (50 mL) at 0° C. was added 4-phenylbenzoyl chloride (4.97 g, 22.9 mmol) followed by N-methylmorpholine (4 mL, 36 mmol). After 1 hour, the cooling bath was removed and the mixture stirred at room temperature for 2 hours. The mixture was then diluted with ethyl acetate and washed with 0.1M hydrochloric acid, saturated sodium bicarbonate and saturated sodium chloride. The organic phase was dried over anhydrous magnesium sulfate, filtered and the filtrate concentrated in vacuo to afford 3.37 g (48%) of the desired amide, mass spectrum: (M+H)$^+$=510/512; $^1$H NMR (300 MHz, CDCl$_3$) d7.9 (2H, d, J=8.3), 7.84 (1H, bs), 7.6 (2H, d, J=8.3), 7.44 (5H, m), 4.37 (1H, m), 3.41 (1H, t, J=6.9), 2.0 (10H, m) 1.49 (3H, s), 1.38 (1H, m), 1.29 (3H, s), 0.91 (3H, s).

Part B: (+)-Pinanediol 4-azido-1(R)-(4-phenylbenzo-yl)-aminobutane-1-boronate.

To a solution of (+)-pinanediol 4-bromo-1(R)-(4-phenylbenzoyl)aminobutane-1-boronate (3.37 g, 6.60 mmol) in dimethylformamide (6 mL) was added sodium azide (547 mg, 8.41 mmol). The resulting mixture was heated at 70° C. for 2 hours, cooled to room temperature, and diluted with ethyl acetate. The mixture was then washed with water, saturated sodium chloride and dried over anhydrous magnesium sulfate. Filtration, followed by concentration of the filtrate in vacuo gave 3.04 g (97%) of the desired azide, mass spectrum: (M+H)$^+$=473; $^1$H NMR (300 MHz, CDCl$_3$) d7.89 (2H, d, J=8.3), 7.75 (1H, bs), 7.3 (7H, m), 4.32 (1H, m), 3.32 (1H, m), 2.0 (10H, m) 1.48 (3H, s), 1.3 (4H, m), 0.9 (3H, s).

Part C: N$^1$-(4-Phenylbenzoyl)boroarginine (+)-pinanediol, hydrochloride

To a solution of (+)-pinanediol 4-azido-1(R)—(4-phenylbenzoyl) aminobutane-1-boronate (3.04 g, 6.44 mmol) in methanol (30 mL) was added Pearlman's catalyst (Pd(OH)$_2$/C, 200 mg) and 1M hydrochloric acid (6.5 mL, 6.5 mmol). The mixture was placed on a Parr apparatus and hydrogenated at 50 psi for 3 hours. The mixture was filtered using Celite™, washed with methanol and the filtrate concentrated in vacuo. The resulting amorphous solid was dissolved in water and washed with ether. The aqueous phase was then concentrated in vacuo and crystallized from ethyl acetate-hexanes, giving 1.52 g (49%) of the desired amine hydrochloride, mass spectrum: (M+H)$^+$=447; mp: 157°–170° C.; $^1$H NMR (400 MHz, CDCl$_3$/DMSO-d$_6$) d9.88 (1H, bs), 8.18, (2H, d, J=8.3), 8.13 (3H, bs), 7.68 (2H, d, J=8.3), 7.61 (2H, d J=7.0), 7.45 (2H, d, J=7.0), 7.37 (1H, d, J=7.30), 4.20 (1H, d, J=6.3), 2.99 (1H, m), 2.87 (2H, m), 2.31 (1H, m), 2.13 (1H, m), 1.84 (7H, m), 1.56 (1H, d, J=10.0), 1.42 (3H, s), 1.29 (3H, s), 0.89 (3H, s).

Part D: N$^1$-(4-Phenylbenzoyl)boroarginine (+)-pinanediol, bisulfite.

To a solution of
N$^1$-(4-phenylbenzoyl)boroarginine (+)-pinanediol, hydrochloride (80 mg, 0.17 mmol) in ethanol (2 mL) was added 4-dimethylaminopyridine (40 mg, 0.33 mmol). After 15 minutes, aminoiminomethanesulfonic acid (40 mg, 0.32 mmol) was added and the resulting mixture heated at reflux for 3 hours. After cooling to room temperature, the mixture was filtered and the filtrate concentrated in vacuo. The residue was dissolved in chloroform and washed with 0.1M hydrochloric acid, water and dried over anhydrous magnesium sulfate. Filtration, followed by concentration of the filtrate in vacuo afforded 73 mg (84%) of the desired guanidine, mass spectrum: (M+H)$^+$=489; $^1$H NMR (400 MHz, CDCl$_3$, 60° C.) d9.48 (1H, bs), 8.10 (2H, d, J=8.1), 8.07 (1H, bs), 7.75 (1H, bs), 7.54 (2H, d, J=8.3), 7.48 (2H, d, J=7.0), 7.35 (3H, m), 7.06 (4H, bs), 4.19 (1H, bd, J=8.3), 3.1 (2H, m), 2.84 (1H, m), 2.29 (1H, m), 2.12 (1H, m), 1.96 (1H, m), 1.75 (6H, m), 1.47 (1H, d, J=10.2), 1.40 (3H, s), 1.24 (3H, s), 0.83 (3H, s).

EXAMPLE 34

(+)-Pinanediol 4-(Formamidino)Thio-1(R)-(4-Phenylbenzoyl)Aminobutane-1-Boronate, Hydrobromide (+)-Pinanediol 4-(formamidino)thio-1(R)-(4-phenylbenzoyl)aminobutane-1-boronate, hydrobromide.

To a solution of (+)-pinanediol 4-bromo-1(R)-(4-phenylbenzoyl)aminobutane-1-boronate (200 mg, 0.392 mmol) in methanol (3 mL) was added thiourea (120 mg, 1.58 mmol). The reaction was stirred at room temperature for 3 days. The mixture was concentrated in vacuo, the residue dissolved in water and washed with ether. Concentration of the aqueous portion afforded 80 mg (35%) of the desired isothiourea, mass spectrum: (M+H)$^+$=506; $^1$H NMR (300 MHz, CDCl$_3$) d8.15 (2H, d, J=8.4), 7.61 (2H, d, J=8.4), 7.52 (2H, m), 7.38 (3H, m), 6.47 (1H, bs), 4.23 (1H, dd, J=6.6, 1.9), 3.24 (1H, m), 3.14, (1H, m), 2.96, (1H, m), 2.32 (1H, m), 2.15 (1H, m), 1.99 (1H, m), 1.78 (6H, m), 1.48 (1H, d, J=10.1), 1.42 (3H, s), 1.27 (3H, s), 0.86 (3H, s).

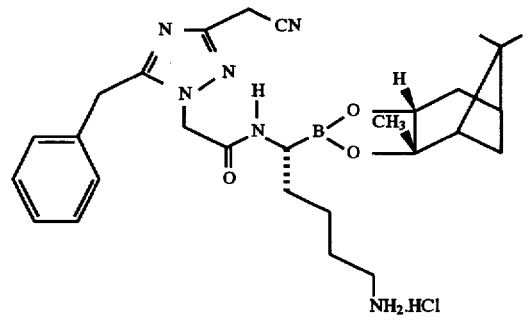

EXAMPLE 898

R-N$^1$-(3-Cyanomethyl-5-phenylmethyl-1,2,4-triazol-1-yl)acetyl-borolysine, (+)-pinanediol ester, hydrochloride; X=—CH$_2$NH$_2$, R$^{13}$=—CH$_2$Ph, R$^{14}$=—CH$_2$CN, Y$^1$, Y$_2$=(+)-pin

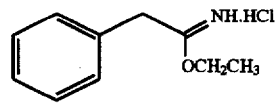

Part A. Ethyl benzylimidate, hydrochloride.

HCl gas (17.1 g, 469 mmol, 1.1 eq) was slowly bubbled into a solution of phenylacetonitrile (50.00 g, 427 mmol, 1 eq) in ethanol (27.6 mL, 469 mmol, 1.1 eq) at 0° C. The reaction was put into the refrigerator over the weekend. After warming to room temperature, ether (300 mL) was added to the reaction mixture which had solidified and the contents were vigorously stirred at 0° C. to pulverize the mixture. The solid material was filtered while cold under an inert atmosphere and the filter cake rinsed with some more ether. The product was dried under high vacuum to yield 60.0 g (mp 94.0°–95.0° C.) of a white solid. A second crop yielded 20.98 g (96.0°–97.5° C.).

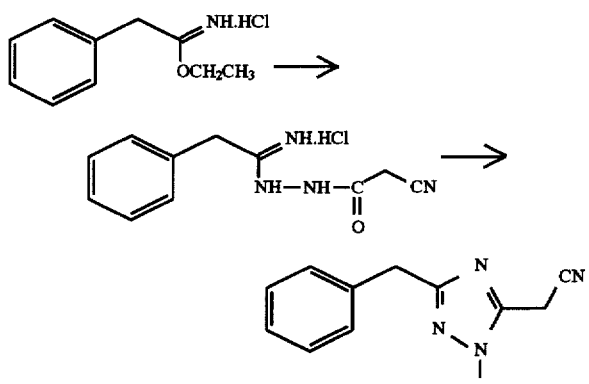

Part B. 3-Cyanomethyl-5-phenylmethyl-1,2,4-triazole.

The imidate from part A (14.92 g, 91 mmol, 1 eq) was dissolved in ethanol (250 mL) and cooled to 0° C. under an inert atmosphere. Cyanoacetohydrazide (9.06 g, 91 mmol, 1 eq) dissolved as best possible in warm ethanol was added, and the resultant mixture stirred at room temperature overnight. The mixture was filtered, and the filtrate concentrated to yield a gummy orange solid. Trituration from hexanes yielded 19.72 g of solid product acylamidrazone (MS detects $(M+H)^+=216$). This intermediate was heated neat (oil bath) at 170° C. under an inert atmosphere for 0.5 h to crack out water. The product was cooled to room temperature and dissolved in ethyl acetate. The solvent was dried (MgSO4) and stripped to yield 11.89 g of an orange solid. Flash chromatography over silica gel in solvent systems consisting of 3:1 pentane/ethyl acetate to 100% ethyl acetate to 4:1 chloroform/methanol yielded 6.76 g (38%) of a light pink solid product; m.p.=140.0°–142.5° C. NMR (DMSO-$d_6$) δ 14.00–13.60 (bs, 1H); 7.40–7.10 (m, 5H); 4.08 (s, 2H); 4.05 (s, 2H). MS: $(M+H)^+=199$.

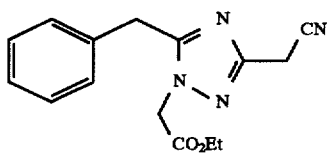

Part C. Ethyl (3-cyanomethyl-5-phenylmethyl-1,2,4-triazol-1-yl)acetate.

The compound from part B (3.36 g, 17 mmol, 1 eq) was added portionwise to a mixture of DMF and 50% NaH (0.81 g, 17 mmol, 1 eq) at 25° C. After $H_2$ evolution had ceased, the mixture was heated a little with a heat gun to ensure complete deprotonation. The mixture was cooled to 0° C. and ethyl bromoacetate (1.88 mL, 17 mmol, 1 eq ) was added. The reaction was allowed to warm to room temperature and was stirred overnight. Ethyl acetate was added and the mixture washed with water (5×) to remove the DMF. The organic layer was dried (MgSO4) and stripped to yield 6.10 g of a reddish oil. Flash chromatography in 3:1 hexanes/ethyl acetate to 1:1 hexanes/ethyl acetate yielded 2.93 g of an amber oil which consisted of a 4:1 mixture of regioisomers as determined by NMR with the major isomer being depicted above. NMR (major isomer) (CDCl3) δ 7.40–7.20 (m, 5H); 4.68 (s, 2H); 4.25–4.05 (m, 4H); 3.84 (s, 2H); 1.23 (t, 3H, J=7 Hz).

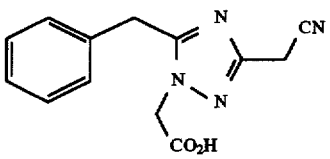

Part D. (3-Cyanomethyl-5-phenylmethyl-1,2,4-triazol-1-yl) acetate acid.

The product of part C (1.00g, 3.52 mmol, 1 eq), 1.000N NaOH (7.03 mL, 7.03 mmol, 2 eq) and methanol (10 mL) were mixed and stirred at room temperature. After 24 h, the methanol was stripped and the aqueous mixture washed with ether (2×). The aqueous layer was then acidified with conc. HCl and extracted with ethyl acetate (3×). The organic layers were combined, dried (MgSO4) and stripped to yield 0.66 g of an off-white glass. MS $(M+H)^+=257$.

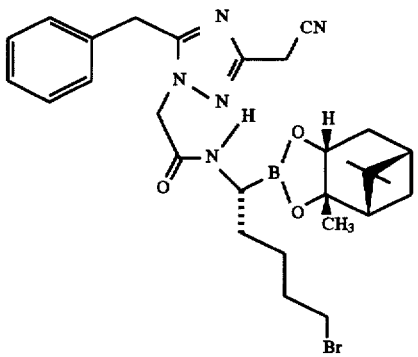

Part E. (+)-Pinanediol 5bromo-1(R)-((3-Cyanomethyl-5-phenylmethyl-1,2,4-triazol-1-yl)acetamido)pentane-1-boronate.

N-methylmorpholine (0.42 mL, 3.86 mmol, 1.5 eq) was added to a solution of the product in part D (0.66 g, 2.58 mmol, 1 eq) in THF at 25° C. The mixture was cooled to −20° C. and isobutylchloroformate (0.50 mL, 3.86 mmol, 1.5 eq) in THF was added dropwise. In a seperate flask, pinanediol 5-bromo-1-R-aminopentane-1-boronate hydrochloride (0.98 g, 2.58 mmol, 1 eq) was dissolved in $CHCl_{13}$ and cooled to −78° C. Triethylamine (0.36 mL, 2.58 mmol, 1 eq) was then added and the mixture syringed immediately into the reaction flask with the mixed anhydride. The reaction was allowed then to warm to room temperature overnight. The next day, the precipitate was filtered off and the solids were rinsed with THF. The filtrate was stripped to yield 410 mg of a white oil. Flash chromatography over silica gel in solvent systems consisting of 3:1 pentane/ethyl acetate to 100% ethyl acetate to 4:1 chloroform/methanol yielded 300 mg of a clear, colorless viscous oil and only one regioisomer by NMR. MS $(M+H)^+=633$ and 635. NMR (CDCl3) δ 7.40–7.10 (m, 5H); 6.13 (d, 1H, J=6 Hz); 4.62 (s, 2H); 4.40–4.20 (m, 1H); 4.17 (s, 2H); 3.86 (s, 1H); 3.50–3.20 (m, 3H); 2.40–2.10 (m, 2H); 2.10–1.75 (m, 4H); 1.75–1.10 (m, 13 H); 0.83 (s, 3H).

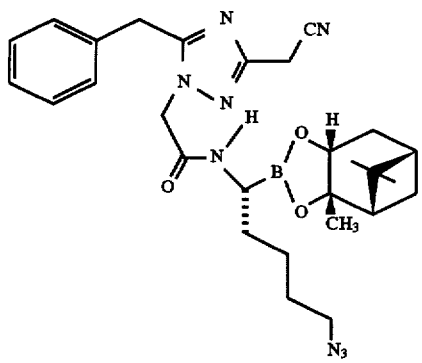

Part F. (+)-Pinanediol 5bromo-1(R)-((3-Cyanomethyl-5-phenylmethyl-1,2,4-triazol-1-yl)acetamido)pentane-1-boronate.

The product from Part E (300 mg, 0.52 mmol, 1 eq), sodium azide (1.03 mmol, 2 eq), and DMSO (5 mL) were mixed and stirred at room temperature under an inert atmosphere for 24 h. Ethyl acetate was added and the mixture rinsed with water (5×). The ethyl acetate layer was dried (MgSO$_4$) and stripped to yield 256 mg of a light amber oil. IR (neat)$_{2096}$ cm-1. NMR (CDCl3) δ 7.40–7.10 (m, 5H); 6.15 (d, 1H, J=6 Hz); 4.62 (s, 2H); 4.40–4.20 (d of d, 1H, J=7, 2 Hz); 4.20–4.10 (m, 2H); 3.85 (s, 2H); 3.40–3.10 (m, 3H); 2.50–1.40 (m, 9H); 1.40–1.00 (m, 9 H); 0.84 (s, 3H).

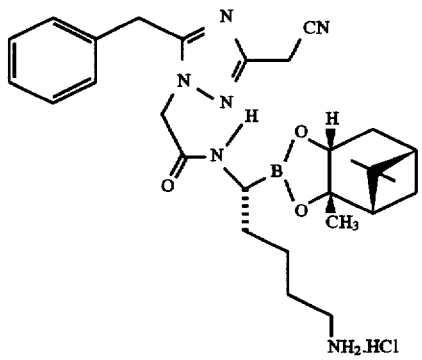

Part G. (+)-Pinanediol 5bromo-1(R)-((3-Cyanomethyl-5-phenylmethyl-1,2,4-triazol-1-yl)acetamido)pentane-1-boronate, hydrochloride salt.

The product from Part F (250 mg, 0.46mmol, 1 eq) and triphenylphosphine (157 mg, 0.6 mmol, 1.3 eq) and THF (5 mL) were mixed and stirred at room temperature. After 1 h, water (11 μM, 0.6 mmol, 1.3 eq) was added and the mixture stirred overnight. After 24 h, the reaction was not finished, and thus 1.3 eq more equivalents of water were added and the reaction stirred for another 24 h. The reaction was now complete and 1 equivalent of 1.000N HCl was added. The reaction was then stripped and water was added and the reaction again stripped. Ethyl ether was added and the mixture stripped once more. The residue was dried under high vacuum to yield 138 mg of a white glass. MS detects (M+H)$^+$=519 and 385 (minus pinanediol). Mass calculated for C$_{28}$H$_{40}$BN$_6$O$_3$: 519.3255. Found: 519.3274. NMR shows a 1:1 mixture of pinanediol ester and free boronic acid.

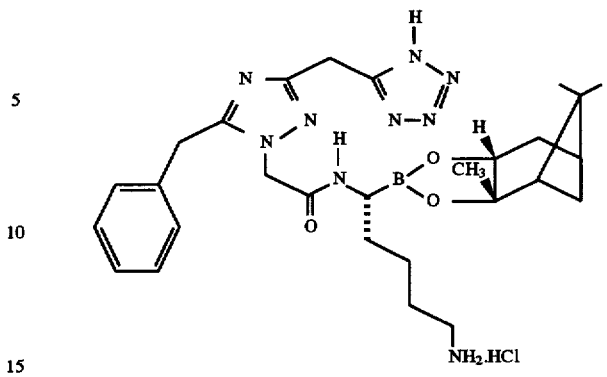

EXAMPLE 908

R-N$^1$-(3-(1H-tetrazol-5-yl)methyl-5-phenylmethyl-1,2,4-triazol-1-yl)acetyl-borolysine, (+)-pinanediol ester, hydrochloride; X=—CH$_2$NH$_2$, R$^{13}$=—CH$_2$Ph, R$^{14}$=—CH$_2$—(CN$^4$H), Y$^1$, Y$^2$=(+)-pin

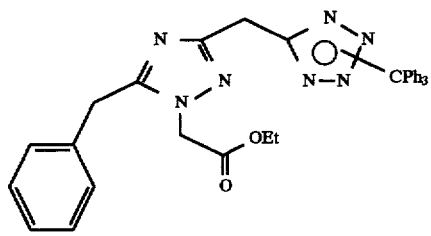

Part A. Ethyl (3)-N-triphenylmethyl)-1H-tetrazol-5-methyl-5-phenylmethyl-1,2,4-triazol-1-yl)acetate The product from Example 360, part C (1.83 g, 6.44 mmol, 1 eq), tributyltin chloride (1.75 mL, 6.44 mmol, 1 eq), sodium azide (0.42 g, 6.44 mmol, 1 eq), and xylenes (15 mL) were mixed and refluxed for 24 h under an inert atmosphere. The mixture was cooled to room temperature and pyridine was then added (0.57 mL, 7.08 mmol, 1.1 eq) followed after 0.5 h by trityl chloride (1.97 g, 7.08 mmol, 1.1 eq). The following day, the reaction was worked up by adding ethyl ether and rinsing the mixture with water (3×). The ether layer was dried (MgSO4), and stripped to yield 5.66 g of an amber oil. Flash chromatography in 3:1 pentane/ethyl acetate to 100% ethyl acetate over silica gel yielded 1.33 g of an amber oil which eventually crystallized. MS detects (M+H)$^+$=570 and 328 (M+H—CPh$_3$)$^+$.

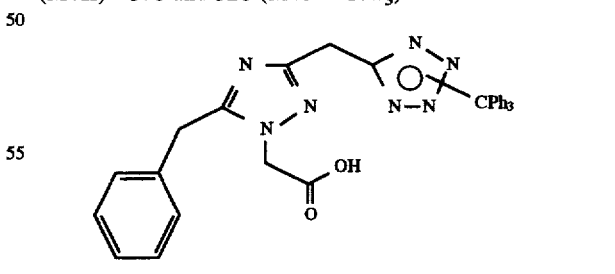

Part B. (3)-N-Triphenylmethyl)-1H-tetrazol-5-yl)methyl-5-phenylmethyl-1,2,4-triazol-1-yl)acetic acid.

The product from part A (200 mg, 0.35 mmol, 1 eq), 1.000N NaOH (0.39 mL, 0.39 mmol, 1.1 eq) and THF (5 mL) were mixed and stirred at room temperature under an inert atmosphere for 24 h. The reaction was not finished and thus 0.5 eq more of 1.000N NaOH were added and stirred overnight. Water was then added and the pH adjusted to 5 with 1N HCl. The mixture was stripped to dryness. THe residue was stirred in ethyl acetate. Some solids were filtered and the filtrate was stripped to yield 190 mg of a white glass. NMR (CDCl₃) δ 7.40–7.15 (m, 12 H); 7.15–7.00 (m, 8 H); 4.55 (s, 2); 4.40 (s, 2H); 4.10 (s, 2H).

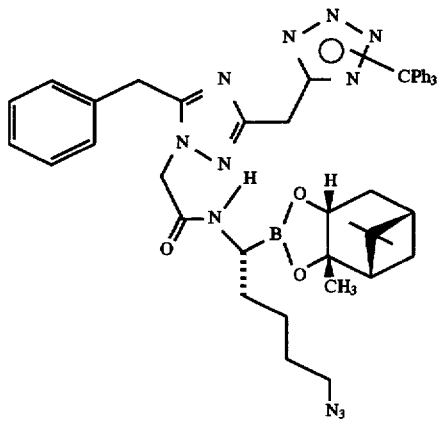

Part C. (+)-Pinanediol 5-azido-1(R)-((3-N-triphenylmethyl)-1H-tetrazol-5-ylmethyl-)5-phenylmethyl1,2,4-triazol-1-yl)acetamido)pentane-1-boronate.

The compound in part B was converted to the corresponding azidoboronic acid pinanediol ester by the methods disclosed in example 360, parts E and F. IR (neat) 2095 cm⁻¹. NMR (CDCl₃) δ 7.45–7.20 (m, 12H); 7.17 (d, 2H, J=7 Hz); 7.12 (d, 6H, J=7 Hz); 6.34 (d, 1H, J=6 Hz); 4.60 (s, 2H); 4.42 (s, 2H); 4.27 (d, 1H, J=7 Hz); 3.13 (t, 2H, J=2 Hz); 3.06 (q, 1H, J=7 Hz); 2.40–2.10 (m, 2H); 2.01 (t, 1H, J=6 Hz); 1.95–1.70 (m, 2H); 1.60–1.40 (m, 4H); 1.37 (s, 3H); 1.35–1.20 (m, 5H); 1.16 (d, 1H, J=11 Hz); 0.82 (s, 3H). MS detects (M+H)⁺=830 and (M+H—CPh₃)⁺=588.

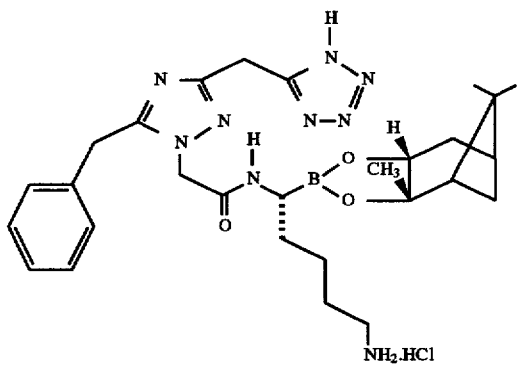

Part D. R-N¹-(3-(1H-tetrazol-5-yl)methyl-5-phenylmethyl-1,2,4-triazol-1-yl)acetyl-borolysine, (+)-pinanediol ester, hydrochloride.

The product from part C (135 mg, 0.16 mmol, 1 eq), 10% Pd on carbon (25 mg), chloroform (39 μL, 0.49 mmol, 3 eq) and methanol (5 mL) were mixed and stirred under hydrogen under balloon pressure for 24 h at room temperature. The mixture was filtered through a Celite® cake rinsing the cake well with methanol afterwards. The filtrate was stripped to yield an off-white glass. This glass was triturated with ethyl ether to yield after drying 50 mg of an off-white solid. Mass calcd. for C₂₈H₄₁BN⁹O₃: 562.3425. Found: 562.3413. NMR (DMSO-d₆) δ 8.75–8.50 (m, 1H); 7.40–7.10 (m, 5H); 4.87 (bs, 2H); 4.30–4.00 (m, 5H); 2.96–2.60 (m, 3H); 2.40–2.00 (m, 2H); 1.91 (t, 1H, J=6 Hz); 1.90–1.75 (m, 1H); 1.75–1.10 (m, 14 H); 0.80 (s, 3H).

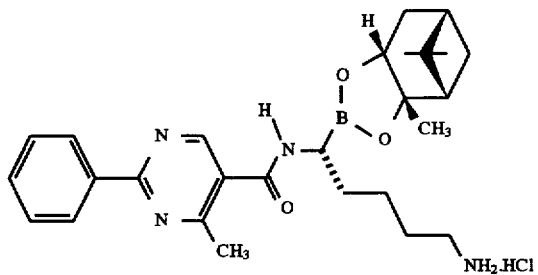

EXAMPLE 3458

R-N¹-((2-phenyl-4-methylpyrimidin-5-yl)carbonyl)borolysine, (+)-pinanediol ester, hydrochloride; X= —CH₂NH₂, R¹³=—Ph, R¹⁴=—CH₃, R¹⁵=H, Y¹, Y²=(+)-pin

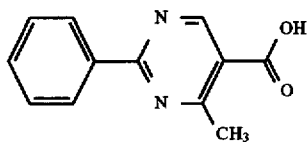

Part A. 2-Phenyl-4-methylpyrimidin-5-carboxylic acid.

The above compound was synthesized by the procedure of P. Schenone, L. Sansebastiano, L. Mosti *J. Heterocyclic Chem.* 1990, 27, 302 which is generally applicable to a wide variety of pyrimidine-5-carboxylic acids.

Part B. R-N¹-((2-phenyl-4-methylpyrimidine-5-yl)carbonyl)borolysine, (+)-pinanediol ester, hydrochloride.

The product was obtained using the procedures described in example 360, parts E and F and example 361, part D followed by prepatory TLC in 4:1 chloroform/methanol. (M+H)⁺=477. NMR (DMSO-d₆) δ 8.86 (s, 1H); 8.50–8.30 (m, 2H); 7.70–7.40 (m, 3H); 4.25 (d, 1H, J=7 Hz); 2.90–2.70 (m, 3H); 2.64 (s, 3H); 2.40–1.00 (m, 15H); 0.84 (s, 3H).

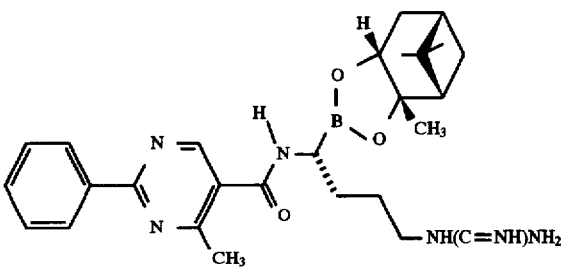

EXAMPLE 3538

R-N¹-((2-phenyl-4-methylpyrimidin-5-yl)carbonyl) boroarginine, (+)-pinanediol ester, hydrochloride;
X=—NH (C=NH) NH$_2$, R$^{13}$=—Ph, R$^{14}$=—CH$_3$, R$^{15}$=H, Y$^1$, Y$^2$=(+)-pin

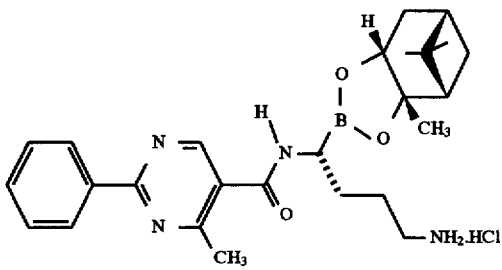

Part A. R-N¹-((2-phenyl-4-methylpyrimidin-5-yl)carbonyl) boroarginine, (+)-pinanediol ester, hydrochloride.

The above intermediate was synthesized by the procedures described for example 361 using the appropriate starting materials.

Part B. R-N¹-((2-phenyl-4-methylpyrimidin-5-yl)carbonyl) boroarginine, (+)-pinanediol ester, hydrochloride.

The product from part A (500 mg, 1 mmol, 1 eq), formamidinesulfonic acid (224 mg, 1.8 mmol, 2 eq), 4-(N, N-dimethylamino)pyridine (220 mg, 1.8 mmol, 2 eq, and ethanol (20 mL) were mixed and refluxed under an inert atmosphere for 5 hours. Some solid material was filtered and the filtrate was stripped to yield a yellow glass. The glass was taken up in chloroform/0.1N HCl. Solids precipitated. These were filtered and dried to yield 144 mg of product as a white powder: mp 132° C. (dec.). (M+H)$^+$=505.

Mass calcd. for C$_{27}$H$_{38}$BN$_6$O$_3$: 505.3086. Found: 505.3098. NMR (DMSO-d$_6$) δ 8.89 (s, 1H); 8.60–8.40 (m, 2H); 8.05–7.80 (m, 1H); 7.65–7.40 (m, 3H); 7.40–6.80 (m, 3H); 4.19 (d, 1H, J=7 HZ); 3.60–3.20 (m, 3H); 2.85–2.40 (m, 4H); 2.40–1.95 (m, 1H); 1.95–1.00 (m, 16 H); 0.80 (t, 3H).

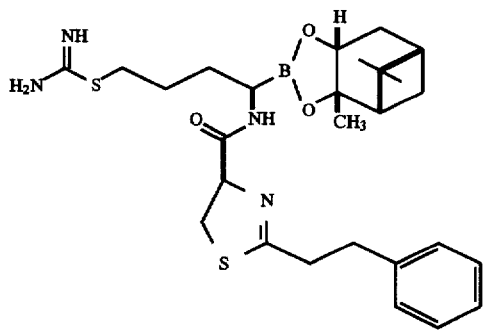

EXAMPLE 5926

N¹-[(4R)-2-(2-Phenyl)ethyl-Thiazoline-4-Carboxy]-R-borothioarginine-(+)-pinanediol ester Part A. (4R )-2-(2-phenyl)-thiazoline-4-carboxylic acid ethyl ester.

Cysteine ethyl ester hydrochloride (950 mg, 5.10 mmol) was added to a solution of ethyl (2-phenyl)ethylimidate (900 mg, 5.10 mmol) [prepared by the method of North, M.; Pattenden, G. *Tetrahedron* 1990, 46, 8267] in EtOH (20 mL) at room temperature. The reaction mixture was stirred for 16 h and concentrated under reduced pressure. The residue was partitioned between H$_2$O (ca. 50 mL) and EtOAc (ca. 100 mL) and the layers were separated; the aqueous phase was extracted with EtOAc (1×20 mL). The combined organic layers were washed with saturated aqueous NaCl$_1$ (1×50 mL), dried (Na$_2$SO$_4$), and concentrated under reduced pressure to give an oil which was purified by flash chromatography, elution with 3:1 hexanes—EtOAc, to afford 885 mg (66%) of the title compound as a colorless oil.
¹H NMR (300 MHz, CDCl$_3$) δ 7.23 (comp, 5H), 5.05 (dd, 1H, J=9.5, 9.1 Hz), 4.27 (dq, 2H, J=7.0, 1.8 Hz), 3.55 (m, 2H), 2.97 (m, 2H), 2.86 (m, 2H), 1.32 (t, 3H, J=7.0 Hz); LRMS 264 (M+1, base).

Part B. (4R)-2-(2-phenyl)ethyl-thiazoline-4carboxylic acid.

A solution of lithium hydroxide monohydrate (96 mg, 2.28 mmol) in H$_2$O (2 mL) was added to a solution of (4R)-2-(2-phenyl)ethyl-thiazoline-4-carboxylic acid ethyl ester (400 mg, 1.52 mmol) in THF (8 mL) and MeOH (5 mL). The reaction mixture was stirred at room temperature for 1 h at which time 2M aqueous HCl was added until pH=2 and the aqueous phase was extracted with EtOAc (2–30 mL). The combined organic layers were washed with saturated aqueous NaCl (1–20 mL), dried (MgSO$_4$), and concentrated under reduced pressure to give 340 mg (95%) of the title compound as an oil. ¹H NMR (300 MHz, CDCl$_3$) δ 7.22 (comp, 5H), 6.86 (br s, 1H), 5.14 (dd, 1H, J=9.5, 9.1 Hz), 3.64 (m, 2H), 2.96 (comp, 4H); LRMS 236 (M+1, base).

Part C. (1R)-4-Bromo-1-[(4R)-2-(2-Phenyl)ethyl-thiazoline-4carbox]amido-1-boronic acid-(+)-pinanediol ester.

A solution of (4R)-2-(2-phenyl)ethyl-thiazoline-4-carboxylic acid (335 mg, 1.43 mmol) and 4-methylmorpholine (0.47 mL, 4.28 mmol) in 10 mL of anhydrous THF at −20° C. was treated with i—butyl chloroformate (0.20 mL, 1.57 mmol) and stirred for 2 min after which a solution of (1R)-4-bromoaminobutane-1-boronic acid (+)-pinanediol ester (522 mg, 1.43 mmol) in 4 mL of anhydrous DMF was added. The reaction mixture was stirred at −20° C. for 15 min, warmed to room temperature over 18 h then poured into EtOAc (ca. 100 mL) and washed with H$_2$O (3–25 mL), and saturated aqueous NaCl (1–25 mL), dried (Na$_2$SO$_4$) and concentrated under reduced pressure. The residue was purified by flash chromatography, elution with 3:2 hexanes—EtOAc, to give 306 mg (39%) of the title compound as an oil. LRMS 549, 547 (M+1, base).

Part D. N¹-[(4R -2-2-Phenyl)ethyl-Thiazoline-4-Carboxy]-R-borothioarginine-(+)-pinanediol ester.

A mixture of (1R)-4-bromo-1-[(4R)-2-(2 -phenyl)ethyl-thiazoline-4-carbox]amido-1-boronic acid (+)-pinanediol ester (295 mg, 0.54 mmol) and thiourea (82 mg, 1.08 mmol) in 10 mL of EtOH was heated at reflux for 14 h then cooled to room temperature and concentrated under reduced pressure. The residue was purified by size exclusion chromatography on Sephadex LH-20, elution with MeOH, to give a glass which was dissolved in 3 mL of THF and treated with Et$_2$O (ca. 10 mL) to give a solid that was washed with Et$_2$O (ca. 5 mL) and dried to afford 230 mg (68%) of the title compound. LRMS 543 (M+1, base); HRMS Calcd for C$_{27}$H$_{40}$BN$_4$O$_3$S$_2$: 543.2635. Found: 543.2643.

The compounds in the following tables were or can be synthesized by the methods discussed previously or by methods familiar to one skilled in the art.

The compounds listed in Tables 1–61 may be prepared using the above examples. It is understood that R$^{14-16}$ and R$^{A-C}$ in the tables correspond to independent R13 groups as described within the scope of this application.

TABLE 1

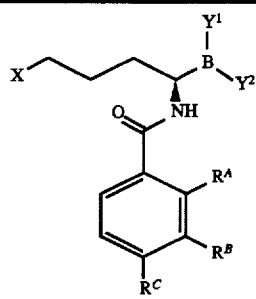

| Ex | X | R^A | R^B | R^C | Y^1, Y^2 | Phys Data |
|---|---|---|---|---|---|---|
| 1 | NHC(NH)NH_2 | H | H | Ph | (+)-pin | A |
| 2 | NHC(NH)NH_2 | H | Ph | H | (+)-pin | BZ |
| 3 | NHC(NH)NH_2 | H | OPh | Ph | (+)-pin | B |
| 4 | NHC(NH)NH_2 | H | H | 4-pyridyl | (+)-pin | C |
| 5 | NHC(NH)NH_2 | COPh | H | H | (+)-pin | |
| 6 | NHC(NH)NH_2 | H | COPh | H | (+)-pin | |
| 7 | NHC(NH)NH_2 | H | H | COPh | (+)-pin | |
| 8 | NHC(NH)NH_2 | H | NHCbz | H | (+)-pin | |
| 9 | NHC(NH)NH_2 | H | NMeCbz | H | (+)-pin | |
| 10 | NHC(NH)NH_2 | H | H | Et | (+)-pin | |
| 11 | NHC(NH)NH_2 | H | H | n-Pr | (+)-pin | |
| 12 | NHC(NH)NH_2 | H | H | i-Pr | (+)-pin | |
| 13 | NHC(NH)NH_2 | H | H | n-Bu | (+)-pin | |
| 14 | NHC(NH)NH_2 | H | H | t-Bu | (+)-pin | |
| 15 | NHC(NH)NH_2 | H | H | n-hexyl | (+)-pin | |
| 16 | NHC(NH)NH_2 | H | H | cyclohexyl | (+)-pin | |
| 17 | NHC(NH)NH_2 | NHCO(CH_2)_2Ph | H | H | (+)-pin | |
| 18 | NHC(NH)NH_2 | H | H | O-n-Bu | (+)-Pin | |
| 19 | NHC(NH)NH_2 | H | H | NHCOcyclopropyl | (+)-pin | |
| 20 | NHC(NH)NH_2 | H | H | NHCO-cyclohexyl | (+)-pin | |
| 21 | NHC(NH)NH_2 | H | H | NHCO(4-C_6H_4OMe) | (+)-pin | |
| 22 | NHC(NH)NH_2 | H | H | 4-C_6H_4OMe | (+)-pin | |
| 23 | NHC(NH)NH_2 | CO_2CH_2(2-C_6H_4Ph) | H | H | (+)-pin | |
| 24 | NHC(NH)NH_2 | H | H | 1-naphthyl | (+)-pin | |
| 25 | NHC(NH)NH_2 | H | H | 4-C_6H_4CO_2H | (+)-pin | |
| 26 | NHC(NH)NH_2 | COPh | H | Me | (+)-pin | |
| 27 | NHC(NH)NH_2 | H | NHCbz | n-Bu | (+)-pin | |
| 28 | NHC(NH)NH_2 | H | NMeCbz | n-Bu | (+)-pin | |
| 29 | NHC(NH)NH_2 | Me | H | Ph | (+)-pin | CB |
| 30 | NHC(NH)NH_2 | Me | H | 4-C_6H_4CO_2H | (+)-pin | |
| 31 | NHC(NH)NH_2 | H | H | 4-C_6H_4CO_2Me | (+)-pin | |
| 32 | NHC(NH)NH_2 | Me | H | 4-C_6H_4CO_2Me | (+)-pin | |
| 33 | NHC(NH)NH_2 | H | OMe | Ph | (+)-pin | |
| 34 | SC(NH)NH_2 | H | H | Ph | (+)-pin | D |
| 35 | SC(NH)NH_2 | H | Ph | H | (+)-pin | E |
| 36 | SC(NH)NH_2 | H | OPh | H | (+)-pin | F |
| 37 | SC(NH)NH_2 | COPh | H | H | (+)-pin | G |
| 38 | SC(NH)NH_2 | H | COPh | H | (+)-pin | H |
| 39 | SC(NH)NH_2 | H | H | COPh | (+)-pin | I |
| 40 | SC(NH)NH_2 | H | NHCbz | H | (+)-pin | J |
| 41 | SC(NH)NH_2 | H | NMeCbz | H | (+)-pin | K |
| 42 | SC(NH)NH_2 | H | H | Et | (+)-pin | L |
| 43 | SC(NH)NH_2 | H | H | n-Pr | (+)-pin | M |
| 44 | SC(NH)NH_2 | H | H | i-Pr | (+)-pin | N |
| 45 | SC(NH)NH_2 | H | H | n-Bu | (+)-pin | O |
| 46 | SC(NH)NH_2 | H | H | t-Bu | (+)-pin | P |
| 47 | SC(NH)NH_2 | H | H | n-hexyl | (+)-pin | Q |
| 48 | SC(NH)NH_2 | H | H | cyclohexyl | (+)-pin | R |
| 49 | SC(NH)NH_2 | NHCOCH_2CH_2Ph | H | H | (+)-pin | S |
| 50 | SC(NH)NH_2 | H | H | O-n-Bu | (+)-pin | P |
| 51 | SC(NH)NH_2 | H | H | NHCOcyclopropyl | (+)-pin | U |
| 52 | SC(NH)NH_2 | H | H | NHCOcyclohexyl | (+)-pin | V |
| 53 | SC(NH)NH_2 | H | H | NHCO(4-C_6H_4OMe) | (+)-pin | W |
| 54 | SC(NH)NH_2 | H | H | 4-C_6H_4OMe | (+)-pin | X |
| 55 | SC(NH)NH_2 | CO_2CH_2(2-C_6H_4Ph) | H | H | (+)-pin | Y |
| 56 | SC(NH)NH_2 | H | H | 1-naphthyl | (+)-pin | |
| 57 | SC(NH)NH_2 | H | H | 4-C_6H_4CO_2H | (+)-pin | |
| 58 | SC(NH)NH_2 | H | NHCbz | n-Bu | (+)-pin | Z |
| 59 | SC(NH)NH_2 | H | NMeCbz | n-Bu | (+)-pin | AA |
| 60 | SC(NH)NH_2 | COPh | H | Me | (+)-pin | BB |
| 61 | SC(NH)NH_2 | H | H | 4-pyridyl | (+)-pin | |
| 62 | SC(NH)NH_2 | Me | H | 4-C_6H_4CO_2H | (+)-pin | |

TABLE 1-continued

| Ex | X | R^A | R^B | R^C | Y^1, Y^2 | Phys Data |
|---|---|---|---|---|---|---|
| 63 | SC(NH)NH$_2$ | H | H | 4-C$_6$H$_4$CO$_2$Me | (+)-pin | |
| 64 | SC(NH)NH$_2$ | Me | H | 4-C$_6$H$_4$CO$_2$Me | (+)-pin | |
| 65 | SC(NH)NH$_2$ | Me | H | Ph | (+)-pin | |
| 66 | SC(NH)NH$_2$ | H | OMe | Ph | (+)-pin | |
| 67 | CH$_2$NH$_2$ | H | H | Ph | (+)-pin | |
| 68 | CH$_2$NH$_2$ | H | Ph | H | (+)-pin | YY |
| 69 | CH$_2$NH$_2$ | H | OPh | H | (+)-pin | |
| 70 | CH$_2$NH$_2$ | COPh | H | H | (+)-pin | |
| 71 | CH$_2$NH$_2$ | H | COPh | H | (+)-pin | |
| 72 | CH$_2$NH$_2$ | H | H | COPh | (+)-pin | |
| 73 | CH$_2$NH$_2$ | H | NHCbz | H | (+)-pin | |
| 74 | CH$_2$NH$_2$ | H | NMeCbz | H | (+)-pin | |
| 75 | CH$_2$NH$_2$ | H | H | Et | (+)-pin | |
| 76 | CH$_2$NH$_2$ | H | H | n-Pr | (+)-pin | |
| 77 | CH$_2$NH$_2$ | H | H | i-Pr | (+)-pin | |
| 78 | CH$_2$NH$_2$ | H | H | n-Bu | (+)-pin | |
| 79 | CH$_2$NH$_2$ | H | H | t-Bu | (+)-pin | |
| 80 | CH$_2$NH$_2$ | H | H | n-hexyl | (+)-pin | |
| 81 | CH$_2$NH$_2$ | H | H | cyclohexyl | (+)-pin | |
| 82 | CH$_2$NH$_2$ | NHCOCH$_2$CH$_2$Ph | H | H | (+)-pin | |
| 83 | CH$_2$NH$_2$ | H | H | O-n-Bu | (+)-pin | |
| 84 | CH$_2$NH$_2$ | H | H | NHCOcyclopropyl | (+)-pin | |
| 85 | CH$_2$NH$_2$ | H | H | NHCOcyclohexyl | (+)-pin | |
| 86 | CH$_2$NH$_2$ | H | H | NHCO(4-C$_6$H$_4$OMe) | (+)-pin | |
| 87 | CH$_2$NH$_2$ | H | H | 4-C$_6$H$_4$OMe | (+)-pin | |
| 88 | CH$_2$NH$_2$ | CO$_2$CH$_2$(2-C$_6$H$_4$Ph) | H | H | (+)-pin | |
| 89 | CH$_2$NH$_2$ | H | H | 1-naphthyl | (+)-pin | |
| 90 | CH$_2$NH$_2$ | H | H | 4-C$_6$H$_4$CO$_2$H | (+)-pin | |
| 91 | CH$_2$NH$_2$ | H | NHCbz | n-Bu | (+)-pin | |
| 92 | CH$_2$NH$_2$ | H | NMeCbz | n-Bu | (+)-pin | |
| 93 | CH$_2$NH$_2$ | COPh | H | Me | (+)-pin | |
| 94 | CH$_2$NH$_2$ | H | H | 4-pyridyl | (+)-pin | |
| 95 | CH$_2$NH$_2$ | Me | H | 4-C$_6$H$_4$CO$_2$H | (+)-pin | |
| 96 | CH$_2$NH$_2$ | H | H | 4-C$_6$H$_4$CO$_2$Me | (+)-pin | |
| 97 | CH$_2$NH$_2$ | Me | H | 4-C$_6$H$_4$CO$_2$Me | (+)-pin | |
| 98 | CH$_2$NH$_2$ | Me | H | Ph | (+)-pin | |
| 99 | CH$_2$NH$_2$ | H | OMe | Ph | (+)-pin | |
| 100 | CH$_2$NH$_2$ | H | OMe | Ph | OH, OH | |
| 101 | NHC(NH)NH$_2$ | H | H | Ph | OH, OH | |
| 102 | NHC(NH)NH$_2$ | H | Ph | H | OH, OH | |
| 103 | NHC(NH)NH$_2$ | H | OPh | Ph | OH, OH | |
| 104 | NHC(NH)NH$_2$ | H | H | 4-pyridyl | OH, OH | |
| 105 | NHC(NH)NH$_2$ | COPh | H | H | OH, OH | |
| 106 | NHC(NH)NH$_2$ | H | COPh | H | OH, OH | |
| 107 | NHC(NH)NH$_2$ | H | H | COPh | OH, OH | |
| 108 | NHC(NH)NH$_2$ | H | NHCbz | H | OH, OH | |
| 109 | NHC(NH)NH$_2$ | H | NMeCbz | H | OH, OH | |
| 110 | NHC(NH)NH$_2$ | H | H | Et | OH, OH | |
| 111 | NHC(NH)NH$_2$ | H | H | n-Pr | OH, OH | |
| 112 | NHC(NH)NH$_2$ | H | H | i-Pr | OH, OH | |
| 113 | NHC(NH)NH$_2$ | H | H | n-Bu | OH, OH | |
| 114 | NHC(NH)NH$_2$ | H | H | t-Bu | OH, OH | |
| 115 | NHC(NH)NH$_2$ | H | H | n-hexyl | OH, OH | |
| 116 | NHC(NH)NH$_2$ | H | H | cyclohexyl | OH, OH | |
| 117 | NHC(NH)NH$_2$ | NHCO(CH$_2$)$_2$Ph | H | H | OH, OH | |
| 118 | NHC(NH)NH$_2$ | H | H | O-n-Bu | OH, OH | |
| 119 | NHC(NH)NH$_2$ | H | H | NHCOcyclopropyl | OH, OH | |
| 120 | NHC(NH)NH$_2$ | H | H | NHCO-cyclohexyl | OH, OH | |
| 121 | NHC(NH)NH$_2$ | H | H | NHCO(4-C$_6$H$_4$OMe) | OH, OH | |
| 122 | NHC(NH)NH$_2$ | H | H | 4-C$_6$H$_4$OMe | OH, OH | |
| 123 | NHC(NH)NH$_2$ | CO$_2$CH$_2$(2-C$_6$H$_4$Ph) | H | H | OH, OH | |
| 124 | NHC(NH)NH$_2$ | H | H | 1-naphthyl | OH, OH | |

TABLE 1-continued

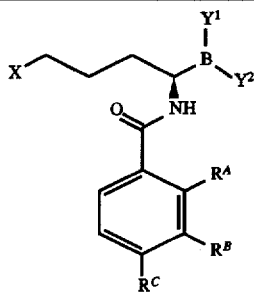

| Ex | X | R^A | R^B | R^C | Y^1, Y^2 | Phys Data |
|---|---|---|---|---|---|---|
| 125 | NHC(NH)NH$_2$ | H | H | 4-C$_6$H$_4$CO$_2$H | OH, OH | |
| 126 | NHC(NH)NH$_2$ | COPh | H | Me | OH, OH | |
| 127 | NHC(NH)NH$_2$ | H | NHCbz | n-Bu | OH, OH | |
| 128 | NHC(NH)NH$_2$ | H | NMeCbz | n-Bu | OH, OH | |
| 129 | NHC(NH)NH$_2$ | Me | H | Ph | OH, OH | CD |
| 130 | NHC(NH)NH$_2$ | Me | H | 4-C$_6$H$_4$CO$_2$H | OH, OH | |
| 131 | NHC(NH)NH$_2$ | H | H | 4-C$_6$H$_4$CO$_2$Me | OH, OH | |
| 132 | NHC(NH)NH$_2$ | Me | H | 4-C$_6$H$_4$CO$_2$Me | OH, OH | |
| 133 | NHC(NH)NH$_2$ | H | OMe | Ph | OH, OH | |
| 134 | SC(NH)NH$_2$ | H | H | Ph | OH, OH | |
| 135 | SC(NH)NH$_2$ | H | Ph | H | OH, OH | |
| 136 | SC(NH)NH$_2$ | H | OPh | H | OH, OH | |
| 137 | SC(NH)NH$_2$ | COPh | H | H | OH, OH | |
| 138 | SC(NH)NH$_2$ | H | COPh | H | OH, OH | |
| 139 | SC(NH)NH$_2$ | H | H | COPh | OH, OH | |
| 140 | SC(NH)NH$_2$ | H | NHCbz | H | OH, OH | |
| 141 | SC(NH)NH$_2$ | H | NMeCbz | H | OH, OH | |
| 142 | SC(NH)NH$_2$ | H | H | Et | OH, OH | |
| 143 | SC(NH)NH$_2$ | H | H | n-Pr | OH, OH | |
| 144 | SC(NH)NH$_2$ | H | H | i-Pr | OH, OH | |
| 145 | SC(NH)NH$_2$ | H | H | n-Bu | OH, OH | |
| 146 | SC(NH)NH$_2$ | H | H | t-Bu | OH, OH | |
| 147 | SC(NH)NH$_2$ | H | H | n-hexyl | OH, OH | |
| 148 | SC(NH)NH$_2$ | H | H | cyclohexyl | OH, OH | |
| 149 | SC(NH)NH$_2$ | NHCOCH$_2$CH$_2$Ph | H | H | OH, OH | |
| 150 | SC(NH)NH$_2$ | H | H | O-n-Bu | OH, OH | |
| 151 | SC(NH)NH$_2$ | H | H | NHCOcyclopropyl | OH, OH | |
| 152 | SC(NH)NH$_2$ | H | H | NHCOcyclohexyl | OH, OH | |
| 153 | SC(NH)NH$_2$ | H | H | NHCO(4-C$_6$H$_4$OMe) | OH, OH | |
| 154 | SC(NH)NH$_2$ | H | H | 4-C$_6$H$_4$OMe | OH, OH | |
| 155 | SC(NH)NH$_2$ | CO$_2$CH$_2$(2-C$_6$H$_4$Ph) | H | H | OH, OH | |
| 156 | SC(NH)NH$_2$ | H | H | 1-naphthyl | OH, OH | |
| 157 | SC(NH)NH$_2$ | H | H | 4-C$_6$H$_4$CO$_2$H | OH, OH | |
| 158 | SC(NH)NH$_2$ | H | NHCbz | n-Bu | OH, OH | |
| 159 | SC(NH)NH$_2$ | H | NMeCbz | n-Bu | OH, OH | |
| 160 | SC(NH)NH$_2$ | COPh | H | Me | OH, OH | |
| 161 | SC(NH)NH$_2$ | H | H | 4-pyridyl | OH, OH | |
| 162 | SC(NH)NH$_2$ | Me | H | 4-C$_6$H$_4$CO$_2$H | OH, OH | |
| 163 | SC(NH)NH$_2$ | H | H | 4-C$_6$H$_4$CO$_2$Me | OH, OH | |
| 164 | SC(NH)NH$_2$ | Me | H | 4-C$_6$H$_4$CO$_2$Me | OH, OH | |
| 165 | SC(NH)NH$_2$ | Me | H | Ph | OH, OH | |
| 166 | SC(NH)NH$_2$ | H | OMe | Ph | OH, OH | |
| 167 | CH$_2$NH$_2$ | H | H | Ph | OH, OH | |
| 168 | CH$_2$NH$_2$ | H | Ph | H | OH, OH | |
| 169 | CH$_2$NH$_2$ | H | OPh | H | OH, OH | |
| 170 | CH$_2$NH$_2$ | COPh | H | H | OH, OH | |
| 171 | CH$_2$NH$_2$ | H | COPh | H | OH, OH | |
| 172 | CH$_2$NH$_2$ | H | H | COPh | OH, OH | |
| 173 | CH$_2$NH$_2$ | H | NHCbz | H | OH, OH | |
| 174 | CH$_2$NH$_2$ | H | NMeCbz | H | OH, OH | |
| 175 | CH$_2$NH$_2$ | H | H | Et | OH, OH | |
| 176 | CH$_2$NH$_2$ | H | H | n-Pr | OH, OH | |
| 177 | CH$_2$NH$_2$ | H | H | i-Pr | OH, OH | |
| 178 | CH$_2$NH$_2$ | H | H | n-Bu | OH, OH | |
| 179 | CH$_2$NH$_2$ | H | H | t-Bu | OH, OH | |
| 180 | CH$_2$NH$_2$ | H | H | n-hexyl | OH, OH | |
| 181 | CH$_2$NH$_2$ | H | H | cyclohexyl | OH, OH | |
| 182 | CH$_2$NH$_2$ | NHCOCH$_2$CH$_2$Ph | H | H | OH, OH | |
| 183 | CH$_2$NH$_2$ | H | H | O-n-Bu | OH, OH | |
| 184 | CH$_2$NH$_2$ | H | H | NHCOcyclopropyl | OH, OH | |
| 185 | CH$_2$NH$_2$ | H | H | NHCOcyclohexyl | OH, OH | |
| 186 | CH$_2$NH$_2$ | H | H | NHCO(4-C$_6$H$_4$OMe) | OH, OH | |

TABLE 1-continued

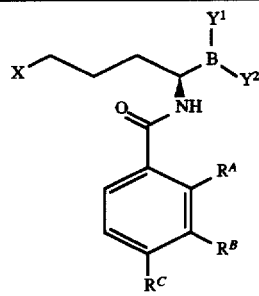

| Ex | X | R^A | R^B | R^C | Y^1, Y^2 | Phys Data |
|---|---|---|---|---|---|---|
| 187 | $CH_2NH_2$ | H | H | $4\text{-}C_6H_4OMe$ | OH, OH | |
| 188 | $CH_2NH_2$ | $CO_2CH_2(2\text{-}C_6H_4Ph)$ | H | H | OH, OH | |
| 189 | $CH_2NH_2$ | H | H | 1-naphthyl | OH, OH | |
| 190 | $CH_2NH_2$ | H | H | $4\text{-}C_6H_4CO_2H$ | OH, OH | |
| 191 | $CH_2NH_2$ | H | NHCbz | n-Bu | OH, OH | |
| 192 | $CH_2NH_2$ | H | NMeCbz | n-Bu | OH, OH | |
| 193 | $CH_2NH_2$ | COPh | H | Me | OH, OH | |
| 194 | $CH_2NH_2$ | H | H | 4-pyridyl | OH, OH | |
| 195 | $CH_2NH_2$ | Me | H | $4\text{-}C_6H_4CO_2H$ | OH, OH | |
| 196 | $CH_2NH_2$ | H | H | $4\text{-}C_6H_4CO_2Me$ | OH, OH | |
| 197 | $CH_2NH_2$ | Me | H | $4\text{-}C_6H_4CO_2Me$ | OH, OH | |
| 198 | $CH_2NH_2$ | Me | H | Ph | OH, OH | |
| 199 | $NH(C=NH)NH_2$ | F | H | Ph | (+)-pin | SS |
| 200 | $NH(C=NH)NH_2$ | F | H | Ph | OH, OH | |
| 201 | $NH(C=NH)NH_2$ | $NH_2$ | H | Ph | (+)-pin | |
| 202 | $NH(C=NH)NH_2$ | $NH_2$ | H | Ph | OH, OH | |
| 203 | $NH(C=NH)NH_2$ | $NO_2$ | H | Ph | (+)-pin | TT |
| 204 | $NH(C=NH)NH_2$ | $NO_2$ | H | Ph | OH, OH | |
| 205 | $NH(C=NH)NH_2$ | OH | H | Ph | (+)-pin | |
| 206 | $NH(C=NH)NH_2$ | OH | H | Ph | OH, OH | |
| 207 | $NH(C=NH)NH_2$ | $-NHSO_2CF_3$ | H | Ph | (+)-pin | |
| 208 | $NH(C=NH)NH_2$ | $-NHSO_2CF_3$ | H | Ph | (+)-pin | |
| 209 | $NH(C=NH)NH_2$ | $-NHSO_2CH_3$ | H | Ph | (+)-pin | |
| 210 | $NH(C=NH)NH_2$ | $-NHSO_2CH_3$ | H | Ph | (+)-pin | |
| 211 | $NH(C=NH)NH_2$ | $CH_2CN$ | H | Ph | (+)-pin | |
| 212 | $NH(C=NH)NH_2$ | $CH_2CN$ | H | Ph | OH, OH | |
| 213 | $NH(C=NH)NH_2$ | $CH_2CH_2CN$ | H | Ph | (+)-pin | |
| 214 | $NH(C=NH)NH_2$ | $CH_2CH_2CN$ | H | Ph | OH, OH | |
| 215 | $NH(C=NH)NH_2$ | $OCH_2CN$ | H | Ph | (+)-pin | |
| 216 | $NH(C=NH)NH_2$ | $OCH_2CN$ | H | Ph | OH, OH | |
| 217 | $NH(C=NH)NH_2$ | $SCH_2CN$ | H | Ph | (+)-pin | |
| 218 | $NH(C=NH)NH_2$ | $SCH_2CN$ | H | Ph | OH, OH | |
| 219 | $NH(C=NH)NH_2$ | $NHCH_2CN$ | H | Ph | (+)-pin | |
| 220 | $NH(C=NH)NH_2$ | $NHCH_2CN$ | H | Ph | OH, OH | |
| 221 | $NH(C=NH)NH_2$ | $CH_2OH$ | H | Ph | (+)-pin | |
| 222 | $NH(C=NH)NH_2$ | $CH_2OH$ | H | Ph | OH, OH | |
| 223 | $NH(C=NH)NH_2$ | $CH_3$ | H | $2\text{-}(t\text{-butyl-}NHSO_2)\text{-}Ph$ | (+)-pin | UU |
| 224 | $NH(C=NH)NH_2$ | $CH_3$ | H | $2\text{-}(t\text{-butyl-}NHSO_2)\text{-}Ph$ | OH, OH | |
| 225 | $NH(C=NH)NH_2$ | $CH_3$ | H | $2\text{-}(ethyl\text{-}NHSO_2)\text{-}Ph$ | (+)-pin | |
| 226 | $NH(C=NH)NH_2$ | $CH_3$ | H | $2\text{-}(ethyl\text{-}NHSO_2)\text{-}Ph$ | OH, OH | |
| 227 | $NH(C=NH)NH_2$ | $CH_3$ | H | $2\text{-}(H_2NSO_2)\text{-}Ph$ | (+)-pin | ZZ |
| 228 | $NH(C=NH)NH_2$ | $CH_3$ | H | $2\text{-}(H_2NSO_2)\text{-}Ph$ | OH, OH | |
| 229 | $NH(C=NH)NH_2$ | $CH_3$ | H | $2\text{-}(MeCO\text{-}NHSO_2)\text{-}Ph$ | (+)-pin | |
| 230 | $NH(C=NH)NH_2$ | $CH_3$ | H | $2\text{-}(MeCO\text{-}NHSO_2)\text{-}Ph$ | OH, OH | |
| 231 | $NH(C=NH)NH_2$ | $CH_3$ | H | $2\text{-}(MeOCO\text{-}NHSO_2)\text{-}Ph$ | (+)-pin | AB |
| 232 | $NH(C=NH)NH_2$ | $CH_3$ | H | $2\text{-}(MeOCO\text{-}NHSO_2)\text{-}Ph$ | OH, OH | |
| 233 | $NH(C=NH)NH_2$ | $CH_3$ | H | $2\text{-}(NH_2)\text{-}Ph$ | (+)-pin | |
| 234 | $NH(C=NH)NH_2$ | $CH_3$ | H | $2\text{-}(NH_2)\text{-}Ph$ | OH, OH | |
| 235 | $NH(C=NH)NH_2$ | $CH_3$ | H | $2\text{-}(CH_3SO_2NH)\text{-}Ph$ | (+)-pin | |
| 236 | $NH(C=NH)NH_2$ | $CH_3$ | H | $2\text{-}(CH_3SO_2NH)\text{-}Ph$ | OH, OH | |
| 237 | $NH(C=NH)NH_2$ | $CH_3$ | H | $2\text{-}(CF_3SO_2NH)\text{-}Ph$ | (+)-pin | |
| 238 | $NH(C=NH)NH_2$ | $CH_3$ | H | $2\text{-}(CF_3SO_2NH)\text{-}Ph$ | OH, OH | |
| 239 | $NH(C=NH)NH_2$ | $CH_3$ | H | $2\text{-}(CN_4H)\text{-}Ph$ | (+)-pin | |
| 240 | $NH(C=NH)NH_2$ | $CH_3$ | H | $2\text{-}(CN_4H)\text{-}Ph$ | OH, OH | |
| 241 | $NH(C=NH)NH_2$ | $CH_3$ | H | $2\text{-}(COOH)\text{-}Ph$ | (+)-pin | |
| 242 | $NH(C=NH)NH_2$ | $CH_3$ | H | $2\text{-}(COOH)\text{-}Ph$ | OH, OH | |
| 243 | $NH(C=NH)NH_2$ | $CH_3$ | H | $3\text{-}(NH_2)\text{-}Ph$ | (+)-pin | |
| 244 | $NH(C=NH)NH_2$ | $CH_3$ | H | $3\text{-}(NH_2)\text{-}Ph$ | OH, OH | |
| 245 | $NH(C=NH)NH_2$ | $CH_3$ | H | $3\text{-}(CH_3SO_2NH)\text{-}Ph$ | (+)-pin | |
| 246 | $NH(C=NH)NH_2$ | $CH_3$ | H | $3\text{-}(CH_3SO_2NH)\text{-}Ph$ | OH, OH | |
| 247 | $NH(C=NH)NH_2$ | $CH_3$ | OH | Ph | (+)-pin | |
| 248 | $NH(C=NH)NH_2$ | $CH_3$ | OH | Ph | OH, OH | |

TABLE 1-continued

| Ex | X | R^A | R^B | R^C | Y¹, Y² | Phys Data |
|---|---|---|---|---|---|---|
| 249 | NH(C=NH)NH₂ | CH₃ | NH₂ | Ph | (+)-pin | |
| 250 | NH(C=NH)NH₂ | CH₃ | NH₂ | Ph | OH, OH | |
| 251 | NH(C=NH)NH₂ | F | H | 2-(t-butyl-NHSO₂)—Ph | (+)-pin | |
| 252 | NH(C=NH)NH₂ | F | H | 2-(t-butyl-NHSO₂)—Ph | OH, OH | |
| 253 | NH(C=NH)NH₂ | F | H | 2-(ethyl-NHSO₂)—Ph | (+)-pin | |
| 254 | NH(C=NH)NH₂ | F | H | 2-(ethyl-NHSO₂)—Ph | OH, OH | |
| 255 | NH(C=NH)NH₂ | F | H | 2-(H₂NSO₂)—Ph | (+)-pin | |
| 256 | NH(C=NH)NH₂ | F | H | 2-(H₂NSO₂)—Ph | OH, OH | |
| 257 | NH(C=NH)NH₂ | F | H | 2-(MeCO—NHSO₂)—Ph | (+)-pin | |
| 258 | NH(C=NH)NH₂ | F | H | 2-(MeCO—NHSO₂)—Ph | OH, OH | |
| 259 | NH(C=NH)NH₂ | F | H | 2-(MeOCO—NHSO₂)—Ph | (+)-pin | |
| 260 | NH(C=NH)NH₂ | F | H | 2-(MeOCO—NHSO₂)—Ph | OH, OH | |
| 261 | NH(C=NH)NH₂ | H | H | 2-(t-butyl-NHSO₂)—Ph | (+)-pin | AC |
| 262 | NH(C=NH)NH₂ | Cl | H | 2-(t-butyl-NHSO₂)—Ph | (+)-pin | CE |
| 263 | NH(C=NH)NH₂ | H | H | 2-(t-butyl-NHSO₂)—Ph | OH, OH | AD |
| 264 | NH(C=NH)NH₂ | Cl | H | 2-(t-butyl-NHSO₂)—Ph | OH, OH | |
| 265 | NH(C=NH)NH₂ | Cl | H | 2-(ethyl-NHSO₂)—Ph | (+)-pin | |
| 266 | NH(C=NH)NH₂ | Cl | H | 2-(ethyl-NHSO₂)—Ph | OH, OH | |
| 267 | NH(C=NH)NH₂ | Cl | H | 2-(H₂NSO₂)—Ph | (+)-pin | |
| 268 | NH(C=NH)NH₂ | Cl | H | 2-(H₂NSO₂)—Ph | OH, OH | |
| 269 | NH(C=NH)NH₂ | Cl | H | 2-(MeCO—NHSO₂)—Ph | (+)-pin | |
| 270 | NH(C=NH)NH₂ | Cl | H | 2-(MeCO—NHSO₂)—Ph | OH, OH | |
| 271 | NH(C=NH)NH₂ | Cl | H | 2-(MeOCO—NHSO₂)—Ph | (+)-pin | |
| 272 | NH(C=NH)NH₂ | Cl | H | 2-(MeOCO—NHSO₂)—Ph | OH, OH | |
| 273 | NH(C=NH)NH₂ | NHSO₂CH₃ | H | 2-(t-butyl-NHSO₂)—Ph | (+)-pin | |
| 274 | NH(C=NH)NH₂ | NHSO₂CH₃ | H | 2-(t-butyl-NHSO₂)—Ph | OH, OH | |
| 275 | NH(C=NH)NH₂ | NHSO₂CH₃ | H | 2-(ethyl-NHSO₂)—Ph | (+)-pin | |
| 276 | NH(C=NH)NH₂ | NHSO₂CH₃ | H | 2-(ethyl-NHSO₂)—Ph | OH, OH | |
| 277 | NH(C=NH)NH₂ | NHSO₂CH₃ | H | 2-(H₂NSO₂)—Ph | (+)-pin | |
| 278 | NH(C=NH)NH₂ | NHSO₂CH₃ | H | 2-(H₂NSO₂)—Ph | OH, OH | |
| 279 | NH(C=NH)NH₂ | NHSO₂CH₃ | H | 2-(MeCO—NHSO₂)—Ph | (+)-pin | |
| 280 | NH(C=NH)NH₂ | NHSO₂CH₃ | H | 2-(MeCO—NHSO₂)—Ph | OH, OH | |
| 281 | NH(C=NH)NH₂ | NHSO₂CH₃ | H | 2-(MeOCO—NHSO₂)—Ph | (+)-pin | |
| 282 | NH(C=NH)NH₂ | NHSO₂CH₃ | H | 2-(MeOCO—NHSO₂)—Ph | OH, OH | |
| 283 | NH(C=NH)NH₂ | CH₃ | H | 3-(t-butylOCO—NH)—Ph | (+)-pin | VV |
| 284 | NH(C=NH)NH₂ | CH₃ | H | 3-(t-butylOCO—NH)—Ph | OH, OH | |
| 285 | NH(C=NH)NH₂ | N(Et)₂ | H | Ph | (+)-pin | |
| 286 | NH(C=NH)NH₂ | CH₃ | H | 2-((ethyl)₂-NSO₂)—Ph | (+)-pin | CF |
| 287 | NH(C=NH)NH₂ | CH₃ | H | 2-(n-BuOCO—NHSO₂)—Ph | (+)-pin | |
| 288 | NH(C=NH)NH₂ | NO₂ | H | 2-(t-butyl-NHSO₂)—Ph | (+)-pin | CG |
| 289 | NH(C=NH)NH₂ | NO₂ | H | 2-(t-butyl-NHSO₂)—Ph | OH, OH | |
| 290 | NH(C=NH)NH₂ | NO₂ | H | 2-(ethyl-NHSO₂)—Ph | (+)-pin | |
| 291 | NH(C=NH)NH₂ | NO₂ | H | 2-(ethyl-NHSO₂)—Ph | OH, OH | |
| 292 | NH(C=NH)NH₂ | NO₂ | H | 2-(H₂NSO₂)—Ph | (+)-pin | |
| 293 | NH(C=NH)NH₂ | NO₂ | H | 2-(H₂NSO₂)—Ph | OH, OH | |
| 294 | NH(C=NH)NH₂ | NO₂ | H | 2-(MeCO—NHSO₂)—Ph | (+)-pin | |
| 295 | NH(C=NH)NH₂ | NO₂ | H | 2-(MeCO—NHSO₂)—Ph | OH, OH | |
| 296 | NH(C=NH)NH₂ | NO₂ | H | 2-(MeOCO—NHSO₂)—Ph | (+)-pin | |
| 297 | NH(C=NH)NH₂ | NO₂ | H | 2-(MeOCO—NHSO₂)—Ph | OH, OH | |
| 298 | NH(C=NH)NH₂ | H | NO₂ | Ph | (+)-pin | AE |
| 299 | NH(C=NH)NH₂ | H | NH₂ | Ph | (+)-pin | AF |
| 300 | NH(C=NH)NH₂ | H | NO₂ | Ph | OH, OH | |
| 301 | NH(C=NH)NH₂ | H | NH₂ | Ph | OH, OH | |
| 302 | NH(C=NH)H | H | H | 2-(t-butyl-NHSO₂)—Ph | (+)-pin | CH |
| 303 | NH(C=NH)NH₂ | 2-NHBOC | H | Ph | (+)-pin | CI |
| 304 | NH(C=NH)NH₂ | 2-NO₂ | H | Ph | (+)-pin | CJ |
| 305 | —OCH₃ | 2-Me | H | 2-(H₂NSO₂)—Ph | (+)-pin | CK |
| 306 | CH₂NH₂ | CH₃ | H | 4-thiophen-2-yl | (+)-pin | |
| 307 | CH₂NH₂ | CH₃ | H | 4-thiophen-3-yl | (+)-pin | |
| 308 | CH₂NH₂ | CH₃ | 3-thiophen-2-yl | H | (+)-pin | |
| 309 | CH₂NH₂ | CH₃ | 3-thiophen-3-yl | H | (+)-pin | |
| 310 | CH₂NH₂ | CH₃ | H | 4-furan-2-yl | (+)-pin | |

TABLE 1-continued

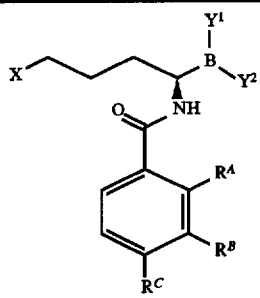

| Ex | X | R^A | R^B | R^C | Y^1, Y^2 | Phys Data |
|---|---|---|---|---|---|---|
| 311 | CH$_2$NH$_2$ | CH$_3$ | H | 4-furan-3-yl | (+)-pin | |
| 312 | CH$_2$NH$_2$ | CH$_3$ | 3-furan-2-yl | H | (+)-pin | |
| 313 | CH$_2$NH$_2$ | CH$_3$ | 3-furan-3-yl | H | (+)-pin | |
| 314 | CH$_2$NH$_2$ | CH$_3$ | H | 4-imidazol-2-yl | (+)-pin | |
| 315 | CH$_2$NH$_2$ | CH$_3$ | H | 4-imidazol-4-yl | (+)-pin | |
| 316 | CH$_2$NH$_2$ | CH$_3$ | 3-imidazol-2-yl | H | (+)-pin | |
| 317 | CH$_2$NH$_2$ | CH$_3$ | 3-imidazol-4-yl | H | (+)-pin | |
| 318 | CH$_2$NH$_2$ | CH$_3$ | H | 4-pyrazol-1-yl | (+)-pin | |
| 319 | CH$_2$NH$_2$ | CH$_3$ | H | 4-pyrazol-2-yl | (+)-pin | |
| 320 | CH$_2$NH$_2$ | CH$_3$ | 3-pyrazol-1-yl | H | (+)-pin | |
| 321 | CH$_2$NH$_2$ | CH$_3$ | 3-pyrazol-2-yl | H | (+)-pin | |
| 322 | CH$_2$NH$_2$ | CH$_3$ | H | 4-pyrrol-1-yl | (+)-pin | |
| 323 | CH$_2$NH$_2$ | CH$_3$ | H | 4-pyrrol-2-yl | (+)-pin | |
| 324 | CH$_2$NH$_2$ | CH$_3$ | 3-pyrrol-1-yl | H | (+)-pin | |
| 325 | CH$_2$NH$_2$ | CH$_3$ | 3-pyrrol-2-yl | H | (+)-pin | |
| 326 | CH$_2$NH$_2$ | CH$_3$ | H | 4-(1,2,4-triazol-1-yl) | (+)-pin | |
| 327 | CH$_2$NH$_2$ | CH$_3$ | H | 4-(1,2,4-triazol-2-yl) | (+)-pin | |
| 328 | CH$_2$NH$_2$ | CH$_3$ | 3-(1,2,4-triazol-1-yl) | H | (+)-pin | |
| 329 | CH$_2$NH$_2$ | CH$_3$ | 3-(1,2,4-triazol-1-yl) | H | (+)-pin | |
| 330 | CH$_2$NH$_2$ | CH$_3$ | H | 4-(1,2,3-triazol-1-yl) | (+)-pin | |
| 331 | CH$_2$NH$_2$ | CH$_3$ | H | 4-(1,2,3-triazol-4-yl) | (+)-pin | |
| 332 | CH$_2$NH$_2$ | CH$_3$ | 3-(1,2,3-triazol-1-yl) | H | (+)-pin | |
| 333 | CH$_2$NH$_2$ | CH$_3$ | 3-(1,2,3-triazol-4-yl) | H | (+)-pin | |
| 334 | CH$_2$NH$_2$ | CH$_3$ | H | 4-tetrazol-1-yl | (+)-pin | |
| 335 | CH$_2$NH$_2$ | CH$_3$ | H | 4-tetrazol-5-yl | (+)-pin | |
| 336 | CH$_2$NH$_2$ | CH$_3$ | 3-tetrazol-1-yl | H | (+)-pin | |
| 337 | CH$_2$NH$_2$ | CH$_3$ | 3-tetrazol-5-yl | H | (+)-pin | |
| 338 | CH$_2$NH$_2$ | CH$_3$ | H | 4-oxazol-2-yl | (+)-pin | |
| 339 | CH$_2$NH$_2$ | CH$_3$ | H | 4-oxazol-4-yl | (+)-pin | |
| 340 | CH$_2$NH$_2$ | CH$_3$ | H | 4-oxazol-5-yl | (+)-pin | |
| 341 | CH$_2$NH$_2$ | CH$_3$ | 3-oxazol-2-yl | H | (+)-pin | |
| 342 | CH$_2$NH$_2$ | CH$_3$ | 3-oxazol-4-yl | H | (+)-pin | |
| 343 | CH$_2$NH$_2$ | CH$_3$ | 3-oxazol-5-yl | H | (+)-pin | |
| 344 | CH$_2$NH$_2$ | CH$_3$ | H | 4-thiazol-2-yl | (+)-pin | |
| 345 | CH$_2$NH$_2$ | CH$_3$ | H | 4-thiazol-4-yl | (+)-pin | |
| 346 | CH$_2$NH$_2$ | CH$_3$ | H | 4-thiazol-5-yl | (+)-pin | |
| 347 | CH$_2$NH$_2$ | CH$_3$ | 3-thiazol-2-yl | H | (+)-pin | |
| 348 | CH$_2$NH$_2$ | CH$_3$ | 3-thiazol-4-yl | H | (+)-pin | |
| 349 | CH$_2$NH$_2$ | CH$_3$ | 3-thiazol-5-yl | H | (+)-pin | |
| 350 | CH$_2$NH$_2$ | CH$_3$ | H | 4-pyridin-2-yl | (+)-pin | |
| 351 | CH$_2$NH$_2$ | CH$_3$ | H | 4-pyridin-3-yl | (+)-pin | |
| 352 | CH$_2$NH$_2$ | CH$_3$ | 3-pyridin-2-yl | H | (+)-pin | |
| 353 | CH$_2$NH$_2$ | CH$_3$ | 3-pyridin-3-yl | H | (+)-pin | |
| 354 | CH$_2$NH$_2$ | CH$_3$ | H | 4-pyrimidin-2-yl | (+)-pin | |
| 355 | CH$_2$NH$_2$ | CH$_3$ | H | 4-pyrimidin-4-yl | (+)-pin | |
| 356 | CH$_2$NH$_2$ | CH$_3$ | H | 4-pyrimidin-5-yl | (+)-pin | |
| 357 | CH$_2$NH$_2$ | CH$_3$ | 3-pyrimidin-2-yl | H | (+)-pin | |
| 358 | CH$_2$NH$_2$ | CH$_3$ | 3-pyrimidin-4-yl | H | (+)-pin | |
| 359 | CH$_2$NH$_2$ | CH$_3$ | 3-pyrimidin-5-yl | H | (+)-pin | |

(+)-pin indicates (+)-pinanediol
A: MS (M + H)$^+$ = 489;
B: MS (DCI—NH$_3$), 505 (M + H)$^+$.
C: MS (M + H)$^+$ = 490.
D: MS (M + H)$^+$ = 506;
E: mp 145–150° C.; MS (DCI—NH$_3$), Calc: 506, Found: 506.
F: MS (DCI—NH$_3$), 522 (M + H)$^+$.
G: HRMS (DCI—NH$_3$), Calc: 534.2597, Found: 534.2609.
H: HRMS (DCI—NH$_3$), Calc: 534.2597, Found: 534.2605.
I: HRMS (DCI—NH$_3$), Calc: 534.2597, Found: 534.2609.
J: [a]$_D$ = −14,85° (c = 0.606, MeOH); MS (CI—NH$_3$), m/e (%) 537.2 (10.2, M + H—H$_2$NCN)$^+$), 429.0 (42.8), 277.0 (100); Anal. Calcd for C$_{30}$H$_{40}$BBrN$_4$O$_5$S: C, 54.64; H, 6.11; N, 8.50; B, 1.64. Found: C, 54.52; H, 6.16; N, 8.45; B, 1.60.

TABLE 1-continued

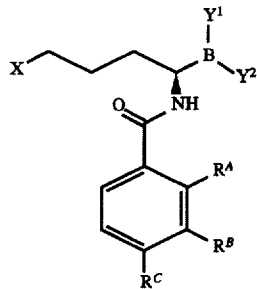

| Ex | X | R^A | R^B | R^C | Y^1, Y^2 | Phys Data |
|---|---|---|---|---|---|---|

K: $[a]_D = -15.07°$ (c = 0.604, MeOH); MS (CI—NH$_3$), m/e (%) 593.2 (1.2, (M + H)$^+$), 568.3 (22, (M + NH$_4$ — H$_2$NCN)$^+$), 551.3 (100, (M + H — H$_2$NCN)$^+$); Anal. Calcd for C$_{31}$H$_{42}$BBrN$_4$O$_5$S: C, 55.29; H, 6.29; N, 8.32; B, 1.61. Found: C, 55.15; H, 6.21; N, 8.22; B, 1.47.

L: $[a]_D = -14.12°$ (c = 0.602, MeOH); MS (DCI—NH$_3$), m/e (%) 458 (100, (M + H)$^+$); Anal. Calcd for C$_{24}$H$_{37}$BBrN$_3$O$_3$S: C, 53.54; H, 6.93; N, 7.81; B, 2.01. Found: C, 53.75; H, 6.98; N, 7.74; B, 1.97.

M: $[a]_D = -14.21°$ (c = 0.556, MeOH); MS (CI—NH$_3$), m/e (%) 472.2 (13.5, (M + H)$^+$), 430.2 (100, (M + H — H$_2$NCN)$^+$), 278.0 (61.9); Anal. Calcd for C$_{25}$H$_{39}$BBrN$_3$O$_3$S: C, 54.36; H, 7.12; N, 7.61; B, 1.96. Found: C, 54.50; H, 7.18; N, 7.83; B, 1.73.

N: $[a]_D = -13.79°$ (c = 0.602, MeOH); MS (DCI—NH$_3$), m/e (%) 472 (100, (M + H)$^+$), 430 (37, (M + H — H$_2$NCN)$^+$); Anal. Calcd for C$_{25}$H$_{39}$BBrN$_3$O$_3$S: C, 54.36; H, 7.12; N, 7.61; B, 1.96. Found: C, 54.64; H, 7.17; N, 7.50; B, 1.74.

O: $[a]_D = -13.19°$ (c = 0.364, MeOH); MS (CI—NH$_3$), m/e (%) 486.2 (3.3, (M + H)$^+$), 444.2 (87.1, (M + H — H$_2$NCN)$^+$), 292.0 (100); Anal. Calcd for C$_{26}$H$_{41}$BBrN$_3$O$_3$S: C, 55.13; H, 7.30; N, 7.42; B, 1.91. Found: C, 54.99; H, 7.22; N, 7.29; B, 2.07.

P: $[a]_D = -12.71°$ (c = 0.598, MeOH); MS (DCI—NH$_3$), m/e (%) 486 (100, (M + H)$^+$), 444 (16, (M + H — H$_2$NCN)$^+$); Anal. Calcd for C$_{26}$H$_{41}$BBrN$_3$O$_3$S: C, 55.13; H, 7.30; N, 7.42; B, 1.91. Found: C, 55.09; H, 7.45; N, 7.40; B, 1.67.

Q: MS (DCIAB,4 NH$_3$), m/e (%) 514 (100, (M + H)$^+$), 472 (16, (M + H — H$_2$NCN)$^+$); Anal. Calcd for C$_{28}$H$_{45}$BBrN$_3$O$_3$S: C, 56.57; H, 7.63; N, 7.07; B, 1.82. Found: C, 56.19; H, 7.53; N, 6.97; B, 1.99.

R: $[a]_D = -12.70°$ (c = 0.530, MeOH); MS (DCI—NH$_3$), m/e (%) 512 (100, (M + H)$^+$), 470 (40, (M + H — H$_2$NCN)$^+$); Anal. Calcd for C$_{28}$H$_{43}$BBrN$_3$O$_3$S: C, 56.77; H, 7.32; N, 7.09; B, 1.82. Found: C, 56.49; H, 7.38; N, 6.96; B, 1.75.

S: HRMS (DCI—NH$_3$), Calc: 577.3019, Found: 577.3025.

T: $[a]_D = -8.31°$ (c = 0.614, MeOH); MS (DCI—NH$_3$), m/e (%) 502 (100, (M + H)$^+$), 460 (28, (M + H — H$_2$NCN)$^+$); Anal. Calcd for C$_{26}$H$_{41}$BBrN$_3$O$_4$S: C, 53.62; H, 7.10; N, 7.21; B, 1.86. Found: C, 53.61; H, 7.09; N, 7.20; B, 1.78.

U: HRMS (DCI—NH$_3$), Calc: 513.2707, Found: 513.2702.

V: HRMS (DCI—NH$_3$), Calc: 555.3165, Found: 555.3176.

W: HRMS (DCI—NH$_3$), Calc: 579.2812, Found: 579.2801.

X: HRMS (DCI—NH$_3$), Calc: 450.2962, Found: 450.2958.

Y: HRMS (DCI—NH$_3$), Calc: 640.3019, Found: 640.3022.

Z: $[a]_D = -8.80°$ (c = 0.602, MeOH); MS (CI—NH$_3$), m/e (%) 593.2 (1.3, (M + H)$^+$), 485.2 (42.7), 333.0 (100); Anal. Calcd for C$_{34}$H$_{48}$BBrN$_4$O$_5$S: C, 57.07; H, 6.76; N, 7.83; B, 1.51. Found: C, 57.17; H, 6.84; N, 7.76; B, 1.41.

AA: MS (CI—NH$_3$), m/e (%) 649.4 (1.9, (M + H)$^+$), 624.4 (31, (M + NH$_4$ — H$_2$NCN)$^+$), 607.2 (100, (M + H — H$_2$NCN)$^+$), 455.0 (39), 444.0 (29.8); Anal. Calcd for C$_{35}$H$_{50}$BBrN$_4$O$_5$S: C, 57.62; H, 6.91; N, 7.68; B, 1.48. Found: C, 57.37; H, 6.86; N, 7.64; B, 1.40.

BB: HRMS (DCI—NH$_3$), Calc: 520.2805, Found: 520.2796.

SS. MS (DCI—NH$_3$), Calc: 507, Found: 507.
TT. MS (DCI—NH$_3$), Calc: 534, Found: 534.
UU. MS (DCI—NH$_3$), Calc: 638, Found: 638.
VV. MS (DCI—NH$_3$), Calc: 618, Found: 618.
XX. MS (DCI—NH$_3$), Calc: 489, Found: 489.
YY. MS (DCI—NH$_3$), Calc: 461, Found: 461.
ZZ. MS (DCI—NH$_3$), Calc: 582, Found: 582.
AB. MS (DCI—NH$_3$), Calc: 641, Found: 641.
AC. MS (DCI—NH$_3$), Calc: 625, Found: 625.
AD. MS (DCI—NH$_3$), Calc: 490, Found: 490.
AE. MS (DCI—NH$_3$), Calc: 534, Found: 534.
AF. MS (DCI—NH$_3$), Calc: 504, Found: 504.
CB. MS (M + H)$^+$, Calc: 503.32, Found: 503.32.
CD. MS (M + H)$^+$, Calc: , Found: .(WITYAK)
CE. MS (M + H)$^+$, Calc: 658, Found: 658.
CF. MS (M + H)$^+$, Calc: 638, Found: 638.
CG. MS (M + H)$^+$, Calc: 669, Found: 669.
CH. MS (M + H)$^+$, Calc: 609, Found: 609.
CI. MS (M + H)$^+$, Calc: 604, Found: 604.
CJ. MS (M + H)$^+$, Calc: 641, Found: 641.
CK. MS (M + H)$^+$, Calc: 555, Found: 555.

TABLE 2

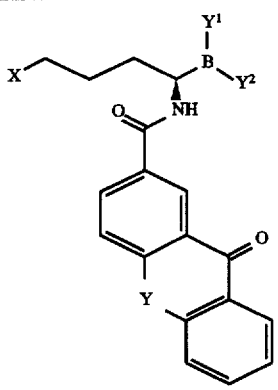

| Ex | X | Y | $Y^1, Y^2$ | Phys Data |
|---|---|---|---|---|
| 365 | $CH_2NH_2$ | CO | (+)-pin | |
| 366 | $CH_2NH_2$ | $SO_2$ | (+)-pin | |
| 367 | $NHC(NH)NH_2$ | CO | (+)-pin | |
| 368 | $NHC(NH)NH_2$ | $SO_2$ | (+)-pin | |
| 369 | $SC(NH)NH_2$ | CO | (+)-pin | CC |
| 370 | $SC(NH)NH_2$ | $SO_2$ | (+)-pin | DD |
| 371 | $CH_2NH_2$ | CO | OH, OH | |
| 372 | $CH_2NH_2$ | $SO_2$ | OH, OH | |
| 373 | $NHC(NH)NH_2$ | CO | OH, OH | |
| 374 | $NHC(NH)NH_2$ | $SO_2$ | OH, OH | |
| 375 | $SC(NH)NH_2$ | CO | OH, OH | |
| 376 | $SC(NH)NH_2$ | $SO_2$ | OH, OH | |

CC: HRMS ($DCI-NH_3$), Calc: 560.2390, Found: 560.2407.
DD: HRMS ($DCI-NH_3$), Calc: 596.2060, Found: 596.2055.

TABLE 3

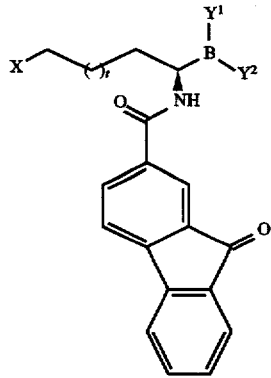

| Ex | X | t | $Y^1, Y^2$ | Phys Data |
|---|---|---|---|---|
| 382 | $NH_2$ | 2 | (+)-pin | |
| 383 | $SC(NH)NH_2$ | 2 | (+)-pin | EE |
| 384 | $SC(NH)NH_2$ | 1 | (+)-pin | FF |
| 385 | $NHC(NH)NH_2$ | 2 | (+)-pin | |
| 386 | $NHC(NH)NH_2$ | 1 | (+)-pin | |
| 387 | $NH_2$ | 2 | OH, OH | |
| 388 | $SC(NH)NH_2$ | 2 | OH, OH | |
| 389 | $SC(NH)NH_2$ | 1 | OH, OH | |
| 390 | $NHC(NH)NH_2$ | 2 | OH, OH | |
| 391 | $NHC(NH)NH_2$ | 1 | OH, OH | |

EE: HRMS ($DCI-NH_3$), Calc: 546.2597, Found: 546.2604.
FF: HRMS ($DCI-NH_3$), Calc: 534.2597, Found: 534.2609.

TABLE 4

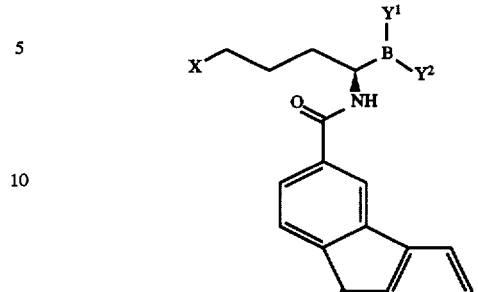

| Ex | X | $Y^1, Y^2$ | Phys Data |
|---|---|---|---|
| 397 | $CH_2NH_2$ | (+)-pin | |
| 398 | $NHC(NH)NH_2$ | (+)-pin | |
| 399 | $SC(NH)NH_2$ | (+)-pin | CG |
| 400 | $CH_2NH_2$ | OH, OH | |
| 401 | $NHC(NH)NH_2$ | OH, OH | |
| 402 | $SC(NH)NH_2$ | OH, OH | |

GG: HRMS ($DCI-NH_3$), Calc: 532.2441, Found: 532.2445.

TABLE 5

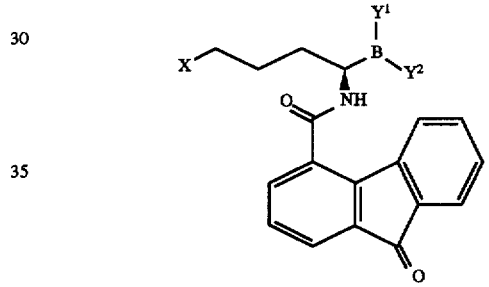

| Ex | X | $Y^1, Y^2$ | Phys Data |
|---|---|---|---|
| 403 | $CH_2NH_2$ | (+)-pin | |
| 404 | $NHC(NH)NH_2$ | (+)-pin | |
| 405 | $SC(NH)NH_2$ | (+)-pin | HH |
| 406 | $CH_2NH_2$ | OH, OH | |
| 407 | $NHC(NH)NH_2$ | OH, OH | |
| 408 | $SC(NH)NH_2$ | OH, OH | |

HH: HRMS ($DCI-NH_3$), Calc: 532.2441, Found: 532.2452.

TABLE 6

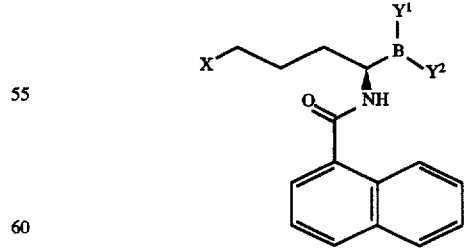

| Ex | X | $Y^1, Y^2$ | Phys Data |
|---|---|---|---|
| 436 | $NHC(NH)NH_2$ | (+)-pin | |
| 437 | $SC(NH)NH_2$ | (+)-pin | II |
| 438 | $CH_2NH_2$ | (+)-pin | |
| 439 | $NHC(NH)NH_2$ | OH, OH | |

TABLE 6-continued

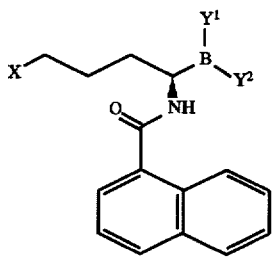

| Ex | X | $Y^1$, $Y^2$ | Phys Data |
|---|---|---|---|
| 440 | SC(NH)NH$_2$ | OH, OH | |
| 441 | CH$_2$NH$_2$ | OH, OH | |

II: HRMS (DCI—NH$_3$), Calc: 480.2493, Found: 480.2492.

TABLE 7

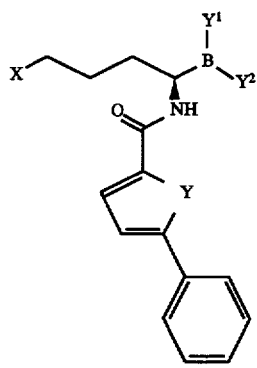

| Ex | X | Y | $Y^1$, $Y^2$ | Phys Data |
|---|---|---|---|---|
| 447 | NHC(NH)NH$_2$ | O | (+)-pin | WW |
| 448 | SC(NH)NH$_2$ | O | (+)-pin | JJ |
| 449 | CH$_2$NH$_2$ | O | (+)-pin | |
| 450 | NHC(NH)NH$_2$ | S | (+)-pin | |
| 451 | SC(NH)NH$_2$ | S | (+)-pin | |
| 452 | CH$_2$NH$_2$ | S | (+)-pin | |
| 453 | NHC(NH)NH$_2$ | O | OH, OH | |
| 454 | SC(NH)NH$_2$ | O | OH, OH | |
| 455 | CH$_2$NH$_2$ | O | OH, OH | |
| 456 | NHC(NH)NH$_2$ | S | OH, OH | |
| 457 | SC(NH)NH$_2$ | S | OH, OH | |
| 458 | CH$_2$NH$_2$ | S | OH, OH | |

JJ: HRMS (DCI—NH$_3$), Calc: 496.2441, Found: 496.2449.
WW: MS (DCI—NH$_3$), Calc: 345, Found: 345.

TABLE 8

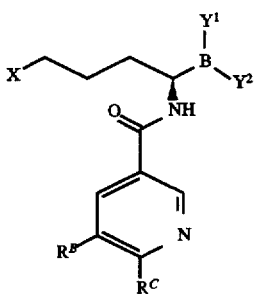

| Ex | X | $R^B$ | $R^C$ | $Y^1$, $Y^2$ | Phys Data |
|---|---|---|---|---|---|
| 464 | NHC(NH)NH$_2$ | H | Ph | (+)-pin | |
| 465 | NHC(NH)NH$_2$ | OBn | H | (+)-pin | |
| 466 | SC(NH)NH$_2$ | H | Ph | (+)-pin | KK |
| 467 | SC(NH)NH$_2$ | OBn | H | (+)-pin | LL |
| 468 | CH$_2$NH$_2$ | H | Ph | (+)-pin | CL |
| 469 | CH$_2$NH$_2$ | OBn | H | (+)-pin | |
| 470 | NHC(NH)NH$_2$ | H | Ph | OH, OH | |
| 471 | NHC(NH)NH$_2$ | OBn | H | OH, OH | |
| 472 | SC(NH)NH$_2$ | H | Ph | OH, OH | |
| 473 | SC(NH)NH$_2$ | OBn | H | OH, OH | |
| 474 | CH$_2$NH$_2$ | H | Ph | OH, OH | CM |
| 475 | CH$_2$NH$_2$ | OBn | H | OH, OH | |

KK: HRMS (DCI—NH$_3$), Calc: 507.2601, Found: 507.2592.
LL: HRMS (DCI—NH$_3$), Calc: 537.2667, Found: 537.2685.
CL: Anal. Calc'd. for $C_{27}H_{36}BN_3O_3 \cdot (HCl)_{1.7} \cdot (H_2O)_{2.2}$: C, 57.60; H, 7.54; Cl, 10.70; N, 7.46. Found: C, 57.40; H, 7.23; Cl, 10.78; N, 7.53. MS (M + H)$^+$: calc. 462, Found 462.
CM: MS (M + H)$^+$: Calc: 328, Found: 328.

TABLE 9

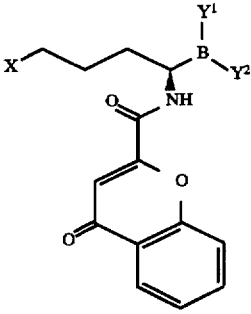

| Ex | X | $Y^1$, $Y^2$ | Phys Data |
|---|---|---|---|
| 476 | NHC(NH)NH$_2$ | (+)-pin | |
| 477 | SC(NH)NH$_2$ | (+)-pin | MM |
| 478 | CH$_2$NH$_2$ | (+)-pin | |
| 479 | NHC(NH)NH$_2$ | OH, OH | |
| 480 | SC(NH)NH$_2$ | OH, OH | |
| 481 | CH$_2$NH$_2$ | OH, OH | |

MM: HRMS (DCI—NH$_3$), Calc: 498.2233, Found: 498.2231.

TABLE 10

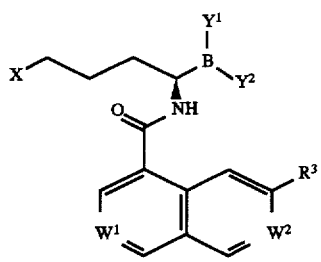

| Ex | X | W¹ | W² | R³ | Y¹, Y² | Phys Data |
|---|---|---|---|---|---|---|
| 482 | NHC(NH)NH₂ | N | CH | H | (+)-pin | |
| 483 | SC(NH)NH₂ | N | CH | H | (+)-pin | NN |
| 484 | CH₂NH₂ | N | CH | H | (+)-pin | |
| 485 | NHC(NH)NH₂ | CH | N | Ph | (+)-pin | |
| 486 | SC(NH)NH₂ | CH | N | Ph | (+)-pin | OO |
| 487 | CH₂NH₂ | CH | N | Ph | (+)-pin | |
| 488 | NHC(NH)NH₂ | N | CH | H | OH, OH | |
| 489 | SC(NH)NH₂ | N | CH | H | OH, OH | |
| 490 | CH₂NH₂ | N | CH | H | OH, OH | |
| 491 | NHC(NH)NH₂ | CH | N | Ph | OH, OH | |
| 492 | SC(NH)NH₂ | CH | N | Ph | OH, OH | |
| 493 | CH₂NH₂ | CH | N | Ph | OH, OH | |

NN: HRMS (DCI—NH₃), Calc: 481.2445, Found: 481.2442.
OO: HRMS (DCI—NH₃), Calc: 557.2758, Found: 557.2754.

TABLE 11

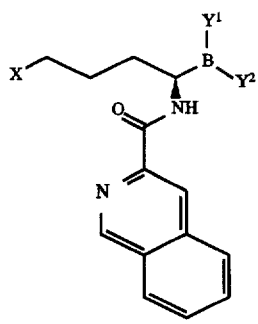

| Ex | X | Y¹, Y² | Phys Data |
|---|---|---|---|
| 499 | NHC(NH)NH₂ | (+)-pin | |
| 500 | SC(NH)NH₂ | (+)-pin | PP |
| 501 | CH₂NH₂ | (+)-pin | |
| 502 | NHC(NH)NH₂ | OH, OH | |
| 503 | SC(NH)NH₂ | OH, OH | |
| 504 | CH₂NH₂ | OH, OH | |

PP: HRMS (DCI—NH₃), Calc: 5481.2445, Found: 481.2440.

TABLE 12

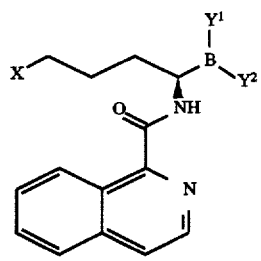

| Ex | X | R³ | Y¹, Y² | Phys Data |
|---|---|---|---|---|
| 510 | SC(NH)NH₂ | H | (+)-pin | QQ |

QQ: HRNS (NH₃—Cl/DEP), Calc: 503.3193, Found: 503.3199.

TABLE 13

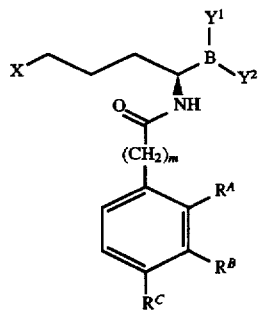

| Ex | m, X | R^A | R^B | R^C | Y¹, Y² | Phys Data |
|---|---|---|---|---|---|---|
| 516 | 2, SC(NH)NH₂ | H | NHCO—(CH₂)₂Ph | H | (+)-pin | RR |
| 517 | 2, SC(NH)NH₂ | H | Ph | H | (+)-pin | |
| 518 | 2, SC(NH)NH₂ | H | OPh | Ph | (+)-pin | |
| 519 | 1, SC(NH)NH₂ | H | H | 4-pyridyl | (+)-pin | |
| 520 | 1, NHC(NH)NH₂ | COPh | H | H | (+)-pin | |
| 521 | 3, NHC(NH)NH₂ | H | COPh | H | (+)-pin | |
| 522 | 3, NHC(NH)NH₂ | H | H | COPh | (+)-pin | |

RR: HRMS (DCI—NH₃), Calc: 605.333, Found: 605.3325.

TABLE 14

| Ex | X | m | R¹³ | R¹⁴ | Y¹Y² | Phys. Data |
|---|---|---|---|---|---|---|
| 528 | CH₂NH₂ | 1 | Ph | H | (+)-pin | |
| 529 | CH₂NH₂ | 1 | Ph | Methyl | (+)-pin | |
| 530 | CH₂NH₂ | 1 | Ph | Ethyl | (+)-pin | |
| 531 | CH₂NH₂ | 1 | Ph | n-Propyl | (+)-pin | |
| 532 | CH₂NH₂ | 1 | Ph | n-Butyl | (+)-pin | |
| 533 | CH₂NH₂ | 1 | Ph | CH₂SCH₃ | (+)-pin | |
| 534 | CH₂NH₂ | 1 | Ph | CH₂(SO)CH₃ | (+)-pin | |
| 535 | CH₂NH₂ | 1 | Ph | CH₂(SO₂)CH₃ | (+)-pin | |
| 536 | CH₂NH₂ | 1 | Ph | CH₂CH₂SCH₃ | (+)-pin | |
| 537 | CH₂NH₂ | 1 | Ph | CH₂CH₂(SO)CH₃ | (+)-pin | |
| 538 | CH₂NH₂ | 1 | Ph | CH₂CH₂(SO)₂CH₃ | (+)-pin | |
| 539 | CH₂NH₂ | 1 | Ph | CH₂CN | (+)-pin | |
| 540 | CH₂NH₂ | 1 | Ph | CH₂CH₂CN | (+)-pin | |
| 541 | CH₂NH₂ | 1 | Ph | CH₂CH₂CH₂CN | (+)-pin | |
| 542 | CH₂NH₂ | 1 | Ph | CF₃ | (+)-pin | |
| 543 | CH₂NH₂ | 1 | Ph | CF₂CF₃ | (+)-pin | |
| 544 | CH₂NH₂ | 1 | Ph | CF₂CF₂CF₃ | (+)-pin | |
| 545 | CH₂NH₂ | 1 | Ph | CF₂CF₂CF₂CF₃ | (+)-pin | |
| 546 | CH₂NH₂ | 1 | Ph | F₅-Ph | (+)-pin | |
| 547 | CH₂NH₂ | 1 | Ph | CH₂CO₂H | (+)-pin | |
| 548 | CH₂NH₂ | 1 | Ph | (CH₂)₂CO₂H | (+)-pin | |
| 549 | CH₂NH₂ | 1 | Ph | (CH₂)₃CO₂H | (+)-pin | |
| 550 | CH₂NH₂ | 1 | Ph | CH₂CN₄H | (+)-pin | |
| 551 | CH₂NH₂ | 1 | Ph | (CH₂)₂CN₄H | (+)-pin | |
| 552 | CH₂NH₂ | 1 | Ph | (CH₂)₃CN₄H | (+)-pin | |
| 553 | CH₂NH₂ | 1 | Ph | CH₂NO₂ | (+)-pin | |
| 554 | CH₂NH₂ | 1 | Ph | (CH₂)₂NO₂ | (+)-pin | |
| 555 | CH₂NH₂ | 1 | Ph | (CH₂)₃NO₂ | (+)-pin | |
| 556 | CH₂NH₂ | 1 | Ph | CH₂OH | (+)-pin | |
| 557 | CH₂NH₂ | 1 | Ph | (CH₂)₂OH | (+)-pin | |
| 558 | CH₂NH₂ | 1 | Ph | (CH₂)₃OH | (+)-pin | |
| 559 | CH₂NH₂ | 1 | Ph | CH₂CO₂Me | (+)-pin | |
| 560 | CH₂NH₂ | 1 | Ph | (CH₂)₂CO₂Me | (+)-pin | |
| 561 | CH₂NH₂ | 1 | Ph | (CH₂)₃CO₂Me | (+)-pin | |
| 562 | CH₂NH₂ | 1 | Ph | Ph | (+)-pin | |
| 563 | CH₂NH₂ | 1 | Ph | PhCH₂ | (+)-pin | AG |
| 564 | CH₂NH₂ | 1 | Ph | Ph(CH₂)₂ | (+)-pin | |
| 565 | CH₂NH₂ | 1 | Ph | 3-NO₂-Ph | (+)-pin | |
| 566 | CH₂NH₂ | 1 | Ph | 4-NO₂-Ph | (+)-pin | |
| 567 | CH₂NH₂ | 1 | Ph | 3-CO₂H-Ph | (+)-pin | |
| 568 | CH₂NH₂ | 1 | Ph | 4-CO₂H-Ph | (+)-pin | |
| 569 | CH₂NH₂ | 1 | Ph | 3-CN₄H-Ph | (+)-pin | |
| 570 | CH₂NH₂ | 1 | Ph | 4-CN₄H-Ph | (+)-pin | |
| 571 | CH₂NH₂ | 1 | Ph | 3-(HOCH₂)-Ph | (+)-pin | |
| 572 | CH₂NH₂ | 1 | Ph | 4-(HOCH₂)-Ph | (+)-pin | |
| 573 | NH(C=NH)NH₂ | 1 | Ph | H | (+)-pin | |
| 574 | NH(C=NH)NH₂ | 1 | Ph | Methyl | (+)-pin | |
| 575 | NH(C=NH)NH₂ | 1 | Ph | Ethyl | (+)-pin | |
| 576 | NH(C=NH)NH₂ | 1 | Ph | n-Propyl | (+)-pin | |
| 577 | NH(C=NH)NH₂ | 1 | Ph | n-Butyl | (+)-pin | |
| 578 | NH(C=NH)NH₂ | 1 | Ph | CH₂SCH₃ | (+)-pin | |
| 579 | NH(C=NH)NH₂ | 1 | Ph | CH₂(SO)CH₃ | (+)-pin | |
| 580 | NH(C=NH)NH₂ | 1 | Ph | CH₂(SO₂)CH₃ | (+)-pin | |
| 581 | NH(C=NH)NH₂ | 1 | Ph | CH₂CH₂SCH₃ | (+)-pin | |
| 582 | NH(C=NH)NH₂ | 1 | Ph | CH₂CH₂(SO)CH₃ | (+)-pin | |
| 583 | NH(C=NH)NH₂ | 1 | Ph | CH₂CH₂(SO)₂CH₃ | (+)-pin | |
| 584 | NH(C=NH)NH₂ | 1 | Ph | CH₂CN | (+)-pin | |
| 585 | NH(C=NH)NH₂ | 1 | Ph | CH₂CH₂CN | (+)-pin | |
| 586 | NH(C=NH)NH₂ | 1 | Ph | CH₂CH₂CH₂CN | (+)-pin | |
| 587 | NH(C=NH)NH₂ | 1 | Ph | CF₃ | (+)-pin | |
| 588 | NH(C=NH)NH₂ | 1 | Ph | CF₂CF₃ | (+)-pin | |
| 589 | NH(C=NH)NH₂ | 1 | Ph | CF₂CF₂CF₃ | (+)-pin | |
| 590 | NH(C=NH)NH₂ | 1 | Ph | CF₂CF₂CF₂CF₃ | (+)-pin | |
| 591 | NH(C=NH)NH₂ | 1 | Ph | F₅-Ph | (+)-pin | |

TABLE 14-continued

[Structure: triazole-N-(CH₂)ₘ-C(O)-NH-CH(CH₂CH₂-X)-B(Y¹)(Y²), with R¹³ and R¹⁴ substituents on the triazole ring]

| Ex | X | m | R¹³ | R¹⁴ | Y¹Y² | Phys. Data |
|---|---|---|---|---|---|---|
| 592 | NH(C=NH)NH₂ | 1 | Ph | CH₂CO₂H | (+)-pin | |
| 593 | NH(C=NH)NH₂ | 1 | Ph | (CH₂)₂CO₂H | (+)-pin | |
| 594 | NH(C=NH)NH₂ | 1 | Ph | (CH₂)₃CO₂H | (+)-pin | |
| 595 | NH(C=NH)NH₂ | 1 | Ph | CH₂CN₄H | (+)-pin | |
| 596 | NH(C=NH)NH₂ | 1 | Ph | (CH₂)₂CN₄H | (+)-pin | |
| 597 | NH(C=NH)NH₂ | 1 | Ph | (CH₂)₃CN₄H | (+)-pin | |
| 598 | NH(C=NH)NH₂ | 1 | Ph | CH₂NO₂ | (+)-pin | |
| 599 | NH(C=NH)NH₂ | 1 | Ph | (CH₂)₂NO₂ | (+)-pin | |
| 600 | NH(C=NH)NH₂ | 1 | Ph | (CH₂)₃NO₂ | (+)-pin | |
| 601 | NH(C=NH)NH₂ | 1 | Ph | CH₂OH | (+)-pin | |
| 602 | NH(C=NH)NH₂ | 1 | Ph | (CH₂)₂OH | (+)-pin | |
| 603 | NH(C=NH)NH₂ | 1 | Ph | (CH₂)₃OH | (+)-pin | |
| 604 | NH(C=NH)NH₂ | 1 | Ph | CH₂CO₂Me | (+)-pin | |
| 605 | NH(C=NH)NH₂ | 1 | Ph | (CH₂)₂CO₂Me | (+)-pin | |
| 606 | NH(C=NH)NH₂ | 1 | Ph | (CH₂)₃CO₂Me | (+)-pin | |
| 607 | NH(C=NH)NH₂ | 1 | Ph | Ph | (+)-pin | |
| 609 | NH(C=NH)NH₂ | 1 | Ph | 3-NO₂-Ph | (+)-pin | |
| 610 | NH(C=NH)NH₂ | 1 | Ph | 4-NO₂-Ph | (+)-pin | |
| 611 | NH(C=NH)NH₂ | 1 | Ph | 3-CO₂H-Ph | (+)-pin | |
| 612 | NH(C=NH)NH₂ | 1 | Ph | 4-CO₂H-Ph | (+)-pin | |
| 613 | NH(C=NH)NH₂ | 1 | Ph | 3-CN₄H-Ph | (+)-pin | |
| 614 | NH(C=NH)NH₂ | 1 | Ph | 4-CN₄H-Ph | (+)-pin | |
| 615 | NH(C=NH)NH₂ | 1 | Ph | 3-(HOCH₂)-Ph | (+)-pin | |
| 616 | NH(C=NH)NH₂ | 1 | Ph | 4-(HOCH₂)-Ph | (+)-pin | |
| 617 | CH₂NH₂ | 1 | Ph | H | OH, OH | |
| 618 | CH₂NH₂ | 1 | Ph | Methyl | OH, OH | |
| 619 | CH₂NH₂ | 1 | Ph | Ethyl | OH, OH | |
| 620 | CH₂NH₂ | 1 | Ph | n-Propyl | OH, OH | |
| 621 | CH₂NH₂ | 1 | Ph | n-Butyl | OH, OH | |
| 622 | CH₂NH₂ | 1 | Ph | CH₂SCH₃ | OH, OH | |
| 623 | CH₂NH₂ | 1 | Ph | CH₂(SO)CH₃ | OH, OH | |
| 624 | CH₂NH₂ | 1 | Ph | CH₂(SO₂)CH₃ | OH, OH | |
| 625 | CH₂NH₂ | 1 | Ph | CH₂CH₂SCH₃ | OH, OH | |
| 626 | CH₂NH₂ | 1 | Ph | CH₂CH₂(SO)CH₃ | OH, OH | |
| 627 | CH₂NH₂ | 1 | Ph | CH₂CH₂(SO)₂CH₃ | OH, OH | |
| 628 | CH₂NH₂ | 1 | Ph | CH₂CN | OH, OH | |
| 629 | CH₂NH₂ | 1 | Ph | CH₂CH₂CN | OH, OH | |
| 630 | CH₂NH₂ | 1 | Ph | CH₂CH₂CH₂CN | OH, OH | |
| 631 | CH₂NH₂ | 1 | Ph | CF₃ | OH, OH | |
| 632 | CH₂NH₂ | 1 | Ph | CF₂CF₃ | OH, OH | |
| 633 | CH₂NH₂ | 1 | Ph | CF₂CF₂CF₃ | OH, OH | |
| 634 | CH₂NH₂ | 1 | Ph | CF₂CF₂CF₂CF₃ | OH, OH | |
| 635 | CH₂NH₂ | 1 | Ph | F₅-Ph | OH, OH | |
| 636 | CH₂NH₂ | 1 | Ph | CH₂CO₂H | OH, OH | |
| 637 | CH₂NH₂ | 1 | Ph | (CH₂)₂CO₂H | OH, OH | |
| 638 | CH₂NH₂ | 1 | Ph | (CH₂)₃CO₂H | OH, OH | |
| 639 | CH₂NH₂ | 1 | Ph | CH₂CN₄H | OH, OH | |
| 640 | CH₂NH₂ | 1 | Ph | (CH₂)₂CN₄H | OH, OH | |
| 641 | CH₂NH₂ | 1 | Ph | (CH₂)₃CN₄H | OH, OH | |
| 642 | CH₂NH₂ | 1 | Ph | CH₂NO₂ | OH, OH | |
| 643 | CH₂NH₂ | 1 | Ph | (CH₂)₂NO₂ | OH, OH | |
| 644 | CH₂NH₂ | 1 | Ph | (CH₂)₃NO₂ | OH, OH | |
| 645 | CH₂NH₂ | 1 | Ph | CH₂OH | OH, OH | |
| 646 | CH₂NH₂ | 1 | Ph | (CH₂)₂OH | OH, OH | |
| 647 | CH₂NH₂ | 1 | Ph | (CH₂)₃OH | OH, OH | |
| 648 | CH₂NH₂ | 1 | Ph | CH₂CO₂Me | OH, OH | |
| 649 | CH₂NH₂ | 1 | Ph | (CH₂)₂CO₂Me | OH, OH | |
| 650 | CH₂NH₂ | 1 | Ph | (CH₂)₃CO₂Me | OH, OH | |
| 651 | CH₂NH₂ | 1 | Ph | Ph | OH, OH | |
| 652 | CH₂NH₂ | 1 | Ph | PhCH₂ | OH, OH | AH |
| 653 | CH₂NH₂ | 1 | Ph | Ph(CH₂)₂ | OH, OH | |
| 654 | CH₂NH₂ | 1 | Ph | 3-NO₂-Ph | OH, OH | |
| 655 | CH₂NH₂ | 1 | Ph | 4-NO₂-Ph | OH, OH | |
| 656 | CH₂NH₂ | 1 | Ph | 3-CO₂H-Ph | OH, OH | |

TABLE 14-continued

| Ex | X | m | R[13] | R[14] | Y[1]Y[2] | Phys. Data |
|---|---|---|---|---|---|---|
| 657 | $CH_2NH_2$ | 1 | Ph | 4-$CO_2$H-Ph | OH, OH | |
| 658 | $CH_2NH_2$ | 1 | Ph | 3-$CN_4$H-Ph | OH, OH | |
| 659 | $CH_2NH_2$ | 1 | Ph | 4-$CN_4$H-Ph | OH, OH | |
| 660 | $CH_2NH_2$ | 1 | Ph | 3-$(HOCH_2)$-Ph | OH, OH | |
| 661 | $CH_2NH_2$ | 1 | Ph | 4-$(HOCH_2)$-Ph | OH, OH | |
| 662 | $NH(C=NH)NH_2$ | 1 | Ph | H | OH, OH | |
| 663 | $NH(C=NH)NH_2$ | 1 | Ph | Methyl | OH, OH | |
| 664 | $NH(C=NH)NH_2$ | 1 | Ph | Ethyl | OH, OH | |
| 665 | $NH(C=NH)NH_2$ | 1 | Ph | n-Propyl | OH, OH | |
| 666 | $NH(C=NH)NH_2$ | 1 | Ph | n-Butyl | OH, OH | |
| 667 | $NH(C=NH)NH_2$ | 1 | Ph | $CH_2SCH_3$ | OH, OH | |
| 668 | $NH(C=NH)NH_2$ | 1 | Ph | $CH_2(SO)CH_3$ | OH, OH | |
| 669 | $NH(C=NH)NH_2$ | 1 | Ph | $CH_2(SO_2)CH_3$ | OH, OH | |
| 670 | $NH(C=NH)NH_2$ | 1 | Ph | $CH_2CH_2SCH_3$ | OH, OH | |
| 671 | $NH(C=NH)NH_2$ | 1 | Ph | $CH_2CH_2(SO)CH_3$ | OH, OH | |
| 672 | $NH(C=NH)NH_2$ | 1 | Ph | $CH_2CH_2(SO)_2CH_3$ | OH, OH | |
| 673 | $NH(C=NH)NH_2$ | 1 | Ph | $CH_2CN$ | OH, OH | |
| 674 | $NH(C=NH)NH_2$ | 1 | Ph | $CH_2CH_2CN$ | OH, OH | |
| 675 | $NH(C=NH)NH_2$ | 1 | Ph | $CH_2CH_2CH_2CN$ | OH, OH | |
| 676 | $NH(C=NH)NH_2$ | 1 | Ph | $CF_3$ | OH, OH | |
| 677 | $NH(C=NH)NH_2$ | 1 | Ph | $CF_2CF_3$ | OH, OH | |
| 678 | $NH(C=NH)NH_2$ | 1 | Ph | $CF_2CF_2CF_3$ | OH, OH | |
| 679 | $NH(C=NH)NH_2$ | 1 | Ph | $CF_2CF_2CF_2CF_3$ | OH, OH | |
| 680 | $NH(C=NH)NH_2$ | 1 | Ph | $F_5$-Ph | OH, OH | |
| 681 | $NH(C=NH)NH_2$ | 1 | Ph | $CH_2CO_2H$ | OH, OH | |
| 682 | $NH(C=NH)NH_2$ | 1 | Ph | $(CH_2)_2CO_2H$ | OH, OH | |
| 683 | $NH(C=NH)NH_2$ | 1 | Ph | $(CH_2)_3CO_2H$ | OH, OH | |
| 684 | $NH(C=NH)NH_2$ | 1 | Ph | $CH_2CN_4H$ | OH, OH | |
| 685 | $NH(C=NH)NH_2$ | 1 | Ph | $(CH_2)_2CN_4H$ | OH, OH | |
| 686 | $NH(C=NH)NH_2$ | 1 | Ph | $(CH_2)_3CN_4H$ | OH, OH | |
| 687 | $NH(C=NH)NH_2$ | 1 | Ph | $CH_2NO_2$ | OH, OH | |
| 688 | $NH(C=NH)NH_2$ | 1 | Ph | $(CH_2)_2NO_2$ | OH, OH | |
| 689 | $NH(C=NH)NH_2$ | 1 | Ph | $(CH_2)_3NO_2$ | OH, OH | |
| 690 | $NH(C=NH)NH_2$ | 1 | Ph | $CH_2OH$ | OH, OH | |
| 691 | $NH(C=NH)NH_2$ | 1 | Ph | $(CH_2)_2OH$ | OH, OH | |
| 692 | $NH(C=NH)NH_2$ | 1 | Ph | $(CH_2)_3OH$ | OH, OH | |
| 693 | $NH(C=NH)NH_2$ | 1 | Ph | $CH_2CO_2Me$ | OH, OH | |
| 694 | $NH(C=NH)NH_2$ | 1 | Ph | $(CH_2)_2CO_2Me$ | OH, OH | |
| 695 | $NH(C=NH)NH_2$ | 1 | Ph | $(CH_2)_3CO_2Me$ | OH, OH | |
| 696 | $NH(C=NH)NH_2$ | 1 | Ph | Ph | OH, OH | |
| 697 | $NH(C=NH)NH_2$ | 1 | Ph | $PhCH_2$ | OH, OH | |
| 698 | $NH(C=NH)NH_2$ | 1 | Ph | $Ph(CH_2)_2$ | OH, OH | |
| 699 | $NH(C=NH)NH_2$ | 1 | Ph | 3-$NO_2$-Ph | OH, OH | |
| 700 | $NH(C=NH)NH_2$ | 1 | Ph | 4-$NO_2$-Ph | OH, OH | |
| 701 | $NH(C=NH)NH_2$ | 1 | Ph | 3-$CO_2$H-Ph | OH, OH | |
| 702 | $NH(C=NH)NH_2$ | 1 | Ph | 4-$CO_2$H-Ph | OH, OH | |
| 703 | $NH(C=NH)NH_2$ | 1 | Ph | 3-$CN_4$H-Ph | OH, OH | |
| 704 | $NH(C=NH)NH_2$ | 1 | Ph | 4-$CN_4$H-Ph | OH, OH | |
| 705 | $NH(C=NH)NH_2$ | 1 | Ph | 3-$(HOCH_2)$-Ph | OH, OH | |
| 706 | $NH(C=NH)NH_2$ | 1 | Ph | 4-$(HOCH_2)$-Ph | OH, OH | |
| 707 | $-S-(C=NH)NH_2$ | 1 | Ph | H | (+)-pin | |
| 708 | $-S-(C=NH)NH_2$ | 1 | Ph | Methyl | (+)-pin | |
| 709 | $-S-(C=NH)NH_2$ | 1 | Ph | Ethyl | (+)-pin | |
| 710 | $-S-(C=NH)NH_2$ | 1 | Ph | n-Propyl | (+)-pin | |
| 711 | $-S-(C=NH)NH_2$ | 1 | Ph | n-Butyl | (+)-pin | |
| 712 | $-S-(C=NH)NH_2$ | 1 | Ph | $CH_2SCH_3$ | (+)-pin | |
| 713 | $-S-(C=NH)NH_2$ | 1 | Ph | $CH_2(SO)CH_3$ | (+)-pin | |
| 714 | $-S-(C=NH)NH_2$ | 1 | Ph | $CH_2(SO_2)CH_3$ | (+)-pin | |
| 715 | $-S-(C=NH)NH_2$ | 1 | Ph | $CH_2CH_2SCH_3$ | (+)-pin | |
| 716 | $-S-(C=NH)NH_2$ | 1 | Ph | $CH_2CH_2(SO)CH_3$ | (+)-pin | |
| 717 | $-S-(C=NH)NH_2$ | 1 | Ph | $CH_2CH_2(SO)_2CH_3$ | (+)-pin | |
| 718 | $-S-(C=NH)NH_2$ | 1 | Ph | $CH_2CN$ | (+)-pin | |
| 719 | $-S-(C=NH)NH_2$ | 1 | Ph | $CH_2CH_2CN$ | (+)-pin | |
| 720 | $-S-(C=NH)NH_2$ | 1 | Ph | $CH_2CH_2CH_2CN$ | (+)-pin | |

TABLE 14-continued

| Ex | X | m | R$^{13}$ | R$^{14}$ | Y$^1$Y$^2$ | Phys. Data |
|---|---|---|---|---|---|---|
| 721 | —S—(C=NH)NH$_2$ | 1 | Ph | CF$_3$ | (+)-pin | |
| 722 | —S—(C=NH)NH$_2$ | 1 | Ph | CF$_2$CF$_3$ | (+)-pin | |
| 723 | —S—(C=NH)NH$_2$ | 1 | Ph | CF$_2$CF$_2$CF$_3$ | (+)-pin | |
| 724 | —S—(C=NH)NH$_2$ | 1 | Ph | CF$_2$CF$_2$CF$_2$CF$_3$ | (+)-pin | |
| 725 | —S—(C=NH)NH$_2$ | 1 | Ph | F$_5$-Ph | (+)-pin | |
| 726 | —S—(C=NH)NH$_2$ | 1 | Ph | CH$_2$CO$_2$H | (+)-pin | |
| 727 | —S—(C=NH)NH$_2$ | 1 | Ph | (CH$_2$)$_2$CO$_2$H | (+)-pin | |
| 728 | —S—(C=NH)NH$_2$ | 1 | Ph | (CH$_2$)$_3$CO$_2$H | (+)-pin | |
| 729 | —S—(C=NH)NH$_2$ | 1 | Ph | CH$_2$CN$_4$H | (+)-pin | |
| 730 | —S—(C=NH)NH$_2$ | 1 | Ph | (CH$_2$)$_2$CN$_4$H | (+)-pin | |
| 731 | —S—(C=NH)NH$_2$ | 1 | Ph | (CH$_2$)$_3$CN$_4$H | (+)-pin | |
| 732 | —S—(C=NH)NH$_2$ | 1 | Ph | CH$_2$NO$_2$ | (+)-pin | |
| 733 | —S—(C=NH)NH$_2$ | 1 | Ph | (CH$_2$)$_2$NO$_2$ | (+)-pin | |
| 734 | —S—(C=NH)NH$_2$ | 1 | Ph | (CH$_2$)$_3$NO$_2$ | (+)-pin | |
| 735 | —S—(C=NH)NH$_2$ | 1 | Ph | CH$_2$OH | (+)-pin | |
| 736 | —S—(C=NH)NH$_2$ | 1 | Ph | (CH$_2$)$_2$OH | (+)-pin | |
| 737 | —S—(C=NH)NH$_2$ | 1 | Ph | (CH$_2$)$_3$OH | (+)-pin | |
| 738 | —S—(C=NH)NH$_2$ | 1 | Ph | CH$_2$CO$_2$Me | (+)-pin | |
| 739 | —S—(C=NH)NH$_2$ | 1 | Ph | (CH$_2$)$_2$CO$_2$Me | (+)-pin | |
| 740 | —S—(C=NH)NH$_2$ | 1 | Ph | (CH$_2$)$_3$CO$_2$Me | (+)-pin | |
| 741 | —S—(C=NH)NH$_2$ | 1 | Ph | Ph | (+)-pin | |
| 742 | —S—(C=NH)NH$_2$ | 1 | Ph | 3-NO$_2$-Ph | (+)-pin | |
| 743 | —S—(C=NH)NH$_2$ | 1 | Ph | 4-NO$_2$-Ph | (+)-pin | |
| 744 | —S—(C=NH)NH$_2$ | 1 | Ph | 3-CO$_2$H-Ph | (+)-pin | |
| 745 | —S—(C=NH)NH$_2$ | 1 | Ph | 4-CO$_2$H-Ph | (+)-pin | |
| 746 | —S—(C=NH)NH$_2$ | 1 | Ph | 3-CN$_4$H-Ph | (+)-pin | |
| 747 | —S—(C=NH)NH$_2$ | 1 | Ph | 4-CN$_4$H-Ph | (+)-pin | |
| 748 | —S—(C=NH)NH$_2$ | 1 | Ph | 3-(HOCH$_2$)-Ph | (+)-pin | |
| 749 | —S—(C=NH)NH$_2$ | 1 | Ph | 4-(HOCH$_2$)-Ph | (+)-pin | |
| 750 | —S—(C=NH)NH$_2$ | 1 | Ph | H | OH, OH | |
| 751 | —S—(C=NH)NH$_2$ | 1 | Ph | Methyl | OH, OH | |
| 752 | —S—(C=NH)NH$_2$ | 1 | Ph | Ethyl | OH, OH | |
| 753 | —S—(C=NH)NH$_2$ | 1 | Ph | n-Propyl | OH, OH | |
| 754 | —S—(C=NH)NH$_2$ | 1 | Ph | n-Butyl | OH, OH | |
| 755 | —S—(C=NH)NH$_2$ | 1 | Ph | CH$_2$SCH$_3$ | OH, OH | |
| 756 | —S—(C=NH)NH$_2$ | 1 | Ph | CH$_2$(SO)CH$_3$ | OH, OH | |
| 757 | —S—(C=NH)NH$_2$ | 1 | Ph | CH$_2$(SO$_2$)CH$_3$ | OH, OH | |
| 758 | —S—(C=NH)NH$_2$ | 1 | Ph | CH$_2$CH$_2$SCH$_3$ | OH, OH | |
| 759 | —S—(C=NH)NH$_2$ | 1 | Ph | CH$_2$CH$_2$(SO)CH$_3$ | OH, OH | |
| 760 | —S—(C=NH)NH$_2$ | 1 | Ph | CH$_2$CH$_2$(SO)$_2$CH$_3$ | OH, OH | |
| 761 | —S—(C=NH)NH$_2$ | 1 | Ph | CH$_2$CN | OH, OH | |
| 762 | —S—(C=NH)NH$_2$ | 1 | Ph | CH$_2$CH$_2$CN | OH, OH | |
| 763 | —S—(C=NH)NH$_2$ | 1 | Ph | CH$_2$CH$_2$CH$_2$CN | OH, OH | |
| 764 | —S—(C=NH)NH$_2$ | 1 | Ph | CF$_3$ | OH, OH | |
| 765 | —S—(C=NH)NH$_2$ | 1 | Ph | CF$_2$CF$_3$ | OH, OH | |
| 766 | —S—(C=NH)NH$_2$ | 1 | Ph | CF$_2$CF$_2$CF$_3$ | OH, OH | |
| 767 | —S—(C=NH)NH$_2$ | 1 | Ph | CF$_2$CF$_2$CF$_2$CF$_3$ | OH, OH | |
| 768 | —S—(C=NH)NH$_2$ | 1 | Ph | F$_5$-Ph | OH, OH | |
| 769 | —S—(C=NH)NH$_2$ | 1 | Ph | CH$_2$CO$_2$H | OH, OH | |
| 770 | —S—(C=NH)NH$_2$ | 1 | Ph | (CH$_2$)$_2$CO$_2$H | OH, OH | |
| 771 | —S—(C=NH)NH$_2$ | 1 | Ph | (CH$_2$)$_3$CO$_2$H | OH, OH | |
| 772 | —S—(C=NH)NH$_2$ | 1 | Ph | CH$_2$CN$_4$H | OH, OH | |
| 773 | —S—(C=NH)NH$_2$ | 1 | Ph | (CH$_2$)$_2$CN$_4$H | OH, OH | |
| 774 | —S—(C=NH)NH$_2$ | 1 | Ph | (CH$_2$)$_3$CN$_4$H | OH, OH | |
| 775 | —S—(C=NH)NH$_2$ | 1 | Ph | CH$_2$NO$_2$ | OH, OH | |
| 776 | —S—(C=NH)NH$_2$ | 1 | Ph | (CH$_2$)$_2$NO$_2$ | OH, OH | |
| 777 | —S—(C=NH)NH$_2$ | 1 | Ph | (CH$_2$)$_3$NO$_2$ | OH, OH | |
| 778 | —S—(C=NH)NH$_2$ | 1 | Ph | CH$_2$OH | OH, OH | |
| 779 | —S—(C=NH)NH$_2$ | 1 | Ph | (CH$_2$)$_2$OH | OH, OH | |
| 780 | —S—(C=NH)NH$_2$ | 1 | Ph | (CH$_2$)$_3$OH | OH, OH | |
| 781 | —S—(C=NH)NH$_2$ | 1 | Ph | CH$_2$CO$_2$Me | OH, OH | |
| 782 | —S—(C=NH)NH$_2$ | 1 | Ph | (CH$_2$)$_2$CO$_2$Me | OH, OH | |
| 783 | —S—(C=NH)NH$_2$ | 1 | Ph | (CH$_2$)$_3$CO$_2$Me | OH, OH | |
| 784 | —S—(C=NH)NH$_2$ | 1 | Ph | Ph | OH, OH | |

TABLE 14-continued

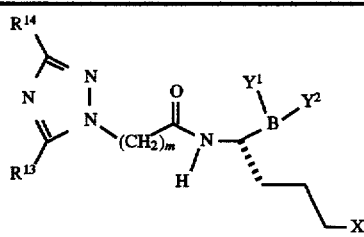

| Ex | X | m | $R^{13}$ | $R^{14}$ | $Y^1Y^2$ | Phys. Data |
|---|---|---|---|---|---|---|
| 785 | $-S-(C=NH)NH_2$ | 1 | Ph | $PhCH_2$ | OH, OH | |
| 786 | $-S-(C=NH)NH_2$ | 1 | Ph | $Ph(CH_2)_2$ | OH, OH | |
| 787 | $-S-(C=NH)NH_2$ | 1 | Ph | $3-NO_2-Ph$ | OH, OH | |
| 788 | $-S-(C=NH)NH_2$ | 1 | Ph | $4-NO_2-Ph$ | OH, OH | |
| 789 | $-S-(C=NH)NH_2$ | 1 | Ph | $3-CO_2H-Ph$ | OH, OH | |
| 790 | $-S-(C=NH)NH_2$ | 1 | Ph | $4-CO_2H-Ph$ | OH, OH | |
| 791 | $-S-(C=NH)NH_2$ | 1 | Ph | $3-CN_4H-Ph$ | OH, OH | |
| 792 | $-S-(C=NH)NH_2$ | 1 | Ph | $4-CN_4H-Ph$ | OH, OH | |
| 793 | $-S-(C=NH)NH_2$ | 1 | Ph | $3-(HOCH_2)-Ph$ | OH, OH | |
| 794 | $-S-(C=NH)NH_2$ | 1 | Ph | $4-(HOCH_2)-Ph$ | OH, OH | |
| 795 | $CH_2NH_2$ | 2 | Ph | H | (+)-pin | |
| 796 | $CH_2NH_2$ | 2 | Ph | H | OH, OH | |
| 797 | OMe | 1 | Ph | H | (+)-pin | |
| 798 | OMe | 1 | Ph | Methyl | (+)-pin | |
| 799 | OMe | 1 | Ph | Ethyl | (+)-pin | |
| 800 | OMe | 1 | Ph | n-Propyl | (+)-pin | |
| 801 | OMe | 1 | Ph | n-Butyl | (+)-pin | |
| 802 | OMe | 1 | Ph | $CH_2SCH_3$ | (+)-pin | |
| 803 | OMe | 1 | Ph | $CH_2(SO)CH_3$ | (+)-pin | |
| 804 | OMe | 1 | Ph | $CH_2(SO_2)CH_3$ | (+)-pin | |
| 805 | OMe | 1 | Ph | $CH_2CH_2SCH_3$ | (+)-pin | |
| 806 | OMe | 1 | Ph | $CH_2CH_2(SO)CH_3$ | (+)-pin | |
| 807 | OMe | 1 | Ph | $CH_2CH_2(SO)_2CH_3$ | (+)-pin | |
| 808 | OMe | 1 | Ph | $CH_2CN$ | (+)-pin | |
| 809 | OMe | 1 | Ph | $CH_2CH_2CN$ | (+)-pin | |
| 810 | OMe | 1 | Ph | $CH_2CH_2CH_2CN$ | (+)-pin | |
| 811 | OMe | 1 | Ph | $CF_3$ | (+)-pin | |
| 812 | OMe | 1 | Ph | $CF_2CF_3$ | (+)-pin | |
| 813 | OMe | 1 | Ph | $CF_2CF_2CF_3$ | (+)-pin | |
| 814 | OMe | 1 | Ph | $CF_2CF_2CF_2CF_3$ | (+)-pin | |
| 815 | OMe | 1 | Ph | $F_5-Ph$ | (+)-pin | |
| 816 | OMe | 1 | Ph | $CH_2CO_2H$ | (+)-pin | |
| 817 | OMe | 1 | Ph | $(CH_2)_2CO_2H$ | (+)-pin | |
| 818 | OMe | 1 | Ph | $(CH_2)_3CO_2H$ | (+)-pin | |
| 819 | OMe | 1 | Ph | $CH_2CN_4H$ | (+)-pin | |
| 820 | OMe | 1 | Ph | $(CH_2)_2CN_4H$ | (+)-pin | |
| 821 | OMe | 1 | Ph | $(CH_2)_3CN_4H$ | (+)-pin | |
| 822 | OMe | 1 | Ph | $CH_2NO_2$ | (+)-pin | |
| 823 | OMe | 1 | Ph | $(CH_2)_2NO_2$ | (+)-pin | |
| 824 | OMe | 1 | Ph | $(CH_2)_3NO_2$ | (+)-pin | |
| 825 | OMe | 1 | Ph | $CH_2OH$ | (+)-pin | |
| 826 | OMe | 1 | Ph | $(CH_2)_2OH$ | (+)-pin | |
| 827 | OMe | 1 | Ph | $(CH_2)_3OH$ | (+)-pin | |
| 828 | OMe | 1 | Ph | $CH_2CO_2Me$ | (+)-pin | |
| 829 | OMe | 1 | Ph | $(CH_2)_2CO_2Me$ | (+)-pin | |
| 830 | OMe | 1 | Ph | $(CH_2)_3CO_2Me$ | (+)-pin | |
| 831 | OMe | 1 | Ph | Ph | (+)-pin | |
| 832 | OMe | 1 | Ph | $PhCH_2$ | (+)-pin | |
| 833 | OMe | 1 | Ph | $Ph(CH_2)_2$ | (+)-pin | |
| 834 | OMe | 1 | Ph | $3-NO_2-Ph$ | (+)-pin | |
| 835 | OMe | 1 | Ph | $4-NO_2-Ph$ | (+)-pin | |
| 836 | OMe | 1 | Ph | $3-CO_2H-Ph$ | (+)-pin | |
| 837 | OMe | 1 | Ph | $4-CO_2H-Ph$ | (+)-pin | |
| 838 | OMe | 1 | Ph | $3-CN_4H-Ph$ | (+)-pin | |
| 839 | OMe | 1 | Ph | $4-CN_4H-Ph$ | (+)-pin | |
| 840 | OMe | 1 | Ph | $3-(HOCH_2)-Ph$ | (+)-pin | |
| 841 | OMe | 1 | Ph | $4-(HOCH_2)-Ph$ | (+)-pin | |
| 842 | OMe | 1 | Ph | H | OH, OH | |
| 843 | OMe | 1 | Ph | Methyl | OH, OH | |
| 844 | OMe | 1 | Ph | Ethyl | OH, OH | |
| 845 | OMe | 1 | Ph | n-Propyl | OH, OH | |
| 846 | OMe | 1 | Ph | n-Butyl | OH, OH | |
| 847 | OMe | 1 | Ph | $CH_2SCH_3$ | OH, OH | |
| 848 | OMe | 1 | Ph | $CH_2(SO)CH_3$ | OH, OH | |

TABLE 14-continued

| Ex | X | m | R¹³ | R¹⁴ | Y¹Y² | Phys. Data |
|---|---|---|---|---|---|---|
| 849 | OMe | 1 | Ph | CH₂(SO₂)CH₃ | OH, OH | |
| 850 | OMe | 1 | Ph | CH₂CH₂SCH₃ | OH, OH | |
| 851 | OMe | 1 | Ph | CH₂CH₂(SO)CH₃ | OH, OH | |
| 852 | OMe | 1 | Ph | CH₂CH₂(SO)₂CH₃ | OH, OH | |
| 853 | OMe | 1 | Ph | CH₂CN | OH, OH | |
| 854 | OMe | 1 | Ph | CH₂CH₂CN | OH, OH | |
| 855 | OMe | 1 | Ph | CH₂CH₂CH₂CN | OH, OH | |
| 856 | OMe | 1 | Ph | CF₃ | OH, OH | |
| 857 | OMe | 1 | Ph | CF₂CF₃ | OH, OH | |
| 858 | OMe | 1 | Ph | CF₂CF₂CF₃ | OH, OH | |
| 859 | OMe | 1 | Ph | CF₂CF₂CF₂CF₃ | OH, OH | |
| 860 | OMe | 1 | Ph | F₅-Ph | OH, OH | |
| 861 | OMe | 1 | Ph | CH₂CO₂H | OH, OH | |
| 862 | OMe | 1 | Ph | (CH₂)₂CO₂H | OH, OH | |
| 863 | OMe | 1 | Ph | (CH₂)₃CO₂H | OH, OH | |
| 864 | OMe | 1 | Ph | CH₂CN₄H | OH, OH | |
| 865 | OMe | 1 | Ph | (CH₂)₂CN₄H | OH, OH | |
| 866 | OMe | 1 | Ph | (CH₂)₃CN₄H | OH, OH | |
| 867 | OMe | 1 | Ph | CH₂NO₂ | OH, OH | |
| 868 | OMe | 1 | Ph | (CH₂)₂NO₂ | OH, OH | |
| 869 | OMe | 1 | Ph | (CH₂)₃NO₂ | OH, OH | |
| 870 | OMe | 1 | Ph | CH₂OH | OH, OH | |
| 871 | OMe | 1 | Ph | (CH₂)₂OH | OH, OH | |
| 872 | OMe | 1 | Ph | (CH₂)₃OH | OH, OH | |
| 873 | OMe | 1 | Ph | CH₂CO₂Me | OH, OH | |
| 874 | OMe | 1 | Ph | (CH₂)₂CO₂Me | OH, OH | |
| 875 | OMe | 1 | Ph | (CH₂)₃CO₂Me | OH, OH | |
| 876 | OMe | 1 | Ph | Ph | OH, OH | |
| 877 | OMe | 1 | Ph | PhCH₂ | OH, OH | |
| 878 | OMe | 1 | Ph | Ph(CH₂)₂ | OH, OH | |
| 879 | OMe | 1 | Ph | 3-NO₂-Ph | OH, OH | |
| 880 | OMe | 1 | Ph | 4-NO₂-Ph | OH, OH | |
| 881 | OMe | 1 | Ph | 3-CO₂H-Ph | OH, OH | |
| 882 | OMe | 1 | Ph | 4-CO₂H-Ph | OH, OH | |
| 883 | OMe | 1 | Ph | 3-CN₄H-Ph | OH, OH | |
| 884 | OMe | 1 | Ph | 4-CN₄H-Ph | OH, OH | |
| 885 | OMe | 1 | Ph | 3-(HOCH₂)-Ph | OH, OH | |
| 886 | OMe | 1 | Ph | 4-(HOCH₂)-Ph | OH, OH | |
| 887 | CH₂NH₂ | 1 | PhCH₂ | H | (+)-pin | AK |
| 888 | CH₂NH₂ | 1 | PhCH₂ | Methyl | (+)-pin | AL |
| 889 | CH₂NH₂ | 1 | PhCH₂ | Ethyl | (+)-pin | |
| 890 | CH₂NH₂ | 1 | PhCH₂ | n-Propyl | (+)-pin | AM |
| 891 | CH₂NH₂ | 1 | PhCH₂ | n-Butyl | (+)-pin | |
| 892 | CH₂NH₂ | 1 | PhCH₂ | CH₂SCH₃ | (+)-pin | AN |
| 893 | CH₂NH₂ | 1 | PhCH₂ | CH₂(SO)CH₃ | (+)-pin | |
| 894 | CH₂NH₂ | 1 | PhCH₂ | CH₂(SO₂)CH₃ | (+)-pin | |
| 895 | CH₂NH₂ | 1 | PhCH₂ | CH₂CH₂SCH₃ | (+)-pin | |
| 896 | CH₂NH₂ | 1 | PhCH₂ | CH₂CH₂(SO)CH₃ | (+)-pin | |
| 897 | CH₂NH₂ | 1 | PhCH₂ | CH₂CH₂(SO)₂CH₃ | (+)-pin | |
| 898 | CH₂NH₂ | 1 | PhCH₂ | CH₂CN | (+)-pin | CN |
| 899 | CH₂NH₂ | 1 | PhCH₂ | CH₂CH₂CH₂CN | (+)-pin | |
| 900 | CH₂NH₂ | 1 | PhCH₂ | CF₃ | (+)-pin | |
| 901 | CH₂NH₂ | 1 | PhCH₂ | CF₂CF₃ | (+)-pin | |
| 902 | CH₂NH₂ | 1 | PhCH₂ | CF₂CF₂CF₃ | (+)-pin | |
| 903 | CH₂NH₂ | 1 | PhCH₂ | CF₂CF₂CF₂CF₃ | (+)-pin | |
| 904 | CH₂NH₂ | 1 | PhCH₂ | F₅-Ph | (+)-pin | |
| 905 | CH₂NH₂ | 1 | PhCH₂ | CH₂CO₂H | (+)-pin | AW |
| 906 | CH₂NH₂ | 1 | PhCH₂ | (CH₂)₂CO₂H | (+)-pin | |
| 907 | CH₂NH₂ | 1 | PhCH₂ | (CH₂)₃CO₂H | (+)-pin | |
| 908 | CH₂NH₂ | 1 | PhCH₂ | (CH₂)₂CN₄H | (+)-pin | |
| 909 | CH₂NH₂ | 1 | PhCH₂ | (CH₂)₃CN₄H | (+)-pin | |
| 910 | CH₂NH₂ | 1 | PhCH₂ | CH₂NO₂ | (+)-pin | |
| 911 | CH₂NH₂ | 1 | PhCH₂ | (CH₂)₂NO₂ | (+)-pin | |
| 912 | CH₂NH₂ | 1 | PhCH₂ | (CH₂)₃NO₂ | (+)-pin | |

TABLE 14-continued

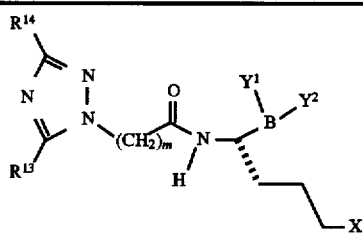

| Ex | X | m | R¹³ | R¹⁴ | Y¹Y² | Phys. Data |
|---|---|---|---|---|---|---|
| 913 | $CH_2NH_2$ | 1 | $PhCH_2$ | $CH_2OH$ | (+)-pin | AO |
| 914 | $CH_2NH_2$ | 1 | $PhCH_2$ | $CH_2OCH_2Ph$ | (+)-pin | AP |
| 915 | $CH_2NH_2$ | 1 | $PhCH_2$ | $(CH_2)_2OH$ | (+)-pin | |
| 916 | $CH_2NH_2$ | 1 | $PhCH_2$ | $(CH_2)_3OH$ | (+)-pin | |
| 917 | $CH_2NH_2$ | 1 | $PhCH_2$ | $CH_2CO_2Me$ | (+)-pin | CP |
| 918 | $CH_2NH_2$ | 1 | $PhCH_2$ | $(CH_2)_2CO_2Me$ | (+)-pin | |
| 919 | $CH_2NH_2$ | 1 | $PhCH_2$ | $(CH_2)_3CO_2Me$ | (+)-pin | |
| 920 | $CH_2NH_2$ | 1 | $PhCH_2$ | Ph | (+)-pin | AQ |
| 921 | $CH_2NH_2$ | 1 | $PhCH_2$ | $PhCH_2$ | (+)-pin | AR |
| 922 | $CH_2NH_2$ | 1 | $PhCH_2$ | $Ph(CH_2)_2$ | (+)-pin | |
| 923 | $CH_2NH_2$ | 1 | $PhCH_2$ | $3-NO_2-Ph$ | (+)-pin | AS |
| 924 | $CH_2NH_2$ | 1 | $PhCH_2$ | $4-NO_2-Ph$ | (+)-pin | |
| 925 | $CH_2NH_2$ | 1 | $PhCH_2$ | $3-CO_2H-Ph$ | (+)-pin | |
| 926 | $CH_2NH_2$ | 1 | $PhCH_2$ | $4-CO_2H-Ph$ | (+)-pin | |
| 927 | $CH_2NH_2$ | 1 | $PhCH_2$ | $3-CN_4H-Ph$ | (+)-pin | |
| 928 | $CH_2NH_2$ | 1 | $PhCH_2$ | $4-CN_4H-Ph$ | (+)-pin | |
| 929 | $CH_2NH_2$ | 1 | $PhCH_2$ | $3-(HOCH_2)-Ph$ | (+)-pin | |
| 930 | $CH_2NH_2$ | 1 | $PhCH_2$ | $4-(HOCH_2)-Ph$ | (+)-pin | |
| 931 | $CH_2NH_2$ | 1 | $PhCH_2$ | $3-NH_2-Ph$ | (+)-pin | CQ |
| 932 | $NH(C=NH)NH_2$ | 1 | $PhCH_2$ | H | (+)-pin | |
| 933 | $NH(C=NH)NH_2$ | 1 | $PhCH_2$ | Methyl | (+)-pin | |
| 934 | $NH(C=NH)NH_2$ | 1 | $PhCH_2$ | Ethyl | (+)-pin | |
| 935 | $NH(C=NH)NH_2$ | 1 | $PhCH_2$ | n-Propyl | (+)-pin | |
| 936 | $NH(C=NH)NH_2$ | 1 | $PhCH_2$ | n-Butyl | (+)-pin | |
| 937 | $NH(C=NH)NH_2$ | 1 | $PhCH_2$ | $CH_2SCH_3$ | (+)-pin | |
| 938 | $NH(C=NH)NH_2$ | 1 | $PhCH_2$ | $CH_2(SO)CH_3$ | (+)-pin | |
| 939 | $NH(C=NH)NH_2$ | 1 | $PhCH_2$ | $CH_2(SO_2)CH_3$ | (+)-pin | |
| 940 | $NH(C=NH)NH_2$ | 1 | $PhCH_2$ | $CH_2CH_2SCH_3$ | (+)-pin | |
| 941 | $NH(C=NH)NH_2$ | 1 | $PhCH_2$ | $CH_2CH_2(SO)CH_3$ | (+)-pin | |
| 942 | $NH(C=NH)NH_2$ | 1 | $PhCH_2$ | $CH_2CH_2(SO)_2CH_3$ | (+)-pin | |
| 943 | $NH(C=NH)NH_2$ | 1 | $PhCH_2$ | $CH_2CN$ | (+)-pin | |
| 944 | $NH(C=NH)NH_2$ | 1 | $PhCH_2$ | $CH_2CH_2CN$ | (+)-pin | |
| 945 | $NH(C=NH)NH_2$ | 1 | $PhCH_2$ | $CH_2CH_2CH_2CN$ | (+)-pin | |
| 946 | $NH(C=NH)NH_2$ | 1 | $PhCH_2$ | $CF_3$ | (+)-pin | |
| 947 | $NH(C=NH)NH_2$ | 1 | $PhCH_2$ | $CF_2CF_3$ | (+)-pin | |
| 948 | $NH(C=NH)NH_2$ | 1 | $PhCH_2$ | $CF_2CF_2CF_3$ | (+)-pin | |
| 949 | $NH(C=NH)NH_2$ | 1 | $PhCH_2$ | $CF_2CF_2CF_2CF_3$ | (+)-pin | |
| 950 | $NH(C=NH)NH_2$ | 1 | $PhCH_2$ | $F_5-Ph$ | (+)-pin | |
| 951 | $NH(C=NH)NH_2$ | 1 | $PhCH_2$ | $CH_2CO_2H$ | (+)-pin | |
| 952 | $NH(C=NH)NH_2$ | 1 | $PhCH_2$ | $(CH_2)_2CO_2H$ | (+)-pin | |
| 953 | $NH(C=NH)NH_2$ | 1 | $PhCH_2$ | $(CH_2)_3CO_2H$ | (+)-pin | |
| 954 | $NH(C=NH)NH_2$ | 1 | $PhCH_2$ | $CH_2CN_4H$ | (+)-pin | |
| 955 | $NH(C=NH)NH_2$ | 1 | $PhCH_2$ | $(CH_2)_2CN_4H$ | (+)-pin | |
| 956 | $NH(C=NH)NH_2$ | 1 | $PhCH_2$ | $(CH_2)CH_3CN_4H$ | (+)-pin | |
| 957 | $NH(C=NH)NH_2$ | 1 | $PhCH_2$ | $CH_2NO_2$ | (+)-pin | |
| 958 | $NH(C=NH)NH_2$ | 1 | $PhCH_2$ | $(CH_2)_2NO_2$ | (+)-pin | |
| 959 | $NH(C=NH)NH_2$ | 1 | $PhCH_2$ | $(CH_2)_3NO_2$ | (+)-pin | |
| 960 | $NH(C=NH)NH_2$ | 1 | $PhCH_2$ | $CH_2OH$ | (+)-pin | |
| 961 | $NH(C=NH)NH_2$ | 1 | $PhCH_2$ | $(CH_2)_2OH$ | (+)-pin | |
| 962 | $NH(C=NH)NH_2$ | 1 | $PhCH_2$ | $(CH_2)_3OH$ | (+)-pin | |
| 963 | $NH(C=NH)NH_2$ | 1 | $PhCH_2$ | $CH_2CO_2Me$ | (+)-pin | |
| 964 | $NH(C=NH)NH_2$ | 1 | $PhCH_2$ | $(CH_2)_2CO_2Me$ | (+)-pin | |
| 965 | $NH(C=NH)NH_2$ | 1 | $PhCH_2$ | $(CH_2)_3CO_2Me$ | (+)-pin | |
| 966 | $NH(C=NH)NH_2$ | 1 | $PhCH_2$ | Ph | (+)-pin | |
| 967 | $NH(C=NH)NH_2$ | 1 | $PhCH_2$ | $PhCH_2$ | (+)-pin | AT |
| 968 | $NH(C=NH)NH_2$ | 1 | $PhCH_2$ | $Ph(CH_2)_2$ | (+)-pin | |
| 969 | $NH(C=NH)NH_2$ | 1 | $PhCH_2$ | $3-NO_2-Ph$ | (+)-pin | AU |
| 970 | $NH(C=NH)NH_2$ | 1 | $PhCH_2$ | $4-NO_2Ph$ | (+)-pin | |
| 971 | $NH(C=NH)NH_2$ | 1 | $PhCH_2$ | $3-CO_2H-Ph$ | (+)-pin | |
| 972 | $NH(C=NH)NH_2$ | 1 | $PhCH_2$ | $4-CO_2H-Ph$ | (+)-pin | |
| 973 | $NH(C=NH)NH_2$ | 1 | $PhCH_2$ | $3-CN_4H-Ph$ | (+)-pin | |
| 974 | $NH(C=NH)NH_2$ | 1 | $PhCH_2$ | $4-CN_4H-Ph$ | (+)-pin | |
| 975 | $NH(C=NH)NH_2$ | 1 | $PhCH_2$ | $3-(HOCH_2)-Ph$ | (+)-pin | |
| 976 | $NH(C=NH)NH_2$ | 1 | $PhCH_2$ | $4-(HOCH_2)-Ph$ | (+)-pin | |

TABLE 14-continued

| Ex | X | m | R¹³ | R¹⁴ | Y¹Y² | Phys. Data |
|---|---|---|---|---|---|---|
| 977 | CH₂NH₂ | 1 | PhCH₂ | H | OH, OH | AI |
| 978 | CH₂NH₂ | 1 | PhCH₂ | Methyl | OH, OH | |
| 979 | CH₂NH₂ | 1 | PhCH₂ | Ethyl | OH, OH | |
| 980 | CH₂NH₂ | 1 | PhCH₂ | n-Propyl | OH, OH | |
| 981 | CH₂NH₂ | 1 | PhCH₂ | n-Butyl | OH, OH | |
| 982 | CH₂NH₂ | 1 | PhCH₂ | CH₂SCH₃ | OH, OH | |
| 983 | CH₂NH₂ | 1 | PhCH₂ | CH₂(SO)CH₃ | OH, OH | |
| 984 | CH₂NH₂ | 1 | PhCH₂ | CH₂(SO₂)CH₃ | OH, OH | |
| 985 | CH₂NH₂ | 1 | PhCH₂ | CH₂CH₂SCH₃ | OH, OH | |
| 986 | CH₂NH₂ | 1 | PhCH₂ | CH₂CH₂(SO)CH₃ | OH, OH | |
| 987 | CH₂NH₂ | 1 | PhCH₂ | CH₂CH₂(SO)₂CH₃ | OH, OH | |
| 988 | CH₂NH₂ | 1 | PhCH₂ | CH₂CN | OH, OH | |
| 989 | CH₂NH₂ | 1 | PhCH₂ | CH₂CH₂CN | OH, OH | |
| 990 | CH₂NH₂ | 1 | PhCH₂ | CH₂CH₂CH₂CN | OH, OH | |
| 991 | CH₂NH₂ | 1 | PhCH₂ | CF₃ | OH, OH | |
| 992 | CH₂NH₂ | 1 | PhCH₂ | CF₂CF₃ | OH, OH | |
| 993 | CH₂NH₂ | 1 | PhCH₂ | CF₂CF₂CF₃ | OH, OH | |
| 994 | CH₂NH₂ | 1 | PhCH₂ | CF₂CF₂CF₂CF₃ | OH, OH | |
| 995 | CH₂NH₂ | 1 | PhCH₂ | F₅-Ph | OH, OH | |
| 996 | CH₂NH₂ | 1 | PhCH₂ | CH₂CO₂H | OH, OH | |
| 997 | CH₂NH₂ | 1 | PhCH₂ | (CH₂)₂CO₂H | OH, OH | |
| 998 | CH₂NH₂ | 1 | PhCH₂ | (CH₂)₃CO₂H | OH, OH | |
| 999 | CH₂NH₂ | 1 | PhCH₂ | CH₂CN₄H | OH, OH | |
| 1000 | CH₂NH₂ | 1 | PhCH₂ | (CH₂)₂CN₄H | OH, OH | |
| 1001 | CH₂NH₂ | 1 | PhCH₂ | (CH₂)₃CN₄H | OH, OH | |
| 1002 | CH₂NH₂ | 1 | PhCH₂ | CH₂NO₂ | OH, OH | |
| 1003 | CH₂NH₂ | 1 | PhCH₂ | (CH₂)₂NO₂ | OH, OH | |
| 1004 | CH₂NH₂ | 1 | PhCH₂ | (CH₂)₃NO₂ | OH, OH | |
| 1005 | CH₂NH₂ | 1 | PhCH₂ | CH₂OH | OH, OH | |
| 1006 | CH₂NH₂ | 1 | PhCH₂ | (CH₂)₂OH | OH, OH | |
| 1007 | CH₂NH₂ | 1 | PhCH₂ | (CH₂)₃OH | OH, OH | |
| 1008 | CH₂NH₂ | 1 | PhCH₂ | CH₂CO₂Me | OH, OH | |
| 1009 | CH₂NH₂ | 1 | PhCH₂ | (CH₂)₂CO₂Me | OH, OH | |
| 1010 | CH₂NH₂ | 1 | PhCH₂ | (CH₂)₃CO₂Me | OH, OH | |
| 1011 | CH₂NH₂ | 1 | PhCH₂ | Ph | OH, OH | AV |
| 1012 | CH₂NH₂ | 1 | PhCH₂ | PhCH₂ | OH, OH | |
| 1013 | CH₂NH₂ | 1 | PhCH₂ | Ph(CH₂)₂ | OH, OH | |
| 1014 | CH₂NH₂ | 1 | PhCH₂ | 3-NO₂-Ph | OH, OH | |
| 1015 | CH₂NH₂ | 1 | PhCH₂ | 4-NO₂-Ph | OH, OH | |
| 1016 | CH₂NH₂ | 1 | PhCH₂ | 3-CO₂H-Ph | OH, OH | |
| 1017 | CH₂NH₂ | 1 | PhCH₂ | 4-CO₂H-Ph | OH, OH | |
| 1018 | CH₂NH₂ | 1 | PhCH₂ | 3-CN₄H-Ph | OH, OH | |
| 1019 | CH₂NH₂ | 1 | PhCH₂ | 4-CN₄H-Ph | OH, OH | |
| 1020 | CH₂NH₂ | 1 | PhCH₂ | 3-(HOCH₂)-Ph | OH, OH | |
| 1021 | CH₂NH₂ | 1 | PhCH₂ | 4-(HOCH₂)-Ph | OH, OH | |
| 1022 | CH₂NH₂ | 1 | PhCH₂ | F | (+)-pin | |
| 1023 | CH₂NH₂ | 1 | PhCH₂ | Cl | (+)-pin | |
| 1024 | CH₂NH₂ | 1 | PhCH₂ | Br | (+)-pin | |
| 1025 | CH₂NH₂ | 1 | PhCH₂ | I | (+)-pin | |
| 1026 | CH₂NH₂ | 1 | PhCH₂ | COOH | (+)-pin | |
| 1027 | CH₂NH₂ | 1 | PhCH₂ | COOMe | (+)-pin | |
| 1028 | CH₂NH₂ | 1 | PhCH₂ | CHO | (+)-pin | |
| 1029 | CH₂NH₂ | 1 | PhCH₂ | COMe | (+)-pin | |
| 1030 | CH₂NH₂ | 1 | PhCH₂ | NO₂ | (+)-pin | |
| 1031 | CH₂NH₂ | 1 | PhCH₂ | CN | (+)-pin | |
| 1032 | CH₂NH₂ | 1 | PhCH₂ | isopropyl | (+)-pin | |
| 1033 | CH₂NH₂ | 1 | PhCH₂ | 3-F-phenyl | (+)-pin | |
| 1034 | CH₂NH₂ | 1 | PhCH₂ | 3-Cl-phenyl | (+)-pin | |
| 1035 | CH₂NH₂ | 1 | PhCH₂ | 4-Br-phenyl | (+)-pin | |
| 1036 | CH₂NH₂ | 1 | PhCH₂ | 4-I-phenyl | (+)-pin | |
| 1037 | CH₂NH₂ | 1 | PhCH₂ | 3-CH₃-phenyl | (+)-pin | |
| 1038 | CH₂NH₂ | 1 | PhCH₂ | 3-MeO-phenyl | (+)-pin | |
| 1039 | CH₂NH₂ | 1 | PhCH₂ | 3-CN-phenyl | (+)-pin | |
| 1040 | CH₂NH₂ | 1 | PhCH₂ | 4-CN-phenyl | (+)-pin | |

TABLE 14-continued

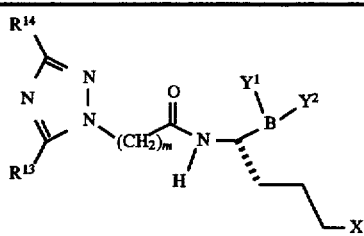

| Ex | X | m | R¹³ | R¹⁴ | Y¹Y² | Phys. Data |
|---|---|---|---|---|---|---|
| 1041 | CH₂NH₂ | 1 | PhCH₂ | 3-NC-phenyl | (+)-pin | |
| 1042 | CH₂NH₂ | 1 | PhCH₂ | 4-NC-phenyl | (+)-pin | |
| 1043 | CH₂NH₂ | 1 | PhCH₂ | 3-CF₃-phenyl | (+)-pin | |
| 1044 | CH₂NH₂ | 1 | PhCH₂ | 3-CH₂S-phenyl | (+)-pin | |
| 1045 | CH₂NH₂ | 1 | PhCH₂ | 3-CH₃SO-phenyl | (+)-pin | |
| 1046 | CH₂NH₂ | 1 | PhCH₂ | 3-CH₃SO₂-phenyl | (+)-pin | |
| 1047 | CH₂NH₂ | 1 | PhCH₂ | 3-N(Me)₂-phenyl | (+)-pin | |
| 1048 | CH₂NH₂ | 1 | PhCH₂ | 3-MeCO-phenyl | (+)-pin | |
| 1049 | CH₂NH₂ | 1 | PhCH₂ | 3-CHO-phenyl | (+)-pin | |
| 1050 | CH₂NH₂ | 1 | PhCH₂ | 3-CO₂Me-phenyl | (+)-pin | |
| 1051 | CH₂NH₂ | 1 | PhCH₂ | 3-CONH₂-phenyl | (+)-pin | |
| 1052 | CH₂NH₂ | 1 | PhCH₂ | CH₂NHSO₂CF₃ | (+)-pin | |
| 1053 | CH₂NH₂ | 1 | PhCH₂ | CH₂NHSO₂CH₃ | (+)-pin | |
| 1054 | CH₂NH₂ | 1 | PhCH₂ | CH₂CO₂-i-propyl | (+)-pin | |
| 1055 | CH₂NH₂ | 1 | PhCH₂ | CH₂CHO | (+)-pin | |
| 1056 | CH₂NH₂ | 1 | PhCH₂ | CH₂CH₂OMe | (+)-pin | |
| 1057 | CH₂NH₂ | 1 | PhCH₂ | CH₂CH₂O-i-propyl | (+)-pin | |
| 1058 | CH₂NH₂ | 1 | PhCH₂ | CH₂OCOMe | (+)-pin | |
| 1059 | CH₂NH₂ | 1 | PhCH₂ | CH₂OCO-i-propyl | (+)-pin | |
| 1060 | CH₂NH₂ | 1 | PhCH₂ | CH₂OCO-Phenyl | (+)-pin | |
| 1061 | CH₂NH₂ | 1 | PhCH₂ | CH₂NHCOMe | (+)-pin | |
| 1062 | CH₂NH₂ | 1 | PhCH₂ | CH₂NHCO-i-propyl | (+)-pin | |
| 1063 | CH₂NH₂ | 1 | PhCH₂ | F | OH, OH | |
| 1064 | CH₂NH₂ | 1 | PhCH₂ | Cl | OH, OH | |
| 1065 | CH₂NH₂ | 1 | PhCH₂ | Br | OH, OH | |
| 1066 | CH₂NH₂ | 1 | PhCH₂ | I | OH, OH | |
| 1067 | CH₂NH₂ | 1 | PhCH₂ | COOH | OH, OH | |
| 1068 | CH₂NH₂ | 1 | PhCH₂ | COOMe | OH, OH | |
| 1069 | CH₂NH₂ | 1 | PhCH₂ | CHO | OH, OH | |
| 1070 | CH₂NH₂ | 1 | PhCH₂ | COMe | OH, OH | |
| 1071 | CH₂NH₂ | 1 | PhCH₂ | NO₂ | OH, OH | |
| 1072 | CH₂NH₂ | 1 | PhCH₂ | CN | OH, OH | |
| 1073 | CH₂NH₂ | 1 | PhCH₂ | isopropyl | OH, OH | |
| 1074 | CH₂NH₂ | 1 | PhCH₂ | 3-F-phenyl | OH, OH | |
| 1075 | CH₂NH₂ | 1 | PhCH₂ | 3-Cl-phenyl | OH, OH | |
| 1076 | CH₂NH₂ | 1 | PhCH₂ | 4-Br-phenyl | OH, OH | |
| 1077 | CH₂NH₂ | 1 | PhCH₂ | 4-I-phenyl | OH, OH | |
| 1078 | CH₂NH₂ | 1 | PhCH₂ | 3-CH₃-phenyl | OH, OH | |
| 1079 | CH₂NH₂ | 1 | PhCH₂ | 3-MeO-phenyl | OH, OH | |
| 1080 | CH₂NH₂ | 1 | PhCH₂ | 3-CN-phenyl | OH, OH | |
| 1081 | CH₂NH₂ | 1 | PhCH₂ | 4-CN-phenyl | OH, OH | |
| 1082 | CH₂NH₂ | 1 | PhCH₂ | 3-NC-phenyl | OH, OH | |
| 1083 | CH₂NH₂ | 1 | PhCH₂ | 4-NC-phenyl | OH, OH | |
| 1084 | CH₂NH₂ | 1 | PhCH₂ | 3-CF₃-phenyl | OH, OH | |
| 1085 | CH₂NH₂ | 1 | PhCH₂ | 3-CH₂S-phenyl | OH, OH | |
| 1086 | CH₂NH₂ | 1 | PhCH₂ | 3-CH₃SO-phenyl | OH, OH | |
| 1087 | CH₂NH₂ | 1 | PhCH₂ | 3-CH₃SO₂-phenyl | OH, OH | |
| 1088 | CH₂NH₂ | 1 | PhCH₂ | 3-N(Me)₂-phenyl | OH, OH | |
| 1089 | CH₂NH₂ | 1 | PhCH₂ | 3-MeCO-phenyl | OH, OH | |
| 1090 | CH₂NH₂ | 1 | PhCH₂ | 3-CHO-phenyl | OH, OH | |
| 1091 | CH₂NH₂ | 1 | PhCH₂ | 3-CO₂Me-phenyl | OH, OH | |
| 1092 | CH₂NH₂ | 1 | PhCH₂ | 3-CONH₂-phenyl | OH, OH | |
| 1093 | CH₂NH₂ | 1 | PhCH₂ | CH₂NHSO₂CF₃ | OH, OH | |
| 1094 | CH₂NH₂ | 1 | PhCH₂ | CH₂NHSO₂CH₃ | OH, OH | |
| 1095 | CH₂NH₂ | 1 | PhCH₂ | CH₂CO₂-i-propyl | OH, OH | |
| 1096 | CH₂NH₂ | 1 | PhCH₂ | CH₂CHO | OH, OH | |
| 1097 | CH₂NH₂ | 1 | PhCH₂ | CH₂CH₂OMe | OH, OH | |
| 1098 | CH₂NH₂ | 1 | PhCH₂ | CH₂CH₂O-i-propyl | OH, OH | |
| 1099 | CH₂NH₂ | 1 | PhCH₂ | CH₂OCOMe | OH, OH | |
| 1100 | CH₂NH₂ | 1 | PhCH₂ | CH₂OCO-i-propyl | OH, OH | |
| 1101 | CH₂NH₂ | 1 | PhCH₂ | CH₂OCO-Phenyl | OH, OH | |
| 1102 | CH₂NH₂ | 1 | PhCH₂ | CH₂NHCOMe | OH, OH | |
| 1103 | CH₂NH₂ | 1 | PhCH₂ | CH₂NHCO-i-propyl | OH, OH | |
| 1104 | CH₂NH₂ | 1 | 3,4-Di-F-PhCH₂ | CH₂CN | (+)-pin | |

TABLE 14-continued

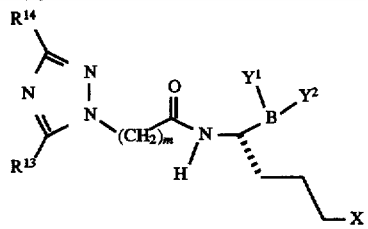

| Ex | X | m | R[13] | R[14] | Y[1]Y[2] | Phys. Data |
|---|---|---|---|---|---|---|
| 1105 | $CH_2NH_2$ | 1 | 3,4-Di-Cl-PhCH$_2$ | $CH_2CN$ | (+)-pin | |
| 1106 | $CH_2NH_2$ | 1 | 4-Br-PhCH$_2$ | $CH_2CN$ | (+)-pin | |
| 1107 | $CH_2NH_2$ | 1 | 4-I-PhCH$_2$ | $CH_2CN$ | (+)-pin | |
| 1108 | $CH_2NH_2$ | 1 | 4-Me-PhCH$_2$ | $CH_2CN$ | (+)-pin | |
| 1109 | $CH_2NH_2$ | 1 | 2-MeO-PhCH$_2$ | $CH_2CN$ | (+)-pin | |
| 1110 | $CH_2NH_2$ | 1 | 2-CN-PhCH$_2$ | $CH_2CN$ | (+)-pin | |
| 1111 | $CH_2NH_2$ | 1 | 2-NC-PhCH$_2$ | $CH_2CN$ | (+)-pin | |
| 1112 | $CH_2NH_2$ | 1 | 2-NO$_2$-PhCH$_2$ | $CH_2CN$ | (+)-pin | |
| 1113 | $CH_2NH_2$ | 1 | 2-CF$_3$-PhCH$_2$ | $CH_2CN$ | (+)-pin | |
| 1114 | $CH_2NH_2$ | 1 | 2-MeS-PhCH$_2$ | $CH_2CN$ | (+)-pin | |
| 1115 | $CH_2NH_2$ | 1 | 3-MeSO-PhCH$_2$ | $CH_2CN$ | (+)-pin | |
| 1116 | $CH_2NH_2$ | 1 | 3-MeSO$_2$-PhCH$_2$ | $CH_2CN$ | (+)-pin | |
| 1117 | $CH_2NH_2$ | 1 | 2-NH$_2$-PhCH$_2$ | $CH_2CN$ | (+)-pin | |
| 1118 | $CH_2NH_2$ | 1 | 3-NHMe-PhCH$_2$ | $CH_2CN$ | (+)-pin | |
| 1119 | $CH_2NH_2$ | 1 | 2-CHO-PhCH$_2$ | $CH_2CN$ | (+)-pin | |
| 1120 | $CH_2NH_2$ | 1 | 3-MeCO-PhCH$_2$ | $CH_2CN$ | (+)-pin | |
| 1121 | $CH_2NH_2$ | 1 | 2-MeO$_2$C-PhCH$_2$ | $CH_2CN$ | (+)-pin | |
| 1122 | $CH_2NH_2$ | 1 | 2-NH$_2$OC-PhCH$_2$ | $CH_2CN$ | (+)-pin | |
| 1123 | $CH_2NH_2$ | 1 | 2-HOCH$_2$-PhCH$_2$ | $CH_2CN$ | (+)-pin | |
| 1124 | $CH_2NH_2$ | 1 | 3,4-Di-F-PhCH$_2$ | $CH_2CN$ | OH, OH | |
| 1125 | $CH_2NH_2$ | 1 | 3,4-Di-Cl-PhCH$_2$ | $CH_2CN$ | OH, OH | |
| 1126 | $CH_2NH_2$ | 1 | 4-Br-PhCH$_2$ | $CH_2CN$ | OH, OH | |
| 1127 | $CH_2NH_2$ | 1 | 4-I-PhCH$_2$ | $CH_2CN$ | OH, OH | |
| 1128 | $CH_2NH_2$ | 1 | 4-Me-PhCH$_2$ | $CH_2CN$ | OH, OH | |
| 1129 | $CH_2NH_2$ | 1 | 2-MeO-PhCH$_2$ | $CH_2CN$ | OH, OH | |
| 1130 | $CH_2NH_2$ | 1 | 2-CN-PhCH$_2$ | $CH_2CN$ | OH, OH | |
| 1131 | $CH_2NH_2$ | 1 | 2-NC-PhCH$_2$ | $CH_2CN$ | OH, OH | |
| 1132 | $CH_2NH_2$ | 1 | 2-NO$_2$-PhCH$_2$ | $CH_2CN$ | OH, OH | |
| 1133 | $CH_2NH_2$ | 1 | 2-CF$_3$-PhCH$_2$ | $CH_2CN$ | OH, OH | |
| 1134 | $CH_2NH_2$ | 1 | 2-MeS-PhCH$_2$ | $CH_2CN$ | OH, OH | |
| 1135 | $CH_2NH_2$ | 1 | 3-MeSO-PhCH$_2$ | $CH_2CN$ | OH, OH | |
| 1136 | $CH_2NH_2$ | 1 | 3-MeSO$_2$-PhCH$_2$ | $CH_2CN$ | OH, OH | |
| 1137 | $CH_2NH_2$ | 1 | 2-NH$_2$-PhCH$_2$ | $CH_2CN$ | OH, OH | |
| 1138 | $CH_2NH_2$ | 1 | 3-NHMe-PhCH$_2$ | $CH_2CN$ | OH, OH | |
| 1139 | $CH_2NH_2$ | 1 | 2-CHO-PhCH$_2$ | $CH_2CN$ | OH, OH | |
| 1140 | $CH_2NH_2$ | 1 | 3-MeCO-PhCH$_2$ | $CH_2CN$ | OH, OH | |
| 1141 | $CH_2NH_2$ | 1 | 2-MeO$_2$C-PhCH$_2$ | $CH_2CN$ | OH, OH | |
| 1142 | $CH_2NH_2$ | 1 | 2-NH$_2$OC-PhCH$_2$ | $CH_2CN$ | OH, OH | |
| 1143 | $CH_2NH_2$ | 1 | 2-HOCH$_2$-PhCH$_2$ | $CH_2CN$ | OH, OH | |
| 1144 | NH(C=NH)NH$_2$ | 1 | PhCH$_2$ | H | OH, OH | |
| 1145 | NH(C=NH)NH$_2$ | 1 | PhCH$_2$ | Methyl | OH, OH | |
| 1146 | NH(C=NH)NH$_2$ | 1 | PhCH$_2$ | Ethyl | OH, OH | |
| 1147 | NH(C=NH)NH$_2$ | 1 | PhCH$_2$ | n-Propyl | OH, OH | |
| 1148 | NH(C=NH)NH$_2$ | 1 | PhCH$_2$ | n-Butyl | OH, OH | |
| 1149 | NH(C=NH)NH$_2$ | 1 | PhCH$_2$ | CH$_2$SCH$_3$ | OH, OH | |
| 1150 | NH(C=NH)NH$_2$ | 1 | PhCH$_2$ | CH$_2$(SO)CH$_3$ | OH, OH | |
| 1151 | NH(C=NH)NH$_2$ | 1 | PhCH$_2$ | CH$_2$(SO$_2$)CH$_3$ | OH, OH | |
| 1152 | NH(C=NH)NH$_2$ | 1 | PhCH$_2$ | CH$_2$CH$_2$SCH$_3$ | OH, OH | |
| 1153 | NH(C=NH)NH$_2$ | 1 | PhCH$_2$ | CH$_2$CH$_2$(SO)CH$_3$ | OH, OH | |
| 1154 | NH(C=NH)NH$_2$ | 1 | PhCH$_2$ | CH$_2$CH$_2$(SO)$_2$CH$_3$ | OH, OH | |
| 1155 | NH(C=NH)NH$_2$ | 1 | PhCH$_2$ | CH$_2$CN | OH, OH | |
| 1156 | NH(C=NH)NH$_2$ | 1 | PhCH$_2$ | CH$_2$CH$_2$CN | OH, OH | |
| 1157 | NH(C=NH)NH$_2$ | 1 | PhCH$_2$ | CH$_2$CH$_2$CH$_2$CN | OH, OH | |
| 1158 | NH(C=NH)NH$_2$ | 1 | PhCH$_2$ | CF$_3$ | OH, OH | |
| 1159 | NH(C=NH)NH$_2$ | 1 | PhCH$_2$ | CF$_2$CF$_3$ | OH, OH | |
| 1160 | NH(C=NH)NH$_2$ | 1 | PhCH$_2$ | CF$_2$CF$_2$CF$_3$ | OH, OH | |
| 1161 | NH(C=NH)NH$_2$ | 1 | PhCH$_2$ | CF$_2$CF$_2$CF$_2$CF$_3$ | OH, OH | |
| 1162 | NH(C=NH)NH$_2$ | 1 | PhCH$_2$ | F$_5$-Ph | OH, OH | |
| 1163 | NH(C=NH)NH$_2$ | 1 | PhCH$_2$ | CH$_2$CO$_2$H | OH, OH | |
| 1164 | NH(C=NH)NH$_2$ | 1 | PhCH$_2$ | (CH$_2$)$_2$CO$_2$H | OH, OH | |
| 1165 | NH(C=NH)NH$_2$ | 1 | PhCH$_2$ | (CH$_2$)$_3$CO$_2$H | OH, OH | |
| 1166 | NH(C=NH)NH$_2$ | 1 | PhCH$_2$ | CH$_2$CN$_4$H | OH, OH | |
| 1167 | NH(C=NH)NH$_2$ | 1 | PhCH$_2$ | (CH$_2$)$_2$CN$_4$H | OH, OH | |
| 1168 | NH(C=NH)NH$_2$ | 1 | PhCH$_2$ | (CH$_2$)$_3$CN$_4$H | OH, OH | |

TABLE 14-continued

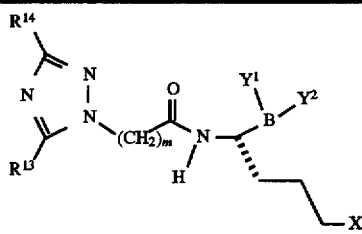

| Ex | X | m | R¹³ | R¹⁴ | Y¹Y² | Phys. Data |
|---|---|---|---|---|---|---|
| 1169 | NH(C=NH)NH₂ | 1 | PhCH₂ | CH₂NO₂ | OH, OH | |
| 1170 | NH(C=NH)NH₂ | 1 | PhCH₂ | (CH₂)₂NO₂ | OH, OH | |
| 1171 | NH(C=NH)NH₂ | 1 | PhCH₂ | (CH₂)₃NO₂ | OH, OH | |
| 1172 | NH(C=NH)NH₂ | 1 | PhCH₂ | CH₂OH | OH, OH | |
| 1173 | NH(C=NH)NH₂ | 1 | PhCH₂ | (CH₂)₂OH | OH, OH | |
| 1174 | NH(C=NH)NH₂ | 1 | PhCH₂ | (CH₂)₃OH | OH, OH | |
| 1175 | NH(C=NH)NH₂ | 1 | PhCH₂ | CH₂CO₂Me | OH, OH | |
| 1176 | NH(C=NH)NH₂ | 1 | PhCH₂ | (CH₂)₂CO₂Me | OH, OH | |
| 1177 | NH(C=NH)NH₂ | 1 | PhCH₂ | (CH₂)₃CO₂Me | OH, OH | |
| 1178 | NH(C=NH)NH₂ | 1 | PhCH₂ | Ph | OH, OH | |
| 1179 | NH(C=NH)NH₂ | 1 | PhCH₂ | PhCH₂ | OH, OH | |
| 1180 | NH(C=NH)NH₂ | 1 | PhCH₂ | Ph(CH₂)₂ | OH, OH | |
| 1181 | NH(C=NH)NH₂ | 1 | PhCH₂ | 3-NO₂-Ph | OH, OH | |
| 1182 | NH(C=NH)NH₂ | 1 | PhCH₂ | 4-NO₂-Ph | OH, OH | |
| 1183 | NH(C=NH)NH₂ | 1 | PhCH₂ | 3-CO₂H-Ph | OH, OH | |
| 1184 | NH(C=NH)NH₂ | 1 | PhCH₂ | 4-CO₂H-Ph | OH, OH | |
| 1185 | NH(C=NH)NH₂ | 1 | PhCH₂ | 3-CN₄H-Ph | OH, OH | |
| 1186 | NH(C=NH)NH₂ | 1 | PhCH₂ | 4-CN₄H-Ph | OH, OH | |
| 1187 | NH(C=NH)NH₂ | 1 | PhCH₂ | 3-(HOCH₂)-Ph | OH, OH | |
| 1188 | NH(C=NH)NH₂ | 1 | PhCH₂ | 4-(HOCH₂)-Ph | OH, OH | |
| 1189 | NH(C=NH)NH₂ | 1 | PhCH₂ | CH₂CHO | (+)-pin | |
| 1190 | NH(C=NH)NH₂ | 1 | PhCH₂ | CH₂CHO | OH, OH | |
| 1191 | CH₂NH₂ | 1 | PhCH₂ | CH₂CHO | (+)-pin | |
| 1192 | CH₂NH₂ | 1 | PhCH₂ | CH₂CHO | OH, OH | |
| 1193 | -S-(C=NH)NH₂ | 1 | PhCH₂ | H | (+)-pin | |
| 1194 | -S-(C=NH)NH₂ | 1 | PhCH₂ | Methyl | (+)-pin | |
| 1195 | -S-(C=NH)NH₂ | 1 | PhCH₂ | Ethyl | (+)-pin | |
| 1196 | -S-(C=NH)NH₂ | 1 | PhCH₂ | n-Propyl | (+)-pin | |
| 1197 | -S-(C=NH)NH₂ | 1 | PhCH₂ | n-Butyl | (+)-pin | |
| 1198 | -S-(C=NH)NH₂ | 1 | PhCH₂ | CH₂SCH₃ | (+)-pin | |
| 1199 | -S-(C=NH)NH₂ | 1 | PhCH₂ | CH₂(SO)CH₃ | (+)-pin | |
| 1200 | -S-(C=NH)NH₂ | 1 | PhCH₂ | CH₂(SO₂)CH₃ | (+)-pin | |
| 1201 | -S-(C=NH)NH₂ | 1 | PhCH₂ | CH₂CH₂SCH₃ | (+)-pin | |
| 1202 | -S-(C=NH)NH₂ | 1 | PhCH₂ | CH₂CH₂(SO)CH₃ | (+)-pin | |
| 1203 | -S-(C=NH)NH₂ | 1 | PhCH₂ | CH₂CH₂(SO)₂CH₃ | (+)-pin | |
| 1204 | -S-(C=NH)NH₂ | 1 | PhCH₂ | CH₂CN | (+)-pin | |
| 1205 | -S-(C=NH)NH₂ | 1 | PhCH₂ | CH₂CH₂CN | (+)-pin | |
| 1206 | -S-(C=NH)NH₂ | 1 | PhCH₂ | CH₂CH₂CH₂CN | (+)-pin | |
| 1207 | -S-(C=NH)NH₂ | 1 | PhCH₂ | CF₃ | (+)-pin | |
| 1208 | -S-(C=NH)NH₂ | 1 | PhCH₂ | CF₂CF₃ | (+)-pin | |
| 1209 | -S-(C=NH)NH₂ | 1 | PhCH₂ | CF₂CF₂CF₃ | (+)-pin | |
| 1210 | -S-(C=NH)NH₂ | 1 | PhCH₂ | CF₂CF₂CF₂CF₃ | (+)-pin | |
| 1211 | -S-(C=NH)NH₂ | 1 | PhCH₂ | F₅-Ph | (+)-pin | |
| 1212 | -S-(C=NH)NH₂ | 1 | PhCH₂ | CH₂CO₂H | (+)-pin | |
| 1213 | -S-(C=NH)NH₂ | 1 | PhCH₂ | (CH₂)₂CO₂H | (+)-pin | |
| 1214 | -S-(C=NH)NH₂ | 1 | PhCH₂ | (CH₂)₃CO₂H | (+)-pin | |
| 1215 | -S-(C=NH)NH₂ | 1 | PhCH₂ | CH₂CN₄H | (+)-pin | |
| 1216 | -S-(C=NH)NH₂ | 1 | PhCH₂ | (CH₂)₂CN₄H | (+)-pin | |
| 1217 | -S-(C=NH)NH₂ | 1 | PhCH₂ | (CH₂)₃CN₄H | (+)-pin | |
| 1218 | -S-(C=NH)NH₂ | 1 | PhCH₂ | CH₂NO₂ | (+)-pin | |
| 1219 | -S-(C=NH)NH₂ | 1 | PhCH₂ | (CH₂)₂NO₂ | (+)-pin | |
| 1220 | -S-(C=NH)NH₂ | 1 | PhCH₂ | (CH₂)₃NO₂ | (+)-pin | |
| 1221 | -S-(C=NH)NH₂ | 1 | PhCH₂ | CH₂OH | (+)-pin | |
| 1222 | -S-(C=NH)NH₂ | 1 | PhCH₂ | (CH₂)₂OH | (+)-pin | |
| 1223 | -S-(C=NH)NH₂ | 1 | PhCH₂ | (CH₂)₃OH | (+)-pin | |
| 1224 | -S-(C=NH)NH₂ | 1 | PhCH₂ | CH₂CO₂Me | (+)-pin | |
| 1225 | -S-(C=NH)NH₂ | 1 | PhCH₂ | (CH₂)₂CO₂Me | (+)-pin | |
| 1226 | -S-(C=NH)NH₂ | 1 | PhCH₂ | (CH₂)₃CO₂Me | (+)-pin | |
| 1227 | -S-(C=NH)NH₂ | 1 | PhCH₂ | Ph | (+)-pin | |
| 1228 | -S-(C=NH)NH₂ | 1 | PhCH₂ | PhCH₂ | (+)-pin | |
| 1229 | -S-(C=NH)NH₂ | 1 | PhCH₂ | Ph(CH₂)₂ | (+)-pin | |
| 1230 | -S-(C=NH)NH₂ | 1 | PhCH₂ | 3-NO₂-Ph | (+)-pin | |
| 1231 | -S-(C=NH)NH₂ | 1 | PhCH₂ | 4-NO₂-Ph | (+)-pin | |
| 1232 | -S-(C=NH)NH₂ | 1 | PhCH₂ | 3-CO₂H-Ph | (+)-pin | |

TABLE 14-continued

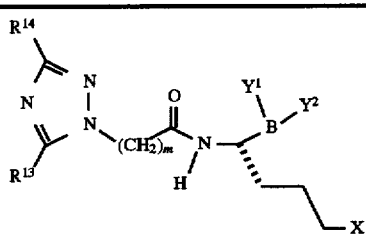

| Ex | X | m | R13 | R14 | Y1Y2 | Phys. Data |
|---|---|---|---|---|---|---|
| 1233 | —S—(C=NH)NH2 | 1 | PhCH2 | 4-CO2H-Ph | (+)-pin | |
| 1234 | —S—(C=NH)NH2 | 1 | PhCH2 | 3-CN4H-Ph | (+)-pin | |
| 1235 | —S—(C=NH)NH2 | 1 | PhCH2 | 4-CN4H-Ph | (+)-pin | |
| 1236 | —S—(C=NH)NH2 | 1 | PhCH2 | 3-(HOCH2)-Ph | (+)-pin | |
| 1237 | —S—(C=NH)NH2 | 1 | PhCH2 | 4-(HOCH2)-Ph | (+)-pin | |
| 1238 | —CN | 1 | PhCH2 | CH2CN | (+)-pin | |
| 1239 | —NO2 | 1 | PhCH2 | CH2CN | (+)-pin | |
| 1240 | —CH2NO2 | 1 | PhCH2 | CH2CN | (+)-pin | |
| 1241 | —CF3 | 1 | PhCH2 | CH2CN | (+)-pin | |
| 1242 | —NH2 | 1 | PhCH2 | CH2CN | (+)-pin | |
| 1243 | —NHOH | 1 | PhCH2 | CH2CN | (+)-pin | |
| 1244 | —NHOME | 1 | PhCH2 | CH2CN | (+)-pin | |
| 1245 | —CH2NHOH | 1 | PhCH2 | CH2CN | (+)-pin | |
| 1246 | —CH2NHOMe | 1 | PhCH2 | CH2CN | (+)-pin | |
| 1247 | —NH(C=NH)CH3 | 1 | PhCH2 | CH2CN | (+)-pin | |
| 1248 | —NH(C=NH)NHOH | 1 | PhCH2 | CH2CN | (+)-pin | |
| 1249 | —NH(C=NH)NHNH2 | 1 | PhCH2 | CH2CN | (+)-pin | |
| 1250 | —NH(C=NH)NHCN | 1 | PhCH2 | CH2CN | (+)-pin | |
| 1251 | —NH(C=NH)NHCH3 | 1 | PhCH2 | CH2CN | (+)-pin | |
| 1252 | —NH(C=NH)NHCOCH3 | 1 | PhCH2 | CH2CN | (+)-pin | |
| 1253 | —C(=NH)NH2 | 1 | PhCH2 | CH2CN | (+)-pin | |
| 1254 | —C(=NH)NHMe | 1 | PhCH2 | CH2CN | (+)-pin | |
| 1255 | —C(=NH)NHCOMe | 1 | PhCH2 | CH2CN | (+)-pin | |
| 1256 | —CONH2 | 1 | PhCH2 | CH2CN | (+)-pin | |
| 1257 | —CONHCH3 | 1 | PhCH2 | CH2CN | (+)-pin | |
| 1258 | —CO2CH3 | 1 | PhCH2 | CH2CN | (+)-pin | |
| 1259 | —OH | 1 | PhCH2 | CH2CN | (+)-pin | |
| 1260 | —CH2OH | 1 | PhCH2 | CH2CN | (+)-pin | |
| 1261 | —SCH3 | 1 | PhCH2 | CH2CN | (+)-pin | |
| 1262 | —SOCH3 | 1 | PhCH2 | CH2CN | (+)-pin | |
| 1263 | —SO2CH3 | 1 | PhCH2 | CH2CN | (+)-pin | |
| 1264 | —S—(C=NH)NHCH3 | 1 | PhCH2 | CH2CN | (+)-pin | |
| 1265 | —S—(C=NH)NHCOCH3 | 1 | PhCH2 | CH2CN | (+)-pin | |
| 1266 | —S—(C=NH)NH2 | 1 | PhCH2 | H | OH, OH | |
| 1267 | —S—(C=NH)NH2 | 1 | PhCH2 | Methyl | OH, OH | |
| 1268 | —S—(C=NH)NH2 | 1 | PhCH2 | Ethyl | OH, OH | |
| 1269 | —S—(C=NH)NH2 | 1 | PhCH2 | n-Propyl | OH, OH | |
| 1270 | —S—(C=NH)NH2 | 1 | PhCH2 | n-Butyl | OH, OH | |
| 1271 | —S—(C=NH)NH2 | 1 | PhCH2 | CH2SCH3 | OH, OH | |
| 1272 | —S—(C=NH)NH2 | 1 | PhCH2 | CH2(SO)CH3 | OH, OH | |
| 1273 | —S—(C=NH)NH2 | 1 | PhCH2 | CH2(SO2)CH3 | OH, OH | |
| 1274 | —S—(C=NH)NH2 | 1 | PhCH2 | CH2CH2SCH3 | OH, OH | |
| 1275 | —S—(C=NH)NH2 | 1 | PhCH2 | CH2CH2(SO)CH3 | OH, OH | |
| 1276 | —S—(C=NH)NH2 | 1 | PhCH2 | CH2CH2(SO)2CH3 | OH, OH | |
| 1277 | —S—(C=NH)NH2 | 1 | PhCH2 | CH2CN | OH, OH | |
| 1278 | —S—(C=NH)NH2 | 1 | PhCH2 | CH2CH2CN | OH, OH | |
| 1279 | —S—(C=NH)NH2 | 1 | PhCH2 | CH2CH2CH2CN | OH, OH | |
| 1280 | —S—(C=NH)NH2 | 1 | PhCH2 | CF3 | OH, OH | |
| 1281 | —S—(C=NH)NH2 | 1 | PhCH2 | CF2CF3 | OH, OH | |
| 1282 | —S—(C=NH)NH2 | 1 | PhCH2 | CF2CF2CF3 | OH, OH | |
| 1283 | —S—(C=NH)NH2 | 1 | PhCH2 | CF2CF2CF2CF3 | OH, OH | |
| 1284 | —S—(C=NH)NH2 | 1 | PhCH2 | F5-Ph | OH, OH | |
| 1285 | —S—(C=NH)NH2 | 1 | PhCH2 | CH2CO2H | OH, OH | |
| 1286 | —S—(C=NH)NH2 | 1 | PhCH2 | (CH2)2CO2H | OH, OH | |
| 1287 | —S—(C=NH)NH2 | 1 | PhCH2 | (CH2)3CO2H | OH, OH | |
| 1288 | —S—(C=NH)NH2 | 1 | PhCH2 | CH2CN4H | OH, OH | |
| 1289 | —S—(C=NH)NH2 | 1 | PhCH2 | (CH2)2CN4H | OH, OH | |
| 1290 | —S—(C=NH)NH2 | 1 | PhCH2 | (CH2)3CN4H | OH, OH | |
| 1291 | —S—(C=NH)NH2 | 1 | PhCH2 | CH2NO2 | OH, OH | |
| 1292 | —S—(C=NH)NH2 | 1 | PhCH2 | (CH2)2NO2 | OH, OH | |
| 1293 | —S—(C=NH)NH2 | 1 | PhCH2 | (CH2)3NO2 | OH, OH | |
| 1294 | —S—(C=NH)NH2 | 1 | PhCH2 | CH2OH | OH, OH | |
| 1295 | —S—(C=NH)NH2 | 1 | PhCH2 | (CH2)2OH | OH, OH | |
| 1296 | —S—(C=NH)NH2 | 1 | PhCH2 | (CH2)3OH | OH, OH | |

TABLE 14-continued

[Structure: R14-C=N-N(-(CH2)m-C(=O)-NH-CH(CH2CH2-X)-B(Y1)(Y2)) with R13-C=N on the other nitrogen of the pyrazole ring]

| Ex | X | m | R¹³ | R¹⁴ | Y¹Y² | Phys. Data |
|---|---|---|---|---|---|---|
| 1297 | —S—(C=NH)NH₂ | 1 | PhCH₂ | CH₂CO₂Me | OH, OH | |
| 1298 | —S—(C=NH)NH₂ | 1 | PhCH₂ | (CH₂)₂CO₂Me | OH, OH | |
| 1299 | —S—(C=NH)NH₂ | 1 | PhCH₂ | (CH₂)₃CO₂Me | OH, OH | |
| 1300 | —S—(C=NH)NH₂ | 1 | PhCH₂ | Ph | OH, OH | |
| 1301 | —S—(C=NH)NH₂ | 1 | PhCH₂ | PhCH₂ | OH, OH | |
| 1302 | —S—(C=NH)NH₂ | 1 | PhCH₂ | Ph(CH₂)₂ | OH, OH | |
| 1303 | —S—(C=NH)NH₂ | 1 | PhCH₂ | 3-NO₂-Ph | OH, OH | |
| 1304 | —S—(C=NH)NH₂ | 1 | PhCH₂ | 4-NO₂-Ph | OH, OH | |
| 1305 | —S—(C=NH)NH₂ | 1 | PhCH₂ | 3-CO₂H-Ph | OH, OH | |
| 1306 | —S—(C=NH)NH₂ | 1 | PhCH₂ | 4-CO₂H-Ph | OH, OH | |
| 1307 | —S—(C=NH)NH₂ | 1 | PhCH₂ | 3-CN₄H-Ph | OH, OH | |
| 1308 | —S—(C=NH)NH₂ | 1 | PhCH₂ | 4-CN₄H-Ph | OH, OH | |
| 1309 | —S—(C=NH)NH₂ | 1 | PhCH₂ | 3-(HOCH₂)-Ph | OH, OH | |
| 1310 | —S—(C=NH)NH₂ | 1 | PhCH₂ | 4-(HOCH₂)-Ph | OH, OH | |
| 1311 | —CN | 1 | PhCH₂ | CH₂CN | OH, OH | |
| 1312 | —NO₂ | 1 | PhCH₂ | CH₂CN | OH, OH | |
| 1313 | —CH₂NO₂ | 1 | PhCH₂ | CH₂CN | OH, OH | |
| 1314 | —CF₃ | 1 | PhCH₂ | CH₂CN | OH, OH | |
| 1315 | —NH₂ | 1 | PhCH₂ | CH₂CN | OH, OH | |
| 1316 | —NHOH | 1 | PhCH₂ | CH₂CN | OH, OH | |
| 1317 | —NHOME | 1 | PhCH₂ | CH₂CN | OH, OH | |
| 1318 | —CH₂NHOH | 1 | PhCH₂ | CH₂CN | OH, OH | |
| 1319 | —CH₂NHOMe | 1 | PhCH₂ | CH₂CN | OH, OH | |
| 1320 | —NH(C=NH)CH₃ | 1 | PhCH₂ | CH₂CN | OH, OH | |
| 1321 | —NH(C=NH)NHOH | 1 | PhCH₂ | CH₂CN | OH, OH | |
| 1322 | —NH(C=NH)NHNH₂ | 1 | PhCH₂ | CH₂CN | OH, OH | |
| 1323 | —NH(C=NH)NHCN | 1 | PhCH₂ | CH₂CN | OH, OH | |
| 1324 | —NH(C=NH)NHCH₃ | 1 | PhCH₂ | CH₂CN | OH, OH | |
| 1325 | —NH(C=NH)NHCOCH₃ | 1 | PhCH₂ | CH₂CN | OH, OH | |
| 1326 | —C(=NH)NH₂ | 1 | PhCH₂ | CH₂CN | OH, OH | |
| 1327 | —C(=NH)NHMe | 1 | PhCH₂ | CH₂CN | OH, OH | |
| 1328 | —C(=NH)NHCOMe | 1 | PhCH₂ | CH₂CN | OH, OH | |
| 1329 | —CONH₂ | 1 | PhCH₂ | CH₂CN | OH, OH | |
| 1330 | —CONHCH₃ | 1 | PhCH₂ | CH₂CN | OH, OH | |
| 1331 | —CO₂CH₃ | 1 | PhCH₂ | CH₂CN | OH, OH | |
| 1332 | —OH | 1 | PhCH₂ | CH₂CN | OH, OH | |
| 1333 | —CH₂OH | 1 | PhCH₂ | CH₂CN | OH, OH | |
| 1334 | —SCH₃ | 1 | PhCH₂ | CH₂CN | OH, OH | |
| 1335 | —SOCH₃ | 1 | PhCH₂ | CH₂CN | OH, OH | |
| 1336 | —SO₂CH₃ | 1 | PhCH₂ | CH₂CN | OH, OH | |
| 1337 | —S—(C=NH)NHCH₃ | 1 | PhCH₂ | CH₂CN | OH, OH | |
| 1338 | —S—(C=NH)NHCOCH₃ | 1 | PhCH₂ | CH₂CN | OH, OH | |
| 1339 | CH₂NH₂ | 2 | PhCH₂ | H | (+)-pin | |
| 1340 | CH₂NH₂ | 2 | PhCH₂ | H | OH, OH | |
| 1341 | OMe | 1 | PhCH₂ | H | (+)-pin | |
| 1342 | OMe | 1 | PhCH₂ | Methyl | (+)-pin | |
| 1343 | OMe | 1 | PhCH₂ | Ethyl | (+)-pin | |
| 1344 | OMe | 1 | PhCH₂ | n-Propyl | (+)-pin | |
| 1345 | OMe | 1 | PhCH₂ | n-Butyl | (+)-pin | |
| 1346 | OMe | 1 | PhCH₂ | CH₂SCH₃ | (+)-pin | |
| 1347 | OMe | 1 | PhCH₂ | CH₂(SO)CH₃ | (+)-pin | |
| 1348 | OMe | 1 | PhCH₂ | CH₂(SO₂)CH₃ | (+)-pin | |
| 1349 | OMe | 1 | PhCH₂ | CH₂CH₂SCH₃ | (+)-pin | |
| 1350 | OMe | 1 | PhCH₂ | CH₂CH₂(SO)CH₃ | (+)-pin | |
| 1351 | OMe | 1 | PhCH₂ | CH₂CH₂(SO)₂CH₃ | (+)-pin | |
| 1352 | OMe | 1 | PhCH₂ | CH₂CN | (+)-pin | CR |
| 1353 | OMe | 1 | PhCH₂ | CH₂CH₂CN | (+)-pin | |
| 1354 | OMe | 1 | PhCH₂ | CH₂CH₂CH₂CN | (+)-pin | |
| 1355 | OMe | 1 | PhCH₂ | CF₃ | (+)-pin | |
| 1356 | OMe | 1 | PhCH₂ | CF₂CF₃ | (+)-pin | |
| 1357 | OMe | 1 | PhCH₂ | CF₂CF₂CF₃ | (+)-pin | |
| 1358 | OMe | 1 | PhCH₂ | CF₂CF₂CF₂CF₃ | (+)-pin | |
| 1359 | OMe | 1 | PhCH₂ | F₅-Ph | (+)-pin | |
| 1360 | OMe | 1 | PhCH₂ | CH₂CO₂H | (+)-pin | |

TABLE 14-continued

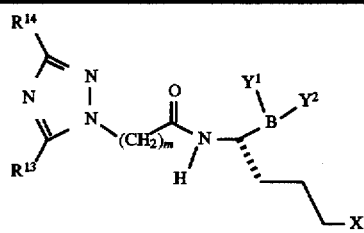

| Ex | X | m | R13 | R14 | Y1Y2 | Phys. Data |
|---|---|---|---|---|---|---|
| 1361 | OMe | 1 | PhCH2 | (CH2)2CO2H | (+)-pin | |
| 1362 | OMe | 1 | PhCH2 | (CH2)3CO2H | (+)-pin | |
| 1363 | OMe | 1 | PhCH2 | CH2CN4H | (+)-pin | |
| 1364 | OMe | 1 | PhCH2 | (CH2)2CN4H | (+)-pin | |
| 1365 | OMe | 1 | PhCH2 | (CH2)3CN4H | (+)-pin | |
| 1366 | OMe | 1 | PhCH2 | CH2NO2 | (+)-pin | |
| 1367 | OMe | 1 | PhCH2 | (CH2)2NO2 | (+)-pin | |
| 1368 | OMe | 1 | PhCH2 | (CH2)3NO2 | (+)-pin | |
| 1369 | OMe | 1 | PhCH2 | CH2OH | (+)-pin | |
| 1370 | OMe | 1 | PhCH2 | (CH2)2OH | (+)-pin | |
| 1371 | OMe | 1 | PhCH2 | (CH2)3OH | (+)-pin | |
| 1372 | OMe | 1 | PhCH2 | CH2CO2Me | (+)-pin | |
| 1373 | OMe | 1 | PhCH2 | (CH2)2CO2Me | (+)-pin | |
| 1374 | OMe | 1 | PhCH2 | (CH2)3CO2Me | (+)-pin | |
| 1375 | OMe | 1 | PhCH2 | Ph | (+)-pin | |
| 1376 | OMe | 1 | PhCH2 | PhCH2 | (+)-pin | |
| 1377 | OMe | 1 | PhCH2 | Ph(CH2)2 | (+)-pin | |
| 1378 | OMe | 1 | PhCH2 | 3-NO2-Ph | (+)-pin | |
| 1379 | OMe | 1 | PhCH2 | 4-NO2-Ph | (+)-pin | |
| 1380 | OMe | 1 | PhCH2 | 3-CO2H-Ph | (+)-pin | |
| 1381 | OMe | 1 | PhCH2 | 4-CO2H-Ph | (+)-pin | |
| 1382 | OMe | 1 | PhCH2 | 3-CN4H-Ph | (+)-pin | |
| 1383 | OMe | 1 | PhCH2 | 4-CN4H-Ph | (+)-pin | |
| 1384 | OMe | 1 | PhCH2 | 3-(HOCH2)-Ph | (+)-pin | |
| 1385 | OMe | 1 | PhCH2 | 4-(HOCH2)-Ph | (+)-pin | |
| 1386 | OMe | 1 | PhCH2 | H | OH, OH | |
| 1387 | OMe | 1 | PhCH2 | Methyl | OH, OH | |
| 1388 | OMe | 1 | PhCH2 | Ethyl | OH, OH | |
| 1389 | OMe | 1 | PhCH2 | n-Propyl | OH, OH | |
| 1390 | OMe | 1 | PhCH2 | n-Butyl | OH, OH | |
| 1391 | OMe | 1 | PhCH2 | CH2SCH3 | OH, OH | |
| 1392 | OMe | 1 | PhCH2 | CH2(SO)CH3 | OH, OH | |
| 1393 | OMe | 1 | PhCH2 | CH2(SO2)CH3 | OH, OH | |
| 1394 | OMe | 1 | PhCH2 | CH2CH2SCH3 | OH, OH | |
| 1395 | OMe | 1 | PhCH2 | CH2CH2(SO)CH3 | OH, OH | |
| 1396 | OMe | 1 | PhCH2 | CH2CH2(SO)2CH3 | OH, OH | |
| 1397 | OMe | 1 | PhCH2 | CH2CN | OH, OH | |
| 1398 | OMe | 1 | PhCH2 | CH2CH2CN | OH, OH | |
| 1399 | OMe | 1 | PhCH2 | CH2CH2CH2CN | OH, OH | |
| 1400 | OMe | 1 | PhCH2 | CF3 | OH, OH | |
| 1401 | OMe | 1 | PhCH2 | CF2CF3 | OH, OH | |
| 1402 | OMe | 1 | PhCH2 | CF2CF2CF3 | OH, OH | |
| 1403 | OMe | 1 | PhCH2 | CF2CF2CF2CF3 | OH, OH | |
| 1404 | OMe | 1 | PhCH2 | F5-Ph | OH, OH | |
| 1405 | OMe | 1 | PhCH2 | CH2CO2H | OH, OH | |
| 1406 | OMe | 1 | PhCH2 | (CH2)2CO2H | OH, OH | |
| 1407 | OMe | 1 | PhCH2 | (CH2)3CO2H | OH, OH | |
| 1408 | OMe | 1 | PhCH2 | CH2CN4H | OH, OH | |
| 1409 | OMe | 1 | PhCH2 | (CH2)2CN4H | OH, OH | |
| 1410 | OMe | 1 | PhCH2 | (CH2)3CN4H | OH, OH | |
| 1411 | OMe | 1 | PhCH2 | CH2NO2 | OH, OH | |
| 1412 | OMe | 1 | PhCH2 | (CH2)2NO2 | OH, OH | |
| 1413 | OMe | 1 | PhCH2 | (CH2)3NO2 | OH, OH | |
| 1414 | OMe | 1 | PhCH2 | CH2OH | OH, OH | |
| 1415 | OMe | 1 | PhCH2 | (CH2)2OH | OH, OH | |
| 1416 | OMe | 1 | PhCH2 | (CH2)3OH | OH, OH | |
| 1417 | OMe | 1 | PhCH2 | CH2CO2Me | OH, OH | |
| 1418 | OMe | 1 | PhCH2 | (CH2)2CO2Me | OH, OH | |
| 1419 | OMe | 1 | PhCH2 | (CH2)3CO2Me | OH, OH | |
| 1420 | OMe | 1 | PhCH2 | PhCH2 | OH, OH | |
| 1421 | OMe | 1 | PhCH2 | PhCH2 | OH, OH | |
| 1422 | OMe | 1 | PhCH2 | Ph(CH2)2 | OH, OH | |
| 1423 | OMe | 1 | PhCH2 | 3-NO2-Ph | OH, OH | |
| 1424 | OMe | 1 | PhCH2 | 4-NO2-Ph | OH, OH | |

TABLE 14-continued

| Ex | X | m | R$^{13}$ | R$^{14}$ | Y$^1$Y$^2$ | Phys. Data |
|---|---|---|---|---|---|---|
| 1425 | OMe | 1 | PhCH$_2$ | 3-CO$_2$H-Ph | OH, OH | |
| 1426 | OMe | 1 | PhCH$_2$ | 4-CO$_2$H-Ph | OH, OH | |
| 1427 | OMe | 1 | PhCH$_2$ | 3-CN$_4$H-Ph | OH, OH | |
| 1428 | OMe | 1 | PhCH$_2$ | 4-CN$_4$H-Ph | OH, OH | |
| 1429 | OMe | 1 | PhCH$_2$ | 3-(HOCH$_2$)-Ph | OH, OH | |
| 1430 | OMe | 1 | PhCH$_2$ | 4-(HOCH$_2$)-Ph | OH, OH | |
| 1431 | CH$_2$NH$_2$ | 1 | PhCH$_2$CH$_2$ | H | (+)-pin | AX |
| 1432 | CH$_2$NH$_2$ | 1 | PhCH$_2$CH$_2$ | Methyl | (+)-pin | |
| 1433 | CH$_2$NH$_2$ | 1 | PhCH$_2$CH$_2$ | Ethyl | (+)-pin | |
| 1434 | CH$_2$NH$_2$ | 1 | PhCH$_2$CH$_2$ | n-Propyl | (+)-pin | |
| 1435 | CH$_2$NH$_2$ | 1 | PhCH$_2$CH$_2$ | n-Butyl | (+)-pin | |
| 1436 | CH$_2$NH$_2$ | 1 | PhCH$_2$CH$_2$ | CH$_2$SCH$_3$ | (+)-pin | |
| 1437 | CH$_2$NH$_2$ | 1 | PhCH$_2$CH$_2$ | CH$_2$(SO)CH$_3$ | (+)-pin | |
| 1438 | CH$_2$NH$_2$ | 1 | PhCH$_2$CH$_2$ | CH$_2$(SO$_2$)CH$_3$ | (+)-pin | |
| 1439 | CH$_2$NH$_2$ | 1 | PhCH$_2$CH$_2$ | CH$_2$CH$_2$SCH$_3$ | (+)-pin | |
| 1440 | CH$_2$NH$_2$ | 1 | PhCH$_2$CH$_2$ | CH$_2$CH$_2$(SO)CH$_3$ | (+)-pin | |
| 1441 | CH$_2$NH$_2$ | 1 | PhCH$_2$CH$_2$ | CH$_2$CH$_2$(SO)$_2$CH$_3$ | (+)-pin | |
| 1442 | CH$_2$NH$_2$ | 1 | PhCH$_2$CH$_2$ | CH$_2$CN | (+)-pin | |
| 1443 | CH$_2$NH$_2$ | 1 | PhCH$_2$CH$_2$ | CH$_2$CH$_2$CN | (+)-pin | |
| 1444 | CH$_2$NH$_2$ | 1 | PhCH$_2$CH$_2$ | CH$_2$CH$_2$CH$_2$CN | (+)-pin | |
| 1445 | CH$_2$NH$_2$ | 1 | PhCH$_2$CH$_2$ | CF$_3$ | (+)-pin | |
| 1446 | CH$_2$NH$_2$ | 1 | PhCH$_2$CH$_2$ | CF$_2$CF$_3$ | (+)-pin | |
| 1447 | CH$_2$NH$_2$ | 1 | PhCH$_2$CH$_2$ | CF$_2$CF$_2$CF$_3$ | (+)-pin | |
| 1448 | CH$_2$NH$_2$ | 1 | PhCH$_2$CH$_2$ | CF$_2$CF$_2$CF$_2$CF$_3$ | (+)-pin | |
| 1449 | CH$_2$NH$_2$ | 1 | PhCH$_2$CH$_2$ | F$_5$-Ph | (+)-pin | |
| 1450 | CH$_2$NH$_2$ | 1 | PhCH$_2$CH$_2$ | CH$_2$CO$_2$H | (+)-pin | |
| 1451 | CH$_2$NH$_2$ | 1 | PhCH$_2$CH$_2$ | (CH$_2$)$_2$CO$_2$H | (+)-pin | |
| 1452 | CH$_2$NH$_2$ | 1 | PhCH$_2$CH$_2$ | (CH$_2$)$_3$CO$_2$H | (+)-pin | |
| 1453 | CH$_2$NH$_2$ | 1 | PhCH$_2$CH$_2$ | CH$_2$CN$_4$H | (+)-pin | |
| 1454 | CH$_2$NH$_2$ | 1 | PhCH$_2$CH$_2$ | (CH$_2$)$_2$CN$_4$H | (+)-pin | |
| 1455 | CH$_2$NH$_2$ | 1 | PhCH$_2$CH$_2$ | (CH$_2$)$_3$CN$_4$H | (+)-pin | |
| 1456 | CH$_2$NH$_2$ | 1 | PhCH$_2$CH$_2$ | CH$_2$NO$_2$ | (+)-pin | |
| 1457 | CH$_2$NH$_2$ | 1 | PhCH$_2$CH$_2$ | (CH$_2$)$_2$NO$_2$ | (+)-pin | |
| 1458 | CH$_2$NH$_2$ | 1 | PhCH$_2$CH$_2$ | (CH$_2$)$_3$NO$_2$ | (+)-pin | |
| 1459 | CH$_2$NH$_2$ | 1 | PhCH$_2$CH$_2$ | CH$_2$OH | (+)-pin | CS |
| 1460 | CH$_2$NH$_2$ | 1 | PhCH$_2$CH$_2$ | (CH$_2$)$_2$OH | (+)-pin | |
| 1461 | CH$_2$NH$_2$ | 1 | PhCH$_2$CH$_2$ | (CH$_2$)$_3$OH | (+)-pin | |
| 1462 | CH$_2$NH$_2$ | 1 | PhCH$_2$CH$_2$ | CH$_2$CO$_2$Me | (+)-pin | |
| 1463 | CH$_2$NH$_2$ | 1 | PhCH$_2$CH$_2$ | (CH$_2$)$_2$CO$_2$Me | (+)-pin | |
| 1464 | CH$_2$NH$_2$ | 1 | PhCH$_2$CH$_2$ | (CH$_2$)$_3$CO$_2$Me | (+)-pin | |
| 1465 | CH$_2$NH$_2$ | 1 | PhCH$_2$CH$_2$ | Ph | (+)-pin | |
| 1466 | CH$_2$NH$_2$ | 1 | PhCH$_2$CH$_2$ | PhCH$_2$ | (+)-pin | |
| 1467 | CH$_2$NH$_2$ | 1 | PhCH$_2$CH$_2$ | Ph(CH$_2$)$_2$ | (+)-pin | AY |
| 1468 | CH$_2$NH$_2$ | 1 | PhCH$_2$CH$_2$ | 3-NO$_2$-Ph | (+)-pin | |
| 1469 | CH$_2$NH$_2$ | 1 | PhCH$_2$CH$_2$ | 4-NO$_2$-Ph | (+)-pin | |
| 1470 | CH$_2$NH$_2$ | 1 | PhCH$_2$CH$_2$ | 3-CO$_2$H-Ph | (+)-pin | |
| 1471 | CH$_2$NH$_2$ | 1 | PhCH$_2$CH$_2$ | 4-CO$_2$H-Ph | (+)-pin | |
| 1472 | CH$_2$NH$_2$ | 1 | PhCH$_2$CH$_2$ | 3-CN$_4$H-Ph | (+)-pin | |
| 1473 | CH$_2$NH$_2$ | 1 | PhCH$_2$CH$_2$ | 4-CN$_4$H-Ph | (+)-pin | |
| 1474 | CH$_2$NH$_2$ | 1 | PhCH$_2$CH$_2$ | 3-(HOCH$_2$)-Ph | (+)-pin | |
| 1475 | CH$_2$NH$_2$ | 1 | PhCH$_2$CH$_2$ | 4-(HOCH$_2$)-Ph | (+)-pin | |
| 1476 | NH(C=NH)NH$_2$ | 1 | PhCH$_2$CH$_2$ | H | (+)-pin | |
| 1477 | NH(C=NH)NH$_2$ | 1 | PhCH$_2$CH$_2$ | Methyl | (+)-pin | |
| 1478 | NH(C=NH)NH$_2$ | 1 | PhCH$_2$CH$_2$ | Ethyl | (+)-pin | |
| 1479 | NH(C=NH)NH$_2$ | 1 | PhCH$_2$CH$_2$ | n-Propyl | (+)-pin | |
| 1480 | NH(C=NH)NH$_2$ | 1 | PhCH$_2$CH$_2$ | n-Butyl | (+)-pin | |
| 1481 | NH(C=NH)NH$_2$ | 1 | PhCH$_2$CH$_2$ | CH$_2$SCH$_3$ | (+)-pin | |
| 1482 | NH(C=NH)NH$_2$ | 1 | PhCH$_2$CH$_2$ | CH$_2$(SO)CH$_3$ | (+)-pin | |
| 1483 | NH(C=NH)NH$_2$ | 1 | PhCH$_2$CH$_2$ | CH$_2$(SO$_2$)CH$_3$ | (+)-pin | |
| 1484 | NH(C=NH)NH$_2$ | 1 | PhCH$_2$CH$_2$ | CH$_2$CH$_2$SCH$_3$ | (+)-pin | |
| 1485 | NH(C=NH)NH$_2$ | 1 | PhCH$_2$CH$_2$ | CH$_2$CH$_2$(SO)CH$_3$ | (+)-pin | |
| 1486 | NH(C=NH)NH$_2$ | 1 | PhCH$_2$CH$_2$ | CH$_2$CH$_2$(SO)$_2$CH$_3$ | (+)-pin | |
| 1487 | NH(C=NH)NH$_2$ | 1 | PhCH$_2$CH$_2$ | CH$_2$CN | (+)-pin | |
| 1488 | NH(C=NH)NH$_2$ | 1 | PhCH$_2$CH$_2$ | CH$_2$CH$_2$CN | (+)-pin | |

TABLE 14-continued

| Ex | X | m | R¹³ | R¹⁴ | Y¹Y² | Phys. Data |
|---|---|---|---|---|---|---|
| 1489 | NH(C=NH)NH₂ | 1 | PhCH₂CH₂ | CH₂CH₂CH₂CN | (+)-pin | |
| 1490 | NH(C=NH)NH₂ | 1 | PhCH₂CH₂ | CF₃ | (+)-pin | |
| 1491 | NH(C=NH)NH₂ | 1 | PhCH₂CH₂ | CF₂CF₃ | (+)-pin | |
| 1492 | NH(C=NH)NH₂ | 1 | PhCH₂CH₂ | CF₂CF₂CF₃ | (+)-pin | |
| 1493 | NH(C=NH)NH₂ | 1 | PhCH₂CH₂ | CF₂CF₂CF₂CF₃ | (+)-pin | |
| 1494 | NH(C=NH)NH₂ | 1 | PhCH₂CH₂ | F₅-Ph | (+)-pin | |
| 1495 | NH(C=NH)NH₂ | 1 | PhCH₂CH₂ | CH₂CO₂H | (+)-pin | |
| 1496 | NH(C=NH)NH₂ | 1 | PhCH₂CH₂ | (CH₂)₂CO₂H | (+)-pin | |
| 1497 | NH(C=NH)NH₂ | 1 | PhCH₂CH₂ | (CH₂)₃CO₂H | (+)-pin | |
| 1498 | NH(C=NH)NH₂ | 1 | PhCH₂CH₂ | CH₂CN₄H | (+)-pin | |
| 1499 | NH(C=NH)NH₂ | 1 | PhCH₂CH₂ | (CH₂)₂CN₄H | (+)-pin | |
| 1500 | NH(C=NH)NH₂ | 1 | PhCH₂CH₂ | (CH₂)₃CN₄H | (+)-pin | |
| 1501 | NH(C=NH)NH₂ | 1 | PhCH₂CH₂ | CH₂NO₂ | (+)-pin | |
| 1502 | NH(C=NH)NH₂ | 1 | PhCH₂CH₂ | (CH₂)₂NO₂ | (+)-pin | |
| 1503 | NH(C=NH)NH₂ | 1 | PhCH₂CH₂ | (CH₂)₃NO₂ | (+)-pin | |
| 1504 | NH(C=NH)NH₂ | 1 | PhCH₂CH₂ | CH₂OH | (+)-pin | |
| 1505 | NH(C=NH)NH₂ | 1 | PhCH₂CH₂ | (CH₂)₂OH | (+)-pin | |
| 1506 | NH(C=NH)NH₂ | 1 | PhCH₂CH₂ | (CH₂)₃OH | (+)-pin | |
| 1507 | NH(C=NH)NH₂ | 1 | PhCH₂CH₂ | CH₂CO₂Me | (+)-pin | |
| 1508 | NH(C=NH)NH₂ | 1 | PhCH₂CH₂ | (CH₂)₂CO₂Me | (+)-pin | |
| 1509 | NH(C=NH)NH₂ | 1 | PhCH₂CH₂ | (CH₂)₃CO₂Me | (+)-pin | |
| 1510 | NH(C=NH)NH₂ | 1 | PhCH₂CH₂ | Ph | (+)-pin | |
| 1511 | NH(C=NH)NH₂ | 1 | PhCH₂CH₂ | PhCH₂ | (+)-pin | |
| 1512 | NH(C=NH)NH₂ | 1 | PhCH₂CH₂ | Ph(CH₂)₂ | (+)-pin | |
| 1513 | NH(C=NH)NH₂ | 1 | PhCH₂CH₂ | 3-NO₂-Ph | (+)-pin | |
| 1514 | NH(C=NH)NH₂ | 1 | PhCH₂CH₂ | 4-NO₂-Ph | (+)-pin | |
| 1515 | NH(C=NH)NH₂ | 1 | PhCH₂CH₂ | 3-CO₂H-Ph | (+)-pin | |
| 1516 | NH(C=NH)NH₂ | 1 | PhCH₂CH₂ | 4-CO₂H-Ph | (+)-pin | |
| 1517 | NH(C=NH)NH₂ | 1 | PhCH₂CH₂ | 3-CN₄H-Ph | (+)-pin | |
| 1518 | NH(C=NH)NH₂ | 1 | PhCH₂CH₂ | 4-CN₄H-Ph | (+)-pin | |
| 1519 | NH(C=NH)NH₂ | 1 | PhCH₂CH₂ | 3-(HOCH₂)-Ph | (+)-pin | |
| 1520 | NH(C=NH)NH₂ | 1 | PhCH₂CH₂ | 4-(HOCH₂)-Ph | (+)-pin | |
| 1521 | CH₂NH₂ | 1 | PhCH₂CH₂ | H | OH, OH | AZ |
| 1522 | CH₂NH₂ | 1 | PhCH₂CH₂ | Methyl | OH, OH | |
| 1523 | CH₂NH₂ | 1 | PhCH₂CH₂ | Ethyl | OH, OH | |
| 1524 | CH₂NH₂ | 1 | PhCH₂CH₂ | n-Propyl | OH, OH | |
| 1525 | CH₂NH₂ | 1 | PhCH₂CH₂ | n-Butyl | OH, OH | |
| 1526 | CH₂NH₂ | 1 | PhCH₂CH₂ | CH₂SCH₃ | OH, OH | |
| 1527 | CH₂NH₂ | 1 | PhCH₂CH₂ | CH₂(SO)CH₃ | OH, OH | |
| 1528 | CH₂NH₂ | 1 | PhCH₂CH₂ | CH₂(SO₂)CH₃ | OH, OH | |
| 1529 | CH₂NH₂ | 1 | PhCH₂CH₂ | CH₂CH₂SCH₃ | OH, OH | |
| 1530 | CH₂NH₂ | 1 | PhCH₂CH₂ | CH₂CH₂(SO)CH₃ | OH, OH | |
| 1531 | CH₂NH₂ | 1 | PhCH₂CH₂ | CH₂CH₂(SO)₂CH₃ | OH, OH | |
| 1532 | CH₂NH₂ | 1 | PhCH₂CH₂ | CH₂CN | OH, OH | |
| 1533 | CH₂NH₂ | 1 | PhCH₂CH₂ | CH₂CH₂CN | OH, OH | |
| 1534 | CH₂NH₂ | 1 | PhCH₂CH₂ | CH₂CH₂CH₂CN | OH, OH | |
| 1535 | CH₂NH₂ | 1 | PhCH₂CH₂ | CF₃ | OH, OH | |
| 1536 | CH₂NH₂ | 1 | PhCH₂CH₂ | CF₂CF₃ | OH, OH | |
| 1537 | CH₂NH₂ | 1 | PhCH₂CH₂ | CF₂CF₂CF₃ | OH, OH | |
| 1538 | CH₂NH₂ | 1 | PhCH₂CH₂ | CF₂CF₂CF₂CF₃ | OH, OH | |
| 1539 | CH₂NH₂ | 1 | PhCH₂CH₂ | F₅-Ph | OH, OH | |
| 1540 | CH₂NH₂ | 1 | PhCH₂CH₂ | CH₂CO₂H | OH, OH | |
| 1541 | CH₂NH₂ | 1 | PhCH₂CH₂ | (CH₂)₂CO₂H | OH, OH | |
| 1542 | CH₂NH₂ | 1 | PhCH₂CH₂ | (CH₂)₃CO₂H | OH, OH | |
| 1543 | CH₂NH₂ | 1 | PhCH₂CH₂ | CH₂CN₄H | OH, OH | |
| 1544 | CH₂NH₂ | 1 | PhCH₂CH₂ | (CH₂)₂CN₄H | OH, OH | |
| 1545 | CH₂NH₂ | 1 | PhCH₂CH₂ | (CH₂)₃CN₄H | OH, OH | |
| 1546 | CH₂NH₂ | 1 | PhCH₂CH₂ | CH₂NO₂ | OH, OH | |
| 1547 | CH₂NH₂ | 1 | PhCH₂CH₂ | (CH₂)₂NO₂ | OH, OH | |
| 1548 | CH₂NH₂ | 1 | PhCH₂CH₂ | (CH₂)₃NO₂ | OH, OH | |
| 1549 | CH₂NH₂ | 1 | PhCH₂CH₂ | CH₂OH | OH, OH | |
| 1550 | CH₂NH₂ | 1 | PhCH₂CH₂ | (CH₂)₂OH | OH, OH | |
| 1551 | CH₂NH₂ | 1 | PhCH₂CH₂ | (CH₂)₃OH | OH, OH | |
| 1552 | CH₂NH₂ | 1 | PhCH₂CH₂ | CH₂CO₂Me | OH, OH | |

TABLE 14-continued

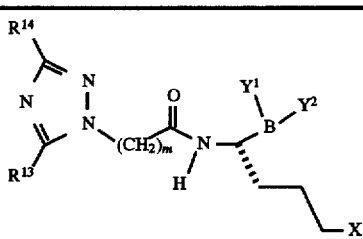

| Ex | X | m | $R^{13}$ | $R^{14}$ | $Y^1Y^2$ | Phys. Data |
|---|---|---|---|---|---|---|
| 1553 | $CH_2NH_2$ | 1 | $PhCH_2CH_2$ | $(CH_2)_2CO_2Me$ | OH, OH | |
| 1554 | $CH_2NH_2$ | 1 | $PhCH_2CH_2$ | $(CH_2)_3CO_2Me$ | OH, OH | |
| 1555 | $CH_2NH_2$ | 1 | $PhCH_2CH_2$ | Ph | OH, OH | |
| 1556 | $CH_2NH_2$ | 1 | $PhCH_2CH_2$ | $PhCH_2$ | OH, OH | |
| 1557 | $CH_2NH_2$ | 1 | $PhCH_2CH_2$ | $Ph(CH_2)_2$ | OH, OH | AJ |
| 1558 | $CH_2NH_2$ | 1 | $PhCH_2CH_2$ | $3-NO_2-Ph$ | OH, OH | |
| 1559 | $CH_2NH_2$ | 1 | $PhCH_2CH_2$ | $4-NO_2-Ph$ | OH, OH | |
| 1560 | $CH_2NH_2$ | 1 | $PhCH_2CH_2$ | $3-CO_2H-Ph$ | OH, OH | |
| 1561 | $CH_2NH_2$ | 1 | $PhCH_2CH_2$ | $4-CO_2H-Ph$ | OH, OH | |
| 1562 | $CH_2NH_2$ | 1 | $PhCH_2CH_2$ | $3-CN_4H-Ph$ | OH, OH | |
| 1563 | $CH_2NH_2$ | 1 | $PhCH_2CH_2$ | $4-CN_4H-Ph$ | OH, OH | |
| 1564 | $CH_2NH_2$ | 1 | $PhCH_2CH_2$ | $3-(HOCH_2)-Ph$ | OH, OH | |
| 1565 | $CH_2NH_2$ | 1 | $PhCH_2CH_2$ | $4-(HOCH_2)-Ph$ | OH, OH | |
| 1566 | $NH(C=NH)NH_2$ | 1 | $PhCH_2CH_2$ | H | OH, OH | |
| 1567 | $NH(C=NH)NH_2$ | 1 | $PhCH_2CH_2$ | Methyl | OH, OH | |
| 1568 | $NH(C=NH)NH_2$ | 1 | $PhCH_2CH_2$ | Ethyl | OH, OH | |
| 1569 | $NH(C=NH)NH_2$ | 1 | $PhCH_2CH_2$ | n-Propyl | OH, OH | |
| 1570 | $NH(C=NH)NH_2$ | 1 | $PhCH_2CH_2$ | n-Butyl | OH, OH | |
| 1571 | $NH(C=NH)NH_2$ | 1 | $PhCH_2CH_2$ | $CH_2SCH_3$ | OH, OH | |
| 1572 | $NH(C=NH)NH_2$ | 1 | $PhCH_2CH_2$ | $CH_2(SO)CH_3$ | OH, OH | |
| 1573 | $NH(C=NH)NH_2$ | 1 | $PhCH_2CH_2$ | $CH_2(SO_2)CH_3$ | OH, OH | |
| 1574 | $NH(C=NH)NH_2$ | 1 | $PhCH_2CH_2$ | $CH_2CH_2SCH_3$ | OH, OH | |
| 1575 | $NH(C=NH)NH_2$ | 1 | $PhCH_2CH_2$ | $CH_2CH_2(SO)CH_3$ | OH, OH | |
| 1576 | $NH(C=NH)NH_2$ | 1 | $PhCH_2CH_2$ | $CH_2CH_2(SO)_2CH_3$ | OH, OH | |
| 1577 | $NH(C=NH)NH_2$ | 1 | $PhCH_2CH_2$ | $CH_2CN$ | OH, OH | |
| 1578 | $NH(C=NH)NH_2$ | 1 | $PhCH_2CH_2$ | $CH_2CH_2CN$ | OH, OH | |
| 1579 | $NH(C=NH)NH_2$ | 1 | $PhCH_2CH_2$ | $CH_2CH_2CH_2CN$ | OH, OH | |
| 1580 | $NH(C=NH)NH_2$ | 1 | $PhCH_2CH_2$ | $CF_3$ | OH, OH | |
| 1581 | $NH(C=NH)NH_2$ | 1 | $PhCH_2CH_2$ | $CF_2CF_3$ | OH, OH | |
| 1582 | $NH(C=NH)NH_2$ | 1 | $PhCH_2CH_2$ | $CF_2CF_2CF_3$ | OH, OH | |
| 1583 | $NH(C=NH)NH_2$ | 1 | $PhCH_2CH_2$ | $CF_2CF_2CF_2CF_3$ | OH, OH | |
| 1584 | $NH(C=NH)NH_2$ | 1 | $PhCH_2CH_2$ | $F_5-Ph$ | OH, OH | |
| 1585 | $NH(C=NH)NH_2$ | 1 | $PhCH_2CH_2$ | $CH_2CO_2H$ | OH, OH | |
| 1586 | $NH(C=NH)NH_2$ | 1 | $PhCH_2CH_2$ | $(CH_2)_2CO_2H$ | OH, OH | |
| 1587 | $NH(C=NH)NH_2$ | 1 | $PhCH_2CH_2$ | $(CH_2)_3CO_2H$ | OH, OH | |
| 1588 | $NH(C=NH)NH_2$ | 1 | $PhCH_2CH_2$ | $CH_2CN_4H$ | OH, OH | |
| 1589 | $NH(C=NH)NH_2$ | 1 | $PhCH_2CH_2$ | $(CH_2)_2CN_4H$ | OH, OH | |
| 1590 | $NH(C=NH)NH_2$ | 1 | $PhCH_2CH_2$ | $(CH_2)_3CN_4H$ | OH, OH | |
| 1591 | $NH(C=NH)NH_2$ | 1 | $PhCH_2CH_2$ | $CH_2NO_2$ | OH, OH | |
| 1592 | $NH(C=NH)NH_2$ | 1 | $PhCH_2CH_2$ | $(CH_2)_2NO_2$ | OH, OH | |
| 1593 | $NH(C=NH)NH_2$ | 1 | $PhCH_2CH_2$ | $(CH_2)_3NO_2$ | OH, OH | |
| 1594 | $NH(C=NH)NH_2$ | 1 | $PhCH_2CH_2$ | $CH_2OH$ | OH, OH | |
| 1595 | $NH(C=NH)NH_2$ | 1 | $PhCH_2CH_2$ | $(CH_2)_2OH$ | OH, OH | |
| 1596 | $NH(C=NH)NH_2$ | 1 | $PhCH_2CH_2$ | $(CH_2)_3OH$ | OH, OH | |
| 1597 | $NH(C=NH)NH_2$ | 1 | $PhCH_2CH_2$ | $CH_2CO_2Me$ | OH, OH | |
| 1598 | $NH(C=NH)NH_2$ | 1 | $PhCH_2CH_2$ | $(CH_2)_2CO_2Me$ | OH, OH | |
| 1599 | $NH(C=NH)NH_2$ | 1 | $PhCH_2CH_2$ | $(CH_2)_3CO_2Me$ | OH, OH | |
| 1600 | $NH(C=NH)NH_2$ | 1 | $PhCH_2CH_2$ | $PhCH_2CH_2$ | OH, OH | |
| 1601 | $NH(C=NH)NH_2$ | 1 | $PhCH_2CH_2$ | $PhCH_2CH_2$ | OH, OH | |
| 1602 | $NH(C=NH)NH_2$ | 1 | $PhCH_2CH_2$ | $Ph(CH_2)_2$ | OH, OH | |
| 1603 | $NH(C=NH)NH_2$ | 1 | $PhCH_2CH_2$ | $3-NO_2-Ph$ | OH, OH | |
| 1604 | $NH(C=NH)NH_2$ | 1 | $PhCH_2CH_2$ | $4-NO_2-Ph$ | OH, OH | |
| 1605 | $NH(C=NH)NH_2$ | 1 | $PhCH_2CH_2$ | $3-CO_2H-Ph$ | OH, OH | |
| 1606 | $NH(C=NH)NH_2$ | 1 | $PhCH_2CH_2$ | $4-CO_2H-Ph$ | OH, OH | |
| 1607 | $NH(C=NH)NH_2$ | 1 | $PhCH_2CH_2$ | $3-CN_4H-Ph$ | OH, OH | |
| 1608 | $NH(C=NH)NH_2$ | 1 | $PhCH_2CH_2$ | $4-CN_4H-Ph$ | OH, OH | |
| 1609 | $NH(C=NH)NH_2$ | 1 | $PhCH_2CH_2$ | $3-(HOCH_2)-Ph$ | OH, OH | |
| 1610 | $NH(C=NH)NH_2$ | 1 | $PhCH_2CH_2$ | $4-(HOCH_2)-Ph$ | OH, OH | |
| 1611 | $-S-(C=NH)NH_2$ | 1 | $PhCH_2CH_2$ | H | (+)-pin | |
| 1612 | $-S-(C=NH)NH_2$ | 1 | $PhCH_2CH_2$ | Methyl | (+)-pin | |
| 1613 | $-S-(C=NH)NH_2$ | 1 | $PhCH_2CH_2$ | Ethyl | (+)-pin | |
| 1614 | $-S-(C=NH)NH_2$ | 1 | $PhCH_2CH_2$ | n-Propyl | (+)-pin | |
| 1615 | $-S-(C=NH)NH_2$ | 1 | $PhCH_2CH_2$ | n-Butyl | (+)-pin | |
| 1616 | $-S-(C=NH)NH_2$ | 1 | $PhCH_2CH_2$ | $CH_2SCH_3$ | (+)-pin | |

TABLE 14-continued

| Ex | X | m | R¹³ | R¹⁴ | Y¹Y² | Phys. Data |
|---|---|---|---|---|---|---|
| 1617 | -S-(C=NH)NH₂ | 1 | PhCH₂CH₂ | CH₂(SO)CH₃ | (+)-pin | |
| 1618 | -S-(C=NH)NH₂ | 1 | PhCH₂CH₂ | CH₂(SO₂)CH₃ | (+)-pin | |
| 1619 | -S-(C=NH)NH₂ | 1 | PhCH₂CH₂ | CH₂CH₂SCH₃ | (+)-pin | |
| 1620 | -S-(C=NH)NH₂ | 1 | PhCH₂CH₂ | CH₂CH₂(SO)CH₃ | (+)-pin | |
| 1621 | -S-(C=NH)NH₂ | 1 | PhCH₂CH₂ | CH₂CH₂(SO)₂CH₃ | (+)-pin | |
| 1622 | -S-(C=NH)NH₂ | 1 | PhCH₂CH₂ | CH₂CN | (+)-pin | |
| 1623 | -S-(C=NH)NH₂ | 1 | PhCH₂CH₂ | CH₂CH₂CN | (+)-pin | |
| 1624 | -S-(C=NH)NH₂ | 1 | PhCH₂CH₂ | CH₂CH₂CH₂CN | (+)-pin | |
| 1625 | -S-(C=NH)NH₂ | 1 | PhCH₂CH₂ | CF₃ | (+)-pin | |
| 1626 | -S-(C=NH)NH₂ | 1 | PhCH₂CH₂ | CF₂CF₃ | (+)-pin | |
| 1627 | -S-(C=NH)NH₂ | 1 | PhCH₂CH₂ | CF₂CF₂CF₃ | (+)-pin | |
| 1628 | -S-(C=NH)NH₂ | 1 | PhCH₂CH₂ | CF₂CF₂CF₂CF₃ | (+)-pin | |
| 1629 | -S-(C=NH)NH₂ | 1 | PhCH₂CH₂ | F₅-Ph | (+)-pin | |
| 1630 | -S-(C=NH)NH₂ | 1 | PhCH₂CH₂ | CH₂CO₂H | (+)-pin | |
| 1631 | -S-(C=NH)NH₂ | 1 | PhCH₂CH₂ | (CH₂)₂CO₂H | (+)-pin | |
| 1632 | -S-(C=NH)NH₂ | 1 | PhCH₂CH₂ | (CH₂)₃CO₂H | (+)-pin | |
| 1633 | -S-(C=NH)NH₂ | 1 | PhCH₂CH₂ | CH₂CN₄H | (+)-pin | |
| 1634 | -S-(C=NH)NH₂ | 1 | PhCH₂CH₂ | (CH₂)₂CN₄H | (+)-pin | |
| 1635 | -S-(C=NH)NH₂ | 1 | PhCH₂CH₂ | (CH₂)₃CN₄H | (+)-pin | |
| 1636 | -S-(C=NH)NH₂ | 1 | PhCH₂CH₂ | CH₂NO₂ | (+)-pin | |
| 1637 | -S-(C=NH)NH₂ | 1 | PhCH₂CH₂ | (CH₂)₂NO₂ | (+)-pin | |
| 1638 | -S-(C=NH)NH₂ | 1 | PhCH₂CH₂ | (CH₂)₃NO₂ | (+)-pin | |
| 1639 | -S-(C=NH)NH₂ | 1 | PhCH₂CH₂ | CH₂OH | (+)-pin | |
| 1640 | -S-(C=NH)NH₂ | 1 | PhCH₂CH₂ | (CH₂)₂OH | (+)-pin | |
| 1641 | -S-(C=NH)NH₂ | 1 | PhCH₂CH₂ | (CH₂)₃OH | (+)-pin | |
| 1642 | -S-(C=NH)NH₂ | 1 | PhCH₂CH₂ | CH₂CO₂Me | (+)-pin | |
| 1643 | -S-(C=NH)NH₂ | 1 | PhCH₂CH₂ | (CH₂)₂CO₂Me | (+)-pin | |
| 1644 | -S-(C=NH)NH₂ | 1 | PhCH₂CH₂ | (CH₂)₃CO₂Me | (+)-pin | |
| 1645 | -S-(C=NH)NH₂ | 1 | PhCH₂CH₂ | Ph | (+)-pin | |
| 1646 | -S-(C=NH)NH₂ | 1 | PhCH₂CH₂ | PhCH₂ | (+)-pin | |
| 1647 | -S-(C=NH)NH₂ | 1 | PhCH₂CH₂ | Ph(CH₂)₂ | (+)-pin | |
| 1648 | -S-(C=NH)NH₂ | 1 | PhCH₂CH₂ | 3-NO₂-Ph | (+)-pin | |
| 1649 | -S-(C=NH)NH₂ | 1 | PhCH₂CH₂ | 4-NO₂-Ph | (+)-pin | |
| 1650 | -S-(C=NH)NH₂ | 1 | PhCH₂CH₂ | 3-CO₂H-Ph | (+)-pin | |
| 1651 | -S-(C=NH)NH₂ | 1 | PhCH₂CH₂ | 4-CO₂H-Ph | (+)-pin | |
| 1652 | -S-(C=NH)NH₂ | 1 | PhCH₂CH₂ | 3-CN₄H-Ph | (+)-pin | |
| 1653 | -S-(C=NH)NH₂ | 1 | PhCH₂CH₂ | 4-CN₄H-Ph | (+)-pin | |
| 1654 | -S-(C=NH)NH₂ | 1 | PhCH₂CH₂ | 3-(HOCH₂)-Ph | (+)-pin | |
| 1655 | -S-(C=NH)NH₂ | 1 | PhCH₂CH₂ | 4-(HOCH₂)-Ph | (+)-pin | |
| 1656 | -S-(C=NH)NH₂ | 1 | PhCH₂CH₂ | H | OH, OH | |
| 1657 | -S-(C=NH)NH₂ | 1 | PhCH₂CH₂ | Methyl | OH, OH | |
| 1658 | -S-(C=NH)NH₂ | 1 | PhCH₂CH₂ | Ethyl | OH, OH | |
| 1659 | -S-(C=NH)NH₂ | 1 | PhCH₂CH₂ | n-Propyl | OH, OH | |
| 1660 | -S-(C=NH)NH₂ | 1 | PhCH₂CH₂ | n-Butyl | OH, OH | |
| 1661 | -S-(C=NH)NH₂ | 1 | PhCH₂CH₂ | CH₂SCH₃ | OH, OH | |
| 1662 | -S-(C=NH)NH₂ | 1 | PhCH₂CH₂ | CH₂(SO)CH₃ | OH, OH | |
| 1663 | -S-(C=NH)NH₂ | 1 | PhCH₂CH₂ | CH₂(SO₂)CH₃ | OH, OH | |
| 1664 | -S-(C=NH)NH₂ | 1 | PhCH₂CH₂ | CH₂CH₂SCH₃ | OH, OH | |
| 1665 | -S-(C=NH)NH₂ | 1 | PhCH₂CH₂ | CH₂CH₂(SO)CH₃ | OH, OH | |
| 1666 | -S-(C=NH)NH₂ | 1 | PhCH₂CH₂ | CH₂CH₂(SO)₂CH₃ | OH, OH | |
| 1667 | -S-(C=NH)NH₂ | 1 | PhCH₂CH₂ | CH₂CN | OH, OH | |
| 1668 | -S-(C=NH)NH₂ | 1 | PhCH₂CH₂ | CH₂CH₂CN | OH, OH | |
| 1669 | -S-(C=NH)NH₂ | 1 | PhCH₂CH₂ | CH₂CH₂CH₂CN | OH, OH | |
| 1670 | -S-(C=NH)NH₂ | 1 | PhCH₂CH₂ | CF₃ | OH, OH | |
| 1671 | -S-(C=NH)NH₂ | 1 | PhCH₂CH₂ | CF₂CF₃ | OH, OH | |
| 1672 | -S-(C=NH)NH₂ | 1 | PhCH₂CH₂ | CF₂CF₂CF₃ | OH, OH | |
| 1673 | -S-(C=NH)NH₂ | 1 | PhCH₂CH₂ | CF₂CF₂CF₂CF₃ | OH, OH | |
| 1674 | -S-(C=NH)NH₂ | 1 | PhCH₂CH₂ | F₅-Ph | OH, OH | |
| 1675 | -S-(C=NH)NH₂ | 1 | PhCH₂CH₂ | CH₂CO₂H | OH, OH | |
| 1676 | -S-(C=NH)NH₂ | 1 | PhCH₂CH₂ | (CH₂)₂CO₂H | OH, OH | |
| 1677 | -S-(C=NH)NH₂ | 1 | PhCH₂CH₂ | (CH₂)₃CO₂H | OH, OH | |
| 1678 | -S-(C=NH)NH₂ | 1 | PhCH₂CH₂ | CH₂CN₄H | OH, OH | |
| 1679 | -S-(C=NH)NH₂ | 1 | PhCH₂CH₂ | (CH₂)₂CN₄H | OH, OH | |
| 1680 | -S-(C=NH)NH₂ | 1 | PhCH₂CH₂ | (CH₂)₃CN₄H | OH, OH | |

TABLE 14-continued

| Ex | X | m | R13 | R14 | Y1Y2 | Phys. Data |
|---|---|---|---|---|---|---|
| 1681 | —S—(C═NH)NH2 | 1 | PhCH2CH2 | CH2NO2 | OH, OH | |
| 1682 | —S—(C═NH)NH2 | 1 | PhCH2CH2 | (CH2)2NO2 | OH, OH | |
| 1683 | —S—(C═NH)NH2 | 1 | PhCH2CH2 | (CH2)3NO2 | OH, OH | |
| 1684 | —S—(C═NH)NH2 | 1 | PhCH2CH2 | CH2OH | OH, OH | |
| 1685 | —S—(C═NH)NH2 | 1 | PhCH2CH2 | (CH2)2OH | OH, OH | |
| 1686 | —S—(C═NH)NH2 | 1 | PhCH2CH2 | (CH2)3OH | OH, OH | |
| 1687 | —S—(C═NH)NH2 | 1 | PhCH2CH2 | CH2CO2Me | OH, OH | |
| 1688 | —S—(C═NH)NH2 | 1 | PhCH2CH2 | (CH2)2CO2Me | OH, OH | |
| 1689 | —S—(C═NH)NH2 | 1 | PhCH2CH2 | (CH2)3CO2Me | OH, OH | |
| 1690 | —S—(C═NH)NH2 | 1 | PhCH2CH2 | Ph | OH, OH | |
| 1691 | —S—(C═NH)NH2 | 1 | PhCH2CH2 | PhCH2 | OH, OH | |
| 1692 | —S—(C═NH)NH2 | 1 | PhCH2CH2 | Ph(CH2)2 | OH, OH | |
| 1693 | —S—(C═NH)NH2 | 1 | PhCH2CH2 | 3-NO2-Ph | OH, OH | |
| 1694 | —S—(C═NH)NH2 | 1 | PhCH2CH2 | 4-NO2-Ph | OH, OH | |
| 1695 | —S—(C═NH)NH2 | 1 | PhCH2CH2 | 3-CO2H-Ph | OH, OH | |
| 1696 | —S—(C═NH)NH2 | 1 | PhCH2CH2 | 4-CO2H-Ph | OH, OH | |
| 1697 | —S—(C═NH)NH2 | 1 | PhCH2CH2 | 3-CN4H-Ph | OH, OH | |
| 1698 | —S—(C═NH)NH2 | 1 | PhCH2CH2 | 4-CN4H-Ph | OH, OH | |
| 1699 | —S—(C═NH)NH2 | 1 | PhCH2CH2 | 3-(HOCH2)-Ph | OH, OH | |
| 1700 | —S—(C═NH)NH2 | 1 | PhCH2CH2 | 4-(HOCH2)-Ph | OH, OH | |
| 1701 | OMe | 1 | PhCH2CH2 | H | (+)-pin | |
| 1702 | OMe | 1 | PhCH2CH2 | Methyl | (+)-pin | |
| 1703 | OMe | 1 | PhCH2CH2 | Ethyl | (+)-pin | |
| 1704 | OMe | 1 | PhCH2CH2 | n-Propyl | (+)-pin | |
| 1705 | OMe | 1 | PhCH2CH2 | n-Butyl | (+)-pin | |
| 1706 | OMe | 1 | PhCH2CH2 | CH2SCH3 | (+)-pin | |
| 1707 | OMe | 1 | PhCH2CH2 | CH2(SO)CH3 | (+)-pin | |
| 1708 | OMe | 1 | PhCH2CH2 | CH2(SO2)CH3 | (+)-pin | |
| 1709 | OMe | 1 | PhCH2CH2 | CH2CH2SCH3 | (+)-pin | |
| 1710 | OMe | 1 | PhCH2CH2 | CH2CH2(SO)CH3 | (+)-pin | |
| 1711 | OMe | 1 | PhCH2CH2 | CH2CH2(SO)2CH3 | (+)-pin | |
| 1712 | OMe | 1 | PhCH2CH2 | CH2CN | (+)-pin | CR |
| 1713 | OMe | 1 | PhCH2CH2 | CH2CH2CN | (+)-pin | |
| 1714 | OMe | 1 | PhCH2CH2 | CH2CH2CH2CN | (+)-pin | |
| 1715 | OMe | 1 | PhCH2CH2 | CF3 | (+)-pin | |
| 1716 | OMe | 1 | PhCH2CH2 | CF2CF3 | (+)-pin | |
| 1717 | OMe | 1 | PhCH2CH2 | CF2CF2CF3 | (+)-pin | |
| 1718 | OMe | 1 | PhCH2CH2 | CF2CF2CF2CF3 | (+)-pin | |
| 1719 | OMe | 1 | PhCH2CH2 | F5-Ph | (+)-pin | |
| 1720 | OMe | 1 | PhCH2CH2 | CH2CO2H | (+)-pin | |
| 1721 | OMe | 1 | PhCH2CH2 | (CH2)2CO2H | (+)-pin | |
| 1722 | OMe | 1 | PhCH2CH2 | (CH2)3CO2H | (+)-pin | |
| 1723 | OMe | 1 | PhCH2CH2 | CH2CN4H | (+)-pin | |
| 1724 | OMe | 1 | PhCH2CH2 | (CH2)2CN4H | (+)-pin | |
| 1725 | OMe | 1 | PhCH2CH2 | (CH2)3CN4H | (+)-pin | |
| 1726 | OMe | 1 | PhCH2CH2 | CH2NO2 | (+)-pin | |
| 1727 | OMe | 1 | PhCH2CH2 | (CH2)2NO2 | (+)-pin | |
| 1728 | OMe | 1 | PhCH2CH2 | (CH2)3NO2 | (+)-pin | |
| 1729 | OMe | 1 | PhCH2CH2 | CH2OH | (+)-pin | |
| 1730 | OMe | 1 | PhCH2CH2 | (CH2)2OH | (+)-pin | |
| 1731 | OMe | 1 | PhCH2CH2 | (CH2)3OH | (+)-pin | |
| 1732 | OMe | 1 | PhCH2CH2 | CH2CO2Me | (+)-pin | |
| 1733 | OMe | 1 | PhCH2CH2 | (CH2)2CO2Me | (+)-pin | |
| 1734 | OMe | 1 | PhCH2CH2 | (CH2)3CO2Me | (+)-pin | |
| 1735 | OMe | 1 | PhCH2CH2 | Ph | (+)-pin | |
| 1736 | OMe | 1 | PhCH2CH2 | PhCH2 | (+)-pin | |
| 1737 | OMe | 1 | PhCH2CH2 | Ph(CH2)2 | (+)-pin | |
| 1738 | OMe | 1 | PhCH2CH2 | 3-NO2-Ph | (+)-pin | |
| 1739 | OMe | 1 | PhCH2CH2 | 4-NO2-Ph | (+)-pin | |
| 1740 | OMe | 1 | PhCH2CH2 | 3-CO2H-Ph | (+)-pin | |
| 1741 | OMe | 1 | PhCH2CH2 | 4-CO2H-Ph | (+)-pin | |
| 1742 | OMe | 1 | PhCH2CH2 | 3-CN4H-Ph | (+)-pin | |
| 1743 | OMe | 1 | PhCH2CH2 | 4-CN4H-Ph | (+)-pin | |
| 1744 | OMe | 1 | PhCH2CH2 | 3-(HOCH2)-Ph | (+)-pin | |

TABLE 14-continued

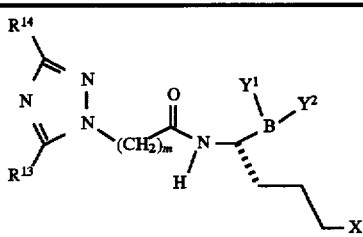

| Ex | X | m | R¹³ | R¹⁴ | Y¹Y² | Phys. Data |
|---|---|---|---|---|---|---|
| 1745 | OMe | 1 | PhCH₂CH₂ | 4-(HOCH₂)-Ph | (+)-pin | |
| 1746 | OMe | 1 | PhCH₂CH₂ | H | OH, OH | |
| 1747 | OMe | 1 | PhCH₂CH₂ | Methyl | OH, OH | |
| 1748 | OMe | 1 | PhCH₂CH₂ | Ethyl | OH, OH | |
| 1749 | OMe | 1 | PhCH₂CH₂ | n-Propyl | OH, OH | |
| 1750 | OMe | 1 | PhCH₂CH₂ | n-Butyl | OH, OH | |
| 1751 | OMe | 1 | PhCH₂CH₂ | CH₂SCH₃ | OH, OH | |
| 1752 | OMe | 1 | PhCH₂CH₂ | CH₂(SO)CH₃ | OH, OH | |
| 1753 | OMe | 1 | PhCH₂CH₂ | CH₂(SO₂)CH₃ | OH, OH | |
| 1754 | OMe | 1 | PhCH₂CH₂ | CH₂CH₂SCH₃ | OH, OH | |
| 1755 | OMe | 1 | PhCH₂CH₂ | CH₂CH₂(SO)CH₃ | OH, OH | |
| 1756 | OMe | 1 | PhCH₂CH₂ | CH₂CH₂(SO)₂CH₃ | OH, OH | |
| 1757 | OMe | 1 | PhCH₂CH₂ | CH₂CN | OH, OH | |
| 1758 | OMe | 1 | PhCH₂CH₂ | CH₂CH₂CN | OH, OH | |
| 1759 | OMe | 1 | PhCH₂CH₂ | CH₂CH₂CH₂CN | OH, OH | |
| 1760 | OMe | 1 | PhCH₂CH₂ | CF₃ | OH, OH | |
| 1761 | OMe | 1 | PhCH₂CH₂ | CF₂CF₃ | OH, OH | |
| 1762 | OMe | 1 | PhCH₂CH₂ | CF₂CF₂CF₃ | OH, OH | |
| 1763 | OMe | 1 | PhCH₂CH₂ | CF₂CF₂CF₂CF₃ | OH, OH | |
| 1764 | OMe | 1 | PhCH₂CH₂ | F₅-Ph | OH, OH | |
| 1765 | OMe | 1 | PhCH₂CH₂ | CH₂CO₂H | OH, OH | |
| 1766 | OMe | 1 | PhCH₂CH₂ | (CH₂)₂CO₂H | OH, OH | |
| 1767 | OMe | 1 | PhCH₂CH₂ | (CH₂)₃CO₂H | OH, OH | |
| 1768 | OMe | 1 | PhCH₂CH₂ | CH₂CN₄H | OH, OH | |
| 1769 | OMe | 1 | PhCH₂CH₂ | (CH₂)₂CN₄H | OH, OH | |
| 1770 | OMe | 1 | PhCH₂CH₂ | (CH₂)₃CN₄H | OH, OH | |
| 1771 | OMe | 1 | PhCH₂CH₂ | CH₂NO₂ | OH, OH | |
| 1772 | OMe | 1 | PhCH₂CH₂ | (CH₂)₂NO₂ | OH, OH | |
| 1773 | OMe | 1 | PhCH₂CH₂ | (CH₂)₃NO₂ | OH, OH | |
| 1774 | OMe | 1 | PhCH₂CH₂ | CH₂OH | OH, OH | |
| 1775 | OMe | 1 | PhCH₂CH₂ | (CH₂)₂OH | OH, OH | |
| 1776 | OMe | 1 | PhCH₂CH₂ | (CH₂)₃OH | OH, OH | |
| 1777 | OMe | 1 | PhCH₂CH₂ | CH₂CO₂Me | OH, OH | |
| 1778 | OMe | 1 | PhCH₂CH₂ | (CH₂)₂CO₂Me | OH, OH | |
| 1779 | OMe | 1 | PhCH₂CH₂ | (CH₂)₃CO₂Me | OH, OH | |
| 1780 | OMe | 1 | PhCH₂CH₂ | Ph | OH, OH | |
| 1781 | OMe | 1 | PhCH₂CH₂ | PhCH₂ | OH, OH | |
| 1782 | OMe | 1 | PhCH₂CH₂ | Ph(CH₂)₂ | OH, OH | |
| 1783 | OMe | 1 | PhCH₂CH₂ | 3-NO₂-Ph | OH, OH | |
| 1784 | OMe | 1 | PhCH₂CH₂ | 4-NO₂-Ph | OH, OH | |
| 1785 | OMe | 1 | PhCH₂CH₂ | 3-CO₂H-Ph | OH, OH | |
| 1786 | OMe | 1 | PhCH₂CH₂ | 4-CO₂H-Ph | OH, OH | |
| 1787 | OMe | 1 | PhCH₂CH₂ | 3-CN₄H-Ph | OH, OH | |
| 1788 | OMe | 1 | PhCH₂CH₂ | 4-CN₄H-Ph | OH, OH | |
| 1789 | OMe | 1 | PhCH₂CH₂ | 3-(HOCH₂)-Ph | OH, OH | |
| 1790 | OMe | 1 | PhCH₂CH₂ | 4-(HOCH₂)-Ph | OH, OH | |
| 1791 | NH(C=NH)H | 1 | Ph | H | (+)-pin | |
| 1792 | NH(C=NH)H | 1 | Ph | Methyl | (+)-pin | |
| 1793 | NH(C=NH)H | 1 | Ph | Ethyl | (+)-pin | |
| 1794 | NH(C=NH)H | 1 | Ph | n-Propyl | (+)-pin | |
| 1795 | NH(C=NH)H | 1 | Ph | n-Butyl | (+)-pin | |
| 1796 | NH(C=NH)H | 1 | Ph | CH₂SCH₃ | (+)-pin | |
| 1797 | NH(C=NH)H | 1 | Ph | CH₂(SO)CH₃ | (+)-pin | |
| 1798 | NH(C=NH)H | 1 | Ph | CH₂(SO₂)CH₃ | (+)-pin | |
| 1799 | NH(C=NH)H | 1 | Ph | CH₂CH₂SCH₃ | (+)-pin | |
| 1800 | NH(C=NH)H | 1 | Ph | CH₂CH₂(SO)CH₃ | (+)-pin | |
| 1801 | NH(C=NH)H | 1 | Ph | CH₂CH₂(SO)₂CH₃ | (+)-pin | |
| 1802 | NH(C=NH)H | 1 | Ph | CH₂CN | (+)-pin | |
| 1803 | NH(C=NH)H | 1 | Ph | CH₂CH₂CN | (+)-pin | |
| 1804 | NH(C=NH)H | 1 | Ph | CH₂CH₂CH₂CN | (+)-pin | |
| 1805 | NH(C=NH)H | 1 | Ph | CF₃ | (+)-pin | |
| 1806 | NH(C=NH)H | 1 | Ph | CF₂CF₃ | (+)-pin | |
| 1807 | NH(C=NH)H | 1 | Ph | CF₂CF₂CF₃ | (+)-pin | |
| 1808 | NH(C=NH)H | 1 | Ph | CF₂CF₂CF₂CF₃ | (+)-pin | |

TABLE 14-continued

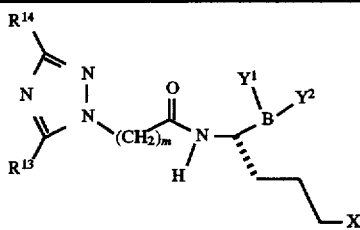

| Ex | X | m | R[13] | R[14] | Y[1]Y[2] | Phys. Data |
|---|---|---|---|---|---|---|
| 1809 | NH(C=NH)H | 1 | Ph | F$_5$-Ph | (+)-pin | |
| 1810 | NH(C=NH)H | 1 | Ph | CH$_2$CO$_2$H | (+)-pin | |
| 1811 | NH(C=NH)H | 1 | Ph | (CH$_2$)$_2$CO$_2$H | (+)-pin | |
| 1812 | NH(C=NH)H | 1 | Ph | (CH$_2$)$_3$CO$_2$H | (+)-pin | |
| 1813 | NH(C=NH)H | 1 | Ph | CH$_2$CN$_4$H | (+)-pin | |
| 1814 | NH(C=NH)H | 1 | Ph | (CH$_2$)$_2$CN$_4$H | (+)-pin | |
| 1815 | NH(C=NH)H | 1 | Ph | (CH$_2$)$_3$CN$_4$H | (+)-pin | |
| 1816 | NH(C=NH)H | 1 | Ph | CH$_2$NO$_2$ | (+)-pin | |
| 1817 | NH(C=NH)H | 1 | Ph | (CH$_2$)$_2$NO$_2$ | (+)-pin | |
| 1818 | NH(C=NH)H | 1 | Ph | (CH$_2$)$_3$NO$_2$ | (+)-pin | |
| 1819 | NH(C=NH)H | 1 | Ph | CH$_2$OH | (+)-pin | |
| 1820 | NH(C=NH)H | 1 | Ph | (CH$_2$)$_2$OH | (+)-pin | |
| 1821 | NH(C=NH)H | 1 | Ph | (CH$_2$)$_3$OH | (+)-pin | |
| 1822 | NH(C=NH)H | 1 | Ph | CH$_2$CO$_2$Me | (+)-pin | |
| 1823 | NH(C=NH)H | 1 | Ph | (CH$_2$)$_2$CO$_2$Me | (+)-pin | |
| 1824 | NH(C=NH)H | 1 | Ph | (CH$_2$)$_3$CO$_2$Me | (+)-pin | |
| 1825 | NH(C=NH)H | 1 | Ph | Ph | (+)-pin | |
| 1826 | NH(C=NH)H | 1 | Ph | PhCH$_2$ | (+)-pin | |
| 1827 | NH(C=NH)H | 1 | Ph | Ph(CH$_2$)$_2$ | (+)-pin | |
| 1828 | NH(C=NH)H | 1 | Ph | 3-NO$_2$-Ph | (+)-pin | |
| 1829 | NH(C=NH)H | 1 | Ph | 4-NO$_2$-Ph | (+)-pin | |
| 1830 | NH(C=NH)H | 1 | Ph | 3-CO$_2$H-Ph | (+)-pin | |
| 1831 | NH(C=NH)H | 1 | Ph | 4-CO$_2$H-Ph | (+)-pin | |
| 1832 | NH(C=NH)H | 1 | Ph | 3-CN$_4$H-Ph | (+)-pin | |
| 1833 | NH(C=NH)H | 1 | Ph | 4-CN$_4$H-Ph | (+)-pin | |
| 1834 | NH(C=NH)H | 1 | Ph | 3-(HOCH$_2$)-Ph | (+)-pin | |
| 1835 | NH(C=NH)H | 1 | Ph | 4-(HOCH$_2$)-Ph | (+)-pin | |
| 1836 | NH(C=NH)H | 1 | Ph | H | OH, OH | |
| 1837 | NH(C=NH)H | 1 | Ph | Methyl | OH, OH | |
| 1838 | NH(C=NH)H | 1 | Ph | Ethyl | OH, OH | |
| 1839 | NH(C=NH)H | 1 | Ph | n-Propyl | OH, OH | |
| 1840 | NH(C=NH)H | 1 | Ph | n-Butyl | OH, OH | |
| 1841 | NH(C=NH)H | 1 | Ph | CH$_2$SCH$_3$ | OH, OH | |
| 1842 | NH(C=NH)H | 1 | Ph | CH$_2$(SO)CH$_3$ | OH, OH | |
| 1843 | NH(C=NH)H | 1 | Ph | CH$_2$(SO$_2$)CH$_3$ | OH, OH | |
| 1844 | NH(C=NH)H | 1 | Ph | CH$_2$CH$_2$SCH$_3$ | OH, OH | |
| 1845 | NH(C=NH)H | 1 | Ph | CH$_2$CH$_2$(SO)CH$_3$ | OH, OH | |
| 1846 | NH(C=NH)H | 1 | Ph | CH$_2$CH$_2$(SO)$_2$CH$_3$ | OH, OH | |
| 1847 | NH(C=NH)H | 1 | Ph | CH$_2$CN | OH, OH | |
| 1848 | NH(C=NH)H | 1 | Ph | CH$_2$CH$_2$CN | OH, OH | |
| 1849 | NH(C=NH)H | 1 | Ph | CH$_2$CH$_2$CH$_2$CN | OH, OH | |
| 1850 | NH(C=NH)H | 1 | Ph | CF$_3$ | OH, OH | |
| 1851 | NH(C=NH)H | 1 | Ph | CF$_2$CF$_3$ | OH, OH | |
| 1852 | NH(C=NH)H | 1 | Ph | CF$_2$CF$_2$CF$_3$ | OH, OH | |
| 1853 | NH(C=NH)H | 1 | Ph | CF$_2$CF$_2$CF$_2$CF$_3$ | OH, OH | |
| 1854 | NH(C=NH)H | 1 | Ph | F$_5$-Ph | OH, OH | |
| 1855 | NH(C=NH)H | 1 | Ph | CH$_2$CO$_2$H | OH, OH | |
| 1856 | NH(C=NH)H | 1 | Ph | (CH$_2$)$_2$CO$_2$H | OH, OH | |
| 1857 | NH(C=NH)H | 1 | Ph | (CH$_2$)$_3$CO$_2$H | OH, OH | |
| 1858 | NH(C=NH)H | 1 | Ph | CH$_2$CN$_4$H | OH, OH | |
| 1859 | NH(C=NH)H | 1 | Ph | (CH$_2$)$_2$CN$_4$H | OH, OH | |
| 1860 | NH(C=NH)H | 1 | Ph | (CH$_2$)$_3$CN$_4$H | OH, OH | |
| 1861 | NH(C=NH)H | 1 | Ph | CH$_2$NO$_2$ | OH, OH | |
| 1862 | NH(C=NH)H | 1 | Ph | (CH$_2$)$_2$NO$_2$ | OH, OH | |
| 1863 | NH(C=NH)H | 1 | Ph | (CH$_2$)$_3$NO$_2$ | OH, OH | |
| 1864 | NH(C=NH)H | 1 | Ph | CH$_2$OH | OH, OH | |
| 1865 | NH(C=NH)H | 1 | Ph | (CH$_2$)$_2$OH | OH, OH | |
| 1866 | NH(C=NH)H | 1 | Ph | (CH$_2$)$_3$OH | OH, OH | |
| 1867 | NH(C=NH)H | 1 | Ph | CH$_2$CO$_2$Me | OH, OH | |
| 1868 | NH(C=NH)H | 1 | Ph | (CH$_2$)$_2$CO$_2$Me | OH, OH | |
| 1869 | NH(C=NH)H | 1 | Ph | (CH$_2$)$_3$CO$_2$Me | OH, OH | |
| 1870 | NH(C=NH)H | 1 | Ph | Ph | OH, OH | |
| 1871 | NH(C=NH)H | 1 | Ph | PhCH$_2$ | OH, OH | |
| 1872 | NH(C=NH)H | 1 | Ph | Ph(CH$_2$)$_2$ | OH, OH | |

TABLE 14-continued

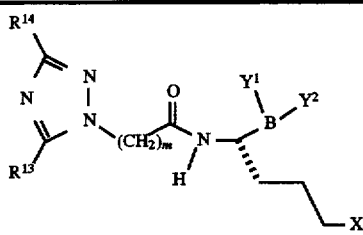

| Ex | X | m | R[13] | R[14] | Y[1]Y[2] | Phys. Data |
|---|---|---|---|---|---|---|
| 1873 | NH(C=NH)H | 1 | Ph | 3-NO$_2$-Ph | OH, OH | |
| 1874 | NH(C=NH)H | 1 | Ph | 4-NO$_2$-Ph | OH, OH | |
| 1875 | NH(C=NH)H | 1 | Ph | 3-CO$_2$H-Ph | OH, OH | |
| 1876 | NH(C=NH)H | 1 | Ph | 4-CO$_2$H-Ph | OH, OH | |
| 1877 | NH(C=NH)H | 1 | Ph | 3-CN$_4$H-Ph | OH, OH | |
| 1878 | NH(C=NH)H | 1 | Ph | 4-CN$_4$H-Ph | OH, OH | |
| 1879 | NH(C=NH)H | 1 | Ph | 3-(HOCH$_2$)-Ph | OH, OH | |
| 1880 | NH(C=NH)H | 1 | Ph | 4-(HOCH$_2$)-Ph | OH, OH | |
| 1881 | NH(C=NH)H | 1 | PhCH$_2$ | H | (+)-pin | |
| 1882 | NH(C=NH)H | 1 | PhCH$_2$ | Methyl | (+)-pin | |
| 1883 | NH(C=NH)H | 1 | PhCH$_2$ | Ethyl | (+)-pin | |
| 1884 | NH(C=NH)H | 1 | PhCH$_2$ | n-Propyl | (+)-pin | |
| 1885 | NH(C=NH)H | 1 | PhCH$_2$ | n-Butyl | (+)-pin | |
| 1886 | NH(C=NH)H | 1 | PhCH$_2$ | CH$_2$SCH$_3$ | (+)-pin | |
| 1887 | NH(C=NH)H | 1 | PhCH$_2$ | CH$_2$(SO)CH$_3$ | (+)-pin | |
| 1888 | NH(C=NH)H | 1 | PhCH$_2$ | CH$_2$(SO$_2$)CH$_3$ | (+)-pin | |
| 1889 | NH(C=NH)H | 1 | PhCH$_2$ | CH$_2$CH$_2$SCH$_3$ | (+)-pin | |
| 1890 | NH(C=NH)H | 1 | PhCH$_2$ | CH$_2$CH$_2$(SO)CH$_3$ | (+)-pin | |
| 1891 | NH(C=NH)H | 1 | PhCH$_2$ | CH$_2$CH$_2$(SO)$_2$CH$_3$ | (+)-pin | |
| 1892 | NH(C=NH)H | 1 | PhCH$_2$ | CH$_2$CN | (+)-pin | |
| 1893 | NH(C=NH)H | 1 | PhCH$_2$ | CH$_2$CH$_2$CN | (+)-pin | |
| 1894 | NH(C=NH)H | 1 | PhCH$_2$ | CH$_2$CH$_2$CH$_2$CN | (+)-pin | |
| 1895 | NH(C=NH)H | 1 | PhCH$_2$ | CF$_3$ | (+)-pin | |
| 1896 | NH(C=NH)H | 1 | PhCH$_2$ | CF$_2$CF$_3$ | (+)-pin | |
| 1897 | NH(C=NH)H | 1 | PhCH$_2$ | CF$_2$CF$_2$CF$_3$ | (+)-pin | |
| 1898 | NH(C=NH)H | 1 | PhCH$_2$ | CF$_2$CF$_2$CF$_2$CF$_3$ | (+)-pin | |
| 1899 | NH(C=NH)H | 1 | PhCH$_2$ | F$_5$-Ph | (+)-pin | |
| 1900 | NH(C=NH)H | 1 | PhCH$_2$ | CH$_2$CO$_2$H | (+)-pin | |
| 1901 | NH(C=NH)H | 1 | PhCH$_2$ | (CH$_2$)$_2$CO$_2$H | (+)-pin | |
| 1902 | NH(C=NH)H | 1 | PhCH$_2$ | (CH$_2$)$_3$CO$_2$H | (+)-pin | |
| 1903 | NH(C=NH)H | 1 | PhCH$_2$ | CH$_2$CN$_4$H | (+)-pin | |
| 1904 | NH(C=NH)H | 1 | PhCH$_2$ | (CH$_2$)$_2$CN$_4$H | (+)-pin | |
| 1905 | NH(C=NH)H | 1 | PhCH$_2$ | (CH$_2$)$_3$CN$_4$H | (+)-pin | |
| 1906 | NH(C=NH)H | 1 | PhCH$_2$ | CH$_2$NO$_2$ | (+)-pin | |
| 1907 | NH(C=NH)H | 1 | PhCH$_2$ | (CH$_2$)$_2$NO$_2$ | (+)-pin | |
| 1908 | NH(C=NH)H | 1 | PhCH$_2$ | (CH$_2$)$_3$NO$_2$ | (+)-pin | |
| 1909 | NH(C=NH)H | 1 | PhCH$_2$ | CH$_2$OH | (+)-pin | |
| 1910 | NH(C=NH)H | 1 | PhCH$_2$ | (CH$_2$)$_2$OH | (+)-pin | |
| 1911 | NH(C=NH)H | 1 | PhCH$_2$ | (CH$_2$)$_3$OH | (+)-pin | |
| 1912 | NH(C=NH)H | 1 | PhCH$_2$ | CH$_2$CO$_2$Me | (+)-pin | |
| 1913 | NH(C=NH)H | 1 | PhCH$_2$ | (CH$_2$)$_2$CO$_2$Me | (+)-pin | |
| 1914 | NH(C=NH)H | 1 | PhCH$_2$ | (CH$_2$)$_3$CO$_2$Me | (+)-pin | |
| 1915 | NH(C=NH)H | 1 | PhCH$_2$ | Ph | (+)-pin | |
| 1916 | NH(C=NH)H | 1 | PhCH$_2$ | PhCH$_2$ | (+)-pin | |
| 1917 | NH(C=NH)H | 1 | PhCH$_2$ | Ph(CH$_2$)$_2$ | (+)-pin | |
| 1918 | NH(C=NH)H | 1 | PhCH$_2$ | 3-NO$_2$-Ph | (+)-pin | |
| 1919 | NH(C=NH)H | 1 | PhCH$_2$ | 4-NO$_2$-Ph | (+)-pin | |
| 1920 | NH(C=NH)H | 1 | PhCH$_2$ | 3-CO$_2$H-Ph | (+)-pin | |
| 1921 | NH(C=NH)H | 1 | PhCH$_2$ | 4-CO$_2$H-Ph | (+)-pin | |
| 1922 | NH(C=NH)H | 1 | PhCH$_2$ | 3-CN$_4$H-Ph | (+)-pin | |
| 1923 | NH(C=NH)H | 1 | PhCH$_2$ | 4-CN$_4$H-Ph | (+)-pin | |
| 1924 | NH(C=NH)H | 1 | PhCH$_2$ | 3-(HOCH$_2$)-Ph | (+)-pin | |
| 1925 | NH(C=NH)H | 1 | PhCH$_2$ | 4-(HOCH$_2$)-Ph | (+)-pin | |
| 1926 | NH(C=NH)H | 1 | PhCH$_2$ | H | OH, OH | |
| 1927 | NH(C=NH)H | 1 | PhCH$_2$ | Methyl | OH, OH | |
| 1928 | NH(C=NH)H | 1 | PhCH$_2$ | Ethyl | OH, OH | |
| 1929 | NH(C=NH)H | 1 | PhCH$_2$ | n-Propyl | OH, OH | |
| 1930 | NH(C=NH)H | 1 | PhCH$_2$ | n-Butyl | OH, OH | |
| 1931 | NH(C=NH)H | 1 | PhCH$_2$ | CH$_2$SCH$_3$ | OH, OH | |
| 1932 | NH(C=NH)H | 1 | PhCH$_2$ | CH$_2$(SO)CH$_3$ | OH, OH | |
| 1933 | NH(C=NH)H | 1 | PhCH$_2$ | CH$_2$(SO$_2$)CH$_3$ | OH, OH | |
| 1934 | NH(C=NH)H | 1 | PhCH$_2$ | CH$_2$CH$_2$SCH$_3$ | OH, OH | |
| 1935 | NH(C=NH)H | 1 | PhCH$_2$ | CH$_2$CH$_2$(SO)CH$_3$ | OH, OH | |
| 1936 | NH(C=NH)H | 1 | PhCH$_2$ | CH$_2$CH$_2$(SO)$_2$CH$_3$ | OH, OH | |

TABLE 14-continued

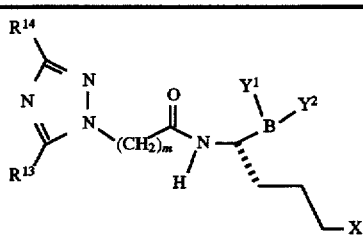

| Ex | X | m | R¹³ | R¹⁴ | Y¹Y² | Phys. Data |
|---|---|---|---|---|---|---|
| 1937 | NH(C=NH)H | 1 | PhCH₂ | CH₂CN | OH, OH | |
| 1938 | NH(C=NH)H | 1 | PhCH₂ | CH₂CH₂CN | OH, OH | |
| 1939 | NH(C=NH)H | 1 | PhCH₂ | CH₂CH₂CH₂CN | OH, OH | |
| 1940 | NH(C=NH)H | 1 | PhCH₂ | CF₃ | OH, OH | |
| 1941 | NH(C=NH)H | 1 | PhCH₂ | CF₂CF₃ | OH, OH | |
| 1942 | NH(C=NH)H | 1 | PhCH₂ | CF₂CF₂CF₃ | OH, OH | |
| 1943 | NH(C=NH)H | 1 | PhCH₂ | CF₂CF₂CF₂CF₃ | OH, OH | |
| 1944 | NH(C=NH)H | 1 | PhCH₂ | F₅-Ph | OH, OH | |
| 1945 | NH(C=NH)H | 1 | PhCH₂ | CH₂CO₂H | OH, OH | |
| 1946 | NH(C=NH)H | 1 | PhCH₂ | (CH₂)₂CO₂H | OH, OH | |
| 1947 | NH(C=NH)H | 1 | PhCH₂ | (CH₂)₃CO₂H | OH, OH | |
| 1948 | NH(C=NH)H | 1 | PhCH₂ | CH₂CN₄H | OH, OH | |
| 1949 | NH(C=NH)H | 1 | PhCH₂ | (CH₂)₂CN₄H | OH, OH | |
| 1950 | NH(C=NH)H | 1 | PhCH₂ | (CH₂)₃CN₄H | OH, OH | |
| 1951 | NH(C=NH)H | 1 | PhCH₂ | CH₂NO₂ | OH, OH | |
| 1952 | NH(C=NH)H | 1 | PhCH₂ | (CH₂)₂NO₂ | OH, OH | |
| 1953 | NH(C=NH)H | 1 | PhCH₂ | (CH₂)₃NO₂ | OH, OH | |
| 1954 | NH(C=NH)H | 1 | PhCH₂ | CH₂OH | OH, OH | |
| 1955 | NH(C=NH)H | 1 | PhCH₂ | (CH₂)₂OH | OH, OH | |
| 1956 | NH(C=NH)H | 1 | PhCH₂ | (CH₂)₃OH | OH, OH | |
| 1957 | NH(C=NH)H | 1 | PhCH₂ | CH₂CO₂Me | OH, OH | |
| 1958 | NH(C=NH)H | 1 | PhCH₂ | (CH₂)₂CO₂Me | OH, OH | |
| 1959 | NH(C=NH)H | 1 | PhCH₂ | (CH₂)₃CO₂Me | OH, OH | |
| 1960 | NH(C=NH)H | 1 | PhCH₂ | Ph | OH, OH | |
| 1961 | NH(C=NH)H | 1 | PhCH₂ | PhCH₂ | OH, OH | |
| 1962 | NH(C=NH)H | 1 | PhCH₂ | Ph(CH₂)₂ | OH, OH | |
| 1963 | NH(C=NH)H | 1 | PhCH₂ | 3-NO₂-Ph | OH, OH | |
| 1964 | NH(C=NH)H | 1 | PhCH₂ | 4-NO₂-Ph | OH, OH | |
| 1965 | NH(C=NH)H | 1 | PhCH₂ | 3-CO₂H-Ph | OH, OH | |
| 1966 | NH(C=NH)H | 1 | PhCH₂ | 4-CO₂H-Ph | OH, OH | |
| 1967 | NH(C=NH)H | 1 | PhCH₂ | 3-CN₄H-Ph | OH, OH | |
| 1968 | NH(C=NH)H | 1 | PhCH₂ | 4-CN₄H-Ph | OH, OH | |
| 1969 | NH(C=NH)H | 1 | PhCH₂ | 3-(HOCH₂)-Ph | OH, OH | |
| 1970 | NH(C=NH)H | 1 | PhCH₂ | 4-(HOCH₂)-Ph | OH, OH | |
| 1971 | NH(C=NH)H | 1 | PhCH₂CH₂ | H | (+)-pin | |
| 1972 | NH(C=NH)H | 1 | PhCH₂CH₂ | Methyl | (+)-pin | |
| 1973 | NH(C=NH)H | 1 | PhCH₂CH₂ | Ethyl | (+)-pin | |
| 1974 | NH(C=NH)H | 1 | PhCH₂CH₂ | n-Propyl | (+)-pin | |
| 1975 | NH(C=NH)H | 1 | PhCH₂CH₂ | n-Butyl | (+)-pin | |
| 1976 | NH(C=NH)H | 1 | PhCH₂CH₂ | CH₂SCH₃ | (+)-pin | |
| 1977 | NH(C=NH)H | 1 | PhCH₂CH₂ | CH₂(SO)CH₃ | (+)-pin | |
| 1978 | NH(C=NH)H | 1 | PhCH₂CH₂ | CH₂(SO₂)CH₃ | (+)-pin | |
| 1979 | NH(C=NH)H | 1 | PhCH₂CH₂ | CH₂CH₂SCH₃ | (+)-pin | |
| 1980 | NH(C=NH)H | 1 | PhCH₂CH₂ | CH₂CH₂(SO)CH₃ | (+)-pin | |
| 1981 | NH(C=NH)H | 1 | PhCH₂CH₂ | CH₂CH₂(SO)₂CH₃ | (+)-pin | |
| 1982 | NH(C=NH)H | 1 | PhCH₂CH₂ | CH₂CN | (+)-pin | |
| 1983 | NH(C=NH)H | 1 | PhCH₂CH₂ | CH₂CH₂CN | (+)-pin | |
| 1984 | NH(C=NH)H | 1 | PhCH₂CH₂ | CH₂CH₂CH₂CN | (+)-pin | |
| 1985 | NH(C=NH)H | 1 | PhCH₂CH₂ | CF₃ | (+)-pin | |
| 1986 | NH(C=NH)H | 1 | PhCH₂CH₂ | CF₂CF₃ | (+)-pin | |
| 1987 | NH(C=NH)H | 1 | PhCH₂CH₂ | CF₂CF₂CF₃ | (+)-pin | |
| 1988 | NH(C=NH)H | 1 | PhCH₂CH₂ | CF₂CF₂CF₂CF₃ | (+)-pin | |
| 1989 | NH(C=NH)H | 1 | PhCH₂CH₂ | F₅-Ph | (+)-pin | |
| 1990 | NH(C=NH)H | 1 | PhCH₂CH₂ | CH₂CO₂H | (+)-pin | |
| 1991 | NH(C=NH)H | 1 | PhCH₂CH₂ | (CH₂)₂CO₂H | (+)-pin | |
| 1992 | NH(C=NH)H | 1 | PhCH₂CH₂ | (CH₂)₃CO₂H | (+)-pin | |
| 1993 | NH(C=NH)H | 1 | PhCH₂CH₂ | CH₂CN₄H | (+)-pin | |
| 1994 | NH(C=NH)H | 1 | PhCH₂CH₂ | (CH₂)₂CN₄H | (+)-pin | |
| 1995 | NH(C=NH)H | 1 | PhCH₂CH₂ | (CH₂)₃CN₄H | (+)-pin | |
| 1996 | NH(C=NH)H | 1 | PhCH₂CH₂ | CH₂NO₂ | (+)-pin | |
| 1997 | NH(C=NH)H | 1 | PhCH₂CH₂ | (CH₂)₂NO₂ | (+)-pin | |
| 1998 | NH(C=NH)H | 1 | PhCH₂CH₂ | (CH₂)₃NO₂ | (+)-pin | |
| 1999 | NH(C=NH)H | 1 | PhCH₂CH₂ | CH₂OH | (+)-pin | |
| 2000 | NH(C=NH)H | 1 | PhCH₂CH₂ | (CH₂)₂OH | (+)-pin | |

TABLE 14-continued

| Ex | X | m | R¹³ | R¹⁴ | Y¹Y² | Phys. Data |
|---|---|---|---|---|---|---|
| 2001 | NH(C=NH)H | 1 | PhCH₂CH₂ | (CH₂)₃OH | (+)-pin | |
| 2002 | NH(C=NH)H | 1 | PhCH₂CH₂ | CH₂CO₂Me | (+)-pin | |
| 2003 | NH(C=NH)H | 1 | PhCH₂CH₂ | (CH₂)₂CO₂Me | (+)-pin | |
| 2004 | NH(C=NH)H | 1 | PhCH₂CH₂ | (CH₂)₃CO₂Me | (+)-pin | |
| 2005 | NH(C=NH)H | 1 | PhCH₂CH₂ | Ph | (+)-pin | |
| 2006 | NH(C=NH)H | 1 | PhCH₂CH₂ | PhCH₂ | (+)-pin | |
| 2007 | NH(C=NH)H | 1 | PhCH₂CH₂ | Ph(CH₂)₂ | (+)-pin | |
| 2008 | NH(C=NH)H | 1 | PhCH₂CH₂ | 3-NO₂-Ph | (+)-pin | |
| 2009 | NH(C=NH)H | 1 | PhCH₂CH₂ | 4-NO₂-Ph | (+)-pin | |
| 2010 | NH(C=NH)H | 1 | PhCH₂CH₂ | 3-CO₂H-Ph | (+)-pin | |
| 2011 | NH(C=NH)H | 1 | PhCH₂CH₂ | 4-CO₂H-Ph | (+)-pin | |
| 2012 | NH(C=NH)H | 1 | PhCH₂CH₂ | 3-CN₄H-Ph | (+)-pin | |
| 2013 | NH(C=NH)H | 1 | PhCH₂CH₂ | 4-CN₄H-Ph | (+)-pin | |
| 2014 | NH(C=NH)H | 1 | PhCH₂CH₂ | 3-(HOCH₂)-Ph | (+)-pin | |
| 2015 | NH(C=NH)H | 1 | PhCH₂CH₂ | 4-(HOCH₂)-Ph | (+)-pin | |
| 2016 | NH(C=NH)H | 1 | PhCH₂CH₂ | H | OH, OH | |
| 2017 | NH(C=NH)H | 1 | PhCH₂CH₂ | Methyl | OH, OH | |
| 2018 | NH(C=NH)H | 1 | PhCH₂CH₂ | Ethyl | OH, OH | |
| 2019 | NH(C=NH)H | 1 | PhCH₂CH₂ | n-Propyl | OH, OH | |
| 2020 | NH(C=NH)H | 1 | PhCH₂CH₂ | n-Butyl | OH, OH | |
| 2021 | NH(C=NH)H | 1 | PhCH₂CH₂ | CH₂SCH₃ | OH, OH | |
| 2022 | NH(C=NH)H | 1 | PhCH₂CH₂ | CH₂(SO)CH₃ | OH, OH | |
| 2023 | NH(C=NH)H | 1 | PhCH₂CH₂ | CH₂(SO₂)CH₃ | OH, OH | |
| 2024 | NH(C=NH)H | 1 | PhCH₂CH₂ | CH₂CH₂SCH₃ | OH, OH | |
| 2025 | NH(C=NH)H | 1 | PhCH₂CH₂ | CH₂CH₂(SO)CH₃ | OH, OH | |
| 2026 | NH(C=NH)H | 1 | PhCH₂CH₂ | CH₂CH₂(SO)₂CH₃ | OH, OH | |
| 2027 | NH(C=NH)H | 1 | PhCH₂CH₂ | CH₂CN | OH, OH | |
| 2028 | NH(C=NH)H | 1 | PhCH₂CH₂ | CH₂CH₂CN | OH, OH | |
| 2029 | NH(C=NH)H | 1 | PhCH₂CH₂ | CH₂CH₂CH₂CN | OH, OH | |
| 2030 | NH(C=NH)H | 1 | PhCH₂CH₂ | CF₃ | OH, OH | |
| 2031 | NH(C=NH)H | 1 | PhCH₂CH₂ | CF₂CF₃ | OH, OH | |
| 2032 | NH(C=NH)H | 1 | PhCH₂CH₂ | CF₂CF₂CF₃ | OH, OH | |
| 2033 | NH(C=NH)H | 1 | PhCH₂CH₂ | CF₂CF₂CF₂CF₃ | OH, OH | |
| 2034 | NH(C=NH)H | 1 | PhCH₂CH₂ | F₅-Ph | OH, OH | |
| 2035 | NH(C=NH)H | 1 | PhCH₂CH₂ | CH₂CO₂H | OH, OH | |
| 2036 | NH(C=NH)H | 1 | PhCH₂CH₂ | (CH₂)₂CO₂H | OH, OH | |
| 2037 | NH(C=NH)H | 1 | PhCH₂CH₂ | (CH₂)₃CO₂H | OH, OH | |
| 2038 | NH(C=NH)H | 1 | PhCH₂CH₂ | CH₂CN₄H | OH, OH | |
| 2039 | NH(C=NH)H | 1 | PhCH₂CH₂ | (CH₂)₂CN₄H | OH, OH | |
| 2040 | NH(C=NH)H | 1 | PhCH₂CH₂ | (CH₂)₃CN₄H | OH, OH | |
| 2041 | NH(C=NH)H | 1 | PhCH₂CH₂ | CH₂NO₂ | OH, OH | |
| 2042 | NH(C=NH)H | 1 | PhCH₂CH₂ | (CH₂)₂NO₂ | OH, OH | |
| 2043 | NH(C=NH)H | 1 | PhCH₂CH₂ | (CH₂)₃NO₂ | OH, OH | |
| 2044 | NH(C=NH)H | 1 | PhCH₂CH₂ | CH₂OH | OH, OH | |
| 2045 | NH(C=NH)H | 1 | PhCH₂CH₂ | (CH₂)₂OH | OH, OH | |
| 2046 | NH(C=NH)H | 1 | PhCH₂CH₂ | (CH₂)₃OH | OH, OH | |
| 2047 | NH(C=NH)H | 1 | PhCH₂CH₂ | CH₂CO₂Me | OH, OH | |
| 2048 | NH(C=NH)H | 1 | PhCH₂CH₂ | (CH₂)₂CO₂Me | OH, OH | |
| 2049 | NH(C=NH)H | 1 | PhCH₂CH₂ | (CH₂)₃CO₂Me | OH, OH | |
| 2050 | NH(C=NH)H | 1 | PhCH₂CH₂ | Ph | OH, OH | |
| 2051 | NH(C=NH)H | 1 | PhCH₂CH₂ | PhCH₂ | OH, OH | |
| 2052 | NH(C=NH)H | 1 | PhCH₂CH₂ | Ph(CH₂)₂ | OH, OH | |
| 2053 | NH(C=NH)H | 1 | PhCH₂CH₂ | 3-NO₂-Ph | OH, OH | |
| 2054 | NH(C=NH)H | 1 | PhCH₂CH₂ | 4-NO₂-Ph | OH, OH | |
| 2055 | NH(C=NH)H | 1 | PhCH₂CH₂ | 3-CO₂H-Ph | OH, OH | |
| 2056 | NH(C=NH)H | 1 | PhCH₂CH₂ | 4-CO₂H-Ph | OH, OH | |
| 2057 | NH(C=NH)H | 1 | PhCH₂CH₂ | 3-CN₄H-Ph | OH, OH | |
| 2058 | NH(C=NH)H | 1 | PhCH₂CH₂ | 4-CN₄H-Ph | OH, OH | |
| 2059 | NH(C=NH)H | 1 | PhCH₂CH₂ | 3-(HOCH₂)-Ph | OH, OH | |
| 2060 | NH(C=NH)H | 1 | PhCH₂CH₂ | 4-(HOCH₂)-Ph | OH, OH | |
| 2061 | CH₂NH₂ | 1 | PhCH₂ | 3-NO₂Ph | (+)-pin | CU |
| 2062 | NH(C=NH)NH₂ | 1 | Ph | PhCH₂ | (+)-pin | |
| 2063 | NH(C=NH)NH₂ | 1 | Ph | PhCH₂CH₂ | (+)-pin | |
| 2064 | —S—(C=NH)NH₂ | 1 | Ph | PhCH₂ | (+)-pin | |

TABLE 14-continued

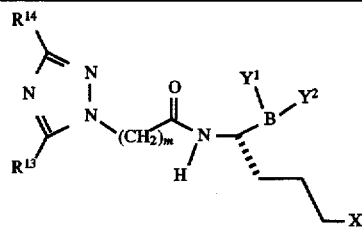

| Ex | X | m | R¹³ | R¹⁴ | Y¹Y² | Phys. Data |
|---|---|---|---|---|---|---|
| 2065 | —S—(C═NH)NH₂ | 1 | Ph | PhCH₂CH₂ | (+)-pin | |
| 2066 | CH₂NH₂ | 1 | PhCH₂ | CH₂CN | (+)-pin | CN |
| 2067 | CH₂NH₂ | 1 | PhCH₂ | CH₂CN₄H | (+)-pin | CO |
| 2068 | CH₂NH₂ | 1 | PhCH₂CH₂ | CH₂OCH₂Ph | (+)-pin | CT |

AG. Anal. calcd. for $C_{32}H_{42}BN_5O_3 \cdot 0.7H_2O \cdot 17HCl$: 6, 61.00; H, 7.21; Cl, 9.56 N, 11.11. Found: C, 60.93; H, 7.20; Cl, 9.57 N, 11.55.
AH. Anal. calcd. for $C_{22}H_{28}BN_5O_3 \cdot 12H_2O \cdot 2.6HCl$: C, 36.09; Cl., 12.59; N, 9.56. Found: C, 36.25; Cl, 12.52; N, 9.32.
AI. Anal. calcd. for $C_{16}H_{24}BN_5O_3 \cdot 1.5H_2O \cdot 1.8HCl$: C, 43.89; H, 6.63; Cl, 14.57; N, 16.06. Found: C, 44.01; H, 6.28; Cl, 14.21; N, 15.59.
AJ. Anal. calcd. for $C_{25}H_{34}BN_5O_3 \cdot 2H_2O \cdot 1.6HCl$: C, 53.84; H, 7.16; Cl, 10.17; N, 12.56. Found: C, 53.71; H, 7.13; Cl, 10.25; N, 12.60.
AK. MS (M+H)⁺: Calc. 480, Found 480.
AL. MS (M+H)⁺: Calc. 494, Found 494.
AM. MS (M+H)⁺: Calc. 522, Found 522.
AN. MS (M+H)⁺: Calc. 540, Found 540.
AO. MS (M+H)⁺: Calc. 510, Found 510.
AP. MS (M+H)⁺: Calc. 600, Found 600.
AQ. MS (M+H)⁺: Calc. 556, Found 556.
AR. MS (M+H)⁺: Calc. 570, Found 570.
AS. MS (M+H)⁺: Calc. 601, Found 601.
AT. MS (M+H)⁺: Calc. 598, Found 598.
AU. MS (M+H)⁺: Calc. 629, Found 629.
AV. MS (M+H)⁺: Calc. 422, Found 422.
AW. MS (M+H)⁺: Calc. 538, Found 538.
AX. MS (M+H)⁺: Calc. 494, Found 494.
AY. MS (M+H)⁺: Calc. 598, Found 598.
AZ. MS (M+H)⁺: Calc. 360, Found 360.
CN. MS (M+H)⁺: Calc. 519, Found 519.
CO. MS (M+H)⁺: Calc. 562, Found 562.
CP. MS (M+H)⁺: Calc. 552, Found 552.
CQ. MS (M+H)⁺: Calc. 571, Found 571.
CR. MS (M+H)⁺: Calc. 520, Found 520.
CS. MS (M+H)⁺: Calc. 524, Found 524.
CT. MS (M+H)⁺: Calc. 614, Found 614.
CU. MS (M+H)⁺: Calc. 571, Found 571.

TABLE 15

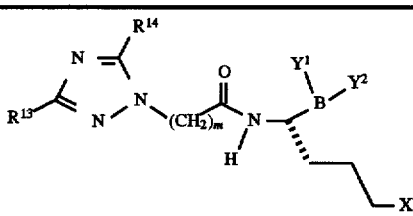

| Ex | X | m | R¹³ | R¹⁴ | Y¹Y² | Phys. Data |
|---|---|---|---|---|---|---|
| 2073 | CH₂NH₂ | 1 | Ph | H | (+)-pin | BW |
| 2074 | CH₂NH₂ | 1 | Ph | Methyl | (+)-pin | BX |
| 2075 | CH₂NH₂ | 1 | Ph | Ethyl | (+)-pin | |
| 2076 | CH₂NH₂ | 1 | Ph | n-Propyl | (+)-pin | |
| 2077 | CH₂NH₂ | 1 | Ph | n-Butyl | (+)-pin | |
| 2078 | CH₂NH₂ | 1 | Ph | CH₂SCH₃ | (+)-pin | |
| 2079 | CH₂NH₂ | 1 | Ph | CH₂(SO)CH₃ | (+)-pin | |
| 2080 | CH₂NH₂ | 1 | Ph | CH₂(SO₂)CH₃ | (+)-pin | |
| 2081 | CH₂NH₂ | 1 | Ph | CH₂CH₂SCH₃ | (+)-pin | |
| 2082 | CH₂NH₂ | 1 | Ph | CH₂CH₂(SO)CH₃ | (+)-pin | |

TABLE 15-continued

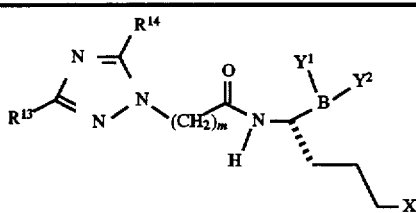

| Ex | X | m | R13 | R14 | Y1Y2 | Phys. Data |
|---|---|---|---|---|---|---|
| 2083 | CH2NH2 | 1 | Ph | CH2CH2(SO)2CH3 | (+)-pin | |
| 2084 | CH2NH2 | 1 | Ph | CH2CN | (+)-pin | |
| 2085 | CH2NH2 | 1 | Ph | CH2CH2CN | (+)-pin | |
| 2086 | CH2NH2 | 1 | Ph | CH2CH2CH2CN | (+)-pin | |
| 2087 | CH2NH2 | 1 | Ph | CF3 | (+)-pin | |
| 2088 | CH2NH2 | 1 | Ph | CF2CF3 | (+)-pin | |
| 2089 | CH2NH2 | 1 | Ph | CF2CF2CF3 | (+)-pin | |
| 2090 | CH2NH2 | 1 | Ph | CF2CF2CF2CF3 | (+)-pin | |
| 2091 | CH2NH2 | 1 | Ph | F5-Ph | (+)-pin | |
| 2092 | CH2NH2 | 1 | Ph | CH2CO2H | (+)-pin | |
| 2093 | CH2NH2 | 1 | Ph | (CH2)2CO2H | (+)-pin | |
| 2094 | CH2NH2 | 1 | Ph | (CH2)3CO2H | (+)-pin | |
| 2095 | CH2NH2 | 1 | Ph | CH2CN4H | (+)-pin | |
| 2096 | CH2NH2 | 1 | Ph | (CH2)2CN4H | (+)-pin | |
| 2097 | CH2NH2 | 1 | Ph | (CH2)3CN4H | (+)-pin | |
| 2098 | CH2NH2 | 1 | Ph | CH2NO2 | (+)-pin | |
| 2099 | CH2NH2 | 1 | Ph | (CH2)2NO2 | (+)-pin | |
| 2100 | CH2NH2 | 1 | Ph | (CH2)3NO2 | (+)-pin | |
| 2101 | CH2NH2 | 1 | Ph | CH2OH | (+)-pin | |
| 2102 | CH2NH2 | 1 | Ph | (CH2)2OH | (+)-pin | |
| 2103 | CH2NH2 | 1 | Ph | (CH2)3OH | (+)-pin | |
| 2104 | CH2NH2 | 1 | Ph | CH2CO2Me | (+)-pin | |
| 2105 | CH2NH2 | 1 | Ph | (CH2)2CO2Me | (+)-pin | |
| 2106 | CH2NH2 | 1 | Ph | (CH2)3CO2Me | (+)-pin | |
| 2107 | CH2NH2 | 1 | Ph | 3-NO2-Ph | (+)-pin | |
| 2108 | CH2NH2 | 1 | Ph | 4-NO2-Ph | (+)-pin | |
| 2109 | CH2NH2 | 1 | Ph | 3-CO2H-Ph | (+)-pin | |
| 2110 | CH2NH2 | 1 | Ph | 4-CO2H-Ph | (+)-pin | |
| 2111 | CH2NH2 | 1 | Ph | 3-CN4H-Ph | (+)-pin | |
| 2112 | CH2NH2 | 1 | Ph | 4-CN4H-Ph | (+)-pin | |
| 2113 | CH2NH2 | 1 | Ph | 3-(HOCH2)-Ph | (+)-pin | |
| 2114 | CH2NH2 | 1 | Ph | 4-(HOCH2)-Ph | (+)-pin | |
| 2115 | NH(C=NH)NH2 | 1 | Ph | H | (+)-pin | |
| 2116 | NH(C=NH)NH2 | 1 | Ph | Methyl | (+)-pin | |
| 2117 | NH(C=NH)NH2 | 1 | Ph | Ethyl | (+)-pin | |
| 2118 | NH(C=NH)NH2 | 1 | Ph | n-Propyl | (+)-pin | |
| 2119 | NH(C=NH)NH2 | 1 | Ph | n-Butyl | (+)-pin | |
| 2120 | NH(C=NH)NH2 | 1 | Ph | CH2SCH3 | (+)-pin | |
| 2121 | NH(C=NH)NH2 | 1 | Ph | CH2(SO)CH3 | (+)-pin | |
| 2122 | NH(C=NH)NH2 | 1 | Ph | CH2(SO2)CH3 | (+)-pin | |
| 2123 | NH(C=NH)NH2 | 1 | Ph | CH2CH2SCH3 | (+)-pin | |
| 2124 | NH(C=NH)NH2 | 1 | Ph | CH2CH2(SO)CH3 | (+)-pin | |
| 2125 | NH(C=NH)NH2 | 1 | Ph | CH2CH2(SO)2CH3 | (+)-pin | |
| 2126 | NH(C=NH)NH2 | 1 | Ph | CH2CN | (+)-pin | |
| 2127 | NH(C=NH)NH2 | 1 | Ph | CH2CH2CN | (+)-pin | |
| 2128 | NH(C=NH)NH2 | 1 | Ph | CH2CH2CH2CN | (+)-pin | |
| 2129 | NH(C=NH)NH2 | 1 | Ph | CF3 | (+)-pin | |
| 2130 | NH(C=NH)NH2 | 1 | Ph | CF2CF3 | (+)-pin | |
| 2131 | NH(C=NH)NH2 | 1 | Ph | CF2CF2CF3 | (+)-pin | |
| 2132 | NH(C=NH)NH2 | 1 | Ph | CF2CF2CF2CF3 | (+)-pin | |
| 2133 | NH(C=NH)NH2 | 1 | Ph | F5-Ph | (+)-pin | |
| 2134 | NH(C=NH)NH2 | 1 | Ph | CH2CO2H | (+)-pin | |
| 2135 | NH(C=NH)NH2 | 1 | Ph | (CH2)2CO2H | (+)-pin | |
| 2136 | NH(C=NH)NH2 | 1 | Ph | (CH2)3CO2H | (+)-pin | |
| 2137 | NH(C=NH)NH2 | 1 | Ph | CH2CN4H | (+)-pin | |
| 2138 | NH(C=NH)NH2 | 1 | Ph | (CH2)2CN4H | (+)-pin | |
| 2139 | NH(C=NH)NH2 | 1 | Ph | (CH2)3CN4H | (+)-pin | |
| 2140 | NH(C=NH)NH2 | 1 | Ph | CH2NO2 | (+)-pin | |
| 2141 | NH(C=NH)NH2 | 1 | Ph | (CH2)2NO2 | (+)-pin | |
| 2142 | NH(C=NH)NH2 | 1 | Ph | (CH2)3NO2 | (+)-pin | |
| 2143 | NH(C=NH)NH2 | 1 | Ph | CH2OH | (+)-pin | |
| 2144 | NH(C=NH)NH2 | 1 | Ph | (CH2)2OH | (+)-pin | |
| 2145 | NH(C=NH)NH2 | 1 | Ph | (CH2)3OH | (+)-pin | |
| 2146 | NH(C=NH)NH2 | 1 | Ph | CH2CO2Me | (+)-pin | |
| 2147 | NH(C=NH)NH2 | 1 | Ph | (CH2)2CO2Me | (+)-pin | |

TABLE 15-continued

| Ex | X | m | R¹³ | R¹⁴ | Y¹Y² | Phys. Data |
|---|---|---|---|---|---|---|
| 2148 | NH(C=NH)NH₂ | 1 | Ph | (CH₂)₃CO₂Me | (+)-pin | |
| 2149 | NH(C=NH)NH₂ | 1 | Ph | 3-NO₂-Ph | (+)-pin | |
| 2150 | NH(C=NH)NH₂ | 1 | Ph | 4-NO₂-Ph | (+)-pin | |
| 2151 | NH(C=NH)NH₂ | 1 | Ph | 3-CO₂H-Ph | (+)-pin | |
| 2152 | NH(C=NH)NH₂ | 1 | Ph | 4-CO₂H-Ph | (+)-pin | |
| 2153 | NH(C=NH)NH₂ | 1 | Ph | 3-CN₄H-Ph | (+)-pin | |
| 2154 | NH(C=NH)NH₂ | 1 | Ph | 4-CN₄H-Ph | (+)-pin | |
| 2155 | NH(C=NH)NH₂ | 1 | Ph | 3-(HOCH₂)-Ph | (+)-pin | |
| 2156 | NH(C=NH)NH₂ | 1 | Ph | 4-(HOCH₂)-Ph | (+)-pin | |
| 2157 | CH₂NH₂ | 1 | Ph | H | OH, OH | |
| 2158 | CH₂NH₂ | 1 | Ph | Methyl | OH, OH | |
| 2159 | CH₂NH₂ | 1 | Ph | Ethyl | OH, OH | |
| 2160 | CH₂NH₂ | 1 | Ph | n-Propyl | OH, OH | |
| 2161 | CH₂NH₂ | 1 | Ph | n-Butyl | OH, OH | |
| 2162 | CH₂NH₂ | 1 | Ph | CH₂SCH₃ | OH, OH | |
| 2163 | CH₂NH₂ | 1 | Ph | CH₂(SO)CH₃ | OH, OH | |
| 2164 | CH₂NH₂ | 1 | Ph | CH₂(SO₂)CH₃ | OH, OH | |
| 2165 | CH₂NH₂ | 1 | Ph | CH₂CH₂SCH₃ | OH, OH | |
| 2166 | CH₂NH₂ | 1 | Ph | CH₂CH₂(SO)CH₃ | OH, OH | |
| 2167 | CH₂NH₂ | 1 | Ph | CH₂CH₂(SO)₂CH₃ | OH, OH | |
| 2168 | CH₂NH₂ | 1 | Ph | CH₂CN | OH, OH | |
| 2169 | CH₂NH₂ | 1 | Ph | CH₂CH₂CN | OH, OH | |
| 2170 | CH₂NH₂ | 1 | Ph | CH₂CH₂CH₂CN | OH, OH | |
| 2171 | CH₂NH₂ | 1 | Ph | CF₃ | OH, OH | |
| 2172 | CH₂NH₂ | 1 | Ph | CF₂CF₃ | OH, OH | |
| 2173 | CH₂NH₂ | 1 | Ph | CF₂CF₂CF₃ | OH, OH | |
| 2174 | CH₂NH₂ | 1 | Ph | CF₂CF₂CF₂CF₃ | OH, OH | |
| 2175 | CH₂NH₂ | 1 | Ph | F₅-Ph | OH, OH | |
| 2176 | CH₂NH₂ | 1 | Ph | CH₂CO₂H | OH, OH | |
| 2177 | CH₂NH₂ | 1 | Ph | (CH₂)₂CO₂H | OH, OH | |
| 2178 | CH₂NH₂ | 1 | Ph | (CH₂)₃CO₂H | OH, OH | |
| 2179 | CH₂NH₂ | 1 | Ph | CH₂CN₄H | OH, OH | |
| 2180 | CH₂NH₂ | 1 | Ph | (CH₂)₂CN₄H | OH, OH | |
| 2181 | CH₂NH₂ | 1 | Ph | (CH₂)₃CN₄H | OH, OH | |
| 2182 | CH₂NH₂ | 1 | Ph | CH₂NO₂ | OH, OH | |
| 2183 | CH₂NH₂ | 1 | Ph | (CH₂)₂NO₂ | OH, OH | |
| 2184 | CH₂NH₂ | 1 | Ph | (CH₂)₃NO₂ | OH, OH | |
| 2185 | CH₂NH₂ | 1 | Ph | CH₂OH | OH, OH | |
| 2186 | CH₂NH₂ | 1 | Ph | (CH₂)₂OH | OH, OH | |
| 2187 | CH₂NH₂ | 1 | Ph | (CH₂)₃OH | OH, OH | |
| 2188 | CH₂NH₂ | 1 | Ph | CH₂CO₂Me | OH, OH | |
| 2189 | CH₂NH₂ | 1 | Ph | (CH₂)₂CO₂Me | OH, OH | |
| 2190 | CH₂NH₂ | 1 | Ph | (CH₂)₃CO₂Me | OH, OH | |
| 2191 | CH₂NH₂ | 1 | Ph | 3-NO₂-Ph | OH, OH | |
| 2192 | CH₂NH₂ | 1 | Ph | 4-NO₂-Ph | OH, OH | |
| 2193 | CH₂NH₂ | 1 | Ph | 3-CO₂H-Ph | OH, OH | |
| 2194 | CH₂NH₂ | 1 | Ph | 4-CO₂H-Ph | OH, OH | |
| 2195 | CH₂NH₂ | 1 | Ph | 3-CN₄H-Ph | OH, OH | |
| 2196 | CH₂NH₂ | 1 | Ph | 4-CN₄H-Ph | OH, OH | |
| 2197 | CH₂NH₂ | 1 | Ph | 3-(HOCH₂)-Ph | OH, OH | |
| 2198 | CH₂NH₂ | 1 | Ph | 4-(HOCH₂)-Ph | OH, OH | |
| 2199 | NH(C=NH)NH₂ | 1 | Ph | H | OH, OH | |
| 2200 | NH(C=NH)NH₂ | 1 | Ph | Methyl | OH, OH | |
| 2201 | NH(C=NH)NH₂ | 1 | Ph | Ethyl | OH, OH | |
| 2202 | NH(C=NH)NH₂ | 1 | Ph | n-Propyl | OH, OH | |
| 2203 | NH(C=NH)NH₂ | 1 | Ph | n-Butyl | OH, OH | |
| 2204 | NH(C=NH)NH₂ | 1 | Ph | CH₂SCH₃ | OH, OH | |
| 2205 | NH(C=NH)NH₂ | 1 | Ph | CH₂(SO)CH₃ | OH, OH | |
| 2206 | NH(C=NH)NH₂ | 1 | Ph | CH₂(SO₂)CH₃ | OH, OH | |
| 2207 | NH(C=NH)NH₂ | 1 | Ph | CH₂CH₂SCH₃ | OH, OH | |
| 2208 | NH(C=NH)NH₂ | 1 | Ph | CH₂CH₂(SO)CH₃ | OH, OH | |
| 2209 | NH(C=NH)NH₂ | 1 | Ph | CH₂CH₂(SO)₂CH₃ | OH, OH | |
| 2210 | NH(C=NH)NH₂ | 1 | Ph | CH₂CN | OH, OH | |
| 2211 | NH(C=NH)NH₂ | 1 | Ph | CH₂CH₂CN | OH, OH | |
| 2212 | NH(C=NH)NH₂ | 1 | Ph | CH₂CH₂CH₂CN | OH, OH | |

TABLE 15-continued

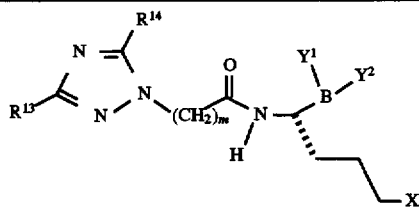

| Ex | X | m | R13 | R14 | Y1Y2 | Phys. Data |
|---|---|---|---|---|---|---|
| 2213 | NH(C=NH)NH2 | 1 | Ph | CF3 | OH, OH | |
| 2214 | NH(C=NH)NH2 | 1 | Ph | CF2CF3 | OH, OH | |
| 2215 | NH(C=NH)NH2 | 1 | Ph | CF2CF2CF3 | OH, OH | |
| 2216 | NH(C=NH)NH2 | 1 | Ph | CF2CF2CF2CF3 | OH, OH | |
| 2217 | NH(C=NH)NH2 | 1 | Ph | F5-Ph | OH, OH | |
| 2218 | NH(C=NH)NH2 | 1 | Ph | CH2CO2H | OH, OH | |
| 2219 | NH(C=NH)NH2 | 1 | Ph | (CH2)2CO2H | OH, OH | |
| 2220 | NH(C=NH)NH2 | 1 | Ph | (CH2)3CO2H | OH, OH | |
| 2221 | NH(C=NH)NH2 | 1 | Ph | CH2CN4H | OH, OH | |
| 2222 | NH(C=NH)NH2 | 1 | Ph | (CH2)2CN4H | OH, OH | |
| 2223 | NH(C=NH)NH2 | 1 | Ph | (CH2)3CN4H | OH, OH | |
| 2224 | NH(C=NH)NH2 | 1 | Ph | CH2NO2 | OH, OH | |
| 2225 | NH(C=NH)NH2 | 1 | Ph | (CH2)2NO2 | OH, OH | |
| 2226 | NH(C=NH)NH2 | 1 | Ph | (CH2)3NO2 | OH, OH | |
| 2227 | NH(C=NH)NH2 | 1 | Ph | CH2OH | OH, OH | |
| 2228 | NH(C=NH)NH2 | 1 | Ph | (CH2)2OH | OH, OH | |
| 2229 | NH(C=NH)NH2 | 1 | Ph | (CH2)3OH | OH, OH | |
| 2230 | NH(C=NH)NH2 | 1 | Ph | CH2CO2Me | OH, OH | |
| 2231 | NH(C=NH)NH2 | 1 | Ph | (CH2)2CO2Me | OH, OH | |
| 2232 | NH(C=NH)NH2 | 1 | Ph | (CH2)3CO2Me | OH, OH | |
| 2233 | NH(C=NH)NH2 | 1 | Ph | 3-NO2-Ph | OH, OH | |
| 2234 | NH(C=NH)NH2 | 1 | Ph | 4-NO2-Ph | OH, OH | |
| 2235 | NH(C=NH)NH2 | 1 | Ph | 3-CO2H-Ph | OH, OH | |
| 2236 | NH(C=NH)NH2 | 1 | Ph | 4-CO2H-Ph | OH, OH | |
| 2237 | NH(C=NH)NH2 | 1 | Ph | 3-CN4H-Ph | OH, OH | |
| 2238 | NH(C=NH)NH2 | 1 | Ph | 4-CN4H-Ph | OH, OH | |
| 2239 | NH(C=NH)NH2 | 1 | Ph | 3-(HOCH2)-Ph | OH, OH | |
| 2240 | NH(C=NH)NH2 | 1 | Ph | 4-(HOCH2)-Ph | OH, OH | |
| 2241 | —S—(C=NH)NH2 | 1 | Ph | H | (+)-pin | |
| 2242 | —S—(C=NH)NH2 | 1 | Ph | Methyl | (+)-pin | |
| 2243 | —S—(C=NH)NH2 | 1 | Ph | Ethyl | (+)-pin | |
| 2244 | —S—(C=NH)NH2 | 1 | Ph | n-Propyl | (+)-pin | |
| 2245 | —S—(C=NH)NH2 | 1 | Ph | n-Butyl | (+)-pin | |
| 2246 | —S—(C=NH)NH2 | 1 | Ph | CH2SCH3 | (+)-pin | |
| 2247 | —S—(C=NH)NH2 | 1 | Ph | CH2(SO)CH3 | (+)-pin | |
| 2248 | —S—(C=NH)NH2 | 1 | Ph | CH2(SO2)CH3 | (+)-pin | |
| 2249 | —S—(C=NH)NH2 | 1 | Ph | CH2CH2SCH3 | (+)-pin | |
| 2250 | —S—(C=NH)NH2 | 1 | Ph | CH2CH2(SO)CH3 | (+)-pin | |
| 2251 | —S—(C=NH)NH2 | 1 | Ph | CH2CH2(SO)2CH3 | (+)-pin | |
| 2252 | —S—(C=NH)NH2 | 1 | Ph | CH2CN | (+)-pin | |
| 2253 | —S—(C=NH)NH2 | 1 | Ph | CH2CH2CN | (+)-pin | |
| 2254 | —S—(C=NH)NH2 | 1 | Ph | CH2CH2CH2CN | (+)-pin | |
| 2255 | —S—(C=NH)NH2 | 1 | Ph | CF3 | (+)-pin | |
| 2256 | —S—(C=NH)NH2 | 1 | Ph | CF2CF3 | (+)-pin | |
| 2257 | —S—(C=NH)NH2 | 1 | Ph | CF2CF2CF3 | (+)-pin | |
| 2258 | —S—(C=NH)NH2 | 1 | Ph | CF2CF2CF2CF3 | (+)-pin | |
| 2259 | —S—(C=NH)NH2 | 1 | Ph | F5-Ph | (+)-pin | |
| 2260 | —S—(C=NH)NH2 | 1 | Ph | CH2CO2H | (+)-pin | |
| 2261 | —S—(C=NH)NH2 | 1 | Ph | (CH2)2CO2H | (+)-pin | |
| 2262 | —S—(C=NH)NH2 | 1 | Ph | (CH2)3CO2H | (+)-pin | |
| 2263 | —S—(C=NH)NH2 | 1 | Ph | CH2CN4H | (+)-pin | |
| 2264 | —S—(C=NH)NH2 | 1 | Ph | (CH2)2CN4H | (+)-pin | |
| 2265 | —S—(C=NH)NH2 | 1 | Ph | (CH2)3CN4H | (+)-pin | |
| 2266 | —S—(C=NH)NH2 | 1 | Ph | CH2NO2 | (+)-pin | |
| 2267 | —S—(C=NH)NH2 | 1 | Ph | (CH2)2NO2 | (+)-pin | |
| 2268 | —S—(C=NH)NH2 | 1 | Ph | (CH2)3NO2 | (+)-pin | |
| 2269 | —S—(C=NH)NH2 | 1 | Ph | CH2OH | (+)-pin | |
| 2270 | —S—(C=NH)NH2 | 1 | Ph | (CH2)2OH | (+)-pin | |
| 2271 | —S—(C=NH)NH2 | 1 | Ph | (CH2)3OH | (+)-pin | |
| 2272 | —S—(C=NH)NH2 | 1 | Ph | CH2CO2Me | (+)-pin | |
| 2273 | —S—(C=NH)NH2 | 1 | Ph | (CH2)2CO2Me | (+)-pin | |
| 2274 | —S—(C=NH)NH2 | 1 | Ph | (CH2)3CO2Me | (+)-pin | |
| 2275 | —S—(C=NH)NH2 | 1 | Ph | 3-NO2-Ph | (+)-pin | |
| 2276 | —S—(C=NH)NH2 | 1 | Ph | 4-NO2-Ph | (+)-pin | |
| 2277 | —S—(C=NH)NH2 | 1 | Ph | 3-CO2H-Ph | (+)-pin | |

TABLE 15-continued

| Ex | X | m | R13 | R14 | Y1Y2 | Phys. Data |
|---|---|---|---|---|---|---|
| 2278 | —S—(C=NH)NH2 | 1 | Ph | 4-CO2H-Ph | (+)-pin | |
| 2279 | —S—(C=NH)NH2 | 1 | Ph | 3-CN4H-Ph | (+)-pin | |
| 2280 | —S—(C=NH)NH2 | 1 | Ph | 4-CN4H-Ph | (+)-pin | |
| 2281 | —S—(C=NH)NH2 | 1 | Ph | 3-(HOCH2)-Ph | (+)-pin | |
| 2282 | —S—(C=NH)NH2 | 1 | Ph | 4-(HOCH2)-Ph | (+)-pin | |
| 2283 | —S—(C=NH)NH2 | 1 | Ph | H | OH, OH | |
| 2284 | —S—(C=NH)NH2 | 1 | Ph | Methyl | OH, OH | |
| 2285 | —S—(C=NH)NH2 | 1 | Ph | Ethyl | OH, OH | |
| 2286 | —S—(C=NH)NH2 | 1 | Ph | n-Propyl | OH, OH | |
| 2287 | —S—(C=NH)NH2 | 1 | Ph | n-Butyl | OH, OH | |
| 2288 | —S—(C=NH)NH2 | 1 | Ph | CH2SCH3 | OH, OH | |
| 2289 | —S—(C=NH)NH2 | 1 | Ph | CH2(SO)CH3 | OH, OH | |
| 2290 | —S—(C=NH)NH2 | 1 | Ph | CH2(SO2)CH3 | OH, OH | |
| 2291 | —S—(C=NH)NH2 | 1 | Ph | CH2CH2SCH3 | OH, OH | |
| 2292 | —S—(C=NH)NH2 | 1 | Ph | CH2CH2(SO)CH3 | OH, OH | |
| 2293 | —S—(C=NH)NH2 | 1 | Ph | CH2CH2(SO)2CH3 | OH, OH | |
| 2294 | —S—(C=NH)NH2 | 1 | Ph | CH2CN | OH, OH | |
| 2295 | —S—(C=NH)NH2 | 1 | Ph | CH2CH2CN | OH, OH | |
| 2296 | —S—(C=NH)NH2 | 1 | Ph | CH2CH2CH2CN | OH, OH | |
| 2297 | —S—(C=NH)NH2 | 1 | Ph | CF3 | OH, OH | |
| 2298 | —S—(C=NH)NH2 | 1 | Ph | CF2CF3 | OH, OH | |
| 2299 | —S—(C=NH)NH2 | 1 | Ph | CF2CF2CF3 | OH, OH | |
| 2300 | —S—(C=NH)NH2 | 1 | Ph | CF2CF2CF2CF3 | OH, OH | |
| 2301 | —S—(C=NH)NH2 | 1 | Ph | F5-Ph | OH, OH | |
| 2302 | —S—(C=NH)NH2 | 1 | Ph | CH2CO2H | OH, OH | |
| 2303 | —S—(C=NH)NH2 | 1 | Ph | (CH2)2CO2H | OH, OH | |
| 2304 | —S—(C=NH)NH2 | 1 | Ph | (CH2)3CO2H | OH, OH | |
| 2305 | —S—(C=NH)NH2 | 1 | Ph | CH2CN4H | OH, OH | |
| 2306 | —S—(C=NH)NH2 | 1 | Ph | (CH2)2CN4H | OH, OH | |
| 2307 | —S—(C=NH)NH2 | 1 | Ph | (CH2)3CN4H | OH, OH | |
| 2308 | —S—(C=NH)NH2 | 1 | Ph | CH2NO2 | OH, OH | |
| 2309 | —S—(C=NH)NH2 | 1 | Ph | (CH2)2NO2 | OH, OH | |
| 2310 | —S—(C=NH)NH2 | 1 | Ph | (CH2)3NO2 | OH, OH | |
| 2311 | —S—(C=NH)NH2 | 1 | Ph | CH2OH | OH, OH | |
| 2312 | —S—(C=NH)NH2 | 1 | Ph | (CH2)2OH | OH, OH | |
| 2313 | —S—(C=NH)NH2 | 1 | Ph | (CH2)3OH | OH, OH | |
| 2314 | —S—(C=NH)NH2 | 1 | Ph | CH2CO2Me | OH, OH | |
| 2315 | —S—(C=NH)NH2 | 1 | Ph | (CH2)2CO2Me | OH, OH | |
| 2316 | —S—(C=NH)NH2 | 1 | Ph | (CH2)3CO2Me | OH, OH | |
| 2317 | —S—(C=NH)NH2 | 1 | Ph | 3-NO2-Ph | OH, OH | |
| 2318 | —S—(C=NH)NH2 | 1 | Ph | 4-NO2-Ph | OH, OH | |
| 2319 | —S—(C=NH)NH2 | 1 | Ph | 3-CO2H-Ph | OH, OH | |
| 2320 | —S—(C=NH)NH2 | 1 | Ph | 4-CO2H-Ph | OH, OH | |
| 2321 | —S—(C=NH)NH2 | 1 | Ph | 3-CN4H-Ph | OH, OH | |
| 2322 | —S—(C=NH)NH2 | 1 | Ph | 4-CN4H-Ph | OH, OH | |
| 2323 | —S—(C=NH)NH2 | 1 | Ph | 3-(HOCH2)-Ph | OH, OH | |
| 2324 | —S—(C=NH)NH2 | 1 | Ph | 4-(HOCH2)-Ph | OH, OH | |
| 2325 | CH2NH2 | 2 | Ph | H | (+)-pin | |
| 2326 | CH2NH2 | 2 | Ph | H | OH, OH | |
| 2327 | OMe | 1 | Ph | H | (+)-pin | |
| 2328 | OMe | 1 | Ph | Methyl | (+)-pin | |
| 2329 | OMe | 1 | Ph | Ethyl | (+)-pin | |
| 2330 | OMe | 1 | Ph | n-Propyl | (+)-pin | |
| 2331 | OMe | 1 | Ph | n-Butyl | (+)-pin | |
| 2332 | OMe | 1 | Ph | CH2SCH3 | (+)-pin | |
| 2333 | OMe | 1 | Ph | CH2(SO)CH3 | (+)-pin | |
| 2334 | OMe | 1 | Ph | CH2(SO2)CH3 | (+)-pin | |
| 2335 | OMe | 1 | Ph | CH2CH2SCH3 | (+)-pin | |
| 2336 | OMe | 1 | Ph | CH2CH2(SO)CH3 | (+)-pin | |
| 2337 | OMe | 1 | Ph | CH2CH2(SO)2CH3 | (+)-pin | |
| 2338 | OMe | 1 | Ph | CH2CN | (+)-pin | |
| 2339 | OMe | 1 | Ph | CH2CH2CN | (+)-pin | |
| 2340 | OMe | 1 | Ph | CH2CH2CH2CN | (+)-pin | |
| 2341 | OMe | 1 | Ph | CF3 | (+)-pin | |
| 2342 | OMe | 1 | Ph | CF2CF3 | (+)-pin | |

TABLE 15-continued

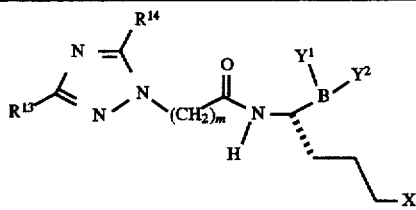

| Ex | X | m | R¹³ | R¹⁴ | Y¹Y² | Phys. Data |
|---|---|---|---|---|---|---|
| 2343 | OMe | 1 | Ph | CF₂CF₂CF₃ | (+)-pin | |
| 2344 | OMe | 1 | Ph | CF₂CF₂CF₂CF₃ | (+)-pin | |
| 2345 | OMe | 1 | Ph | F₅-Ph | (+)-pin | |
| 2346 | OMe | 1 | Ph | CH₂CO₂H | (+)-pin | |
| 2347 | OMe | 1 | Ph | (CH₂)₂CO₂H | (+)-pin | |
| 2348 | OMe | 1 | Ph | (CH₂)₃CO₂H | (+)-pin | |
| 2349 | OMe | 1 | Ph | CH₂CN₄H | (+)-pin | |
| 2350 | OMe | 1 | Ph | (CH₂)₂CN₄H | (+)-pin | |
| 2351 | OMe | 1 | Ph | (CH₂)₃CN₄H | (+)-pin | |
| 2352 | OMe | 1 | Ph | CH₂NO₂ | (+)-pin | |
| 2353 | OMe | 1 | Ph | (CH₂)₂NO₂ | (+)-pin | |
| 2354 | OMe | 1 | Ph | (CH₂)₃NO₂ | (+)-pin | |
| 2355 | OMe | 1 | Ph | CH₂OH | (+)-pin | |
| 2356 | OMe | 1 | Ph | (CH₂)₂OH | (+)-pin | |
| 2357 | OMe | 1 | Ph | (CH₂)₃OH | (+)-pin | |
| 2358 | OMe | 1 | Ph | CH₂CO₂Me | (+)-pin | |
| 2359 | OMe | 1 | Ph | (CH₂)₂CO₂Me | (+)-pin | |
| 2360 | OMe | 1 | Ph | (CH₂)₃CO₂Me | (+)-pin | |
| 2361 | OMe | 1 | Ph | 3-NO₂-Ph | (+)-pin | |
| 2362 | OMe | 1 | Ph | 4-NO₂-Ph | (+)-pin | |
| 2363 | OMe | 1 | Ph | 3-CO₂H-Ph | (+)-pin | |
| 2364 | OMe | 1 | Ph | 4-CO₂H-Ph | (+)-pin | |
| 2365 | OMe | 1 | Ph | 3-CN₄H-Ph | (+)-pin | |
| 2366 | OMe | 1 | Ph | 4-CN₄H-Ph | (+)-pin | |
| 2367 | OMe | 1 | Ph | 3-(HOCH₂)-Ph | (+)-pin | |
| 2368 | OMe | 1 | Ph | 4-(HOCH₂)-Ph | (+)-pin | |
| 2369 | OMe | 1 | Ph | H | OH, OH | |
| 2370 | OMe | 1 | Ph | Methyl | OH, OH | |
| 2371 | OMe | 1 | Ph | Ethyl | OH, OH | |
| 2372 | OMe | 1 | Ph | n-Propyl | OH, OH | |
| 2373 | OMe | 1 | Ph | n-Butyl | OH, OH | |
| 2374 | OMe | 1 | Ph | CH₂SCH₃ | OH, OH | |
| 2375 | OMe | 1 | Ph | CH₂(SO)CH₃ | OH, OH | |
| 2376 | OMe | 1 | Ph | CH₂(SO₂)CH₃ | OH, OH | |
| 2377 | OMe | 1 | Ph | CH₂CH₂SCH₃ | OH, OH | |
| 2378 | OMe | 1 | Ph | CH₂CH₂(SO)CH₃ | OH, OH | |
| 2379 | OMe | 1 | Ph | CH₂CH₂(SO)₂CH₃ | OH, OH | |
| 2380 | OMe | 1 | Ph | CH₂CN | OH, OH | |
| 2381 | OMe | 1 | Ph | CH₂CH₂CN | OH, OH | |
| 2382 | OMe | 1 | Ph | CH₂CH₂CH₂CN | OH, OH | |
| 2383 | OMe | 1 | Ph | CF₃ | OH, OH | |
| 2384 | OMe | 1 | Ph | CF₂CF₃ | OH, OH | |
| 2385 | OMe | 1 | Ph | CF₂CF₂CF₃ | OH, OH | |
| 2386 | OMe | 1 | Ph | CF₂CF₂CF₂CF₃ | OH, OH | |
| 2387 | OMe | 1 | Ph | F₅-Ph | OH, OH | |
| 2388 | OMe | 1 | Ph | CH₂CO₂H | OH, OH | |
| 2389 | OMe | 1 | Ph | (CH₂)₂CO₂H | OH, OH | |
| 2390 | OMe | 1 | Ph | (CH₂)₃CO₂H | OH, OH | |
| 2391 | OMe | 1 | Ph | CH₂CN₄H | OH, OH | |
| 2392 | OMe | 1 | Ph | (CH₂)₂CN₄H | OH, OH | |
| 2393 | OMe | 1 | Ph | (CH₂)₃CN₄H | OH, OH | |
| 2394 | OMe | 1 | Ph | CH₂NO₂ | OH, OH | |
| 2395 | OMe | 1 | Ph | (CH₂)₂NO₂ | OH, OH | |
| 2396 | OMe | 1 | Ph | (CH₂)₃NO₂ | OH, OH | |
| 2397 | OMe | 1 | Ph | CH₂OH | OH, OH | |
| 2398 | OMe | 1 | Ph | (CH₂)₂OH | OH, OH | |
| 2399 | OMe | 1 | Ph | (CH₂)₃OH | OH, OH | |
| 2400 | OMe | 1 | Ph | CH₂CO₂Me | OH, OH | |
| 2401 | OMe | 1 | Ph | (CH₂)₂CO₂Me | OH, OH | |
| 2402 | OMe | 1 | Ph | (CH₂)₃CO₂Me | OH, OH | |
| 2403 | OMe | 1 | Ph | 3-NO₂-Ph | OH, OH | |
| 2404 | OMe | 1 | Ph | 4-NO₂-Ph | OH, OH | |
| 2405 | OMe | 1 | Ph | 3-CO₂H-Ph | OH, OH | |
| 2406 | OMe | 1 | Ph | 4-CO₂H-Ph | OH, OH | |
| 2407 | OMe | 1 | Ph | 3-CN₄H-Ph | OH, OH | |

TABLE 15-continued

| Ex | X | m | R$^{13}$ | R$^{14}$ | Y$^1$Y$^2$ | Phys. Data |
|---|---|---|---|---|---|---|
| 2408 | OMe | 1 | Ph | 4-CN$_4$H-Ph | OH, OH | |
| 2409 | OMe | 1 | Ph | 3-(HOCH$_2$)-Ph | OH, OH | |
| 2410 | OMe | 1 | Ph | 4-(HOCH$_2$)-Ph | OH, OH | |
| 2411 | CH$_2$NH$_2$ | 1 | PhCH$_2$ | H | (+)-pin | BA |
| 2412 | CH$_2$NH$_2$ | 1 | PhCH$_2$ | Methyl | (+)-pin | BC |
| 2413 | CH$_2$NH$_2$ | 1 | PhCH$_2$ | Ethyl | (+)-pin | |
| 2414 | CH$_2$NH$_2$ | 1 | PhCH$_2$ | n-Propyl | (+)-pin | BD |
| 2415 | CH$_2$NH$_2$ | 1 | PhCH$_2$ | n-Butyl | (+)-pin | |
| 2416 | CH$_2$NH$_2$ | 1 | PhCH$_2$ | CH$_2$SCH$_3$ | (+)-pin | BE |
| 2417 | CH$_2$NH$_2$ | 1 | PhCH$_2$ | CH$_2$(SO)CH$_3$ | (+)-pin | |
| 2418 | CH$_2$NH$_2$ | 1 | PhCH$_2$ | CH$_2$(SO$_2$)CH$_3$ | (+)-pin | |
| 2419 | CH$_2$NH$_2$ | 1 | PhCH$_2$ | CH$_2$CH$_2$SCH$_3$ | (+)-pin | |
| 2420 | CH$_2$NH$_2$ | 1 | PhCH$_2$ | CH$_2$CH$_2$(SO)CH$_3$ | (+)-pin | |
| 2421 | CH$_2$NH$_2$ | 1 | PhCH$_2$ | CH$_2$CH$_2$(SO)$_2$CH$_3$ | (+)-pin | |
| 2422 | CH$_2$NH$_2$ | 1 | PhCH$_2$ | CH$_2$CN | (+)-pin | BF |
| 2423 | CH$_2$NH$_2$ | 1 | PhCH$_2$ | CH$_2$CH$_2$CN | (+)-pin | |
| 2424 | CH$_2$NH$_2$ | 1 | PhCH$_2$ | CH$_2$CH$_2$CH$_2$CN | (+)-pin | |
| 2425 | CH$_2$NH$_2$ | 1 | PhCH$_2$ | CF$_3$ | (+)-pin | |
| 2426 | CH$_2$NH$_2$ | 1 | PhCH$_2$ | CF$_2$CF$_3$ | (+)-pin | |
| 2427 | CH$_2$NH$_2$ | 1 | PhCH$_2$ | CF$_2$CF$_2$CF$_3$ | (+)-pin | |
| 2428 | CH$_2$NH$_2$ | 1 | PhCH$_2$ | CF$_2$CF$_2$CF$_2$CF$_3$ | (+)-pin | |
| 2429 | CH$_2$NH$_2$ | 1 | PhCH$_2$ | F$_5$-Ph | (+)-pin | |
| 2430 | CH$_2$NH$_2$ | 1 | PhCH$_2$ | CH$_2$CO$_2$H | (+)-pin | BG |
| 2431 | CH$_2$NH$_2$ | 1 | PhCH$_2$ | (CH$_2$)$_2$CO$_2$H | (+)-pin | |
| 2432 | CH$_2$NH$_2$ | 1 | PhCH$_2$ | (CH$_2$)$_3$CO$_2$H | (+)-pin | |
| 2433 | CH$_2$NH$_2$ | 1 | PhCH$_2$ | CH$_2$CN$_4$H | (+)-pin | |
| 2434 | CH$_2$NH$_2$ | 1 | PhCH$_2$ | (CH$_2$)$_2$CN$_4$H | (+)-pin | |
| 2435 | CH$_2$NH$_2$ | 1 | PhCH$_2$ | (CH$_2$)$_3$CN$_4$H | (+)-pin | |
| 2436 | CH$_2$NH$_2$ | 1 | PhCH$_2$ | CH$_2$NO$_2$ | (+)-pin | |
| 2437 | CH$_2$NH$_2$ | 1 | PhCH$_2$ | (CH$_2$)$_2$NO$_2$ | (+)-pin | |
| 2438 | CH$_2$NH$_2$ | 1 | PhCH$_2$ | (CH$_2$)$_3$NO$_2$ | (+)-pin | |
| 2439 | CH$_2$NH$_2$ | 1 | PhCH$_2$ | CH$_2$OH | (+)-pin | CV |
| 2440 | CH$_2$NH$_2$ | 1 | PhCH$_2$ | CH$_2$OCH$_2$Ph | (+)-pin | CW |
| 2441 | CH$_2$NH$_2$ | 1 | PhCH$_2$ | (CH$_2$)$_2$OH | (+)-pin | |
| 2442 | CH$_2$NH$_2$ | 1 | PhCH$_2$ | (CH$_2$)$_3$OH | (+)-pin | |
| 2443 | CH$_2$NH$_2$ | 1 | PhCH$_2$ | CH$_2$CO$_2$Me | (+)-pin | |
| 2444 | CH$_2$NH$_2$ | 1 | PhCH$_2$ | (CH$_2$)$_2$CO$_2$Me | (+)-pin | CX |
| 2445 | CH$_2$NH$_2$ | 1 | PhCH$_2$ | (CH$_2$)$_3$CO$_2$Me | (+)-pin | |
| 2446 | CH$_2$NH$_2$ | 1 | PhCH$_2$ | Ph | (+)-pin | |
| 2447 | CH$_2$NH$_2$ | 1 | PhCH$_2$ | PhCH$_2$ | (+)-pin | |
| 2448 | CH$_2$NH$_2$ | 1 | PhCH$_2$ | 3-NO$_2$-Ph | (+)-pin | |
| 2449 | CH$_2$NH$_2$ | 1 | PhCH$_2$ | 4-NO$_2$-Ph | (+)-pin | |
| 2450 | CH$_2$NH$_2$ | 1 | PhCH$_2$ | 3-CO$_2$H-Ph | (+)-pin | |
| 2451 | CH$_2$NH$_2$ | 1 | PhCH$_2$ | 4-CO$_2$H-Ph | (+)-pin | |
| 2452 | CH$_2$NH$_2$ | 1 | PhCH$_2$ | 3-CN$_4$H-Ph | (+)-pin | |
| 2453 | CH$_2$NH$_2$ | 1 | PhCH$_2$ | 4-CN$_4$H-Ph | (+)-pin | |
| 2454 | CH$_2$NH$_2$ | 1 | PhCH$_2$ | 3-(HOCH$_2$)-Ph | (+)-pin | |
| 2455 | CH$_2$NH$_2$ | 1 | PhCH$_2$ | 4-(HOCH$_2$)-Ph | (+)-pin | |
| 2456 | NH(C=NH)NH$_2$ | 1 | PhCH$_2$ | H | (+)-pin | |
| 2457 | NH(C=NH)NH$_2$ | 1 | PhCH$_2$ | Methyl | (+)-pin | |
| 2458 | NH(C=NH)NH$_2$ | 1 | PhCH$_2$ | Ethyl | (+)-pin | |
| 2459 | NH(C=NH)NH$_2$ | 1 | PhCH$_2$ | n-Propyl | (+)-pin | |
| 2460 | NH(C=NH)NH$_2$ | 1 | PhCH$_2$ | n-Butyl | (+)-pin | |
| 2461 | NH(C=NH)NH$_2$ | 1 | PhCH$_2$ | CH$_2$SCH$_3$ | (+)-pin | |
| 2462 | NH(C=NH)NH$_2$ | 1 | PhCH$_2$ | CH$_2$(SO)CH$_3$ | (+)-pin | |
| 2463 | NH(C=NH)NH$_2$ | 1 | PhCH$_2$ | CH$_2$(SO$_2$)CH$_3$ | (+)-pin | |
| 2464 | NH(C=NH)NH$_2$ | 1 | PhCH$_2$ | CH$_2$CH$_2$SCH$_3$ | (+)-pin | |
| 2465 | NH(C=NH)NH$_2$ | 1 | PhCH$_2$ | CH$_2$CH$_2$(SO)CH$_3$ | (+)-pin | |
| 2466 | NH(C=NH)NH$_2$ | 1 | PhCH$_2$ | CH$_2$CH$_2$(SO)$_2$CH$_3$ | (+)-pin | |
| 2467 | NH(C=NH)NH$_2$ | 1 | PhCH$_2$ | CH$_2$CN | (+)-pin | |
| 2468 | NH(C=NH)NH$_2$ | 1 | PhCH$_2$ | CH$_2$CH$_2$CN | (+)-pin | |
| 2469 | NH(C=NH)NH$_2$ | 1 | PhCH$_2$ | CH$_2$CH$_2$CH$_2$CN | (+)-pin | |
| 2470 | NH(C=NH)NH$_2$ | 1 | PhCH$_2$ | CF$_3$ | (+)-pin | |
| 2471 | NH(C=NH)NH$_2$ | 1 | PhCH$_2$ | CF$_2$CF$_3$ | (+)-pin | |
| 2472 | NH(C=NH)NH$_2$ | 1 | PhCH$_2$ | CF$_2$CF$_2$CF$_3$ | (+)-pin | |

TABLE 15-continued

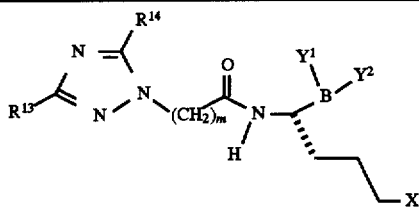

| Ex | X | m | R¹³ | R¹⁴ | Y¹Y² | Phys. Data |
|---|---|---|---|---|---|---|
| 2473 | NH(C=NH)NH₂ | 1 | PhCH₂ | CF₂CF₂CF₂CF₃ | (+)-pin | |
| 2474 | NH(C=NH)NH₂ | 1 | PhCH₂ | F₅-Ph | (+)-pin | |
| 2475 | NH(C=NH)NH₂ | 1 | PhCH₂ | CH₂CO₂H | (+)-pin | |
| 2476 | NH(C=NH)NH₂ | 1 | PhCH₂ | (CH₂)₂CO₂H | (+)-pin | |
| 2477 | NH(C=NH)NH₂ | 1 | PhCH₂ | (CH₂)₃CO₂H | (+)-pin | |
| 2478 | NH(C=NH)NH₂ | 1 | PhCH₂ | CH₂CN₄H | (+)-pin | |
| 2479 | NH(C=NH)NH₂ | 1 | PhCH₂ | (CH₂)₂CN₄H | (+)-pin | |
| 2480 | NH(C=NH)NH₂ | 1 | PhCH₂ | (CH₂)₃CN₄H | (+)-pin | |
| 2481 | NH(C=NH)NH₂ | 1 | PhCH₂ | CH₂NO₂ | (+)-pin | |
| 2482 | NH(C=NH)NH₂ | 1 | PhCH₂ | (CH₂)₂NO₂ | (+)-pin | |
| 2483 | NH(C=NH)NH₂ | 1 | PhCH₂ | (CH₂)₃NO₂ | (+)-pin | |
| 2484 | NH(C=NH)NH₂ | 1 | PhCH₂ | CH₂OH | (+)-pin | |
| 2485 | NH(C=NH)NH₂ | 1 | PhCH₂ | (CH₂)₂OH | (+)-pin | |
| 2486 | NH(C=NH)NH₂ | 1 | PhCH₂ | (CH₂)₃OH | (+)-pin | |
| 2487 | NH(C=NH)NH₂ | 1 | PhCH₂ | CH₂CO₂Me | (+)-pin | |
| 2488 | NH(C=NH)NH₂ | 1 | PhCH₂ | (CH₂)₂CO₂Me | (+)-pin | |
| 2489 | NH(C=NH)NH₂ | 1 | PhCH₂ | (CH₂)₃CO₂Me | (+)-pin | |
| 2490 | NH(C=NH)NH₂ | 1 | PhCH₂ | Ph | (+)-pin | |
| 2491 | NH(C=NH)NH₂ | 1 | PhCH₂ | 3-NO₂-Ph | (+)-pin | CY |
| 2492 | NH(C=NH)NH₂ | 1 | PhCH₂ | 4-NO₂-Ph | (+)-pin | |
| 2493 | NH(C=NH)NH₂ | 1 | PhCH₂ | 3-CO₂H-Ph | (+)-pin | |
| 2494 | NH(C=NH)NH₂ | 1 | PhCH₂ | 4-CO₂H-Ph | (+)-pin | |
| 2495 | NH(C=NH)NH₂ | 1 | PhCH₂ | 3-CN₄H-Ph | (+)-pin | |
| 2496 | NH(C=NH)NH₂ | 1 | PhCH₂ | 4-CN₄H-Ph | (+)-pin | |
| 2497 | NH(C=NH)NH₂ | 1 | PhCH₂ | 3-(HOCH₂)-Ph | (+)-pin | |
| 2498 | NH(C=NH)NH₂ | 1 | PhCH₂ | 4-(HOCH₂)-Ph | (+)-pin | |
| 2499 | CH₂NH₂ | 1 | PhCH₂ | H | OH, OH | BH |
| 2500 | CH₂NH₂ | 1 | PhCH₂ | Methyl | OH, OH | |
| 2501 | CH₂NH₂ | 1 | PhCH₂ | Ethyl | OH, OH | |
| 2502 | CH₂NH₂ | 1 | PhCH₂ | n-Propyl | OH, OH | |
| 2503 | CH₂NH₂ | 1 | PhCH₂ | n-Butyl | OH, OH | |
| 2504 | CH₂NH₂ | 1 | PhCH₂ | CH₂SCH₃ | OH, OH | |
| 2505 | CH₂NH₂ | 1 | PhCH₂ | CH₂(SO)CH₃ | OH, OH | |
| 2506 | CH₂NH₂ | 1 | PhCH₂ | CH₂(SO₂)CH₃ | OH, OH | |
| 2507 | CH₂NH₂ | 1 | PhCH₂ | CH₂CH₂SCH₃ | OH, OH | |
| 2508 | CH₂NH₂ | 1 | PhCH₂ | CH₂CH₂(SO)CH₃ | OH, OH | |
| 2509 | CH₂NH₂ | 1 | PhCH₂ | CH₂CH₂(SO)₂CH₃ | OH, OH | |
| 2510 | CH₂NH₂ | 1 | PhCH₂ | CH₂CN | OH, OH | |
| 2511 | CH₂NH₂ | 1 | PhCH₂ | CH₂CH₂CN | OH, OH | |
| 2512 | CH₂NH₂ | 1 | PhCH₂ | CH₂CH₂CH₂CN | OH, OH | |
| 2513 | CH₂NH₂ | 1 | PhCH₂ | CF₃ | OH, OH | |
| 2514 | CH₂NH₂ | 1 | PhCH₂ | CF₂CF₃ | OH, OH | |
| 2515 | CH₂NH₂ | 1 | PhCH₂ | CF₂CF₂CF₃ | OH, OH | |
| 2516 | CH₂NH₂ | 1 | PhCH₂ | CF₂CF₂CF₂CF₃ | OH, OH | |
| 2517 | CH₂NH₂ | 1 | PhCH₂ | F₅-Ph | OH, OH | |
| 2518 | CH₂NH₂ | 1 | PhCH₂ | CH₂CO₂H | OH, OH | |
| 2519 | CH₂NH₂ | 1 | PhCH₂ | (CH₂)₂CO₂H | OH, OH | |
| 2520 | CH₂NH₂ | 1 | PhCH₂ | (CH₂)₃CO₂H | OH, OH | |
| 2521 | CH₂NH₂ | 1 | PhCH₂ | CH₂CN₄H | OH, OH | |
| 2522 | CH₂NH₂ | 1 | PhCH₂ | (CH₂)₂CN₄H | OH, OH | |
| 2523 | CH₂NH₂ | 1 | PhCH₂ | (CH₂)₃CN₄H | OH, OH | |
| 2524 | CH₂NH₂ | 1 | PhCH₂ | CH₂NO₂ | OH, OH | |
| 2525 | CH₂NH₂ | 1 | PhCH₂ | (CH₂)₂NO₂ | OH, OH | |
| 2526 | CH₂NH₂ | 1 | PhCH₂ | (CH₂)₃NO₂ | OH, OH | |
| 2527 | CH₂NH₂ | 1 | PhCH₂ | CH₂OH | OH, OH | |
| 2528 | CH₂NH₂ | 1 | PhCH₂ | (CH₂)₂OH | OH, OH | |
| 2529 | CH₂NH₂ | 1 | PhCH₂ | (CH₂)₃OH | OH, OH | |
| 2530 | CH₂NH₂ | 1 | PhCH₂ | CH₂CO₂Me | OH, OH | |
| 2531 | CH₂NH₂ | 1 | PhCH₂ | (CH₂)₂CO₂Me | OH, OH | |
| 2532 | CH₂NH₂ | 1 | PhCH₂ | (CH₂)₃CO₂Me | OH, OH | |
| 2533 | CH₂NH₂ | 1 | PhCH₂ | Ph | OH, OH | |
| 2534 | CH₂NH₂ | 1 | PhCH₂ | 3-NO₂-Ph | OH, OH | |
| 2535 | CH₂NH₂ | 1 | PhCH₂ | 4-NO₂-Ph | OH, OH | |
| 2536 | CH₂NH₂ | 1 | PhCH₂ | 3-CO₂H-Ph | OH, OH | |
| 2537 | CH₂NH₂ | 1 | PhCH₂ | 4-CO₂H-Ph | OH, OH | |

TABLE 15-continued

| Ex | X | m | R$^{13}$ | R$^{14}$ | Y$^1$Y$^2$ | Phys. Data |
|---|---|---|---|---|---|---|
| 2538 | CH$_2$NH$_2$ | 1 | PhCH$_2$ | 3-CN$_4$H-Ph | OH, OH | |
| 2539 | CH$_2$NH$_2$ | 1 | PhCH$_2$ | 4-CN$_4$H-Ph | OH, OH | |
| 2540 | CH$_2$NH$_2$ | 1 | PhCH$_2$ | 3-(HOCH$_2$)-Ph | OH, OH | |
| 2541 | CH$_2$NH$_2$ | 1 | PhCH$_2$ | 4-(HOCH$_2$)-Ph | OH, OH | |
| 2542 | NH(C=NH)NH$_2$ | 1 | PhCH$_2$ | H | OH, OH | |
| 2543 | NH(C=NH)NH$_2$ | 1 | PhCH$_2$ | Methyl | OH, OH | |
| 2544 | NH(C=NH)NH$_2$ | 1 | PhCH$_2$ | Ethyl | OH, OH | |
| 2545 | NH(C=NH)NH$_2$ | 1 | PhCH$_2$ | n-Propyl | OH, OH | |
| 2546 | NH(C=NH)NH$_2$ | 1 | PhCH$_2$ | n-Butyl | OH, OH | |
| 2547 | NH(C=NH)NH$_2$ | 1 | PhCH$_2$ | CH$_2$SCH$_3$ | OH, OH | |
| 2548 | NH(C=NH)NH$_2$ | 1 | PhCH$_2$ | CH$_2$(SO)CH$_3$ | OH, OH | |
| 2549 | NH(C=NH)NH$_2$ | 1 | PhCH$_2$ | CH$_2$(SO$_2$)CH$_3$ | OH, OH | |
| 2550 | NH(C=NH)NH$_2$ | 1 | PhCH$_2$ | CH$_2$CH$_2$SCH$_3$ | OH, OH | |
| 2551 | NH(C=NH)NH$_2$ | 1 | PhCH$_2$ | CH$_2$CH$_2$(SO)CH$_3$ | OH, OH | |
| 2552 | NH(C=NH)NH$_2$ | 1 | PhCH$_2$ | CH$_2$CH$_2$(SO)$_2$CH$_3$ | OH, OH | |
| 2553 | NH(C=NH)NH$_2$ | 1 | PhCH$_2$ | CH$_2$CN | OH, OH | |
| 2554 | NH(C=NH)NH$_2$ | 1 | PhCH$_2$ | CH$_2$CH$_2$CN | OH, OH | |
| 2555 | NH(C=NH)NH$_2$ | 1 | PhCH$_2$ | CH$_2$CH$_2$CH$_2$CN | OH, OH | |
| 2556 | NH(C=NH)NH$_2$ | 1 | PhCH$_2$ | CF$_3$ | OH, OH | |
| 2557 | NH(C=NH)NH$_2$ | 1 | PhCH$_2$ | CF$_2$CF$_3$ | OH, OH | |
| 2558 | NH(C=NH)NH$_2$ | 1 | PhCH$_2$ | CF$_2$CF$_2$CF$_3$ | OH, OH | |
| 2559 | NH(C=NH)NH$_2$ | 1 | PhCH$_2$ | CF$_2$CF$_2$CF$_2$CF$_3$ | OH, OH | |
| 2560 | NH(C=NH)NH$_2$ | 1 | PhCH$_2$ | F$_5$-Ph | OH, OH | |
| 2561 | NH(C=NH)NH$_2$ | 1 | PhCH$_2$ | CH$_2$CO$_2$H | OH, OH | |
| 2562 | NH(C=NH)NH$_2$ | 1 | PhCH$_2$ | (CH$_2$)$_2$CO$_2$H | OH, OH | |
| 2563 | NH(C=NH)NH$_2$ | 1 | PhCH$_2$ | (CH$_2$)$_3$CO$_2$H | OH, OH | |
| 2564 | NH(C=NH)NH$_2$ | 1 | PhCH$_2$ | CH$_2$CN$_4$H | OH, OH | |
| 2565 | NH(C=NH)NH$_2$ | 1 | PhCH$_2$ | (CH$_2$)$_2$CN$_4$H | OH, OH | |
| 2566 | NH(C=NH)NH$_2$ | 1 | PhCH$_2$ | (CH$_2$)$_3$CN$_4$H | OH, OH | |
| 2567 | NH(C=NH)NH$_2$ | 1 | PhCH$_2$ | CH$_2$NO$_2$ | OH, OH | |
| 2568 | NH(C=NH)NH$_2$ | 1 | PhCH$_2$ | (CH$_2$)$_2$NO$_2$ | OH, OH | |
| 2569 | NH(C=NH)NH$_2$ | 1 | PhCH$_2$ | (CH$_2$)$_3$NO$_2$ | OH, OH | |
| 2570 | NH(C=NH)NH$_2$ | 1 | PhCH$_2$ | CH$_2$OH | OH, OH | |
| 2571 | NH(C=NH)NH$_2$ | 1 | PhCH$_2$ | (CH$_2$)$_2$OH | OH, OH | |
| 2572 | NH(C=NH)NH$_2$ | 1 | PhCH$_2$ | (CH$_2$)$_3$OH | OH, OH | |
| 2573 | NH(C=NH)NH$_2$ | 1 | PhCH$_2$ | CH$_2$CO$_2$Me | OH, OH | |
| 2574 | NH(C=NH)NH$_2$ | 1 | PhCH$_2$ | (CH$_2$)$_2$CO$_2$Me | OH, OH | |
| 2575 | NH(C=NH)NH$_2$ | 1 | PhCH$_2$ | (CH$_2$)$_3$CO$_2$Me | OH, OH | |
| 2576 | NH(C=NH)NH$_2$ | 1 | PhCH$_2$ | 3-NO$_2$-Ph | OH, OH | |
| 2577 | NH(C=NH)NH$_2$ | 1 | PhCH$_2$ | 4-NO$_2$-Ph | OH, OH | |
| 2578 | NH(C=NH)NH$_2$ | 1 | PhCH$_2$ | 3-CO$_2$H-Ph | OH, OH | |
| 2579 | NH(C=NH)NH$_2$ | 1 | PhCH$_2$ | 4-CO$_2$H-Ph | OH, OH | |
| 2580 | NH(C=NH)NH$_2$ | 1 | PhCH$_2$ | 3-CN$_4$H-Ph | OH, OH | |
| 2581 | NH(C=NH)NH$_2$ | 1 | PhCH$_2$ | 4-CN$_4$H-Ph | OH, OH | |
| 2582 | NH(C=NH)NH$_2$ | 1 | PhCH$_2$ | 3-(HOCH$_2$)-Ph | OH, OH | |
| 2583 | NH(C=NH)NH$_2$ | 1 | PhCH$_2$ | 4-(HOCH$_2$)-Ph | OH, OH | |
| 2584 | —S—(C=NH)NH$_2$ | 1 | PhCH$_2$ | H | (+)-pin | |
| 2585 | —S—(C=NH)NH$_2$ | 1 | PhCH$_2$ | Methyl | (+)-pin | |
| 2586 | —S—(C=NH)NH$_2$ | 1 | PhCH$_2$ | Ethyl | (+)-pin | |
| 2587 | —S—(C=NH)NH$_2$ | 1 | PhCH$_2$ | n-Propyl | (+)-pin | |
| 2588 | —S—(C=NH)NH$_2$ | 1 | PhCH$_2$ | n-Butyl | (+)-pin | |
| 2589 | —S—(C=NH)NH$_2$ | 1 | PhCH$_2$ | CH$_2$SCH$_3$ | (+)-pin | |
| 2590 | —S—(C=NH)NH$_2$ | 1 | PhCH$_2$ | CH$_2$(SO)CH$_3$ | (+)-pin | |
| 2591 | —S—(C=NH)NH$_2$ | 1 | PhCH$_2$ | CH$_2$(SO$_2$)CH$_3$ | (+)-pin | |
| 2592 | —S—(C=NH)NH$_2$ | 1 | PhCH$_2$ | CH$_2$CH$_2$SCH$_3$ | (+)-pin | |
| 2593 | —S—(C=NH)NH$_2$ | 1 | PhCH$_2$ | CH$_2$CH$_2$(SO)CH$_3$ | (+)-pin | |
| 2594 | —S—(C=NH)NH$_2$ | 1 | PhCH$_2$ | CH$_2$CH$_2$(SO)$_2$CH$_3$ | (+)-pin | |
| 2595 | —S—(C=NH)NH$_2$ | 1 | PhCH$_2$ | CH$_2$CN | (+)-pin | |
| 2596 | —S—(C=NH)NH$_2$ | 1 | PhCH$_2$ | CH$_2$CH$_2$CN | (+)-pin | |
| 2597 | —S—(C=NH)NH$_2$ | 1 | PhCH$_2$ | CH$_2$CH$_2$CH$_2$CN | (+)-pin | |
| 2598 | —S—(C=NH)NH$_2$ | 1 | PhCH$_2$ | CF$_3$ | (+)-pin | |
| 2599 | —S—(C=NH)NH$_2$ | 1 | PhCH$_2$ | CF$_2$CF$_3$ | (+)-pin | |
| 2600 | —S—(C=NH)NH$_2$ | 1 | PhCH$_2$ | CF$_2$CF$_2$CF$_3$ | (+)-pin | |
| 2601 | —S—(C=NH)NH$_2$ | 1 | PhCH$_2$ | CF$_2$CF$_2$CF$_2$CF$_3$ | (+)-pin | |
| 2602 | —S—(C=NH)NH$_2$ | 1 | PhCH$_2$ | F$_5$-Ph | (+)-pin | |

TABLE 15-continued

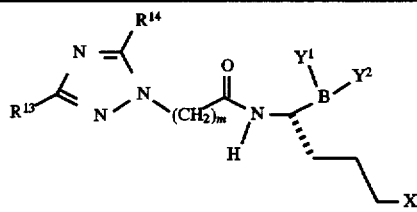

| Ex | X | m | R¹³ | R¹⁴ | Y¹Y² | Phys. Data |
|---|---|---|---|---|---|---|
| 2603 | —S—(C=NH)NH₂ | 1 | PhCH₂ | CH₂CO₂H | (+)-pin | |
| 2604 | —S—(C=NH)NH₂ | 1 | PhCH₂ | (CH₂)₂CO₂H | (+)-pin | |
| 2605 | —S—(C=NH)NH₂ | 1 | PhCH₂ | (CH₂)₃CO₂H | (+)-pin | |
| 2606 | —S—(C=NH)NH₂ | 1 | PhCH₂ | CH₂CN₄H | (+)-pin | |
| 2607 | —S—(C=NH)NH₂ | 1 | PhCH₂ | (CH₂)₂CN₄H | (+)-pin | |
| 2608 | —S—(C=NH)NH₂ | 1 | PhCH₂ | (CH₂)₃CN₄H | (+)-pin | |
| 2609 | —S—(C=NH)NH₂ | 1 | PhCH₂ | CH₂NO₂ | (+)-pin | |
| 2610 | —S—(C=NH)NH₂ | 1 | PhCH₂ | (CH₂)₂NO₂ | (+)-pin | |
| 2611 | —S—(C=NH)NH₂ | 1 | PhCH₂ | (CH₂)₃NO₂ | (+)-pin | |
| 2612 | —S—(C=NH)NH₂ | 1 | PhCH₂ | CH₂OH | (+)-pin | |
| 2613 | —S—(C=NH)NH₂ | 1 | PhCH₂ | (CH₂)₂OH | (+)-pin | |
| 2614 | —S—(C=NH)NH₂ | 1 | PhCH₂ | (CH₂)₃OH | (+)-pin | |
| 2615 | —S—(C=NH)NH₂ | 1 | PhCH₂ | CH₂CO₂Me | (+)-pin | |
| 2616 | —S—(C=NH)NH₂ | 1 | PhCH₂ | (CH₂)₂CO₂Me | (+)-pin | |
| 2617 | —S—(C=NH)NH₂ | 1 | PhCH₂ | (CH₂)₃CO₂Me | (+)-pin | |
| 2618 | —S—(C=NH)NH₂ | 1 | PhCH₂ | 3-NO₂-Ph | (+)-pin | |
| 2619 | —S—(C=NH)NH₂ | 1 | PhCH₂ | 4-NO₂-Ph | (+)-pin | |
| 2620 | —S—(C=NH)NH₂ | 1 | PhCH₂ | 3-CO₂H-Ph | (+)-pin | |
| 2621 | —S—(C=NH)NH₂ | 1 | PhCH₂ | 4-CO₂H-Ph | (+)-pin | |
| 2622 | —S—(C=NH)NH₂ | 1 | PhCH₂ | 3-CN₄H-Ph | (+)-pin | |
| 2623 | —S—(C=NH)NH₂ | 1 | PhCH₂ | 4-CN₄H-Ph | (+)-pin | |
| 2624 | —S—(C=NH)NH₂ | 1 | PhCH₂ | 3-(HOCH₂)-Ph | (+)-pin | |
| 2625 | —S—(C=NH)NH₂ | 1 | PhCH₂ | 4-(HOCH₂)-Ph | (+)-pin | |
| 2626 | —S—(C=NH)NH₂ | 1 | PhCH₂ | H | OH, OH | |
| 2627 | —S—(C=NH)NH₂ | 1 | PhCH₂ | Methyl | OH, OH | |
| 2628 | —S—(C=NH)NH₂ | 1 | PhCH₂ | Ethyl | OH, OH | |
| 2629 | —S—(C=NH)NH₂ | 1 | PhCH₂ | n-Propyl | OH, OH | |
| 2630 | —S—(C=NH)NH₂ | 1 | PhCH₂ | n-Butyl | OH, OH | |
| 2631 | —S—(C=NH)NH₂ | 1 | PhCH₂ | CH₂SCH₃ | OH, OH | |
| 2632 | —S—(C=NH)NH₂ | 1 | PhCH₂ | CH₂(SO)CH₃ | OH, OH | |
| 2633 | —S—(C=NH)NH₂ | 1 | PhCH₂ | CH₂(SO₂)CH₃ | OH, OH | |
| 2634 | —S—(C=NH)NH₂ | 1 | PhCH₂ | CH₂CH₂SCH₃ | OH, OH | |
| 2635 | —S—(C=NH)NH₂ | 1 | PhCH₂ | CH₂CH₂(SO)CH₃ | OH, OH | |
| 2636 | —S—(C=NH)NH₂ | 1 | PhCH₂ | CH₂CH₂(SO)₂CH₃ | OH, OH | |
| 2637 | —S—(C=NH)NH₂ | 1 | PhCH₂ | CH₂CN | OH, OH | |
| 2638 | —S—(C=NH)NH₂ | 1 | PhCH₂ | CH₂CH₂CN | OH, OH | |
| 2639 | —S—(C=NH)NH₂ | 1 | PhCH₂ | CH₂CH₂CH₂CN | OH, OH | |
| 2640 | —S—(C=NH)NH₂ | 1 | PhCH₂ | CF₃ | OH, OH | |
| 2641 | —S—(C=NH)NH₂ | 1 | PhCH₂ | CF₂CF₃ | OH, OH | |
| 2642 | —S—(C=NH)NH₂ | 1 | PhCH₂ | CF₂CF₂CF₃ | OH, OH | |
| 2643 | —S—(C=NH)NH₂ | 1 | PhCH₂ | CF₂CF₂CF₂CF₃ | OH, OH | |
| 2644 | —S—(C=NH)NH₂ | 1 | PhCH₂ | F₅-Ph | OH, OH | |
| 2645 | —S—(C=NH)NH₂ | 1 | PhCH₂ | CH₂CO₂H | OH, OH | |
| 2646 | —S—(C=NH)NH₂ | 1 | PhCH₂ | (CH₂)₂CO₂H | OH, OH | |
| 2647 | —S—(C=NH)NH₂ | 1 | PhCH₂ | (CH₂)₃CO₂H | OH, OH | |
| 2648 | —S—(C=NH)NH₂ | 1 | PhCH₂ | CH₂CN₄H | OH, OH | |
| 2649 | —S—(C=NH)NH₂ | 1 | PhCH₂ | (CH₂)₂CN₄H | OH, OH | |
| 2650 | —S—(C=NH)NH₂ | 1 | PhCH₂ | (CH₂)₃CN₄H | OH, OH | |
| 2651 | —S—(C=NH)NH₂ | 1 | PhCH₂ | CH₂NO₂ | OH, OH | |
| 2652 | —S—(C=NH)NH₂ | 1 | PhCH₂ | (CH₂)₂NO₂ | OH, OH | |
| 2653 | —S—(C=NH)NH₂ | 1 | PhCH₂ | (CH₂)₃NO₂ | OH, OH | |
| 2654 | —S—(C=NH)NH₂ | 1 | PhCH₂ | CH₂OH | OH, OH | |
| 2655 | —S—(C=NH)NH₂ | 1 | PhCH₂ | (CH₂)₂OH | OH, OH | |
| 2656 | —S—(C=NH)NH₂ | 1 | PhCH₂ | (CH₂)₃OH | OH, OH | |
| 2657 | —S—(C=NH)NH₂ | 1 | PhCH₂ | CH₂CO₂Me | OH, OH | |
| 2658 | —S—(C=NH)NH₂ | 1 | PhCH₂ | (CH₂)₂CO₂Me | OH, OH | |
| 2659 | —S—(C=NH)NH₂ | 1 | PhCH₂ | (CH₂)₃CO₂Me | OH, OH | |
| 2660 | —S—(C=NH)NH₂ | 1 | PhCH₂ | 3-NO₂-Ph | OH, OH | |
| 2661 | —S—(C=NH)NH₂ | 1 | PhCH₂ | 4-NO₂-Ph | OH, OH | |
| 2662 | —S—(C=NH)NH₂ | 1 | PhCH₂ | 3-CO₂H-Ph | OH, OH | |
| 2663 | —S—(C=NH)NH₂ | 1 | PhCH₂ | 4-CO₂H-Ph | OH, OH | |
| 2664 | —S—(C=NH)NH₂ | 1 | PhCH₂ | 3-CN₄H-Ph | OH, OH | |
| 2665 | —S—(C=NH)NH₂ | 1 | PhCH₂ | 4-CN₄H-Ph | OH, OH | |
| 2666 | —S—(C=NH)NH₂ | 1 | PhCH₂ | 3-(HOCH₂)-Ph | OH, OH | |
| 2667 | —S—(C=NH)NH₂ | 1 | PhCH₂ | 4-(HOCH₂)-Ph | OH, OH | |

TABLE 15-continued

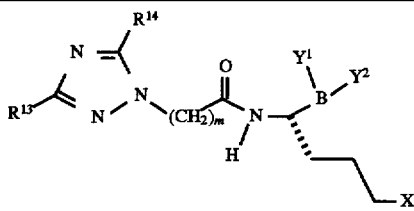

| Ex | X | m | R$^{13}$ | R$^{14}$ | Y$^1$Y$^2$ | Phys. Data |
|---|---|---|---|---|---|---|
| 2668 | OMe | 1 | PhCH$_2$ | H | (+)-pin | |
| 2669 | OMe | 1 | PhCH$_2$ | Methyl | (+)-pin | |
| 2670 | OMe | 1 | PhCH$_2$ | Ethyl | (+)-pin | |
| 2671 | OMe | 1 | PhCH$_2$ | n-Propyl | (+)-pin | |
| 2672 | OMe | 1 | PhCH$_2$ | n-Butyl | (+)-pin | |
| 2673 | OMe | 1 | PhCH$_2$ | CH$_2$SCH$_3$ | (+)-pin | |
| 2674 | OMe | 1 | PhCH$_2$ | CH$_2$(SO)CH$_3$ | (+)-pin | |
| 2675 | OMe | 1 | PhCH$_2$ | CH$_2$(SO$_2$)CH$_3$ | (+)-pin | |
| 2676 | OMe | 1 | PhCH$_2$ | CH$_2$CH$_2$SCH$_3$ | (+)-pin | |
| 2677 | OMe | 1 | PhCH$_2$ | CH$_2$CH$_2$(SO)CH$_3$ | (+)-pin | |
| 2678 | OMe | 1 | PhCH$_2$ | CH$_2$CH$_2$(SO)$_2$CH$_3$ | (+)-pin | |
| 2679 | OMe | 1 | PhCH$_2$ | CH$_2$CN | (+)-pin | |
| 2680 | OMe | 1 | PhCH$_2$ | CH$_2$CH$_2$CN | (+)-pin | |
| 2681 | OMe | 1 | PhCH$_2$ | CH$_2$CH$_2$CH$_2$CN | (+)-pin | |
| 2682 | OMe | 1 | PhCH$_2$ | CF$_3$ | (+)-pin | |
| 2683 | OMe | 1 | PhCH$_2$ | CF$_2$CF$_3$ | (+)-pin | |
| 2684 | OMe | 1 | PhCH$_2$ | CF$_2$CF$_2$CF$_3$ | (+)-pin | |
| 2685 | OMe | 1 | PhCH$_2$ | CF$_2$CF$_2$CF$_2$CF$_3$ | (+)-pin | |
| 2686 | OMe | 1 | PhCH$_2$ | F$_5$-Ph | (+)-pin | |
| 2687 | OMe | 1 | PhCH$_2$ | CH$_2$CO$_2$H | (+)-pin | |
| 2688 | OMe | 1 | PhCH$_2$ | (CH$_2$)$_2$CO$_2$H | (+)-pin | |
| 2689 | OMe | 1 | PhCH$_2$ | (CH$_2$)$_3$CO$_2$H | (+)-pin | |
| 2690 | OMe | 1 | PhCH$_2$ | CH$_2$CN$_4$H | (+)-pin | |
| 2691 | OMe | 1 | PhCH$_2$ | (CH$_2$)$_2$CN$_4$H | (+)-pin | |
| 2692 | OMe | 1 | PhCH$_2$ | (CH$_2$)$_3$CN$_4$H | (+)-pin | |
| 2693 | OMe | 1 | PhCH$_2$ | CH$_2$NO$_2$ | (+)-pin | |
| 2694 | OMe | 1 | PhCH$_2$ | (CH$_2$)$_2$NO$_2$ | (+)-pin | |
| 2695 | OMe | 1 | PhCH$_2$ | (CH$_2$)$_3$NO$_2$ | (+)-pin | |
| 2696 | OMe | 1 | PhCH$_2$ | CH$_2$OH | (+)-pin | |
| 2697 | OMe | 1 | PhCH$_2$ | (CH$_2$)$_2$OH | (+)-pin | |
| 2698 | OMe | 1 | PhCH$_2$ | (CH$_2$)$_3$OH | (+)-pin | |
| 2699 | OMe | 1 | PhCH$_2$ | CH$_2$CO$_2$Me | (+)-pin | |
| 2700 | OMe | 1 | PhCH$_2$ | (CH$_2$)$_2$CO$_2$Me | (+)-pin | |
| 2701 | OMe | 1 | PhCH$_2$ | (CH$_2$)$_3$CO$_2$Me | (+)-pin | |
| 2702 | OMe | 1 | PhCH$_2$ | 3-NO$_2$-Ph | (+)-pin | |
| 2703 | OMe | 1 | PhCH$_2$ | 4-NO$_2$-Ph | (+)-pin | |
| 2704 | OMe | 1 | PhCH$_2$ | 3-CO$_2$H-Ph | (+)-pin | |
| 2705 | OMe | 1 | PhCH$_2$ | 4-CO$_2$H-Ph | (+)-pin | |
| 2706 | OMe | 1 | PhCH$_2$ | 3-CN$_4$H-Ph | (+)-pin | |
| 2707 | OMe | 1 | PhCH$_2$ | 4-CN$_4$H-Ph | (+)-pin | |
| 2708 | OMe | 1 | PhCH$_2$ | 3-(HOCH$_2$)-Ph | (+)-pin | |
| 2709 | OMe | 1 | PhCH$_2$ | 4-(HOCH$_2$)-Ph | (+)-pin | |
| 2710 | OMe | 1 | PhCH$_2$ | H | OH, OH | |
| 2711 | OMe | 1 | PhCH$_2$ | Methyl | OH, OH | |
| 2712 | OMe | 1 | PhCH$_2$ | Ethyl | OH, OH | |
| 2713 | OMe | 1 | PhCH$_2$ | n-Propyl | OH, OH | |
| 2714 | OMe | 1 | PhCH$_2$ | n-Butyl | OH, OH | |
| 2715 | OMe | 1 | PhCH$_2$ | CH$_2$SCH$_3$ | OH, OH | |
| 2716 | OMe | 1 | PhCH$_2$ | CH$_2$(SO)CH$_3$ | OH, OH | |
| 2717 | OMe | 1 | PhCH$_2$ | CH$_2$(SO$_2$)CH$_3$ | OH, OH | |
| 2718 | OMe | 1 | PhCH$_2$ | CH$_2$CH$_2$SCH$_3$ | OH, OH | |
| 2719 | OMe | 1 | PhCH$_2$ | CH$_2$CH$_2$(SO)CH$_3$ | OH, OH | |
| 2720 | OMe | 1 | PhCH$_2$ | CH$_2$CH$_2$(SO)$_2$CH$_3$ | OH, OH | |
| 2721 | OMe | 1 | PhCH$_2$ | CH$_2$CN | OH, OH | |
| 2722 | OMe | 1 | PhCH$_2$ | CH$_2$CH$_2$CN | OH, OH | |
| 2723 | OMe | 1 | PhCH$_2$ | CH$_2$CH$_2$CH$_2$CN | OH, OH | |
| 2724 | OMe | 1 | PhCH$_2$ | CF$_3$ | OH, OH | |
| 2725 | OMe | 1 | PhCH$_2$ | CF$_2$CF$_3$ | OH, OH | |
| 2726 | OMe | 1 | PhCH$_2$ | CF$_2$CF$_2$CF$_3$ | OH, OH | |
| 2727 | OMe | 1 | PhCH$_2$ | CF$_2$CF$_2$CF$_2$CF$_3$ | OH, OH | |
| 2728 | OMe | 1 | PhCH$_2$ | F$_5$-Ph | OH, OH | |
| 2729 | OMe | 1 | PhCH$_2$ | CH$_2$CO$_2$H | OH, OH | |
| 2730 | OMe | 1 | PhCH$_2$ | (CH$_2$)$_2$CO$_2$H | OH, OH | |
| 2731 | OMe | 1 | PhCH$_2$ | (CH$_2$)$_3$CO$_2$H | OH, OH | |
| 2732 | OMe | 1 | PhCH$_2$ | CH$_2$CN$_4$H | OH, OH | |

TABLE 15-continued

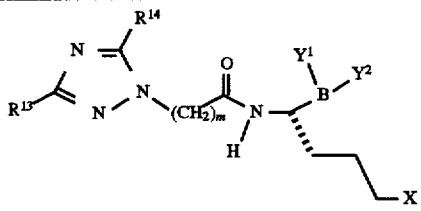

| Ex | X | m | R[13] | R[14] | Y[1]Y[2] | Phys. Data |
|---|---|---|---|---|---|---|
| 2733 | OMe | 1 | PhCH$_2$ | (CH$_2$)$_2$CN$_4$H | OH, OH | |
| 2734 | OMe | 1 | PhCH$_2$ | (CH$_2$)$_3$CN$_4$H | OH, OH | |
| 2735 | OMe | 1 | PhCH$_2$ | CH$_2$NO$_2$ | OH, OH | |
| 2736 | OMe | 1 | PhCH$_2$ | (CH$_2$)$_2$NO$_2$ | OH, OH | |
| 2737 | OMe | 1 | PhCH$_2$ | (CH$_2$)$_3$NO$_2$ | OH, OH | |
| 2738 | OMe | 1 | PhCH$_2$ | CH$_2$OH | OH, OH | |
| 2739 | OMe | 1 | PhCH$_2$ | (CH$_2$)$_2$OH | OH, OH | |
| 2740 | OMe | 1 | PhCH$_2$ | (CH$_2$)$_3$OH | OH, OH | |
| 2741 | OMe | 1 | PhCH$_2$ | CH$_2$CO$_2$Me | OH, OH | |
| 2742 | OMe | 1 | PhCH$_2$ | (CH$_2$)$_2$CO$_2$Me | OH, OH | |
| 2743 | OMe | 1 | PhCH$_2$ | (CH$_2$)$_3$CO$_2$Me | OH, OH | |
| 2744 | OMe | 1 | PhCH$_2$ | 3-NO$_2$-Ph | OH, OH | |
| 2745 | OMe | 1 | PhCH$_2$ | 4-NO$_2$-Ph | OH, OH | |
| 2746 | OMe | 1 | PhCH$_2$ | 3-CO$_2$H-Ph | OH, OH | |
| 2747 | OMe | 1 | PhCH$_2$ | 4-CO$_2$H-Ph | OH, OH | |
| 2748 | OMe | 1 | PhCH$_2$ | 3-CN$_4$H-Ph | OH, OH | |
| 2749 | OMe | 1 | PhCH$_2$ | 4-CN$_4$H-Ph | OH, OH | |
| 2750 | OMe | 1 | PhCH$_2$ | 3-(HOCH$_2$)-Ph | OH, OH | |
| 2751 | OMe | 1 | PhCH$_2$ | 4-(HOCH$_2$)-Ph | OH, OH | |
| 2752 | CH$_2$NH$_2$ | 1 | PhCH$_2$CH$_2$ | H | (+)-pin | BI |
| 2753 | CH$_2$NH$_2$ | 1 | PhCH$_2$CH$_2$ | Methyl | (+)-pin | |
| 2754 | CH$_2$NH$_2$ | 1 | PhCH$_2$CH$_2$ | Ethyl | (+)-pin | |
| 2755 | CH$_2$NH$_2$ | 1 | PhCH$_2$CH$_2$ | n-Propyl | (+)-pin | |
| 2756 | CH$_2$NH$_2$ | 1 | PhCH$_2$CH$_2$ | n-Butyl | (+)-pin | |
| 2757 | CH$_2$NH$_2$ | 1 | PhCH$_2$CH$_2$ | CH$_2$SCH$_3$ | (+)-pin | |
| 2758 | CH$_2$NH$_2$ | 1 | PhCH$_2$CH$_2$ | CH$_2$(SO)CH$_3$ | (+)-pin | |
| 2759 | CH$_2$NH$_2$ | 1 | PhCH$_2$CH$_2$ | CH$_2$(SO$_2$)CH$_3$ | (+)-pin | |
| 2760 | CH$_2$NH$_2$ | 1 | PhCH$_2$CH$_2$ | CH$_2$CH$_2$SCH$_3$ | (+)-pin | |
| 2761 | CH$_2$NH$_2$ | 1 | PhCH$_2$CH$_2$ | CH$_2$CH$_2$(SO)CH$_3$ | (+)-pin | |
| 2762 | CH$_2$NH$_2$ | 1 | PhCH$_2$CH$_2$ | CH$_2$CH$_2$(SO)$_2$CH$_3$ | (+)-pin | |
| 2763 | CH$_2$NH$_2$ | 1 | PhCH$_2$CH$_2$ | CH$_2$CN | (+)-pin | |
| 2764 | CH$_2$NH$_2$ | 1 | PhCH$_2$CH$_2$ | CH$_2$CH$_2$CN | (+)-pin | |
| 2765 | CH$_2$NH$_2$ | 1 | PhCH$_2$CH$_2$ | CH$_2$CH$_2$CH$_2$CN | (+)-pin | |
| 2766 | CH$_2$NH$_2$ | 1 | PhCH$_2$CH$_2$ | CF$_3$ | (+)-pin | |
| 2767 | CH$_2$NH$_2$ | 1 | PhCH$_2$CH$_2$ | CF$_2$CF$_3$ | (+)-pin | |
| 2768 | CH$_2$NH$_2$ | 1 | PhCH$_2$CH$_2$ | CF$_2$CF$_2$CF$_3$ | (+)-pin | |
| 2769 | CH$_2$NH$_2$ | 1 | PhCH$_2$CH$_2$ | CF$_2$CF$_2$CF$_2$CF$_3$ | (+)-pin | |
| 2770 | CH$_2$NH$_2$ | 1 | PhCH$_2$CH$_2$ | F$_5$-Ph | (+)-pin | |
| 2771 | CH$_2$NH$_2$ | 1 | PhCH$_2$CH$_2$ | CH$_2$CO$_2$H | (+)-pin | |
| 2772 | CH$_2$NH$_2$ | 1 | PhCH$_2$CH$_2$ | (CH$_2$)$_2$CO$_2$H | (+)-pin | |
| 2773 | CH$_2$NH$_2$ | 1 | PhCH$_2$CH$_2$ | (CH$_2$)$_3$CO$_2$H | (+)-pin | |
| 2774 | CH$_2$NH$_2$ | 1 | PhCH$_2$CH$_2$ | CH$_2$CN$_4$H | (+)-pin | |
| 2775 | CH$_2$NH$_2$ | 1 | PhCH$_2$CH$_2$ | (CH$_2$)$_2$CN$_4$H | (+)-pin | |
| 2776 | CH$_2$NH$_2$ | 1 | PhCH$_2$CH$_2$ | (CH$_2$)$_3$CN$_4$H | (+)-pin | |
| 2777 | CH$_2$NH$_2$ | 1 | PhCH$_2$CH$_2$ | CH$_2$NO$_2$ | (+)-pin | |
| 2778 | CH$_2$NH$_2$ | 1 | PhCH$_2$CH$_2$ | (CH$_2$)$_2$NO$_2$ | (+)-pin | |
| 2779 | CH$_2$NH$_2$ | 1 | PhCH$_2$CH$_2$ | (CH$_2$)$_3$NO$_2$ | (+)-pin | |
| 2780 | CH$_2$NH$_2$ | 1 | PhCH$_2$CH$_2$ | CH$_2$OH | (+)-pin | CZ |
| 2781 | CH$_2$NH$_2$ | 1 | CH$_2$ | CH$_2$OCH$_2$Ph | (+)-pin | DA |
| 2782 | CH$_2$NH$_2$ | 1 | PhCH$_2$CH$_2$ | (CH$_2$)$_2$OH | (+)-pin | |
| 2783 | CH$_2$NH$_2$ | 1 | PhCH$_2$CH$_2$ | (CH$_2$)$_3$OH | (+)-pin | |
| 2784 | CH$_2$NH$_2$ | 1 | PhCH$_2$CH$_2$ | CH$_2$CO$_2$Me | (+)-pin | |
| 2785 | CH$_2$NH$_2$ | 1 | PhCH$_2$CH$_2$ | (CH$_2$)$_2$CO$_2$Me | (+)-pin | |
| 2786 | CH$_2$NH$_2$ | 1 | PhCH$_2$CH$_2$ | (CH$_2$)$_3$CO$_2$Me | (+)-pin | |
| 2787 | CH$_2$NH$_2$ | 1 | PhCH$_2$CH$_2$ | 3-NO$_2$-Ph | (+)-pin | |
| 2788 | CH$_2$NH$_2$ | 1 | PhCH$_2$CH$_2$ | 4-NO$_2$-Ph | (+)-pin | |
| 2789 | CH$_2$NH$_2$ | 1 | PhCH$_2$CH$_2$ | 3-CO$_2$H-Ph | (+)-pin | |
| 2790 | CH$_2$NH$_2$ | 1 | PhCH$_2$CH$_2$ | 4-CO$_2$H-Ph | (+)-pin | |
| 2791 | CH$_2$NH$_2$ | 1 | PhCH$_2$CH$_2$ | 3-CN$_4$H-Ph | (+)-pin | |
| 2792 | CH$_2$NH$_2$ | 1 | PhCH$_2$CH$_2$ | 4-CN$_4$H-Ph | (+)-pin | |
| 2793 | CH$_2$NH$_2$ | 1 | PhCH$_2$CH$_2$ | 3-(HOCH$_2$)-Ph | (+)-pin | |
| 2794 | CH$_2$NH$_2$ | 1 | PhCH$_2$CH$_2$ | 4-(HOCH$_2$)-Ph | (+)-pin | |
| 2795 | NH(C=NH)NH$_2$ | 1 | PhCH$_2$CH$_2$ | H | (+)-pin | |
| 2796 | NH(C=NH)NH$_2$ | 1 | PhCH$_2$CH$_2$ | Methyl | (+)-pin | |
| 2797 | NH(C=NH)NH$_2$ | 1 | PhCH$_2$CH$_2$ | Ethyl | (+)-pin | |

TABLE 15-continued

Structure: R13-C(=N-N(-(CH2)m-C(=O)-NH-CH(-CH2CH2-X)-B(Y1)(Y2))-N=C-R14

| Ex | X | m | R13 | R14 | Y1Y2 | Phys. Data |
|---|---|---|---|---|---|---|
| 2798 | NH(C=NH)NH2 | 1 | PhCH2CH2 | n-Propyl | (+)-pin | |
| 2799 | NH(C=NH)NH2 | 1 | PhCH2CH2 | n-Butyl | (+)-pin | |
| 2800 | NH(C=NH)NH2 | 1 | PhCH2CH2 | CH2SCH3 | (+)-pin | |
| 2801 | NH(C=NH)NH2 | 1 | PhCH2CH2 | CH2(SO)CH3 | (+)-pin | |
| 2802 | NH(C=NH)NH2 | 1 | PhCH2CH2 | CH2(SO2)CH3 | (+)-pin | |
| 2803 | NH(C=NH)NH2 | 1 | PhCH2CH2 | CH2CH2SCH3 | (+)-pin | |
| 2804 | NH(C=NH)NH2 | 1 | PhCH2CH2 | CH2CH2(SO)CH3 | (+)-pin | |
| 2805 | NH(C=NH)NH2 | 1 | PhCH2CH2 | CH2CH2(SO)2CH3 | (+)-pin | |
| 2806 | NH(C=NH)NH2 | 1 | PhCH2CH2 | CH2CN | (+)-pin | |
| 2807 | NH(C=NH)NH2 | 1 | PhCH2CH2 | CH2CH2CN | (+)-pin | |
| 2808 | NH(C=NH)NH2 | 1 | PhCH2CH2 | CH2CH2CH2CN | (+)-pin | |
| 2809 | NH(C=NH)NH2 | 1 | PhCH2CH2 | CF3 | (+)-pin | |
| 2810 | NH(C=NH)NH2 | 1 | PhCH2CH2 | CF2CF3 | (+)-pin | |
| 2811 | NH(C=NH)NH2 | 1 | PhCH2CH2 | CF2CF2CF3 | (+)-pin | |
| 2812 | NH(C=NH)NH2 | 1 | PhCH2CH2 | CF2CF2CF2CF3 | (+)-pin | |
| 2813 | NH(C=NH)NH2 | 1 | PhCH2CH2 | F5-Ph | (+)-pin | |
| 2814 | NH(C=NH)NH2 | 1 | PhCH2CH2 | CH2CO2H | (+)-pin | |
| 2815 | NH(C=NH)NH2 | 1 | PhCH2CH2 | (CH2)2CO2H | (+)-pin | |
| 2816 | NH(C=NH)NH2 | 1 | PhCH2CH2 | (CH2)3CO2H | (+)-pin | |
| 2817 | NH(C=NH)NH2 | 1 | PhCH2CH2 | CH2CN4H | (+)-pin | |
| 2818 | NH(C=NH)NH2 | 1 | PhCH2CH2 | (CH2)2CN4H | (+)-pin | |
| 2819 | NH(C=NH)NH2 | 1 | PhCH2CH2 | (CH2)3CN4H | (+)-pin | |
| 2820 | NH(C=NH)NH2 | 1 | PhCH2CH2 | CH2NO2 | (+)-pin | |
| 2821 | NH(C=NH)NH2 | 1 | PhCH2CH2 | (CH2)2NO2 | (+)-pin | |
| 2822 | NH(C=NH)NH2 | 1 | PhCH2CH2 | (CH2)3NO2 | (+)-pin | |
| 2823 | NH(C=NH)NH2 | 1 | PhCH2CH2 | CH2OH | (+)-pin | |
| 2824 | NH(C=NH)NH2 | 1 | PhCH2CH2 | (CH2)2OH | (+)-pin | |
| 2825 | NH(C=NH)NH2 | 1 | PhCH2CH2 | (CH2)3OH | (+)-pin | |
| 2826 | NH(C=NH)NH2 | 1 | PhCH2CH2 | CH2CO2Me | (+)-pin | |
| 2827 | NH(C=NH)NH2 | 1 | PhCH2CH2 | (CH2)2CO2Me | (+)-pin | |
| 2828 | NH(C=NH)NH2 | 1 | PhCH2CH2 | (CH2)3CO2Me | (+)-pin | |
| 2829 | NH(C=NH)NH2 | 1 | PhCH2CH2 | 3-NO2-Ph | (+)-pin | |
| 2830 | NH(C=NH)NH2 | 1 | PhCH2CH2 | 4-NO2-Ph | (+)-pin | |
| 2831 | NH(C=NH)NH2 | 1 | PhCH2CH2 | 3-CO2H-Ph | (+)-pin | |
| 2832 | NH(C=NH)NH2 | 1 | PhCH2CH2 | 4-CO2H-Ph | (+)-pin | |
| 2833 | NH(C=NH)NH2 | 1 | PhCH2CH2 | 3-CN4H-Ph | (+)-pin | |
| 2834 | NH(C=NH)NH2 | 1 | PhCH2CH2 | 4-CN4H-Ph | (+)-pin | |
| 2835 | NH(C=NH)NH2 | 1 | PhCH2CH2 | 3-(HOCH2)-Ph | (+)-pin | |
| 2836 | NH(C=NH)NH2 | 1 | PhCH2CH2 | 4-(HOCH2)-Ph | (+)-pin | |
| 2837 | CH2NH2 | 1 | PhCH2CH2 | H | OH, OH | BJ |
| 2838 | CH2NH2 | 1 | PhCH2CH2 | Methyl | OH, OH | |
| 2839 | CH2NH2 | 1 | PhCH2CH2 | Ethyl | OH, OH | |
| 2840 | CH2NH2 | 1 | PhCH2CH2 | n-Propyl | OH, OH | |
| 2841 | CH2NH2 | 1 | PhCH2CH2 | n-Butyl | OH, OH | |
| 2842 | CH2NH2 | 1 | PhCH2CH2 | CH2SCH3 | OH, OH | |
| 2843 | CH2NH2 | 1 | PhCH2CH2 | CH2(SO)CH3 | OH, OH | |
| 2844 | CH2NH2 | 1 | PhCH2CH2 | CH2(SO2)CH3 | OH, OH | |
| 2845 | CH2NH2 | 1 | PhCH2CH2 | CH2CH2SCH3 | OH, OH | |
| 2846 | CH2NH2 | 1 | PhCH2CH2 | CH2CH2(SO)CH3 | OH, OH | |
| 2847 | CH2NH2 | 1 | PhCH2CH2 | CH2CH2(SO)2CH3 | OH, OH | |
| 2848 | CH2NH2 | 1 | PhCH2CH2 | CH2CN | OH, OH | |
| 2849 | CH2NH2 | 1 | PhCH2CH2 | CH2CH2CN | OH, OH | |
| 2850 | CH2NH2 | 1 | PhCH2CH2 | CH2CH2CH2CN | OH, OH | |
| 2851 | CH2NH2 | 1 | PhCH2CH2 | CF3 | OH, OH | |
| 2852 | CH2NH2 | 1 | PhCH2CH2 | CF2CF3 | OH, OH | |
| 2853 | CH2NH2 | 1 | PhCH2CH2 | CF2CF2CF3 | OH, OH | |
| 2854 | CH2NH2 | 1 | PhCH2CH2 | CF2CF2CF2CF3 | OH, OH | |
| 2855 | CH2NH2 | 1 | PhCH2CH2 | F5-Ph | OH, OH | |
| 2856 | CH2NH2 | 1 | PhCH2CH2 | CH2CO2H | OH, OH | |
| 2857 | CH2NH2 | 1 | PhCH2CH2 | (CH2)2CO2H | OH, OH | |
| 2858 | CH2NH2 | 1 | PhCH2CH2 | (CH2)3CO2H | OH, OH | |
| 2859 | CH2NH2 | 1 | PhCH2CH2 | CH2CN4H | OH, OH | |
| 2860 | CH2NH2 | 1 | PhCH2CH2 | (CH2)2CN4H | OH, OH | |
| 2861 | CH2NH2 | 1 | PhCH2CH2 | (CH2)3CN4H | OH, OH | |
| 2862 | CH2NH2 | 1 | PhCH2CH2 | CH2NO2 | OH, OH | |

TABLE 15-continued

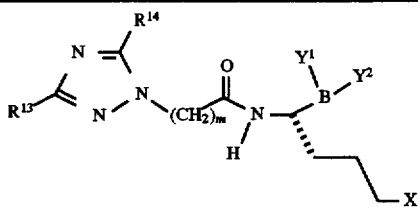

| Ex | X | m | R[13] | R[14] | Y[1]Y[2] | Phys. Data |
|---|---|---|---|---|---|---|
| 2863 | $CH_2NH_2$ | 1 | $PhCH_2CH_2$ | $(CH_2)_2NO_2$ | OH, OH | |
| 2864 | $CH_2NH_2$ | 1 | $PhCH_2CH_2$ | $(CH_2)_3NO_2$ | OH, OH | |
| 2865 | $CH_2NH_2$ | 1 | $PhCH_2CH_2$ | $CH_2OH$ | OH, OH | |
| 2866 | $CH_2NH_2$ | 1 | $PhCH_2CH_2$ | $(CH_2)_2OH$ | OH, OH | |
| 2867 | $CH_2NH_2$ | 1 | $PhCH_2CH_2$ | $(CH_2)_3OH$ | OH, OH | |
| 2868 | $CH_2NH_2$ | 1 | $PhCH_2CH_2$ | $CH_2CO_2Me$ | OH, OH | |
| 2869 | $CH_2NH_2$ | 1 | $PhCH_2CH_2$ | $(CH_2)_2CO_2Me$ | OH, OH | |
| 2870 | $CH_2NH_2$ | 1 | $PhCH_2CH_2$ | $(CH_2)_3CO_2Me$ | OH, OH | |
| 2871 | $CH_2NH_2$ | 1 | $PhCH_2CH_2$ | $3\text{-}NO_2\text{-}Ph$ | OH, OH | |
| 2872 | $CH_2NH_2$ | 1 | $PhCH_2CH_2$ | $4\text{-}NO_2\text{-}Ph$ | OH, OH | |
| 2873 | $CH_2NH_2$ | 1 | $PhCH_2CH_2$ | $3\text{-}CO_2H\text{-}Ph$ | OH, OH | |
| 2874 | $CH_2NH_2$ | 1 | $PhCH_2CH_2$ | $4\text{-}CO_2H\text{-}Ph$ | OH, OH | |
| 2875 | $CH_2NH_2$ | 1 | $PhCH_2CH_2$ | $3\text{-}CN_4H\text{-}Ph$ | OH, OH | |
| 2876 | $CH_2NH_2$ | 1 | $PhCH_2CH_2$ | $4\text{-}CN_4H\text{-}Ph$ | OH, OH | |
| 2877 | $CH_2NH_2$ | 1 | $PhCH_2CH_2$ | $3\text{-}(HOCH_2)\text{-}Ph$ | OH, OH | |
| 2878 | $CH_2NH_2$ | 1 | $PhCH_2CH_2$ | $4\text{-}(HOCH_2)\text{-}Ph$ | OH, OH | |
| 2879 | $NH(C=NH)NH_2$ | 1 | $PhCH_2CH_2$ | H | OH, OH | |
| 2880 | $NH(C=NH)NH_2$ | 1 | $PhCH_2CH_2$ | Methyl | OH, OH | |
| 2881 | $NH(C=NH)NH_2$ | 1 | $PhCH_2CH_2$ | Ethyl | OH, OH | |
| 2882 | $NH(C=NH)NH_2$ | 1 | $PhCH_2CH_2$ | n-Propyl | OH, OH | |
| 2883 | $NH(C=NH)NH_2$ | 1 | $PhCH_2CH_2$ | n-Butyl | OH, OH | |
| 2884 | $NH(C=NH)NH_2$ | 1 | $PhCH_2CH_2$ | $CH_2SCH_3$ | OH, OH | |
| 2885 | $NH(C=NH)NH_2$ | 1 | $PhCH_2CH_2$ | $CH_2(SO)CH_3$ | OH, OH | |
| 2886 | $NH(C=NH)NH_2$ | 1 | $PhCH_2CH_2$ | $CH_2(SO_2)CH_3$ | OH, OH | |
| 2887 | $NH(C=NH)NH_2$ | 1 | $PhCH_2CH_2$ | $CH_2CH_2SCH_3$ | OH, OH | |
| 2888 | $NH(C=NH)NH_2$ | 1 | $PhCH_2CH_2$ | $CH_2CH_2(SO)CH_3$ | OH, OH | |
| 2889 | $NH(C=NH)NH_2$ | 1 | $PhCH_2CH_2$ | $CH_2CH_2(SO)_2CH_3$ | OH, OH | |
| 2890 | $NH(C=NH)NH_2$ | 1 | $PhCH_2CH_2$ | $CH_2CN$ | OH, OH | |
| 2891 | $NH(C=NH)NH_2$ | 1 | $PhCH_2CH_2$ | $CH_2CH_2CN$ | OH, OH | |
| 2892 | $NH(C=NH)NH_2$ | 1 | $PhCH_2CH_2$ | $CH_2CH_2CH_2CN$ | OH, OH | |
| 2893 | $NH(C=NH)NH_2$ | 1 | $PhCH_2CH_2$ | $CF_3$ | OH, OH | |
| 2894 | $NH(C=NH)NH_2$ | 1 | $PhCH_2CH_2$ | $CF_2CF_3$ | OH, OH | |
| 2895 | $NH(C=NH)NH_2$ | 1 | $PhCH_2CH_2$ | $CF_2CF_2CF_3$ | OH, OH | |
| 2896 | $NH(C=NH)NH_2$ | 1 | $PhCH_2CH_2$ | $CF_2CF_2CF_2CF_3$ | OH, OH | |
| 2897 | $NH(C=NH)NH_2$ | 1 | $PhCH_2CH_2$ | $F_5\text{-}Ph$ | OH, OH | |
| 2898 | $NH(C=NH)NH_2$ | 1 | $PhCH_2CH_2$ | $CH_2CO_2H$ | OH, OH | |
| 2899 | $NH(C=NH)NH_2$ | 1 | $PhCH_2CH_2$ | $(CH_2)_2CO_2H$ | OH, OH | |
| 2900 | $NH(C=NH)NH_2$ | 1 | $PhCH_2CH_2$ | $(CH_2)_3CO_2H$ | OH, OH | |
| 2901 | $NH(C=NH)NH_2$ | 1 | $PhCH_2CH_2$ | $CH_2CN_4H$ | OH, OH | |
| 2902 | $NH(C=NH)NH_2$ | 1 | $PhCH_2CH_2$ | $(CH_2)_2CN_4H$ | OH, OH | |
| 2903 | $NH(C=NH)NH_2$ | 1 | $PhCH_2CH_2$ | $(CH_2)_3CN_4H$ | OH, OH | |
| 2904 | $NH(C=NH)NH_2$ | 1 | $PhCH_2CH_2$ | $CH_2NO_2$ | OH, OH | |
| 2905 | $NH(C=NH)NH_2$ | 1 | $PhCH_2CH_2$ | $(CH_2)_2NO_2$ | OH, OH | |
| 2906 | $NH(C=NH)NH_2$ | 1 | $PhCH_2CH_2$ | $(CH_2)_3NO_2$ | OH, OH | |
| 2907 | $NH(C=NH)NH_2$ | 1 | $PhCH_2CH_2$ | $CH_2OH$ | OH, OH | |
| 2908 | $NH(C=NH)NH_2$ | 1 | $PhCH_2CH_2$ | $(CH_2)_2OH$ | OH, OH | |
| 2909 | $NH(C=NH)NH_2$ | 1 | $PhCH_2CH_2$ | $(CH_2)_3OH$ | OH, OH | |
| 2910 | $NH(C=NH)NH_2$ | 1 | $PhCH_2CH_2$ | $CH_2CO_2Me$ | OH, OH | |
| 2911 | $NH(C=NH)NH_2$ | 1 | $PhCH_2CH_2$ | $(CH_2)_2CO_2Me$ | OH, OH | |
| 2912 | $NH(C=NH)NH_2$ | 1 | $PhCH_2CH_2$ | $(CH_2)_3CO_2Me$ | OH, OH | |
| 2913 | $NH(C=NH)NH_2$ | 1 | $PhCH_2CH_2$ | $3\text{-}NO_2\text{-}Ph$ | OH, OH | |
| 2914 | $NH(C=NH)NH_2$ | 1 | $PhCH_2CH_2$ | $4\text{-}NO_2\text{-}Ph$ | OH, OH | |
| 2915 | $NH(C=NH)NH_2$ | 1 | $PhCH_2CH_2$ | $3\text{-}CO_2H\text{-}Ph$ | OH, OH | |
| 2916 | $NH(C=NH)NH_2$ | 1 | $PhCH_2CH_2$ | $4\text{-}CO_2H\text{-}Ph$ | OH, OH | |
| 2917 | $NH(C=NH)NH_2$ | 1 | $PhCH_2CH_2$ | $3\text{-}CN_4H\text{-}Ph$ | OH, OH | |
| 2918 | $NH(C=NH)NH_2$ | 1 | $PhCH_2CH_2$ | $4\text{-}CN_4H\text{-}Ph$ | OH, OH | |
| 2919 | $NH(C=NH)NH_2$ | 1 | $PhCH_2CH_2$ | $3\text{-}(HOCH_2)\text{-}Ph$ | OH, OH | |
| 2920 | $NH(C=NH)NH_2$ | 1 | $PhCH_2CH_2$ | $4\text{-}(HOCH_2)\text{-}Ph$ | OH, OH | |
| 2921 | $-S-(C=NH)NH_2$ | 1 | $PhCH_2CH_2$ | H | (+)-pin | |
| 2922 | $-S-(C=NH)NH_2$ | 1 | $PhCH_2CH_2$ | Methyl | (+)-pin | |
| 2923 | $-S-(C=NH)NH_2$ | 1 | $PhCH_2CH_2$ | Ethyl | (+)-pin | |
| 2924 | $-S-(C=NH)NH_2$ | 1 | $PhCH_2CH_2$ | n-Propyl | (+)-pin | |
| 2925 | $-S-(C=NH)NH_2$ | 1 | $PhCH_2CH_2$ | n-Butyl | (+)-pin | |
| 2926 | $-S-(C=NH)NH_2$ | 1 | $PhCH_2CH_2$ | $CH_2SCH_3$ | (+)-pin | |
| 2927 | $-S-(C=NH)NH_2$ | 1 | $PhCH_2CH_2$ | $CH_2(SO)CH_3$ | (+)-pin | |

TABLE 15-continued

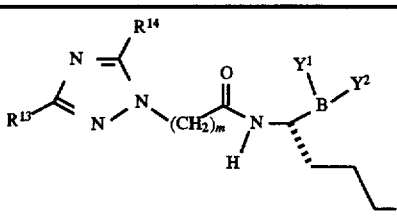

| Ex | X | m | R[13] | R[14] | Y[1]Y[2] | Phys. Data |
|---|---|---|---|---|---|---|
| 2928 | $-S-(C=NH)NH_2$ | 1 | $PhCH_2CH_2$ | $CH_2(SO_2)CH_3$ | (+)-pin | |
| 2929 | $-S-(C=NH)NH_2$ | 1 | $PhCH_2CH_2$ | $CH_2CH_2SCH_3$ | (+)-pin | |
| 2930 | $-S-(C=NH)NH_2$ | 1 | $PhCH_2CH_2$ | $CH_2CH_2(SO)CH_3$ | (+)-pin | |
| 2931 | $-S-(C=NH)NH_2$ | 1 | $PhCH_2CH_2$ | $CH_2CH_2(SO)_2CH_3$ | (+)-pin | |
| 2932 | $-S-(C=NH)NH_2$ | 1 | $PhCH_2CH_2$ | $CH_2CN$ | (+)-pin | |
| 2933 | $-S-(C=NH)NH_2$ | 1 | $PhCH_2CH_2$ | $CH_2CH_2CN$ | (+)-pin | |
| 2934 | $-S-(C=NH)NH_2$ | 1 | $PhCH_2CH_2$ | $CH_2CH_2CH_2CN$ | (+)-pin | |
| 2935 | $-S-(C=NH)NH_2$ | 1 | $PhCH_2CH_2$ | $CF_3$ | (+)-pin | |
| 2936 | $-S-(C=NH)NH_2$ | 1 | $PhCH_2CH_2$ | $CF_2CF_3$ | (+)-pin | |
| 2937 | $-S-(C=NH)NH_2$ | 1 | $PhCH_2CH_2$ | $CF_2CF_2CF_3$ | (+)-pin | |
| 2938 | $-S-(C=NH)NH_2$ | 1 | $PhCH_2CH_2$ | $CF_2CF_2CF_2CF_3$ | (+)-pin | |
| 2939 | $-S-(C=NH)NH_2$ | 1 | $PhCH_2CH_2$ | $F_5$-Ph | (+)-pin | |
| 2940 | $-S-(C=NH)NH_2$ | 1 | $PhCH_2CH_2$ | $CH_2CO_2H$ | (+)-pin | |
| 2941 | $-S-(C=NH)NH_2$ | 1 | $PhCH_2CH_2$ | $(CH_2)_2CO_2H$ | (+)-pin | |
| 2942 | $-S-(C=NH)NH_2$ | 1 | $PhCH_2CH_2$ | $(CH_2)_3CO_2H$ | (+)-pin | |
| 2943 | $-S-(C=NH)NH_2$ | 1 | $PhCH_2CH_2$ | $CH_2CN_4H$ | (+)-pin | |
| 2944 | $-S-(C=NH)NH_2$ | 1 | $PhCH_2CH_2$ | $(CH_2)_2CN_4H$ | (+)-pin | |
| 2945 | $-S-(C=NH)NH_2$ | 1 | $PhCH_2CH_2$ | $(CH_2)_3CN_4H$ | (+)-pin | |
| 2946 | $-S-(C=NH)NH_2$ | 1 | $PhCH_2CH_2$ | $CH_2NO_2$ | (+)-pin | |
| 2947 | $-S-(C=NH)NH_2$ | 1 | $PhCH_2CH_2$ | $(CH_2)_2NO_2$ | (+)-pin | |
| 2948 | $-S-(C=NH)NH_2$ | 1 | $PhCH_2CH_2$ | $(CH_2)_3NO_2$ | (+)-pin | |
| 2949 | $-S-(C=NH)NH_2$ | 1 | $PhCH_2CH_2$ | $CH_2OH$ | (+)-pin | |
| 2950 | $-S-(C=NH)NH_2$ | 1 | $PhCH_2CH_2$ | $(CH_2)_2OH$ | (+)-pin | |
| 2951 | $-S-(C=NH)NH_2$ | 1 | $PhCH_2CH_2$ | $(CH_2)_3OH$ | (+)-pin | |
| 2952 | $-S-(C=NH)NH_2$ | 1 | $PhCH_2CH_2$ | $CH_2CO_2Me$ | (+)-pin | |
| 2953 | $-S-(C=NH)NH_2$ | 1 | $PhCH_2CH_2$ | $(CH_2)_2CO_2Me$ | (+)-pin | |
| 2954 | $-S-(C=NH)NH_2$ | 1 | $PhCH_2CH_2$ | $(CH_2)_3CO_2Me$ | (+)-pin | |
| 2955 | $-S-(C=NH)NH_2$ | 1 | $PhCH_2CH_2$ | 3-$NO_2$-Ph | (+)-pin | |
| 2956 | $-S-(C=NH)NH_2$ | 1 | $PhCH_2CH_2$ | 4-$NO_2$-Ph | (+)-pin | |
| 2957 | $-S-(C=NH)NH_2$ | 1 | $PhCH_2CH_2$ | 3-$CO_2H$-Ph | (+)-pin | |
| 2958 | $-S-(C=NH)NH_2$ | 1 | $PhCH_2CH_2$ | 4-$CO_2H$-Ph | (+)-pin | |
| 2959 | $-S-(C=NH)NH_2$ | 1 | $PhCH_2CH_2$ | 3-$CN_4H$-Ph | (+)-pin | |
| 2960 | $-S-(C=NH)NH_2$ | 1 | $PhCH_2CH_2$ | 4-$CN_4H$-Ph | (+)-pin | |
| 2961 | $-S-(C=NH)NH_2$ | 1 | $PhCH_2CH_2$ | 3-$(HOCH_2)$-Ph | (+)-pin | |
| 2962 | $-S-(C=NH)NH_2$ | 1 | $PhCH_2CH_2$ | 4-$(HOCH_2)$-Ph | (+)-pin | |
| 2963 | $-S-(C=NH)NH_2$ | 1 | $PhCH_2CH_2$ | H | OH, OH | |
| 2964 | $-S-(C=NH)NH_2$ | 1 | $PhCH_2CH_2$ | Methyl | OH, OH | |
| 2965 | $-S-(C=NH)NH_2$ | 1 | $PhCH_2CH_2$ | Ethyl | OH, OH | |
| 2966 | $-S-(C=NH)NH_2$ | 1 | $PhCH_2CH_2$ | n-Propyl | OH, OH | |
| 2967 | $-S-(C=NH)NH_2$ | 1 | $PhCH_2CH_2$ | n-Butyl | OH, OH | |
| 2968 | $-S-(C=NH)NH_2$ | 1 | $PhCH_2CH_2$ | $CH_2SCH_3$ | OH, OH | |
| 2969 | $-S-(C=NH)NH_2$ | 1 | $PhCH_2CH_2$ | $CH_2(SO)CH_3$ | OH, OH | |
| 2970 | $-S-(C=NH)NH_2$ | 1 | $PhCH_2CH_2$ | $CH_2(SO_2)CH_3$ | OH, OH | |
| 2971 | $-S-(C=NH)NH_2$ | 1 | $PhCH_2CH_2$ | $CH_2CH_2SCH_3$ | OH, OH | |
| 2972 | $-S-(C=NH)NH_2$ | 1 | $PhCH_2CH_2$ | $CH_2CH_2(SO)CH_3$ | OH, OH | |
| 2973 | $-S-(C=NH)NH_2$ | 1 | $PhCH_2CH_2$ | $CH_2CH_2(SO)_2CH_3$ | OH, OH | |
| 2974 | $-S-(C=NH)NH_2$ | 1 | $PhCH_2CH_2$ | $CH_2CN$ | OH, OH | |
| 2975 | $-S-(C=NH)NH_2$ | 1 | $PhCH_2CH_2$ | $CH_2CH_2CN$ | OH, OH | |
| 2976 | $-S-(C=NH)NH_2$ | 1 | $PhCH_2CH_2$ | $CH_2CH_2CH_2CN$ | OH, OH | |
| 2977 | $-S-(C=NH)NH_2$ | 1 | $PhCH_2CH_2$ | $CF_3$ | OH, OH | |
| 2978 | $-S-(C=NH)NH_2$ | 1 | $PhCH_2CH_2$ | $CF_2CF_3$ | OH, OH | |
| 2979 | $-S-(C=NH)NH_2$ | 1 | $PhCH_2CH_2$ | $CF_2CF_2CF_3$ | OH, OH | |
| 2980 | $-S-(C=NH)NH_2$ | 1 | $PhCH_2CH_2$ | $CF_2CF_2CF_2CF_3$ | OH, OH | |
| 2981 | $-S-(C=NH)NH_2$ | 1 | $PhCH_2CH_2$ | $F_5$-Ph | OH, OH | |
| 2982 | $-S-(C=NH)NH_2$ | 1 | $PhCH_2CH_2$ | $CH_2CO_2H$ | OH, OH | |
| 2983 | $-S-(C=NH)NH_2$ | 1 | $PhCH_2CH_2$ | $(CH_2)_2CO_2H$ | OH, OH | |
| 2984 | $-S-(C=NH)NH_2$ | 1 | $PhCH_2CH_2$ | $(CH_2)_3CO_2H$ | OH, OH | |
| 2985 | $-S-(C=NH)NH_2$ | 1 | $PhCH_2CH_2$ | $CH_2CN_4H$ | OH, OH | |
| 2986 | $-S-(C=NH)NH_2$ | 1 | $PhCH_2CH_2$ | $(CH_2)_2CN_4H$ | OH, OH | |
| 2987 | $-S-(C=NH)NH_2$ | 1 | $PhCH_2CH_2$ | $(CH_2)_3CN_4H$ | OH, OH | |
| 2988 | $-S-(C=NH)NH_2$ | 1 | $PhCH_2CH_2$ | $CH_2NO_2$ | OH, OH | |
| 2989 | $-S-(C=NH)NH_2$ | 1 | $PhCH_2CH_2$ | $(CH_2)_2NO_2$ | OH, OH | |
| 2990 | $-S-(C=NH)NH_2$ | 1 | $PhCH_2CH_2$ | $(CH_2)_3NO_2$ | OH, OH | |
| 2991 | $-S-(C=NH)NH_2$ | 1 | $PhCH_2CH_2$ | $CH_2OH$ | OH, OH | |
| 2992 | $-S-(C=NH)NH_2$ | 1 | $PhCH_2CH_2$ | $(CH_2)_2OH$ | OH, OH | |

TABLE 15-continued

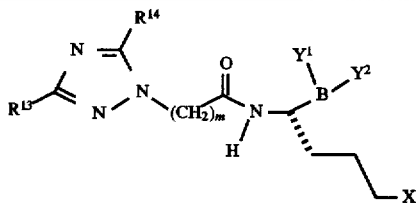

| Ex | X | m | R¹³ | R¹⁴ | Y¹Y² | Phys. Data |
|---|---|---|---|---|---|---|
| 2993 | —S—(C=NH)NH₂ | 1 | PhCH₂CH₂ | (CH₂)₃OH | OH, OH | |
| 2994 | —S—(C=NH)NH₂ | 1 | PhCH₂CH₂ | CH₂CO₂Me | OH, OH | |
| 2995 | —S—(C=NH)NH₂ | 1 | PhCH₂CH₂ | (CH₂)₂CO₂Me | OH, OH | |
| 2996 | —S—(C=NH)NH₂ | 1 | PhCH₂CH₂ | (CH₂)₃CO₂Me | OH, OH | |
| 2997 | —S—(C=NH)NH₂ | 1 | PhCH₂CH₂ | 3-NO₂-Ph | OH, OH | |
| 2998 | —S—(C=NH)NH₂ | 1 | PhCH₂CH₂ | 4-NO₂-Ph | OH, OH | |
| 2999 | —S—(C=NH)NH₂ | 1 | PhCH₂CH₂ | 3-CO₂H-Ph | OH, OH | |
| 3000 | —S—(C=NH)NH₂ | 1 | PhCH₂CH₂ | 4-CO₂H-Ph | OH, OH | |
| 3001 | —S—(C=NH)NH₂ | 1 | PhCH₂CH₂ | 3-CN₄H-Ph | OH, OH | |
| 3002 | —S—(C=NH)NH₂ | 1 | PhCH₂CH₂ | 4-CN₄H-Ph | OH, OH | |
| 3003 | —S—(C=NH)NH₂ | 1 | PhCH₂CH₂ | 3-(HOCH₂)-Ph | OH, OH | |
| 3004 | —S—(C=NH)NH₂ | 1 | PhCH₂CH₂ | 4-(HOCH₂)-Ph | OH, OH | |
| 3005 | OMe | 1 | PhCH₂CH₂ | H | (+)-pin | |
| 3006 | OMe | 1 | PhCH₂CH₂ | Methyl | (+)-pin | |
| 3007 | OMe | 1 | PhCH₂CH₂ | Ethyl | (+)-pin | |
| 3008 | OMe | 1 | PhCH₂CH₂ | n-Propyl | (+)-pin | |
| 3009 | OMe | 1 | PhCH₂CH₂ | n-Butyl | (+)-pin | |
| 3010 | OMe | 1 | PhCH₂CH₂ | CH₂SCH₃ | (+)-pin | |
| 3011 | OMe | 1 | PhCH₂CH₂ | CH₂(SO)CH₃ | (+)-pin | |
| 3012 | OMe | 1 | PhCH₂CH₂ | CH₂(SO₂)CH₃ | (+)-pin | |
| 3013 | OMe | 1 | PhCH₂CH₂ | CH₂CH₂SCH₃ | (+)-pin | |
| 3014 | OMe | 1 | PhCH₂CH₂ | CH₂CH₂(SO)CH₃ | (+)-pin | |
| 3015 | OMe | 1 | PhCH₂CH₂ | CH₂CH₂(SO)₂CH₃ | (+)-pin | |
| 3016 | OMe | 1 | PhCH₂CH₂ | CH₂CN | (+)-pin | |
| 3017 | OMe | 1 | PhCH₂CH₂ | CH₂CH₂CN | (+)-pin | |
| 3018 | OMe | 1 | PhCH₂CH₂ | CH₂CH₂CH₂CN | (+)-pin | |
| 3019 | OMe | 1 | PhCH₂CH₂ | CF₃ | (+)-pin | |
| 3020 | OMe | 1 | PhCH₂CH₂ | CF₂CF₃ | (+)-pin | |
| 3021 | OMe | 1 | PhCH₂CH₂ | CF₂CF₂CF₃ | (+)-pin | |
| 3022 | OMe | 1 | PhCH₂CH₂ | CF₂CF₂CF₂CF₃ | (+)-pin | |
| 3023 | OMe | 1 | PhCH₂CH₂ | F₅-Ph | (+)-pin | |
| 3024 | OMe | 1 | PhCH₂CH₂ | CH₂CO₂H | (+)-pin | |
| 3025 | OMe | 1 | PhCH₂CH₂ | (CH₂)₂CO₂H | (+)-pin | |
| 3026 | OMe | 1 | PhCH₂CH₂ | (CH₂)₃CO₂H | (+)-pin | |
| 3027 | OMe | 1 | PhCH₂CH₂ | CH₂CN₄H | (+)-pin | |
| 3028 | OMe | 1 | PhCH₂CH₂ | (CH₂)₂CN₄H | (+)-pin | |
| 3029 | OMe | 1 | PhCH₂CH₂ | (CH₂)₃CN₄H | (+)-pin | |
| 3030 | OMe | 1 | PhCH₂CH₂ | CH₂NO₂ | (+)-pin | |
| 3031 | OMe | 1 | PhCH₂CH₂ | (CH₂)₂NO₂ | (+)-pin | |
| 3032 | OMe | 1 | PhCH₂CH₂ | (CH₂)₃NO₂ | (+)-pin | |
| 3033 | OMe | 1 | PhCH₂CH₂ | CH₂OH | (+)-pin | |
| 3034 | OMe | 1 | PhCH₂CH₂ | (CH₂)₂OH | (+)-pin | |
| 3035 | OMe | 1 | PhCH₂CH₂ | (CH₂)₃OH | (+)-pin | |
| 3036 | OMe | 1 | PhCH₂CH₂ | CH₂CO₂Me | (+)-pin | |
| 3037 | OMe | 1 | PhCH₂CH₂ | (CH₂)₂CO₂Me | (+)-pin | |
| 3038 | OMe | 1 | PhCH₂CH₂ | (CH₂)₃CO₂Me | (+)-pin | |
| 3039 | OMe | 1 | PhCH₂CH₂ | 3-NO₂-Ph | (+)-pin | |
| 3040 | OMe | 1 | PhCH₂CH₂ | 4-NO₂-Ph | (+)-pin | |
| 3041 | OMe | 1 | PhCH₂CH₂ | 3-CO₂H-Ph | (+)-pin | |
| 3042 | OMe | 1 | PhCH₂CH₂ | 4-CO₂H-Ph | (+)-pin | |
| 3043 | OMe | 1 | PhCH₂CH₂ | 3-CN₄H-Ph | (+)-pin | |
| 3044 | OMe | 1 | PhCH₂CH₂ | 4-CN₄H-Ph | (+)-pin | |
| 3045 | OMe | 1 | PhCH₂CH₂ | 3-(HOCH₂)-Ph | (+)-pin | |
| 3046 | OMe | 1 | PhCH₂CH₂ | 4-(HOCH₂)-Ph | (+)-pin | |
| 3047 | OMe | 1 | PhCH₂CH₂ | H | OH, OH | |
| 3048 | OMe | 1 | PhCH₂CH₂ | Methyl | OH, OH | |
| 3049 | OMe | 1 | PhCH₂CH₂ | Ethyl | OH, OH | |
| 3050 | OMe | 1 | PhCH₂CH₂ | n-Propyl | OH, OH | |
| 3051 | OMe | 1 | PhCH₂CH₂ | n-Butyl | OH, OH | |
| 3052 | OMe | 1 | PhCH₂CH₂ | CH₂SCH₃ | OH, OH | |
| 3053 | OMe | 1 | PhCH₂CH₂ | CH₂(SO)CH₃ | OH, OH | |
| 3054 | OMe | 1 | PhCH₂CH₂ | CH₂(SO₂)CH₃ | OH, OH | |
| 3055 | OMe | 1 | PhCH₂CH₂ | CH₂CH₂SCH₃ | OH, OH | |
| 3056 | OMe | 1 | PhCH₂CH₂ | CH₂CH₂(SO)CH₃ | OH, OH | |
| 3057 | OMe | 1 | PhCH₂CH₂ | CH₂CH₂(SO)₂CH₃ | OH, OH | |

TABLE 15-continued

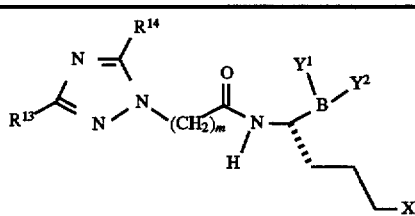

| Ex | X | m | R¹³ | R¹⁴ | Y¹Y² | Phys. Data |
|---|---|---|---|---|---|---|
| 3058 | OMe | 1 | PhCH₂CH₂ | CH₂CN | OH, OH | |
| 3059 | OMe | 1 | PhCH₂CH₂ | CH₂CH₂CN | OH, OH | |
| 3060 | OMe | 1 | PhCH₂CH₂ | CH₂CH₂CH₂CN | OH, OH | |
| 3061 | OMe | 1 | PhCH₂CH₂ | CF₃ | OH, OH | |
| 3062 | OMe | 1 | PhCH₂CH₂ | CF₂CF₃ | OH, OH | |
| 3063 | OMe | 1 | PhCH₂CH₂ | CF₂CF₂CF₃ | OH, OH | |
| 3064 | OMe | 1 | PhCH₂CH₂ | CF₂CF₂CF₂CF₃ | OH, OH | |
| 3065 | OMe | 1 | PhCH₂CH₂ | F₅-Ph | OH, OH | |
| 3066 | OMe | 1 | PhCH₂CH₂ | CH₂CO₂H | OH, OH | |
| 3067 | OMe | 1 | PhCH₂CH₂ | (CH₂)₂CO₂H | OH, OH | |
| 3068 | OMe | 1 | PhCH₂CH₂ | (CH₂)₃CO₂H | OH, OH | |
| 3069 | OMe | 1 | PhCH₂CH₂ | CH₂CN₄H | OH, OH | |
| 3070 | OMe | 1 | PhCH₂CH₂ | (CH₂)₂CN₄H | OH, OH | |
| 3071 | OMe | 1 | PhCH₂CH₂ | (CH₂)₃CN₄H | OH, OH | |
| 3072 | OMe | 1 | PhCH₂CH₂ | CH₂NO₂ | OH, OH | |
| 3073 | OMe | 1 | PhCH₂CH₂ | (CH₂)₂NO₂ | OH, OH | |
| 3074 | OMe | 1 | PhCH₂CH₂ | (CH₂)₃NO₂ | OH, OH | |
| 3075 | OMe | 1 | PhCH₂CH₂ | CH₂OH | OH, OH | |
| 3076 | OMe | 1 | PhCH₂CH₂ | (CH₂)₂OH | OH, OH | |
| 3077 | OMe | 1 | PhCH₂CH₂ | (CH₂)₃OH | OH, OH | |
| 3078 | OMe | 1 | PhCH₂CH₂ | CH₂CO₂Me | OH, OH | |
| 3079 | OMe | 1 | PhCH₂CH₂ | (CH₂)₂CO₂Me | OH, OH | |
| 3080 | OMe | 1 | PhCH₂CH₂ | (CH₂)₃CO₂Me | OH, OH | |
| 3081 | OMe | 1 | PhCH₂CH₂ | 3-NO₂-Ph | OH, OH | |
| 3082 | OMe | 1 | PhCH₂CH₂ | 4-NO₂-Ph | OH, OH | |
| 3083 | OMe | 1 | PhCH₂CH₂ | 3-CO₂H-Ph | OH, OH | |
| 3084 | OMe | 1 | PhCH₂CH₂ | 4-CO₂H-Ph | OH, OH | |
| 3085 | OMe | 1 | PhCH₂CH₂ | 3-CN₄H-Ph | OH, OH | |
| 3086 | OMe | 1 | PhCH₂CH₂ | 4-CN₄H-Ph | OH, OH | |
| 3087 | OMe | 1 | PhCH₂CH₂ | 3-(HOCH₂)-Ph | OH, OH | |
| 3088 | OMe | 1 | PhCH₂CH₂ | 4-(HOCH₂)-Ph | OH, OH | |
| 3089 | NH(C=NH)NH₂ | 1 | Ph | H | (+)-pin | |
| 3090 | NH(C=NH)NH₂ | 1 | Ph | Methyl | (+)-pin | |
| 3091 | NH(C=NH)NH₂ | 1 | Ph | Ethyl | (+)-pin | |
| 3092 | NH(C=NH)NH₂ | 1 | Ph | n-Propyl | (+)-pin | |
| 3093 | NH(C=NH)NH₂ | 1 | Ph | n-Butyl | (+)-pin | |
| 3094 | NH(C=NH)NH₂ | 1 | Ph | CH₂SCH₃ | (+)-pin | |
| 3095 | NH(C=NH)NH₂ | 1 | Ph | CH₂(SO)CH₃ | (+)-pin | |
| 3096 | NH(C=NH)NH₂ | 1 | Ph | CH₂(SO₂)CH₃ | (+)-pin | |
| 3097 | NH(C=NH)NH₂ | 1 | Ph | CH₂CH₂SCH₃ | (+)-pin | |
| 3098 | NH(C=NH)NH₂ | 1 | Ph | CH₂CH₂(SO)CH₃ | (+)-pin | |
| 3099 | NH(C=NH)NH₂ | 1 | Ph | CH₂CH₂(SO)₂CH₃ | (+)-pin | |
| 3100 | NH(C=NH)NH₂ | 1 | Ph | CH₂CN | (+)-pin | |
| 3101 | NH(C=NH)NH₂ | 1 | Ph | CH₂CH₂CN | (+)-pin | |
| 3102 | NH(C=NH)NH₂ | 1 | Ph | CH₂CH₂CH₂CN | (+)-pin | |
| 3103 | NH(C=NH)NH₂ | 1 | Ph | CF₃ | (+)-pin | |
| 3104 | NH(C=NH)NH₂ | 1 | Ph | CF₂CF₃ | (+)-pin | |
| 3105 | NH(C=NH)NH₂ | 1 | Ph | CF₂CF₂CF₃ | (+)-pin | |
| 3106 | NH(C=NH)NH₂ | 1 | Ph | CF₂CF₂CF₂CF₃ | (+)-pin | |
| 3107 | NH(C=NH)NH₂ | 1 | Ph | F₅-Ph | (+)-pin | |
| 3108 | NH(C=NH)NH₂ | 1 | Ph | CH₂CO₂H | (+)-pin | |
| 3109 | NH(C=NH)NH₂ | 1 | Ph | (CH₂)₂CO₂H | (+)-pin | |
| 3110 | NH(C=NH)NH₂ | 1 | Ph | (CH₂)₃CO₂H | (+)-pin | |
| 3111 | NH(C=NH)NH₂ | 1 | Ph | CH₂CN₄H | (+)-pin | |
| 3112 | NH(C=NH)NH₂ | 1 | Ph | (CH₂)₂CN₄H | (+)-pin | |
| 3113 | NH(C=NH)NH₂ | 1 | Ph | (CH₂)₃CN₄H | (+)-pin | |
| 3114 | NH(C=NH)NH₂ | 1 | Ph | CH₂NO₂ | (+)-pin | |
| 3115 | NH(C=NH)NH₂ | 1 | Ph | (CH₂)₂NO₂ | (+)-pin | |
| 3116 | NH(C=NH)NH₂ | 1 | Ph | (CH₂)₃NO₂ | (+)-pin | |
| 3117 | NH(C=NH)NH₂ | 1 | Ph | CH₂OH | (+)-pin | |
| 3118 | NH(C=NH)NH₂ | 1 | Ph | (CH₂)₂OH | (+)-pin | |
| 3119 | NH(C=NH)NH₂ | 1 | Ph | (CH₂)₃OH | (+)-pin | |
| 3120 | NH(C=NH)NH₂ | 1 | Ph | CH₂CO₂Me | (+)-pin | |
| 3121 | NH(C=NH)NH₂ | 1 | Ph | (CH₂)₂CO₂Me | (+)-pin | |
| 3122 | NH(C=NH)NH₂ | 1 | Ph | (CH₂)₃CO₂Me | (+)-pin | |

TABLE 15-continued

| Ex | X | m | R[13] | R[14] | Y[1]Y[2] | Phys. Data |
|---|---|---|---|---|---|---|
| 3123 | NH(C=NH)NH$_2$ | 1 | Ph | 3-NO$_2$-Ph | (+)-pin | |
| 3124 | NH(C=NH)NH$_2$ | 1 | Ph | 4-NO$_2$-Ph | (+)-pin | |
| 3125 | NH(C=NH)NH$_2$ | 1 | Ph | 3-CO$_2$H-Ph | (+)-pin | |
| 3126 | NH(C=NH)NH$_2$ | 1 | Ph | 4-CO$_2$H-Ph | (+)-pin | |
| 3127 | NH(C=NH)NH$_2$ | 1 | Ph | 3-CN$_4$H-Ph | (+)-pin | |
| 3128 | NH(C=NH)NH$_2$ | 1 | Ph | 4-CN$_4$H-Ph | (+)-pin | |
| 3129 | NH(C=NH)NH$_2$ | 1 | Ph | 3-(HOCH$_2$)-Ph | (+)-pin | |
| 3130 | NH(C=NH)NH$_2$ | 1 | Ph | 4-(HOCH$_2$)-Ph | (+)-pin | |
| 3131 | NH(C=NH)NH$_2$ | 1 | Ph | H | OH, OH | |
| 3132 | NH(C=NH)NH$_2$ | 1 | Ph | Methyl | OH, OH | |
| 3133 | NH(C=NH)NH$_2$ | 1 | Ph | Ethyl | OH, OH | |
| 3134 | NH(C=NH)NH$_2$ | 1 | Ph | n-Propyl | OH, OH | |
| 3135 | NH(C=NH)NH$_2$ | 1 | Ph | n-Butyl | OH, OH | |
| 3136 | NH(C=NH)NH$_2$ | 1 | Ph | CH$_2$SCH$_3$ | OH, OH | |
| 3137 | NH(C=NH)NH$_2$ | 1 | Ph | CH$_2$(SO)CH$_3$ | OH, OH | |
| 3138 | NH(C=NH)NH$_2$ | 1 | Ph | CH$_2$(SO$_2$)CH$_3$ | OH, OH | |
| 3139 | NH(C=NH)NH$_2$ | 1 | Ph | CH$_2$CH$_2$SCH$_3$ | OH, OH | |
| 3140 | NH(C=NH)NH$_2$ | 1 | Ph | CH$_2$CH$_2$(SO)CH$_3$ | OH, OH | |
| 3141 | NH(C=NH)NH$_2$ | 1 | Ph | CH$_2$CH$_2$(SO)$_2$CH$_3$ | OH, OH | |
| 3142 | NH(C=NH)NH$_2$ | 1 | Ph | CH$_2$CN | OH, OH | |
| 3143 | NH(C=NH)NH$_2$ | 1 | Ph | CH$_2$CH$_2$CN | OH, OH | |
| 3144 | NH(C=NH)NH$_2$ | 1 | Ph | CH$_2$CH$_2$CH$_2$CN | OH, OH | |
| 3145 | NH(C=NH)NH$_2$ | 1 | Ph | CF$_3$ | OH, OH | |
| 3146 | NH(C=NH)NH$_2$ | 1 | Ph | CF$_2$CF$_3$ | OH, OH | |
| 3147 | NH(C=NH)NH$_2$ | 1 | Ph | CF$_2$CF$_2$CF$_3$ | OH, OH | |
| 3148 | NH(C=NH)NH$_2$ | 1 | Ph | CF$_2$CF$_2$CF$_2$CF$_3$ | OH, OH | |
| 3149 | NH(C=NH)NH$_2$ | 1 | Ph | F$_5$-Ph | OH, OH | |
| 3150 | NH(C=NH)NH$_2$ | 1 | Ph | CH$_2$CO$_2$H | OH, OH | |
| 3151 | NH(C=NH)NH$_2$ | 1 | Ph | (CH$_2$)$_2$CO$_2$H | OH, OH | |
| 3152 | NH(C=NH)NH$_2$ | 1 | Ph | (CH$_2$)$_3$CO$_2$H | OH, OH | |
| 3153 | NH(C=NH)NH$_2$ | 1 | Ph | CH$_2$CN$_4$H | OH, OH | |
| 3154 | NH(C=NH)NH$_2$ | 1 | Ph | (CH$_2$)$_2$CN$_4$H | OH, OH | |
| 3155 | NH(C=NH)NH$_2$ | 1 | Ph | (CH$_2$)$_3$CN$_4$H | OH, OH | |
| 3156 | NH(C=NH)NH$_2$ | 1 | Ph | CH$_2$NO$_2$ | OH, OH | |
| 3157 | NH(C=NH)NH$_2$ | 1 | Ph | (CH$_2$)$_2$NO$_2$ | OH, OH | |
| 3158 | NH(C=NH)NH$_2$ | 1 | Ph | (CH$_2$)$_3$NO$_2$ | OH, OH | |
| 3159 | NH(C=NH)NH$_2$ | 1 | Ph | CH$_2$OH | OH, OH | |
| 3160 | NH(C=NH)NH$_2$ | 1 | Ph | (CH$_2$)$_2$OH | OH, OH | |
| 3161 | NH(C=NH)NH$_2$ | 1 | Ph | (CH$_2$)$_3$OH | OH, OH | |
| 3162 | NH(C=NH)NH$_2$ | 1 | Ph | CH$_2$CO$_2$Me | OH, OH | |
| 3163 | NH(C=NH)NH$_2$ | 1 | Ph | (CH$_2$)$_2$CO$_2$Me | OH, OH | |
| 3164 | NH(C=NH)NH$_2$ | 1 | Ph | (CH$_2$)$_3$CO$_2$Me | OH, OH | |
| 3165 | NH(C=NH)NH$_2$ | 1 | Ph | 3-NO$_2$-Ph | OH, OH | |
| 3166 | NH(C=NH)NH$_2$ | 1 | Ph | 4-NO$_2$-Ph | OH, OH | |
| 3167 | NH(C=NH)NH$_2$ | 1 | Ph | 3-CO$_2$H-Ph | OH, OH | |
| 3168 | NH(C=NH)NH$_2$ | 1 | Ph | 4-CO$_2$H-Ph | OH, OH | |
| 3169 | NH(C=NH)NH$_2$ | 1 | Ph | 3-CN$_4$H-Ph | OH, OH | |
| 3170 | NH(C=NH)NH$_2$ | 1 | Ph | 4-CN$_4$H-Ph | OH, OH | |
| 3171 | NH(C=NH)NH$_2$ | 1 | Ph | 3-(HOCH$_2$)-Ph | OH, OH | |
| 3172 | NH(C=NH)NH$_2$ | 1 | Ph | 4-(HOCH$_2$)-Ph | OH, OH | |
| 3173 | NH(C=NH)NH$_2$ | 1 | PhCH$_2$ | H | (+)-pin | |
| 3174 | NH(C=NH)NH$_2$ | 1 | PhCH$_2$ | Methyl | (+)-pin | |
| 3175 | NH(C=NH)NH$_2$ | 1 | PhCH$_2$ | Ethyl | (+)-pin | |
| 3176 | NH(C=NH)NH$_2$ | 1 | PhCH$_2$ | n-Propyl | (+)-pin | |
| 3177 | NH(C=NH)NH$_2$ | 1 | PhCH$_2$ | n-Butyl | (+)-pin | |
| 3178 | NH(C=NH)NH$_2$ | 1 | PhCH$_2$ | CH$_2$SCH$_3$ | (+)-pin | |
| 3179 | NH(C=NH)NH$_2$ | 1 | PhCH$_2$ | CH$_2$(SO)CH$_3$ | (+)-pin | |
| 3180 | NH(C=NH)NH$_2$ | 1 | PhCH$_2$ | CH$_2$(SO$_2$)CH$_3$ | (+)-pin | |
| 3181 | NH(C=NH)NH$_2$ | 1 | PhCH$_2$ | CH$_2$CH$_2$SCH$_3$ | (+)-pin | |
| 3182 | NH(C=NH)NH$_2$ | 1 | PhCH$_2$ | CH$_2$CH$_2$(SO)CH$_3$ | (+)-pin | |
| 3183 | NH(C=NH)NH$_2$ | 1 | PhCH$_2$ | CH$_2$CH$_2$(SO)$_2$CH$_3$ | (+)-pin | |
| 3184 | NH(C=NH)NH$_2$ | 1 | PhCH$_2$ | CH$_2$CN | (+)-pin | |
| 3185 | NH(C=NH)NH$_2$ | 1 | PhCH$_2$ | CH$_2$CH$_2$CN | (+)-pin | |
| 3186 | NH(C=NH)NH$_2$ | 1 | PhCH$_2$ | CH$_2$CH$_2$CH$_2$CN | (+)-pin | |
| 3187 | NH(C=NH)NH$_2$ | 1 | PhCH$_2$ | CF$_3$ | (+)-pin | |

TABLE 15-continued

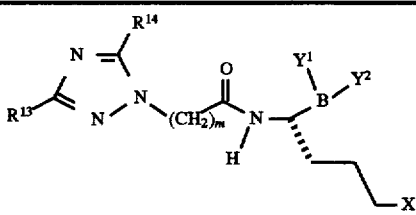

| Ex | X | m | R13 | R14 | Y1Y2 | Phys. Data |
|---|---|---|---|---|---|---|
| 3188 | NH(C=NH)NH2 | 1 | PhCH2 | CF2CF3 | (+)-pin | |
| 3189 | NH(C=NH)NH2 | 1 | PhCH2 | CF2CF2CF3 | (+)-pin | |
| 3190 | NH(C=NH)NH2 | 1 | PhCH2 | CF2CF2CF2CF3 | (+)-pin | |
| 3191 | NH(C=NH)NH2 | 1 | PhCH2 | F5-Ph | (+)-pin | |
| 3192 | NH(C=NH)NH2 | 1 | PhCH2 | CH2CO2H | (+)-pin | |
| 3193 | NH(C=NH)NH2 | 1 | PhCH2 | (CH2)2CO2H | (+)-pin | |
| 3194 | NH(C=NH)NH2 | 1 | PhCH2 | (CH2)3CO2H | (+)-pin | |
| 3195 | NH(C=NH)NH2 | 1 | PhCH2 | CH2CN4H | (+)-pin | |
| 3196 | NH(C=NH)NH2 | 1 | PhCH2 | (CH2)2CN4H | (+)-pin | |
| 3197 | NH(C=NH)NH2 | 1 | PhCH2 | (CH2)3CN4H | (+)-pin | |
| 3198 | NH(C=NH)NH2 | 1 | PhCH2 | CH2NO2 | (+)-pin | |
| 3199 | NH(C=NH)NH2 | 1 | PhCH2 | (CH2)2NO2 | (+)-pin | |
| 3200 | NH(C=NH)NH2 | 1 | PhCH2 | (CH2)3NO2 | (+)-pin | |
| 3201 | NH(C=NH)NH2 | 1 | PhCH2 | CH2OH | (+)-pin | |
| 3202 | NH(C=NH)NH2 | 1 | PhCH2 | (CH2)2OH | (+)-pin | |
| 3203 | NH(C=NH)NH2 | 1 | PhCH2 | (CH2)3OH | (+)-pin | |
| 3204 | NH(C=NH)NH2 | 1 | PhCH2 | CH2CO2Me | (+)-pin | |
| 3205 | NH(C=NH)NH2 | 1 | PhCH2 | (CH2)2CO2Me | (+)-pin | |
| 3206 | NH(C=NH)NH2 | 1 | PhCH2 | (CH2)3CO2Me | (+)-pin | |
| 3207 | NH(C=NH)NH2 | 1 | PhCH2 | 3-NO2-Ph | (+)-pin | |
| 3208 | NH(C=NH)NH2 | 1 | PhCH2 | 4-NO2-Ph | (+)-pin | |
| 3209 | NH(C=NH)NH2 | 1 | PhCH2 | 3-CO2H-Ph | (+)-pin | |
| 3210 | NH(C=NH)NH2 | 1 | PhCH2 | 4-CO2H-Ph | (+)-pin | |
| 3211 | NH(C=NH)NH2 | 1 | PhCH2 | 3-CN4H-Ph | (+)-pin | |
| 3212 | NH(C=NH)NH2 | 1 | PhCH2 | 4-CN4H-Ph | (+)-pin | |
| 3213 | NH(C=NH)NH2 | 1 | PhCH2 | 3-(HOCH2)-Ph | (+)-pin | |
| 3214 | NH(C=NH)NH2 | 1 | PhCH2 | 4-(HOCH2)-Ph | (+)-pin | |
| 3215 | NH(C=NH)NH2 | 1 | PhCH2 | H | OH, OH | |
| 3216 | NH(C=NH)NH2 | 1 | PhCH2 | Methyl | OH, OH | |
| 3217 | NH(C=NH)NH2 | 1 | PhCH2 | Ethyl | OH, OH | |
| 3218 | NH(C=NH)NH2 | 1 | PhCH2 | n-Propyl | OH, OH | |
| 3219 | NH(C=NH)NH2 | 1 | PhCH2 | n-Butyl | OH, OH | |
| 3220 | NH(C=NH)NH2 | 1 | PhCH2 | CH2SCH3 | OH, OH | |
| 3221 | NH(C=NH)NH2 | 1 | PhCH2 | CH2(SO)CH3 | OH, OH | |
| 3222 | NH(C=NH)NH2 | 1 | PhCH2 | CH2(SO2)CH3 | OH, OH | |
| 3223 | NH(C=NH)NH2 | 1 | PhCH2 | CH2CH2SCH3 | OH, OH | |
| 3224 | NH(C=NH)NH2 | 1 | PhCH2 | CH2CH2(SO)CH3 | OH, OH | |
| 3225 | NH(C=NH)NH2 | 1 | PhCH2 | CH2CH2(SO)2CH3 | OH, OH | |
| 3226 | NH(C=NH)NH2 | 1 | PhCH2 | CH2CN | OH, OH | |
| 3227 | NH(C=NH)NH2 | 1 | PhCH2 | CH2CH2CN | OH, OH | |
| 3228 | NH(C=NH)NH2 | 1 | PhCH2 | CH2CH2CH2CN | OH, OH | |
| 3229 | NH(C=NH)NH2 | 1 | PhCH2 | CF3 | OH, OH | |
| 3230 | NH(C=NH)NH2 | 1 | PhCH2 | CF2CF3 | OH, OH | |
| 3231 | NH(C=NH)NH2 | 1 | PhCH2 | CF2CF2CF3 | OH, OH | |
| 3232 | NH(C=NH)NH2 | 1 | PhCH2 | CF2CF2CF2CF3 | OH, OH | |
| 3233 | NH(C=NH)NH2 | 1 | PhCH2 | F5-Ph | OH, OH | |
| 3234 | NH(C=NH)NH2 | 1 | PhCH2 | CH2CO2H | OH, OH | |
| 3235 | NH(C=NH)NH2 | 1 | PhCH2 | (CH2)2CO2H | OH, OH | |
| 3236 | NH(C=NH)NH2 | 1 | PhCH2 | (CH2)3CO2H | OH, OH | |
| 3237 | NH(C=NH)NH2 | 1 | PhCH2 | CH2CN4H | OH, OH | |
| 3238 | NH(C=NH)NH2 | 1 | PhCH2 | (CH2)2CN4H | OH, OH | |
| 3239 | NH(C=NH)NH2 | 1 | PhCH2 | (CH2)3CN4H | OH, OH | |
| 3240 | NH(C=NH)NH2 | 1 | PhCH2 | CH2NO2 | OH, OH | |
| 3241 | NH(C=NH)NH2 | 1 | PhCH2 | (CH2)2NO2 | OH, OH | |
| 3242 | NH(C=NH)NH2 | 1 | PhCH2 | (CH2)3NO2 | OH, OH | |
| 3243 | NH(C=NH)NH2 | 1 | PhCH2 | CH2OH | OH, OH | |
| 3244 | NH(C=NH)NH2 | 1 | PhCH2 | (CH2)2OH | OH, OH | |
| 3245 | NH(C=NH)NH2 | 1 | PhCH2 | (CH2)3OH | OH, OH | |
| 3246 | NH(C=NH)NH2 | 1 | PhCH2 | CH2CO2Me | OH, OH | |
| 3247 | NH(C=NH)NH2 | 1 | PhCH2 | (CH2)2CO2Me | OH, OH | |
| 3248 | NH(C=NH)NH2 | 1 | PhCH2 | (CH2)3CO2Me | OH, OH | |
| 3249 | NH(C=NH)NH2 | 1 | PhCH2 | 3-NO2-Ph | OH, OH | |
| 3250 | NH(C=NH)NH2 | 1 | PhCH2 | 4-NO2-Ph | OH, OH | |
| 3251 | NH(C=NH)NH2 | 1 | PhCH2 | 3-CO2H-Ph | OH, OH | |
| 3252 | NH(C=NH)NH2 | 1 | PhCH2 | 4-CO2H-Ph | OH, OH | |

TABLE 15-continued

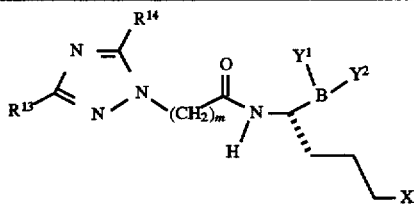

| Ex | X | m | R[13] | R[14] | Y[1]Y[2] | Phys. Data |
|---|---|---|---|---|---|---|
| 3253 | NH(C=NH)NH$_2$ | 1 | PhCH$_2$ | 3-CN$_4$H-Ph | OH, OH | |
| 3254 | NH(C=NH)NH$_2$ | 1 | PhCH$_2$ | 4-CN$_4$H-Ph | OH, OH | |
| 3255 | NH(C=NH)NH$_2$ | 1 | PhCH$_2$ | 3-(HOCH$_2$)-Ph | OH, OH | |
| 3256 | NH(C=NH)NH$_2$ | 1 | PhCH$_2$ | 4-(HOCH$_2$)-Ph | OH, OH | |
| 3257 | NH(C=NH)NH$_2$ | 1 | PhCH$_2$CH$_2$ | H | (+)-pin | |
| 3258 | NH(C=NH)NH$_2$ | 1 | PhCH$_2$CH$_2$ | Methyl | (+)-pin | |
| 3259 | NH(C=NH)NH$_2$ | 1 | PhCH$_2$CH$_2$ | Ethyl | (+)-pin | |
| 3260 | NH(C=NH)NH$_2$ | 1 | PhCH$_2$CH$_2$ | n-Propyl | (+)-pin | |
| 3261 | NH(C=NH)NH$_2$ | 1 | PhCH$_2$CH$_2$ | n-Butyl | (+)-pin | |
| 3262 | NH(C=NH)NH$_2$ | 1 | PhCH$_2$CH$_2$ | CH$_2$SCH$_3$ | (+)-pin | |
| 3263 | NH(C=NH)NH$_2$ | 1 | PhCH$_2$CH$_2$ | CH$_2$(SO)CH$_3$ | (+)-pin | |
| 3264 | NH(C=NH)NH$_2$ | 1 | PhCH$_2$CH$_2$ | CH$_2$(SO$_2$)CH$_3$ | (+)-pin | |
| 3265 | NH(C=NH)NH$_2$ | 1 | PhCH$_2$CH$_2$ | CH$_2$CH$_2$SCH$_3$ | (+)-pin | |
| 3266 | NH(C=NH)NH$_2$ | 1 | PhCH$_2$CH$_2$ | CH$_2$CH$_2$(SO)CH$_3$ | (+)-pin | |
| 3267 | NH(C=NH)NH$_2$ | 1 | PhCH$_2$CH$_2$ | CH$_2$CH$_2$(SO)$_2$CH$_3$ | (+)-pin | |
| 3268 | NH(C=NH)NH$_2$ | 1 | PhCH$_2$CH$_2$ | CH$_2$CN | (+)-pin | |
| 3269 | NH(C=NH)NH$_2$ | 1 | PhCH$_2$CH$_2$ | CH$_2$CH$_2$CN | (+)-pin | |
| 3270 | NH(C=NH)NH$_2$ | 1 | PhCH$_2$CH$_2$ | CH$_2$CH$_2$CH$_2$CN | (+)-pin | |
| 3271 | NH(C=NH)NH$_2$ | 1 | PhCH$_2$CH$_2$ | CF$_3$ | (+)-pin | |
| 3272 | NH(C=NH)NH$_2$ | 1 | PhCH$_2$CH$_2$ | CF$_2$CF$_3$ | (+)-pin | |
| 3273 | NH(C=NH)NH$_2$ | 1 | PhCH$_2$CH$_2$ | CF$_2$CF$_2$CF$_3$ | (+)-pin | |
| 3274 | NH(C=NH)NH$_2$ | 1 | PhCH$_2$CH$_2$ | CF$_2$CF$_2$CF$_2$CF$_3$ | (+)-pin | |
| 3275 | NH(C=NH)NH$_2$ | 1 | PhCH$_2$CH$_2$ | F$_5$-Ph | (+)-pin | |
| 3276 | NH(C=NH)NH$_2$ | 1 | PhCH$_2$CH$_2$ | CH$_2$CO$_2$H | (+)-pin | |
| 3277 | NH(C=NH)NH$_2$ | 1 | PhCH$_2$CH$_2$ | (CH$_2$)$_2$CO$_2$H | (+)-pin | |
| 3278 | NH(C=NH)NH$_2$ | 1 | PhCH$_2$CH$_2$ | (CH$_2$)$_3$CO$_2$H | (+)-pin | |
| 3279 | NH(C=NH)NH$_2$ | 1 | PhCH$_2$CH$_2$ | CH$_2$CN$_4$H | (+)-pin | |
| 3280 | NH(C=NH)NH$_2$ | 1 | PhCH$_2$CH$_2$ | (CH$_2$)$_2$CN$_4$H | (+)-pin | |
| 3281 | NH(C=NH)NH$_2$ | 1 | PhCH$_2$CH$_2$ | (CH$_2$)$_3$CN$_4$H | (+)-pin | |
| 3282 | NH(C=NH)NH$_2$ | 1 | PhCH$_2$CH$_2$ | CH$_2$NO$_2$ | (+)-pin | |
| 3283 | NH(C=NH)NH$_2$ | 1 | PhCH$_2$CH$_2$ | (CH$_2$)$_2$NO$_2$ | (+)-pin | |
| 3284 | NH(C=NH)NH$_2$ | 1 | PhCH$_2$CH$_2$ | (CH$_2$)$_3$NO$_2$ | (+)-pin | |
| 3285 | NH(C=NH)NH$_2$ | 1 | PhCH$_2$CH$_2$ | CH$_2$OH | (+)-pin | |
| 3286 | NH(C=NH)NH$_2$ | 1 | PhCH$_2$CH$_2$ | (CH$_2$)$_2$OH | (+)-pin | |
| 3287 | NH(C=NH)NH$_2$ | 1 | PhCH$_2$CH$_2$ | (CH$_2$)$_3$OH | (+)-pin | |
| 3288 | NH(C=NH)NH$_2$ | 1 | PhCH$_2$CH$_2$ | CH$_2$CO$_2$Me | (+)-pin | |
| 3289 | NH(C=NH)NH$_2$ | 1 | PhCH$_2$CH$_2$ | (CH$_2$)$_2$CO$_2$Me | (+)-pin | |
| 3290 | NH(C=NH)NH$_2$ | 1 | PhCH$_2$CH$_2$ | (CH$_2$)$_3$CO$_2$Me | (+)-pin | |
| 3291 | NH(C=NH)NH$_2$ | 1 | PhCH$_2$CH$_2$ | 3-NO$_2$-Ph | (+)-pin | |
| 3292 | NH(C=NH)NH$_2$ | 1 | PhCH$_2$CH$_2$ | 4-NO$_2$-Ph | (+)-pin | |
| 3293 | NH(C=NH)NH$_2$ | 1 | PhCH$_2$CH$_2$ | 3-CO$_2$H-Ph | (+)-pin | |
| 3294 | NH(C=NH)NH$_2$ | 1 | PhCH$_2$CH$_2$ | 4-CO$_2$H-Ph | (+)-pin | |
| 3295 | NH(C=NH)NH$_2$ | 1 | PhCH$_2$CH$_2$ | 3-CN$_4$H-Ph | (+)-pin | |
| 3296 | NH(C=NH)NH$_2$ | 1 | PhCH$_2$CH$_2$ | 4-CN$_4$H-Ph | (+)-pin | |
| 3297 | NH(C=NH)NH$_2$ | 1 | PhCH$_2$CH$_2$ | 3-(HOCH$_2$)-Ph | (+)-pin | |
| 3298 | NH(C=NH)NH$_2$ | 1 | PhCH$_2$CH$_2$ | 4-(HOCH$_2$)-Ph | (+)-pin | |
| 3299 | NH(C=NH)NH$_2$ | 1 | PhCH$_2$CH$_2$ | H | OH, OH | |
| 3300 | NH(C=NH)NH$_2$ | 1 | PhCH$_2$CH$_2$ | Methyl | OH, OH | |
| 3301 | NH(C=NH)NH$_2$ | 1 | PhCH$_2$CH$_2$ | Ethyl | OH, OH | |
| 3302 | NH(C=NH)NH$_2$ | 1 | PhCH$_2$CH$_2$ | n-Propyl | OH, OH | |
| 3303 | NH(C=NH)NH$_2$ | 1 | PhCH$_2$CH$_2$ | n-Butyl | OH, OH | |
| 3304 | NH(C=NH)NH$_2$ | 1 | PhCH$_2$CH$_2$ | CH$_2$SCH$_3$ | OH, OH | |
| 3305 | NH(C=NH)NH$_2$ | 1 | PhCH$_2$CH$_2$ | CH$_2$(SO)CH$_3$ | OH, OH | |
| 3306 | NH(C=NH)NH$_2$ | 1 | PhCH$_2$CH$_2$ | CH$_2$(SO$_2$)CH$_3$ | OH, OH | |
| 3307 | NH(C=NH)NH$_2$ | 1 | PhCH$_2$CH$_2$ | CH$_2$CH$_2$SCH$_3$ | OH, OH | |
| 3308 | NH(C=NH)NH$_2$ | 1 | PhCH$_2$CH$_2$ | CH$_2$CH$_2$(SO)CH$_3$ | OH, OH | |
| 3309 | NH(C=NH)NH$_2$ | 1 | PhCH$_2$CH$_2$ | CH$_2$CH$_2$(SO)$_2$CH$_3$ | OH, OH | |
| 3310 | NH(C=NH)NH$_2$ | 1 | PhCH$_2$CH$_2$ | CH$_2$CN | OH, OH | |
| 3311 | NH(C=NH)NH$_2$ | 1 | PhCH$_2$CH$_2$ | CH$_2$CH$_2$CN | OH, OH | |
| 3312 | NH(C=NH)NH$_2$ | 1 | PhCH$_2$CH$_2$ | CH$_2$CH$_2$CH$_2$CN | OH, OH | |
| 3313 | NH(C=NH)NH$_2$ | 1 | PhCH$_2$CH$_2$ | CF$_3$ | OH, OH | |
| 3314 | NH(C=NH)NH$_2$ | 1 | PhCH$_2$CH$_2$ | CF$_2$CF$_3$ | OH, OH | |
| 3315 | NH(C=NH)NH$_2$ | 1 | PhCH$_2$CH$_2$ | CF$_2$CF$_2$CF$_3$ | OH, OH | |
| 3316 | NH(C=NH)NH$_2$ | 1 | PhCH$_2$CH$_2$ | CF$_2$CF$_2$CF$_2$CF$_3$ | OH, OH | |
| 3317 | NH(C=NH)NH$_2$ | 1 | PhCH$_2$CH$_2$ | F$_5$-Ph | OH, OH | |

TABLE 15-continued

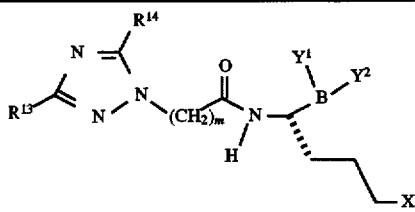

| Ex | X | m | R13 | R14 | Y1Y2 | Phys. Data |
|---|---|---|---|---|---|---|
| 3318 | NH(C=NH)NH2 | 1 | PhCH2CH2 | CH2CO2H | OH, OH | |
| 3319 | NH(C=NH)NH2 | 1 | PhCH2CH2 | (CH2)2CO2H | OH, OH | |
| 3320 | NH(C=NH)NH2 | 1 | PhCH2CH2 | (CH2)3CO2H | OH, OH | |
| 3321 | NH(C=NH)NH2 | 1 | PhCH2CH2 | CH2CN4H | OH, OH | |
| 3322 | NH(C=NH)NH2 | 1 | PhCH2CH2 | (CH2)2CN4H | OH, OH | |
| 3323 | NH(C=NH)NH2 | 1 | PhCH2CH2 | (CH2)3CN4H | OH, OH | |
| 3324 | NH(C=NH)NH2 | 1 | PhCH2CH2 | CH2NO2 | OH, OH | |
| 3325 | NH(C=NH)NH2 | 1 | PhCH2CH2 | (CH2)2NO2 | OH, OH | |
| 3326 | NH(C=NH)NH2 | 1 | PhCH2CH2 | (CH2)3NO2 | OH, OH | |
| 3327 | NH(C=NH)NH2 | 1 | PhCH2CH2 | CH2OH | OH, OH | |
| 3328 | NH(C=NH)NH2 | 1 | PhCH2CH2 | (CH2)2OH | OH, OH | |
| 3329 | NH(C=NH)NH2 | 1 | PhCH2CH2 | (CH2)3OH | OH, OH | |
| 3330 | NH(C=NH)NH2 | 1 | PhCH2CH2 | CH2CO2Me | OH, OH | |
| 3331 | NH(C=NH)NH2 | 1 | PhCH2CH2 | (CH2)2CO2Me | OH, OH | |
| 3332 | NH(C=NH)NH2 | 1 | PhCH2CH2 | (CH2)3CO2Me | OH, OH | |
| 3333 | NH(C=NH)NH2 | 1 | PhCH2CH2 | 3-NO2-Ph | OH, OH | |
| 3334 | NH(C=NH)NH2 | 1 | PhCH2CH2 | 4-NO2-Ph | OH, OH | |
| 3335 | NH(C=NH)NH2 | 1 | PhCH2CH2 | 3-CO2H-Ph | OH, OH | |
| 3336 | NH(C=NH)NH2 | 1 | PhCH2CH2 | 4-CO2H-Ph | OH, OH | |
| 3337 | NH(C=NH)NH2 | 1 | PhCH2CH2 | 3-CN4H-Ph | OH, OH | |
| 3338 | NH(C=NH)NH2 | 1 | PhCH2CH2 | 4-CN4H-Ph | OH, OH | |
| 3339 | NH(C=NH)NH2 | 1 | PhCH2CH2 | 3-(HOCH2)-Ph | OH, OH | |
| 3340 | NH(C=NH)NH2 | 1 | PhCH2CH2 | 4-(HOCH2)-Ph | OH, OH | |

BA. MS (M+H)+: Calc. 480, Found 480.
BC. MS (M+H)+: Calc. 494, Found 494.
BD. MS (M+H)+: Calc. 522, Found 522.
BE. MS (M+H)+: Calc. 540, Found 540.
BF. MS (M+H)+: Calc. 519, Found 519.
BG. MS (M+H)+: Calc. 538, Found 538.
BH. MS (M+H)+: Calc. 346, Found 346.
BI. MS (M+H)+: Calc. 494, Found 494.
BJ. Anal. calcd. for $C_{17}H_{26}BN_5O_3 \cdot 2H_2O \cdot 1.8HCl$: C, 44.30; H, 6.95; Cl, 13.84; N, 15.20. Found: C, 44.22; H, 6.66; Cl, 14.03; N, 14.03.
BW. MS (M+H)+: Calc. 466, Found 466.
BX. MS (M+H)+: Calc. 480, Found 480.
CV. MS (M+H)+: Calc. 510, Found 510.
CW. MS (M+H)+: Calc. 600, Found 600.
CX. MS (M+H)+: Calc. 552, Found 552.
CY. MS (M+H)+: Calc. 629, Found 629.
CZ. MS (M+H)+: Calc. 524, Found 524.
DA. MS (M+H)+: Calc. 614, Found 614.

TABLE 16

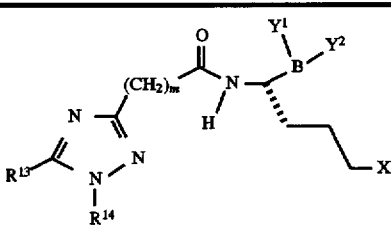

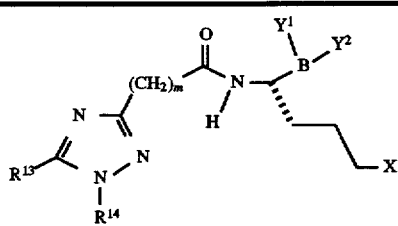

| Ex | X | m | R13 | R14 | Y1Y2 | Phys. Data |
|---|---|---|---|---|---|---|
| 3345 | CH2NH2 | 1 | Ph | Ph | (+)-pin | |
| 3346 | CH2NH2 | 1 | Ph | PhCH2 | (+)-pin | |
| 3347 | CH2NH2 | 1 | Ph | Ph(CH2)2 | (+)-pin | |
| 3348 | CH2NH2 | 1 | PhCH2 | Ph | (+)-pin | |
| 3349 | CH2NH2 | 1 | PhCH2 | PhCH2 | (+)-pin | BY |
| 3350 | CH2NH2 | 1 | PhCH2 | Ph(CH2)2 | (+)-pin | |
| 3351 | CH2NH2 | 1 | Ph(CH2)2 | Ph | (+)-pin | |
| 3352 | CH2NH2 | 1 | Ph(CH2)2 | PhCH2 | (+)-pin | |

TABLE 16-continued

| Ex | X | m | R13 | R14 | Y1Y2 | Phys. Data |
|---|---|---|---|---|---|---|
| 3353 | CH2NH2 | 1 | Ph(CH2)2 | Ph(CH2)2 | (+)-pin | |
| 3354 | CH2NH2 | 1 | Ph | Ph | OH, OH | |
| 3355 | CH2NH2 | 1 | Ph | PhCH2 | OH, OH | |
| 3356 | CH2NH2 | 1 | Ph | Ph(CH2)2 | OH, OH | |
| 3357 | CH2NH2 | 1 | PhCH2 | Ph | OH, OH | |
| 3358 | CH2NH2 | 1 | PhCH2 | PhCH2 | OH, OH | |
| 3359 | CH2NH2 | 1 | PhCH2 | Ph(CH2)2 | OH, OH | |
| 3360 | CH2NH2 | 1 | Ph(CH2)2 | Ph | OH, OH | |
| 3361 | CH2NH2 | 1 | Ph(CH2)2 | PhCH2 | OH, OH | |
| 3362 | CH2NH2 | 1 | Ph(CH2)2 | Ph(CH2)2 | OH, OH | |
| 3363 | NH(C=NH)NH2 | 1 | Ph | Ph | (+)-pin | |
| 3364 | NH(C=NH)NH2 | 1 | Ph | PhCH2 | (+)-pin | |
| 3365 | NH(C=NH)NH2 | 1 | Ph | Ph(CH2)2 | (+)-pin | |
| 3366 | NH(C=NH)NH2 | 1 | PhCH2 | Ph | (+)-pin | |
| 3367 | NH(C=NH)NH2 | 1 | PhCH2 | PhCH2 | (+)-pin | |
| 3368 | NH(C=NH)NH2 | 1 | PhCH2 | Ph(CH2)2 | (+)-pin | |
| 3369 | NH(C=NH)NH2 | 1 | Ph(CH2)2 | Ph | (+)-pin | |
| 3370 | NH(C=NH)NH2 | 1 | Ph(CH2)2 | PhCH2 | (+)-pin | |
| 3371 | NH(C=NH)NH2 | 1 | Ph(CH2)2 | Ph(CH2)2 | (+)-pin | |
| 3372 | NH(C=NH)NH2 | 1 | Ph | Ph | OH, OH | |
| 3373 | NH(C=NH)NH2 | 1 | Ph | PhCH2 | OH, OH | |
| 3374 | NH(C=NH)NH2 | 1 | Ph | Ph(CH2)2 | OH, OH | |
| 3375 | NH(C=NH)NH2 | 1 | PhCH2 | Ph | OH, OH | |
| 3376 | NH(C=NH)NH2 | 1 | PhCH2 | PhCH2 | OH, OH | |
| 3377 | NH(C=NH)NH2 | 1 | PhCH2 | Ph(CH2)2 | OH, OH | |
| 3378 | NH(C=NH)NH2 | 1 | Ph(CH2)2 | Ph | OH, OH | |
| 3379 | NH(C=NH)NH2 | 1 | Ph(CH2)2 | PhCH2 | OH, OH | |
| 3380 | NH(C=NH)NH2 | 1 | Ph(CH2)2 | Ph(CH2)2 | OH, OH | |
| 3381 | OMe | 1 | Ph | Ph | (+)-pin | |
| 3382 | OMe | 1 | Ph | PhCH2 | (+)-pin | |
| 3383 | OMe | 1 | Ph | Ph(CH2)2 | (+)-pin | |
| 3384 | OMe | 1 | PhCH2 | Ph | (+)-pin | |
| 3385 | OMe | 1 | PhCH2 | PhCH2 | (+)-pin | |
| 3386 | OMe | 1 | PhCH2 | Ph(CH2)2 | (+)-pin | |
| 3387 | OMe | 1 | Ph(CH2)2 | Ph | (+)-pin | |
| 3388 | OMe | 1 | Ph(CH2)2 | PhCH2 | (+)-pin | |
| 3389 | OMe | 1 | Ph(CH2)2 | Ph(CH2)2 | (+)-pin | |
| 3390 | OMe | 1 | Ph | Ph | OH, OH | |
| 3391 | OMe | 1 | Ph | PhCH2 | OH, OH | |
| 3392 | OMe | 1 | Ph | Ph(CH2)2 | OH, OH | |
| 3393 | OMe | 1 | PhCH2 | Ph | OH, OH | |
| 3394 | OMe | 1 | PhCH2 | PhCH2 | OH, OH | |
| 3395 | OMe | 1 | PhCH2 | Ph(CH2)2 | OH, OH | |
| 3396 | OMe | 1 | Ph(CH2)2 | Ph | OH, OH | |
| 3397 | OMe | 1 | Ph(CH2)2 | PhCH2 | OH, OH | |
| 3398 | OMe | 1 | Ph(CH2)2 | Ph(CH2)2 | OH, OH | |
| 3399 | NH(C=NH)H | 1 | Ph | Ph | (+)-pin | |
| 3400 | NH(C=NH)H | 1 | Ph | PhCH2 | (+)-pin | |
| 3401 | NH(C=NH)H | 1 | Ph | Ph(CH2)2 | (+)-pin | |
| 3402 | NH(C=NH)H | 1 | PhCH2 | Ph | (+)-pin | |
| 3403 | NH(C=NH)H | 1 | PhCH2 | PhCH2 | (+)-pin | |
| 3404 | NH(C=NH)H | 1 | PhCH2 | Ph(CH2)2 | (+)-pin | |
| 3405 | NH(C=NH)H | 1 | Ph(CH2)2 | Ph | (+)-pin | |
| 3406 | NH(C=NH)H | 1 | Ph(CH2)2 | PhCH2 | (+)-pin | |
| 3407 | NH(C=NH)H | 1 | Ph(CH2)2 | Ph(CH2)2 | (+)-pin | |
| 3408 | NH(C=NH)H | 1 | Ph | Ph | OH, OH | |
| 3409 | NH(C=NH)H | 1 | Ph | PhCH2 | OH, OH | |
| 3410 | NH(C=NH)H | 1 | Ph | Ph(CH2)2 | OH, OH | |
| 3411 | NH(C=NH)H | 1 | PhCH2 | Ph | OH, OH | |
| 3412 | NH(C=NH)H | 1 | PhCH2 | PhCH2 | OH, OH | |
| 3413 | NH(C=NH)H | 1 | PhCH2 | Ph(CH2)2 | OH, OH | |
| 3414 | NH(C=NH)H | 1 | Ph(CH2)2 | Ph | OH, OH | |
| 3415 | NH(C=NH)H | 1 | Ph(CH2)2 | PhCH2 | OH, OH | |
| 3416 | NH(C=NH)H | 1 | Ph(CH2)2 | Ph(CH2)2 | OH, OH | |
| 3417 | CH2NH2 | 2 | Ph | Ph | (+)-pin | |
| 3418 | CH2NH2 | 2 | Ph | PhCH2 | (+)-pin | |
| 3419 | CH2NH2 | 2 | Ph | Ph(CH2)2 | (+)-pin | |
| 3420 | CH2NH2 | 2 | PhCH2 | Ph | (+)-pin | |
| 3421 | CH2NH2 | 2 | PhCH2 | PhCH2 | (+)-pin | |
| 3422 | CH2NH2 | 2 | PhCH2 | Ph(CH2)2 | (+)-pin | |
| 3423 | CH2NH2 | 2 | Ph(CH2)2 | Ph | (+)-pin | |
| 3424 | CH2NH2 | 2 | Ph(CH2)2 | PhCH2 | (+)-pin | |
| 3425 | CH2NH2 | 2 | Ph(CH2)2 | Ph(CH2)2 | (+)-pin | |
| 3426 | CH2NH2 | 2 | Ph | Ph | OH, OH | |
| 3427 | CH2NH2 | 2 | Ph | PhCH2 | OH, OH | |
| 3428 | CH2NH2 | 2 | Ph | Ph(CH2)2 | OH, OH | |
| 3429 | CH2NH2 | 2 | PhCH2 | Ph | OH, OH | |
| 3430 | CH2NH2 | 2 | PhCH2 | PhCH2 | OH, OH | |
| 3431 | CH2NH2 | 2 | PhCH2 | Ph(CH2)2 | OH, OH | |
| 3432 | CH2NH2 | 2 | Ph(CH2)2 | Ph | OH, OH | |
| 3433 | CH2NH2 | 2 | Ph(CH2)2 | PhCH2 | OH, OH | |
| 3434 | CH2NH2 | 2 | Ph(CH2)2 | Ph(CH2)2 | OH, OH | |
| 3435 | NH(C=NH)NH2 | 2 | Ph | Ph | (+)-pin | |
| 3436 | NH(C=NH)NH2 | 2 | Ph | PhCH2 | (+)-pin | |
| 3437 | NH(C=NH)NH2 | 2 | Ph | Ph(CH2)2 | (+)-pin | |
| 3438 | NH(C=NH)NH2 | 2 | PhCH2 | Ph | (+)-pin | |
| 3439 | NH(C=NH)NH2 | 2 | PhCH2 | PhCH2 | (+)-pin | |
| 3440 | NH(C=NH)NH2 | 2 | PhCH2 | Ph(CH2)2 | (+)-pin | |
| 3441 | NH(C=NH)NH2 | 2 | Ph(CH2)2 | Ph | (+)-pin | |
| 3442 | NH(C=NH)NH2 | 2 | Ph(CH2)2 | PhCH2 | (+)-pin | |
| 3443 | NH(C=NH)NH2 | 2 | Ph(CH2)2 | Ph(CH2)2 | (+)-pin | |
| 3444 | NH(C=NH)NH2 | 2 | Ph | Ph | OH, OH | |
| 3445 | NH(C=NH)NH2 | 2 | Ph | PhCH2 | OH, OH | |
| 3446 | NH(C=NH)NH2 | 2 | Ph | Ph(CH2)2 | OH, OH | |
| 3447 | NH(C=NH)NH2 | 2 | PhCH2 | Ph | OH, OH | |
| 3448 | NH(C=NH)NH2 | 2 | PhCH2 | PhCH2 | OH, OH | |
| 3449 | NH(C=NH)NH2 | 2 | PhCH2 | Ph(CH2)2 | OH, OH | |
| 3450 | NH(C=NH)NH2 | 2 | Ph(CH2)2 | Ph | OH, OH | |
| 3451 | NH(C=NH)NH2 | 2 | Ph(CH2)2 | PhCH2 | OH, OH | |
| 3452 | NH(C=NH)NH2 | 2 | Ph(CH2)2 | Ph(CH2)2 | OH, OH | |

BY. MS (M+H)+: Calc. 570, Found 570.

TABLE 17

| Ex | X | R[13] | R[14] | R[15] | Y[1]Y[2] | Phys. Data |
|---|---|---|---|---|---|---|
| 3457 | CH$_2$NH$_2$ | Ph | H | H | (+)-pin | |
| 3458 | CH$_2$NH$_2$ | Ph | methyl | H | (+)-pin | BK |
| 3459 | CH$_2$NH$_2$ | Ph | methyl | H | (+)-pin | |
| 3460 | CH$_2$NH$_2$ | Ph | methyl | methyl | (+)-pin | |
| 3461 | CH$_2$NH$_2$ | Ph | ethyl | H | (+)-pin | |
| 3462 | CH$_2$NH$_2$ | Ph | ethyl | methyl | (+)-pin | |
| 3463 | CH$_2$NH$_2$ | Ph | ethyl | ethyl | (+)-pin | |
| 3464 | CH$_2$NH$_2$ | Ph | isopropyl | H | (+)-pin | |
| 3465 | CH$_2$NH$_2$ | Ph | phenyl | H | (+)-pin | BL |
| 3466 | CH$_2$NH$_2$ | Ph | CH$_2$CN | H | (+)-pin | |
| 3467 | CH$_2$NH$_2$ | Ph | CH$_2$NC | H | (+)-pin | |
| 3468 | CH$_2$NH$_2$ | Ph | CH$_2$NO$_2$ | H | (+)-pin | |
| 3469 | CH$_2$NH$_2$ | Ph | CH$_2$SCH$_3$ | H | (+)-pin | |
| 3470 | CH$_2$NH$_2$ | Ph | CH$_2$SOCH$_3$ | H | (+)-pin | |
| 3471 | CH$_2$NH$_2$ | Ph | CH$_2$SO$_2$CH$_3$ | H | (+)-pin | |
| 3472 | CH$_2$NH$_2$ | Ph | CH$_2$OH | H | (+)-pin | |
| 3473 | CH$_2$NH$_2$ | Ph | CH$_2$COOH | H | (+)-pin | |
| 3474 | CH$_2$NH$_2$ | Ph | (CH$_2$)$_2$COOH | H | (+)-pin | |
| 3475 | CH$_2$NH$_2$ | Ph | (CH$_2$)$_2$CN | H | (+)-pin | |
| 3476 | CH$_2$NH$_2$ | Ph | CH=CHCOOMe | H | (+)-pin | |
| 3477 | CH$_2$NH$_2$ | Ph | CH=CHCOOH | H | (+)-pin | |
| 3478 | CH$_2$NH$_2$ | Ph | CH=CHCN | H | (+)-pin | |
| 3479 | CH$_2$NH$_2$ | Ph | CH$_2$CN$_4$H | H | (+)-pin | |
| 3480 | CH$_2$NH$_2$ | Ph | CH$_2$NHSO$_2$CF$_3$ | H | (+)-pin | |
| 3481 | CH$_2$NH$_2$ | Ph | CH$_2$CH$_2$CN | H | (+)-pin | |
| 3482 | CH$_2$NH$_2$ | Ph | CH$_2$CH$_2$NC | H | (+)-pin | |
| 3483 | CH$_2$NH$_2$ | Ph | CH$_2$CH$_2$NO$_2$ | H | (+)-pin | |
| 3484 | CH$_2$NH$_2$ | Ph | CH$_2$CH$_2$SCH$_3$ | H | (+)-pin | |
| 3485 | CH$_2$NH$_2$ | Ph | CH$_2$CH$_2$SOCH$_3$ | H | (+)-pin | |
| 3486 | CH$_2$NH$_2$ | Ph | CH$_2$CH$_2$SO$_2$CH$_3$ | H | (+)-pin | |
| 3487 | CH$_2$NH$_2$ | Ph | CH$_2$CH$_2$CH$_2$OH | H | (+)-pin | |
| 3488 | CH$_2$NH$_2$ | Ph | NO$_2$ | H | (+)-pin | |
| 3489 | CH$_2$NH$_2$ | Ph | F | H | (+)-pin | |
| 3490 | CH$_2$NH$_2$ | Ph | OH | H | (+)-pin | |
| 3491 | CH$_2$NH$_2$ | Ph | H | H | OH, OH | |
| 3492 | CH$_2$NH$_2$ | Ph | methyl | H | OH, OH | |
| 3493 | CH$_2$NH$_2$ | Ph | methyl | methyl | OH, OH | |
| 3494 | CH$_2$NH$_2$ | Ph | ethyl | H | OH, OH | |
| 3495 | CH$_2$NH$_2$ | Ph | ethyl | methyl | OH, OH | |
| 3496 | CH$_2$NH$_2$ | Ph | ethyl | ethyl | OH, OH | |
| 3497 | CH$_2$NH$_2$ | Ph | isopropyl | H | OH, OH | |
| 3498 | CH$_2$NH$_2$ | Ph | phenyl | H | OH, OH | |
| 3499 | CH$_2$NH$_2$ | Ph | CH$_2$CN | H | OH, OH | |
| 3500 | CH$_2$NH$_2$ | Ph | CH$_2$NC | H | OH, OH | |
| 3501 | CH$_2$NH$_2$ | Ph | CH$_2$NO$_2$ | H | OH, OH | |
| 3502 | CH$_2$NH$_2$ | Ph | CH$_2$SCH$_3$ | H | OH, OH | |
| 3503 | CH$_2$NH$_2$ | Ph | CH$_2$SOCH$_3$ | H | OH, OH | |
| 3504 | CH$_2$NH$_2$ | Ph | CH$_2$SO$_2$CH$_3$ | H | OH, OH | |
| 3505 | CH$_2$NH$_2$ | Ph | CH$_2$OH | H | OH, OH | |
| 3506 | CH$_2$NH$_2$ | Ph | CH$_2$COOH | H | OH, OH | |
| 3507 | CH$_2$NH$_2$ | Ph | (CH$_2$)$_2$COOH | H | OH, OH | |
| 3508 | CH$_2$NH$_2$ | Ph | (CH$_2$)$_2$CN | H | OH, OH | |
| 3509 | CH$_2$NH$_2$ | Ph | CH=CHCOOMe | H | OH, OH | |
| 3510 | CH$_2$NH$_2$ | Ph | CH=CHCOOH | H | OH, OH | |
| 3511 | CH$_2$NH$_2$ | Ph | CH$_2$CN$_4$H | H | OH, OH | |
| 3512 | CH$_2$NH$_2$ | Ph | CH$_2$NHSO$_2$CF$_3$ | H | OH, OH | |
| 3513 | CH$_2$NH$_2$ | Ph | CH$_2$CH$_2$CN | H | OH, OH | |
| 3514 | CH$_2$NH$_2$ | Ph | CH$_2$CH$_2$NC | H | OH, OH | |
| 3515 | CH$_2$NH$_2$ | Ph | CH$_2$CH$_2$NO$_2$ | H | OH, OH | |
| 3516 | CH$_2$NH$_2$ | Ph | CH$_2$CH$_2$SCH$_3$ | H | OH, OH | |
| 3517 | CH$_2$NH$_2$ | Ph | CH$_2$CH$_2$SOCH$_3$ | H | OH, OH | |
| 3518 | CH$_2$NH$_2$ | Ph | CH$_2$CH$_2$SO$_2$CH$_3$ | H | OH, OH | |
| 3519 | CH$_2$NH$_2$ | Ph | CH$_2$CH$_2$OH | H | OH, OH | |
| 3520 | CH$_2$NH$_2$ | Ph | CH$_2$CH$_2$COOH | H | OH, OH | |
| 3521 | CH$_2$NH$_2$ | Ph | CH$_2$CH$_2$CN$_4$H | H | OH, OH | |

TABLE 17-continued

Structure: R13 and R14 substituted pyrimidine with R15, connected via C=O-NH to a chiral center bearing a B(Y1)(Y2) group and a propyl chain ending in X.

| Ex | X | R13 | R14 | R15 | Y1Y2 | Phys. Data |
|---|---|---|---|---|---|---|
| 3522 | CH$_2$NH$_2$ | Ph | CH$_2$CH$_2$NHSO$_2$CF$_3$ | H | OH, OH | |
| 3523 | CH$_2$NH$_2$ | PhCH$_2$ | H | H | (+)-pin | |
| 3524 | CH$_2$NH$_2$ | PhO | methyl | H | (+)-pin | |
| 3525 | CH$_2$NH$_2$ | PhS | methyl | methyl | (+)-pin | |
| 3526 | CH$_2$NH$_2$ | PhNH | ethyl | H | (+)-pin | |
| 3527 | CH$_2$NH$_2$ | PhCONH | ethyl | methyl | (+)-pin | |
| 3528 | CH$_2$NH$_2$ | PhNHCO | ethyl | ethyl | (+)-pin | |
| 3529 | CH$_2$NH$_2$ | Ph | isopropyl | H | (+)-pin | |
| 3530 | CH$_2$NH$_2$ | PhCH$_2$ | phenyl | H | (+)-pin | |
| 3531 | CH$_2$NH$_2$ | PhO | CH$_2$CN | H | (+)-pin | |
| 3532 | CH$_2$NH$_2$ | PhS | CH$_2$NC | H | (+)-pin | |
| 3533 | CH$_2$NH$_2$ | PhNH | CH$_2$NO$_2$ | H | (+)-pin | |
| 3534 | CH$_2$NH$_2$ | PhCONH | CH$_2$SCH$_3$ | H | (+)-pin | |
| 3535 | CH$_2$NH$_2$ | PhNHCO | CH$_2$SOCH$_3$ | H | (+)-pin | |
| 3536 | CH$_2$NH$_2$ | Ph(CH$_2$)$_2$ | CH$_2$SO$_2$CH$_3$ | H | (+)-pin | |
| 3537 | NH(C=NH)NH$_2$ | Ph | H | H | (+)-pin | |
| 3538 | NH(C=NH)NH$_2$ | Ph | methyl | H | (+)-pin | BM |
| 3539 | NH(C=NH)NH$_2$ | Ph | methyl | H | (+)-pin | |
| 3540 | NH(C=NH)NH$_2$ | Ph | methyl | methyl | (+)-pin | |
| 3541 | NH(C=NH)NH$_2$ | Ph | ethyl | H | (+)-pin | |
| 3542 | NH(C=NH)NH$_2$ | Ph | ethyl | methyl | (+)-pin | |
| 3543 | NH(C=NH)NH$_2$ | Ph | ethyl | ethyl | (+)-pin | |
| 3544 | NH(C=NH)NH$_2$ | Ph | isopropyl | H | (+)-pin | |
| 3545 | NH(C=NH)NH$_2$ | Ph | phenyl | H | (+)-pin | |
| 3546 | NH(C=NH)NH$_2$ | Ph | CH$_2$CN | H | (+)-pin | |
| 3547 | NH(C=NH)NH$_2$ | Ph | CH$_2$NC | H | (+)-pin | |
| 3548 | NH(C=NH)NH$_2$ | Ph | CH$_2$NO$_2$ | H | (+)-pin | |
| 3549 | NH(C=NH)NH$_2$ | Ph | CH$_2$SCH$_3$ | H | (+)-pin | |
| 3550 | NH(C=NH)NH$_2$ | Ph | CH$_2$SOCH$_3$ | H | (+)-pin | |
| 3551 | NH(C=NH)NH$_2$ | Ph | CH$_2$SO$_2$CH$_3$ | H | (+)-pin | |
| 3552 | NH(C=NH)NH$_2$ | Ph | CH$_2$OH | H | (+)-pin | |
| 3553 | NH(C=NH)NH$_2$ | Ph | CH$_2$COOH | H | (+)-pin | |
| 3554 | NH(C=NH)NH$_2$ | Ph | (CH$_2$)$_2$COOH | H | (+)-pin | |
| 3555 | NH(C=NH)NH$_2$ | Ph | (CH$_2$)$_2$CN | H | (+)-pin | |
| 3556 | NH(C=NH)NH$_2$ | Ph | CH=CHCOOMe | H | (+)-pin | |
| 3557 | NH(C=NH)NH$_2$ | Ph | CH=CHCOOH | H | (+)-pin | |
| 3558 | NH(C=NH)NH$_2$ | Ph | CH$_2$CN$_4$H | H | (+)-pin | |
| 3559 | NH(C=NH)NH$_2$ | Ph | CH$_2$NHSO$_2$CF$_3$ | H | (+)-pin | |
| 3560 | NH(C=NH)NH$_2$ | Ph | CH$_2$CH$_2$CN | H | (+)-pin | |
| 3561 | NH(C=NH)NH$_2$ | Ph | CH$_2$CH$_2$NC | H | (+)-pin | |
| 3562 | NH(C=NH)NH$_2$ | Ph | CH$_2$CH$_2$NO$_2$ | H | (+)-pin | |
| 3563 | NH(C=NH)NH$_2$ | Ph | CH$_2$CH$_2$SCH$_3$ | H | (+)-pin | |
| 3564 | NH(C=NH)NH$_2$ | Ph | CH$_2$CH$_2$SOCH$_3$ | H | (+)-pin | |
| 3565 | NH(C=NH)NH$_2$ | Ph | CH$_2$CH$_2$SO$_2$CH$_3$ | H | (+)-pin | |
| 3566 | NH(C=NH)NH$_2$ | Ph | CH$_2$CH$_2$OH | H | (+)-pin | |
| 3567 | NH(C=NH)NH$_2$ | Ph | NO$_2$ | H | (+)-pin | |
| 3568 | NH(C=NH)NH$_2$ | Ph | F | H | (+)-pin | |
| 3569 | NH(C=NH)NH$_2$ | Ph | OH | H | (+)-pin | |
| 3570 | NH(C=NH)NH$_2$ | Ph | H | H | OH, OH | |
| 3571 | NH(C=NH)NH$_2$ | Ph | methyl | H | OH, OH | |
| 3572 | NH(C=NH)NH$_2$ | Ph | methyl | methyl | OH, OH | |
| 3573 | NH(C=NH)NH$_2$ | Ph | ethyl | H | OH, OH | |
| 3574 | NH(C=NH)NH$_2$ | Ph | ethyl | methyl | OH, OH | |
| 3575 | NH(C=NH)NH$_2$ | Ph | ethyl | ethyl | OH, OH | |
| 3576 | NH(C=NH)NH$_2$ | Ph | isopropyl | H | OH, OH | |
| 3577 | NH(C=NH)NH$_2$ | Ph | phenyl | H | OH, OH | |
| 3578 | NH(C=NH)NH$_2$ | Ph | CH$_2$CN | H | OH, OH | |
| 3579 | NH(C=NH)NH$_2$ | Ph | CH$_2$NC | H | OH, OH | |
| 3580 | NH(C=NH)NH$_2$ | Ph | CH$_2$NO$_2$ | H | OH, OH | |
| 3581 | NH(C=NH)NH$_2$ | Ph | CH$_2$SCH$_3$ | H | OH, OH | |
| 3582 | NH(C=NH)NH$_2$ | Ph | CH$_2$SOCH$_3$ | H | OH, OH | |
| 3583 | NH(C=NH)NH$_2$ | Ph | CH$_2$SO$_2$CH$_3$ | H | OH, OH | |
| 3584 | NH(C=NH)NH$_2$ | Ph | CH$_2$OH | H | OH, OH | |
| 3585 | NH(C=NH)NH$_2$ | Ph | CH$_2$COOH | H | OH, OH | |
| 3586 | NH(C=NH)NH$_2$ | Ph | (CH$_2$)$_2$COOH | H | OH, OH | |

TABLE 17-continued

| Ex | X | R¹³ | R¹⁴ | R¹⁵ | Y¹Y² | Phys. Data |
|---|---|---|---|---|---|---|
| 3587 | NH(C=NH)NH₂ | Ph | (CH₂)₂CN | H | OH, OH | |
| 3588 | NH(C=NH)NH₂ | Ph | CH=CHCOOMe | H | OH, OH | |
| 3589 | NH(C=NH)NH₂ | Ph | CH=CHCOOH | H | OH, OH | |
| 3590 | NH(C=NH)NH₂ | Ph | CH₂CN₄H | H | OH, OH | |
| 3591 | NH(C=NH)NH₂ | Ph | CH₂NHSO₂CF₃ | H | OH, OH | |
| 3592 | NH(C=NH)NH₂ | Ph | CH₂CH₂CN | H | OH, OH | |
| 3593 | NH(C=NH)NH₂ | Ph | CH₂CH₂NC | H | OH, OH | |
| 3594 | NH(C=NH)NH₂ | Ph | CH₂CH₂NO₂ | H | OH, OH | |
| 3595 | NH(C=NH)NH₂ | Ph | CH₂CH₂SCH₃ | H | OH, OH | |
| 3596 | NH(C=NH)NH₂ | Ph | CH₂CH₂SOCH₃ | H | OH, OH | |
| 3597 | NH(C=NH)NH₂ | Ph | CH₂CH₂SO₂CH₃ | H | OH, OH | |
| 3598 | NH(C=NH)NH₂ | Ph | CH₂CH₂OH | H | OH, OH | |
| 3599 | NH(C=NH)NH₂ | Ph | CH₂CH₂COOH | H | OH, OH | |
| 3600 | NH(C=NH)NH₂ | Ph | CH₂CH₂CN₄H | H | OH, OH | |
| 3601 | NH(C=NH)NH₂ | Ph | CH₂CH₂NHSO₂CF₃ | H | OH, OH | |
| 3602 | NH(C=NH)NH₂ | PhCH₂ | H | H | (+)-pin | |
| 3603 | NH(C=NH)NH₂ | PhO | methyl | H | (+)-pin | |
| 3604 | NH(C=NH)NH₂ | PhS | methyl | methyl | (+)-pin | |
| 3605 | NH(C=NH)NH₂ | PhNH | ethyl | H | (+)-pin | |
| 3606 | NH(C=NH)NH₂ | PhCONH | ethyl | methyl | (+)-pin | |
| 3607 | NH(C=NH)NH₂ | PhNHCO | ethyl | ethyl | (+)-pin | |
| 3608 | NH(C=NH)NH₂ | Ph | isopropyl | H | (+)-pin | |
| 3609 | NH(C=NH)NH₂ | PhCH₂ | phenyl | H | (+)-pin | |
| 3610 | NH(C=NH)NH₂ | PhO | CH₂CN | H | (+)-pin | |
| 3611 | NH(C=NH)NH₂ | PhS | CH₂NC | H | (+)-pin | |
| 3612 | NH(C=NH)NH₂ | PhNH | CH₂NO₂ | H | (+)-pin | |
| 3613 | NH(C=NH)NH₂ | PhCONH | CH₂SCH₃ | H | (+)-pin | |
| 3614 | NH(C=NH)NH₂ | PhNHCO | CH₂SOCH₃ | H | (+)-pin | |
| 3615 | NH(C=NH)NH₂ | Ph(CH₂)₂ | CH₂SO₂CH₃ | H | (+)-pin | |
| 3616 | OMe | Ph | CH₃ | H | (+)-pin | |
| 3617 | NH(C=NH)H | Ph | CH₃ | H | (+)-pin | |
| 3618 | OMe | Ph | CH₃ | H | OH, OH | |
| 3619 | NH(C=NH)H | Ph | CH₃ | H | OH, OH | |

BK. MS (M=H)⁺: Calc. 477, Found 477.
BL. MS (M=H)⁺: Calc. 539, Found 539.
BM. MS (M=H)⁺: Calc. 505, Found 505.

TABLE 18

| Ex | X | R¹³ | R¹⁴ | R¹⁵ | Y¹Y² | Phys. Data |
|---|---|---|---|---|---|---|
| 3624 | CH₂NH₂ | Ph | H | H | (+)-pin | |
| 3625 | CH₂NH₂ | Ph | methyl | H | (+)-pin | |
| 3626 | CH₂NH₂ | Ph | ethyl | H | (+)-pin | |
| 3627 | CH₂NH₂ | Ph | ethyl | methyl | (+)-pin | |
| 3628 | CH₂NH₂ | Ph | ethyl | ethyl | (+)-pin | |
| 3629 | CH₂NH₂ | Ph | isopropyl | H | (+)-pin | |
| 3630 | CH₂NH₂ | Ph | phenyl | H | (+)-pin | |
| 3631 | CH₂NH₂ | Ph | CH₂CN | H | (+)-pin | |
| 3632 | CH₂NH₂ | Ph | CH₂NC | H | (+)-pin | |
| 3633 | CH₂NH₂ | Ph | CH₂NO₂ | H | (+)-pin | |

TABLE 18-continued

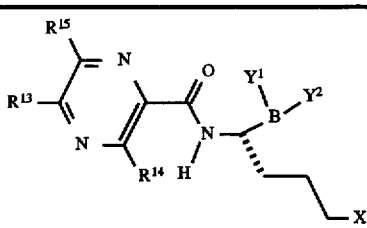

| Ex | X | R13 | R14 | R15 | Y1Y2 | Phys. Data |
|---|---|---|---|---|---|---|
| 3634 | CH2NH2 | Ph | CH2SCH3 | H | (+)-pin | |
| 3635 | CH2NH2 | Ph | CH2SOCH3 | H | (+)-pin | |
| 3636 | CH2NH2 | Ph | CH2SO2CH3 | H | (+)-pin | |
| 3637 | CH2NH2 | Ph | CH2OH | H | (+)-pin | |
| 3638 | CH2NH2 | Ph | CH2COOH | H | (+)-pin | |
| 3639 | CH2NH2 | Ph | CH2CN4H | H | (+)-pin | |
| 3640 | CH2NH2 | Ph | CH2NHSO2CF3 | H | (+)-pin | |
| 3641 | CH2NH2 | Ph | CH2CH2CN | H | (+)-pin | |
| 3642 | CH2NH2 | Ph | CH2CH2NC | H | (+)-pin | |
| 3643 | CH2NH2 | Ph | CH2CH2NO2 | H | (+)-pin | |
| 3644 | CH2NH2 | Ph | CH2CH2SCH3 | H | (+)-pin | |
| 3645 | CH2NH2 | Ph | CH2CH2SOCH3 | H | (+)-pin | |
| 3646 | CH2NH2 | Ph | CH2CH2SO2CH3 | H | (+)-pin | |
| 3647 | CH2NH2 | Ph | CH2CH2CH2OH | H | (+)-pin | |
| 3648 | CH2NH2 | Ph | NO2 | H | (+)-pin | |
| 3649 | CH2NH2 | Ph | F | H | (+)-pin | |
| 3650 | CH2NH2 | Ph | OH | H | (+)-pin | |
| 3651 | CH2NH2 | Ph | H | H | OH, OH | |
| 3652 | CH2NH2 | Ph | methyl | H | OH, OH | |
| 3653 | CH2NH2 | Ph | methyl | methyl | OH, OH | |
| 3654 | CH2NH2 | Ph | ethyl | H | OH, OH | |
| 3655 | CH2NH2 | Ph | ethyl | methyl | OH, OH | |
| 3656 | CH2NH2 | Ph | ethyl | ethyl | OH, OH | |
| 3657 | CH2NH2 | Ph | isopropyl | H | OH, OH | |
| 3658 | CH2NH2 | Ph | phenyl | H | OH, OH | |
| 3659 | CH2NH2 | Ph | CH2CN | H | OH, OH | |
| 3660 | CH2NH2 | Ph | CH2NC | H | OH, OH | |
| 3661 | CH2NH2 | Ph | CH2NO2 | H | OH, OH | |
| 3662 | CH2NH2 | Ph | CH2SCH3 | H | OH, OH | |
| 3663 | CH2NH2 | Ph | CH2SOCH3 | H | OH, OH | |
| 3664 | CH2NH2 | Ph | CH2SO2CH3 | H | OH, OH | |
| 3665 | CH2NH2 | Ph | CH2OH | H | OH, OH | |
| 3666 | CH2NH2 | Ph | CH2COOH | H | OH, OH | |
| 3667 | CH2NH2 | Ph | CH2CN4H | H | OH, OH | |
| 3668 | CH2NH2 | Ph | CH2NHSO2CF3 | H | OH, OH | |
| 3669 | CH2NH2 | Ph | CH2CH2CN | H | OH, OH | |
| 3670 | CH2NH2 | Ph | CH2CH2NC | H | OH, OH | |
| 3671 | CH2NH2 | Ph | CH2CH2NO2 | H | OH, OH | |
| 3672 | CH2NH2 | Ph | CH2CH2SCH3 | H | OH, OH | |
| 3673 | CH2NH2 | Ph | CH2CH2SOCH3 | H | OH, OH | |
| 3674 | CH2NH2 | Ph | CH2CH2SO2CH3 | H | OH, OH | |
| 3675 | CH2NH2 | Ph | CH2CH2OH | H | OH, OH | |
| 3676 | CH2NH2 | Ph | CH2CH2COOH | H | OH, OH | |
| 3677 | CH2NH2 | Ph | CH2CH2CN4H | H | OH, OH | |
| 3678 | CH2NH2 | Ph | CH2CH2NHSO2CF3 | H | OH, OH | |
| 3679 | CH2NH2 | PhCH2 | H | H | (+)-pin | |
| 3680 | CH2NH2 | PhO | methyl | H | (+)-pin | |
| 3681 | CH2NH2 | PhS | methyl | methyl | (+)-pin | |
| 3682 | CH2NH2 | PhNH | ethyl | H | (+)-pin | |
| 3683 | CH2NH2 | PhCONH | ethyl | methyl | (+)-pin | |
| 3684 | CH2NH2 | PhNHCO | ethyl | ethyl | (+)-pin | |
| 3685 | CH2NH2 | Ph | isopropyl | H | (+)-pin | |
| 3686 | CH2NH2 | PhCH2 | phenyl | H | (+)-pin | |
| 3687 | CH2NH2 | PhO | CH2CN | H | (+)-pin | |
| 3688 | CH2NH2 | PhS | CH2NC | H | (+)-pin | |
| 3689 | CH2NH2 | PhNH | CH2NO2 | H | (+)-pin | |
| 3690 | CH2NH2 | PhCONH | CH2SCH3 | H | (+)-pin | |
| 3691 | CH2NH2 | PhNHCO | CH2SOCH3 | H | (+)-pin | |
| 3692 | CH2NH2 | Ph(CH2)2 | CH2SO2CH3 | H | (+)-pin | |
| 3693 | NH(C=NH)NH2 | Ph | H | H | (+)-pin | |
| 3694 | NH(C=NH)NH2 | Ph | methyl | methyl | (+)-pin | |
| 3695 | NH(C=NH)NH2 | Ph | ethyl | H | (+)-pin | |
| 3696 | NH(C=NH)NH2 | Ph | ethyl | methyl | (+)-pin | |
| 3697 | NH(C=NH)NH2 | Ph | ethyl | ethyl | (+)-pin | |
| 3698 | NH(C=NH)NH2 | Ph | isopropyl | H | (+)-pin | |

TABLE 18-continued

| Ex | X | R¹³ | R¹⁴ | R¹⁵ | Y¹Y² | Phys. Data |
|---|---|---|---|---|---|---|
| 3699 | NH(C=NH)NH₂ | Ph | phenyl | H | (+)-pin | |
| 3700 | NH(C=NH)NH₂ | Ph | CH₂CN | H | (+)-pin | |
| 3701 | NH(C=NH)NH₂ | Ph | CH₂NC | H | (+)-pin | |
| 3702 | NH(C=NH)NH₂ | Ph | CH₂NO₂ | H | (+)-pin | |
| 3703 | NH(C=NH)NH₂ | Ph | CH₂SCH₃ | H | (+)-pin | |
| 3704 | NH(C=NH)NH₂ | Ph | CH₂SOCH₃ | H | (+)-pin | |
| 3705 | NH(C=NH)NH₂ | Ph | CH₂SO₂CH₃ | H | (+)-pin | |
| 3706 | NH(C=NH)NH₂ | Ph | CH₂OH | H | (+)-pin | |
| 3707 | NH(C=NH)NH₂ | Ph | CH₂COOH | H | (+)-pin | |
| 3708 | NH(C=NH)NH₂ | Ph | CH₂CN₄H | H | (+)-pin | |
| 3709 | NH(C=NH)NH₂ | Ph | CH₂NHSO₂CF₃ | H | (+)-pin | |
| 3710 | NH(C=NH)NH₂ | Ph | CH₂CH₂CN | H | (+)-pin | |
| 3711 | NH(C=NH)NH₂ | Ph | CH₂CH₂NC | H | (+)-pin | |
| 3712 | NH(C=NH)NH₂ | Ph | CH₂CH₂NO₂ | H | (+)-pin | |
| 3713 | NH(C=NH)NH₂ | Ph | CH₂CH₂SCH₃ | H | (+)-pin | |
| 3714 | NH(C=NH)NH₂ | Ph | CH₂CH₂SOCH₃ | H | (+)-pin | |
| 3715 | NH(C=NH)NH₂ | Ph | CH₂CH₂SO₂CH₃ | H | (+)-pin | |
| 3716 | NH(C=NH)NH₂ | Ph | CH₂CH₂OH | H | (+)-pin | |
| 3717 | NH(C=NH)NH₂ | Ph | NO₂ | H | (+)-pin | |
| 3718 | NH(C=NH)NH₂ | Ph | F | H | (+)-pin | |
| 3719 | NH(C=NH)NH₂ | Ph | OH | H | (+)-pin | |
| 3720 | NH(C=NH)NH₂ | Ph | H | H | OH, OH | |
| 3721 | NH(C=NH)NH₂ | Ph | methyl | H | OH, OH | |
| 3722 | NH(C=NH)NH₂ | Ph | methyl | methyl | OH, OH | |
| 3723 | NH(C=NH)NH₂ | Ph | ethyl | H | OH, OH | |
| 3724 | NH(C=NH)NH₂ | Ph | ethyl | methyl | OH, OH | |
| 3725 | NH(C=NH)NH₂ | Ph | ethyl | ethyl | OH, OH | |
| 3726 | NH(C=NH)NH₂ | Ph | isopropyl | H | OH, OH | |
| 3727 | NH(C=NH)NH₂ | Ph | phenyl | H | OH, OH | |
| 3728 | NH(C=NH)NH₂ | Ph | CH₂CN | H | OH, OH | |
| 3729 | NH(C=NH)NH₂ | Ph | CH₂NC | H | OH, OH | |
| 3730 | NH(C=NH)NH₂ | Ph | CH₂NO₂ | H | OH, OH | |
| 3731 | NH(C=NH)NH₂ | Ph | CH₂SCH₃ | H | OH, OH | |
| 3732 | NH(C=NH)NH₂ | Ph | CH₂SOCH₃ | H | OH, OH | |
| 3733 | NH(C=NH)NH₂ | Ph | CH₂SO₂CH₃ | H | OH, OH | |
| 3734 | NH(C=NH)NH₂ | Ph | CH₂OH | H | OH, OH | |
| 3735 | NH(C=NH)NH₂ | Ph | CH₂COOH | H | OH, OH | |
| 3736 | NH(C=NH)NH₂ | Ph | CH₂CN₄H | H | OH, OH | |
| 3737 | NH(C=NH)NH₂ | Ph | CH₂NHSO₂CF₃ | H | OH, OH | |
| 3738 | NH(C=NH)NH₂ | Ph | CH₂CH₂CN | H | OH, OH | |
| 3739 | NH(C=NH)NH₂ | Ph | CH₂CH₂NC | H | OH, OH | |
| 3740 | NH(C=NH)NH₂ | Ph | CH₂CH₂NO₂ | H | OH, OH | |
| 3741 | NH(C=NH)NH₂ | Ph | CH₂CH₂SCH₃ | H | OH, OH | |
| 3742 | NH(C=NH)NH₂ | Ph | CH₂CH₂SOCH₃ | H | OH, OH | |
| 3743 | NH(C=NH)NH₂ | Ph | CH₂CH₂SO₂CH₃ | H | OH, OH | |
| 3744 | NH(C=NH)NH₂ | Ph | CH₂CH₂OH | H | OH, OH | |
| 3745 | NH(C=NH)NH₂ | Ph | CH₂CH₂COOH | H | OH, OH | |
| 3746 | NH(C=NH)NH₂ | Ph | CH₂CH₂CN₄H | H | OH, OH | |
| 3747 | NH(C=NH)NH₂ | Ph | CH₂CH₂NHSO₂CF₃ | H | OH, OH | |
| 3748 | NH(C=NH)NH₂ | PhCH₂ | H | H | (+)-pin | |
| 3749 | NH(C=NH)NH₂ | PhO | methyl | H | (+)-pin | |
| 3750 | NH(C=NH)NH₂ | PhS | methyl | methyl | (+)-pin | |
| 3751 | NH(C=NH)NH₂ | PhNH | ethyl | H | (+)-pin | |
| 3752 | NH(C=NH)NH₂ | PhCONH | ethyl | methyl | (+)-pin | |
| 3753 | NH(C=NH)NH₂ | PhNHCO | ethyl | ethyl | (+)-pin | |
| 3754 | NH(C=NH)NH₂ | Ph | isopropyl | H | (+)-pin | |
| 3755 | NH(C=NH)NH₂ | PhCH₂ | phenyl | H | (+)-pin | |
| 3756 | NH(C=NH)NH₂ | PhO | CH₂CN | H | (+)-pin | |
| 3757 | NH(C=NH)NH₂ | PhS | CH₂NC | H | (+)-pin | |
| 3758 | NH(C=NH)NH₂ | PhNH | CH₂NO₂ | H | (+)-pin | |
| 3759 | NH(C=NH)NH₂ | PhCONH | CH₂SCH₃ | H | (+)-pin | |
| 3760 | NH(C=NH)NH₂ | PhNHCO | CH₂SOCH₃ | H | (+)-pin | |
| 3761 | NH(C=NH)NH₂ | Ph(CH₂)₂ | CH₂SO₂CH₃ | H | (+)-pin | |
| 3762 | OMe | Ph | CH₃ | H | (+)-pin | |
| 3763 | NH(C=NH)H | Ph | CH₃ | H | (+)-pin | |

TABLE 18-continued

| Ex | X | R¹³ | R¹⁴ | R¹⁵ | Y¹Y² | Phys. Data |
|---|---|---|---|---|---|---|
| 3764 | OMe | Ph | CH₃ | H | OH, OH | |
| 3765 | NH(C=NH)H | Ph | CH₃ | H | OH, OH | |

TABLE 19

| Ex | X | R¹³ | R¹⁴ | R¹⁵ | Y¹Y² | Phys. Data |
|---|---|---|---|---|---|---|
| 3770 | CH₂NH₂ | Ph | H | H | (+)-pin | |
| 3771 | CH₂NH₂ | Ph | methyl | H | (+)-pin | |
| 3772 | CH₂NH₂ | Ph | H | H | OH, OH | |
| 3773 | CH₂NH₂ | Ph | methyl | H | OH, OH | |
| 3774 | NH(C=NH)NH₂ | Ph | H | H | (+)-pin | |
| 3775 | NH(C=NH)NH₂ | Ph | methyl | H | (+)-pin | |
| 3776 | NH(C=NH)NH₂ | Ph | H | H | OH, OH | |
| 3777 | NH(C=NH)NH₂ | Ph | methyl | H | OH, OH | |
| 3778 | OMe | Ph | CH₃ | H | (+)-pin | |
| 3779 | NH(C=NH)H | Ph | CH₃ | H | (+)-pin | |
| 3780 | OMe | Ph | CH₃ | H | OH, OH | |
| 3781 | NH(C=NH)H | Ph | CH₃ | H | OH, OH | |

TABLE 20

| Ex | X | R¹³ | R¹⁴ | R¹⁵ | Y¹Y² | Phys. Data |
|---|---|---|---|---|---|---|
| 3786 | CH₂NH₂ | Ph | H | H | (+)-pin | |
| 3787 | CH₂NH₂ | Ph | methyl | methyl | (+)-pin | |
| 3788 | CH₂NH₂ | Ph | ethyl | H | (+)-pin | |
| 3789 | CH₂NH₂ | Ph | ethyl | methyl | (+)-pin | |
| 3790 | CH₂NH₂ | Ph | ethyl | ethyl | (+)-pin | |
| 3791 | CH₂NH₂ | Ph | isopropyl | H | (+)-pin | |
| 3792 | CH₂NH₂ | Ph | phenyl | H | (+)-pin | |
| 3793 | CH₂NH₂ | Ph | CH₂CN | H | (+)-pin | |
| 3794 | CH₂NH₂ | Ph | CH₂NC | H | (+)-pin | |
| 3795 | CH₂NH₂ | Ph | CH₂NO₂ | H | (+)-pin | |
| 3796 | CH₂NH₂ | Ph | CH₂SCH₃ | H | (+)-pin | |

TABLE 20-continued

| Ex | X | R13 | R14 | R15 | Y1Y2 | Phys. Data |
|---|---|---|---|---|---|---|
| 3797 | CH2NH2 | Ph | CH2SOCH3 | H | (+)-pin | |
| 3798 | CH2NH2 | Ph | CH2SO2CH3 | H | (+)-pin | |
| 3799 | CH2NH2 | Ph | CH2OH | H | (+)-pin | |
| 3800 | CH2NH2 | Ph | CH2COOH | H | (+)-pin | |
| 3801 | CH2NH2 | Ph | CH2CN4H | H | (+)-pin | |
| 3802 | CH2NH2 | Ph | CH2NHSO2CF3 | H | (+)-pin | |
| 3803 | CH2NH2 | Ph | CH2CH2CN | H | (+)-pin | |
| 3804 | CH2NH2 | Ph | CH2CH2NC | H | (+)-pin | |
| 3805 | CH2NH2 | Ph | CH2CH2NO2 | H | (+)-pin | |
| 3806 | CH2NH2 | Ph | CH2CH2SCH3 | H | (+)-pin | |
| 3807 | CH2NH2 | Ph | CH2CH2SOCH3 | H | (+)-pin | |
| 3808 | CH2NH2 | Ph | CH2CH2SO2CH3 | H | (+)-pin | |
| 3809 | CH2NH2 | Ph | CH2CH2OH | H | (+)-pin | |
| 3810 | CH2NH2 | Ph | NO2 | H | (+)-pin | |
| 3811 | CH2NH2 | Ph | F | H | (+)-pin | |
| 3812 | CH2NH2 | Ph | OH | H | (+)-pin | |
| 3813 | CH2NH2 | Ph | H | H | OH, OH | |
| 3814 | CH2NH2 | Ph | methyl | H | OH, OH | |
| 3815 | CH2NH2 | Ph | methyl | methyl | OH, OH | |
| 3816 | CH2NH2 | Ph | ethyl | H | OH, OH | |
| 3817 | CH2NH2 | Ph | ethyl | methyl | OH, OH | |
| 3818 | CH2NH2 | Ph | ethyl | ethyl | OH, OH | |
| 3819 | CH2NH2 | Ph | isopropyl | H | OH, OH | |
| 3820 | CH2NH2 | Ph | phenyl | H | OH, OH | |
| 3821 | CH2NH2 | Ph | CH2CN | H | OH, OH | |
| 3822 | CH2NH2 | Ph | CH2NC | H | OH, OH | |
| 3823 | CH2NH2 | Ph | CH2NO2 | H | OH, OH | |
| 3824 | CH2NH2 | Ph | CH2SCH3 | H | OH, OH | |
| 3825 | CH2NH2 | Ph | CH2SOCH3 | H | OH, OH | |
| 3826 | CH2NH2 | Ph | CH2SO2CH3 | H | OH, OH | |
| 3827 | CH2NH2 | Ph | CH2OH | H | OH, OH | |
| 3828 | CH2NH2 | Ph | CH2COOH | H | OH, OH | |
| 3829 | CH2NH2 | Ph | CH2CN4H | H | OH, OH | |
| 3830 | CH2NH2 | Ph | CH2NHSO2CF3 | H | OH, OH | |
| 3831 | CH2NH2 | Ph | CH2CH2CN | H | OH, OH | |
| 3832 | CH2NH2 | Ph | CH2CH2NC | H | OH, OH | |
| 3833 | CH2NH2 | Ph | CH2CH2NO2 | H | OH, OH | |
| 3834 | CH2NH2 | Ph | CH2CH2SCH3 | H | OH, OH | |
| 3835 | CH2NH2 | Ph | CH2CH2SOCH3 | H | OH, OH | |
| 3836 | CH2NH2 | Ph | CH2CH2SO2CH3 | H | OH, OH | |
| 3837 | CH2NH2 | Ph | CH2CH2OH | H | OH, OH | |
| 3838 | CH2NH2 | Ph | CH2CH2COOH | H | OH, OH | |
| 3839 | CH2NH2 | Ph | CH2CH2CN4H | H | OH, OH | |
| 3840 | CH2NH2 | Ph | CH2CH2NHSO2CF3 | H | OH, OH | |
| 3841 | CH2NH2 | PhCH2 | H | H | (+)-pin | |
| 3842 | CH2NH2 | PhO | methyl | H | (+)-pin | |
| 3843 | CH2NH2 | PhS | methyl | methyl | (+)-pin | |
| 3844 | CH2NH2 | PhNH | ethyl | H | (+)-pin | |
| 3845 | CH2NH2 | PhCONH | ethyl | methyl | (+)-pin | |
| 3846 | CH2NH2 | PhNHCO | ethyl | ethyl | (+)-pin | |
| 3847 | CH2NH2 | Ph | isopropyl | H | (+)-pin | |
| 3848 | CH2NH2 | PhCH2 | phenyl | H | (+)-pin | |
| 3849 | CH2NH2 | PhO | CH2CN | H | (+)-pin | |
| 3850 | CH2NH2 | PhS | CH2NC | H | (+)-pin | |
| 3851 | CH2NH2 | PhNH | CH2NO2 | H | (+)-pin | |
| 3852 | CH2NH2 | PhCONH | CH2SCH3 | H | (+)-pin | |
| 3853 | CH2NH2 | PhNHCO | CH2SOCH3 | H | (+)-pin | |
| 3854 | CH2NH2 | Ph(CH2)2 | CH2SO2CH3 | H | (+)-pin | |
| 3855 | NH(C=NH)NH2 | Ph | H | H | (+)-pin | |
| 3856 | NH(C=NH)NH2 | Ph | methyl | methyl | (+)-pin | |
| 3857 | NH(C=NH)NH2 | Ph | ethyl | H | (+)-pin | |
| 3858 | NH(C=NH)NH2 | Ph | ethyl | methyl | (+)-pin | |
| 3859 | NH(C=NH)NH2 | Ph | ethyl | ethyl | (+)-pin | |
| 3860 | NH(C=NH)NH2 | Ph | isopropyl | H | (+)-pin | |
| 3861 | NH(C=NH)NH2 | Ph | phenyl | H | (+)-pin | |

TABLE 20-continued

| Ex | X | R¹³ | R¹⁴ | R¹⁵ | Y¹Y² | Phys. Data |
|---|---|---|---|---|---|---|
| 3862 | NH(C=NH)NH₂ | Ph | CH₂CN | H | (+)-pin | |
| 3863 | NH(C=NH)NH₂ | Ph | CH₂NC | H | (+)-pin | |
| 3864 | NH(C=NH)NH₂ | Ph | CH₂NO₂ | H | (+)-pin | |
| 3865 | NH(C=NH)NH₂ | Ph | CH₂SCH₃ | H | (+)-pin | |
| 3866 | NH(C=NH)NH₂ | Ph | CH₂SOCH₃ | H | (+)-pin | |
| 3867 | NH(C=NH)NH₂ | Ph | CH₂SO₂CH₃ | H | (+)-pin | |
| 3868 | NH(C=NH)NH₂ | Ph | CH₂OH | H | (+)-pin | |
| 3869 | NH(C=NH)NH₂ | Ph | CH₂COOH | H | (+)-pin | |
| 3870 | NH(C=NH)NH₂ | Ph | CH₂CN₄H | H | (+)-pin | |
| 3871 | NH(C=NH)NH₂ | Ph | CH₂NHSO₂CF₃ | H | (+)-pin | |
| 3872 | NH(C=NH)NH₂ | Ph | CH₂CH₂CN | H | (+)-pin | |
| 3873 | NH(C=NH)NH₂ | Ph | CH₂CH₂NC | H | (+)-pin | |
| 3874 | NH(C=NH)NH₂ | Ph | CH₂CH₂NO₂ | H | (+)-pin | |
| 3875 | NH(C=NH)NH₂ | Ph | CH₂CH₂SCH₃ | H | (+)-pin | |
| 3876 | NH(C=NH)NH₂ | Ph | CH₂CH₂SOCH₃ | H | (+)-pin | |
| 3877 | NH(C=NH)NH₂ | Ph | CH₂CH₂SO₂CH₃ | H | (+)-pin | |
| 3878 | NH(C=NH)NH₂ | Ph | CH₂CH₂OH | H | (+)-pin | |
| 3879 | NH(C=NH)NH₂ | Ph | NO₂ | H | (+)-pin | |
| 3880 | NH(C=NH)NH₂ | Ph | F | H | (+)-pin | |
| 3881 | NH(C=NH)NH₂ | Ph | OH | H | (+)-pin | |
| 3882 | NH(C=NH)NH₂ | Ph | H | H | OH, OH | |
| 3883 | NH(C=NH)NH₂ | Ph | methyl | H | OH, OH | |
| 3884 | NH(C=NH)NH₂ | Ph | methyl | methyl | OH, OH | |
| 3885 | NH(C=NH)NH₂ | Ph | ethyl | H | OH, OH | |
| 3886 | NH(C=NH)NH₂ | Ph | ethyl | methyl | OH, OH | |
| 3887 | NH(C=NH)NH₂ | Ph | ethyl | ethyl | OH, OH | |
| 3888 | NH(C=NH)NH₂ | Ph | isopropyl | H | OH, OH | |
| 3889 | NH(C=NH)NH₂ | Ph | phenyl | H | OH, OH | |
| 3890 | NH(C=NH)NH₂ | Ph | CH₂CN | H | OH, OH | |
| 3891 | NH(C=NH)NH₂ | Ph | CH₂NC | H | OH, OH | |
| 3892 | NH(C=NH)NH₂ | Ph | CH₂NO₂ | H | OH, OH | |
| 3893 | NH(C=NH)NH₂ | Ph | CH₂SCH₃ | H | OH, OH | |
| 3894 | NH(C=NH)NH₂ | Ph | CH₂SOCH₃ | H | OH, OH | |
| 3895 | NH(C=NH)NH₂ | Ph | CH₂SO₂CH₃ | H | OH, OH | |
| 3896 | NH(C=NH)NH₂ | Ph | CH₂OH | H | OH, OH | |
| 3897 | NH(C=NH)NH₂ | Ph | CH₂COOH | H | OH, OH | |
| 3898 | NH(C=NH)NH₂ | Ph | CH₂CN₄H | H | OH, OH | |
| 3899 | NH(C=NH)NH₂ | Ph | CH₂NHSO₂CF₃ | H | OH, OH | |
| 3900 | NH(C=NH)NH₂ | Ph | CH₂CH₂CN | H | OH, OH | |
| 3901 | NH(C=NH)NH₂ | Ph | CH₂CH₂NC | H | OH, OH | |
| 3902 | NH(C=NH)NH₂ | Ph | CH₂CH₂NO₂ | H | OH, OH | |
| 3903 | NH(C=NH)NH₂ | Ph | CH₂CH₂SCH₃ | H | OH, OH | |
| 3904 | NH(C=NH)NH₂ | Ph | CH₂CH₂SOCH₃ | H | OH, OH | |
| 3905 | NH(C=NH)NH₂ | Ph | CH₂CH₂SO₂CH₃ | H | OH, OH | |
| 3906 | NH(C=NH)NH₂ | Ph | CH₂CH₂OH | H | OH, OH | |
| 3907 | NH(C=NH)NH₂ | Ph | CH₂CH₂COOH | H | OH, OH | |
| 3908 | NH(C=NH)NH₂ | Ph | CH₂CH₂CN₄H | H | OH, OH | |
| 3909 | NH(C=NH)NH₂ | Ph | CH₂CH₂NHSO₂CF₃ | H | OH, OH | |
| 3910 | NH(C=NH)NH₂ | PhCH₂ | H | H | (+)-pin | |
| 3911 | NH(C=NH)NH₂ | PhO | methyl | H | (+)-pin | |
| 3912 | NH(C=NH)NH₂ | PhS | methyl | methyl | (+)-pin | |
| 3913 | NH(C=NH)NH₂ | PhNH | ethyl | H | (+)-pin | |
| 3914 | NH(C=NH)NH₂ | PhCONH | ethyl | methyl | (+)-pin | |
| 3915 | NH(C=NH)NH₂ | PhNHCO | ethyl | ethyl | (+)-pin | |
| 3916 | NH(C=NH)NH₂ | Ph | isopropyl | H | (+)-pin | |
| 3917 | NH(C=NH)NH₂ | PhCH₂ | phenyl | H | (+)-pin | |
| 3918 | NH(C=NH)NH₂ | PhO | CH₂CN | H | (+)-pin | |
| 3919 | NH(C=NH)NH₂ | PhS | CH₂NC | H | (+)-pin | |
| 3920 | NH(C=NH)NH₂ | PhNH | CH₂NO₂ | H | (+)-pin | |
| 3921 | NH(C=NH)NH₂ | PhCONH | CH₂SCH₃ | H | (+)-pin | |
| 3922 | NH(C=NH)NH₂ | PhNHCO | CH₂SOCH₃ | H | (+)-pin | |
| 3923 | NH(C=NH)NH₂ | Ph(CH₂)₂ | CH₂SO₂CH₃ | H | (+)-pin | |
| 3924 | OMe | Ph | CH₃ | H | (+)-pin | |
| 3925 | NH(C=NH)H | Ph | CH₃ | H | (+)-pin | |

TABLE 20-continued

| Ex | X | R¹³ | R¹⁴ | R¹⁵ | Y¹Y² | Phys. Data |
|---|---|---|---|---|---|---|
| 3926 | OMe | Ph | CH₃ | H | OH, OH | |
| 3927 | NH(C=NH)H | Ph | CH₃ | H | OH, OH | |

TABLE 21

| Ex | X | R¹³ | R¹⁴ | R¹⁵ | Y¹Y² | Phys. Data |
|---|---|---|---|---|---|---|
| 3932 | CH₂NH₂ | Ph | H | H | (+)-pin | |
| 3933 | CH₂NH₂ | Ph | methyl | H | (+)-pin | |
| 3934 | CH₂NH₂ | Ph | H | H | OH, OH | |
| 3935 | CH₂NH₂ | Ph | methyl | H | OH, OH | |
| 3936 | NH(C=NH)NH₂ | Ph | H | H | (+)-pin | |
| 3937 | NH(C=NH)NH₂ | Ph | methyl | H | (+)-pin | |
| 3938 | NH(C=NH)NH₂ | Ph | H | H | OH, OH | |
| 3939 | NH(C=NH)NH₂ | Ph | methyl | H | OH, OH | |
| 3940 | OMe | Ph | CH₃ | H | (+)-pin | |
| 3941 | NH(C=NH)H | Ph | CH₃ | H | (+)-pin | |
| 3942 | OMe | Ph | CH₃ | H | OH, OH | |
| 3943 | NH(C=NH)H | Ph | CH₃ | H | OH, OH | |

TABLE 22

| Ex | X | R¹³ | R¹⁴ | R¹⁵ | Y¹Y² | Phys. Data |
|---|---|---|---|---|---|---|
| 3948 | CH₂NH₂ | Ph | H | H | (+)-pin | |
| 3949 | CH₂NH₂ | Ph | methyl | H | (+)-pin | |
| 3950 | CH₂NH₂ | Ph | H | H | OH, OH | |
| 3951 | CH₂NH₂ | Ph | methyl | H | OH, OH | |
| 3952 | NH(C=NH)NH₂ | Ph | H | H | (+)-pin | |
| 3953 | NH(C=NH)NH₂ | Ph | methyl | H | (+)-pin | |
| 3954 | NH(C=NH)NH₂ | Ph | H | H | OH, OH | |
| 3955 | NH(C=NH)NH₂ | Ph | methyl | H | OH, OH | |
| 3956 | OMe | Ph | CH₃ | H | (+)-pin | |
| 3957 | NH(C=NH)H | Ph | CH₃ | H | (+)-pin | |
| 3958 | OMe | Ph | CH₃ | H | OH, OH | |
| 3959 | NH(C=NH)H | Ph | CH₃ | H | OH, OH | |

TABLE 23

| Ex | X | R¹³ | R¹⁴ | R¹⁵ | Y¹Y² | Phys. Data |
|---|---|---|---|---|---|---|
| 3964 | CH₂NH₂ | Ph | H | H | (+)-pin | |
| 3965 | CH₂NH₂ | Ph | methyl | H | (+)-pin | |
| 3966 | CH₂NH₂ | Ph | H | H | OH, OH | |
| 3967 | CH₂NH₂ | Ph | methyl | H | OH, OH | |
| 3968 | NH(C=NH)NH₂ | Ph | H | H | (+)-pin | |
| 3969 | NH(C=NH)NH₂ | Ph | methyl | H | (+)-pin | |
| 3970 | NH(C=NH)NH₂ | Ph | H | H | OH, OH | |
| 3971 | NH(C=NH)NH₂ | Ph | methyl | H | OH, OH | |
| 3972 | OMe | Ph | CH₃ | H | (+)-pin | |
| 3973 | NH(C=NH)H | Ph | CH₃ | H | (+)-pin | |
| 3974 | OMe | Ph | CH₃ | H | OH, OH | |
| 3975 | NH(C=NH)H | Ph | CH₃ | H | OH, OH | |

TABLE 24

| Ex | X | R¹³ | R¹⁴ | R¹⁵ | Y¹Y² | Phys. Data |
|---|---|---|---|---|---|---|
| 3980 | CH₂NH₂ | Ph | H | H | (+)-pin | |
| 3981 | CH₂NH₂ | Ph | methyl | H | (+)-pin | |
| 3982 | CH₂NH₂ | Ph | H | H | OH, OH | |
| 3983 | CH₂NH₂ | Ph | methyl | H | OH, OH | |
| 3984 | NH(C=NH)NH₂ | Ph | H | H | (+)-pin | |
| 3985 | NH(C=NH)NH₂ | Ph | methyl | H | (+)-pin | |
| 3986 | NH(C=NH)NH₂ | Ph | H | H | OH, OH | |
| 3987 | NH(C=NH)NH₂ | Ph | methyl | H | OH, OH | |
| 3988 | OMe | Ph | CH₃ | H | (+)-pin | |
| 3989 | NH(C=NH)H | Ph | CH₃ | H | (+)-pin | |
| 3990 | OMe | Ph | CH₃ | H | OH, OH | |
| 3991 | NH(C=NH)H | Ph | CH₃ | H | OH, OH | |

TABLE 25

| Ex | X | R¹³ | R¹⁴ | R¹⁵ | Y¹Y² | Phys. Data |
|---|---|---|---|---|---|---|
| 3996 | CH₂NH₂ | Ph | H | H | (+)-pin | |
| 3997 | CH₂NH₂ | Ph | methyl | H | (+)-pin | |
| 3998 | CH₂NH₂ | Ph | H | H | OH, OH | |
| 3999 | CH₂NH₂ | Ph | methyl | H | OH, OH | |
| 4000 | NH(C=NH)NH₂ | Ph | H | H | (+)-pin | |
| 4001 | NH(C=NH)NH₂ | Ph | methyl | H | (+)-pin | |
| 4002 | NH(C=NH)NH₂ | Ph | H | H | OH, OH | |
| 4003 | NH(C=NH)NH₂ | Ph | methyl | H | OH, OH | |
| 4004 | OMe | Ph | CH₃ | H | (+)-pin | |
| 4005 | NH(C=NH)H | Ph | CH₃ | H | (+)-pin | |
| 4006 | OMe | Ph | CH₃ | H | OH, OH | |
| 4007 | NH(C=NH)H | Ph | CH₃ | H | OH, OH | |

TABLE 26

| Ex | X | R¹³ | R¹⁴ | R¹⁵ | Y¹Y² | Phys. Data |
|---|---|---|---|---|---|---|
| 4012 | CH₂NH₂ | Ph | H | H | (+)-pin | |
| 4013 | CH₂NH₂ | Ph | methyl | H | (+)-pin | |
| 4014 | CH₂NH₂ | Ph | H | H | OH, OH | |
| 4015 | CH₂NH₂ | Ph | methyl | H | OH, OH | |
| 4016 | CH₂NH₂ | Ph | H | Ph | (+)-pin | |
| 4017 | CH₂NH₂ | Ph | H | Ph | OH, OH | |
| 4018 | NH(C=NH)NH₂ | Ph | H | H | (+)-pin | |
| 4019 | NH(C=NH)NH₂ | Ph | methyl | H | (+)-pin | |
| 4020 | NH(C=NH)NH₂ | Ph | H | H | OH, OH | |
| 4021 | NH(C=NH)NH₂ | Ph | methyl | H | OH, OH | |
| 4022 | NH(C=NH)NH₂ | Ph | H | Ph | (+)-pin | |
| 4023 | NH(C=NH)NH₂ | Ph | H | Ph | OH, OH | |
| 4024 | OMe | Ph | CH₃ | H | (+)-pin | |
| 4025 | NH(C=NH)H | Ph | CH₃ | H | (+)-pin | |
| 4026 | OMe | Ph | CH₃ | H | OH, OH | |
| 4027 | NH(C=NH)H | Ph | CH₃ | H | OH, OH | |

TABLE 27

| Ex | X | R¹³ | R¹⁴ | R¹⁵ | R¹⁶ | Y¹Y² | Phys. Data |
|---|---|---|---|---|---|---|---|
| 4032 | CH₂NH₂ | Ph | H | H | H | (+)-pin | |
| 4033 | CH₂NH₂ | Ph | methyl | H | H | (+)-pin | |
| 4034 | CH₂NH₂ | Ph | H | H | H | OH, OH | |
| 4035 | CH₂NH₂ | Ph | methyl | H | H | OH, OH | |
| 4036 | NH(C=NH)NH₂ | Ph | H | H | H | (+)-pin | |
| 4037 | NH(C=NH)NH₂ | Ph | methyl | H | H | (+)-pin | |
| 4038 | NH(C=NH)NH₂ | Ph | H | H | H | OH, OH | |
| 4039 | NH(C=NH)NH₂ | Ph | methyl | H | H | OH, OH | |
| 4040 | NH(C=NH)NH₂ | Ph | H | CH₃ | CH₃ | (+)-pin | |
| 4041 | NH(C=NH)NH₂ | Ph | H | CH₃ | CH₃ | OH, OH | |
| 4042 | OMe | Ph | CH₃ | H | H | (+)-pin | |
| 4043 | NH(C=NH)H | Ph | CH₃ | H | H | (+)-pin | |
| 4044 | OMe | Ph | CH₃ | H | H | OH, OH | |
| 4045 | NH(C=NH)H | Ph | CH₃ | H | H | OH, OH | |

TABLE 28

[Structure: pyridine with R16, R14, R13, R15 substituents and C(=O)NH-CH(CH2CH2-X)-B(Y1)(Y2)]

| Ex | X | R$^{13}$ | R$^{14}$ | R$^{15}$ | R$^{16}$ | Y$^1$Y$^2$ | Phys. Data |
|---|---|---|---|---|---|---|---|
| 4050 | CH$_2$NH$_2$ | Ph | CH$_2$CO$_2$H | H | H | (+)-pin | |
| 4051 | CH$_2$NH$_2$ | Ph | methyl | H | H | (+)-pin | |
| 4052 | CH$_2$NH$_2$ | Ph | CH$_2$CO$_2$H | H | H | OH, OH | |
| 4053 | CH$_2$NH$_2$ | Ph | methyl | H | H | OH, OH | |
| 4054 | NH(C=NH)NH$_2$ | Ph | CH$_2$CN | H | H | (+)-pin | |
| 4055 | NH(C=NH)NH$_2$ | Ph | methyl | H | H | (+)-pin | |
| 4056 | NH(C=NH)NH$_2$ | Ph | CH$_2$CN | H | H | OH, OH | |
| 4057 | NH(C=NH)NH$_2$ | Ph | methyl | H | H | OH, OH | |
| 4058 | NH(C=NH)NH$_2$ | Ph | CH$_3$ | CH$_3$ | H | (+)-pin | |
| 4059 | NH(C=NH)NH$_2$ | Ph | CH$_3$ | CH$_3$ | H | OH, OH | |
| 4060 | OMe | Ph | CH$_3$ | H | H | (+)-pin | |
| 4061 | NH(C=NH)H | Ph | CH$_3$ | H | H | (+)-pin | |
| 4062 | OMe | Ph | CH$_3$ | H | H | OH, OH | |
| 4063 | N(C=NH)H | Ph | CH$_3$ | H | H | OH, OH | |
| 4064 | CH$_2$NH$_2$ | Ph | H | H | H | (+)-pin | |
| 4065 | CH$_2$NH$_2$ | Ph | H | H | H | OH, OH | |

TABLE 29

[Structure: pyridine with R16, R14, R13, R15 substituents and C(=O)NH-CH(CH2CH2-X)-B(Y1)(Y2)]

| Ex | X | R$^{13}$ | R$^{14}$ | R$^{15}$ | R$^{16}$ | Y$^1$Y$^2$ | Phys. Data |
|---|---|---|---|---|---|---|---|
| 4070 | CH$_2$NH$_2$ | Ph | H | H | H | (+)-pin | |
| 4071 | CH$_2$NH$_2$ | Ph | methyl | H | H | (+)-pin | |
| 4072 | CH$_2$NH$_2$ | Ph | H | H | H | OH, OH | |
| 4073 | CH$_2$NH$_2$ | Ph | methyl | H | H | OH, OH | |
| 4074 | NH(C=NH)NH$_2$ | Ph | H | H | H | (+)-pin | |
| 4075 | NH(C=NH)NH$_2$ | Ph | methyl | H | H | (+)-pin | |
| 4076 | NH(C=NH)NH$_2$ | Ph | H | H | H | OH, OH | |
| 4077 | NH(C=NH)NH$_2$ | Ph | methyl | H | H | OH, OH | |
| 4078 | NH(C=NH)NH$_2$ | Ph | CH$_3$ | CH$_3$ | H | (+)-pin | |
| 4079 | NH(C=NH)NH$_2$ | Ph | CH$_3$ | CH$_3$ | H | OH, OH | |
| 4080 | OMe | Ph | H | H | OH | (+)-pin | |
| 4081 | NH(C=NH)H | Ph | H | H | F | (+)-pin | |
| 4082 | OMe | Ph | H | H | Me | OH, OH | |
| 4083 | NH(C=NH)H | Ph | H | H | Et | OH, OH | |

TABLE 30

Ex | X | R¹³ | R¹⁴ | R¹⁵ | R¹⁶ | Y¹Y² | Phys. Data
---|---|---|---|---|---|---|---
4088 | CH₂NH₂ | PhCH₂ | H | H | Cl | (+)-pin |
4089 | CH₂NH₂ | PhCH₂ | H | methyl | H | (+)-pin |
4090 | CH₂NH₂ | PhCH₂ | H | CH₂CN | H | (+)-pin |
4091 | CH₂NH₂ | PhCH₂ | H | CH₂COOH | H | (+)-pin |
4092 | CH₂NH₂ | PhCH₂ | H | CH₂NC | H | (+)-pin |
4093 | CH₂NH₂ | PhCH₂ | H | CH₂NO₂ | H | (+)-pin |
4094 | CH₂NH₂ | PhCH₂ | H | (CH₂)₂OH | H | (+)-pin |
4095 | CH₂NH₂ | PhCH₂ | H | CH₂SOCH₃ | H | (+)-pin |
4096 | CH₂NH₂ | PhCH₂ | H | H | NO₂ | OH, OH |
4097 | CH₂NH₂ | PhCH₂ | H | methyl | H | OH, OH |
4098 | CH₂NH₂ | PhCH₂ | H | CH₂CN | H | OH, OH |
4099 | CH₂NH₂ | PhCH₂ | H | CH₂COOH | H | OH, OH |
4100 | CH₂NH₂ | PhCH₂ | H | CH₂NC | H | OH, OH |
4101 | CH₂NH₂ | PhCH₂ | H | CH₂NO₂ | H | OH, OH |
4102 | CH₂NH₂ | PhCH₂ | H | (CH₂)₂OH | H | OH, OH |
4103 | CH₂NH₂ | PhCH₂ | H | CH₂SOCH₃ | H | OH, OH |
4104 | NH(C—NH)NH₂ | PhCH₂ | H | H | H | (+)-pin |
4105 | NH(C—NH)NH₂ | PhCH₂ | H | methyl | H | (+)-pin |
4106 | NH(C—NH)NH₂ | PhCH₂ | H | CH₂CN | H | (+)-pin |
4107 | NH(C—NH)NH₂ | PhCH₂ | H | CH₂COOH | H | (+)-pin |
4108 | NH(C—NH)NH₂ | PhCH₂ | H | CH₂NC | H | (+)-pin |
4109 | NH(C—NH)NH₂ | PhCH₂ | H | CH₂NO₂ | H | (+)-pin |
4110 | NH(C—NH)NH₂ | PhCH₂ | H | (CH₂)₂OH | H | (+)-pin |
4111 | NH(C—NH)NH₂ | PhCH₂ | H | CH₂SOCH₃ | H | (+)-pin |
4112 | NH(C—NH)NH₂ | PhCH₂ | H | H | H | OH, OH |
4113 | NH(C—NH)NH₂ | PhCH₂ | H | methyl | H | OH, OH |
4114 | NH(C—NH)NH₂ | PhCH₂ | H | CH₂CN | H | OH, OH |
4115 | NH(C—NH)NH₂ | PhCH₂ | H | CH₂COOH | H | OH, OH |
4116 | NH(C—NH)NH₂ | PhCH₂ | H | CH₂NC | H | OH, OH |
4117 | NH(C—NH)NH₂ | PhCH₂ | H | CH₂NO₂ | H | OH, OH |
4118 | NH(C—NH)NH₂ | PhCH₂ | H | (CH₂)₂OH | H | OH, OH |
4119 | NH(C—NH)NH₂ | PhCH₂ | H | CH₂SOCH₃ | H | OH, OH |

TABLE 31

Ex | X | R¹³ | R¹⁴ | R¹⁵ | Y¹Y² | Phys. Data
---|---|---|---|---|---|---
4124 | CH₂NH₂ | PhCH₂ | H | H | (+)-pin |
4125 | CH₂NH₂ | PhCH₂ | H | methyl | (+)-pin |
4126 | CH₂NH₂ | PhCH₂ | H | CH₂CN | (+)-pin |
4127 | CH₂NH₂ | PhCH₂ | H | CH₂COOH | (+)-pin |
4128 | CH₂NH₂ | PhCH₂ | H | CH₂NC | (+)-pin |
4129 | CH₂NH₂ | PhCH₂ | H | CH₂NO₂ | (+)-pin |
4130 | CH₂NH₂ | PhCH₂ | H | (CH₂)₂OH | (+)-pin |
4131 | CH₂NH₂ | PhCH₂ | H | CH₂SOCH₃ | (+)-pin |
4132 | CH₂NH₂ | PhCH₂ | H | H | OH, OH |
4133 | CH₂NH₂ | PhCH₂ | H | methyl | OH, OH |
4134 | CH₂NH₂ | PhCH₂ | H | CH₂CN | OH, OH |

TABLE 31-continued

Structure: Pyrazole ring with R13, R14, R15 substituents, connected via (CH2)m-C(O)-NH-CH(CH2CH2-X)-B(Y1)(Y2), and m = 1

| Ex | X | R13 | R14 | R15 | Y1Y2 | Phys. Data |
|---|---|---|---|---|---|---|
| 4135 | CH2NH2 | PhCH2 | H | CH2COOH | OH, OH | |
| 4136 | CH2NH2 | PhCH2 | H | CH2NC | OH, OH | |
| 4137 | CH2NH2 | PhCH2 | H | CH2NO2 | OH, OH | |
| 4138 | CH2NH2 | PhCH2 | H | (CH2)2OH | OH, OH | |
| 4139 | CH2NH2 | PhCH2 | H | CH2SOCH3 | OH, OH | |
| 4140 | NH(C—NH)NH2 | PhCH2 | H | H | (+)-pin | |
| 4141 | NH(C—NH)NH2 | PhCH2 | H | methyl | (+)-pin | |
| 4142 | NH(C—NH)NH2 | PhCH2 | H | CH2CN | (+)-pin | |
| 4143 | NH(C—NH)NH2 | PhCH2 | H | CH2COOH | (+)-pin | |
| 4144 | NH(C—NH)NH2 | PhCH2 | H | CH2NC | (+)-pin | |
| 4145 | NH(C—NH)NH2 | PhCH2 | H | CH2NO2 | (+)-pin | |
| 4146 | NH(C—NH)NH2 | PhCH2 | H | (CH2)2OH | (+)-pin | |
| 4147 | NH(C—NH)NH2 | PhCH2 | H | CH2SOCH3 | (+)-pin | |
| 4148 | NH(C—NH)NH2 | PhCH2 | H | H | OH, OH | |
| 4149 | NH(C—NH)NH2 | PhCH2 | H | methyl | OH, OH | |
| 4150 | NH(C—NH)NH2 | PhCH2 | H | CH2CN | OH, OH | |
| 4151 | NH(C—NH)NH2 | PhCH2 | H | CH2COOH | OH, OH | |
| 4152 | NH(C—NH)NH2 | PhCH2 | H | CH2NC | OH, OH | |
| 4153 | NH(C—NH)NH2 | PhCH2 | H | CH2NO2 | OH, OH | |
| 4154 | NH(C—NH)NH2 | PhCH2 | H | (CH2)2OH | OH, OH | |
| 4155 | NH(C—NH)NH2 | PhCH2 | H | CH2SOCH3 | OH, OH | |

TABLE 32

Structure: Imidazole ring with R13, R14, R15 substituents, connected via (CH2)m-C(O)-NH-CH(CH2CH2-X)-B(Y1)(Y2), and m = 1

| Ex | X | R13 | R14 | R15 | Y1Y2 | Phys. Data |
|---|---|---|---|---|---|---|
| 4160 | CH2NH2 | PhCH2 | H | H | (+)-pin | |
| 4161 | CH2NH2 | PhCH2 | Cl | H | (+)-pin | |
| 4162 | CH2NH2 | PhCH2 | H | methyl | (+)-pin | |
| 4163 | CH2NH2 | PhCH2 | H | CH2CN | (+)-pin | |
| 4164 | CH2NH2 | PhCH2 | Cl | CH2CN | (+)-pin | |
| 4165 | CH2NH2 | PhCH2 | H | CH2COOH | (+)-pin | |
| 4166 | CH2NH2 | PhCH2 | H | CH2NC | (+)-pin | |
| 4167 | CH2NH2 | PhCH2 | H | CH2NO2 | (+)-pin | |
| 4168 | CH2NH2 | PhCH2 | H | (CH2)2OH | (+)-pin | |
| 4169 | CH2NH2 | PhCH2 | H | CH2SOCH3 | (+)-pin | |
| 4170 | CH2NH2 | PhCH2 | H | H | OH, OH | |
| 4171 | CH2NH2 | PhCH2 | Cl | H | OH, OH | |
| 4172 | CH2NH2 | PhCH2 | H | methyl | OH, OH | |
| 4173 | CH2NH2 | PhCH2 | H | CH2CN | OH, OH | |
| 4174 | CH2NH2 | PhCH2 | Cl | CH2CN | OH, OH | |
| 4175 | CH2NH2 | PhCH2 | H | CH2COOH | OH, OH | |
| 4176 | CH2NH2 | PhCH2 | H | CH2NC | OH, OH | |
| 4177 | CH2NH2 | PhCH2 | H | CH2NO2 | OH, OH | |
| 4178 | CH2NH2 | PhCH2 | H | (CH2)2OH | OH, OH | |
| 4179 | CH2NH2 | PhCH2 | H | CH2SOCH3 | OH, OH | |
| 4180 | NH(C—NH)NH2 | PhCH2 | H | H | (+)-pin | |
| 4181 | NH(C—NH)NH2 | PhCH2 | H | methyl | (+)-pin | |

TABLE 32-continued

Structure: imidazole ring with R14, R15 substituents, N-(CH2)m-C(O)-NH-CH(B(Y1)(Y2))-CH2CH2-X, R13 on imidazole, and m = 1

| Ex | X | R13 | R14 | R15 | Y1Y2 | Phys. Data |
|---|---|---|---|---|---|---|
| 4182 | NH(C—NH)NH2 | PhCH2 | H | CH2CN | (+)-pin | |
| 4183 | NH(C—NH)NH2 | PhCH2 | H | CH2COOH | (+)-pin | |
| 4184 | NH(C—NH)NH2 | PhCH2 | H | CH2NC | (+)-pin | |
| 4185 | NH(C—NH)NH2 | PhCH2 | H | CH2NO2 | (+)-pin | |
| 4186 | NH(C—NH)NH2 | PhCH2 | H | (CH2)2OH | (+)-pin | |
| 4187 | NH(C—NH)NH2 | PhCH2 | H | CH2SOCH3 | (+)-pin | |
| 4188 | NH(C—NH)NH2 | PhCH2 | H | H | OH, OH | |
| 4189 | NH(C—NH)NH2 | PhCH2 | H | methyl | OH, OH | |
| 4190 | NH(C—NH)NH2 | PhCH2 | H | CH2CN | OH, OH | |
| 4191 | NH(C—NH)NH2 | PhCH2 | H | CH2COOH | OH, OH | |
| 4192 | NH(C—NH)NH2 | PhCH2 | H | CH2NC | OH, OH | |
| 4193 | NH(C—NH)NH2 | PhCH2 | H | CH2NO2 | OH, OH | |
| 4194 | NH(C—NH)NH2 | PhCH2 | H | (CH2)2OH | OH, OH | |
| 4195 | NH(C—NH)NH2 | PhCH2 | H | CH2SOCH3 | OH, OH | |

TABLE 33

Structure: triazole ring with R13, R14 substituents, N-(CH2)m-C(O)-NH-CH(B(Y1)(Y2))-CH2CH2-X, and m = 1

| Ex | X | R13 | R14 | Y1Y2 | Phys. Data |
|---|---|---|---|---|---|
| 4200 | CH2NH2 | PhCH2 | H | (+)-pin | |
| 4201 | CH2NH2 | PhCH2 | methyl | (+)-pin | |
| 4202 | CH2NH2 | PhCH2 | CH2CN | (+)-pin | |
| 4203 | CH2NH2 | PhCH2 | CH2CN | (+)-pin | |
| 4204 | CH2NH2 | PhCH2 | CH2COOH | (+)-pin | |
| 4205 | CH2NH2 | PhCH2 | CH2NC | (+)-pin | |
| 4206 | CH2NH2 | PhCH2 | CH2NO2 | (+)-pin | |
| 4207 | CH2NH2 | PhCH2 | (CH2)2OH | (+)-pin | |
| 4208 | CH2NH2 | PhCH2 | CH2SOCH3 | (+)-pin | |
| 4209 | CH2NH2 | PhCH2 | H | OH, OH | |
| 4210 | CH2NH2 | PhCH2 | methyl | OH, OH | |
| 4211 | CH2NH2 | PhCH2 | CH2CN | OH, OH | |
| 4212 | CH2NH2 | PhCH2 | CH2CN | OH, OH | |
| 4213 | CH2NH2 | PhCH2 | CH2COOH | OH, OH | |
| 4214 | CH2NH2 | PhCH2 | CH2NC | OH, OH | |
| 4215 | CH2NH2 | PhCH2 | CH2NO2 | OH, OH | |
| 4216 | CH2NH2 | PhCH2 | (CH2)2OH | OH, OH | |
| 4217 | CH2NH2 | PhCH2 | CH2SOCH3 | OH, OH | |
| 4218 | NH(C=NH)NH2 | PhCH2 | H | (+)-pin | |
| 4219 | NH(C=NH)NH2 | PhCH2 | methyl | (+)-pin | |
| 4220 | NH(C=NH)NH2 | PhCH2 | CH2CN | (+)-pin | |
| 4221 | NH(C=NH)NH2 | PhCH2 | (CH2)2CN | (+)-pin | |
| 4222 | NH(C=NH)NH2 | PhCH2 | CH2COOH | (+)-pin | |
| 4223 | NH(C=NH)NH2 | PhCH2 | (CH2)2COOH | (+)-pin | |
| 4224 | NH(C=NH)NH2 | PhCH2 | CH2NC | (+)-pin | |
| 4225 | NH(C=NH)NH2 | PhCH2 | CH2NO2 | (+)-pin | |
| 4226 | NH(C=NH)NH2 | PhCH2 | (CH2)2OH | (+)-pin | |
| 4227 | NH(C=NH)NH2 | PhCH2 | CH2SOCH3 | (+)-pin | |
| 4228 | NH(C=NH)NH2 | PhCH2 | H | OH, OH | |
| 4229 | NH(C=NH)NH2 | PhCH2 | methyl | OH, OH | |
| 4230 | NH(C=NH)NH2 | PhCH2 | CH2CN | OH, OH | |
| 4231 | NH(C=NH)NH2 | PhCH2 | (CH2)2CN | OH, OH | |
| 4232 | NH(C=NH)NH2 | PhCH2 | CH2COOH | OH, OH | |
| 4233 | NH(C=NH)NH2 | PhCH2 | (CH2)2COOH | OH, OH | |
| 4234 | NH(C=NH)NH2 | PhCH2 | CH2NC | OH, OH | |
| 4235 | NH(C=NH)NH2 | PhCH2 | CH2NO2 | OH, OH | |
| 4236 | NH(C=NH)NH2 | PhCH2 | (CH2)2OH | OH, OH | |
| 4237 | NH(C=NH)NH2 | PhCH2 | CH2SOCH3 | OH, OH | |

TABLE 34

| Ex | X | R13 | Y1Y2 | Phys. Data |
|---|---|---|---|---|
| | | m = 1 | | |
| 4242 | CH2NH2 | PhCH2 | (+)-pin | |
| 4243 | CH2NH2 | PhCH2 | OH, OH | |
| 4244 | NH(C=NH)NH2 | PhCH2 | (+)-pin | |
| 4245 | NH(C=NH)NH2 | PhCH2 | OH, OH | |
| 4246 | OMe | PhCH2 | (+)-pin | |
| 4247 | OMe | PhCH2 | OH, OH | |
| 4248 | NH(C=NH)H | PhCH2 | (+)-pin | |
| 4249 | NH(C=NH)H | PhCH2 | OH, OH | |
| 4250 | CH2NH2 | PhCH2CH2 | (+)-pin | DB |
| 4251 | CH2NH2 | PhCH2CH2 | OH, OH | |
| 4252 | NH(C=NH)NH2 | PhCH2CH2 | (+)-pin | |
| 4253 | NH(C=NH)NH2 | PhCH2CH2 | OH, OH | |
| 4254 | OMe | PhCH2CH2 | (+)-pin | |
| 4255 | OMe | PhCH2CH2 | OH, OH | |
| 4256 | NH(C=NH)H | PhCH2CH2 | (+)-pin | |
| 4257 | NH(C=NH)H | PhCH2CH2 | OH, OH | DC |
| 4258 | CH2NH2 | Ph | (+)-pin | |
| 4259 | CH2NH2 | Ph | OH, OH | |
| 4260 | NH(C=NH)NH2 | Ph | (+)-pin | |
| 4261 | NH(C=NH)NH2 | Ph | OH, OH | |
| 4262 | OMe | Ph | (+)-pin | |
| 4263 | OMe | Ph | OH, OH | |
| 4264 | NH(C=NH)H | Ph | (+)-pin | |
| 4265 | NH(C=NH)H | Ph | OH, OH | |
| 4266 | CH2NH2 | PhCH2CH2S | (+)-pin | |
| 4267 | CH2NH2 | PhCH2S | (+)-pin | |
| 4268 | CH2NH2 | PhCH2CH2S | OH, OH | |
| 4269 | CH2NH2 | PhCH2S | OH, OH | |
| 4270 | | m = 2 | | |
| 4271 | CH2NH2 | PhCH2 | (+)-pin | |
| 4272 | CH2NH2 | PhCH2 | OH, OH | |
| 4273 | NH(C=NH)NH2 | PhCH2 | (+)-pin | |
| 4274 | NH(C=NH)NH2 | PhCH2 | OH, OH | |
| 4275 | OMe | PhCH2 | (+)-pin | |
| 4276 | OMe | PhCH2 | OH, OH | |
| 4277 | NH(C=NH)H | PhCH2 | (+)-pin | |
| 4278 | NH(C=NH)H | PhCH2 | OH, OH | |
| 4279 | CH2NH2 | PhCH2CH2 | (+)-pin | |
| 4280 | CH2NH2 | PhCH2CH2 | OH, OH | |
| 4281 | NH(C=NH)NH2 | PhCH2CH2 | (+)-pin | |
| 4282 | NH(C=NH)NH2 | PhCH2CH2 | OH, OH | |
| 4283 | OMe | PhCH2CH2 | (+)-pin | |
| 4284 | OMe | PhCH2CH2 | OH, OH | |
| 4285 | NH(C=NH)H | PhCH2CH2 | (+)-pin | |
| 4286 | NH(C=NH)H | PhCH2CH2 | OH, OH | |
| 4287 | CH2NH2 | Ph | (+)-pin | |
| 4288 | CH2NH2 | Ph | OH, OH | |
| 4289 | NH(C=NH)NH2 | Ph | (+)-pin | |
| 4290 | NH(C=NH)NH2 | Ph | OH, OH | |
| 4291 | OMe | Ph | (+)-pin | |
| 4292 | OMe | Ph | OH, OH | |
| 4293 | NH(C=NH)H | Ph | (+)-pin | |
| 4294 | NH(C=NH)H | Ph | OH, OH | |

DB. HRMS Calc'd. 495.3255, Found 495.3257
DC. HRMS Calc'd. 467.2442, Found 467.2950

TABLE 35

| Ex | X | R13 | Y1Y2 | Phys. Data |
|---|---|---|---|---|
| | | m = 1 | | |
| 4299 | CH2NH2 | PhCH2 | (+)-pin | |
| 4300 | CH2NH2 | PhCH2 | OH, OH | |
| 4301 | NH(C=NH)NH2 | PhCH2 | (+)-pin | |
| 4302 | NH(C=NH)NH2 | PhCH2 | OH, OH | |
| 4303 | OMe | PhCH2 | (+)-pin | |
| 4304 | OMe | PhCH2 | OH, OH | |
| 4305 | NH(C=NH)H | PhCH2 | (+)-pin | |
| 4306 | NH(C=NH)H | PhCH2 | OH, OH | |
| 4307 | CH2NH2 | PhCH2CH2 | (+)-pin | DE |
| 4308 | CH2NH2 | PhCH2CH2 | OH, OH | |
| 4309 | NH(C=NH)NH2 | PhCH2CH2 | (+)-pin | |
| 4310 | NH(C=NH)NH2 | PhCH2CH2 | OH, OH | |
| 4311 | OMe | PhCH2CH2 | (+)-pin | |
| 4312 | OMe | PhCH2CH2 | OH, OH | |
| 4313 | NH(C=NH)H | PhCH2CH2 | (+)-pin | |
| 4314 | NH(C=NH)H | PhCH2CH2 | OH, OH | |
| 4315 | CH2NH2 | Ph | (+)-pin | |
| 4316 | CH2NH2 | Ph | OH, OH | |
| 4317 | NH(C=NH)NH2 | Ph | (+)-pin | |
| 4318 | NH(C=NH)NH2 | Ph | OH, OH | |
| 4319 | OMe | Ph | (+)-pin | |
| 4320 | OMe | Ph | OH, OH | |
| 4321 | NH(C=NH)H | Ph | (+)-pin | |
| 4322 | NH(C=NH)H | Ph | OH, OH | |
| 4323 | | m = 2 | | |
| 4324 | CH2NH2 | PhCH2 | (+)-pin | |
| 4325 | CH2NH2 | PhCH2 | OH, OH | |
| 4326 | NH(C=NH)NH2 | PhCH2 | (+)-pin | |
| 4327 | NH(C=NH)NH2 | PhCH2 | OH, OH | |
| 4328 | OMe | PhCH2 | (+)-pin | |
| 4329 | OMe | PhCH2 | OH, OH | |
| 4330 | NH(C=NH)H | PhCH2 | (+)-pin | |
| 4331 | NH(C=NH)H | PhCH2 | OH, OH | |
| 4332 | CH2NH2 | PhCH2CH2 | (+)-pin | |
| 4333 | CH2NH2 | PhCH2CH2 | OH, OH | |
| 4334 | NH(C=NH)NH2 | PhCH2CH2 | (+)-pin | |
| 4335 | NH(C=NH)NH2 | PhCH2CH2 | OH, OH | |
| 4336 | OMe | PhCH2CH2 | (+)-pin | |
| 4337 | OMe | PhCH2CH2 | OH, OH | |
| 4338 | NH(C=NH)H | PhCH2CH2 | (+)-pin | |
| 4339 | NH(C=NH)H | PhCH2CH2 | OH, OH | |
| 4340 | CH2NH2 | Ph | (+)-pin | |
| 4341 | CH2NH2 | Ph | OH, OH | |
| 4342 | NH(C=NH)NH2 | Ph | (+)-pin | |
| 4343 | NH(C=NH)NH2 | Ph | OH, OH | |
| 4344 | OMe | Ph | (+)-pin | |
| 4345 | OMe | Ph | OH, OH | |
| 4346 | NH(C=NH)H | Ph | (+)-pin | |
| 4347 | NH(C=NH)H | Ph | OH, OH | |

DE. HRMS Calc'd. 495.3255, Found 495.3249

TABLE 36

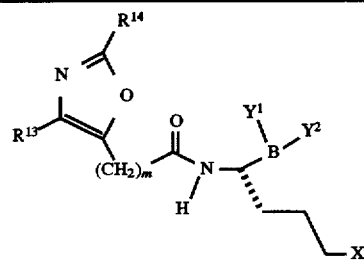

| Ex | X | R¹³ | R¹⁴ | Y¹Y² | Phys. Data |
|---|---|---|---|---|---|
| | | | m = 1 | | |
| 4348 | $CH_2NH_2$ | $PhCH_2$ | H | (+)-pin | |
| 4349 | $CH_2NH_2$ | $PhCH_2$ | methyl | (+)-pin | |
| 4350 | $CH_2NH_2$ | $PhCH_2$ | $CH_2CN$ | (+)-pin | |
| 4351 | $CH_2NH_2$ | $PhCH_2$ | $CH_2COOH$ | (+)-pin | |
| 4352 | $CH_2NH_2$ | $PhCH_2$ | $CH_2NC$ | (+)-pin | |
| 4353 | $CH_2NH_2$ | $PhCH_2$ | $CH_2NO_2$ | (+)-pin | |
| 4354 | $CH_2NH_2$ | $PhCH_2$ | $(CH_2)_2OH$ | (+)-pin | |
| 4355 | $CH_2NH_2$ | $PhCH_2$ | $CH_2SOCH_3$ | (+)-pin | |
| 4356 | $CH_2NH_2$ | $PhCH_2$ | H | OH, OH | |
| 4357 | $CH_2NH_2$ | $PhCH_2$ | methyl | OH, OH | |
| 4358 | $CH_2NH_2$ | $PhCH_2$ | $CH_2CN$ | OH, OH | |
| 4359 | $CH_2NH_2$ | $PhCH_2$ | $CH_2COOH$ | OH, OH | |
| 4360 | $CH_2NH_2$ | $PhCH_2$ | $CH_2NC$ | OH, OH | |
| 4361 | $CH_2NH_2$ | $PhCH_2$ | $CH_2NO_2$ | OH, OH | |
| 4362 | $CH_2NH_2$ | $PhCH_2$ | $(CH_2)_2OH$ | OH, OH | |
| 4363 | $CH_2NH_2$ | $PhCH_2$ | $CH_2SOCH_3$ | OH, OH | |
| 4364 | $NH(C=NH)NH_2$ | $PhCH_2$ | H | (+)-pin | |
| 4365 | $NH(C=NH)NH_2$ | $PhCH_2$ | methyl | (+)-pin | |
| 4366 | $NH(C=NH)NH_2$ | $PhCH_2$ | $CH_2CN$ | (+)-pin | |
| 4367 | $NH(C=NH)NH_2$ | $PhCH_2$ | $(CH_2)_2CN$ | (+)-pin | |
| 4368 | $NH(C=NH)NH_2$ | $PhCH_2$ | $CH_2COOH$ | (+)-pin | |
| 4369 | $NH(C=NH)NH_2$ | $PhCH_2$ | $(CH_2)_2COOH$ | (+)-pin | |
| 4370 | $NH(C=NH)NH_2$ | $PhCH_2$ | $CH_2NC$ | (+)-pin | |
| 4371 | $NH(C=NH)NH_2$ | $PhCH_2$ | $CH_2NO_2$ | (+)-pin | |
| 4372 | $NH(C=NH)NH_2$ | $PhCH_2$ | $(CH_2)_2OH$ | (+)-pin | |
| 4373 | $NH(C=NH)NH_2$ | $PhCH_2$ | $CH_2SOCH_3$ | (+)-pin | |
| 4374 | $NH(C=NH)NH_2$ | $PhCH_2$ | H | H, OH | |
| 4375 | $NH(C=NH)NH_2$ | $PhCH_2$ | methyl | OH, OH | |
| 4376 | $NH(C=NH)NH_2$ | $PhCH_2$ | $CH_2CN$ | OH, OH | |
| 4377 | $NH(C=NH)NH_2$ | $PhCH_2$ | $(CH_2)_2CN$ | OH, OH | |
| 4378 | $NH(C=NH)NH_2$ | $PhCH_2$ | $CH_2COOH$ | OH, OH | |
| 4379 | $NH(C=NH)NH_2$ | $PhCH_2$ | $(CH_2)_2COOH$ | OH, OH | |
| 4380 | $NH(C=NH)NH_2$ | $PhCH_2$ | $CH_2NC$ | OH, OH | |
| 4381 | $NH(C=NH)NH_2$ | $PhCH_2$ | $CH_2NO_2$ | OH, OH | |
| 4382 | $NH(C=NH)NH_2$ | $PhCH_2$ | $(CH_2)_2OH$ | OH, OH | |
| 4383 | $NH(C=NH)NH_2$ | $PhCH_2$ | $CH_2SOCH_3$ | OH, OH | |
| 4384 | | | m = 2 | | |
| 4385 | $CH_2NH_2$ | $PhCH_2$ | H | (+)-pin | |
| 4386 | $CH_2NH_2$ | $PhCH_2$ | methyl | (+)-pin | |
| 4387 | $CH_2NH_2$ | $PhCH_2$ | $CH_2CN$ | (+)-pin | |
| 4388 | $CH_2NH_2$ | $PhCH_2$ | $CH_2COOH$ | (+)-pin | |
| 4389 | $CH_2NH_2$ | $PhCH_2$ | $CH_2NC$ | (+)-pin | |
| 4390 | $CH_2NH_2$ | $PhCH_2$ | $CH_2NO_2$ | (+)-pin | |
| 4391 | $CH_2NH_2$ | $PhCH_2$ | $(CH_2)_2OH$ | (+)-pin | |
| 4392 | $CH_2NH_2$ | $PhCH_2$ | $CH_2SOCH_3$ | (+)-pin | |
| 4393 | $CH_2NH_2$ | $PhCH_2$ | H | OH, OH | |
| 4394 | $CH_2NH_2$ | $PhCH_2$ | methyl | OH, OH | |
| 4395 | $CH_2NH_2$ | $PhCH_2$ | $CH_2CN$ | OH, OH | |
| 4396 | $CH_2NH_2$ | $PhCH_2$ | $CH_2COOH$ | OH, OH | |
| 4397 | $CH_2NH_2$ | $PhCH_2$ | $CH_2NC$ | OH, OH | |
| 4398 | $CH_2NH_2$ | $PhCH_2$ | $CH_2NO_2$ | OH, OH | |
| 4399 | $CH_2NH_2$ | $PhCH_2$ | $(CH_2)_2OH$ | OH, OH | |
| 4400 | $CH_2NH_2$ | $PhCH_2$ | $CH_2SOCH_3$ | OH, OH | |
| 4401 | $NH(C=NH)NH_2$ | $PhCH_2$ | | (+)-pin | |
| 4402 | $NH(C=NH)NH_2$ | $PhCH_2$ | ethyl | (+)-pin | |
| 4403 | $NH(C=NH)NH_2$ | $PhCH_2$ | $CH_2CN$ | (+)-pin | |
| 4404 | $NH(C=NH)NH_2$ | $PhCH_2$ | $(CH_2)_2CN$ | (+)-pin | |
| 4405 | $NH(C=NH)NH_2$ | $PhCH_2$ | $CH_2COOH$ | (+)-pin | |
| 4406 | $NH(C=NH)NH_2$ | $PhCH_2$ | $(CH_2)_2COOH$ | (+)-pin | |
| 4407 | $NH(C=NH)NH_2$ | $PhCH_2$ | $CH_2NC$ | (+)-pin | |
| 4408 | $NH(C=NH)NH_2$ | $PhCH_2$ | $CH_2NO_2$ | (+)-pin | |
| 4409 | $NH(C=NH)NH_2$ | $PhCH_2$ | $(CH_2)_2OH$ | (+)-pin | |
| 4410 | $NH(C=NH)NH_2$ | $PhCH_2$ | $CH_2SOCH_3$ | (+)-pin | |
| 4411 | $NH(C=NH)NH_2$ | $PhCH_2$ | H | OH, OH | |
| 4412 | $NH(C=NH)NH_2$ | $PhCH_2$ | methyl | OH, OH | |
| 4413 | $NH(C=NH)NH_2$ | $PhCH_2$ | $CH_2CN$ | OH, OH | |
| 4414 | $NH(C=NH)NH_2$ | $PhCH_2$ | $(CH_2)_2CN$ | OH, OH | |
| 4415 | $NH(C=NH)NH_2$ | $PhCH_2$ | $CH_2COOH$ | OH, OH | |
| 4416 | $NH(C=NH)NH_2$ | $PhCH_2$ | $(CH_2)_2COOH$ | OH, OH | |
| 4417 | $NH(C=NH)NH_2$ | $PhCH_2$ | $CH_2NC$ | OH, OH | |
| 4418 | $NH(C=NH)NH_2$ | $PhCH_2$ | $CH_2NO_2$ | OH, OH | |
| 4419 | $NH(C=NH)NH_2$ | $PhCH_2$ | $(CH_2)_2OH$ | OH, OH | |
| 4420 | $NH(C=NH)NH_2$ | $PhCH_2$ | $CH_2SOCH_3$ | OH, OH | |
| 4421 | | | m = 0 | | |
| 4422 | $CH_2NH_2$ | $PhCH_2$ | H | (+)-pin | |
| 4423 | $CH_2NH_2$ | $PhCH_2$ | methyl | (+)-pin | |
| 4424 | $CH_2NH_2$ | $PhCH_2$ | $CH_2CN$ | (+)-pin | |
| 4425 | $CH_2NH_2$ | $PhCH_2$ | $CH_2COOH$ | (+)-pin | |
| 4426 | $CH_2NH_2$ | $PhCH_2$ | $CH_2NC$ | (+)-pin | |
| 4427 | $CH_2NH_2$ | $PhCH_2$ | $CH_2NO_2$ | (+)-pin | |
| 4428 | $CH_2NH_2$ | $PhCH_2$ | $(CH_2)_2OH$ | (+)-pin | |
| 4429 | $CH_2NH_2$ | $PhCH_2$ | $CH_2SOCH_3$ | (+)-pin | |
| 4430 | $CH_2NH_2$ | $PhCH_2$ | H | OH, OH | |
| 4431 | $CH_2NH_2$ | $PhCH_2$ | methyl | OH, OH | |
| 4432 | $CH_2NH_2$ | $PhCH_2$ | $CH_2CN$ | OH, OH | |
| 4433 | $CH_2NH_2$ | $PhCH_2$ | $CH_2COOH$ | OH, OH | |
| 4434 | $CH_2NH_2$ | $PhCH_2$ | $CH_2NC$ | OH, OH | |
| 4435 | $CH_2NH_2$ | $PhCH_2$ | $CH_2NO_2$ | OH, OH | |
| 4436 | $CH_2NH_2$ | $PhCH_2$ | $(CH_2)_2OH$ | OH, OH | |
| 4437 | $CH_2NH_2$ | $PhCH_2$ | $CH_2SOCH_3$ | OH, OH | |
| 4438 | $NH(C=NH)NH_2$ | $PhCH_2$ | H | (+)-pin | |
| 4439 | $NH(C=NH)NH_2$ | $PhCH_2$ | methyl | (+)-pin | |
| 4440 | $NH(C=NH)NH_2$ | $PhCH_2$ | $CH_2CN$ | (+)-pin | |
| 4441 | $NH(C=NH)NH_2$ | $PhCH_2$ | $(CH_2)_2CN$ | (+)-pin | |
| 4442 | $NH(C=NH)NH_2$ | $PhCH_2$ | $CH_2COOH$ | (+)-pin | |
| 4443 | $NH(C=NH)NH_2$ | $PhCH_2$ | $(CH_2)_2COOH$ | (+)-pin | |
| 4444 | $NH(C=NH)NH_2$ | $PhCH_2$ | $CH_2NC$ | (+)-pin | |
| 4445 | $NH(C=NH)NH_2$ | $PhCH_2$ | $CH_2NO_2$ | (+)-pin | |
| 4446 | $NH(C=NH)NH_2$ | $PhCH_2$ | $(CH_2)_2OH$ | (+)-pin | |
| 4447 | $NH(C=NH)NH_2$ | $PhCH_2$ | $CH_2SOCH_3$ | (+)-pin | |
| 4448 | $NH(C=NH)NH_2$ | $PhCH_2$ | H | H, OH | |
| 4449 | $NH(C=NH)NH_2$ | $PhCH_2$ | methyl | OH, OH | |
| 4450 | $NH(C=NH)NH_2$ | $PhCH_2$ | $CH_2CN$ | OH, OH | |
| 4451 | $NH(C=NH)NH_2$ | $PhCH_2$ | $(CH_2)_2CN$ | OH, OH | |
| 4452 | $NH(C=NH)NH_2$ | $PhCH_2$ | $CH_2COOH$ | OH, OH | |
| 4453 | $NH(C=NH)NH_2$ | $PhCH_2$ | $(CH_2)_2COOH$ | OH, OH | |
| 4454 | $NH(C=NH)NH_2$ | $PhCH_2$ | $CH_2NC$ | OH, OH | |
| 4455 | $NH(C=NH)NH_2$ | $PhCH_2$ | $CH_2NO_2$ | OH, OH | |
| 4456 | $NH(C=NH)NH_2$ | $PhCH_2$ | $(CH_2)_2OH$ | OH, OH | |
| 4457 | $NH(C=NH)NH_2$ | $PhCH_2$ | $CH_2SOCH_3$ | OH, OH | |

TABLE 37

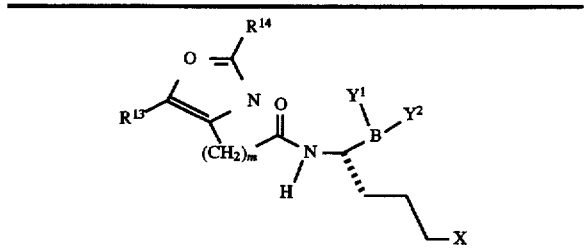

| Ex | X | $R^{13}$ | $R^{14}$ | $Y^1Y^2$ | Phys. Data |
|---|---|---|---|---|---|
| | | | m = 1 | | |
| 4462 | $CH_2NH_2$ | $PhCH_2$ | H | (+)-pin | |
| 4463 | $CH_2NH_2$ | $PhCH_2$ | methyl | (+)-pin | |
| 4464 | $CH_2NH_2$ | $PhCH_2$ | $CH_2CN$ | (+)-pin | |
| 4465 | $CH_2NH_2$ | $PhCH_2$ | $CH_2COOH$ | (+)-pin | |
| 4466 | $CH_2NH_2$ | $PhCH_2$ | $CH_2NC$ | (+)-pin | |
| 4467 | $CH_2NH_2$ | $PhCH_2$ | $CH_2NO_2$ | (+)-pin | |
| 4468 | $CH_2NH_2$ | $PhCH_2$ | $(CH_2)_2OH$ | (+)-pin | |
| 4469 | $CH_2NH_2$ | $PhCH_2$ | $CH_2SOCH_3$ | (+)-pin | |
| 4470 | $CH_2NH_2$ | $PhCH_2$ | H | OH, OH | |
| 4471 | $CH_2NH_2$ | $PhCH_2$ | methyl | OH, OH | |
| 4472 | $CH_2NH_2$ | $PhCH_2$ | $CH_2CN$ | OH, OH | |
| 4473 | $CH_2NH_2$ | $PhCH_2$ | $CH_2COOH$ | OH, OH | |
| 4474 | $CH_2NH_2$ | $PhCH_2$ | $CH_2NC$ | OH, OH | |
| 4475 | $CH_2NH_2$ | $PhCH_2$ | $CH_2NO_2$ | OH, OH | |
| 4476 | $CH_2NH_2$ | $PhCH_2$ | $(CH_2)_2OH$ | OH, OH | |
| 4477 | $CH_2NH_2$ | $PhCH_2$ | $CH_2SOCH_3$ | OH, OH | |
| 4478 | $NH(C=NH)NH_2$ | $PhCH_2$ | H | (+)-pin | |
| 4479 | $NH(C=NH)NH_2$ | $PhCH_2$ | methyl | (+)-pin | |
| 4480 | $NH(C=NH)NH_2$ | $PhCH_2$ | $CH_2CN$ | (+)-pin | |
| 4481 | $NH(C=NH)NH_2$ | $PhCH_2$ | $(CH_2)_2CN$ | (+)-pin | |
| 4482 | $NH(C=NH)NH_2$ | $PhCH_2$ | $CH_2COOH$ | (+)-pin | |
| 4483 | $NH(C=NH)NH_2$ | $PhCH_2$ | $(CH_2)_2COOH$ | (+)-pin | |
| 4484 | $NH(C=NH)NH_2$ | $PhCH_2$ | $CH_2NC$ | (+)-pin | |
| 4485 | $NH(C=NH)NH_2$ | $PhCH_2$ | $CH_2NO_2$ | (+)-pin | |
| 4486 | $NH(C=NH)NH_2$ | $PhCH_2$ | $(CH_2)_2OH$ | (+)-pin | |
| 4487 | $NH(C=NH)NH_2$ | $PhCH_2$ | $CH_2SOCH_3$ | (+)-pin | |
| 4488 | $NH(C=NH)NH_2$ | $PhCH_2$ | H | OH, OH | |
| 4489 | $NH(C=NH)NH_2$ | $PhCH_2$ | methyl | OH, OH | |
| 4490 | $NH(C=NH)NH_2$ | $PhCH_2$ | $CH_2CN$ | OH, OH | |
| 4491 | $NH(C=NH)NH_2$ | $PhCH_2$ | $(CH_2)_2CN$ | OH, OH | |
| 4492 | $NH(C=NH)NH_2$ | $PhCH_2$ | $CH_2COOH$ | OH, OH | |
| 4493 | $NH(C=NH)NH_2$ | $PhCH_2$ | $(CH_2)_2COOH$ | OH, OH | |
| 4494 | $NH(C=NH)NH_2$ | $PhCH_2$ | $CH_2NC$ | OH, OH | |
| 4495 | $NH(C=NH)NH_2$ | $PhCH_2$ | $CH_2NO_2$ | OH, OH | |
| 4496 | $NH(C=NH)NH_2$ | $PhCH_2$ | $(CH_2)_2OH$ | OH, OH | |
| 4497 | $NH(C=NH)NH_2$ | $PhCH_2$ | $CH_2SOCH_3$ | OH, OH | |
| 4498 | | | m = 2 | | |
| 4499 | $CH_2NH_2$ | $PhCH_2$ | H | (+)-pin | |
| 4500 | $CH_2NH_2$ | $PhCH_2$ | methyl | (+)-pin | |
| 4501 | $CH_2NH_2$ | $PhCH_2$ | $CH_2CN$ | (+)-pin | |
| 4502 | $CH_2NH_2$ | $PhCH_2$ | $CH_2COOH$ | (+)-pin | |
| 4503 | $CH_2NH_2$ | $PhCH_2$ | $CH_2NC$ | (+)-pin | |
| 4504 | $CH_2NH_2$ | $PhCH_2$ | $CH_2NO_2$ | (+)-pin | |
| 4505 | $CH_2NH_2$ | $PhCH_2$ | $(CH_2)_2OH$ | (+)-pin | |
| 4506 | $CH_2NH_2$ | $PhCH_2$ | $CH_2SOCH_3$ | (+)-pin | |
| 4507 | $CH_2NH_2$ | $PhCH_2$ | H | OH, OH | |
| 4508 | $CH_2NH_2$ | $PhCH_2$ | methyl | OH, OH | |
| 4509 | $CH_2NH_2$ | $PhCH_2$ | $CH_2CN$ | OH, OH | |
| 4510 | $CH_2NH_2$ | $PhCH_2$ | $CH_2COOH$ | OH, OH | |
| 4511 | $CH_2NH_2$ | $PhCH_2$ | $CH_2NC$ | OH, OH | |
| 4512 | $CH_2NH_2$ | $PhCH_2$ | $CH_2NO_2$ | OH, OH | |
| 4513 | $CH_2NH_2$ | $PhCH_2$ | $(CH_2)_2OH$ | OH, OH | |
| 4514 | $CH_2NH_2$ | $PhCH_2$ | $CH_2SOCH_3$ | OH, OH | |
| 4515 | $NH(C=NH)NH_2$ | $PhCH_2$ | H | (+)-pin | |
| 4516 | $NH(C=NH)NH_2$ | $PhCH_2$ | methyl | (+)-pin | |
| 4517 | $NH(C=NH)NH_2$ | $PhCH_2$ | $CH_2CN$ | (+)-pin | |
| 4518 | $NH(C=NH)NH_2$ | $PhCH_2$ | $(CH_2)_2CN$ | (+)-pin | |
| 4519 | $NH(C=NH)NH_2$ | $PhCH_2$ | $CH_2COOH$ | (+)-pin | |
| 4520 | $NH(C=NH)NH_2$ | $PhCH_2$ | $(CH_2)_2COOH$ | (+)-pin | |
| 4521 | $NH(C=NH)NH_2$ | $PhCH_2$ | $CH_2NC$ | (+)-pin | |
| 4522 | $NH(C=NH)NH_2$ | $PhCH_2$ | $CH_2NO_2$ | (+)-pin | |
| 4523 | $NH(C=NH)NH_2$ | $PhCH_2$ | $(CH_2)_2OH$ | (+)-pin | |
| 4524 | $NH(C=NH)NH_2$ | $PhCH_2$ | $CH_2SOCH_3$ | (+)-pin | |
| 4525 | $NH(C=NH)NH_2$ | $PhCH_2$ | H | OH, OH | |
| 4526 | $NH(C=NH)NH_2$ | $PhCH_2$ | methyl | OH, OH | |
| 4527 | $NH(C=NH)NH_2$ | $PhCH_2$ | $CH_2CN$ | OH, OH | |
| 4528 | $NH(C=NH)NH_2$ | $PhCH_2$ | $(CH_2)_2CN$ | OH, OH | |
| 4529 | $NH(C=NH)NH_2$ | $PhCH_2$ | $CH_2COOH$ | OH, OH | |
| 4530 | $NH(C=NH)NH_2$ | $PhCH_2$ | $(CH_2)_2COOH$ | OH, OH | |
| 4531 | $NH(C=NH)NH_2$ | $PhCH_2$ | $CH_2NC$ | OH, OH | |
| 4532 | $NH(C=NH)NH_2$ | $PhCH_2$ | $CH_2NO_2$ | OH, OH | |
| 4533 | $NH(C=NH)NH_2$ | $PhCH_2$ | $(CH_2)_2OH$ | OH, OH | |
| 4534 | $NH(C=NH)NH_2$ | $PhCH_2$ | $CH_2SOCH_3$ | OH, OH | |
| | | | m = 0 | | |
| 4535 | $CH_2NH_2$ | $PhCH_2$ | H | (+)-pin | |
| 4536 | $CH_2NH_2$ | $PhCH_2$ | methyl | (+)-pin | |
| 4537 | $CH_2NH_2$ | $PhCH_2$ | $CH_2CN$ | (+)-pin | |
| 4538 | $CH_2NH_2$ | $PhCH_2$ | $CH_2COOH$ | (+)-pin | |
| 4539 | $CH_2NH_2$ | $PhCH_2$ | $CH_2NC$ | (+)-pin | |
| 4540 | $CH_2NH_2$ | $PhCH_2$ | $CH_2NO_2$ | (+)-pin | |
| 4541 | $CH_2NH_2$ | $PhCH_2$ | $(CH_2)_2OH$ | (+)-pin | |
| 4542 | $CH_2NH_2$ | $PhCH_2$ | $CH_2SOCH_3$ | (+)-pin | |
| 4543 | $CH_2NH_2$ | $PhCH_2$ | H | OH, OH | |
| 4544 | $CH_2NH_2$ | $PhCH_2$ | methyl | OH, OH | |
| 4545 | $CH_2NH_2$ | $PhCH_2$ | $CH_2CN$ | OH, OH | |
| 4546 | $CH_2NH_2$ | $PhCH_2$ | $CH_2COOH$ | OH, OH | |
| 4547 | $CH_2NH_2$ | $PhCH_2$ | $CH_2NC$ | OH, OH | |
| 4548 | $CH_2NH_2$ | $PhCH_2$ | $CH_2NO_2$ | OH, OH | |
| 4549 | $CH_2NH_2$ | $PhCH_2$ | $(CH_2)_2OH$ | OH, OH | |
| 4550 | $CH_2NH_2$ | $PhCH_2$ | $CH_2SOCH_3$ | OH, OH | |
| 4551 | $NH(C=NH)NH_2$ | $PhCH_2$ | H | (+)-pin | |
| 4552 | $NH(C=NH)NH_2$ | $PhCH_2$ | methyl | (+)-pin | |
| 4553 | $NH(C=NH)NH_2$ | $PhCH_2$ | $CH_2CN$ | (+)-pin | |
| 4554 | $NH(C=NH)NH_2$ | $PhCH_2$ | $(CH_2)_2CN$ | (+)-pin | |
| 4555 | $NH(C=NH)NH_2$ | $PhCH_2$ | $CH_2COOH$ | (+)-pin | |
| 4556 | $NH(C=NH)NH_2$ | $PhCH_2$ | $(CH_2)_2COOH$ | (+)-pin | |
| 4557 | $NH(C=NH)NH_2$ | $PhCH_2$ | $CH_2NC$ | (+)-pin | |
| 4558 | $NH(C=NH)NH_2$ | $PhCH_2$ | $CH_2NO_2$ | (+)-pin | |
| 4559 | $NH(C=NH)NH_2$ | $PhCH_2$ | $(CH_2)_2OH$ | (+)-pin | |
| 4560 | $NH(C=NH)NH_2$ | $PhCH_2$ | $CH_2SOCH_3$ | (+)-pin | |
| 4561 | $NH(C=NH)NH_2$ | $PhCH_2$ | H | OH, OH | |
| 4562 | $NH(C=NH)NH_2$ | $PhCH_2$ | methyl | OH, OH | |
| 4563 | $NH(C=NH)NH_2$ | $PhCH_2$ | $CH_2CN$ | OH, OH | |
| 4564 | $NH(C=NH)NH_2$ | $PhCH_2$ | $(CH_2)_2CN$ | OH, OH | |
| 4565 | $NH(C=NH)NH_2$ | $PhCH_2$ | $CH_2COOH$ | OH, OH | |
| 4566 | $NH(C=NH)NH_2$ | $PhCH_2$ | $(CH_2)_2COOH$ | OH, OH | |
| 4567 | $NH(C=NH)NH_2$ | $PhCH_2$ | $CH_2NC$ | OH, OH | |
| 4568 | $NH(C=NH)NH_2$ | $PhCH_2$ | $CH_2NO_2$ | OH, OH | |
| 4569 | $NH(C=NH)NH_2$ | $PhCH_2$ | $(CH_2)_2OH$ | OH, OH | |
| 4570 | $NH(C=NH)NH_2$ | $PhCH_2$ | $CH_2SOCH_3$ | OH, OH | |

TABLE 38

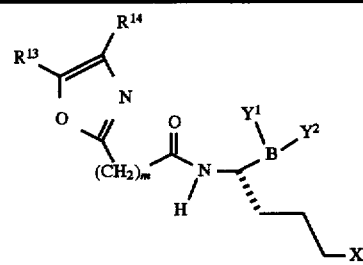

| Ex | X | R13 | R14 | Y1Y2 | Phys. Data |
|---|---|---|---|---|---|
| | | | m = 1 | | |
| 4575 | CH2NH2 | PhCH2 | H | | (+)-pin |
| 4576 | CH2NH2 | PhCH2 | methyl | | (+)-pin |
| 4577 | CH2NH2 | PhCH2 | CH2CN | | (+)-pin |
| 4578 | CH2NH2 | PhCH2 | CH2COOH | | (+)-pin |
| 4579 | CH2NH2 | PhCH2 | CH2NC | | (+)-pin |
| 4580 | CH2NH2 | PhCH2 | CH2NO2 | | (+)-pin |
| 4581 | CH2NH2 | PhCH2 | (CH2)2OH | | (+)-pin |
| 4582 | CH2NH2 | PhCH2 | CH2SOCH3 | | (+)-pin |
| 4583 | CH2NH2 | PhCH2 | H | | OH, OH |
| 4584 | CH2NH2 | PhCH2 | methyl | | OH, OH |
| 4585 | CH2NH2 | PhCH2 | CH2CN | | OH, OH |
| 4586 | CH2NH2 | PhCH2 | CH2COOH | | OH, OH |
| 4587 | CH2NH2 | PhCH2 | CH2NC | | OH, OH |
| 4588 | CH2NH2 | PhCH2 | CH2NO2 | | OH, OH |
| 4589 | CH2NH2 | PhCH2 | (CH2)2OH | | OH, OH |
| 4590 | CH2NH2 | PhCH2 | CH2SOCH3 | | OH, OH |
| 4591 | NH(C=NH)NH2 | PhCH2 | H | | (+)-pin |
| 4592 | NH(C=NH)NH2 | PhCH2 | methyl | | (+)-pin |
| 4593 | NH(C=NH)NH2 | PhCH2 | CH2CN | | (+)-pin |
| 4594 | NH(C=NH)NH2 | PhCH2 | (CH2)2CN | | (+)-pin |
| 4595 | NH(C=NH)NH2 | PhCH2 | CH2COOH | | (+)-pin |
| 4596 | NH(C=NH)NH2 | PhCH2 | (CH2)2COOH | | (+)-pin |
| 4597 | NH(C=NH)NH2 | PhCH2 | CH2NC | | (+)-pin |
| 4598 | NH(C=NH)NH2 | PhCH2 | CH2NO2 | | (+)-pin |
| 4599 | NH(C=NH)NH2 | PhCH2 | (CH2)2OH | | (+)-pin |
| 4600 | NH(C=NH)NH2 | PhCH2 | CH2SOCH3 | | (+)-pin |
| 4601 | NH(C=NH)NH2 | PhCH2 | H | | OH, OH |
| 4602 | NH(C=NH)NH2 | PhCH2 | methyl | | OH, OH |
| 4603 | NH(C=NH)NH2 | PhCH2 | CH2CN | | OH, OH |
| 4604 | NH(C=NH)NH2 | PhCH2 | (CH2)2CN | | OH, OH |
| 4605 | NH(C=NH)NH2 | PhCH2 | CH2COOH | | OH, OH |
| 4606 | NH(C=NH)NH2 | PhCH2 | (CH2)2COOH | | OH, OH |
| 4607 | NH(C=NH)NH2 | PhCH2 | CH2NC | | OH, OH |
| 4608 | NH(C=NH)NH2 | PhCH2 | CH2NO2 | | OH, OH |
| 4609 | NH(C=NH)NH2 | PhCH2 | (CH2)2OH | | OH, OH |
| 4610 | NH(C=NH)NH2 | PhCH2 | CH2SOCH3 | | OH, OH |
| | | | m = 0 | | |
| 4611 | CH2NH2 | PhCH2 | H | | (+)-pin |
| 4612 | CH2NH2 | PhCH2 | methyl | | (+)-pin |
| 4613 | CH2NH2 | PhCH2 | CH2CN | | (+)-pin |
| 4614 | CH2NH2 | PhCH2 | CH2COOH | | (+)-pin |
| 4615 | CH2NH2 | PhCH2 | CH2NC | | (+)-pin |
| 4616 | CH2NH2 | PhCH2 | CH2NO2 | | (+)-pin |
| 4617 | CH2NH2 | PhCH2 | (CH2)2OH | | (+)-pin |
| 4618 | CH2NH2 | PhCH2 | CH2SOCH3 | | (+)-pin |
| 4619 | CH2NH2 | PhCH2 | H | | OH, OH |
| 4620 | CH2NH2 | PhCH2 | methyl | | OH, OH |
| 4621 | CH2NH2 | PhCH2 | CH2CN | | OH, OH |
| 4622 | CH2NH2 | PhCH2 | CH2COOH | | OH, OH |
| 4623 | CH2NH2 | PhCH2 | CH2NC | | OH, OH |
| 4624 | CH2NH2 | PhCH2 | CH2NO2 | | OH, OH |
| 4625 | CH2NH2 | PhCH2 | (CH2)2OH | | OH, OH |
| 4626 | CH2NH2 | PhCH2 | CH2SOCH3 | | OH, OH |
| 4627 | NH(C=NH)NH2 | PhCH2 | H | | (+)-pin |
| 4628 | NH(C=NH)NH2 | PhCH2 | methyl | | (+)-pin |
| 4629 | NH(C=NH)NH2 | PhCH2 | CH2CN | | (+)-pin |
| 4630 | NH(C=NH)NH2 | PhCH2 | (CH2)2CN | | (+)-pin |
| 4631 | NH(C=NH)NH2 | PhCH2 | CH2COOH | | (+)-pin |
| 4632 | NH(C=NH)NH2 | PhCH2 | (CH2)2COOH | | (+)-pin |
| 4633 | NH(C=NH)NH2 | PhCH2 | CH2NC | | (+)-pin |
| 4634 | NH(C=NH)NH2 | PhCH2 | CH2NO2 | | (+)-pin |
| 4635 | NH(C=NH)NH2 | PhCH2 | (CH2)2OH | | (+)-pin |
| 4636 | NH(C=NH)NH2 | PhCH2 | CH2SOCH3 | | (+)-pin |
| 4637 | NH(C=NH)NH2 | PhCH2 | H | | OH, OH |
| 4638 | NH(C=NH)NH2 | PhCH2 | methyl | | OH, OH |
| 4639 | NH(C=NH)NH2 | PhCH2 | CH2CN | | OH, OH |
| 4640 | NH(C=NH)NH2 | PhCH2 | (CH2)2CN | | OH, OH |
| 4641 | NH(C=NH)NH2 | PhCH2 | CH2COOH | | OH, OH |
| 4642 | NH(C=NH)NH2 | PhCH2 | (CH2)2COOH | | OH, OH |
| 4643 | NH(C=NH)NH2 | PhCH2 | CH2NC | | OH, OH |
| 4644 | NH(C=NH)NH2 | PhCH2 | CH2NO2 | | OH, OH |
| 4645 | NH(C=NH)NH2 | PhCH2 | (CH2)2OH | | OH, OH |
| 4646 | NH(C=NH)NH2 | PhCH2 | CH2SOCH3 | | OH, OH |

TABLE 39

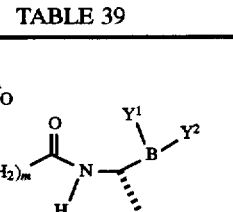

| Ex | X | R13 | R14 | Y1Y2 | Phys. Data |
|---|---|---|---|---|---|
| | | | m = 1 | | |
| 4651 | CH2NH2 | PhCH2 | H | | (+)-pin |
| 4652 | CH2NH2 | PhCH2 | methyl | | (+)-pin |
| 4653 | CH2NH2 | PhCH2 | CH2CN | | (+)-pin |
| 4654 | CH2NH2 | PhCH2 | CH2COOH | | (+)-pin |
| 4655 | CH2NH2 | PhCH2 | CH2NC | | (+)-pin |
| 4656 | CH2NH2 | PhCH2 | CH2NO2 | | (+)-pin |
| 4657 | CH2NH2 | PhCH2 | (CH2)2OH | | (+)-pin |
| 4658 | CH2NH2 | PhCH2 | CH2SOCH3 | | (+)-pin |
| 4659 | CH2NH2 | PhCH2 | H | | OH, OH |
| 4660 | CH2NH2 | PhCH2 | methyl | | OH, OH |
| 4661 | CH2NH2 | PhCH2 | CH2CN | | OH, OH |
| 4662 | CH2NH2 | PhCH2 | CH2COOH | | OH, OH |
| 4663 | CH2NH2 | PhCH2 | CH2NC | | OH, OH |
| 4664 | CH2NH2 | PhCH2 | CH2NO2 | | OH, OH |
| 4665 | CH2NH2 | PhCH2 | (CH2)2OH | | OH, OH |
| 4666 | CH2NH2 | PhCH2 | CH2SOCH3 | | OH, OH |
| 4667 | NH(C=NH)NH2 | PhCH2 | H | | (+)-pin |
| 4668 | NH(C=NH)NH2 | PhCH2 | methyl | | (+)-pin |
| 4669 | NH(C=NH)NH2 | PhCH2 | CH2CN | | (+)-pin |
| 4670 | NH(C=NH)NH2 | PhCH2 | (CH2)2CN | | (+)-pin |
| 4671 | NH(C=NH)NH2 | PhCH2 | CH2COOH | | (+)-pin |
| 4672 | NH(C=NH)NH2 | PhCH2 | (CH2)2COOH | | (+)-pin |
| 4673 | NH(C=NH)NH2 | PhCH2 | CH2NC | | (+)-pin |
| 4674 | NH(C=NH)NH2 | PhCH2 | CH2NO2 | | (+)-pin |
| 4675 | NH(C=NH)NH2 | PhCH2 | (CH2)2OH | | (+)-pin |
| 4676 | NH(C=NH)NH2 | PhCH2 | CH2SOCH3 | | (+)-pin |
| 4677 | NH(C=NH)NH2 | PhCH2 | H | | OH, OH |
| 4678 | NH(C=NH)NH2 | PhCH2 | methyl | | OH, OH |

TABLE 39-continued

| Ex | X | R¹³ | R¹⁴ | Y¹Y² | Phys. Data |
|---|---|---|---|---|---|
| 4679 | NH(C=NH)NH₂ | PhCH₂ | CH₂CN | OH, OH | |
| 4680 | NH(C=NH)NH₂ | PhCH₂ | (CH₂)₂CN | OH, OH | |
| 4681 | NH(C=NH)NH₂ | PhCH₂ | CH₂COOH | OH, OH | |
| 4682 | NH(C=NH)NH₂ | PhCH₂ | (CH₂)₂COOH | OH, OH | |
| 4683 | NH(C=NH)NH₂ | PhCH₂ | CH₂NC | OH, OH | |
| 4684 | NH(C=NH)NH₂ | PhCH₂ | CH₂NO₂ | OH, OH | |
| 4685 | NH(C=NH)NH₂ | PhCH₂ | (CH₂)₂OH | OH, OH | |
| 4686 | NH(C=NH)NH₂ | PhCH₂ | CH₂SOCH₃ | OH, OH | |
| | | | m = 0 | | |
| 4687 | CH₂NH₂ | PhCH₂ | H | (+)-pin | |
| 4688 | CH₂NH₂ | PhCH₂ | methyl | (+)-pin | |
| 4689 | CH₂NH₂ | PhCH₂ | CH₂CN | (+)-pin | |
| 4690 | CH₂NH₂ | PhCH₂ | CH₂COOH | (+)-pin | |
| 4691 | CH₂NH₂ | PhCH₂ | CH₂NC | (+)-pin | |
| 4692 | CH₂NH₂ | PhCH₂ | CH₂NO₂ | (+)-pin | |
| 4693 | CH₂NH₂ | PhCH₂ | (CH₂)₂OH | (+)-pin | |
| 4694 | CH₂NH₂ | PhCH₂ | CH₂SOCH₃ | (+)-pin | |
| 4695 | CH₂NH₂ | PhCH₂ | H | OH, OH | |
| 4696 | CH₂NH₂ | PhCH₂ | methyl | OH, OH | |
| 4697 | CH₂NH₂ | PhCH₂ | CH₂CN | OH, OH | |
| 4698 | CH₂NH₂ | PhCH₂ | CH₂COOH | OH, OH | |
| 4699 | CH₂NH₂ | PhCH₂ | CH₂NC | OH, OH | |
| 4700 | CH₂NH₂ | PhCH₂ | CH₂NO₂ | OH, OH | |
| 4701 | CH₂NH₂ | PhCH₂ | (CH₂)₂OH | OH, OH | |
| 4702 | CH₂NH₂ | PhCH₂ | CH₂SOCH₃ | OH, OH | |
| 4703 | NH(C=NH)NH₂ | PhCH₂ | H | (+)-pin | |
| 4704 | NH(C=NH)NH₂ | PhCH₂ | methyl | (+)-pin | |
| 4705 | NH(C=NH)NH₂ | PhCH₂ | CH₂CN | (+)-pin | |
| 4706 | NH(C=NH)NH₂ | PhCH₂ | (CH₂)₂CN | (+)-pin | |
| 4707 | NH(C=NH)NH₂ | PhCH₂ | CH₂COOH | (+)-pin | |
| 4708 | NH(C=NH)NH₂ | PhCH₂ | (CH₂)₂COOH | (+)-pin | |
| 4709 | NH(C=NH)NH₂ | PhCH₂ | CH₂NC | (+)-pin | |
| 4710 | NH(C=NH)NH₂ | PhCH₂ | CH₂NO₂ | (+)-pin | |
| 4711 | NH(C=NH)NH₂ | PhCH₂ | (CH₂)₂OH | (+)-pin | |
| 4712 | NH(C=NH)NH₂ | PhCH₂ | CH₂SOCH₃ | (+)-pin | |
| 4713 | NH(C=NH)NH₂ | PhCH₂ | H | OH, OH | |
| 4714 | NH(C=NH)NH₂ | PhCH₂ | methyl | OH, OH | |
| 4715 | NH(C=NH)NH₂ | PhCH₂ | CH₂CN | OH, OH | |
| 4716 | NH(C=NH)NH₂ | PhCH₂ | (CH₂)₂CN | OH, OH | |
| 4717 | NH(C=NH)NH₂ | PhCH₂ | CH₂COOH | OH, OH | |
| 4718 | NH(C=NH)NH₂ | PhCH₂ | (CH₂)₂COOH | OH, OH | |
| 4719 | NH(C=NH)NH₂ | PhCH₂ | CH₂NC | OH, OH | |
| 4720 | NH(C=NH)NH₂ | PhCH₂ | CH₂NO₂ | OH, OH | |
| 4721 | NH(C=NH)NH₂ | PhCH₂ | (CH₂)₂OH | OH, OH | |
| 4722 | NH(C=NH)NH₂ | PhCH₂ | CH₂SOCH₃ | OH, OH | |

TABLE 40

| Ex | X | R¹³ | R¹⁴ | Y¹Y² | Phys. Data |
|---|---|---|---|---|---|
| | | | m = 1 | | |
| 4727 | CH₂NH₂ | PhCH₂ | H | (+)-pin | |
| 4728 | CH₂NH₂ | PhCH₂ | methyl | (+)-pin | |
| 4729 | CH₂NH₂ | PhCH₂ | CH₂CN | (+)-pin | |
| 4730 | CH₂NH₂ | PhCH₂ | CH₂COOH | (+)-pin | |
| 4731 | CH₂NH₂ | PhCH₂ | CH₂NC | (+)-pin | |
| 4732 | CH₂NH₂ | PhCH₂ | CH₂NO₂ | (+)-pin | |
| 4733 | CH₂NH₂ | PhCH₂ | (CH₂)₂OH | (+)-pin | |
| 4734 | CH₂NH₂ | PhCH₂ | CH₂SOCH₃ | (+)-pin | |
| 4735 | CH₂NH₂ | PhCH₂ | H | OH, OH | |
| 4736 | CH₂NH₂ | PhCH₂ | methyl | OH, OH | |
| 4737 | CH₂NH₂ | PhCH₂ | CH₂CN | OH, OH | |
| 4738 | CH₂NH₂ | PhCH₂ | CH₂COOH | OH, OH | |
| 4739 | CH₂NH₂ | PhCH₂ | CH₂NC | OH, OH | |
| 4740 | CH₂NH₂ | PhCH₂ | CH₂NO₂ | OH, OH | |
| 4741 | CH₂NH₂ | PhCH₂ | (CH₂)₂OH | OH, OH | |
| 4742 | CH₂NH₂ | PhCH₂ | CH₂SOCH₃ | OH, OH | |
| 4743 | NH(C=NH)NH₂ | PhCH₂ | H | (+)-pin | |
| 4744 | NH(C=NH)NH₂ | PhCH₂ | methyl | (+)-pin | |
| 4745 | NH(C=NH)NH₂ | PhCH₂ | CH₂CN | (+)-pin | |
| 4746 | NH(C=NH)NH₂ | PhCH₂ | (CH₂)₂CN | (+)-pin | |
| 4747 | NH(C=NH)NH₂ | PhCH₂ | CH₂COOH | (+)-pin | |
| 4748 | NH(C=NH)NH₂ | PhCH₂ | (CH₂)₂COOH | (+)-pin | |
| 4749 | NH(C=NH)NH₂ | PhCH₂ | CH₂NC | (+)-pin | |
| 4750 | NH(C=NH)NH₂ | PhCH₂ | CH₂NO₂ | (+)-pin | |
| 4751 | NH(C=NH)NH₂ | PhCH₂ | (CH₂)₂OH | (+)-pin | |
| 4752 | NH(C=NH)NH₂ | PhCH₂ | CH₂SOCH₃ | (+)-pin | |
| 4753 | NH(C=NH)NH₂ | PhCH₂ | H | OH, OH | |
| 4754 | NH(C=NH)NH₂ | PhCH₂ | methyl | OH, OH | |
| 4755 | NH(C=NH)NH₂ | PhCH₂ | CH₂CN | OH, OH | |
| 4756 | NH(C=NH)NH₂ | PhCH₂ | (CH₂)₂CN | OH, OH | |
| 4757 | NH(C=NH)NH₂ | PhCH₂ | CH₂COOH | OH, OH | |
| 4758 | NH(C=NH)NH₂ | PhCH₂ | (CH₂)₂COOH | OH, OH | |
| 4759 | NH(C=NH)NH₂ | PhCH₂ | CH₂NC | OH, OH | |
| 4760 | NH(C=NH)NH₂ | PhCH₂ | CH₂NO₂ | OH, OH | |
| 4761 | NH(C=NH)NH₂ | PhCH₂ | (CH₂)₂OH | OH, OH | |
| 4762 | NH(C=NH)NH₂ | PhCH₂ | CH₂SOCH₃ | OH, OH | |
| | | | m = 0 | | |
| 4763 | CH₂NH₂ | PhCH₂ | H | (+)-pin | |
| 4764 | CH₂NH₂ | PhCH₂ | methyl | (+)-pin | |
| 4765 | CH₂NH₂ | PhCH₂ | CH₂CN | (+)-pin | |
| 4766 | CH₂NH₂ | PhCH₂ | CH₂COOH | (+)-pin | |
| 4767 | CH₂NH₂ | PhCH₂ | CH₂NC | (+)-pin | |
| 4768 | CH₂NH₂ | PhCH₂ | CH₂NO₂ | (+)-pin | |
| 4769 | CH₂NH₂ | PhCH₂ | (CH₂)₂OH | (+)-pin | |
| 4770 | CH₂NH₂ | PhCH₂ | CH₂SOCH₃ | (+)-pin | |
| 4771 | CH₂NH₂ | PhCH₂ | H | OH, OH | |
| 4772 | CH₂NH₂ | PhCH₂ | methyl | OH, OH | |
| 4773 | CH₂NH₂ | PhCH₂ | CH₂CN | OH, OH | |
| 4774 | CH₂NH₂ | PhCH₂ | CH₂COOH | OH, OH | |
| 4775 | CH₂NH₂ | PhCH₂ | CH₂NC | OH, OH | |
| 4776 | CH₂NH₂ | PhCH₂ | CH₂NO₂ | OH, OH | |
| 4777 | CH₂NH₂ | PhCH₂ | (CH₂)₂OH | OH, OH | |
| 4778 | CH₂NH₂ | PhCH₂ | CH₂SOCH₃ | OH, OH | |
| 4779 | NH(C=NH)NH₂ | PhCH₂ | H | (+)-pin | |
| 4780 | NH(C=NH)NH₂ | PhCH₂ | methyl | (+)-pin | |
| 4781 | NH(C=NH)NH₂ | PhCH₂ | CH₂CN | (+)-pin | |
| 4782 | NH(C=NH)NH₂ | PhCH₂ | (CH₂)₂CN | (+)-pin | |
| 4783 | NH(C=NH)NH₂ | PhCH₂ | CH₂COOH | (+)-pin | |
| 4784 | NH(C=NH)NH₂ | PhCH₂ | (CH₂)₂COOH | (+)-pin | |
| 4785 | NH(C=NH)NH₂ | PhCH₂ | CH₂NC | (+)-pin | |
| 4786 | NH(C=NH)NH₂ | PhCH₂ | CH₂NO₂ | (+)-pin | |

TABLE 40-continued

| Ex | X | R¹³ | R¹⁴ | Y¹Y² | Phys. Data |
|---|---|---|---|---|---|
| 4787 | NH(C=NH)NH₂ | PhCH₂ | (CH₂)₂OH | (+)-pin | |
| 4788 | NH(C=NH)NH₂ | PhCH₂ | CH₂SOCH₃ | (+)-pin | |
| 4789 | NH(C=NH)NH₂ | PhCH₂ | H | OH, OH | |
| 4790 | NH(C=NH)NH₂ | PhCH₂ | methyl | OH, OH | |
| 4791 | NH(C=NH)NH₂ | PhCH₂ | CH₂CN | OH, OH | |
| 4792 | NH(C=NH)NH₂ | PhCH₂ | (CH₂)₂CN | OH, OH | |
| 4793 | NH(C=NH)NH₂ | PhCH₂ | CH₂COOH | OH, OH | |
| 4794 | NH(C=NH)NH₂ | PhCH₂ | (CH₂)₂COOH | OH, OH | |
| 4795 | NH(C=NH)NH₂ | PhCH₂ | CH₂NC | OH, OH | |
| 4796 | NH(C=NH)NH₂ | PhCH₂ | CH₂NO₂ | OH, OH | |
| 4797 | NH(C=NH)NH₂ | PhCH₂ | (CH₂)₂OH | OH, OH | |
| 4798 | NH(C=NH)NH₂ | PhCH₂ | CH₂SOCH₃ | OH, OH | |

TABLE 41

| Ex | X | R¹³ | R¹⁴ | Y¹Y² | Phys. Data |
|---|---|---|---|---|---|
| | | | m = 1 | | |
| 4803 | CH₂NH₂ | PhCH₂ | H | (+)-pin | |
| 4804 | CH₂NH₂ | PhCH₂ | methyl | (+)-pin | |
| 4805 | CH₂NH₂ | PhCH₂ | CH₂CN | (+)-pin | |
| 4806 | CH₂NH₂ | PhCH₂ | CH₂COOH | (+)-pin | |
| 4807 | CH₂NH₂ | PhCH₂ | CH₂NC | (+)-pin | |
| 4808 | CH₂NH₂ | PhCH₂ | CH₂NO₂ | (+)-pin | |
| 4809 | CH₂NH₂ | PhCH₂ | (CH₂)₂OH | (+)-pin | |
| 4810 | CH₂NH₂ | PhCH₂ | CH₂SOCH₃ | (+)-pin | |
| 4811 | CH₂NH₂ | PhCH₂ | H | OH, OH | |
| 4812 | CH₂NH₂ | PhCH₂ | methyl | OH, OH | |
| 4813 | CH₂NH₂ | PhCH₂ | CH₂CN | OH, OH | |
| 4814 | CH₂NH₂ | PhCH₂ | CH₂COOH | OH, OH | |
| 4815 | CH₂NH₂ | PhCH₂ | CH₂NC | OH, OH | |
| 4816 | CH₂NH₂ | PhCH₂ | CH₂NO₂ | OH, OH | |
| 4817 | CH₂NH₂ | PhCH₂ | (CH₂)₂OH | OH, OH | |
| 4818 | CH₂NH₂ | PhCH₂ | CH₂SOCH₃ | OH, OH | |
| 4819 | NH(C=NH)NH₂ | PhCH₂ | H | (+)-pin | |
| 4820 | NH(C=NH)NH₂ | PhCH₂ | methyl | (+)-pin | |
| 4821 | NH(C=NH)NH₂ | PhCH₂ | CH₂CN | (+)-pin | |
| 4822 | NH(C=NH)NH₂ | PhCH₂ | (CH₂)₂CN | (+)-pin | |
| 4823 | NH(C=NH)NH₂ | PhCH₂ | CH₂COOH | (+)-pin | |
| 4824 | NH(C=NH)NH₂ | PhCH₂ | (CH₂)₂COOH | (+)-pin | |
| 4825 | NH(C=NH)NH₂ | PhCH₂ | CH₂NC | (+)-pin | |
| 4826 | NH(C=NH)NH₂ | PhCH₂ | CH₂NO₂ | (+)-pin | |
| 4827 | NH(C=NH)NH₂ | PhCH₂ | (CH₂)₂OH | (+)-pin | |
| 4828 | NH(C=NH)NH₂ | PhCH₂ | CH₂SOCH₃ | (+)-pin | |
| 4829 | NH(C=NH)NH₂ | PhCH₂ | H | OH, OH | |
| 4830 | NH(C=NH)NH₂ | PhCH₂ | methyl | OH, OH | |
| 4831 | NH(C=NH)NH₂ | PhCH₂ | CH₂CN | OH, OH | |
| 4832 | NH(C=NH)NH₂ | PhCH₂ | (CH₂)₂CN | OH, OH | |
| 4833 | NH(C=NH)NH₂ | PhCH₂ | CH₂COOH | OH, OH | |
| 4834 | NH(C=NH)NH₂ | PhCH₂ | (CH₂)₂COOH | OH, OH | |
| 4835 | NH(C=NH)NH₂ | PhCH₂ | CH₂NC | OH, OH | |
| 4836 | NH(C=NH)NH₂ | PhCH₂ | CH₂NO₂ | OH, OH | |
| 4837 | NH(C=NH)NH₂ | PhCH₂ | (CH₂)₂OH | OH, OH | |
| 4838 | NH(C=NH)NH₂ | PhCH₂ | CH₂SOCH₃ | OH, OH | |
| | | | m = 0 | | |
| 4839 | CH₂NH₂ | PhCH₂ | H | (+)-pin | |
| 4840 | CH₂NH₂ | PhCH₂ | methyl | (+)-pin | |
| 4841 | CH₂NH₂ | PhCH₂ | CH₂CN | (+)-pin | |
| 4842 | CH₂NH₂ | PhCH₂ | CH₂COOH | (+)-pin | |
| 4843 | CH₂NH₂ | PhCH₂ | CH₂NC | (+)-pin | |
| 4844 | CH₂NH₂ | PhCH₂ | CH₂NO₂ | (+)-pin | |
| 4845 | CH₂NH₂ | PhCH₂ | (CH₂)₂OH | (+)-pin | |
| 4846 | CH₂NH₂ | PhCH₂ | CH₂SOCH₃ | (+)-pin | |
| 4847 | CH₂NH₂ | PhCH₂ | H | OH, OH | |
| 4848 | CH₂NH₂ | PhCH₂ | methyl | OH, OH | |
| 4849 | CH₂NH₂ | PhCH₂ | CH₂CN | OH, OH | |
| 4850 | CH₂NH₂ | PhCH₂ | CH₂COOH | OH, OH | |
| 4851 | CH₂NH₂ | PhCH₂ | CH₂NC | OH, OH | |
| 4852 | CH₂NH₂ | PhCH₂ | CH₂NO₂ | OH, OH | |
| 4853 | CH₂NH₂ | PhCH₂ | (CH₂)₂OH | OH, OH | |
| 4854 | CH₂NH₂ | PhCH₂ | CH₂SOCH₃ | OH, OH | |
| 4855 | NH(C=NH)NH₂ | PhCH₂ | H | (+)-pin | |
| 4856 | NH(C=NH)NH₂ | PhCH₂ | methyl | (+)-pin | |
| 4857 | NH(C=NH)NH₂ | PhCH₂ | CH₂CN | (+)-pin | |
| 4858 | NH(C=NH)NH₂ | PhCH₂ | (CH₂)₂CN | (+)-pin | |
| 4859 | NH(C=NH)NH₂ | PhCH₂ | CH₂COOH | (+)-pin | |
| 4860 | NH(C=NH)NH₂ | PhCH₂ | (CH₂)₂COOH | (+)-pin | |
| 4861 | NH(C=NH)NH₂ | PhCH₂ | CH₂NC | (+)-pin | |
| 4862 | NH(C=NH)NH₂ | PhCH₂ | CH₂NO₂ | (+)-pin | |
| 4863 | NH(C=NH)NH₂ | PhCH₂ | (CH₂)₂OH | (+)-pin | |
| 4864 | NH(C=NH)NH₂ | PhCH₂ | CH₂SOCH₃ | (+)-pin | |
| 4865 | NH(C=NH)NH₂ | PhCH₂ | H | OH, OH | |
| 4866 | NH(C=NH)NH₂ | PhCH₂ | methyl | OH, OH | |
| 4867 | NH(C=NH)NH₂ | PhCH₂ | CH₂CN | OH, OH | |
| 4868 | NH(C=NH)NH₂ | PhCH₂ | (CH₂)₂CN | OH, OH | |
| 4869 | NH(C=NH)NH₂ | PhCH₂ | CH₂COOH | OH, OH | |
| 4870 | NH(C=NH)NH₂ | PhCH₂ | (CH₂)₂COOH | OH, OH | |
| 4871 | NH(C=NH)NH₂ | PhCH₂ | CH₂NC | OH, OH | |
| 4872 | NH(C=NH)NH₂ | PhCH₂ | CH₂NO₂ | OH, OH | |
| 4873 | NH(C=NH)NH₂ | PhCH₂ | (CH₂)₂OH | OH, OH | |
| 4874 | NH(C=NH)NH₂ | PhCH₂ | CH₂SOCH₃ | OH, OH | |

TABLE 42

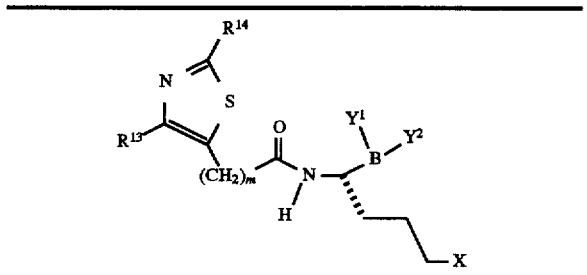

| Ex | X | R13 | R14 | Y1Y2 | Phys. Data |
|---|---|---|---|---|---|
| m = 1 | | | | | |
| 4879 | CH2NH2 | PhCH2 | H | (+)-pin | |
| 4880 | CH2NH2 | PhCH2 | methyl | (+)-pin | |
| 4881 | CH2NH2 | PhCH2 | CH2CN | (+)-pin | |
| 4882 | CH2NH2 | PhCH2 | CH2COOH | (+)-pin | |
| 4883 | CH2NH2 | PhCH2 | CH2NC | (+)-pin | |
| 4884 | CH2NH2 | PhCH2 | CH2NO2 | (+)-pin | |
| 4885 | CH2NH2 | PhCH2 | (CH2)2OH | (+)-pin | |
| 4886 | CH2NH2 | PhCH2 | CH2SOCH3 | (+)-pin | |
| 4887 | CH2NH2 | PhCH2 | H | OH, OH | |
| 4888 | CH2NH2 | PhCH2 | methyl | OH, OH | |
| 4889 | CH2NH2 | PhCH2 | CH2CN | OH, OH | |
| 4890 | CH2NH2 | PhCH2 | CH2COOH | OH, OH | |
| 4891 | CH2NH2 | PhCH2 | CH2NC | OH, OH | |
| 4892 | CH2NH2 | PhCH2 | CH2NO2 | OH, OH | |
| 4893 | CH2NH2 | PhCH2 | (CH2)2OH | OH, OH | |
| 4894 | CH2NH2 | PhCH2 | CH2SOCH3 | OH, OH | |
| 4895 | NH(C=NH)NH2 | PhCH2 | H | (+)-pin | |
| 4896 | NH(C=NH)NH2 | PhCH2 | methyl | (+)-pin | |
| 4897 | NH(C=NH)NH2 | PhCH2 | CH2CN | (+)-pin | |
| 4898 | NH(C=NH)NH2 | PhCH2 | (CH2)2CN | (+)-pin | |
| 4899 | NH(C=NH)NH2 | PhCH2 | CH2COOH | (+)-pin | |
| 4900 | NH(C=NH)NH2 | PhCH2 | (CH2)2COOH | (+)-pin | |
| 4901 | NH(C=NH)NH2 | PhCH2 | CH2NC | (+)-pin | |
| 4902 | NH(C=NH)NH2 | PhCH2 | CH2NO2 | (+)-pin | |
| 4903 | NH(C=NH)NH2 | PhCH2 | (CH2)2OH | (+)-pin | |
| 4904 | NH(C=NH)NH2 | PhCH2 | CH2SOCH3 | (+)-pin | |
| 4905 | NH(C=NH)NH2 | PhCH2 | H | OH, OH | |
| 4906 | NH(C=NH)NH2 | PhCH2 | methyl | OH, OH | |
| 4907 | NH(C=NH)NH2 | PhCH2 | CH2CN | OH, OH | |
| 4908 | NH(C=NH)NH2 | PhCH2 | (CH2)2CN | OH, OH | |
| 4909 | NH(C=NH)NH2 | PhCH2 | CH2COOH | OH, OH | |
| 4910 | NH(C=NH)NH2 | PhCH2 | (CH2)2COOH | OH, OH | |
| 4911 | NH(C=NH)NH2 | PhCH2 | CH2NC | OH, OH | |
| 4912 | NH(C=NH)NH2 | PhCH2 | CH2NO2 | OH, OH | |
| 4913 | NH(C=NH)NH2 | PhCH2 | (CH2)2OH | OH, OH | |
| 4914 | NH(C=NH)NH2 | PhCH2 | CH2SOCH3 | OH, OH | |
| m = 2 | | | | | |
| 4915 | CH2NH2 | PhCH2 | H | (+)-pin | |
| 4916 | CH2NH2 | PhCH2 | methyl | (+)-pin | |
| 4917 | CH2NH2 | PhCH2 | CH2CN | (+)-pin | |
| 4918 | CH2NH2 | PhCH2 | CH2COOH | (+)-pin | |
| 4919 | CH2NH2 | PhCH2 | CH2NC | (+)-pin | |
| 4920 | CH2NH2 | PhCH2 | CH2NO2 | (+)-pin | |
| 4921 | CH2NH2 | PhCH2 | (CH2)2OH | (+)-pin | |
| 4922 | CH2NH2 | PhCH2 | CH2SOCH3 | (+)-pin | |
| 4923 | CH2NH2 | PhCH2 | H | OH, OH | |
| 4924 | CH2NH2 | PhCH2 | methyl | OH, OH | |
| 4925 | CH2NH2 | PhCH2 | CH2CN | OH, OH | |
| 4926 | CH2NH2 | PhCH2 | CH2COOH | OH, OH | |
| 4927 | CH2NH2 | PhCH2 | CH2NC | OH, OH | |
| 4928 | CH2NH2 | PhCH2 | CH2NO2 | OH, OH | |
| 4929 | CH2NH2 | PhCH2 | (CH2)2OH | OH, OH | |
| 4930 | CH2NH2 | PhCH2 | CH2SOCH3 | OH, OH | |
| 4931 | NH(C=NH)NH2 | PhCH2 | H | (+)-pin | |
| 4932 | NH(C=NH)NH2 | PhCH2 | methyl | (+)-pin | |
| 4933 | NH(C=NH)NH2 | PhCH2 | CH2CN | (+)-pin | |
| 4934 | NH(C=NH)NH2 | PhCH2 | (CH2)2CN | (+)-pin | |
| 4935 | NH(C=NH)NH2 | PhCH2 | CH2COOH | (+)-pin | |
| 4936 | NH(C=NH)NH2 | PhCH2 | (CH2)2COOH | (+)-pin | |
| 4937 | NH(C=NH)NH2 | PhCH2 | CH2NC | (+)-pin | |
| 4938 | NH(C=NH)NH2 | PhCH2 | CH2NO2 | (+)-pin | |
| 4939 | NH(C=NH)NH2 | PhCH2 | (CH2)2OH | (+)-pin | |
| 4940 | NH(C=NH)NH2 | PhCH2 | CH2SOCH3 | (+)-pin | |
| 4941 | NH(C=NH)NH2 | PhCH2 | H | OH, OH | |
| 4942 | NH(C=NH)NH2 | PhCH2 | methyl | OH, OH | |
| 4943 | NH(C=NH)NH2 | PhCH2 | CH2CN | OH, OH | |
| 4944 | NH(C=NH)NH2 | PhCH2 | (CH2)2CN | OH, OH | |
| 4945 | NH(C=NH)NH2 | PhCH2 | CH2COOH | OH, OH | |
| 4946 | NH(C=NH)NH2 | PhCH2 | (CH2)2COOH | OH, OH | |
| 4947 | NH(C=NH)NH2 | PhCH2 | CH2NC | OH, OH | |
| 4948 | NH(C=NH)NH2 | PhCH2 | CH2NO2 | OH, OH | |
| 4949 | NH(C=NH)NH2 | PhCH2 | (CH2)2OH | OH, OH | |
| 4950 | NH(C=NH)NH2 | PhCH2 | CH2SOCH3 | OH, OH | |
| m = 0 | | | | | |
| 4951 | CH2NH2 | PhCH2 | H | (+)-pin | |
| 4952 | CH2NH2 | PhCH2 | methyl | (+)-pin | |
| 4953 | CH2NH2 | PhCH2 | CH2CN | (+)-pin | |
| 4954 | CH2NH2 | PhCH2 | CH2COOH | (+)-pin | |
| 4955 | CH2NH2 | PhCH2 | CH2NC | (+)-pin | |
| 4956 | CH2NH2 | PhCH2 | CH2NO2 | (+)-pin | |
| 4957 | CH2NH2 | PhCH2 | (CH2)2OH | (+)-pin | |
| 4958 | CH2NH2 | PhCH2 | CH2SOCH3 | (+)-pin | |
| 4959 | CH2NH2 | PhCH2 | H | OH, OH | |
| 4960 | CH2NH2 | PhCH2 | methyl | OH, OH | |
| 4961 | CH2NH2 | PhCH2 | CH2CN | OH, OH | |
| 4962 | CH2NH2 | PhCH2 | CH2COOH | OH, OH | |
| 4963 | CH2NH2 | PhCH2 | CH2NC | OH, OH | |
| 4964 | CH2NH2 | PhCH2 | CH2NO2 | OH, OH | |
| 4965 | CH2NH2 | PhCH2 | (CH2)2OH | OH, OH | |
| 4966 | CH2NH2 | PhCH2 | CH2SOCH3 | OH, OH | |
| 4967 | NH(C=NH)NH2 | PhCH2 | H | (+)-pin | |
| 4968 | NH(C=NH)NH2 | PhCH2 | methyl | (+)-pin | |
| 4969 | NH(C=NH)NH2 | PhCH2 | CH2CN | (+)-pin | |
| 4970 | NH(C=NH)NH2 | PhCH2 | (CH2)2CN | (+)-pin | |
| 4971 | NH(C=NH)NH2 | PhCH2 | CH2COOH | (+)-pin | |
| 4972 | NH(C=NH)NH2 | PhCH2 | (CH2)2COOH | (+)-pin | |
| 4973 | NH(C=NH)NH2 | PhCH2 | CH2NC | (+)-pin | |
| 4974 | NH(C=NH)NH2 | PhCH2 | CH2NO2 | (+)-pin | |
| 4975 | NH(C=NH)NH2 | PhCH2 | (CH2)2OH | (+)-pin | |
| 4976 | NH(C=NH)NH2 | PhCH2 | CH2SOCH3 | (+)-pin | |
| 4977 | NH(C=NH)NH2 | PhCH2 | H | OH, OH | |
| 4978 | NH(C=NH)NH2 | PhCH2 | methyl | OH, OH | |
| 4979 | NH(C=NH)NH2 | PhCH2 | CH2CN | OH, OH | |
| 4980 | NH(C=NH)NH2 | PhCH2 | (CH2)2CN | OH, OH | |
| 4981 | NH(C=NH)NH2 | PhCH2 | CH2COOH | OH, OH | |
| 4982 | NH(C=NH)NH2 | PhCH2 | (CH2)2COOH | OH, OH | |
| 4983 | NH(C=NH)NH2 | PhCH2 | CH2NC | OH, OH | |
| 4984 | NH(C=NH)NH2 | PhCH2 | CH2NO2 | OH, OH | |
| 4985 | NH(C=NH)NH2 | PhCH2 | (CH2)2OH | OH, OH | |
| 4986 | NH(C=NH)NH2 | PhCH2 | CH2SOCH3 | OH, OH | |

TABLE 43

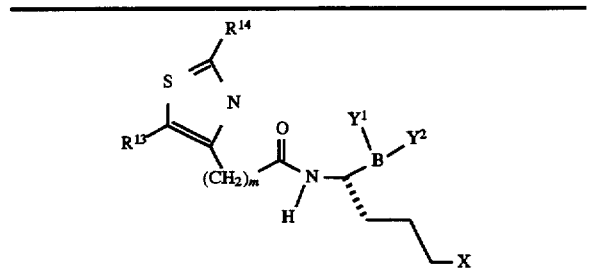

| Ex | X | R13 | R14 | Y1Y2 | Phys. Data |
|---|---|---|---|---|---|
| m = 1 ||||||
| 4991 | CH2NH2 | PhCH2 | H | (+)-pin | |
| 4992 | CH2NH2 | PhCH2 | methyl | (+)-pin | |
| 4993 | CH2NH2 | PhCH2 | CH2CN | (+)-pin | |
| 4994 | CH2NH2 | PhCH2 | CH2COOH | (+)-pin | |
| 4995 | CH2NH2 | PhCH2 | CH2NC | (+)-pin | |
| 4996 | CH2NH2 | PhCH2 | CH2NO2 | (+)-pin | |
| 4997 | CH2NH2 | PhCH2 | (CH2)2OH | (+)-pin | |
| 4998 | CH2NH2 | PhCH2 | CH2SOCH3 | (+)-pin | |
| 4999 | CH2NH2 | PhCH2 | H | OH, OH | |
| 5000 | CH2NH2 | PhCH2 | methyl | OH, OH | |
| 5001 | CH2NH2 | PhCH2 | CH2CN | OH, OH | |
| 5002 | CH2NH2 | PhCH2 | CH2COOH | OH, OH | |
| 5003 | CH2NH2 | PhCH2 | CH2NC | OH, OH | |
| 5004 | CH2NH2 | PhCH2 | CH2NO2 | OH, OH | |
| 5005 | CH2NH2 | PhCH2 | (CH2)2OH | OH, OH | |
| 5006 | CH2NH2 | PhCH2 | CH2SOCH3 | OH, OH | |
| 5007 | NH(C=NH)NH2 | PhCH2 | H | (+)-pin | |
| 5008 | NH(C=NH)NH2 | PhCH2 | methyl | (+)-pin | |
| 5009 | NH(C=NH)NH2 | PhCH2 | CH2CN | (+)-pin | |
| 5010 | NH(C=NH)NH2 | PhCH2 | (CH2)2CN | (+)-pin | |
| 5011 | NH(C=NH)NH2 | PhCH2 | CH2COOH | (+)-pin | |
| 5012 | NH(C=NH)NH2 | PhCH2 | (CH2)2COOH | (+)-pin | |
| 5013 | NH(C=NH)NH2 | PhCH2 | CH2NC | (+)-pin | |
| 5014 | NH(C=NH)NH2 | PhCH2 | CH2NO2 | (+)-pin | |
| 5015 | NH(C=NH)NH2 | PhCH2 | (CH2)2OH | (+)-pin | |
| 5016 | NH(C=NH)NH2 | PhCH2 | CH2SOCH3 | (+)-pin | |
| 5017 | NH(C=NH)NH2 | PhCH2 | H | OH, OH | |
| 5018 | NH(C=NH)NH2 | PhCH2 | methyl | OH, OH | |
| 5019 | NH(C=NH)NH2 | PhCH2 | CH2CN | OH, OH | |
| 5020 | NH(C=NH)NH2 | PhCH2 | (CH2)2CN | OH, OH | |
| 5021 | NH(C=NH)NH2 | PhCH2 | CH2COOH | OH, OH | |
| 5022 | NH(C=NH)NH2 | PhCH2 | (CH2)2COOH | OH, OH | |
| 5023 | NH(C=NH)NH2 | PhCH2 | CH2NC | OH, OH | |
| 5024 | NH(C=NH)NH2 | PhCH2 | CH2NO2 | OH, OH | |
| 5025 | NH(C=NH)NH2 | PhCH2 | (CH2)2OH | OH, OH | |
| 5026 | NH(C=NH)NH2 | PhCH2 | CH2SOCH3 | OH, OH | |
| m = 2 ||||||
| 5027 | CH2NH2 | PhCH2 | H | (+)-pin | |
| 5028 | CH2NH2 | PhCH2 | methyl | (+)-pin | |
| 5029 | CH2NH2 | PhCH2 | CH2CN | (+)-pin | |
| 5030 | CH2NH2 | PhCH2 | CH2COOH | (+)-pin | |
| 5031 | CH2NH2 | PhCH2 | CH2NC | (+)-pin | |
| 5032 | CH2NH2 | PhCH2 | CH2NO2 | (+)-pin | |
| 5033 | CH2NH2 | PhCH2 | (CH2)2OH | (+)-pin | |
| 5034 | CH2NH2 | PhCH2 | CH2SOCH3 | (+)-pin | |
| 5035 | CH2NH2 | PhCH2 | H | OH, OH | |
| 5036 | CH2NH2 | PhCH2 | methyl | OH, OH | |
| 5037 | CH2NH2 | PhCH2 | CH2CN | OH, OH | |
| 5038 | CH2NH2 | PhCH2 | CH2COOH | OH, OH | |
| 5039 | CH2NH2 | PhCH2 | CH2NC | OH, OH | |
| 5040 | CH2NH2 | PhCH2 | CH2NO2 | OH, OH | |
| 5041 | CH2NH2 | PhCH2 | (CH2)2OH | OH, OH | |
| 5042 | CH2NH2 | PhCH2 | CH2SOCH3 | OH, OH | |
| 5043 | NH(C=NH)NH2 | PhCH2 | H | (+)-pin | |
| 5044 | NH(C=NH)NH2 | PhCH2 | methyl | (+)-pin | |
| 5045 | NH(C=NH)NH2 | PhCH2 | CH2CN | (+)-pin | |
| 5046 | NH(C=NH)NH2 | PhCH2 | (CH2)2CN | (+)-pin | |
| 5047 | NH(C=NH)NH2 | PhCH2 | CH2COOH | (+)-pin | |
| 5048 | NH(C=NH)NH2 | PhCH2 | (CH2)2COOH | (+)-pin | |
| 5049 | NH(C=NH)NH2 | PhCH2 | CH2NC | (+)-pin | |
| 5050 | NH(C=NH)NH2 | PhCH2 | CH2NO2 | (+)-pin | |
| 5051 | NH(C=NH)NH2 | PhCH2 | (CH2)2OH | (+)-pin | |
| 5052 | NH(C=NH)NH2 | PhCH2 | CH2SOCH3 | (+)-pin | |
| 5053 | NH(C=NH)NH2 | PhCH2 | H | OH, OH | |
| 5054 | NH(C=NH)NH2 | PhCH2 | methyl | OH, OH | |
| 5055 | NH(C=NH)NH2 | PhCH2 | CH2CN | OH, OH | |
| 5056 | NH(C=NH)NH2 | PhCH2 | (CH2)2CN | OH, OH | |
| 5057 | NH(C=NH)NH2 | PhCH2 | CH2COOH | OH, OH | |
| 5058 | NH(C=NH)NH2 | PhCH2 | (CH2)2COOH | OH, OH | |
| 5059 | NH(C=NH)NH2 | PhCH2 | CH2NC | OH, OH | |
| 5060 | NH(C=NH)NH2 | PhCH2 | CH2NO2 | OH, OH | |
| 5061 | NH(C=NH)NH2 | PhCH2 | (CH2)2OH | OH, OH | |
| 5062 | NH(C=NH)NH2 | PhCH2 | CH2SOCH3 | OH, OH | |
| m = 0 ||||||
| 5063 | CH2NH2 | PhCH2 | H | (+)-pin | |
| 5064 | CH2NH2 | PhCH2 | methyl | (+)-pin | |
| 5065 | CH2NH2 | PhCH2 | CH2CN | (+)-pin | |
| 5066 | CH2NH2 | PhCH2 | CH2COOH | (+)-pin | |
| 5067 | CH2NH2 | PhCH2 | CH2NC | (+)-pin | |
| 5068 | CH2NH2 | PhCH2 | CH2NO2 | (+)-pin | |
| 5069 | CH2NH2 | PhCH2 | (CH2)2OH | (+)-pin | |
| 5070 | CH2NH2 | PhCH2 | CH2SOCH3 | (+)-pin | |
| 5071 | CH2NH2 | PhCH2 | H | OH, OH | |
| 5072 | CH2NH2 | PhCH2 | methyl | OH, OH | |
| 5073 | CH2NH2 | PhCH2 | CH2CN | OH, OH | |
| 5074 | CH2NH2 | PhCH2 | CH2COOH | OH, OH | |
| 5075 | CH2NH2 | PhCH2 | CH2NC | OH, OH | |
| 5076 | CH2NH2 | PhCH2 | CH2NO2 | OH, OH | |
| 5077 | CH2NH2 | PhCH2 | (CH2)2OH | OH, OH | |
| 5078 | CH2NH2 | PhCH2 | CH2SOCH3 | OH, OH | |
| 5079 | NH(C=NH)NH2 | PhCH2 | H | (+)-pin | |
| 5080 | NH(C=NH)NH2 | PhCH2 | methyl | (+)-pin | |
| 5081 | NH(C=NH)NH2 | PhCH2 | CH2CN | (+)-pin | |
| 5082 | NH(C=NH)NH2 | PhCH2 | (CH2)2CN | (+)-pin | |
| 5083 | NH(C=NH)NH2 | PhCH2 | CH2COOH | (+)-pin | |
| 5084 | NH(C=NH)NH2 | PhCH2 | (CH2)2COOH | (+)-pin | |
| 5085 | NH(C=NH)NH2 | PhCH2 | CH2NC | (+)-pin | |
| 5086 | NH(C=NH)NH2 | PhCH2 | CH2NO2 | (+)-pin | |
| 5087 | NH(C=NH)NH2 | PhCH2 | (CH2)2OH | (+)-pin | |
| 5088 | NH(C=NH)NH2 | PhCH2 | CH2SOCH3 | (+)-pin | |
| 5089 | NH(C=NH)NH2 | PhCH2 | H | OH, OH | |
| 5090 | NH(C=NH)NH2 | PhCH2 | methyl | OH, OH | |
| 5091 | NH(C=NH)NH2 | PhCH2 | CH2CN | OH, OH | |
| 5092 | NH(C=NH)NH2 | PhCH2 | (CH2)2CN | OH, OH | |
| 5093 | NH(C=NH)NH2 | PhCH2 | CH2COOH | OH, OH | |
| 5094 | NH(C=NH)NH2 | PhCH2 | (CH2)2COOH | OH, OH | |
| 5095 | NH(C=NH)NH2 | PhCH2 | CH2NC | OH, OH | |
| 5096 | NH(C=NH)NH2 | PhCH2 | CH2NO2 | OH, OH | |
| 5097 | NH(C=NH)NH2 | PhCH2 | (CH2)2OH | OH, OH | |
| 5098 | NH(C=NH)NH2 | PhCH2 | CH2SOCH3 | OH, OH | |

TABLE 44

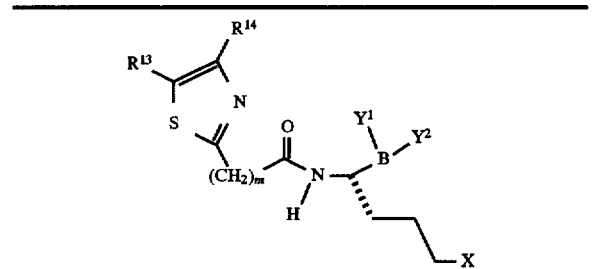

| Ex | X | R13 | R14 | Y1Y2 | Phys. Data |
|---|---|---|---|---|---|
| m = 1 | | | | | |
| 5103 | CH2NH2 | PhCH2 | H | (+)-pin | |
| 5104 | CH2NH2 | PhCH2 | methyl | (+)-pin | |
| 5105 | CH2NH2 | PhCH2 | CH2CN | (+)-pin | |
| 5106 | CH2NH2 | PhCH2 | CH2COOH | (+)-pin | |
| 5107 | CH2NH2 | PhCH2 | CH2NC | (+)-pin | |
| 5108 | CH2NH2 | PhCH2 | CH2NO2 | (+)-pin | |
| 5109 | CH2NH2 | PhCH2 | (CH2)2OH | (+)-pin | |
| 5110 | CH2NH2 | PhCH2 | CH2SOCH3 | (+)-pin | |
| 5111 | CH2NH2 | PhCH2 | H | OH, OH | |
| 5112 | CH2NH2 | PhCH2 | methyl | OH, OH | |
| 5113 | CH2NH2 | PhCH2 | CH2CN | OH, OH | |
| 5114 | CH2NH2 | PhCH2 | CH2COOH | OH, OH | |
| 5115 | CH2NH2 | PhCH2 | CH2NC | OH, OH | |
| 5116 | CH2NH2 | PhCH2 | CH2NO2 | OH, OH | |
| 5117 | CH2NH2 | PhCH2 | (CH2)2OH | OH, OH | |
| 5118 | CH2NH2 | PhCH2 | CH2SOCH3 | OH, OH | |
| 5119 | NH(C=NH)NH2 | PhCH2 | H | (+)-pin | |
| 5120 | NH(C=NH)NH2 | PhCH2 | methyl | (+)-pin | |
| 5121 | NH(C=NH)NH2 | PhCH2 | CH2CN | (+)-pin | |
| 5122 | NH(C=NH)NH2 | PhCH2 | (CH2)2CN | (+)-pin | |
| 5123 | NH(C=NH)NH2 | PhCH2 | CH2COOH | (+)-pin | |
| 5124 | NH(C=NH)NH2 | PhCH2 | (CH2)2COOH | (+)-pin | |
| 5125 | NH(C=NH)NH2 | PhCH2 | CH2NC | (+)-pin | |
| 5126 | NH(C=NH)NH2 | PhCH2 | CH2NO2 | (+)-pin | |
| 5127 | NH(C=NH)NH2 | PhCH2 | (CH2)2OH | (+)-pin | |
| 5128 | NH(C=NH)NH2 | PhCH2 | CH2SOCH3 | (+)-pin | |
| 5129 | NH(C=NH)NH2 | PhCH2 | H | OH, OH | |
| 5130 | NH(C=NH)NH2 | PhCH2 | methyl | OH, OH | |
| 5131 | NH(C=NH)NH2 | PhCH2 | CH2CN | OH, OH | |
| 5132 | NH(C=NH)NH2 | PhCH2 | (CH2)2CN | OH, OH | |
| 5133 | NH(C=NH)NH2 | PhCH2 | CH2COOH | OH, OH | |
| 5134 | NH(C=NH)NH2 | PhCH2 | (CH2)2COOH | OH, OH | |
| 5135 | NH(C=NH)NH2 | PhCH2 | CH2NC | OH, OH | |
| 5136 | NH(C=NH)NH2 | PhCH2 | CH2NO2 | OH, OH | |
| 5137 | NH(C=NH)NH2 | PhCH2 | (CH2)2OH | OH, OH | |
| 5138 | NH(C=NH)NH2 | PhCH2 | CH2SOCH3 | OH, OH | |
| m = 2 | | | | | |
| 5139 | CH2NH2 | PhCH2 | H | (+)-pin | |
| 5140 | CH2NH2 | PhCH2 | methyl | (+)-pin | |
| 5141 | CH2NH2 | PhCH2 | CH2CN | (+)-pin | |
| 5142 | CH2NH2 | PhCH2 | CH2COOH | (+)-pin | |
| 5143 | CH2NH2 | PhCH2 | CH2NC | (+)-pin | |
| 5144 | CH2NH2 | PhCH2 | CH2NO2 | (+)-pin | |
| 5145 | CH2NH2 | PhCH2 | (CH2)2OH | (+)-pin | |
| 5146 | CH2NH2 | PhCH2 | CH2SOCH3 | (+)-pin | |
| 5147 | CH2NH2 | PhCH2 | H | OH, OH | |
| 5148 | CH2NH2 | PhCH2 | methyl | OH, OH | |
| 5149 | CH2NH2 | PhCH2 | CH2CN | OH, OH | |
| 5150 | CH2NH2 | PhCH2 | CH2COOH | OH, OH | |
| 5151 | CH2NH2 | PhCH2 | CH2NC | OH, OH | |
| 5152 | CH2NH2 | PhCH2 | CH2NO2 | OH, OH | |
| 5153 | CH2NH2 | PhCH2 | (CH2)2OH | OH, OH | |
| 5154 | CH2NH2 | PhCH2 | CH2SOCH3 | OH, OH | |
| 5155 | NH(C=NH)NH2 | PhCH2 | H | (+)-pin | |
| 5156 | NH(C=NH)NH2 | PhCH2 | methyl | (+)-pin | |
| 5157 | NH(C=NH)NH2 | PhCH2 | CH2CN | (+)-pin | |
| 5158 | NH(C=NH)NH2 | PhCH2 | (CH2)2CN | (+)-pin | |
| 5159 | NH(C=NH)NH2 | PhCH2 | CH2COOH | (+)-pin | |
| 5160 | NH(C=NH)NH2 | PhCH2 | (CH2)2COOH | (+)-pin | |
| 5161 | NH(C=NH)NH2 | PhCH2 | CH2NC | (+)-pin | |
| 5162 | NH(C=NH)NH2 | PhCH2 | CH2NO2 | (+)-pin | |
| 5163 | NH(C=NH)NH2 | PhCH2 | (CH2)2OH | (+)-pin | |
| 5164 | NH(C=NH)NH2 | PhCH2 | CH2SOCH3 | (+)-pin | |
| 5165 | NH(C=NH)NH2 | PhCH2 | H | OH, OH | |
| 5166 | NH(C=NH)NH2 | PhCH2 | methyl | OH, OH | |
| 5167 | NH(C=NH)NH2 | PhCH2 | CH2CN | OH, OH | |
| 5168 | NH(C=NH)NH2 | PhCH2 | (CH2)2CN | OH, OH | |
| 5169 | NH(C=NH)NH2 | PhCH2 | CH2COOH | OH, OH | |
| 5170 | NH(C=NH)NH2 | PhCH2 | (CH2)2COOH | OH, OH | |
| 5171 | NH(C=NH)NH2 | PhCH2 | CH2NC | OH, OH | |
| 5172 | NH(C=NH)NH2 | PhCH2 | CH2NO2 | OH, OH | |
| 5173 | NH(C=NH)NH2 | PhCH2 | (CH2)2OH | OH, OH | |
| 5174 | NH(C=NH)NH2 | PhCH2 | CH2SOCH3 | OH, OH | |
| m = 0 | | | | | |
| 5175 | CH2NH2 | PhCH2 | H | (+)-pin | |
| 5176 | CH2NH2 | PhCH2 | methyl | (+)-pin | |
| 5177 | CH2NH2 | PhCH2 | CH2CN | (+)-pin | |
| 5178 | CH2NH2 | PhCH2 | CH2COOH | (+)-pin | |
| 5179 | CH2NH2 | PhCH2 | CH2NC | (+)-pin | |
| 5180 | CH2NH2 | PhCH2 | CH2NO2 | (+)-pin | |
| 5181 | CH2NH2 | PhCH2 | (CH2)2OH | (+)-pin | |
| 5182 | CH2NH2 | PhCH2 | CH2SOCH3 | (+)-pin | |
| 5183 | CH2NH2 | PhCH2 | H | OH, OH | |
| 5184 | CH2NH2 | PhCH2 | methyl | OH, OH | |
| 5185 | CH2NH2 | PhCH2 | CH2CN | OH, OH | |
| 5186 | CH2NH2 | PhCH2 | CH2COOH | OH, OH | |
| 5187 | CH2NH2 | PhCH2 | CH2NC | OH, OH | |
| 5188 | CH2NH2 | PhCH2 | CH2NO2 | OH, OH | |
| 5189 | CH2NH2 | PhCH2 | (CH2)2OH | OH, OH | |
| 5190 | CH2NH2 | PhCH2 | CH2SOCH3 | OH, OH | |
| 5191 | NH(C=NH)NH2 | PhCH2 | H | (+)-pin | |
| 5192 | NH(C=NH)NH2 | PhCH2 | methyl | (+)-pin | |
| 5193 | NH(C=NH)NH2 | PhCH2 | CH2CN | (+)-pin | |
| 5194 | NH(C=NH)NH2 | PhCH2 | (CH2)2CN | (+)-pin | |
| 5195 | NH(C=NH)NH2 | PhCH2 | CH2COOH | (+)-pin | |
| 5196 | NH(C=NH)NH2 | PhCH2 | (CH2)2COOH | (+)-pin | |
| 5197 | NH(C=NH)NH2 | PhCH2 | CH2NC | (+)-pin | |
| 5198 | NH(C=NH)NH2 | PhCH2 | CH2NO2 | (+)-pin | |
| 5199 | NH(C=NH)NH2 | PhCH2 | (CH2)2OH | (+)-pin | |
| 5200 | NH(C=NH)NH2 | PhCH2 | CH2SOCH3 | (+)-pin | |
| 5201 | NH(C=NH)NH2 | PhCH2 | H | OH, OH | |
| 5202 | NH(C=NH)NH2 | PhCH2 | methyl | OH, OH | |
| 5203 | NH(C=NH)NH2 | PhCH2 | CH2CN | OH, OH | |
| 5204 | NH(C=NH)NH2 | PhCH2 | (CH2)2CN | OH, OH | |
| 5205 | NH(C=NH)NH2 | PhCH2 | CH2COOH | OH, OH | |
| 5206 | NH(C=NH)NH2 | PhCH2 | (CH2)2COOH | OH, OH | |
| 5207 | NH(C=NH)NH2 | PhCH2 | CH2NC | OH, OH | |
| 5208 | NH(C=NH)NH2 | PhCH2 | CH2NO2 | OH, OH | |
| 5209 | NH(C=NH)NH2 | PhCH2 | (CH2)2OH | OH, OH | |
| 5210 | NH(C=NH)NH2 | PhCH2 | CH2SOCH3 | OH, OH | |

TABLE 45

| Ex | X | R¹³ | Y¹Y² | Phys. Data |
|---|---|---|---|---|
| | | m = 1 | | |
| 5215 | CH$_2$NH$_2$ | PhCH$_2$ | (+)-pin | |
| 5216 | CH$_2$NH$_2$ | PhCH$_2$ | OH, OH | |
| 5217 | NH(C=NH)NH$_2$ | PhCH$_2$ | (+)-pin | |
| 5218 | NH(C=NH)NH$_2$ | PhCH$_2$ | OH, OH | |
| 5219 | OMe | PhCH$_2$ | (+)-pin | |
| 5220 | OMe | PhCH$_2$ | OH, OH | |
| 5221 | NH(C=NH)H | PhCH$_2$ | (+)-pin | |
| 5222 | NH(C=NH)H | PhCH$_2$ | OH, OH | |
| 5223 | CH$_2$NH$_2$ | PhCH$_2$CH$_2$ | (+)-pin | |
| 5224 | CH$_2$NH$_2$ | PhCH$_2$CH$_2$ | OH, OH | |
| 5225 | NH(C=NH)NH$_2$ | PhCH$_2$CH$_2$ | (+)-pin | |
| 5226 | NH(C=NH)NH$_2$ | PhCH$_2$CH$_2$ | OH, OH | |
| 5227 | OMe | PhCH$_2$CH$_2$ | (+)-pin | |
| 5228 | OMe | PhCH$_2$CH$_2$ | OH, OH | |
| 5229 | NH(C=NH)H | PhCH$_2$CH$_2$ | (+)-pin | |
| 5230 | NH(C=NH)H | PhCH$_2$CH$_2$ | OH, OH | |
| 5231 | CH$_2$NH$_2$ | Ph | (+)-pin | |
| 5232 | CH$_2$NH$_2$ | Ph | OH, OH | |
| 5233 | NH(C=NH)NH$_2$ | Ph | (+)-pin | |
| 5234 | NH(C=NH)NH$_2$ | Ph | OH, OH | |
| 5235 | OMe | Ph | (+)-pin | |
| 5236 | OMe | Ph | OH, OH | |
| 5237 | NH(C=NH)H | Ph | (+)-pin | |
| 5238 | NH(C=NH)H | Ph | OH, OH | |
| | | m = 0 | | |
| 5239 | CH$_2$NH$_2$ | PhCH$_2$ | (+)-pin | |
| 5240 | CH$_2$NH$_2$ | PhCH$_2$ | OH, OH | |
| 5241 | NH(C=NH)NH$_2$ | PhCH$_2$ | (+)-pin | |
| 5242 | NH(C=NH)NH$_2$ | PhCH$_2$ | OH, OH | |
| 5243 | OMe | PhCH$_2$ | (+)-pin | |
| 5244 | OMe | PhCH$_2$ | OH, OH | |
| 5245 | NH(C=NH)H | PhCH$_2$ | (+)-pin | |
| 5246 | NH(C=NH)H | PhCH$_2$ | OH, OH | |
| 5247 | CH$_2$NH$_2$ | PhCH$_2$CH$_2$ | (+)-pin | |
| 5248 | CH$_2$NH$_2$ | PhCH$_2$CH$_2$ | OH, OH | |
| 5249 | NH(C=NH)NH$_2$ | PhCH$_2$CH$_2$ | (+)-pin | |
| 5250 | NH(C=NH)NH$_2$ | PhCH$_2$CH$_2$ | OH, OH | |
| 5251 | OMe | PhCH$_2$CH$_2$ | (+)-pin | |
| 5252 | OMe | PhCH$_2$CH$_2$ | OH, OH | |
| 5253 | NH(C=NH)H | PhCH$_2$CH$_2$ | (+)-pin | |
| 5254 | NH(C=NH)H | PhCH$_2$CH$_2$ | OH, OH | |
| 5255 | CH$_2$NH$_2$ | Ph | (+)-pin | |
| 5256 | CH$_2$NH$_2$ | Ph | OH, OH | |
| 5257 | NH(C=NH)NH$_2$ | Ph | (+)-pin | |
| 5258 | NH(C=NH)NH$_2$ | Ph | OH, OH | |
| 5259 | OMe | Ph | (+)-pin | |
| 5260 | OMe | Ph | OH, OH | |
| 5261 | NH(C=NH)H | Ph | (+)-pin | |
| 5262 | NH(C=NH)H | Ph | OH, OH | |

TABLE 46

| Ex | X | R¹³ | Y¹Y² | Phys. Data |
|---|---|---|---|---|
| | | m = 1 | | |
| 5267 | CH$_2$NH$_2$ | PhCH$_2$ | (+)-pin | |
| 5268 | CH$_2$NH$_2$ | PhCH$_2$ | OH, OH | |
| 5269 | NH(C=NH)NH$_2$ | PhCH$_2$ | (+)-pin | |
| 5270 | NH(C=NH)NH$_2$ | PhCH$_2$ | OH, OH | |
| 5271 | OMe | PhCH$_2$ | (+)-pin | |
| 5272 | OMe | PhCH$_2$ | OH, OH | |
| 5273 | NH(C=NH)H | PhCH$_2$ | (+)-pin | |
| 5274 | NH(C=NH)H | PhCH$_2$ | OH, OH | |
| 5275 | CH$_2$NH$_2$ | PhCH$_2$CH$_2$ | (+)-pin | |
| 5276 | CH$_2$NH$_2$ | PhCH$_2$CH$_2$ | OH, OH | |
| 5277 | NH(C=NH)NH$_2$ | PhCH$_2$CH$_2$ | (+)-pin | |
| 5278 | NH(C=NH)NH$_2$ | PhCH$_2$CH$_2$ | OH, OH | |
| 5279 | OMe | PhCH$_2$CH$_2$ | (+)-pin | |
| 5280 | OMe | PhCH$_2$CH$_2$ | OH, OH | |
| 5281 | NH(C=NH)H | PhCH$_2$CH$_2$ | (+)-pin | |
| 5282 | NH(C=NH)H | PhCH$_2$CH$_2$ | OH, OH | |
| 5283 | CH$_2$NH$_2$ | Ph | (+)-pin | |
| 5284 | CH$_2$NH$_2$ | Ph | OH, OH | |
| 5285 | NH(C=NH)NH$_2$ | Ph | (+)-pin | |
| 5286 | NH(C=NH)NH$_2$ | Ph | OH, OH | |
| 5287 | OMe | Ph | (+)-pin | |
| 5288 | OMe | Ph | OH, OH | |
| 5289 | NH(C=NH)H | Ph | (+)-pin | |
| 5290 | NH(C=NH)H | Ph | OH, OH | |
| | | m = 0 | | |
| 5291 | CH$_2$NH$_2$ | PhCH$_2$ | (+)-pin | |
| 5292 | CH$_2$NH$_2$ | PhCH$_2$ | OH, OH | |
| 5293 | NH(C=NH)NH$_2$ | PhCH$_2$ | (+)-pin | |
| 5294 | NH(C=NH)NH$_2$ | PhCH$_2$ | OH, OH | |
| 5295 | OMe | PhCH$_2$ | (+)-pin | |
| 5296 | OMe | PhCH$_2$ | OH, OH | |
| 5297 | NH(C=NH)H | PhCH$_2$ | (+)-pin | |
| 5298 | NH(C=NH)H | PhCH$_2$ | OH, OH | |
| 5299 | CH$_2$NH$_2$ | PhCH$_2$CH$_2$ | (+)-pin | |
| 5300 | CH$_2$NH$_2$ | PhCH$_2$CH$_2$ | OH, OH | |
| 5301 | NH(C=NH)NH$_2$ | PhCH$_2$CH$_2$ | (+)-pin | |
| 5302 | NH(C=NH)NH$_2$ | PhCH$_2$CH$_2$ | OH, OH | |
| 5303 | OMe | PhCH$_2$CH$_2$ | (+)-pin | |
| 5304 | OMe | PhCH$_2$CH$_2$ | OH, OH | |
| 5305 | NH(C=NH)H | PhCH$_2$CH$_2$ | (+)-pin | |
| 5306 | NH(C=NH)H | PhCH$_2$CH$_2$ | OH, OH | |
| 5307 | CH$_2$NH$_2$ | Ph | (+)-pin | |
| 5308 | CH$_2$NH$_2$ | Ph | OH, OH | |
| 5309 | NH(C=NH)NH$_2$ | Ph | (+)-pin | |
| 5310 | NH(C=NH)NH$_2$ | Ph | OH, OH | |
| 5311 | OMe | Ph | (+)-pin | |
| 5312 | OMe | Ph | OH, OH | |
| 5313 | NH(C=NH)H | Ph | (+)-pin | |
| 5314 | NH(C=NH)H | Ph | OH, OH | |

TABLE 47

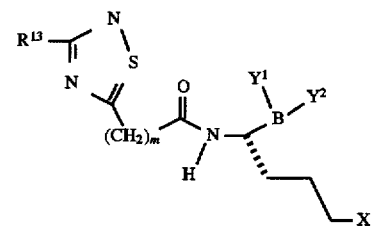

| Ex | X | R[13] | Y[1]Y[2] | Phys. Data |
|---|---|---|---|---|
| m = 1 | | | | |
| 5319 | CH₂NH₂ | PhCH₂ | (+)-pin | |
| 5320 | CH₂NH₂ | PhCH₂ | OH, OH | |
| 5321 | NH(C=NH)NH₂ | PhCH₂ | (+)-pin | |
| 5322 | NH(C=NH)NH₂ | PhCH₂ | OH, OH | |
| 5323 | OMe | PhCH₂ | (+)-pin | |
| 5324 | OMe | PhCH₂ | OH, OH | |
| 5325 | NH(C=NH)H | PhCH₂ | (+)-pin | |
| 5326 | NH(C=NH)H | PhCH₂ | OH, OH | |
| 5327 | CH₂NH₂ | PhCH₂CH₂ | (+)-pin | |
| 5328 | CH₂NH₂ | PhCH₂CH₂ | OH, OH | |
| 5329 | NH(C=NH)NH₂ | PhCH₂CH₂ | (+)-pin | |
| 5330 | NH(C=NH)NH₂ | PhCH₂CH₂ | OH, OH | |
| 5331 | OMe | PhCH₂CH₂ | (+)-pin | |
| 5332 | OMe | PhCH₂CH₂ | OH, OH | |
| 5333 | NH(C=NH)H | PhCH₂CH₂ | (+)-pin | |
| 5334 | NH(C=NH)H | PhCH₂CH₂ | OH, OH | |
| 5335 | CH₂NH₂ | Ph | (+)-pin | |
| 5336 | CH₂NH₂ | Ph | OH, OH | |
| 5337 | NH(C=NH)NH₂ | Ph | (+)-pin | |
| 5338 | NH(C=NH)NH₂ | Ph | OH, OH | |
| 5339 | OMe | Ph | (+)-pin | |
| 5340 | OMe | Ph | OH, OH | |
| 5341 | NH(C=NH)H | Ph | (+)-pin | |
| 5342 | NH(C=NH)H | Ph | OH, OH | |
| m = 0 | | | | |
| 5343 | CH₂NH₂ | PhCH₂ | (+)-pin | |
| 5344 | CH₂NH₂ | PhCH₂ | OH, OH | |
| 5345 | NH(C=NH)NH₂ | PhCH₂ | (+)-pin | |
| 5346 | NH(C=NH)NH₂ | PhCH₂ | OH, OH | |
| 5347 | OMe | PhCH₂ | (+)-pin | |

TABLE 47-continued

| Ex | X | R[13] | Y[1]Y[2] | Phys. Data |
|---|---|---|---|---|
| 5348 | OMe | PhCH₂ | OH, OH | |
| 5349 | NH(C=NH)H | PhCH₂ | (+)-pin | |
| 5350 | NH(C=NH)H | PhCH₂ | OH, OH | |
| 5351 | CH₂NH₂ | PhCH₂CH₂ | (+)-pin | |
| 5352 | CH₂NH₂ | PhCH₂CH₂ | OH, OH | |
| 5353 | NH(C=NH)NH₂ | PhCH₂CH₂ | (+)-pin | |
| 5354 | NH(C=NH)NH₂ | PhCH₂CH₂ | OH, OH | |
| 5355 | OMe | PhCH₂CH₂ | (+)-pin | |
| 5356 | OMe | PhCH₂CH₂ | OH, OH | |
| 5357 | NH(C=NH)H | PhCH₂CH₂ | (+)-pin | |
| 5358 | NH(C=NH)H | PhCH₂CH₂ | OH, OH | |
| 5359 | CH₂NH₂ | Ph | (+)-pin | |
| 5360 | CH₂NH₂ | Ph | OH, OH | |
| 5361 | NH(C=NH)NH₂ | Ph | (+)-pin | |
| 5362 | NH(C=NH)NH₂ | Ph | OH, OH | |
| 5363 | OMe | Ph | (+)-pin | |
| 5364 | OMe | Ph | OH, OH | |
| 5365 | NH(C=NH)H | Ph | (+)-pin | |
| 5366 | NH(C=NH)H | Ph | OH, OH | |

TABLE 48

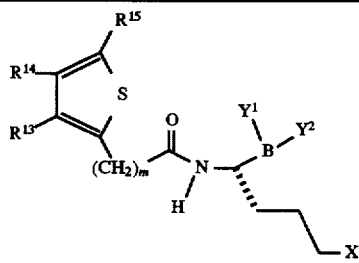

| Ex | X | R[13] | R[14] | R[15] | Y[1]Y[2] | Phys. Data |
|---|---|---|---|---|---|---|
| 5371 | CH₂NH₂ | PhCH₂ | H | H | (+)-pin | |
| 5372 | CH₂NH₂ | PhCH₂ | H | methyl | (+)-pin | |
| 5373 | CH₂NH₂ | PhCH₂ | H | CH₂CN | (+)-pin | |
| 5374 | CH₂NH₂ | PhCH₂ | H | CH₂COOH | (+)-pin | |
| 5375 | CH₂NH₂ | PhCH₂ | H | CH₂NC | (+)-pin | |
| 5376 | CH₂NH₂ | PhCH₂ | H | CH₂NO₂ | (+)-pin | |
| 5377 | CH₂NH₂ | PhCH₂ | H | (CH₂)₂OH | (+)-pin | |
| 5378 | CH₂NH₂ | PhCH₂ | H | CH₂SOCH₃ | (+)-pin | |
| 5379 | CH₂NH₂ | PhCH₂ | H | H | OH, OH | |
| 5380 | CH₂NH₂ | PhCH₂ | H | methyl | OH, OH | |

TABLE 48-continued

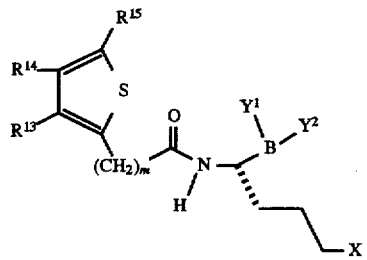

| Ex | X | $R^{13}$ | $R^{14}$ | $R^{15}$ | $Y^1Y^2$ | Phys. Data |
|---|---|---|---|---|---|---|
| 5381 | $CH_2NH_2$ | $PhCH_2$ | H | $CH_2CN$ | OH, OH | |
| 5382 | $CH_2NH_2$ | $PhCH_2$ | H | $CH_2COOH$ | OH, OH | |
| 5383 | $CH_2NH_2$ | $PhCH_2$ | H | $CH_2NC$ | OH, OH | |
| 5384 | $CH_2NH_2$ | $PhCH_2$ | H | $CH_2NO_2$ | OH, OH | |
| 5385 | $CH_2NH_2$ | $PhCH_2$ | H | $(CH_2)_2OH$ | OH, OH | |
| 5386 | $CH_2NH_2$ | $PhCH_2$ | H | $CH_2SOCH_3$ | OH, OH | |
| 5387 | $NH(C=NH)NH_2$ | $PhCH_2$ | H | H | (+)-pin | |
| 5388 | $NH(C=NH)NH_2$ | $PhCH_2$ | H | methyl | (+)-pin | |
| 5389 | $NH(C=NH)NH_2$ | $PhCH_2$ | H | $CH_2CN$ | (+)-pin | |
| 5390 | $NH(C=NH)NH_2$ | $PhCH_2$ | H | $CH_2COOH$ | (+)-pin | |
| 5391 | $NH(C=NH)NH_2$ | $PhCH_2$ | H | $CH_2NC$ | (+)-pin | |
| 5392 | $NH(C=NH)NH_2$ | $PhCH_2$ | H | $CH_2NO_2$ | (+)-pin | |
| 5393 | $NH(C=NH)NH_2$ | $PhCH_2$ | H | $(CH_2)_2OH$ | (+)-pin | |
| 5394 | $NH(C=NH)NH_2$ | $PhCH_2$ | H | $CH_2SOCH_3$ | (+)-pin | |
| 5395 | $NH(C=NH)NH_2$ | $PhCH_2$ | H | H | OH, OH | |
| 5396 | $NH(C=NH)NH_2$ | $PhCH_2$ | H | methyl | OH, OH | |
| 5397 | $NH(C=NH)NH_2$ | $PhCH_2$ | H | $CH_2CN$ | OH, OH | |
| 5398 | $NH(C=NH)NH_2$ | $PhCH_2$ | H | $CH_2COOH$ | OH, OH | |
| 5399 | $NH(C=NH)NH_2$ | $PhCH_2$ | H | $CH_2NC$ | OH, OH | |
| 5400 | $NH(C=NH)NH_2$ | $PhCH_2$ | H | $CH_2NO_2$ | OH, OH | |
| 5401 | $NH(C=NH)NH_2$ | $PhCH_2$ | H | $(CH_2)_2OH$ | OH, OH | |
| 5402 | $NH(C=NH)NH_2$ | $PhCH_2$ | H | $CH_2SOCH_3$ | OH, OH | |
| 5403 | | | | m = 0 | | |
| 5404 | $NH(C=NH)NH_2$ | H | H | 3-(t-butyl-$O_2$CNH)-Ph | (+)-pin | BS |
| 5405 | $NH(C=NH)NH_2$ | H | H | 3-(t-butyl-$O_2$CNH)-Ph | OH, OH | |
| 5406 | $NH(C=NH)NH_2$ | H | H | 3-($NH_2$)-Ph | (+)-pin | |
| 5407 | $NH(C=NH)NH_2$ | H | H | 3-($NH_2$)-Ph | OH, OH | |
| 5408 | $NH(C=NH)NH_2$ | H | H | 3-($CH_3SO_2NH$)-Ph | (+)-pin | |
| 5409 | $NH(C=NH)NH_2$ | H | H | 3-($CH_3SO_2NH$)-Ph | OH, OH | |
| 5410 | $NH(C=NH)NH_2$ | H | methyl | Ph | (+)-pin | |
| 5411 | $NH(C=NH)NH_2$ | H | methyl | Ph | OH, OH | |
| 5412 | $NH(C=NH)NH_2$ | H | $CH_2CN$ | Ph | (+)-pin | |
| 5413 | $NH(C=NH)NH_2$ | H | $CH_2CN$ | Ph | OH, OH | |
| 5414 | $NH(C=NH)NH_2$ | H | methyl | 3-($CH_3SO_2NH$)-Ph | (+)-pin | |
| 5415 | $NH(C=NH)NH_2$ | H | methyl | 3-($CH_3SO_2NH$)-Ph | OH, OH | |
| 5416 | $NH(C=NH)NH_2$ | H | $CH_3$ | 2-($CH_3SO_2NH$)-Ph | (+)-pin | |
| 5417 | $NH(C=NH)NH_2$ | H | $CH_3$ | 2-($CH_3SO_2NH$)-Ph | OH, OH | |
| 5418 | $NH(C=NH)NH_2$ | H | $CH_2CN$ | 3-($CH_3SO_2NH$)-Ph | (+)-pin | |
| 5419 | $NH(C=NH)NH_2$ | H | $CH_2CN$ | 3-($CH_3SO_2NH$)-Ph | OH, OH | |
| 5420 | $NH(C=NH)NH_2$ | H | $CH_2CN$ | 2-($CH_3SO_2NH$)-Ph | (+)-pin | |
| 5421 | $NH(C=NH)NH_2$ | H | $CH_2CN$ | 2-($CH_3SO_2NH$)-Ph | OH, OH | |
| 5422 | $NH(C=NH)NH_2$ | H | $CH_2COOH$ | 3-($CH_3SO_2NH$)-Ph | (+)-pin | |
| 5423 | $NH(C=NH)NH_2$ | H | $CH_2COOH$ | 3-($CH_3SO_2NH$)-Ph | OH, OH | |
| 5424 | $NH(C=NH)NH_2$ | H | $CH_2COOH$ | 2-($CH_3SO_2NH$)-Ph | (+)-pin | |
| 5425 | $NH(C=NH)NH_2$ | H | $CH_2COOH$ | 2-($CH_3SO_2NH$)-Ph | OH, OH | |
| 5426 | $NH(C=NH)NH_2$ | H | H | 3-(t-butylOCO—NH)-Ph | (+)-pin | BP |

BP. MS (M+H)+: Calc 610, Found 610.
BS. MS (M+H)+: Calc 610, Found 610.

TABLE 49

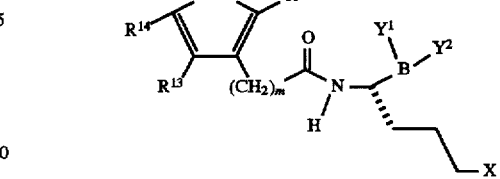

| Ex | X | R[13] | R[14] | Y[1]Y[2] | Phys. Data |
|---|---|---|---|---|---|
| | | m = 1 | | | |
| 5431 | CH$_2$NH$_2$ | PhCH$_2$ | H | (+)-pin | |
| 5432 | CH$_2$NH$_2$ | PhCH$_2$ | methyl | (+)-pin | |
| 5433 | CH$_2$NH$_2$ | PhCH$_2$ | CH$_2$CN | (+)-pin | |
| 5434 | CH$_2$NH$_2$ | PhCH$_2$ | CH$_2$COOH | (+)-pin | |
| 5435 | CH$_2$NH$_2$ | PhCH$_2$ | CH$_2$NC | (+)-pin | |
| 5436 | CH$_2$NH$_2$ | PhCH$_2$ | CH$_2$NO$_2$ | (+)-pin | |
| 5437 | CH$_2$NH$_2$ | PhCH$_2$ | (CH$_2$)$_2$OH | (+)-pin | |
| 5438 | CH$_2$NH$_2$ | PhCH$_2$ | CH$_2$SOCH$_3$ | (+)-pin | |
| 5439 | CH$_2$NH$_2$ | PhCH$_2$ | H | OH, OH | |
| 5440 | CH$_2$NH$_2$ | PhCH$_2$ | methyl | OH, OH | |
| 5441 | CH$_2$NH$_2$ | PhCH$_2$ | CH$_2$CN | OH, OH | |
| 5442 | CH$_2$NH$_2$ | PhCH$_2$ | CH$_2$COOH | OH, OH | |
| 5443 | CH$_2$NH$_2$ | PhCH$_2$ | CH$_2$NC | OH, OH | |
| 5444 | CH$_2$NH$_2$ | PhCH$_2$ | CH$_2$NO$_2$ | OH, OH | |
| 5445 | CH$_2$NH$_2$ | PhCH$_2$ | (CH$_2$)$_2$OH | OH, OH | |
| 5446 | CH$_2$NH$_2$ | PhCH$_2$ | CH$_2$SOCH$_3$ | OH, OH | |
| 5447 | NH(C=NH)NH$_2$ | PhCH$_2$ | H | (+)-pin | |
| 5448 | NH(C=NH)NH$_2$ | PhCH$_2$ | methyl | (+)-pin | |
| 5449 | NH(C=NH)NH$_2$ | PhCH$_2$ | CH$_2$CN | (+)-pin | |
| 5450 | NH(C=NH)NH$_2$ | PhCH$_2$ | CH$_2$COOH | (+)-pin | |
| 5451 | NH(C=NH)NH$_2$ | PhCH$_2$ | CH$_2$NC | (+)-pin | |
| 5452 | NH(C=NH)NH$_2$ | PhCH$_2$ | CH$_2$NO$_2$ | (+)-pin | |
| 5453 | NH(C=NH)NH$_2$ | PhCH$_2$ | (CH$_2$)$_2$OH | (+)-pin | |
| 5454 | NH(C=NH)NH$_2$ | PhCH$_2$ | CH$_2$SOCH$_3$ | (+)-pin | |
| 5455 | NH(C=NH)NH$_2$ | PhCH$_2$ | H | OH, OH | |
| 5456 | NH(C=NH)NH$_2$ | PhCH$_2$ | methyl | OH, OH | |
| 5457 | NH(C=NH)NH$_2$ | PhCH$_2$ | CH$_2$CN | OH, OH | |
| 5458 | NH(C=NH)NH$_2$ | PhCH$_2$ | CH$_2$COOH | OH, OH | |
| 5459 | NH(C=NH)NH$_2$ | PhCH$_2$ | CH$_2$NC | OH, OH | |
| 5460 | NH(C=NH)NH$_2$ | PhCH$_2$ | CH$_2$NO$_2$ | OH, OH | |
| 5461 | NH(C=NH)NH$_2$ | PhCH$_2$ | (CH$_2$)$_2$OH | OH, OH | |
| 5462 | NH(C=NH)NH$_2$ | PhCH$_2$ | CH$_2$SOCH$_3$ | OH, OH | |
| | | m = 0 | | | |
| 5463 | CH$_2$NH$_2$ | PhCH$_2$ | H | (+)-pin | |
| 5464 | CH$_2$NH$_2$ | PhCH$_2$ | methyl | (+)-pin | |

TABLE 49-continued

| Ex | X | R[13] | R[14] | Y[1]Y[2] | Phys. Data |
|---|---|---|---|---|---|
| 5465 | CH$_2$NH$_2$ | PhCH$_2$ | CH$_2$CN | (+)-pin | |
| 5466 | CH$_2$NH$_2$ | PhCH$_2$ | CH$_2$COOH | (+)-pin | |
| 5465 | CH$_2$NH$_2$ | PhCH$_2$ | CH$_2$NC | (+)-pin | |
| 5466 | CH$_2$NH$_2$ | PhCH$_2$ | CH$_2$NO$_2$ | (+)-pin | |
| 5467 | CH$_2$NH$_2$ | PhCH$_2$ | (CH$_2$)$_2$OH | (+)-pin | |
| 5468 | CH$_2$NH$_2$ | PhCH$_2$ | CH$_2$SOCH$_3$ | (+)-pin | |
| 5469 | CH$_2$NH$_2$ | PhCH$_2$ | H | OH, OH | |
| 5470 | CH$_2$NH$_2$ | PhCH$_2$ | methyl | OH, OH | |
| 5471 | CH$_2$NH$_2$ | PhCH$_2$ | CH$_2$CN | OH, OH | |
| 5472 | CH$_2$NH$_2$ | PhCH$_2$ | CH$_2$COOH | OH, OH | |
| 5473 | CH$_2$NH$_2$ | PhCH$_2$ | CH$_2$NC | OH, OH | |
| 5474 | CH$_2$NH$_2$ | PhCH$_2$ | CH$_2$NO$_2$ | OH, OH | |
| 5475 | CH$_2$NH$_2$ | PhCH$_2$ | (CH$_2$)$_2$OH | OH, OH | |
| 5476 | CH$_2$NH$_2$ | PhCH$_2$ | CH$_2$SOCH$_3$ | OH, OH | |
| 5477 | NH(C=NH)NH$_2$ | PhCH$_2$ | H | (+)-pin | |
| 5478 | NH(C=NH)NH$_2$ | PhCH$_2$ | methyl | (+)-pin | |
| 5479 | NH(C=NH)NH$_2$ | PhCH$_2$ | CH$_2$CN | (+)-pin | |
| 5480 | NH(C=NH)NH$_2$ | PhCH$_2$ | CH$_2$COOH | (+)-pin | |
| 5481 | NH(C=NH)NH$_2$ | PhCH$_2$ | CH$_2$NC | (+)-pin | |
| 5482 | NH(C=NH)NH$_2$ | PhCH$_2$ | CH$_2$NO$_2$ | (+)-pin | |
| 5483 | NH(C=NH)NH$_2$ | PhCH$_2$ | (CH$_2$)$_2$OH | (+)-pin | |
| 5484 | NH(C=NH)NH$_2$ | PhCH$_2$ | CH$_2$SOCH$_3$ | (+)-pin | |
| 5485 | NH(C=NH)NH$_2$ | PhCH$_2$ | H | OH, OH | |
| 5486 | NH(C=NH)NH$_2$ | PhCH$_2$ | methyl | OH, OH | |
| 5487 | NH(C=NH)NH$_2$ | PhCH$_2$ | CH$_2$CN | OH, OH | |
| 5488 | NH(C=NH)NH$_2$ | PhCH$_2$ | CH$_2$COOH | OH, OH | |
| 5489 | NH(C=NH)NH$_2$ | PhCH$_2$ | CH$_2$NC | OH, OH | |
| 5490 | NH(C=NH)NH$_2$ | PhCH$_2$ | CH$_2$NO$_2$ | OH, OH | |
| 5491 | NH(C=NH)NH$_2$ | PhCH$_2$ | (CH$_2$)$_2$OH | OH, OH | |
| 5492 | NH(C=NH)NH$_2$ | PhCH$_2$ | CH$_2$SOCH$_3$ | OH, OH | |

TABLE 50

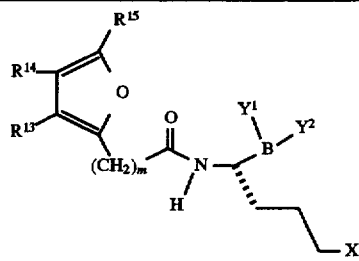

| Ex | X | R[13] | R[14] | R[15] | Y[1]Y[2] | Phys. Data |
|---|---|---|---|---|---|---|
| 5497 | CH$_2$NH$_2$ | PhCH$_2$ | H | H | (+)-pin | |
| 5498 | CH$_2$NH$_2$ | PhCH$_2$ | H | methyl | (+)-pin | |
| 5499 | CH$_2$NH$_2$ | PhCH$_2$ | H | CH$_2$CN | (+)-pin | |
| 5500 | CH$_2$NH$_2$ | PhCH$_2$ | H | CH$_2$COOH | (+)-pin | |
| 5501 | CH$_2$NH$_2$ | PhCH$_2$ | H | CH$_2$NC | (+)-pin | |
| 5502 | CH$_2$NH$_2$ | PhCH$_2$ | H | CH$_2$NO$_2$ | (+)-pin | |

TABLE 50-continued

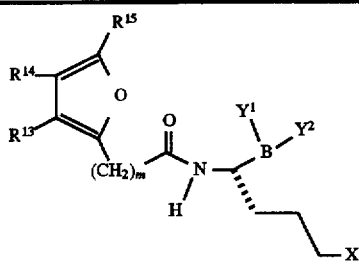

| Ex | X | R13 | R14 | R15 | Y1Y2 | Phys. Data |
|---|---|---|---|---|---|---|
| 5503 | CH2NH2 | PhCH2 | H | (CH2)2OH | (+)-pin | |
| 5504 | CH2NH2 | PhCH2 | H | CH2SOCH3 | (+)-pin | |
| 5505 | CH2NH2 | PhCH2 | H | H | OH, OH | |
| 5506 | CH2NH2 | PhCH2 | H | methyl | OH, OH | |
| 5507 | CH2NH2 | PhCH2 | H | CH2CN | OH, OH | |
| 5508 | CH2NH2 | PhCH2 | H | CH2COOH | OH, OH | |
| 5509 | CH2NH2 | PhCH2 | H | CH2NC | OH, OH | |
| 5510 | CH2NH2 | PhCH2 | H | CH2NO2 | OH, OH | |
| 5511 | CH2NH2 | PhCH2 | H | (CH2)2OH | OH, OH | |
| 5512 | CH2NH2 | PhCH2 | H | CH2SOCH3 | OH, OH | |
| 5513 | NH(C=NH)NH2 | PhCH2 | H | H | (+)-pin | |
| 5514 | NH(C=NH)NH2 | PhCH2 | H | methyl | (+)-pin | |
| 5515 | NH(C=NH)NH2 | PhCH2 | H | CH2CN | (+)-pin | |
| 5516 | NH(C=NH)NH2 | PhCH2 | H | CH2COOH | (+)-pin | |
| 5517 | NH(C=NH)NH2 | PhCH2 | H | CH2NC | (+)-pin | |
| 5518 | NH(C=NH)NH2 | PhCH2 | H | CH2NO2 | (+)-pin | |
| 5519 | NH(C=NH)NH2 | PhCH2 | H | (CH2)2OH | (+)-pin | |
| 5520 | NH(C=NH)NH2 | PhCH2 | H | CH2SOCH3 | (+)-pin | |
| 5521 | NH(C=NH)NH2 | PhCH2 | H | H | OH, OH | |
| 5522 | NH(C=NH)NH2 | PhCH2 | H | methyl | OH, OH | |
| 5523 | NH(C=NH)NH2 | PhCH2 | H | CH2CN | OH, OH | |
| 5524 | NH(C=NH)NH2 | PhCH2 | H | CH2COOH | OH, OH | |
| 5525 | NH(C=NH)NH2 | PhCH2 | H | CH2NC | OH, OH | |
| 5526 | NH(C=NH)NH2 | PhCH2 | H | CH2NO2 | OH, OH | |
| 5527 | NH(C=NH)NH2 | PhCH2 | H | (CH2)2OH | OH, OH | |
| 5528 | NH(C=NH)NH2 | PhCH2 | H | CH2SOCH3 | OH, OH | |
| | | | | m = 0 | | |
| 5529 | NH(C=NH)NH2 | H | H | 3-(t-butyl-O2CNH)-Ph | (+)-pin | BT |
| 5530 | NH(C=NH)NH2 | H | H | 3-(t-butyl-O2CNH)-Ph | OH, OH | |
| 5531 | NH(C=NH)NH2 | H | H | 3-(NH2)-Ph | (+)-pin | |
| 5532 | NH(C=NH)NH2 | H | H | 3-(NH2)-Ph | OH, OH | |
| 5533 | NH(C=NH)NH2 | H | H | 3-(CH3SO2NH)-Ph | (+)-pin | |
| 5534 | NH(C=NH)NH2 | H | H | 3-(CH3SO2NH)-Ph | OH, OH | |
| 5535 | NH(C=NH)NH2 | H | H | Ph | (+)-pin | BU |
| 5536 | NH(C=NH)NH2 | H | H | Ph | OH, OH | BV |
| 5537 | NH(C=NH)NH2 | H | CH3 | Ph | (+)-pin | |
| 5538 | NH(C=NH)NH2 | H | CH3 | Ph | OH, OH | |
| 5539 | NH(C=NH)NH2 | H | CH2CN | Ph | (+)-pin | |
| 5540 | NH(C=NH)NH2 | H | CH2CN | Ph | OH, OH | |
| 5541 | NH(C=NH)NH2 | H | CH2COOH | Ph | (+)-pin | |
| 5542 | NH(C=NH)NH2 | H | CH2COOH | Ph | OH, OH | |
| 5543 | NH(C=NH)NH2 | H | CH2SO2NH2 | Ph | (+)-pin | |
| 5544 | NH(C=NH)NH2 | H | CH2SO2NH2 | Ph | OH, OH | |
| 5545 | NH(C=NH)NH | H | CH2CN | 3-(CH3SO2NH)-Ph | (+)-pin | |
| 5546 | NH(C=NH)NH | H | CH2CN | 3-(CH3SO2NH)-Ph | OH, OH | |
| 5547 | NH(C=NH)NH | H | CH2COOH | 3-(CH3SO2NH)-Ph | (+)-pin | |
| 5548 | NH(C=NH)NH | H | CH2COOH | 3-(CH3SO2NH)-Ph | OH, OH | |
| 5549 | NH(C=NH)NH | H | CH2COOH | 2-(CH3SO2NH)-Ph | (+)-pin | |
| 5550 | NH(C=NH)NH | H | CH2COOH | 2-(CH3SO2NH)-Ph | OH, OH | |
| 5551 | NH(C=NH)NH2 | H | H | 3-(t-butylOCO—NH)-Ph | (+)-pin | BO |
| 5552 | NH(C=NH)NH2 | H | H | Ph | (+)-pin | BQ |
| 5553 | NH(C=NH)NH2 | H | H | Ph | OH | BR |

BO. MS (M+H)+: Calc. 594, Found 594.
BQ. MS (M+H)+: Calc. 479, Found 479.
BS. MS (M+H)+: Calc. 345, Found 345.
BT. MS (M+H)+: Calc. 594, Found 594.
BU. MS (M+H)+: Calc. 479, Found 479.
BV. MS (M+H)+: Calc. 345, Found 345.

TABLE 51

| Ex | X | R13 | R14 | R15 | Y1Y2 | Phys. Data |
|---|---|---|---|---|---|---|
| m = 1 | | | | | | |
| 5558 | CH2NH2 | PhCH2 | H | H | (+)-pin | |
| 5559 | CH2NH2 | PhCH2 | H | methyl | (+)-pin | |
| 5560 | CH2NH2 | PhCH2 | H | CH2CN | (+)-pin | |
| 5561 | CH2NH2 | PhCH2 | H | CH2COOH | (+)-pin | |
| 5562 | CH2NH2 | PhCH2 | H | CH2NC | (+)-pin | |
| 5563 | CH2NH2 | PhCH2 | H | CH2NO2 | (+)-pin | |
| 5564 | CH2NH2 | PhCH2 | H | (CH2)2OH | (+)-pin | |
| 5565 | CH2NH2 | PhCH2 | H | CH2SOCH3 | (+)-pin | |
| 5566 | CH2NH2 | PhCH2 | H | H | OH, OH | |
| 5567 | CH2NH2 | PhCH2 | H | methyl | OH, OH | |
| 5568 | CH2NH2 | PhCH2 | H | CH2CN | OH, OH | |
| 5569 | CH2NH2 | PhCH2 | H | CH2COOH | OH, OH | |
| 5570 | CH2NH2 | PhCH2 | H | CH2NC | OH, OH | |
| 5571 | CH2NH2 | PhCH2 | H | CH2NO2 | OH, OH | |
| 5572 | CH2NH2 | PhCH2 | H | (CH2)2OH | OH, OH | |
| 5573 | CH2NH2 | PhCH2 | H | CH2SOCH3 | OH, OH | |
| 5574 | NH(C=NH)NH2 | PhCH2 | H | H | (+)-pin | |
| 5575 | NH(C=NH)NH2 | PhCH2 | H | methyl | (+)-pin | |
| 5576 | NH(C=NH)NH2 | PhCH2 | H | CH2CN | (+)-pin | |
| 5577 | NH(C=NH)NH2 | PhCH2 | H | CH2COOH | (+)-pin | |
| 5578 | NH(C=NH)NH2 | PhCH2 | H | CH2NC | (+)-pin | |
| 5579 | NH(C=NH)NH2 | PhCH2 | H | CH2NO2 | (+)-pin | |
| 5580 | NH(C=NH)NH2 | PhCH2 | H | (CH2)2OH | (+)-pin | |
| 5581 | NH(C=NH)NH2 | PhCH2 | H | CH2SOCH3 | (+)-pin | |
| 5582 | NH(C=NH)NH2 | PhCH2 | H | H | OH, OH | |
| 5583 | NH(C=NH)NH2 | PhCH2 | H | methyl | OH, OH | |
| 5584 | NH(C=NH)NH2 | PhCH2 | H | CH2CN | OH, OH | |
| 5585 | NH(C=NH)NH2 | PhCH2 | H | CH2COOH | OH, OH | |
| 5586 | NH(C=NH)NH2 | PhCH2 | H | CH2NC | OH, OH | |
| 5587 | NH(C=NH)NH2 | PhCH2 | H | CH2NO2 | OH, OH | |
| 5588 | NH(C=NH)NH2 | PhCH2 | H | (CH2)2OH | OH, OH | |
| 5589 | NH(C=NH)NH2 | PhCH2 | H | CH2SOCH3 | OH, OH | |
| m = 0 | | | | | | |
| 5590 | CH2NH2 | PhCH2 | H | H | (+)-pin | |
| 5591 | CH2NH2 | PhCH2 | H | methyl | (+)-pin | |
| 5592 | CH2NH2 | PhCH2 | H | CH2CN | (+)-pin | |
| 5593 | CH2NH2 | PhCH2 | H | CH2COOH | (+)-pin | |
| 5594 | CH2NH2 | PhCH2 | H | CH2NC | (+)-pin | |
| 5595 | CH2NH2 | PhCH2 | H | CH2NO2 | (+)-pin | |
| 5596 | CH2NH2 | PhCH2 | H | (CH2)2OH | (+)-pin | |
| 5597 | CH2NH2 | PhCH2 | H | CH2SOCH3 | (+)-pin | |
| 5598 | CH2NH2 | PhCH2 | H | H | OH, OH | |
| 5599 | CH2NH2 | PhCH2 | H | methyl | OH, OH | |
| 5600 | CH2NH2 | PhCH2 | H | CH2CN | OH, OH | |
| 5601 | CH2NH2 | PhCH2 | H | CH2COOH | OH, OH | |
| 5602 | CH2NH2 | PhCH2 | H | CH2NC | OH, OH | |
| 5603 | CH2NH2 | PhCH2 | H | CH2NO2 | OH, OH | |
| 5604 | CH2NH2 | PhCH2 | H | (CH2)2OH | OH, OH | |
| 5605 | CH2NH2 | PhCH2 | H | CH2SOCH3 | OH, OH | |
| 5606 | NH(C=NH)NH2 | PhCH2 | H | H | (+)-pin | |
| 5607 | NH(C=NH)NH2 | PhCH2 | H | methyl | (+)-pin | |
| 5608 | NH(C=NH)NH2 | PhCH2 | H | CH2CN | (+)-pin | |
| 5609 | NH(C=NH)NH2 | PhCH2 | H | CH2COOH | (+)-pin | |
| 5610 | NH(C=NH)NH2 | PhCH2 | H | CH2NC | (+)-pin | |
| 5611 | NH(C=NH)NH2 | PhCH2 | H | CH2NO2 | (+)-pin | |
| 5612 | NH(C=NH)NH2 | PhCH2 | H | (CH2)2OH | (+)-pin | |
| 5613 | NH(C=NH)NH2 | PhCH2 | H | CH2SOCH3 | (+)-pin | |
| 5614 | NH(C=NH)NH2 | PhCH2 | H | H | OH, OH | |
| 5615 | NH(C=NH)NH2 | PhCH2 | H | methyl | OH, OH | |
| 5616 | NH(C=NH)NH2 | PhCH2 | H | CH2CN | OH, OH | |
| 5617 | NH(C=NH)NH2 | PhCH2 | H | CH2COOH | OH, OH | |
| 5618 | NH(C=NH)NH2 | PhCH2 | H | CH2NC | OH, OH | |

TABLE 51-continued

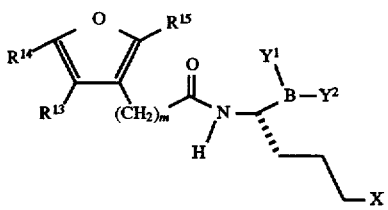

| Ex | X | R13 | R14 | R15 | Y1Y2 | Phys. Data |
|---|---|---|---|---|---|---|
| 5619 | NH(C=NH)NH2 | PhCH2 | H | CH2NO2 | OH, OH | |
| 5620 | NH(C=NH)NH2 | PhCH2 | H | (CH2)2OH | OH, OH | |
| 5621 | NH(C=NH)NH2 | PhCH2 | H | CH2SOCH3 | OH, OH | |

TABLE 52

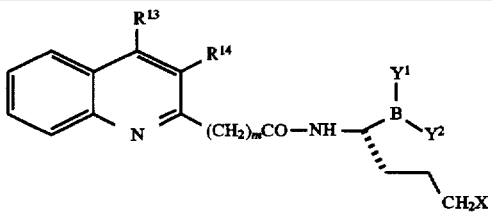

| Ex | X | R13 | R14 | Y1Y2 | Phys. Data |
|---|---|---|---|---|---|
| m = 1 | | | | | |
| 5626 | CH2NH2 | H | H | (+)-pin | |
| 5627 | CH2NH2 | H | methyl | (+)-pin | |
| 5628 | CH2NH2 | H | H | OH, OH | |
| 5629 | CH2NH2 | H | methyl | OH, OH | |
| 5630 | CH2NH2 | H | CH2CN | (+)-pin | |
| 5631 | CH2NH2 | H | (CH2)2COOH | (+)-pin | |
| 5632 | CH2NH2 | H | CH2CN | OH, OH | |
| 5633 | CH2NH2 | H | (CH2)2COOH | OH, OH | |
| 5634 | CH2NH2 | H | CH2COOMe | (+)-pin | |
| 5635 | CH2NH2 | H | (CH2)COOH | (+)-pin | |
| 5636 | CH2NH2 | H | CH2COOMe | OH, OH | |
| 5637 | CH2NH2 | H | (CH2)COOH | OH, OH | |
| 5638 | CH2NH2 | H | (CH2)2CN4H | (+)-pin | |
| 5639 | CH2NH2 | H | (CH2)CN4H | (+)-pin | |
| 5640 | CH2NH2 | H | (CH2)2CN4H | OH, OH | |
| 5641 | CH2NH2 | H | (CH2)CN4H | OH, OH | |
| 5642 | NH(C=NH)NH2 | H | H | (+)-pin | |
| 5643 | NH(C=NH)NH2 | H | methyl | (+)-pin | |
| 5644 | NH(C=NH)NH2 | H | H | OH, OH | |
| 5645 | NH(C=NH)NH2 | H | methyl | OH, OH | |
| 5646 | NH(C=NH)NH2 | H | CH2CN | (+)-pin | |
| 5647 | NH(C=NH)NH2 | H | (CH2)2COOH | (+)-pin | |
| 5648 | NH(C=NH)NH2 | H | CH2CN | OH, OH | |
| 5649 | NH(C=NH)NH2 | H | (CH2)2COOH | OH, OH | |
| 5650 | NH(C=NH)NH2 | H | CH2COOMe | (+)-pin | |
| 5651 | NH(C=NH)NH2 | H | (CH2)COOH | (+)-pin | |
| 5652 | NH(C=NH)NH2 | H | CH2COOMe | OH, OH | |
| 5653 | NH(C=NH)NH2 | H | (CH2)COOH | OH, OH | |
| 5654 | NH(C=NH)NH2 | H | (CH2)2CN4H | (+)-pin | |
| 5655 | NH(C=NH)NH2 | H | (CH2)CN4H | (+)-pin | |
| 5656 | NH(C=NH)NH2 | H | (CH2)2CN4H | OH, OH | |
| 5657 | NH(C=NH)NH2 | H | (CH2)CN4H | OH, OH | |
| 5658 | OMe | H | H | (+)-pin | |
| 5659 | OMe | H | H | OH, OH | |
| 5660 | NH(C=NH)H | H | H | (+)-pin | |
| 5661 | NH(C=NH)H | H | H | OH, OH | |
| 5662 | CH2NH2 | CH2CN | H | (+)-pin | |
| 5663 | CH2NH2 | CH2CN | H | OH, OH | |
| 5664 | NH(C=NH)NH2 | (CH2)2COOH | H | (+)-pin | |
| 5665 | NH(C=NH)NH2 | (CH2)2COOH | H | OH, OH | |
| 5666 | OMe | CH2COOMe | H | (+)-pin | |
| 5667 | OMe | CH2COOMe | H | OH, OH | |

TABLE 52-continued

[Structure: quinoline with R13 at position 4, R14 at position 3, and 2-(CH2)m-CO-NH-CH(CH2CH2X)-B(Y1)(Y2)]

| Ex | X | R13 | R14 | Y1Y2 | Phys. Data |
|---|---|---|---|---|---|
| 5668 | NH(C=NH)H | (CH2)2CN4H | H | OH, OH | |
| 5669 | NH(C=NH)H | (CH2)2CN4H | H | (+)-pin | | m = 1

| Ex | X | R13 | R14 | Y1Y2 | Phys. Data |
|---|---|---|---|---|---|
| 5670 | CH2NH2 | H | H | (+)-pin | |
| 5671 | CH2NH2 | H | methyl | (+)-pin | |
| 5672 | CH2NH2 | H | H | OH, OH | |
| 5673 | CH2NH2 | H | methyl | OH, OH | |
| 5674 | CH2NH2 | H | CH2CN | (+)-pin | |
| 5675 | CH2NH2 | H | (CH2)2COOH | (+)-pin | |
| 5676 | CH2NH2 | H | CH2CN | OH, OH | |
| 5677 | CH2NH2 | H | (CH2)2COOH | OH, OH | |
| 5678 | CH2NH2 | H | CH2COOMe | (+)-pin | |
| 5679 | CH2NH2 | H | (CH2)COOH | (+)-pin | |
| 5680 | CH2NH2 | H | CH2COOMe | OH, OH | |
| 5681 | CH2NH2 | H | (CH2)COOH | OH, OH | |
| 5682 | CH2NH2 | H | (CH2)2CN4H | (+)-pin | |
| 5683 | CH2NH2 | H | (CH2)CN4H | (+)-pin | |
| 5684 | CH2NH2 | H | (CH2)2CN4H | OH, OH | |
| 5685 | CH2NH2 | H | (CH2)CN4H | OH, OH | |
| 5686 | NH(C=NH)NH2 | H | H | (+)-pin | |
| 5687 | NH(C=NH)NH2 | H | methyl | (+)-pin | |
| 5688 | NH(C=NH)NH2 | H | H | OH, OH | |
| 5689 | NH(C=NH)NH2 | H | methyl | OH, OH | |
| 5690 | NH(C=NH)NH2 | H | CH2CN | (+)-pin | |
| 5691 | NH(C=NH)NH2 | H | (CH2)2COOH | (+)-pin | |
| 5692 | NH(C=NH)NH2 | H | CH2CN | OH, OH | |
| 5693 | NH(C=NH)NH2 | H | (CH2)2COOH | OH, OH | |
| 5694 | NH(C=NH)NH2 | H | CH2COOMe | (+)-pin | |
| 5695 | NH(C=NH)NH2 | H | (CH2)COOH | (+)-pin | |
| 5696 | NH(C=NH)NH2 | H | CH2COOMe | OH, OH | |
| 5697 | NH(C=NH)NH2 | H | (CH2)COOH | OH, OH | |
| 5698 | NH(C=NH)NH2 | H | (CH2)2CN4H | (+)-pin | |
| 5699 | NH(C=NH)NH2 | H | (CH2)CN4H | (+)-pin | |
| 5700 | NH(C=NH)NH2 | H | (CH2)2CN4H | OH, OH | |
| 5701 | NH(C=NH)NH2 | H | (CH2)CN4H | OH, OH | |
| 5702 | OMe | H | H | (+)-pin | |
| 5703 | OMe | H | H | OH, OH | |
| 5704 | NH(C=NH)H | H | H | (+)-pin | |
| 5705 | NH(C=NH)H | H | H | OH, OH | |
| 5706 | CH2NH2 | CH2CN | H | (+)-pin | |
| 5707 | CH2NH2 | CH2CN | H | OH, OH | |
| 5708 | NH(C=NH)NH2 | (CH2)2COOH | H | (+)-pin | |
| 5709 | NH(C=NH)NH2 | (CH2)2COOH | H | OH, OH | |
| 5710 | OMe | CH2COOMe | H | (+)-pin | |
| 5711 | OMe | CH2COOMe | H | OH, OH | |
| 5712 | NH(C=NH)H | (CH2)2CN4H | H | OH, OH | |
| 5713 | NH(C=NH)H | (CH2)2CN4H | H | (+)-pin | | m = 0

| Ex | X | R13 | R14 | Y1Y2 | Phys. Data |
|---|---|---|---|---|---|
| 5714 | CH2NH2 | H | H | (+)-pin | |
| 5715 | CH2NH2 | H | methyl | (+)-pin | |
| 5716 | CH2NH2 | H | H | OH, OH | |
| 5717 | CH2NH2 | H | methyl | OH, OH | |
| 5718 | CH2NH2 | H | CH2CN | (+)-pin | |
| 5719 | CH2NH2 | H | (CH2)2COOH | (+)-pin | |
| 5720 | CH2NH2 | H | CH2CN | OH, OH | |
| 5721 | CH2NH2 | H | (CH2)2COOH | OH, OH | |
| 5722 | CH2NH2 | H | CH2COOMe | (+)-pin | |
| 5723 | CH2NH2 | H | (CH2)COOH | (+)-pin | |
| 5724 | CH2NH2 | H | CH2COOMe | OH, OH | |
| 5725 | CH2NH2 | H | (CH2)COOH | OH, OH | |
| 5726 | CH2NH2 | H | (CH2)2CN4H | (+)-pin | |
| 5727 | CH2NH2 | H | (CH2)CN4H | (+)-pin | |
| 5728 | CH2NH2 | H | (CH2)2CN4H | OH, OH | |
| 5729 | CH2NH2 | H | (CH2)CN4H | OH, OH | |

TABLE 52-continued

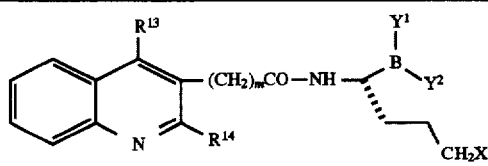

| Ex | X | R¹³ | R¹⁴ | Y¹Y² | Phys. Data |
|---|---|---|---|---|---|
| 5730 | NH(C=NH)NH$_2$ | H | H | (+)-pin | |
| 5731 | NH(C=NH)NH$_2$ | H | methyl | (+)-pin | |
| 5732 | NH(C=NH)NH$_2$ | H | H | OH, OH | |
| 5733 | NH(C=NH)NH$_2$ | H | methyl | OH, OH | |
| 5734 | NH(C=NH)NH$_2$ | H | CH$_2$CN | (+)-pin | |
| 5735 | NH(C=NH)NH$_2$ | H | (CH$_2$)$_2$COOH | (+)-pin | |
| 5736 | NH(C=NH)NH$_2$ | H | CH$_2$CN | OH, OH | |
| 5737 | NH(C=NH)NH$_2$ | H | (CH$_2$)$_2$COOH | OH, OH | |
| 5738 | NH(C=NH)NH$_2$ | H | CH$_2$COOMe | (+)-pin | |
| 5739 | NH(C=NH)NH$_2$ | H | (CH$_2$)COOH | (+)-pin | |
| 5740 | NH(C=NH)NH$_2$ | H | CH$_2$COOMe | OH, OH | |
| 5741 | NH(C=NH)NH$_2$ | H | (CH$_2$)COOH | OH, OH | |
| 5742 | NH(C=NH)NH$_2$ | H | (CH$_2$)$_2$CN$_4$H | (+)-pin | |
| 5743 | NH(C=NH)NH$_2$ | H | (CH$_2$)CN$_4$H | (+)-pin | |
| 5744 | NH(C=NH)NH$_2$ | H | (CH$_2$)$_2$CN$_4$H | OH, OH | |
| 5745 | NH(C=NH)NH$_2$ | H | (CH$_2$)CN$_4$H | OH, OH | |
| 5746 | OMe | H | H | (+)-pin | |
| 5747 | OMe | H | H | OH, OH | |
| 5748 | NH(C=NH)H | H | H | (+)-pin | |
| 5749 | NH(C=NH)H | H | H | OH, OH | |
| 5750 | CH$_2$NH$_2$ | CH$_2$CN | H | (+)-pin | |
| 5751 | CH$_2$NH$_2$ | CH$_2$CN | H | OH, OH | |
| 5752 | NH(C=NH)NH$_2$ | (CH$_2$)$_2$COOH | H | (+)-pin | |
| 5753 | NH(C=NH)NH$_2$ | (CH$_2$)$_2$COOH | H | OH, OH | |
| 5754 | OMe | CH$_2$COOMe | H | (+)-pin | |
| 5755 | OMe | CH$_2$COOMe | H | OH, OH | |
| 5756 | NH(C=NH)H | (CH$_2$)$_2$CN$_4$H | H | OH, OH | |
| 5757 | NH(C=NH)H | (CH$_2$)$_2$CN$_4$H | H | (+)-pin | |

TABLE 53

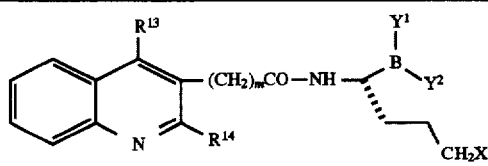

and m = 0

| Ex | X | R¹³ | R¹⁴ | Y¹Y² | Phys. Data |
|---|---|---|---|---|---|
| 5762 | CH$_2$NH$_2$ | H | H | (+)-pin | |
| 5763 | CH$_2$NH$_2$ | H | H | OH, OH | |
| 5764 | NH(C=NH)NH$_2$ | H | H | (+)-pin | |
| 5765 | NH(C=NH)NH$_2$ | H | H | OH, OH | |
| 5766 | OMe | H | H | (+)-pin | |
| 5767 | OMe | H | H | OH, OH | |
| 5768 | NH(C=NH)H | H | H | OH, OH | |
| 5769 | NH(C=NH)H | H | H | (+)-pin | |
| 5770 | CH$_2$NH$_2$ | CH$_2$CN | H | (+)-pin | |
| 5771 | CH$_2$NH$_2$ | CH$_2$CN | H | OH, OH | |
| 5772 | NH(C=NH)NH$_2$ | (CH$_2$)COOH | H | (+)-pin | |
| 5773 | NH(C=NH)NH$_2$ | (CH$_2$)COOH | H | OH, OH | |
| 5774 | OMe | CH$_2$COOMe | H | (+)-pin | |
| 5775 | OMe | CH$_2$COOMe | H | OH, OH | |
| 5776 | NH(C=NH)H | (CH$_2$)CN$_4$H | H | OH, OH | |
| 5777 | NH(C=NH)H | (CH$_2$)CN$_4$H | H | (+)-pin | |

TABLE 54

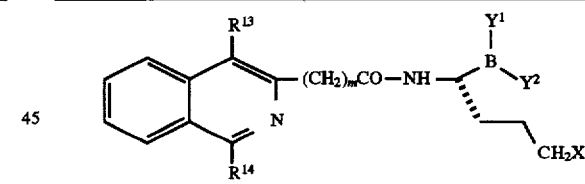

and m = 0

| Ex | X | R¹³ | R¹⁴ | Y¹Y² | Phys. Data |
|---|---|---|---|---|---|
| 5782 | CH$_2$NH$_2$ | H | H | (+)-pin | |
| 5783 | CH$_2$NH$_2$ | H | H | OH, OH | |
| 5784 | NH(C=NH)NH$_2$ | H | H | (+)-pin | |
| 5785 | NH(C=NH)NH$_2$ | H | H | OH, OH | |
| 5786 | OMe | H | H | (+)-pin | |
| 5787 | OMe | H | H | OH, OH | |
| 5788 | NH(C=NH)H | H | H | OH, OH | |
| 5789 | NH(C=NH)H | H | H | (+)-pin | |
| 5790 | CH$_2$NH$_2$ | CH$_2$CN | H | (+)-pin | |
| 5791 | CH$_2$NH$_2$ | CH$_2$CN | H | OH, OH | |
| 5792 | NH(C=NH)NH$_2$ | (CH$_2$)COOH | H | (+)-pin | |
| 5793 | NH(C=NH)NH$_2$ | (CH$_2$)COOH | H | OH, OH | |
| 5794 | OMe | CH$_2$COOMe | H | (+)-pin | |
| 5795 | OMe | CH$_2$COOMe | H | OH, OH | |
| 5796 | NH(C=NH)H | (CH$_2$)CN$_4$H | H | OH, OH | |
| 5797 | NH(C=NH)H | (CH$_2$)CN$_4$H | H | (+)-pin | |

TABLE 55

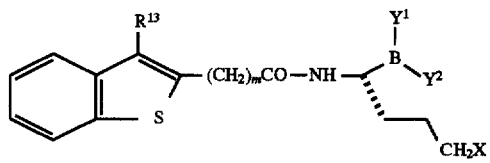

and m = 0

| Ex | X | R13 | R14 | Y1Y2 | Phys. Data |
|---|---|---|---|---|---|
| 5802 | CH2NH2 | H | H | (+)-pin | |
| 5803 | CH2NH2 | H | H | OH, OH | |
| 5804 | NH(C=NH)NH2 | H | H | (+)-pin | |
| 5805 | NH(C=NH)NH2 | H | H | OH, OH | |
| 5806 | OMe | H | H | (+)-pin | |
| 5807 | OMe | H | H | OH, OH | |
| 5808 | NH(C=NH)H | H | H | OH, OH | |
| 5809 | NH(C=NH)H | H | H | (+)-pin | |
| 5810 | CH2NH2 | CH2CN | H | (+)-pin | |
| 5811 | CH2NH2 | CH2CN | H | OH, OH | |
| 5812 | NH(C=NH)NH2 | (CH2)COOH | H | (+)-pin | |
| 5813 | NH(C=NH)NH2 | (CH2)COOH | H | OH, OH | |
| 5814 | OMe | CH2COOMe | H | (+)-pin | |
| 5815 | OMe | CH2COOMe | H | OH, OH | |
| 5816 | NH(C=NH)H | (CH2)CN4H | H | OH, OH | |
| 5817 | NH(C=NH)H | (CH2)CN4H | H | (+)-pin | |

TABLE 56

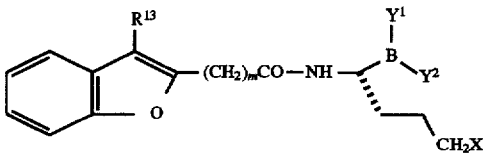

and m = 0

| Ex | X | R13 | R14 | Y1Y2 | Phys. Data |
|---|---|---|---|---|---|
| 5822 | CH2NH2 | H | H | (+)-pin | |
| 5823 | CH2NH2 | H | H | OH, OH | |
| 5824 | NH(C=NH)NH2 | H | H | (+)-pin | |
| 5825 | NH(C=NH)NH2 | H | H | OH, OH | |
| 5826 | OMe | H | H | (+)-pin | |
| 5827 | OMe | H | H | OH, OH | |
| 5828 | NH(C=NH)H | H | H | OH, OH | |
| 5829 | NH(C=NH)H | H | H | (+)-pin | |
| 5830 | CH2NH2 | CH2CN | H | (+)-pin | |
| 5831 | CH2NH2 | CH2CN | H | OH, OH | |
| 5832 | NH(C=NH)NH2 | (CH2)COOH | H | (+)-pin | |
| 5833 | NH(C=NH)NH2 | (CH2)COOH | H | OH, OH | |
| 5834 | OMe | CH2COOMe | H | (+)-pin | |
| 5835 | OMe | CH2COOMe | H | OH, OH | |
| 5836 | NH(C=NH)H | (CH2)CN4H | H | OH, OH | |
| 5837 | NH(C=NH)H | (CH2)CN4H | H | (+)-pin | |

TABLE 57

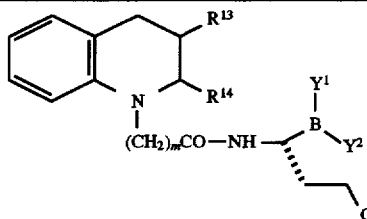

| Ex | X | R13 | R14 | Y1Y2 | Phys. Data |
|---|---|---|---|---|---|
| | | m = 1 | | | |
| 5842 | CH2NH2 | H | H | (+)-pin | |
| 5843 | CH2NH2 | H | H | OH, OH | |
| 5844 | NH(C=NH)NH2 | H | H | (+)-pin | |
| 5845 | NH(C=NH)NH2 | H | H | OH, OH | |
| 5846 | OMe | H | H | (+)-pin | |
| 5847 | OMe | H | H | OH, OH | |
| 5848 | NH(C=NH)H | H | H | OH, OH | |
| 5849 | NH(C=NH)H | H | H | (+)-pin | |
| 5850 | CH2NH2 | CH2CN | H | (+)-pin | |
| 5851 | CH2NH2 | CH2CN | H | OH, OH | |
| 5852 | NH(C=NH)NH2 | (CH2)COOH | H | (+)-pin | |
| 5853 | NH(C=NH)NH2 | (CH2)COOH | H | OH, OH | |
| 5854 | OMe | CH2COOMe | H | (+)-pin | |
| 5855 | OMe | CH2COOMe | H | OH, OH | |
| 5856 | NH(C=NH)H | (CH2)CN4H | H | OH, OH | |
| 5857 | NH(C=NH)H | (CH2)CN4H | H | (+)-pin | |
| | | m = 0 | | | |
| 5858 | CH2NH2 | H | H | (+)-pin | |
| 5859 | CH2NH2 | H | H | OH, OH | |
| 5860 | NH(C=NH)NH2 | H | H | (+)-pin | |
| 5861 | NH(C=NH)NH2 | H | H | OH, OH | |
| 5862 | OMe | H | H | (+)-pin | |
| 5863 | OMe | H | H | OH, OH | |
| 5864 | NH(C=NH)H | H | H | OH, OH | |
| 5865 | NH(C=NH)H | H | H | (+)-pin | |
| 5866 | CH2NH2 | CH2CN | H | (+)-pin | |
| 5867 | CH2NH2 | CH2CN | H | OH, OH | |
| 5868 | NH(C=NH)NH2 | (CH2)COOH | H | (+)-pin | |
| 5869 | NH(C=NH)NH2 | (CH2)COOH | H | OH, OH | |
| 5870 | OMe | CH2COOMe | H | (+)-pin | |
| 5871 | OMe | CH2COOMe | H | OH, OH | |
| 5872 | NH(C=NH)H | (CH2)CN4H | H | OH, OH | |
| 5873 | NH(C=NH)H | (CH2)CN4H | H | (+)-pin | |

TABLE 58

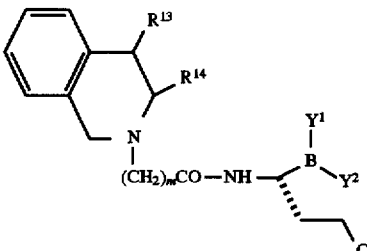

| Ex | X | R13 | R14 | Y1Y2 | Phys. Data |
|---|---|---|---|---|---|
| | | m = 1 | | | |
| 5878 | CH2NH2 | H | H | (+)-pin | |
| 5879 | CH2NH2 | H | H | OH, OH | |
| 5880 | NH(C=NH)NH2 | H | H | (+)-pin | |
| 5881 | NH(C=NH)NH2 | H | H | OH, OH | |
| 5882 | OMe | H | H | (+)-pin | |
| 5883 | OMe | H | H | OH, OH | |
| 5884 | NH(C=NH)H | H | H | OH, OH | |

TABLE 58-continued

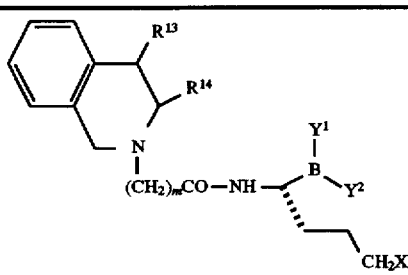

| Ex | X | R13 | R14 | Y1Y2 | Phys. Data |
|---|---|---|---|---|---|
| 5885 | NH(C=NH)H | H | H | (+)-pin | |
| 5886 | CH2NH2 | CH2CN | H | (+)-pin | |
| 5887 | CH2NH2 | CH2CN | H | OH, OH | |
| 5888 | NH(C=NH)NH2 | (CH2)COOH | H | (+)-pin | |
| 5889 | NH(C=NH)NH2 | (CH2)COOH | H | OH, OH | |
| 5890 | OMe | CH2COOMe | H | (+)-pin | |
| 5891 | OMe | CH2COOMe | H | OH, OH | |
| 5892 | NH(C=NH)H | (CH2)CN4H | H | OH, OH | |
| 5893 | NH(C=NH)H | (CH2)CN4H | H | (+)-pin | | m = 0

| 5894 | CH2NH2 | H | H | (+)-pin | |
| 5895 | CH2NH2 | H | H | OH, OH | |
| 5896 | NH(C=NH)NH2 | H | H | (+)-pin | |
| 5897 | NH(C=NH)NH2 | H | H | OH, OH | |
| 5898 | OMe | H | H | (+)-pin | |
| 5899 | OMe | H | H | OH, OH | |
| 5900 | NH(C=NH)H | H | H | OH, OH | |
| 5901 | NH(C=NH)H | H | H | (+)-pin | |
| 5902 | CH2NH2 | CH2CN | H | (+)-pin | |
| 5903 | CH2NH2 | CH2CN | H | OH, OH | |
| 5904 | NH(C=NH)NH2 | (CH2)COOH | H | (+)-pin | |
| 5905 | NH(C=NH)NH2 | (CH2)COOH | H | OH, OH | |
| 5906 | OMe | CH2COOMe | H | (+)-pin | |
| 5907 | OMe | CH2COOMe | H | OH, OH | |
| 5908 | NH(C=NH)H | (CH2)CN4H | H | OH, OH | |
| 5909 | NH(C=NH)H | (CH2)CN4H | H | (+)-pin | |

TABLE 59

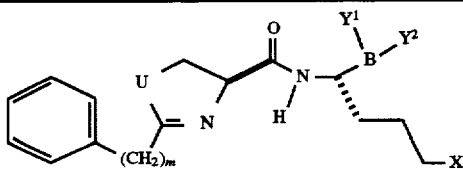

| Ex | H | U | Y1Y2 | Phys. Data |
|---|---|---|---|---|
| | | m = 1 | | |
| 5914 | CH2NH2 | S | (+)-pin | |
| 5915 | NHC(=NH)NH2 | S | (+)-pin | |
| 5916 | SC(=NH)NH2 | S | (+)-pin | |
| 5917 | CH2NH2 | S | OH, OH | |
| 5918 | NHC(=NH)NH2 | S | OH, OH | |
| 5919 | SC(=NH)NH2 | S | OH, OH | |
| 5920 | CH2NH2 | O | (+)-pin | |
| 5921 | NHC(=NH)NH2 | O | (+)-pin | |
| 5922 | SC(=NH)NH2 | O | (+)-pin | |
| 5923 | CH2NH2 | O | OH, OH | |
| 5924 | NHC(=NH)NH2 | O | OH, OH | |
| 5925 | SC(=NH)NH2 | O | OH, OH | |
| | | m = 2 | | |
| 5926 | CH2NH2 | S | (+)-pin | CA |
| 5927 | NHC(=NH)NH2 | S | (+)-pin | |
| 5928 | SC(=NH)NH2 | S | (+)-pin | |
| 5929 | CH2NH2 | S | OH, OH | |
| 5930 | NHC(=NH)NH2 | S | OH, OH | |

TABLE 59-continued

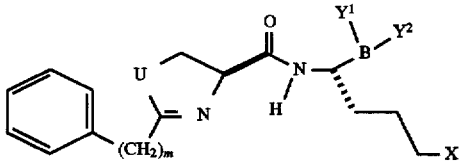

| Ex | H | U | Y1Y2 | Phys. Data |
|---|---|---|---|---|
| 5931 | SC(=NH)NH2 | S | OH, OH | |
| 5932 | CH2NH2 | O | (+)-pin | |
| 5933 | NHC(=NH)NH2 | O | (+)-pin | |
| 5934 | SC(=NH)NH2 | O | (+)-pin | |
| 5935 | CH2NH2 | O | OH, OH | |
| 5936 | NHC(=NH)NH2 | O | OH, OH | |
| 5937 | SC(=NH)NH2 | O | OH, OH | |

CA: HRMS Calc.: 543.2635, Found: 543.2643

TABLE 60

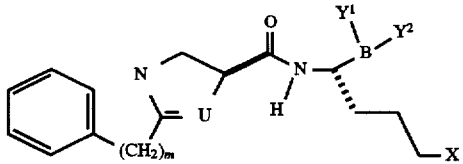

| Ex | H | U | Y1Y2 | Phys. Data |
|---|---|---|---|---|
| | | m = 1 | | |
| 5942 | CH2NH2 | S | (+)-pin | |
| 5943 | NHC(=NH)NH2 | S | (+)-pin | |
| 5944 | SC(=NH)NH2 | S | (+)-pin | |
| 5945 | CH2NH2 | S | OH, OH | |
| 5946 | NHC(=NH)NH2 | S | OH, OH | |
| 5947 | SC(=NH)NH2 | S | OH, OH | |
| 5948 | CH2NH2 | O | (+)-pin | |
| 5949 | NHC(=NH)NH2 | O | (+)-pin | |
| 5950 | SC(=NH)NH2 | O | (+)-pin | |
| 5951 | CH2NH2 | O | OH, OH | |
| 5952 | NHC(=NH)NH2 | O | OH, OH | |
| 5953 | SC(=NH)NH2 | O | OH, OH | |
| | | m = 2 | | |
| 5954 | CH2NH2 | S | (+)-pin | |
| 5955 | NHC(=NH)NH2 | S | (+)-pin | |
| 5956 | SC(=NH)NH2 | S | (+)-pin | |
| 5957 | CH2NH2 | S | OH, OH | |
| 5958 | NHC(=NH)NH2 | S | OH, OH | |
| 5959 | SC(=NH)NH2 | S | OH, OH | |
| 5960 | CH2NH2 | O | (+)-pin | |
| 5961 | NHC(=NH)NH2 | O | (+)-pin | |
| 5962 | SC(=NH)NH2 | O | (+)-pin | |
| 5963 | CH2NH2 | O | OH, OH | |
| 5964 | NHC(=NH)NH2 | O | OH, OH | |
| 5965 | SC(=NH)NH2 | O | OH, OH | |

TABLE 61

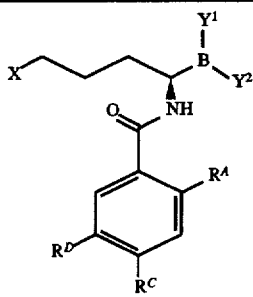

| Ex | X | R^A | R^C | R^D | Y^1, Y^2 | Phys Data |
|---|---|---|---|---|---|---|
| 5970 | NHC(NH)NH_2 | Me | Ph | OMe | (+)-pin | |
| 5971 | NHC(NH)NH_2 | Me | Ph | CONH_2 | (+)-pin | |
| 5972 | NHC(NH)NH_2 | Me | Ph | F | (+)-pin | |
| 5973 | NHC(NH)NH_2 | Me | Ph | CF_3 | (+)-pin | |
| 5974 | NHC(NH)NH_2 | Me | Ph | Cl | (+)-pin | |
| 5975 | NHC(NH)NH_2 | Me | Ph | OH | (+)-pin | |
| 5976 | NHC(NH)NH_2 | Me | 4-C_6H_4CO_2H | OMe | (+)-pin | |
| 5977 | NHC(NH)NH_2 | Me | 4-C_6H_4CO_2H | CONH_2 | (+)-pin | |
| 5978 | NHC(NH)NH_2 | Me | 4-C_6H_4CO_2H | F | (+)-pin | |
| 5979 | NHC(NH)NH_2 | Me | 4-C_6H_4CO_2H | CF_3 | (+)-pin | |
| 5980 | NHC(NH)NH_2 | Me | 4-C_6H_4CO_2H | Cl | (+)-pin | |
| 5981 | NHC(NH)NH_2 | Me | 4-C_6H_4CO_2H | OH | (+)-pin | |
| 5982 | SC(NH)NH_2 | Me | Ph | OMe | (+)-pin | |
| 5983 | SC(NH)NH_2 | Me | Ph | CONH_2 | (+)-pin | |
| 5984 | SC(NH)NH_2 | Me | Ph | F | (+)-pin | |
| 5985 | SC(NH)NH_2 | Me | Ph | CF_3 | (+)-pin | |
| 5986 | SC(NH)NH_2 | Me | Ph | Cl | (+)-pin | |
| 5987 | SC(NH)NH_2 | Me | Ph | OH | (+)-pin | |
| 5988 | SC(NH)NH_2 | Me | 4-C_6H_4CO_2H | OMe | (+)-pin | |
| 5989 | SC(NH)NH_2 | Me | 4-C_6H_4CO_2H | CONH_2 | (+)-pin | |
| 5990 | SC(NH)NH_2 | Me | 4-C_6H_4CO_2H | F | (+)-pin | |
| 5991 | SC(NH)NH_2 | Me | 4-C_6H_4CO_2H | CF_3 | (+)-pin | |
| 5992 | SC(NH)NH_2 | Me | 4-C_6H_4CO_2H | Cl | (+)-pin | |
| 5993 | SC(NH)NH_2 | Me | 4-C_6H_4CO_2H | OH | (+)-pin | |
| 5994 | CH_2NH_2 | Me | Ph | OMe | (+)-pin | |
| 5995 | CH_2NH_2 | Me | Ph | CONH_2 | (+)-pin | |
| 5996 | CH_2NH_2 | Me | Ph | F | (+)-pin | |
| 5997 | CH_2NH_2 | Me | Ph | CF_3 | (+)-pin | |
| 5998 | CH_2NH_2 | Me | Ph | Cl | (+)-pin | |
| 5999 | CH_2NH_2 | Me | Ph | OH | (+)-pin | |
| 6000 | CH_2NH_2 | Me | 4-C_6H_4CO_2H | OMe | (+)-pin | |
| 6001 | CH_2NH_2 | Me | 4-C_6H_4CO_2H | CONH_2 | (+)-pin | |
| 6002 | CH_2NH_2 | Me | 4-C_6H_4CO_2H | F | (+)-pin | |
| 6003 | CH_2NH_2 | Me | 4-C_6H_4CO_2H | CF_3 | (+)-pin | |
| 6004 | CH_2NH_2 | Me | 4-C_6H_4CO_2H | Cl | (+)-pin | |
| 6005 | CH_2NH_2 | Me | 4-C_6H_4CO_2H | OH | (+)-pin | |
| 6006 | NHC(NH)NH_2 | Me | Ph | OMe | OH, OH | |
| 6007 | NHC(NH)NH_2 | Me | Ph | CONH_2 | OH, OH | |
| 6008 | NHC(NH)NH_2 | Me | Ph | F | OH, OH | |
| 6009 | NHC(NH)NH_2 | Me | Ph | CF_3 | OH, OH | |
| 6010 | NHC(NH)NH_2 | Me | Ph | Cl | OH, OH | |
| 6011 | NHC(NH)NH_2 | Me | Ph | OH | OH, OH | |
| 6012 | NHC(NH)NH_2 | Me | 4-C_6H_4CO_2H | OMe | OH, OH | |
| 6013 | NHC(NH)NH_2 | Me | 4-C_6H_4CO_2H | CONH_2 | OH, OH | |
| 6014 | NHC(NH)NH_2 | Me | 4-C_6H_4CO_2H | F | OH, OH | |
| 6015 | NHC(NH)NH_2 | Me | 4-C_6H_4CO_2H | CF_3 | OH, OH | |
| 6016 | NHC(NH)NH_2 | Me | 4-C_6H_4CO_2H | Cl | OH, OH | |
| 6017 | NHC(NH)NH_2 | Me | 4-C_6H_4CO_2H | OH | OH, OH | |
| 6018 | SC(NH)NH_2 | Me | Ph | OMe | OH, OH | |
| 6019 | SC(NH)NH_2 | Me | Ph | CONH_2 | OH, OH | |
| 6020 | SC(NH)NH_2 | Me | Ph | F | OH, OH | |
| 6021 | SC(NH)NH_2 | Me | Ph | CF_3 | OH, OH | |
| 6022 | SC(NH)NH_2 | Me | Ph | Cl | OH, OH | |
| 6023 | SC(NH)NH_2 | Me | Ph | OH | OH, OH | |
| 6024 | SC(NH)NH_2 | Me | 4-C_6H_4CO_2H | OMe | OH, OH | |
| 6025 | SC(NH)NH_2 | Me | 4-C_6H_4CO_2H | CONH_2 | OH, OH | |
| 6026 | SC(NH)NH_2 | Me | 4-C_6H_4CO_2H | F | OH, OH | |
| 6027 | SC(NH)NH_2 | Me | 4-C_6H_4CO_2H | CF_3 | OH, OH | |
| 6028 | SC(NH)NH_2 | Me | 4-C_6H_4CO_2H | Cl | OH, OH | |
| 6029 | SC(NH)NH_2 | Me | 4-C_6H_4CO_2H | OH | OH, OH | |
| 6030 | CH_2NH_2 | Me | Ph | OMe | OH, OH | |
| 6031 | CH_2NH_2 | Me | Ph | CONH_2 | OH, OH | |
| 6032 | CH_2NH_2 | Me | Ph | F | OH, OH | |
| 6033 | CH_2NH_2 | Me | Ph | CF_3 | OH, OH | |
| 6034 | CH_2NH_2 | Me | Ph | Cl | OH, OH | |
| 6035 | CH_2NH_2 | Me | Ph | OH | OH, OH | |
| 6036 | CH_2NH_2 | Me | 4-C_6H_4CO_2H | OMe | OH, OH | |
| 6037 | CH_2NH_2 | Me | 4-C_6H_4CO_2H | CONH_2 | OH, OH | |
| 6038 | CH_2NH_2 | Me | 4-C_6H_4CO_2H | F | OH, OH | |
| 6039 | CH_2NH_2 | Me | 4-C_6H_4CO_2H | CF_3 | OH, OH | |
| 6040 | CH_2NH_2 | Me | 4-C_6H_4CO_2H | Cl | OH, OH | |
| 6041 | CH_2NH_2 | Me | 4-C_6H_4CO_2H | OH | OH, OH | |

UTILITY

The compounds of formula (I) are useful as inhibitors of trypsin-like enzymes, notably human thrombin, Factor VIIa, Factor IXa, Factor Xa, plasma kallikrein and plasmin. Because of their inhibitory action, these compounds are indicated for use in the prevention or treatment of physiological reactions catalyzed by the aforesaid enzymes such as blood coagulation and inflammation. These compounds are also useful as anticoagulants for the processing of blood for therapeutic or diagnostic purposes or for the production of blood products of fragments, since contact of blood with the surfaces commonly used for blood collection and storage causes activation of coagulation leading to thrombin formation and clot formation.

The effectiveness of compounds of the present invention as inhibitors of blood coagulation proteases was determined using purified human proteases and synthetic substrates following procedures similar to those described in Kettner et al. (1990).

For these assays, the rate of enzymatic (thrombin, Factor Xa, and Factor VIIa) hydrolysis of chromogenic substrates (S2238 (H-D-Phe-Pip-Arg-pNA), S2222, and S2288, respectively; Kabi Pharmacia, Franklin, Ohio.) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Thrombin and Xa determinations were made in 0.10M sodium phosphate buffer, pH 7.5, containing 0.20M NaCl, and 0.5% PEG 8000. VIIa determinations were made in 0.05M tris buffer, pH 7.6, containing 0.10M NaCl, 4 mM $CaCl_2$, and 0.1% bovine serum albumin. The Michaelis constant, $K_m$, for substrate hydrolysis was determined at 5° C. using the method of Lineweaver and Burk.

Values of $K_i$ were determined by allowing 0.2–0.5 nM human thrombin or human factor Xa (Enzyme Research Laboratories, South Bend, Ind.), or 50 nM human factor VIIa (BioSpacific, Emeryville, Calif.) react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values.

$$\frac{v_o - v_s}{v_s} = \frac{I}{K_i(1 + S/K_m)}$$

where:

$v_o$ is the velocity of the control in the absence of inhibitor;

$v_s$ is the velocity in the presence of inhibitor;

I is the concentration of inhibitor;

$K_i$ is the dissociation constant of the enzyme: inhibitor complex;

S is the concentration of substrate;

$K_m$ is the Michaelis constant.

Using the methodology described above, representative compounds of this invention were evaluated and found to exhibit a Ki of less 500 μM thereby confirming the utility of compounds of the invention as effective inhibitors of human blood coagulation proteases. The results of these assays are summarized in Table 62, where +++ indicates a $K_i$<500 nM; ++ indicates a $K_i$<50,000 nM; and + indicates a $K_i$500,000<nM; − indicates inactive.

TABLE 62

$K_i$ values for inhibition of Serine Proteases by compounds of the present invention.

| EXAMPLE | Thrombin | Factor Xa | Factor VIIa |
|---|---|---|---|
| 1 | +++ | ++ | NT |
| 2 | +++ | +++ | +++ |
| 29 | +++ | NT | NT |
| 35 | +++ | +++ | ++ |
| 68 | ++ | ++ | +++ |
| 129 | +++ | +++ | NT |
| 199 | +++ | +++ | +++ |
| 203 | +++ | +++ | +++ |
| 224 | +++ | +++ | +++ |
| 227 | +++ | +++ | ++ |
| 231 | +++ | +++ | ++ |
| 261 | +++ | +++ | +++ |
| 262 | +++ | +++ | +++ |
| 263 | +++ | +++ | +++ |
| 283 | +++ | +++ | ++ |
| 286 | +++ | +++ | +++ |
| 288 | +++ | NT | +++ |
| 298 | +++ | +++ | +++ |
| 299 | +++ | +++ | +++ |
| 302 | +++ | +++ | ++ |
| 303 | +++ | ++ | ++ |
| 304 | ++ | ++ | ++ |
| 305 | ++ | ++ | ++ |
| 468 | ++ | ++ | ++ |
| 474 | ++ | ++ | ++ |
| 887 | +++ | NT | NT |
| 888 | +++ | ++ | ++ |
| 890 | +++ | ++ | ++ |
| 892 | +++ | ++ | ++ |
| 898 | +++ | ++ | ++ |
| 905 | ++ | ++ | − |
| 913 | +++ | − | ++ |
| 914 | +++ | ++ | ++ |
| 917 | +++ | ++ | ++ |
| 920 | +++ | NT | NT |
| 921 | +++ | ++ | ++ |
| 923 | +++ | ++ | ++ |
| 931 | +++ | ++ | ++ |

TABLE 62-continued $K_i$ values for inhibition of Serine Proteases by compounds of the present invention.

| EXAMPLE | Thrombin | Factor Xa | Factor VIIa |
|---|---|---|---|
| 967 | +++ | ++ | +++ |
| 969 | +++ | ++ | ++ |
| 977 | +++ | NT | NT |
| 1352 | +++ | ++ | NT |
| 1431 | +++ | NT | NT |
| 1459 | ++ | ++ | ++ |
| 1467 | +++ | NT | ++ |
| 1521 | +++ | NT | NT |
| 1557 | +++ | NT | ++ |
| 2066 | NT | NT | NT |
| 2067 | +++ | NT | NT |
| 2068 | ++ | ++ | ++ |
| 2073 | +++ | ++ | ++ |
| 2074 | +++ | ++ | ++ |
| 2411 | +++ | NT | NT |
| 2412 | +++ | ++ | ++ |
| 2414 | +++ | ++ | ++ |
| 2416 | +++ | ++ | ++ |
| 2422 | +++ | ++ | ++ |
| 2430 | ++ | ++ | − |
| 2439 | +++ | ++ | ++ |
| 2440 | +++ | ++ | ++ |
| 2443 | +++ | ++ | ++ |
| 2446 | +++ | ++ | ++ |
| 2447 | +++ | ++ | ++ |
| 2490 | +++ | ++ | +++ |
| 2491 | +++ | +++ | ++ |
| 2499 | +++ | ++ | ++ |
| 2533 | +++ | ++ | − |
| 2752 | +++ | NT | NT |
| 2780 | +++ | ++ | +++ |
| 2781 | +++ | ++ | ++ |
| 2837 | ++ | NT | NT |
| 3349 | +++ | ++ | NT |
| 3458 | +++ | − | ++ |
| 3465 | +++ | ++ | ++ |
| 3538 | +++ | ++ | ++ |
| 4064 | ++ | ++ | ++ |
| 4065 | ++ | ++ | ++ |
| 5426 | +++ | +++ | NT |
| 5529 | +++ | +++ | NT |
| 5551 | NT | NT | NT |

The final concentration of thrombin was 4 NIH units/mL. The effectiveness of compounds in prolonging clotting times is reported as $K_iTT$ (nM; level of inhibitor required to prolong clotting to the time observed for 2 NIH units/mL thrombin in the absence of inhibitor) o Compounds of the present invention were found to have $K_iTT$ values in the range of 100–6000 nm.

Generally, these compounds may be administered orally or parenterally to a hose to obtain an anti-thrombogenic effect. The dosage of the active compound depends on the mammalian species, body weight, age, and mode of administration as will be obvious to one skilled in the art. In the case of large mammals such as humans, the compounds may be administered alone or in combination with pharmaceutical carriers or diluents at a dose of from 0.02 to 15 mg/Kg to obtain the anti-thrombogenic effect, and may be given as a single dose or in divided doses or as a sustained release formulation.

Pharmaceutical carriers or diluents are well known and include sugars, starches and water, which may be used to make tablets, capsules, injectable solutions or the like which can serve as suitable dosage forms for administration of the compounds of this invention. *Remington's Pharmaceutical Sciences*, A. Osol, is a standard reference text which discloses suitable pharmaceutical carriers and dosage forms. The disclosure of this text is hereby incorporated by reference for a more complete teaching of suitable dosage forms for administration of the compounds of this invention.

What is claimed is:

1. A compound of formula:

R¹—Z—CHR²—A    (I)

wherein:

A is -BY¹Y²;

Y¹ and Y² are independently
  a) —OH,
  b) —F
  c) —NR³R⁴, or
  d) $C_1$-$C_8$ alkoxy;

Y¹ and y² are taken together to form:
  e) a cyclic boron ester where said chain or ring contains from 2 to 20 carbon atoms and, from 0–3 heteroatoms which are N, S, or O,
  f) a cyclic boron amide where said chain or ring contains from 2 to 20 carbon atoms and, from 0–3 heteroatoms which are N, S, or O,
  g) a cyclic boron amide-ester where said chain or ring contains from 2 to 20 carbon atoms and from 0–3 heteroatoms which are N, S, or O;

Z is
  a) —$(CH_2)_m$CONR⁸—,
  b) —$(CH_2)_m$CSNR⁸—,
  c) —$(CH_2)_m$SO₂NR⁸—,
  d) —$(CH_2)_m$CO₂—,
  e) —$(CH_2)_m$C(S)O—, or
  f) —$(CH_2)_m$SO₂O—;

R¹ is —$(CH_2)_p$-aryl, wherein aryl is phenyl, naphthyl or biphenyl substituted with one, two or three substituents selected from the group consisting of:
halo, methylenedioxy, -R⁸, —NR⁸COR⁹, $C_2$-$C_6$-alkenyl, $C_2$-$C_6$-alkynyl, —$(CH_2)_w$—OR⁸, -($C_1$-$C_6$)-perfluoroalkyl, —$(CH_2)_w$CN, —$(CH_2)_w$NC, —$(CH_2)_w$NO₂, —$(CH_2)_w$CF₃, —$(CH_2)_w$S(O)ᵣR⁷, —$(CH_2)_w$NR⁸R⁹, —$(CH_2)_w$COR⁸, —$(CH_2)_w$CHO, —$(CH_2)_w$CO₂R⁸, —$(CH_2)_w$CONR⁸R⁹, —$(CH_2)_w$SO₂NH—($C_1$-$C_5$)-alkyl, —$(CH_2)_w$SO₂NH₂, —$(CH_2)_w$SO₂NH—CO—($C_1$-$C_6$)-alkyl, —$(CH_2)_w$SO₂NH—CO₂—($C_1$-$C_6$)-alkyl, —$(CH_2)_w$NHSO₂—($C_1$-$C_6$)-alkyl, —$(CH_2)_w$NHSO₂—($C_1$-$C_6$)-perfluoroalkyl, —$(CH_2)_w$NHSO₂-phenyl, —$(CH_2)_w$NHSO₂-perfluorophenyl, —$(CH_2)_w$CN₄H, —O$(CH_2)_w$CN, —NH$(CH_2)_w$CN, —S$(CH_2)_w$CN, —$(CH_2)_w$NH—CO—($C_1$-$C_6$-alkyl), —$(CH_2)_w$NH—CO—($C_1$-$C_6$-perfluoroalkyl), —$(CH_2)_w$NH—CO—(phenyl), —$(CH_2)_w$NH—CO₂—($C_1$-$C_6$-alkyl), —$(CH_2)_w$NH—CO₂—($C_1$-$C_6$-perfluoroalkyl), —$(CH_2)_w$NH—CO₂—(phenyl), —O(C=O)—($C_1$-$C_5$-alkyl),

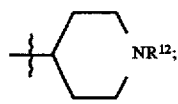

R² is
  a) -($C_1$-$C_{12}$ alkyl)-X,
  b) -($C_2$-$C_{12}$ alkenyl)-X, or
  c)

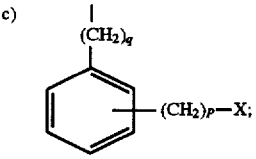

X is
  a) halogen,
  b) —CN,
  c) —NO₂,
  d) —CF₃,
  e) —S(O)ᵣR14,
  f) —NHR¹⁴
  g) —NHS(O)ᵣR¹⁴,
  h) —NHC(NH)H,
  i) —NHC(NH)NHOH,
  j) —NHC(NH)NHCN,
  k) —NHC(NH)NHR¹⁴,
  l) —NHC(NH)NHCOR¹⁴,
  m) —C(NH)NHR¹⁴,
  n) —C(NH)NHCOR¹⁴,
  o) —C(O)NHR¹⁴,
  p) —C(O)NHC(O)R¹⁴,
  q) —C(O)OR¹⁴,
  r) —OR¹⁴,
  s) —OC(O)R¹⁴,
  t) —OC(O)OR¹⁴,
  u) —OC(O)NHR¹⁴,
  v) —OC(O)NHC(O)R¹⁴,
  w) —SC(=NH)$^{NHR14}$, or
  x) —SC(=NH)NHC(=O)R¹⁴;

R³ is
  a) hydrogen,
  b) $C_1$-$C_8$ alkyl,
  c) -($C_1$-$C_4$ alkyl)-aryl,
  d) $C_5$-$C_7$ cycloalkyl, or
  e) phenyl;

R⁴ is
  a) hydrogen,
  b) $C_1$-$C_8$ alkyl,
  c) —($C_1$-$C_4$ alkyl)-aryl,
  d) $C_5$-$C_7$ cycloalkyl,
  e) phenyl, or
  f) phenylsulfonyl;

R⁷ is
  a) phenyl,
  b) $C_1$-$C_8$-alkyl,
  c) $C_1$-$C_4$-alkoxy,
  d) —CF₃, or
  e) benzyl;

R⁸ and R⁹ are independently
  a) H, b) 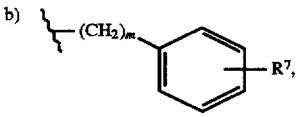

c) $C_3$-$C_7$ cycloalkyl,
  d) $C_1$-$C_8$-alkyl, or

R¹¹ is
  a) halo, b) —CN,
c) $C_1$-$C_{10}$-alkyl,
d) $C_3$-$C_8$-cycloalkyl,
e) $C_2$-$C_{10}$-alkenyl,
f) $C_2$-$C_{10}$-alkynyl,
g) —$OR^8$,
h) —$NO_2$,
i) —$CF_3$,
j) —$S(O)_rR^7$,
k) —$NR^8R^9$,
l) —$CO_2R^8$,
l) —$COR^8$,
n) —$CONR^8R^9$, or
o) H $R^{12}$ is H, $C_1$-$C_4$ alkyl, phenyl, benzyl, —$COR^7$, or —$S(O)_rR^7$;

R14 is
a) —H,
b) —$CF_3$
c) —$C_1$-$C_4$ alkyl,
d) —$(CH_2)_q$-aryl, wherein aryl is phenyl, biphenyl, naphthyl, or fluorenyl unsubstituted or substituted with one to three substituents selected from the group consisting of:
halogen,
—$CF_3$,
-($C_1$-$C_4$ alkyl),
—$(CH_2)_xR^{15}$,
—$(CH_2)_xCO(CH_2)_yR^{15}$,
—$(CH_2)_xC(O)O(CH_2)_yR^{15}$,
—$(CH_2)_xC(O)N[(CH_2)_yR^{15}][(CH_2)_yR^{16}]$,
-methylenedioxy,
-($C_1$-$C_4$ alkoxy),
—$(CH_2)_xO(CH_2)_yR^{15}$,
—$(CH_2)_xOCO(CH_2)_yR^{15}$,
—$(CH_2)_xOC(O)O(CH_2)_yR^{15}$,
—$(CH_2)_xOC(O)N[(CH_2)_yR^{15}][(CH_2)_yR^{16}]$,
—$(CH_2)_xOC(O)N[(CH_2)_yR^{15}][CO(CH_2)_yR^{16}]$,
—$(CH_2)_xS(O)_r(CH_2)_yR^{15}$,
—$(CH_2)_xS(O)_r(CH_2)_yCOR^{15}$,
—$(CH_2)_xS(O)_r(CH_2)_yC(O)OR^{15}$,
—$(CH_2)_xS(O)_rN[(CH_2)_yR^{15}][(CH_2)_yR^{16}]$
—$(CH_2)_xN[(CH_2)_yR^{15}][(CH_2)_yR^{16}]$,
—$(CH_2)_xN[(CH_2)_yR^{15}][CO(CH_2)_yR^{16}]$,
—$(CH_2)_xN[(CH_2)_yR^{15}][C(O)O(CH_2)_yR^{16}]$,
—$(CH_2)_xN[(CH_2)_yR^{15}]CON[(CH_2)_yR^{15}][(CH_2)_yR^{16}]$,
—$(CH_2)_xN[(CH_2)_yR^{15}]CON[(CH_2)_yR^{15}]$—[$CO(CH_2)_yR^{16}$],
—$(CH_2)_xN[(CH_2)_yR^{15}][S(O)_r(CH_2)_yR^{16}]$;

$R^{15}$ and $R^{16}$ are independently
a) hydrogen,
b) $C_1$-$C_8$ alkyl,
c) -($C_1$-$C_4$ alkyl)-aryl, where aryl is defined above,
d) $C_5$-$C_7$ cycloalkyl,
e) phenyl, substituted by 0–3 $R^{18}$,
f) benzyl, substituted by 0–3 $R^{18}$, or
g) —($C_1$-$C_4$ alkoxy);

$R^{15}$ and $R^{16}$ are taken together to form a ring:

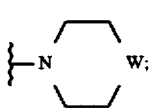

m is 0 to 6;
n is 1 to 2;
p is 0 to 2;
q is 0 to 4;
r is 0 to 2;
s is 0 to 3;
t is 1 to 5;
u is 0 to 5;
w is 0 to 5;
x is 0 to 6;
y is 0 to 6;
W is
a) —O—,
b) —$S(O)_r$,
c) —$NR^4$—,
d) —$NC(=O)R^3$—,
e) a bond, or
f) —$(CH_2)_n$—;

or pharmaceutically acceptable salts thereof.

2. A compound of claim 1 wherein:

Z is
a) —$(CH_2)_mCONR^8$—,
b) —$(CH_2)_mCSNR^8$—,
c) —$(CH_2)_mSO_2NR^8$—, $R^1$ is —$(CH_2)_p$-aryl, wherein aryl is phenyl, naphthyl or biphenyl substituted with one, two or three substituents selected from the group consisting of:
halo, methylenedioxy, -$R^8$, —$NR^8COR^9$, $C_2$-$C_6$-alkenyl, $C_2$-$C_6$-alkynyl, —$(CH_2)_w$—$OR^8$, —($C_1$-$C_6$)-perfluoroalkyl, —$(CH_2)_wCN$, —$(CH_2)_wNC$, —$(CH_2)_wNO_2$, —$(CH_2)_wCF_3$, —$(CH_2)_wS(O)_rR^7$, —$(CH_2)_wNR^8R^9$, —$(CH_2)_wCOR^8$, —$(CH_2)_wCO_2R^8$, —$(CH_2)_wCONR^8R^9$, —$(CH_2)_wSO_2NH$—($C_1$-$C_6$)-alkyl, —$(CH_2)_wSO_2NH_2$, —$(CH_2)_wSO_2NH$—CO—($C_1$-$C_6$)—alkyl, —$(CH_2)_wSO_2NH$—$CO_2$—($C_1$-$C_6$)-alkyl, —$(CH_2)_wNHSO_2$—($C_1$-$C_6$)-alkyl, —$(CH_2)_wNHSO_2$—($C_1$-$C_6$)-perfluoroalkyl, —$(CH_2)_wNHSO_2$-phenyl, —$(CH_2)_wNHSO_2$-perfluorophenyl, —$(CH_2)_wCN_4H$, —$O(CH_2)_wCN$, —$NH(CH_2)_wCN$, —$S(CH_2)_wCN$, —$(CH_2)_wNH$—CO—($C_1$-$C_6$-alkyl), —$(CH_2)_wNH$—CO—($C_1$-$C_6$-perfluoroalkyl), —$(CH_2)_wNH$—CO—(phenyl), —$(CH_2)_wNH$—$CO_2$—($C_1$-$C_6$-alkyl), —$(CH_2)_wNH$—$CO_2$—($C_1$-$C_6$-perfluoroalkyl), or —$(CH_2)_wNH$—$CO_2$—(phenyl), —$O(C=O$—($C_1$-$C_5$ alkyl);

$R^{14}$ is:
a) —H,
b) —$CF_3$
c) -$C_1$-$C_4$ alkyl,
d) —$(CH_2)_q$-aryl, wherein aryl is phenyl, biphenyl, naphthyl, or fluorenyl unsubstituted or substituted with one to three substituents selected from the group consisting of:
halogen
—$CF_3$,
-($C_1$-$C_4$ alkyl),
-methylenedioxy,
-($C_1$-$C_4$ alkoxy),
—$(CH_2)_xN[(CH_2)_yR^{15}][(CH_2)_yR^{16}]$; and all other required substituents of formula (I) are as defined in claim 1.

3. A compound of claim 2 wherein

A is -$BY^1Y^2$;

$Y^1$ and $Y^2$ are independently
a) —OH, or
b) $C_1$-$C_8$ alkoxy;

$Y^1$ and $Y^2$ are taken together to form a cyclic boron ester where said chain or ring contains from 2 to 20 carbon atoms and from 0–3 heteroatoms which are N, S, or O, X is
  a) halogen
  b) —CN,
  c) —NO$_2$,
  d) —CF$_3$,
  e) —NHR$^{14}$
  f) —NHS(O)$_r$R$^{14}$,
  g) —NHC(NH)H,
  h) —NHC(NH)NHOH,
  i) —NHC(NH)NHCN,
  j) —NHC(NH)NHR$^{14}$,
  k) —NHC(NH)NHCOR$^{14}$,
  l) —C(NH)NHR$^{14}$,
  m) —C(NH)NHCOR$^{14}$,
  n) —C(O)NHR$^{14}$,
  o) —C(O)NHC(O) R$^{14}$,
  p) —C(O)OR$^{14}$,
  q) —OR$^{14}$,
  r) —OC(O)R$^{14}$,
  s) —OC(O)OR$^{14}$,
  t) —OC(O)NHR$^{14}$,
  u) —OC(O)NHC(O) R$^{14}$,
  v) —SC(=NH)NHR$^{14}$, or
  w) —SC(=NH)NHC(=O) R$^{14}$;

W is
  a) —O—,
  b) —NR$^4$—,
  c) a bond, or
  d) —(CH$_2$)$_n$—;

and all other required substituents of formula (I) are as in claim 2.

4. A compound of claim 3 wherein:
Z is —(CH$_2$)$_m$CONR$^8$—;
R$^2$ is
  a) -(C1–C12 alkyl)-X, or b) 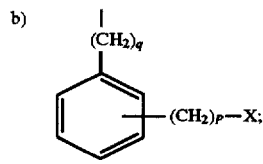

X is
  a) halogen (F, Cl, Br, I),
  b) —CN,
  c) —NHR$^{14}$
  d) —NHC(NH) H,
  e) —NHC(NH) NHR$^{14}$,
  f) —C(NH)NHR$^{14}$,
  g) —OR$^{14}$, or
  h) —SC(=NH) NHR$^{14}$;
R$^{14}$ is —H;
and all other required substituents of formula (I) are defined as in claim 3.

5. A compound of claim 4 selected from the group consisting of:

N$^1$-(4-phenylbenzoyl)-(R)-boroarginine, hydrochloride
N$^1$-(3-phenoxybenzoyl)-(R)-boroarginine, hydrochloride
N$^1$-(1-fluorenonyl)-(R)-boroarginine, hydrochloride
N$^1$-(4-[1-butyl]benzoyl)-(R)-boroarginine, hydrochloride
N$^1$-(2-benzoylbenzoyl)-(R)-boroarginine, hydrochloride
N$^1$-(3-[N-benzyloxycarbonyl-N-methylamino]-4-[1-butyl]-benzoyl)-(R)-boroarginine, hydrochloride
N$^1$-(4-cyclohexylbenzoyl)-(R)-boroarginine, hydrochloride
N$^1$-(2-methyl-4-phenylbenzoyl)-(R)-boroarginine, hydrochloride
N$^1$-[4-phenyl-2-nitrobenzoyl]boroArg, (+)-pinanediol ester
N$^1$-[4-phenyl-2-fluorobenzoyl]boroArg, (+)-pinanediol ester
N$^1$-[4-phenyl-2-aminobenzoyl]boroArg, (+)-pinanediol ester
N$^1$-[4-phenyl-2-(methylsulfonamido)benzoyl]boroArg, (+)-pinanediol ester
N$^1$-[4-phenyl-2-(cyanomethylamino)benzoyl]boroArg, (+)-pinanediol ester
N$^1$-[4-phenyl-2-(cyanomethyl)benzoyl]boroArg, (+)-pinanediol ester
N$^1$-[4-phenyl-2-(diethylamino)benzoyl]boroArg, (+)-pinanediol ester
N$^1$-[4-[2-(t-butylaminosulfonyl)phenyl]-2-methyl-benzoyl]boroArg, (+)pinanediol ester
N$^1$-[4-[2-(aminosulfonyl)phenyl]-2-methyl-benzoyl]boroArg, (+)pinanediol ester
N$^1$-[4-[2-(methoxycarbonylaminosulfonyl)phenyl]-2-methyl-benzoyl]boroArg, (+)-pinanediol ester
N$^1$-[4-[2-(t-butylaminosulfonyl)phenyl]benzoyl]boroArg, (+)-pinanediol ester
N$^1$-[4-[2-(t-butylaminosulfonyl)phenyl]benzoyl]boroArg—OH
N$^1$-[4-[2-(n-butoxycarbonylaminosulfonyl)phenyl]-2-methyl-benzoyl]boroArg, (+)-pinanediol ester
N$^1$-[4-[2-(diethylaminosulfonyl)phenyl]-2-methyl-benzoyl]boroArg, (+)pinanediol ester
N$^1$-[4-[2-(t-butylaminosulfonyl)phenyl]-2-fluoro-benzoyl]boroArg, (+)pinanediol ester
N$^1$-[4-[2-(aminosulfonyl)phenyl]-2-fluoro-benzoyl]boroArg, (+)pinanediol ester
N$^1$-[4-[2-(methoxycarbonylaminosulfonyl)phenyl]-2-fluoro-benzoyl]boroArg, (+)-pinanediol ester
N$^1$-[4-[2-(t-butylaminosulfonyl)phenyl]-2-nitro-benzoyl]boroArg, (+)pinanediol ester
N$^1$-[4-[2-(aminosulfonyl)phenyl]-2-nitro-benzoyl]boroArg, (+)pinanediol ester
N$^1$-[4-[2-(methoxycarbonylaminosulfonyl)phenyl]-2-nitro-benzoyl]boroArg, (+)-pinanediol ester
N$^1$-(3-phenylbenzoyl)boroarg, (+)-pinanediol
N$^1$-[4-(3-BOCNHphenyl)$_2$-methylbenzoyl]boroarg, (+)-pinanediol
N$^1$-[4-(3-nitrophenyl)benzoyl]boroarg, (+)-pinanediol
N$^1$-[4-(3-aminophenyl)benzoyl]boroarg, (+)-pinanediol
N$^1$-(3-phenylbenzoyl)borolys, (+)-pinanediol and
N$^1$-(3-phenylbenzoyl)boroIrg, (+)-pinanediol.

6. A pharmaceutical composition comprising a pharmaceutically acceptable carrier and a therapeutically effective amount of a compound of any one of claims 1 through 5.

7. A method of treating a physiological disorder in a warm blooded animal catalyzed by trypsin-like enzymes comprising administering to an animal in need of such treatment an effective amount of a compound of any one of claims 1 through 5.

* * * * *